US009686971B2

(12) United States Patent
Diacovo et al.

(10) Patent No.: US 9,686,971 B2
(45) Date of Patent: Jun. 27, 2017

(54) METHODS FOR TESTING ANTI-THROMBOTIC AGENTS

(71) Applicant: The Trustees of Columbia University in the City of New York, New York, NY (US)

(72) Inventors: Thomas Diacovo, Larchmont, NY (US); Jianchun Chen, Edgewater, NJ (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 15/047,978

(22) Filed: Feb. 19, 2016

(65) Prior Publication Data
US 2016/0345550 A1 Dec. 1, 2016

Related U.S. Application Data

(63) Continuation of application No. 12/345,363, filed on Dec. 29, 2008, now abandoned, which is a continuation-in-part of application No. PCT/US2007/015043, filed on Jun. 28, 2007.

(60) Provisional application No. 60/817,600, filed on Jun. 29, 2006.

(51) Int. Cl.
| | |
|---|---|
| *A01K 67/00* | (2006.01) |
| *A01K 67/027* | (2006.01) |
| *C07K 14/755* | (2006.01) |
| *C12N 15/85* | (2006.01) |
| *G01N 33/566* | (2006.01) |

(52) U.S. Cl.
CPC ...... *A01K 67/0278* (2013.01); *A01K 67/0275* (2013.01); *C07K 14/755* (2013.01); *C12N 15/8509* (2013.01); *G01N 33/566* (2013.01); *A01K 2207/15* (2013.01); *A01K 2217/072* (2013.01); *A01K 2227/105* (2013.01); *A01K 2267/0381* (2013.01); *A01K 2267/0393* (2013.01); *G01N 2333/70596* (2013.01); *G01N 2500/02* (2013.01)

(58) Field of Classification Search
None
See application file for complete search history.

(56) References Cited

U.S. PATENT DOCUMENTS

| 4,873,191 A | 10/1989 | Wagner et al. |
|---|---|---|
| 5,096,815 A | 3/1992 | Ladner et al. |
| 5,198,346 A | 3/1993 | Ladner et al. |
| 5,223,409 A | 6/1993 | Ladner et al. |
| 5,712,171 A | 1/1998 | Zambias et al. |
| 5,721,121 A | 2/1998 | Etcheverry et al. |
| 6,927,278 B1 | 8/2005 | Diamond |
| 7,087,411 B2 | 8/2006 | Daly et al. |
| 2004/0014667 A1 | 1/2004 | Daly et al. |
| 2005/0009163 A1 | 1/2005 | Tong et al. |
| 2005/0169899 A1 | 8/2005 | Diamond |
| 2005/0175610 A1 | 8/2005 | Wiegand et al. |
| 2005/0260203 A1 | 11/2005 | Wieqand et al. |
| 2006/0030529 A1 | 2/2006 | Wiegand et al. |
| 2006/0058234 A1 | 3/2006 | Daly et al. |
| 2016/0345550 A1* | 12/2016 | Diacovo ............ A01K 67/0278 |

FOREIGN PATENT DOCUMENTS

| WO | WO-91/05058 | 4/1991 |
|---|---|---|
| WO | WO-93/20242 | 10/1993 |
| WO | WO-94/18318 | 8/1994 |
| WO | WO-95/18972 | 7/1995 |
| WO | WO-96/22529 | 7/1996 |
| WO | WO-01/92337 | 12/2001 |
| WO | WO-2008/005290 | 1/2008 |

OTHER PUBLICATIONS

"Animal Cell Culture,. A Practical Approach", R. I. Freshney, ed., 1986.
"DNA Cloning: A Practical Approach," vols. I and II, D. N. Glover, ed., IRL Press Limited, Oxford, England (1985).
"Immobilized Cells and Enzymes", J. Woodward Ed., IRL Press Limited, Oxford, England (1985).
"Nucleic Acid Hybridization", B. D. Hames & S. J. Higgins, eds. IRL Press Limited, Oxford, England ( 1985).
"Oligonucleotide Synthesis" (M. J. Gait, ed., 1984).
"Transcription and Translation", B. D. Hames & S. J. Higgenseds, IRL Press Limited, Oxford, England ( 1984).
Ajzenberg et al., "Effect of recomb. von Willebrand factor reproducing Type 2B . . . 2M mutations on shear-induced platelet aggregation," Blood, vol. 95, pp. 3796-3803(Jun. 2000).
Alon et al., "The kinetics and shear threshold of transient and rolling interactions of L-selectin with its ligand on leukocvtes," PNAS USA, vol. 95, DD. 11631-11636(Sep. 1998).
Andre et al., "CD40L stabilizes arterial thrombi by f:13 integrin-dependent mechanism," Nature Medicine, vol. 8, pp. 247-252 (Mar. 2002).
Andrews et al., "Platelet physiology and thrombosis," Thrombosis Research, vol. 114, pp. 447-453 (2004).
Andrews et al., "Purific. botrocetin from bothrops jararaca Venom. Anal. Botrocetin-Mediated Inter. btwn von Willebrand Fr amd Human . . . Cmplx" Biocem v28 pp. 8317-8326 (1989).

(Continued)

*Primary Examiner* — Michael Burkhart
(74) *Attorney, Agent, or Firm* — Potomac Law Group, PLLC; Mark Catan

(57) ABSTRACT

The invention provides a transgenic non-human animal expressing von Willebrand Factor A1 protein containing at least one mutation selected from the group consisting of: 1263P>S, 1269N>D, 1274K>R, 1287M>R, 1302G>D, 1308H>R, 1313R>W, 1314I>V, 1326R>H, 1329L>I, 1330E>G, 1333A>D, 1344T>A, 1347I>V, 1350T>A, 1370G>S, 1379H>R, 1381T>A, 1385T>M 1391P>Q, 1394A>S, 1397L>F, 1421S>N, 1439L>V, 1442G>S, 1449R>Q, 1466A>P, 1469Q>L, 1472Q>H, 1473V>M, 1475H>Q, 1479S>G, and any combination thereof.

4 Claims, 70 Drawing Sheets

(56) References Cited

OTHER PUBLICATIONS

B. Perbal, "A Practical Guide to Molecular Cloning", John Wiley & Sons, Inc., Printed in the USA (1984).
Bennett J.S.,"Novel Platelet Inhibitors," Annu Rev. Med., vol. 52, pp. 161-184 (2001).
Bergmeier et al., "The role of platelet adhesion receptor GPIba far exceeds that of its main ligand, von Willebrand fator in . . . " PNAS, vol. 103, pp. 16900-16905 (Nov. 2006).
Blondelle et al., "Novel antimicrobial compounds identified using synthetic combinatorial library technoloqv," Tib Tech 14:60-65 (1996).
Bogan et al.,"Anatomy of Hot spots in Protein Interfaces," J. Mol. Biol; vol. 280, pp. 1-9 (1998).
Bonnefoy et al., "Shielding the front-strand f:l3 of the von Willebrand factor A 1 domain inhibits its binding to platelet glycoprotein Iba," Blood, vol. 101, pp. 1375-1383 (2003.
Bonthron et al., "Structure of pre-pro-von Willebrand factor and its expression in heterologous cells," Nature vol. 324, pp. 270-273 (Nov. 1986).
Bradley, et al., "Formation of germ-line Chimaeras from embryo-derived teratocarcinoma cell lines," Nature 309:255-258 (1984).
Brenner et al., "Encoded Combinatorial Chemistry," Proc. Natl. Acad. Sci. USA 89:5381-5383 (1992).
Brinster, et al.,"Factors affecting the efficiency of introducing foreign DNA into mice by microinjecting eggs," Proc. Natl. Acad. Sci. USA 82:4438-4442 (1985).
Celikel et al., "von Willebrand factor conformation and adhesive function is modulated by an internalized water . . . " Nature Structural biology, vol. 10, pp. 881-884 (Oct. 2000).
Chen et al., "An Automatic Braking System that stabilizes Leukocyte Rolling by an Increase in Selectin Bond . . . " The Journal of Cell Biolgy, vol. 144, pp. 185-200 (Jan. 1999).
Chen et al., "Selectin receptor-ligand bonds: Formation limited by shear rate and dissociation governed by bell model," PNAS, vol. 98, pp. 950-955 (Jan. 2001).
Chesla et al., "Measuring two-dimensional Receptor-ligand binding kinetics by Micropipette," Biophysical Journal, vol. 75, pp. 1553-1572 (Sep. 1998).
Collaborative Computational Project, No. 4,"The CCP4 Suite: Programs for Protein Crystallography," Acta Cryst, D50, pp. 760-763 (1994).
Cooney et al., "Comparative Analysis of Type 2b von Willebrand Disease Mutations: Implications for Mechanism of von Willebrand . . . " Blood, vol. 87, pp. 2322-2328 (Mar. 1996).
Coxon et al., "A Novel role for the f:l2 Integrin CD11b/CD18 in Neutrophil Apoptosis: A Homeostatic Mechanism in Inflammation," Immunity, vol. 5, pp. 653-666 (Dec. 1996).
Cruz et al., "Interaction of the vonWFactor with Collagen. Localization of the primary collagen-binding . . . " The Jour. of Biological Chemistry, vol. 270, pp. 10822-10827 (1995).
Cruz et al., "Mapping the Glycoprotein Ib-binding Site in the von Willebrand Factor A1 Domain," J. Biol. Chem. 275, 19098-19105 (2000).
Davis et al., "Isolation of Angiopoietin-1, a ligand for the TIE2 Receptor, by Secretion-Trap Expression Cloning," Cell, vol. 87, pp. 1161-1169 (Dec. 1996).
Denis et al.,"A mouse model of severe von Willebrand disease: Defects in hemostatis and thrombosis," PNAS USA,vol. 95,pp. 9524-9529 (Aug. 1998).
Denis et al., "Insights from Von Willebrand disease animal models," Cell Mol Life Sci., vol. 56, pp. 977-990 (1999).
Diacovo et al.,"Platelet-Mediated Lymphocyte Delivery to High Endothelial Venules," Science, vol. 273,pp. 252-255 (Jul. 1996).
Diamond S.L., "Engineering Design of Optimal Strategies for blood clot dissolution," Annu. Rev. Biomed Eng., vol. 1, pp. 427-461 (1999).
Doggett et al., "Alterations in the intrinsic properties of the GPIba-VWF tether bond define the kinetics of of the platelet-type VWF . . . " Blood, vol. 102; pp. 152-160 (2003).
Doggett et al.,"Selectin-Like Kinetics and Biomechanics Promote Rapid Platelet Adhesion in Flow: . . . " Biophysical Journal, vol. 83, pp. 194-205 (Jul. 2002).
Dulak et al., "New Strategies for Cardiovascular Gene Therapy" Cell Biochemistry and Biophysics, vol. 44, pp. 31-42 (2006).
Dumas et al., "Crystal Structure of the Wild-type von Willebrand Factor A1-Glycoprotein . . . " The Journal of Biological Chemistry, vol. 279, DD. 23327-23334 (2004).
Edge et al., "Total synthesis of a Human Leukocyte interferon gene," (1981) Nature, 292:756-762.
Emsley et al., "Crystal Structure of the von Willebrand factor A1 Domain and Implications for the Binding of platelet Glycoprotein Ib," J Biol Chem. 273:10396-401 (1998).
Emsley et al., "Structural Basis of Collagen Recognition by integrin a2f:l1," Cell vol. 101, pp. 47-56 (Mar. 2000).
Erb et al., "Recursive deconvolution of combinatorial chemical libraries," Proc. Natl. Acad. Sci. USA 91:11422-11426 (1994).
Esnouf R.M., "An extensively modified version of MolScript that includes greatly enhanced coloring capabilities," Journal of Molecular Graphics and Modelling,15, 132-134 (1997).
Espirito Santo et al., "Absence of an atheroprotective effect of the garlic powder printanor in APOE*3-Leiden transgenic mice," Atherosclerosis, vol. 177, pp. 291-297 (2004).
Evans et al., "Chemically distinct transition states govern rapid dissociation of single L-selectin bonds under force," PNAS, vol. 98, pp. 3784-3789 (Mar. 2001).
Evans et al., "Detachment of agglutinin-bounded red blood cells," Biophys Biophysical Society, vol. 59, pp. 838-848 (Apr. 1991).
Evans et al., Establishment in culture of pluripotential cells fro, et al., "Establishment in culture of pluripotential cells from mouse embryos," Nature292:154-156 (1981).
Ewenstein B.M., "Von Willebrand's Disease," Annu. Rev. Med., vol. 48; oo.552-42 (1997).
Ausubel, F.M.et al."Current Protocols in Molecular Biology", John Wiley & Sons, New York, N.Y. (1989).
Falati et al., "Real-time in vivo imaging of platelets, tissue factor and fibrin during arterial thrombus formation in the mouse," Nature Medicine,vol. 8, pp. 1175-1180(Oct. 2002).
Fodor et al., "Light-Directed, Spatially Addressable Parallel Chemical Synthesis," Science 251:767-773 (1991).
Franchini et al., "Von Willebrand factor and thrombosis," Ann Hematol, vol. 85, pp. 415-423 (2006).
Fredrickson et al., "Shear-Dependent rolling on von Willebrand Factor of Mammalian Cells Expressing the Platelet Glycoprotein . . . ," Blood, vol. 92, pp. 3684-3693 (Nov. 1998).
Fukuda et al., "The snake venom protein botrocetin acts as a biological brace to promote dysfunctional . . . ," Nature Structural & Molecular Biology,vol. 12, pp. 152-159 (Feb. 2005).
Fukuda et al., "Structural Basis of von Willebrand Factor Acivation by the snake toxin botrocetin," Structure, vol. 10, pp. 943-950 (Jul. 2002).
Furie et al., "Thrombus formation in vivo," The Journal of Clinical Investigation, vol. 115, pp. 3355-3362 (Dec. 2005).
Gachet et al., "The Platelet P2 Receptors in Thrombosis," Seminars in thrombosis and Hemostasis, vol. 31, pp. 162-167 (2005).
Gallop et al.,"Applications of Combinatorial Technologies to Drug Discovery. 1. Background and Peptide Combinatorial Libraries," J. Medicinal Chemistry 37(9):1233-1251 (1994).
Gillespie et al., "A General Method for numerically Simulating the stochastic Time Evolution of coupled . . . ," Journal of Computational Physics, vol. 22, DD. 403-434 (1976).
Goeddel D.V., "Systems for Heterologous Gene Expression," Gene Expression Technology, Methods in Enzymology 185, pp. 3-5, Academic Press, San Diego, CA (1990).
Goodeve et al., "A standard nomenclature for von Willebrand factor gene mutations and polymorphisms." Thromb Haemost 85(5):929-31 (2001).
Gassler, et al.,"Transgenesis by means of blastocyst-derived embryonic stem cell lines," Proc. Acad. Sci. USA 83:9065-9069 (1986).
Graham et al., "Characteristics of a Human Cell Line Transformed by DNA from Human Adenovirus Type 5," J. Gen. Viral., 36:59-72 (1977).

(56) References Cited

OTHER PUBLICATIONS

Greenberg et al., "Cell-free rolling mediated by L-Selectin and Sialyl Lewis Reveals the Shear Threshold effect," Biophysical Journal, vol. 79, pp. 2391-2402 (Nov. 2000).
Handa et al., "The von Willebrand Factor-binding Domain of Platelet membrane Glycoprotein Ib," The journal of Biological Chemistry, vol. 261, pp. 12579-12585 (1986).
Hankey et al., "New Drugs, old drugs. Antiplatelet drugs," MJA, vol. 178, pp. 568-574 (Jun. 2003).
Haskell et al., "Efficient Production of transgenic Cattle by Retroviral Infection of Early Embryos," Mol. Reprod. Dev. 40:386-390 (1995).
Hillery et al., "Type 2M von Willebrand Disease: F6061 and 1662F Mutations in the Glycoprotein Ib Binding Domain Selectively Impair . . . " Blood, vol. 91,pp. 1572-1581 (Mar. 1998).
Hogan et al., "In Manipulating the Mouse Embryo", Cold Spring Harbor Laboratory Press, Plainview, N.Y. (1986).
Holash et al., "VEGF-Trap: A VEGF blocker with potent antitumor effects," PNAS, vol. 99, pp. 11393-11398 (Aug. 2002).
Houghten et al., "Generation and use of synthetic peptide combinatorial libraries for basic research and drug discovery," Nature 354:84-86 (1991).
Houghten et al., "The use of Synthetic Peptide Combinatorial Libraries for the Identification of Bioactive Peptides," Biotechniques 13:412 (1992).
Howard et al., Variant von Willebrand's disease Type B-Revisited, Blood, vol. 60, pp. 1420-1428 (1982).
Huizinga, E.G. et al., "Structures of Glycoprotein I Ba and its Complex with von Willebrand Factor A 1 Domain," Science 297, 1176-1179 (2002).
Inouye et al., "Up-promoter mutations in the Ipp gene of *Escherichia coli*," Nucleic Acids Res. 13:3101-3109 (1985).
Italiano et al. "Mechanisms and implications of platelet discoid shape," Blood, vol. 10, pp. 4789-4796 (Jun. 2003).
Sambrook, J. et al., "Molecular Cloning, A Labratory Manual", Cold Spring Harbor Press, Plainview, N.Y. (1989).
Jaenisch R., "Germ Line integration and mendelian transmission of the exogenous Moloney leukemia virus," PNAS USA, vol. 73, pp. 1260-1264 (Apr. 1976).
Jaenisch, "Transgenic Animals," Science 240:1468-1474 (1988).
Jaffe et al., "Synthesis of Antihemophilic factor Antigen by cultured human endothelial cells," The Journal of Clinical Investigation, vol. 52, pp. 2757-2764 (Nov. 1973).
Jahner, D. et al., "De Novo methylation and expression of retroviral genomes during mouse embryogenesis," Nature 298:623-628 (1982).
Jahner, D. et al., "Insertion of the bacterial gpt gene into the germ line of mice by retroviral infection," Proc. Natl. Acad Sci. USA 82:6927-6931 (1985).
Jay et al., "Chemical Synthesis of a Biologically Active Gene for human Immune Interferon-y," J. Biol. Chem., 259:6311 (1984).
Jayawickreme et al., "Creation and functional screening of a Multi-use peptide library," Proc. Natl. Acad. Sci. USA 91:1614-1618 (1994).
Jenkins et al. (1998) "Molecular Modeling of Ligand and Mutation Sites of the Type A Domains of Human von Willebrand Factor and Their . . . ," Blood, vol. 91, No. 6, pp. 2032-2044.
Johnsson et al., "Chemical Tools for biomolecular Imaging," ACS Chemical Biology, vol. 2, pp. 31-38 (2007).
Kaji et al., "Quantum dots for single bio-molecule imaging," Analytical Sciences, vol. 23, pp. 21-24 (Jan. 2007).
Kalfitis et al. "Localization of a Collagen-Interactive Domain of Human von Willebrand Factor Between Amino Acid Resi. Gly 911 . . . ," Blood vol. 70,pp. 1577-1583 (Nov. 1987).
King et al., "Multiparticle adhesive dynamics: Hydrodynamic recruitment of rolling leukocytes," PNAS, vol. 98, pp. 14919-14924 (Dec. 2001).
Kitaguchi et al., "Establishment and Characterization of Transgenic mice expressing human platelet glycoprotein Iba," Biochemical and . . . , vol. 220, pp. 418-424 (1996).

Kohler et al., "Continuous cultures of used cells secreting antibody of predefined specificity," Nature vol. 256, pp. 495-497 (Aug. 1975).
Kolkekar et al., "Peptidyglycine a-hydroxylating monooxygenase:Active site, disulfide linkages, and a two-domain model of the catalytic . . . ," Biochemistry,36:10901-10909 (1997).
Kroner et al., "Analysis of the structure and function of the von Willebrand factor A 1 domain using target deletions and . . . ," Biochemistry, vol. 35, pp. 13460-13468 (1996).
Lam et al., "A New type of synthetic peptide library for identifying ligand-binding activity," Nature 354:82-84 (1991).
Lanza et al., "High-Frequency Ultrasonic detection of thrombi with a target contrast system," Ultrasound in Med & Bio, vol. 23, pp. 863-870 (1997).
Lanza et al., "Molecular imaging of stretch-induced tissue Factor expression in carotid Arteries with intravascular . . . ," Investigate Radiology, vol. 35, DD. 227-234 (Apr. 2000).
Laurenzi et al., "Monte Carlo Simulation of the heterotypic aggregation kinetics of platelets and neutrophils," Biophysical Journal, vol. 77, DD. 1733-1746 (Sep. 1999).
Lenain et al.,"Inhibition of localized thrombosis in P2Y1-deficient mice and rodents treated with MRS2179 . . . ," Journal of Thrombosis and haemostasis,vol. 1, pp. 1144-1149 (2003).
Lenling et al.,"An experimental model to study the in vivo survival of von Willebrand factor," The journal of bioloqical chemistry, vol. 279, pp. 12102-12109 (Mar. 2004).
Leon et al., "Defective platelet aggregation and increased resistance to thrombosis in purinergic PSY1 receptor-null mice," J. Clin Invest., vol. 104, pp. 1731-1737 (1999).
Lew et al., "Discovery and development of GS 4104 (oseltamivir): An orally Active Influenza Neuraminidase Inhibitor," Curr. Med. Chem. 7(6):663-72 (2000).
Innis, M.A., et al., "PCR Protocols: A Guide to Methods and Applications," Academic Press, San Diego, California, (1990).
Mancuso et al., "Structure of the Gene for human von Willebrand factor," The journal of Biological chemistry, VOi 264, pp. 19514-19527 (1989).
Mancuso et al.,"Type 2M: Milwaukee-1 von Willebrand Disease: An in-frames deletion in the Cys509 loop of the von Willebrand Factor A1 . . . " Blood, vol. 88, pp. 2559-2568, (1996).
Maniatis, et al., "Molecular Cloning: A Laboratory Manual", Cold Spring Harbor Laboratory, Printed in the USA (1982).
Marshall et al., "Direct observation of catch bonds invovling cell-adhesion molecules," Nature, vol. 423, pp. 190-193 (May 2003).
Mather et al., "Culture of testicular cells in Hormone-supplemented serum-free medium," Annals NY Acad. Sci., 383:44-68 (1982).
Mather, J., "Establishment and Characterization of two distinct Mouse Testicular Epithelial Cell lines," Biol. Reprod., 23:243-252 (1980).
Matsushita et al., "Identification of Amino Acid Residues essential for von Willebrand Factor binding . . . ," The Journal of Biological Chemistry, vol. 270, pp. 13406-13414 (1995).
Matsushita et al., "Localization of von Willebrand factor-binding sites for platelet glycoprotein Ib and . . . ," The Jour.of Biological Chem.,vol. 275, pp. 11044-11049 (Apr. 2000).
Medynski, "Synthesis Peptide Combinatorial Libraries," BioTechnology 12:709-710 (1994).
Melo et al., Endothelium-targeted gene and cell-based therapies for cardiovascular disease, Arterioscler Thromb Vase Biol, vol. 24, pp. 1761-1774, (2004).
Merkel et al., "Energy landscapes of receptor-ligand bonds explored with dynamic force spectroscopy," Nature, vol. 397, pp. 50-53 (Jan. 1999).
Michiels et al., "Characterization, classification, and treatment of von Willebrand diseases: A critical Appraisal of . . . ," Seminars in throm.and hemo. vol. 31,pp. 577-601 (2005).
Miura et al., "Interaction of von Willebrand factor domain A 1 with platelet glycoprotein Iba-(1-289)," The journal of bioloqical chemistry, vol. 275, pp. 7539-7546 (2000).
Mody et al., "Mechanics of transient platelet adhesion to von Willebrand factor under flow," Biophysical Journal, vol. 88, pp. 1432-1443 (Feb. 2005).

(56) References Cited

OTHER PUBLICATIONS

Nachman et al., "Synthesis of Factor VIII Antigen by cultured Guinea Pig Megakaryocytes," The Journal of Clinical Investiaation, VOi 60, DD. 914-921 (Oct. 1977).
Nambiar, et al., "Total Synthesis and cloning of a Gene Coding for Ribonuclease S Protein," Science, 223:1299-1301 (1984).
Napoli et al., "In vivo veritas: Thrombosis mechanisms in animal models," Scand J. Clin Lab invest, vol. 66, DD. 407-428 (2006).
Ni et al., "Increased Thrombogenesis and embolus formation in mice lacking glycoprotein V," Blood, vol. 98, pp. 368-373 (Jul. 2001).
Nitu-Whalley et al., "Identification of Type 2 von Willebrand Disease in Previously Diagnosed Type 1 Patients: A Reappraisal . . . ," Thromb Haemost, vol. 84, pp. 998-1004 (2000).
Offermanns, S., "Activation of Platelet Function through G Protein-Coupled Receptors," Cir Res., vol. 99, DD. 1293-1304 (2006).
Ohlmeyer et al., "Complex synthetic chemical libraries indexed with molecular tags," Proc. Natl. Acad. Sci. USA 90:10922-10926 (1993).
Pareti et al.,"Isolation and Characterization of two domains of human von Willebrand factor that interact with . . . ,"The Jour.of Bio.Chem.,vol. 262, pp. 13835-13841 (1987).
Pareti et al., "Isolation and Characterzation of a Collagen Binding Domain in Human von Willebrand Factor," The Journal of Biological Chemistry, vol. 261, pp. 15310-15315 (1996).
Partlow et al., "19F magnetic resonance imaging for stem/progenitor cell tracking with multiple uniaue perfluorocarbon nanobeacons," FASEB J., vol. 21, DD. 1647-1654 (2007).
Perbal, B. et al., "Organization of chicken DNA Sequence Homologous to the transforming Gene of Avian Myeloblastosis Virus. II Isolation . . . " J. Virol. Mar.45(3):925-40 (1983).
Pletu et al., "Production in *Escherichia coli* of a biologically active subfragnnent of von Willebrand . . . " Biochenn.and Biophys. Res. Com. vol. 164, pp. 1339-1347 (Nov. 1989).
Pozgajova et al., "Reduced thrombus stability in mice lacking the a2A-adrenergic receptor," Blood, vol. 108, pp. 510-514 (2006).
Rabinowitz, I. et al., "von Willebrand disease type B: A missense mutation selectively abolishes ristocetin-induced . . . ," Proc.Natl. Acad.Sci. USA 89, 9846-9849 (1992).
Read et al., "Role of botrocetin in Platelet Agglutination: Formation of an Activated Complex . . . ," Dept. of Path., University of N.C. Chap.Hill., Blood,74(3):1031 (Sep. 1998).
Ribba et al., "Characterization of Recombinant von Willebrand Factor corresponding to mutations in Type IIA and . . . ," The Jour. of Biol.Chem, vol. 267, pp. 23209-23215 (1992).
Robertson, et al., "Germ-line transmission of genes introduced into cultured pluripotential cells by retroviral vector," Nature 322:445-448 (1986).
Roth et al., "Localization of binding sites within human von Willebrand factor for Monomeric Type III Collagen," Biochemistry, vol. 25, pp. 8357-8361 (1986).
Roth,G., "Developing Relationships: Arterial Platelet adhesion, Glycoprotein Ib, and Leucine-Rich Glycproteins," Blood, vol. 77, DD. 5-19 (1991).
Ruggeri et al., "The Complex multimeric Composition of Faction VIII/ von Willebrand Factor," Blood, vol. 57, pp. 1140-1143 (1981).
Ruggeri, Z.M. et al.., "Activation-independent platelet adhesion and aggregation under elevated shear stress," Blood. 108, 1903-1910 (2006).
Ruther et al., "Easy identification of cDNA clones," EMBO 12:1791-1794 (1983).
Sadler et al., "Cloning and characterization of two cDNAs coding for human von Willebrand factor," PNAS USA, vol. 82, pp. 6394-6398 (Oct. 1985).
Sadler, J.E. et al., "Update on the pathophysiology and classification of von Willebrand disease: a report of the Subcommittee . . . ," J. Thromb. Haemost. 4, 2103-2114 (2006).
Sakariassen et al., "Human blood platelet adhesion to artery subendothelium is mediated by factor VIII-Von Willebrand factor bound . . . ," Nature, vol. 279, pp. 636-638 (Jun. 1979).
Salmon et al., Discovery of biologically active peptides in random libraries: Solution-phase testing after staged . . . , Proc. Natl. Acad. Sci. USA 90:11708-11712 (1993).
Sambrook, et al., "Chaperones, paperones," Nature Nov. 16;342 (6247):224-5 (1989).
Sauer et al., "Site-specific DNA recombination in mammalian cells bu the CRE recombinase of bacteriophage P1," Proc. Natl. Acad. Sci. USA 85:5166 (1988).
Savage et al., "Initiation of Platelet Adhesion by arrest onto Fibrogen or translacation on von Willebrand Factor," Cell, vol. 84, DD. 289-297 (Jan. 26, 1995).
Schmidtke et al., "Direct Observation of Membrane Tethers formed during Neutrophil attachment to Platelets or . . . ," The Jour. of Cell Bio, vol. 149, pp. 719-729 (May 1, 2000).
Schulte Am Esch II et al., "Platelet aggregation by membrane-expressed A 1 domains of von Willebrand Factor . . . ," Biochem.and Biophys.Research Comm. vol. 302, pp. 873-877 (2003).
Scott et al., "Dimeric Ristocetin Flocculates Proteins, binds to Platelets, and Medicated von Willebrand Factor-dependent . . . ," The Jour.Biol.Chem. vol. 266. pp. 8149-8155 (1991).
Sen et al., "Crystal Structure of the von Willebrand Factor Modulator Botrocetin," Biochemistry, vol. 40,pp. 345-352 (2001).
Shelton-Inloes et al., "cDNA Sequences for Human von Willebrand Factor Reaveal Five Types of Repeated Domains and Five Possible . . . " Biochemistry, vol. 25, 3164-3171 (1986).
Shen et al., "Requirement of leucine-rich repeats of glycoprotein (GP) I Ba for shear-dependent and static binding of von Willebrand factor . . . ,"Blood, vol. 95, pp. 903-910 (2000).
Sherman et al., "Use of an Induced fit Receptor structure in Virtual Screening," Chem Biol Drug Des, vol. 67, pp. 83-84 (2006).
Siedleicki et al., "Shear-Dependent Changes in the Three-Dimensional Structures of Human von Willebrand Factor," Blood, vol. 88, pp. 2939-2950 (1996).
Simson et al., "Micropipet-Based Pico Force Transducer: In Depth Analysis and Experimental Verification," Biophysical Journal, vol. 74, pp. 2080-2088 (Apr. 1998).
Sixma et al., "Effect of deletion of the A1 domain of von Willebrand factor on its binding to heparin, collagen and platelets in the . . . ," Eur J Biochem. 196:369-75 (1991).
Smith et al., "Mapping the Collagen-binding Site in the I Domain of the Glycoprotein Ia/IIa (Integrin a2131 )," The Jour. of Biol. Chem., vol. 275, pp. 4205-4209 (2000).
Sporn et al., "Biosynthesis of von Willebrand Protein by human Megakaryocytes," J. Clin. Invest., vol. 76, DD. 1102-1106 (Sep. 1985).
Stepanian et al., "A new mutation, S1285F, within the A1 loop ofvon Willebrand factor induces a conformational . . . ," British Jour.of Haematology, vol. 120, pp. 643-651 (2003).
Stewart, et al., "Expression of retroviral vectors in transgenic mice obtained by embryo infection," EMBO J. 6:383-388 (1987).
Sugimoto et al., "Analysis of Structure-Function relationships in the Platelet Membrane Glycoprotein Ib-binding Domain . . . ," Jour. Biological Chemistry 268:12185-92 (1993).
Tees et al., "Kinetics and locus of failure of Receptor-ligand-mediated Adhesion between latex spheres. I. Protein-Carbohydrate Bond," Biophysical Journal, vol. 71, pp. 1102-1111.
Thom et al., "Heart Disease and stroke statistics—2006 Update. A report from the American Heart Association Statistics Committee . . . ," Circulation vol. 113, e86-e151 (2006).
Thomas, J.S., "Von Willebrand's disease in the dog and cat," VEt. Clin North Am Small Amin Practice; vol. 26; pp. 1089-1110 (Sep. 1996).
Uff et al., "Crystal Structure of the Platelet Glycoprotein I Ba N-terminal Domain Reveals and Unmasking Mechansinn . . . ," Jour.of Biolog.Chemistry, vol. 277,pp. 35657-35663 (2002).
Urlaub et al., "Effect of Gamma Rays at the Dihydrofolate Reductase Locus: Deletions and Inversions," Som. Cell Malec. Genet, 12:555-556 (1986).
Urlaub et al., "Isolation of Chinese hamster cell mutants deficient in dihydrofolate reductase activity," Proc. Natl. Acad. Sci. U.S.A., 77:4216-4220 (1980).

(56) References Cited

OTHER PUBLICATIONS

Valgimigli et al., "Tirofiban and Sirolinnus-Eluting Stent vs Abciximab and bare-metal Stent for acute Myocardial Infarction . . . ," JAMA,vol. 293, pp. 2109-2117 (2005).
Van Der Pullen, et al., "Efficient insertion of genes into the mouse germ line via retroviral vectors," Proc. Natl. Acad Sci. USA 82:6148-6152 (1985).
Van Heeke et al., "Expression of Human Asparagine Synthetase in *Escherichia coli*," Chem. 24:5503-5509 (1989).
Vanhoorelbeke et al., "Inhibition of Platelet Adhesion to Collagen as a New Target for Antithrombotic . . . ," Curr.Drugs targ.—Cardio.& Haemato.Disord., vol. 3, pp. 125-140 (2003).
Varughese et al., "Structure and Function of the Von Willebrand Factor A 1 Domain," Current Protein and Peptide Scienc, vol. 3, pp. 301-312 (2002).
Vasudevan et al., "Modeling and functional Analysis of the Interaction between von Willbrand Factor A1 Domain and . . . ," Jour.of Biolog.Chem., vol. 275,pp. 12763-12768 (2000).
Verweij et al., "Full-length von Willebrand factor (vWF) cDNA encodes a highly repetitive protein considerably larger than . . . ," The EMBo Journal, vol. 5, pp. 1839-1847 (1986).
Wachsberger et al., "VEGF trap in combination with Radiotherapy improve tumor control in U87 Glioblastoma," Int. J. Radiation Oncoloay Biol Phys., vol. 67, DD.1526-1357 (2007).
Ware et al., "Generation and rescue of a murine model of platelet dysfunction: the Bernard-Soulier syndrome," PNAS, vol. 97, pp. 2803-2808 (Mar. 2000).
Weiss et al., "Stabilization of Factor VIII in Plasma by the von Willebrand factor. Studies on postransfusion . . . ," Jour.of Clin. Investigation, vol. 60, pp. 390-404 (Aug. 1977).
Werner et al., "Joining high-throughput technology with in silica modelling advances genonnewide screening towards tarqeted . . . ," Brief Fune!.Genonnic Proteomic 5(1 ):32-6 (2006).
Wu D. et al., "Inhibition of the von Willebrand (VWF)-collagen interactionby an antihuman VWF monoclonal antibody results in abolition . . . ," Blood, vol. 99, pp. 3623-3626 (2002).
Xu et al.,"Platelet-derived or soluble CD154 induces vascularized allograft rejection independent of cell-bound CD154," Jour.of Clin. Invest, vol. 116, pp. 769-774 (Mar. 2006).
Yamamoto et al., "Antagonism ofVWF inhibits both injury induced Arterial and Venous Thrombosis in the Hamster," Thromb Haemost, vol. 79; pp. 202-210 (Jan. 1998).
Yoon et al., "A boundary collocation method for the motion of two spheroids in stokes flow: hydrodynamic . . . ," Int. J. Multiphase Flow, vol. 16, pp. 639-649 (1990).
Yoshida et al., "Alboaggregin-B and botrocetin, two snake venom proteins with highly homologous amino acid . . . " Biochem.and Biophys. Res.Comm, vol. 191 pp. 1386-1392 (Mar. 1993).
Yu et al., "High-Resolution MRI characterization of Human Thrombus Using a novel fibrintargeted paramagnetic Nanoparticle . . . ," Mag. Res. in Med., vol. 44, pp. 867-872 (2002).
Zuckerbraun et al., "Vascular Gene Therapy. A reality of the 21st Century," Arch Surg/ vol. 137; pp. 854-861 (Jul. 2002).
Chen et al., "Modifying murine von Willebrand factor A1 domain for in vivo assessment of human platelet therapies," Nature Biotech.,vol. 26, pp. 114-116 (Jan. 2008).
International Search Report and Written Opinion mailed on Sep. 22, 2008 for International Patent Application No. PCT/US07/15043 filed Jun. 28, 2007.

\* cited by examiner

| * standard vWF nomenclature | aa designation in image |
|---|---|
| D1323 | D560 |
| G1324 | G561 |
| H1326 | H563 |
| E1359 | E596 |
| K1362 | K599 |
| Q1367 | Q604 |
| F1369 | F606 |
| S1370 | S607 |

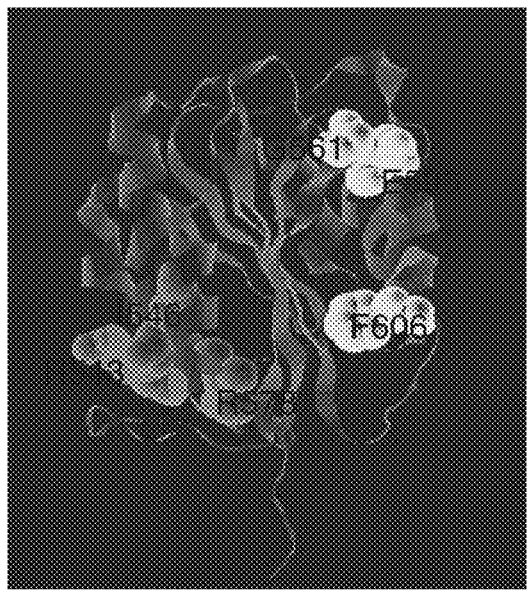
FIG. 3A
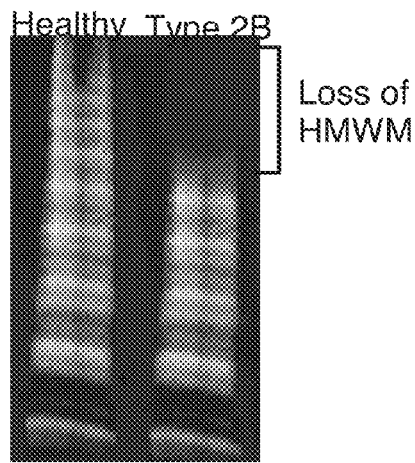
FIG. 3B
| * standard vWF nomenclature | aa designation in image |
|---|---|
| R1306 | R543 |
| I1309 | I546 |
| G1324 | G561 |
| R1341 | R578 |
| E1359 | E596 |
| F1369 | F606 |
FIG. 3C

| * standard vWF nomenclature | aa designation in image |
| I1309 | I546 |

```
                                              ↓1272
M vWF  QEPGGLVAPPTDAPVSSTTPYVEDTPEPPLHNFYCSKLLDLVFLLDGSSMLSEAE
H vWF  QEPGGLVVPPTDAPVSPTTLYVEDISEPPLHDFYCSRLLDLVFLLDGSSRLSEAE

Φ   Φ                      γ * γ   ←—1326             Φ
       FEVLKAFVVGMMERLHISQKRIRVAVVEYHDGSRAYLELKARKRPSELRRITSQIKYTGS
       FEVLKAFVVDMMERLRISQKWVRVAVVEYHDGSHAYIGLKDRKRPSELRRIASQVKYAGS

*  γ       * γ
       QVASTSEVLKYTLFQIFGKIDRPEASHITLLLTASQEPPRMARNLVRYVQGLKKKKVIVI
       QVASTSEVLKYTLFQIFSKIDRPEASRIALLLMASQEPQRMSRNFVRYVQGLKKKKVIVI

*
       PVGIGPHASLKQIRLIEKQAPENKAFLLSGVDELEQRRDEIVSYLCDLAPEAPAPTQPPQ
       PVGIGPHANLKQIRLIEKQAPENKAFVLSSVDELEQQRDEIVSYLCDLAPEAPPPTLPPH
                                                       ↑
                                                      1458
```

VAHVTV    ☐ * = location of type 2M mutations in man  
MAQVTV    Φ = location of type 2B mutations in man  
            χ = location of residue for GPIb alpha binding to HA1

FIG. 9

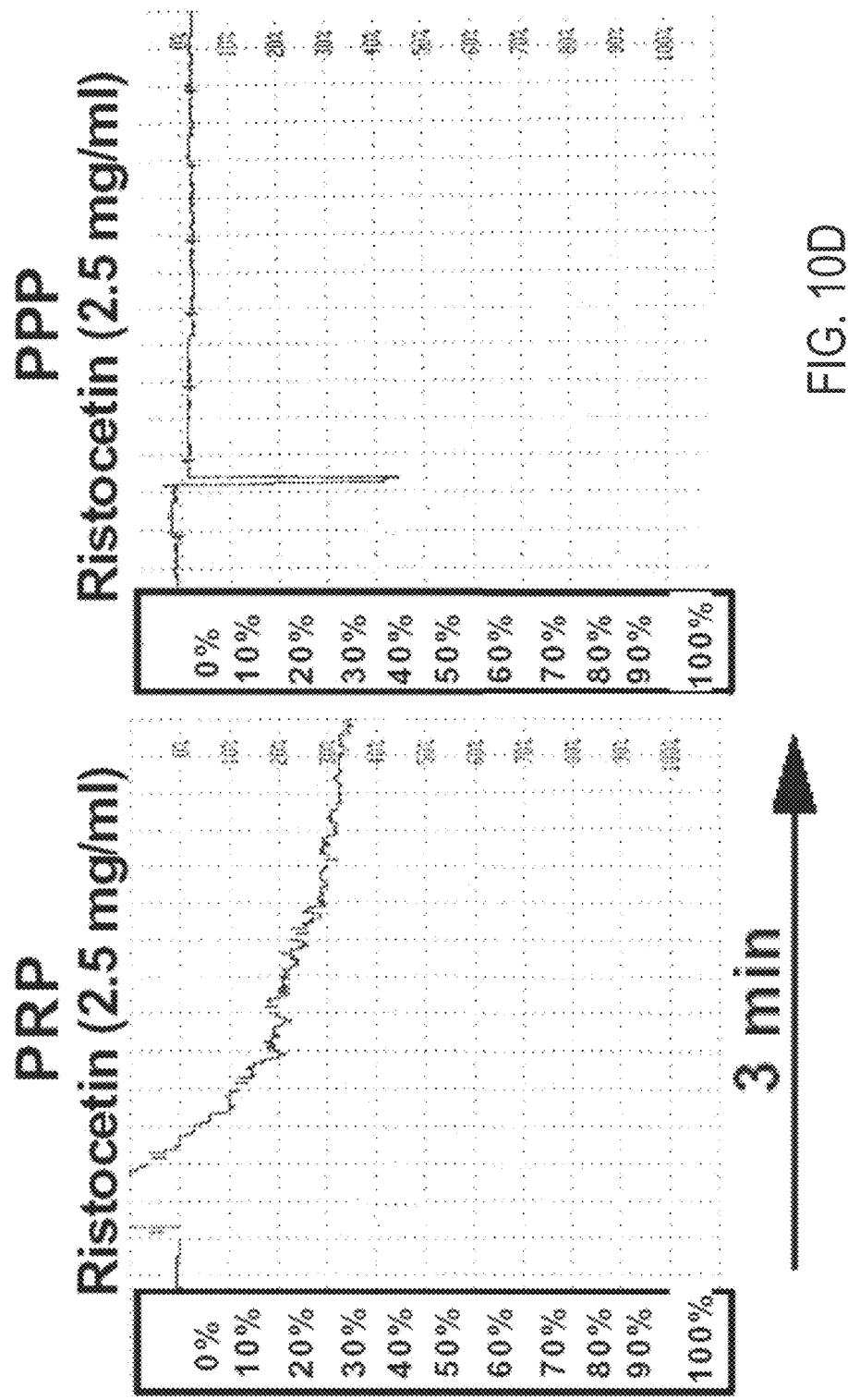

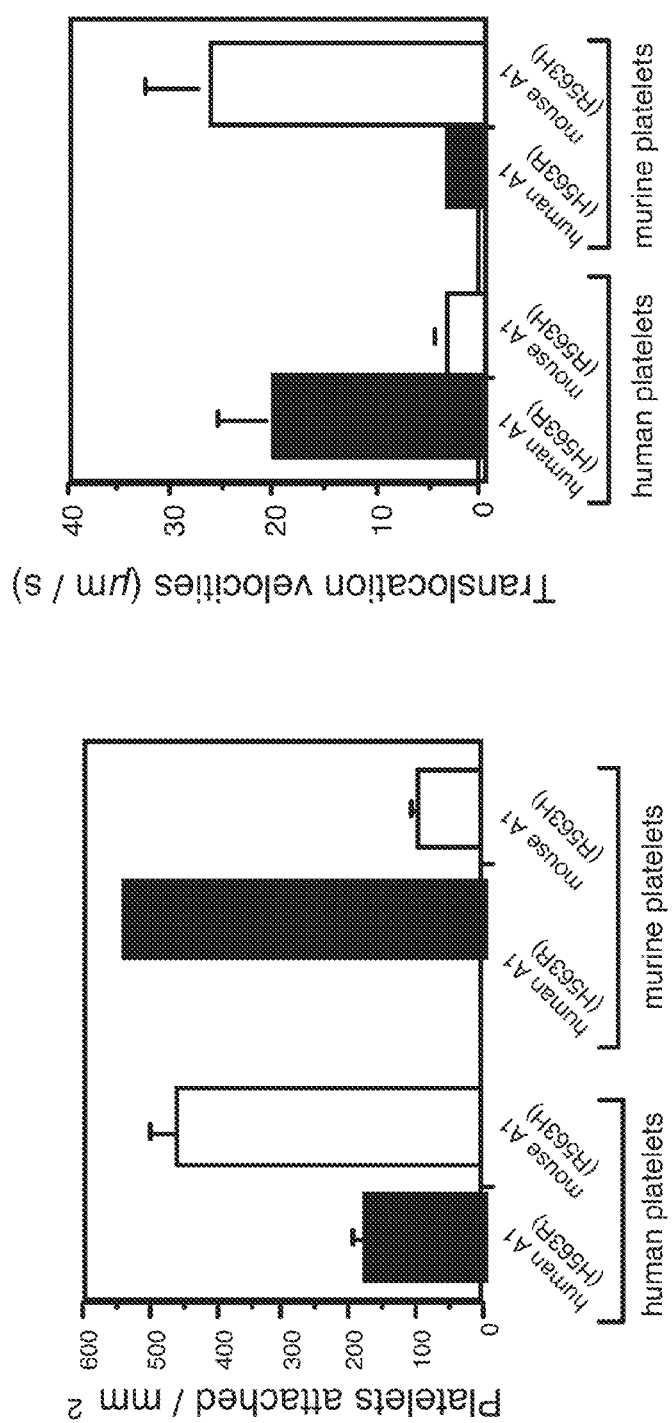

Knock-in construct for proposed mutations in vWF-A1

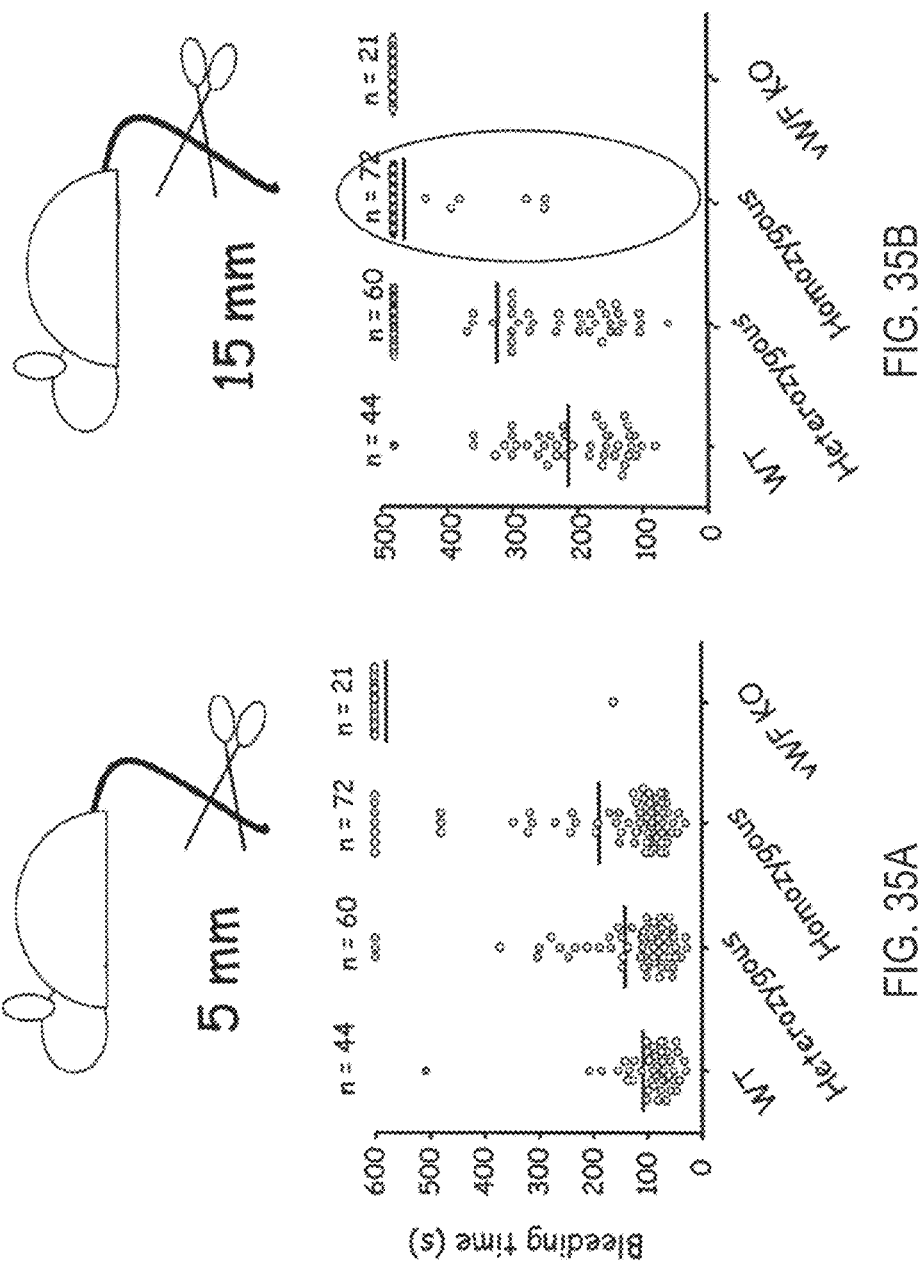

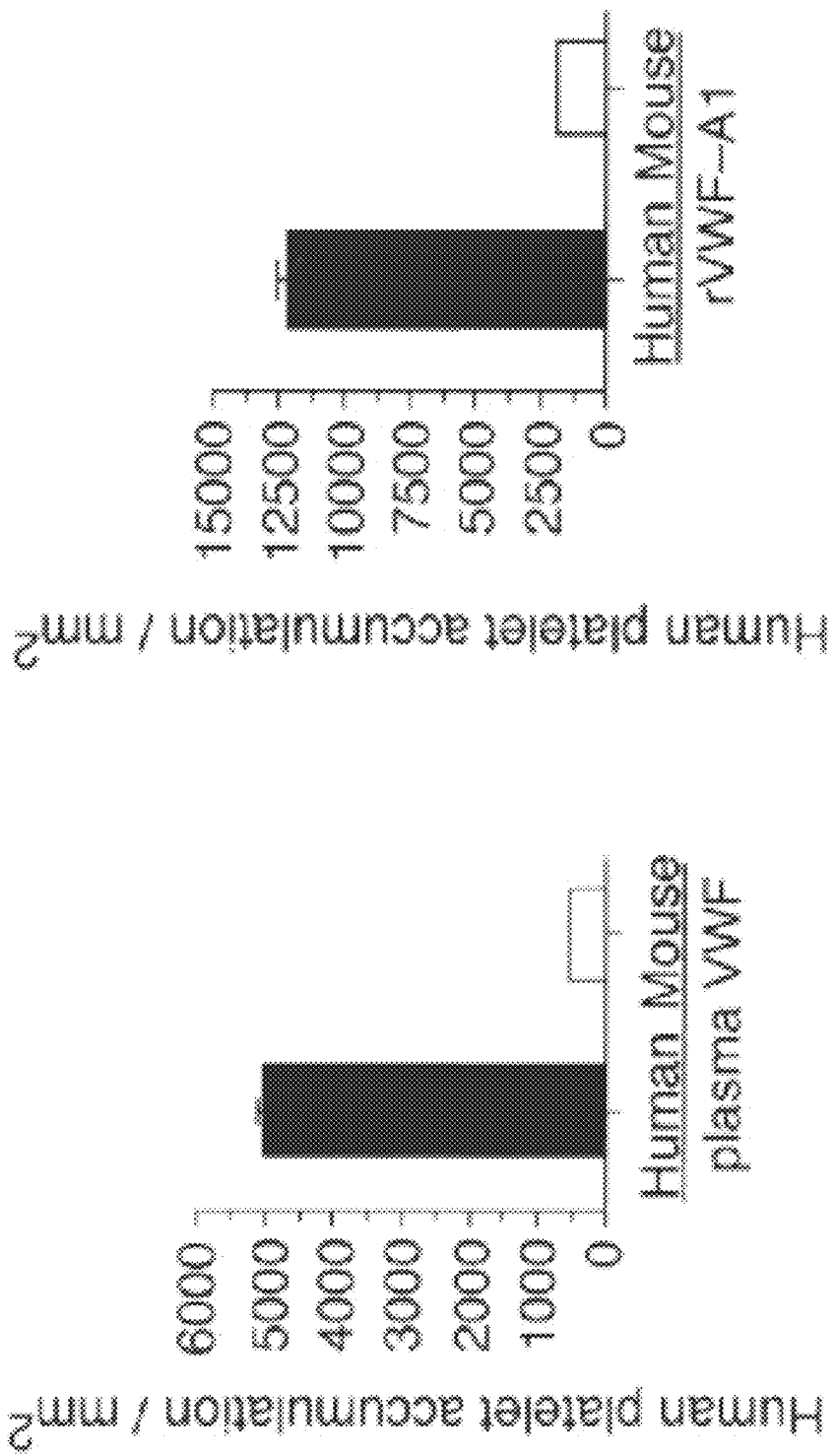

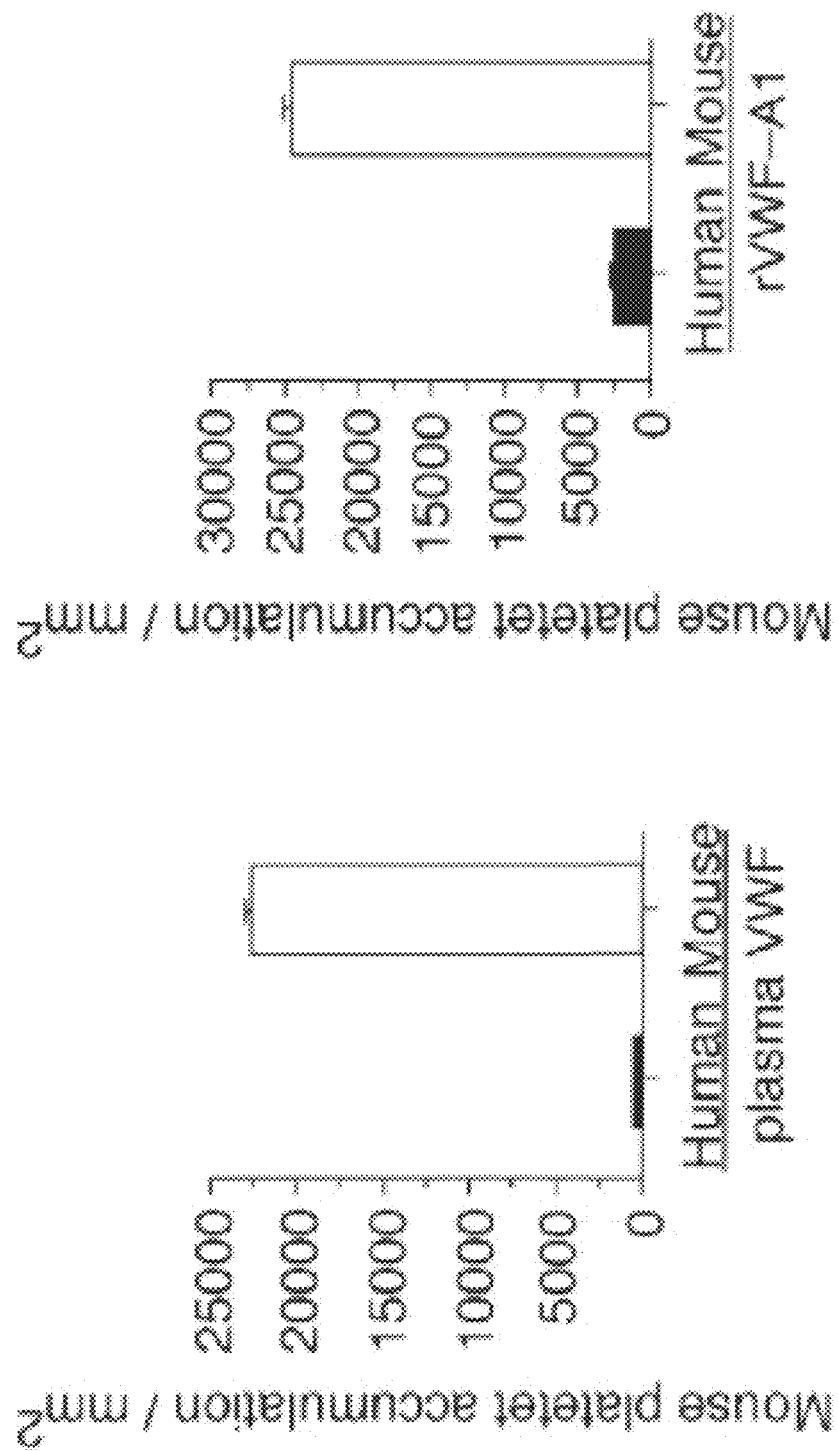

1

METHODS FOR TESTING ANTI-THROMBOTIC AGENTS

This application is continuation of U.S. patent application Ser. No. 12/345,363, filed Dec. 29, 2008, which is a continuation-in-part of International Application No. PCT/US2007/015043 filed on Jun. 28, 2007, which claims the benefit of priority of U.S. Application No. 60/817,600 filed on Jun. 29, 2006, the contents of which are hereby incorporated in their entirety.

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

GOVERNMENT INTERESTS

This invention was made with support from the U.S. Federal Government under Grant No. 5RO1HL63244-7 awarded by the National Heart, Lung, and Blood Institute (NHLBI). As such, the United States government has certain rights in this invention.

BACKGROUND OF THE INVENTION

The ability of platelets to rapidly stick to the damaged wall of arterial blood vessels is critical for preventing blood loss (hemorrhage). Inappropriate deposition of these hemostatic cells in arterial blood vessels due to pathological disease processes such as artherosclerosis can result in lack of blood flow to vital organs such as the heart and brain. Thus a delicate balance exists between providing adequate hemostasis without causing blockage of blood vessels by excessive platelet deposition (a.k.a. thrombus formation).

von Willebrand Factor (VWF) is a multidomain, plasma glycoprotein of complex multimeric structure which is synthesized by vascular endothelial cells and megakaryocytes (1-3) (FIG. 1A). Its presence in the blood is vital to maintaining the integrity of the vasculature. To accomplish this task, VWF forms a "bridge" between the injured vessel wall and platelets by virtue of its ability to interact with extracellular matrix components, such as collagen, and receptors expressed on platelets, such as glycoprotein Ib alpha (4-9). It also binds to and confers stability to factor VIII (10). The importance of this glycoprotein in hemostasis is underscored by the occurrence of clinical bleeding when the plasma VWF levels fall below 50 IU/dL (type I von Willebrand's disease, VWD), or when functional defects in the protein occur (type 2 VWD) (11,12).

Upon surface immobilization of VWF at sites of vascular injury, it is the role of the A1 domain of VWF (residues 1260-1480) to initiate the process of platelet deposition at sites of vascular injury and under conditions of high rates of shear flow (>1,000 $s^{-1}$; Ruggeri, Z. M. et al., Blood. 108, 1903-1910 (2006)). The critical nature of this interaction is exemplified by the bleeding disorder, termed type 2M VWD, which results from the incorporation of loss-of-function mutations within this domain that perturb interactions with GPIb alpha (Sadler, J. E. et al. (2006) J. Thromb. Haemost.

4, 2103-2114; Rabinowitz, I. et al. (1992) Proc. Natl. Acad. Sci. USA 89, 9846-9849; Cruz et al., (2000) J. Biol. Chem. 275, 19098-19105). In addition, recombinant VWF multimers lacking the A1 domain cannot support platelet adhesion at high rates of flow despite retaining the ability to interact with collagen (Sixma et al., (1991) Eur J Biochem. 196:369-75).

The structure of the A1 domain includes the α/β fold with a central β-sheet flanked by α-helices on each side as well as one intra-disulfide bond (Cys1272-Cys 1458), but no MIDAS motif (Emsley et al., (1998) J Biol Chem. 273: 10396-401). Its overall shape is cuboid, with the top and bottom faces forming the major and minor binding sites, respectively, that interact with the concave surface of GPIbα. The most extensive contact site buries ~1700 $Å^2$ of surface area, interacting with LRR five to eight and the C-terminal flank of the GPIbα (Huizinga, E. G. et al. (2002) Science 297, 1176-1179). For this to occur, the β-switch region of this platelet receptor undergoes a conformation change so that it aligns itself with the central beta sheet of the A1 domain. The smaller site (~900 $Å^2$) accommodates the binding of the β-finger and the first LRR of GPIbα, an event that appears to require the displacement of the amino-terminal extension of the A1 domain. Based on these findings as well as the preferential localization of mutations in humans within this region, which enhance GPIbα binding, it is speculated that the amino-terminal extension regulates the adhesive properties of this domain. This is also supported by the fact that recombinant A1 proteins lacking this extension have a higher affinity for this platelet receptor (Sugimoto et al., (1993) J Biol Chem. 268:12185-92). Despite these observations, the physiological relevance of such structural changes in this receptor-ligand pair remains to be determined as well as the contribution of other domains to this process.

In addition to its role in hemostasis, VWF also contributes to pathological thrombus formation on the arterial side of the circulation. This may be the consequence of injury to the blood vessel wall from inflammatory disease states and/or medical/surgical interventions. Pathological thrombus formation is the leading cause of death in the Western world. Thus, pharmaceutical companies have committed considerable resources towards the research and design of drugs to prevent or treat thrombosis. However, there remains an urgent need to develop new and improved therapies such as those aimed at reducing platelet and/or VWF interactions with the injured arterial wall. One major hurdle hindering drug development in this field is the lack of an appropriate small animal model of thrombosis to test promising therapies. For instance, differences in the structure or isoform of protein receptors or ligands on mouse vs. human platelets that are critical for the activation and/or binding of these cells to the injured vessel wall preclude testing of drugs developed against human platelets in a mouse model of thrombosis. Moreover, this issue cannot be overcome by simply transfusing mice with human platelets as we have observed that mouse VWF does not support significant interactions with human cells (see below). Thus, the development of a "humanized" mouse model of hemostasis and thrombosis would potentially expedite drug discovery and testing.

That said, we have discovered that only one amino acid difference between mouse and human VWF-A1 domains accounts for most of the inability of the former to interact with human platelets and vice versa. With this knowledge in hand, we have genetically altered a mouse to express VWF that contains this amino acid found in human VWF-A1, imparting on it the ability to support adhesion of human platelets to a level observed for its human counterpart. As a result, not only are we uniquely poised to better understand the molecular mechanisms governing human platelet binding at sites of vascular injury in vivo, but now have the capability to perform pre-clinical testing of anti-thrombotic agents and targeted molecular imaging agents directed against human platelet cells in a living animal. The material contained within this document describes the features of this unique biological platform for drug testing the testing of drugs and targeted molecular imaging agents.

BRIEF DESCRIPTION OF THE FIGURES

FIG. 3A shows a structure model depicting residues associated with type 2M (red) or type 2B (yellow) VWD.

FIG. 3B represents a silver stained gel that clinically depicts a type 2B VWD disease state individual, which is characterized by a loss of circulating high molecular weight VWF multimers (HMWM, FIG. 3B, Lane 2).

FIG. 3C shows a legend correlating standard nomenclature with nomenclature in the image of FIG. 3A.

FIGS. 8A and 8B demonstrates the direct visualization of bead-platelet interaction under flow (60×DIC microscopy). An approaching bead moving at a velocity of 609±97 um/sec (wall shear stress of 1.5 dyn cm$^{-2}$) is captured by a surface-immobilized platelet at (t=12.8 msec), pivots a distance of less than 3 μm in under 40 msec, and is then released after a pause time of $t_p$=228.2 msec into the flow stream (escape velocity=288+/−90.4 μm/sec). FIG. 8C depicts representative experiments of $k_{off}$ values for WT human VWF-A1 coated beads based on a distribution of interaction (pause) times. FIG. 8D shows that the kinetics of the GPIb alpha tether bond are identical whether platelets are metabolically inactivated or fixed in paraformaldehyde to prevent activation upon surface-immobilization.

FIG. 9 represents the deduced single-letter amino acid sequence of mouse VWF-A1 domain (M VWF) compared to its human counterpart (H VWF) from amino acid 1260 to 1480. The locations of cysteines forming the loop structure are numbered (1238 and 1472) and differences in residues are highlighted in red. Conversion of the arginine (R) in the mouse A1 domain to histidine (H) as found in its human counterpart (blue χ) enables mouse VWF to bind human platelets.

FIGS. 10A through 10D represent graphs of ristocetin-induced platelet aggregation assays (RIPA). Concentrations of the ristocetin modulator known to cause agglutination of human platelets (~1.0 mg/ml) had no effect using murine platelet rich plasma (FIG. 10B, FIG. 10D). Incubation of murine platelet rich plasma (PRP) with thrombin resulted in >90% platelet aggregation (FIG. 10A). Concentrations of ≥2.5 mg/ml of modulator resulted in murine platelet aggregation (~30%, FIG. 10C).

FIG. 14B depicts a bar graph of a human platelet adhesion assay to recombinant VWF proteins with and without the presence of a His-tag at a shear rate of 800 $s^{-1}$.

FIG. 15B demonstrates that the C-alpha atoms of human (red) and mouse (blue) VWF-A1 domains closely overlap. FIG. 15C shows the model of the murine VWF-A1 domain and the residues that purportedly interact with GPIb alpha, wherein amino acid residue 1326 of mouse (M) VWF-A1 was mutated to the corresponding amino acid at the identical location in its human counterpart (from Arg to His).

FIGS. 16A and 16B show graphs that depict platelet adhesion assays (FIG. 16A) and platelet translocation measurements (FIG. 16B). The ability of murine and human platelets to interact with a mutant protein substrate (human VWF-A1 domain wherein amino acid residue 1326 was mutated from His to Arg and mouse VWF-A1 domain wherein amino acid residue 1326 was mutated from Arg to His) was evaluated at a wall shear rate of 800 $s^{-1}$. FIG. 16C identifies the amino acid position designations in FIGS. 16A and 16B relative to the standard vWF nomenclature.

FIG. 20A is a diagram of a knock-in construct for proposed mutations in the VWF-A1 domain of mice. FIG. 20B represents Southern blot hybridization with probe "a" or "b", respectively, to determine if the construct was appropriately targeted.

FIG. 28B is a graph that depicts the amount of human platelets that bound to WT murine VWF or R1326H mutant murine VWF.

FIG. 33A are representative intravital photomicrographs that depict the range of platelet interactions that occur at a site of vascular injury (60×). Platelets were observed to either transiently pause (*) or rapidly tether to and translocate (TP) on damaged arterial endothelium. A composite image demonstrates translocation of two platelets over a 3 s interval of time (panel 6). FIG. 33B depicts interacting platelets at the site of arterial injury that were classified as either undergoing translocation or firm adhesion (sticking) during an observation period of 1 min.

FIGS. 35A and 35B are graphical representations of the bleeding phenotype observed in the mutant VWF-A1 1326R>H heterozygous or homozgygous mouse compared to its WT counterpart when tails were cut either 5 mm (FIG. 35A) or 15 mm (FIG. 35B) from the tip of the tail.

FIGS. 36A and 36B are graphs that depict ex vivo analysis of human platelet interactions with plasma VWF or recombinant VWF-A1 proteins. Accumulation of human platelets on surface-immobilized plasma human or mouse VWF (FIG. 36A) or recombinant human or mouse A1 domain proteins (FIG. 36B) after 4 min of perfusion with whole blood (shear rate of 1600 $s^{-1}$) is shown. Data are representative of three separate experiments performed in triplicate (mean±s.e.m.).

FIGS. 36C and 36D are graphs that depict ex vivo analysis of mouse platelet interactions with plasma VWF or recombinant VWF-A1 proteins. Accumulation of murine platelets on surface-immobilized human or mouse plasma VWF (FIG. 36C) or recombinant human or mouse A1 domain proteins (FIG. 36D) after 4 min of perfusion with whole blood (shear rate of 1600 $s^{-1}$) is shown. Data are representative of three separate experiments performed in triplicate (mean±s.e.m.).

FIG. 37A depicts the alignment of Cα atoms for human (blue) and murine (red) A1 domains. Key residues described in EXAMPLE 4 are shown as red spheres or as ball- and stick side-chains. FIG. 37B is a 90° rotation about a horizontal axis to reveal the packing of residue 1397 (Phe in human, Leu in mouse) that results in a 3 Å shift (blue arrow) of helix α4.

FIG. 37C depicts the model of the murine-murine complex. FIG. 37D depicts the crystal structure of the human-human complex. Salt bridges are circled and key residue differences are boxed. Zooms reveal details of the electrostatic interactions at the β-switch contact region. The region of contact involving helix α3 of the A1 domain and one face of the LRR repeats of GPIbα is highly conserved botweens species, except for two residue changes that do not participate in bond formation: GPIbαE151K and VWF-A1 G1370S (human:mouse). Thus, minor differences in this region are unlikely to contribute to a reduction in binding between the murine and human proteins. This is also the case with the contact area located at the bottom of the A1 domain, which is invariant in both species and participates in salt-bridge formation (red circle).

FIG. 39A is a gel of RT-PCR of lung tissue from WT or mutant VWF mice to detect for A1, A2, and/or A3 domain message. β-actin analyzed to demonstrate use of equivalent amounts of mRNA. FIG. 39B is a graph demonstrating VWF antigen levels in plasma obtained from WT littermates (pooled) or six individual mice homozygous for 1326R>H mutation as detected by ELISA. Data are representative of two independent experiments performed in triplicate.

FIG. 44A is a ribbon representation; GPIb alpha, green; botrocetin, red; A1, cyan. FIG. 44B demonstrates the location of the previously unknown interface between GPIb alpha and botrocetin.

SUMMARY OF THE INVENTION

Figure 1A:
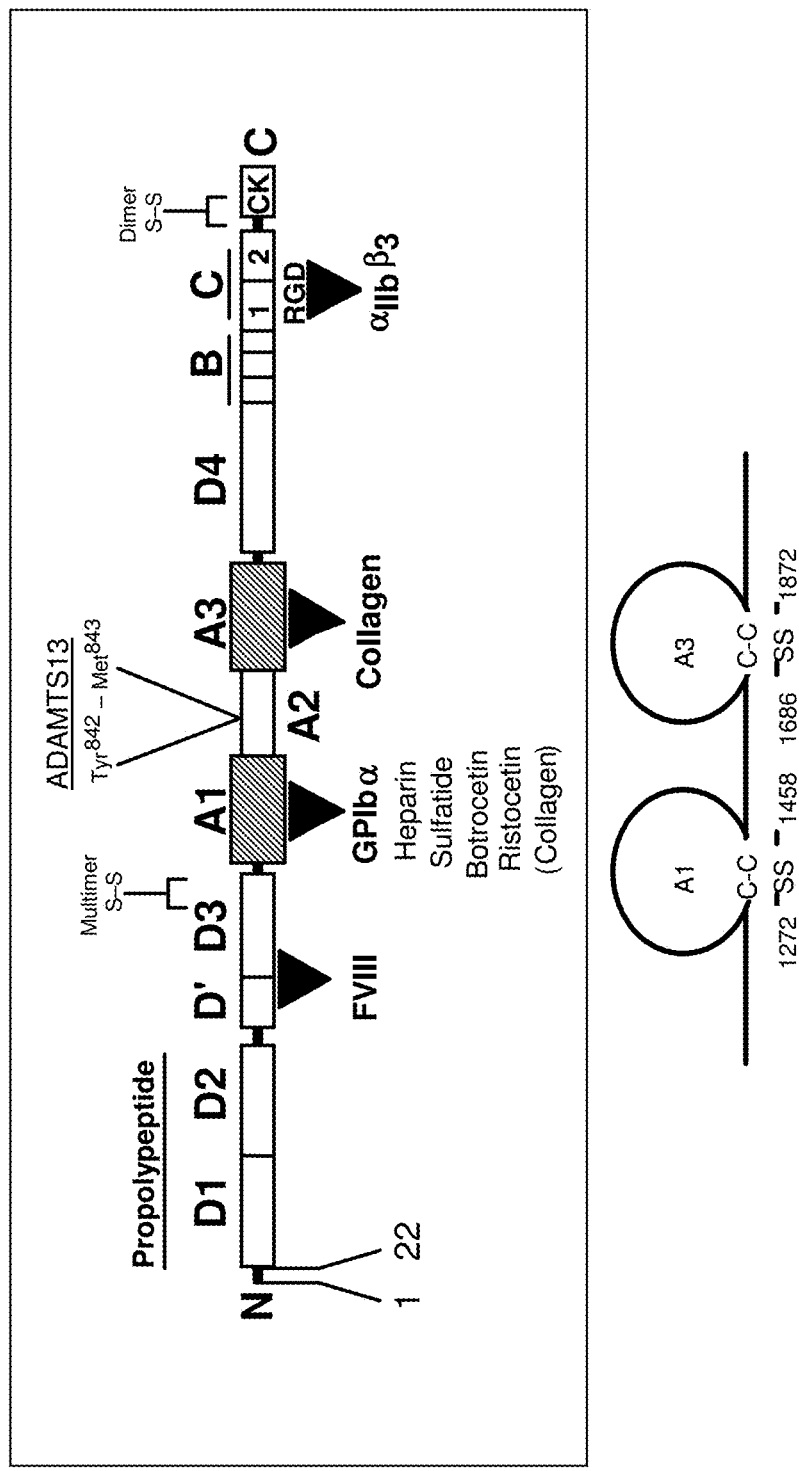
FIG. 1A is a schematic representation of the prepro form of VWF. From top to bottom: repeated homologous regions; A1 and A3 disulfide loops and functional domains of the mature VWF subunit.

The invention provides for a mouse model for pre-clinical screening and testing of candidate compounds, wherein the model comprises a mouse expressing plasma von Willebrand Factor protein that contains a mutation or combination of mutations in its A1 domain that change the mouse protein's binding specificity from being specific for mouse platelets to being specific for human platelets. Thus, the mutant A1 domain contained within mouse plasma VWF particularly supports the binding of human platelets in vivo and ex-vivo. In one embodiment, the mouse model is infused with human platelets. In another embodiment, human platelets are labeled ex-vivo or in vivo so as to be detected while in the animal.

The invention provides for where the mutation in the A1 domain of mouse VWF comprises 1263P>S, 1269N>D, 1274K>R, 1287M>R, 1302G>D, 1308H>R, 1313R>W, 1314I>V, 1326R>H, 1329L>I, 1330E>G, 1333A>D, 1344T>A, 1347I>V, 1350T>A, 1370G>S, 1379H>R, 1381T>A, 1385T>M 1391P>Q, 1394A>S, 1397L>F, 1421S>N, 1439L>V, 1442G>S, 1449R>Q, 1466A>P, 1469Q>L, 1472Q>H, 1473V>M, 1475H>Q, 1479S>G, and any combination thereof, wherein the mutation corresponds to an amino acid position of human von Willebrand Factor A1 protein shown in SEQ ID NO: 6. In addition, the mouse VWF A1 domain can be fully or partially replaced with the human VWF A1 domain. In one embodiment, the mutation in mouse VWF-A1 is 1326R>H. In another embodiment, the mouse model comprises a device within a vessel, such as a stent or a graft, or mechanical, chemical, or heat-induced disruption of vascular endothelium in vivo. This model system is useful for testing compounds in an in vivo environment. The compounds can be tested for an effect on the interaction between human platelets and human-like (the mutant VWF-A1, 1326R>H, for example), or the actual human VWF-A1 domain. For example, the animal model can be used for pre-clinical testing of drugs in order to determine whether 1) there is a desired effect on hemostasis and/or thrombus formation or anti-thrombotic effect by the test drug or 2) there is an undesired effect on hemostasis and/or thrombus formation or anti-thrombotic effect by a test drug not specifically designed to alter hemostasis and/or thrombus formation. In the latter case, many drugs are only identified as having an effect on clotting or bleeding once they are in human clinical trials, this animal model will fill an unmet need, which is to test such effects prior to clinical trials. The invention also permits testing of compounds targeted to the VWF-A1 domain that can correct the bleeding phenotype associated with a loss-of-function mutations (1326R>H, for example) by altering the kinetics of the interaction between GPIbα and VWF-A1 (for example, enhancing the on-rate and/or prolonging the bond lifetime as shown for the snake venom protein botrocetin.

The invention also provides for an isolated mutant human von Willebrand Factor A1 protein comprising one or more mutations selected from the group consisting of: 1263S>P, 1269D>N, 1274R>K, 1287R>M, 1302D>G, 1308R>H, 1313W>R, 1314V>I, 1326H>R, 1329I>L, 1330G>E, 1333D>A, 1344A>T, 1347V>I, 1350A>T, 1370S>G, 1379R>H, 1381A>T, 1385M>T, 1391Q>P, 1394S>A, 1397F>L, 1421N>S, 1439V>L, 1442S>G, 1449Q>R, 1466P>A, 1469L>Q, 1472H>Q, 1473M>V, 1475Q>H, 1479G>S, wherein each amino acid position corresponds to a position in SEQ ID NO: 6. The invention also provides for an isolated mutant human von Willebrand Factor A1 protein consisting of a 1263S>P mutation in an amino acid sequence of SEQ ID NO: 1. The invention also provides for an isolated mutant human von Willebrand Factor A1 protein consisting of a 1269D>N mutation in an amino acid sequence of SEQ ID NO: 1. The invention also provides for an isolated mutant human von Willebrand Factor A1 protein consisting of a 1274R>K mutation in an amino acid sequence of SEQ ID NO: 1. The invention also provides for an isolated mutant human von Willebrand Factor A1 protein consisting of a 1287R>M mutation in an amino acid sequence of SEQ ID NO: 1. The invention also provides for an isolated mutant human von Willebrand Factor A1 protein consisting of a 1302D>G mutation in an amino acid sequence of SEQ ID NO: 1. The invention also provides for an isolated mutant human von Willebrand Factor A1 protein consisting of a 1308R>H mutation in an amino acid sequence of SEQ ID NO: 1. The invention also provides for an isolated mutant human von Willebrand Factor A1 protein consisting of a 1313W>R mutation in an amino acid sequence of SEQ ID NO: 1. The invention also provides for an isolated mutant human von Willebrand Factor A1 protein consisting of a 1314V>I mutation in an amino acid sequence of SEQ ID NO: 1. The invention also provides for an isolated mutant human von Willebrand Factor A1 protein consisting of a 1326H>R mutation in an amino acid sequence of SEQ ID NO: 1. The invention also provides for an isolated mutant human von Willebrand Factor A1 protein consisting of a 1329I>L mutation in an amino acid sequence of SEQ ID NO: 1. The invention also provides for an isolated mutant human von Willebrand Factor A1 protein consisting of a 1330G>E mutation in an amino acid sequence of SEQ ID NO: 1. The invention also provides for an isolated mutant human von Willebrand Factor A1 protein consisting of a 1333D>A mutation in an amino acid sequence of SEQ ID NO: 1. The invention also provides for an isolated mutant human von Willebrand Factor A1 protein consisting of a 1344A>T mutation in an amino acid sequence of SEQ ID NO: 1. The invention also provides for an isolated mutant human von Willebrand Factor A1 protein consisting of a 1347V>I mutation in an amino acid sequence of SEQ ID NO: 1. The invention also provides for an isolated mutant human von Willebrand Factor A1 protein consisting of a 1350A>T mutation in an amino acid sequence of SEQ ID NO: 1. The invention also provides for an isolated mutant human von Willebrand Factor A1 protein consisting of a 1370S>G mutation in an amino acid sequence of SEQ ID NO: 1. The invention also provides for an isolated mutant human von Willebrand Factor A1 protein consisting of a 1379R>H mutation in an amino acid sequence of SEQ ID NO: 1. The invention also provides for an isolated mutant human von Willebrand Factor A1 protein consisting of a 1381A>T mutation in an amino acid sequence of SEQ ID NO: 1. The invention also provides for an isolated mutant human von Willebrand Factor A1 protein consisting of a 1385M>T mutation in an amino acid sequence of SEQ ID NO: 1. The invention also provides for an isolated mutant human von Willebrand Factor A1 protein consisting of a 1391Q>P mutation in an amino acid sequence of SEQ ID NO: 1. The invention also provides for an isolated mutant human von Willebrand Factor A1 protein consisting of a 1394S>A mutation in an amino acid sequence of SEQ ID NO: 1. The invention also provides for an isolated mutant human von Willebrand Factor A1 protein consisting of a 1397F>L mutation in an amino acid sequence of SEQ ID NO: 1. The invention also provides for an isolated mutant human von Willebrand Factor A1 protein consisting of a 1421N>S mutation in an amino acid sequence of SEQ ID NO: 1. The invention also provides for an isolated mutant human von Willebrand Factor A1 protein consisting of a 1439V>L mutation in an amino acid sequence of SEQ ID NO: 1. The invention also provides for an isolated mutant human von Willebrand Factor A1 protein consisting of a 1442S>G mutation in an amino acid sequence of SEQ ID NO: 1. The invention also provides for an isolated mutant human von Willebrand Factor A1 protein consisting of a 1449Q>R mutation in an amino acid sequence of SEQ ID NO: 1. The invention also provides for an isolated mutant human von Willebrand Factor A1 protein consisting of a 1466P>A mutation in an amino acid sequence of SEQ ID NO: 1. The invention also provides for an isolated mutant human von Willebrand Factor A1 protein consisting of a 1469L>Q mutation in an amino acid sequence of SEQ ID NO: 1. The invention also provides for an isolated mutant human von Willebrand Factor A1 protein consisting of a 1472H>Q mutation in an amino acid sequence of SEQ ID NO: 1. The invention also provides for an isolated mutant human von Willebrand Factor A1 protein consisting of a 1473M>V mutation in an amino acid sequence of SEQ ID NO: 1. The invention also provides for an isolated mutant human von Willebrand Factor A1 protein consisting of a 1475Q>H mutation in an amino acid sequence of SEQ ID NO: 1. The invention also provides for an isolated mutant human von Willebrand Factor A1 protein consisting of a 1479G>S mutation in an amino acid sequence of SEQ ID NO: 1.

The invention also provides for an isolated mutant human von Willebrand Factor A1 protein having SEQ ID NO: 6, wherein the protein comprises a mutation selected from the group consisting of: 1263S>P, 1269D>N, 1274R>K, 1287R>M, 1302D>G, 1308R>H, 1313W>R, 1314V>I, 1326H>R, 1329I>L, 1330G>E, 1333D>A, 1344A>T, 1347V>I, 1350A>T, 1370S>G, 1379R>H, 1381A>T, 1385M>T, 1391Q>P, 1394S>A, 1397F>L, 1421N>S, 1439V>L, 1442S>G, 1449Q>R, 1466P>A, 1469L>Q, 1472H>Q, 1473M>V, 1475Q>H, or a 1479G>S.

The invention provides for a transgenic non-human animal expressing von Willebrand Factor A1 protein containing mutation(s) at one of more amino acid position selected from the group consisting of: 1263, 1269, 1274, 1287, 1302, 1308, 1313, 1314, 1326, 1329, 1330, 1333, 1344, 1347, 1350, 1370, 1379, 1381, 1385, 1391, 1394, 1397, 1421, 1439, 1442, 1449, 1466, 1469, 1472, 1473, 1475, and 1479, wherein the position corresponds to an amino acid position of human von Willebrand Factor A1 protein shown in SEQ ID NO: 6. In one embodiment, the animal is a murine, a porcine, a canine, a feline, a rabbit, or a primate. In another embodiment, the animal is a mouse, a rat, a dog, a sheep, a goat, a horse, a cow, a cat, a monkey, a primate, a pig, a llama, an alpaca, a chicken, etc. In other embodiments, the protein comprises a single mutation. In further embodiments, the protein comprises two or more mutations. In yet another embodiment, the protein comprises at least one mutation selected from the group consisting of: 1263>S, 1269>D, 1274>R, 1287>R, 1302>D, 1308>R, 1313R>W, 1314>V, 1326>H, 1329>1, 1330>G, 1333>D, 1344>A, 1347>V, 1350>A, 1370>S, 1379>R, 1381>A, 1385>M 1391>Q, 1394>S, 1397>F, 1421>N, 1439>V, 1442>S, 1449>Q, 1466>P, 1469>L, 1472>H, 1473>M, 1475>Q, 1479>G, and any combination thereof. In particular embodiments, the protein comprises a 1326R>H mutation. In other embodiments, the protein comprises a 1314I>V mutation. In yet other embodiments, the protein comprises a 1326R>H mutation, a 1314I>V mutation, or a combination of the two mutations listed previously. In some embodiments of the invention, the animal is a mouse. In further embodiments, the protein comprises SEQ ID NO: 5. In other embodiments, the VWF protein is at least 5%, 10%, 15%, 20%, 25%, 30%, 40%, 50%, 60%, 70%, 75%, 80%, 85%, 90%, 95%, 99%, or 100% identical to the A1 domain of human VWF protein as shown in SEQ ID NO: 1. In particular embodiments, the von Willebrand Factor A1 protein of the transgenic animal comprises the human A1 domain shown in SEQ ID NO: 1. In some embodiments, the von Willebrand Factor A1 protein is partially or completely replaced with a human von Willebrand Factor A1 protein comprising SEQ ID NO: 1. In other embodiments, the animal is a model for pre-clinical testing of compounds that expresses a mutant von Willebrand Factor (VWF) A1 protein containing one or more mutations, wherein the binding specificity of the mutant VWF-A1 protein changes from being specific for the animal platelets to being specific for human platelets. In further embodiments the mutant VWF-A1 protein in the animal binds to human platelets.

The invention provides a method for identifying a compound that modulates binding of VWF-A1 protein to GPIb-alpha protein. The method comprises: providing an electronic library of test compounds; providing atomic coordinates listed in Table 8 for at least 10 amino acid residues for the A1 domain of the VWF protein, wherein the coordinates have a root mean square deviation therefrom, with respect to at least 50% of Ca atoms, of not greater than about 2.5 Å, in a computer readable format; converting the atomic coordinates into electrical signals readable by a computer processor to generate a three dimensional model of the VWF-A1 domain; performing a data processing method, wherein electronic test compounds from the library are superimposed upon the three dimensional model of the VWF-A1 domain; and determining which test compound fits into the binding pocket of the three dimensional model of the VWF-A1 protein, thereby identifying which compound would modulate the binding of VWF-A1 protein to GPIb-alpha protein. Alternatively, the method can comprise: providing an electronic library of test compounds; providing atomic coordinates listed in Table 8 in a computer readable format for at least 10, 15, 20, 25, 30, 35, or 40 amino acid residues for the A1 domain of the VWF protein, wherein the residues comprise two or more of the following residues: Pro1391, Arg1392, Arg1395, Val1398, Arg1399, Gln1402, Lys1406, Lys1423, Gln1424, Leu1427, Lys1430, or Glu1431; converting the atomic coordinates into electrical signals readable by a computer processor to generate a three dimensional model of the VWF-A1 domain; performing a data processing method, wherein electronic test compounds from the library are superimposed upon the three dimensional model of the VWF-A1 domain; and determining which test compound fits into the binding pocket of the three dimensional model of the VWF-A1 protein, thereby identifying which compound would modulate the binding of VWF-A1 protein to GPIb-alpha protein.

In one embodiment, determining comprises detecting an $IC_{50}$ of less than about 7.5 µg/ml for a test compound. In another embodiment, the method can further comprise: obtaining or synthesizing a compound; contacting VWF-A1 protein with the compound under a condition suitable for GPIb-alpha-VWF-A1 binding; and determining whether the compound modulates GPIb-alpha-VWF-A1 protein binding using a diagnostic assay. In a further embodiment, contacting comprises perfusing platelets into a flow chamber at a shear flow rate of at least 100 $s^{-1}$, wherein mutant murine VWF-A1 protein is immobilized on a bottom surface of the chamber, while in another embodiment contacting comprises perfusing platelets into the transgenic non-human animal described above. In some embodiments, contacting occurs sequentially. In other embodiments, the perfusing of platelets occurs prior to administration of the compound. In one embodiment, the platelets are human platelets, while in other embodiments, the platelets are not murine platelets. In further embodiments, the determining comprises detecting an increase or decrease in the dissociation rate between VWF-A1 protein and GPIb-alpha protein by at least two-fold. In other embodiments, the determining comprises detecting an increase or decrease of platelet adhesion to a surface expressing VWF-A1 protein, while in some embodiments the determining comprises detecting an increase or decrease in a stabilization of an interaction between VWF-A1 protein and GPIb-alpha protein. In particular embodiments, the determining comprises detecting thrombosis formation. In some embodiments, the determining comprises identifying an occurrence of an abnormal thrombotic event in the subject. In further embodiments of the invention, an abnormal thrombotic event comprises abnormal bleeding, abnormal clotting, death, or a combination of the events listed. In some embodiments, the determining comprises dynamic force microscopy, a coagulation factor assay, a platelet adhesion assay, thrombus imaging, a bleeding time assay, aggregometry, review of real-time video of blood flow, a Doppler ultrasound vessel occlusion assay, or a combination thereof. In particular embodiments of the invention, perfusing platelets is followed by perfusion of a labeled agent. In some embodiments, the labeled agent comprises one or more of a nanoparticle, a fluorophore, a quantum dot, a microcrystal, a radiolabel, a dye, a gold biolabel, an antibody, or a small molecule ligand. In other embodiments, the agent targets a platelet receptor, a VWF protein, or a portion thereof. In another embodiment, the animal is injected with nanoparticles, and/or peptides, and/or small molecules, which label the human platelets, at some time prior testing, wherein the nanoparticles, and/or peptides, and/or small molecules are capable of being imaged while in the animal. In another embodiment, the testing comprises tracking of human platelet deposition in the animal. In another embodiment, the compound or agent is an anti-thrombotic, such as an anti-platelet drug, e.g., PLAVIX, an ADP inhibitor, and/or a humanized antibody and/or small molecule that inhibits human alpha IIb and/or beta 3 integrin function, human alpha2 and/or beta 1 integrin function, human glycoprotein VI (GPVI) function, human thrombin receptors function, and/or intracellular signaling pathways (for example, phosphoinositide 3-kinases (PI3K)) vital to platelet function in hemostasis and thrombosis.

The invention provides for a method for testing a compound or agent, the method comprising: (a) providing a candidate agent or compound to be tested; (b) administering the agent or compound to an animal in an effective amount, wherein the animal expresses a mutant von Willebrand Factor A1 protein containing a mutation, combination of mutations that change the animal protein's binding specificity from being specific for animal platelets to being specific for human platelets, so that the mutant VWF-A1 protein in the animal binds to human platelets, and wherein the animal is perfused with human platelets; (c) testing the animal to determine whether the animal experiences any abnormal hemostatic and/or thrombotic events, thereby testing the compound or agent.

The invention provides for a nucleic acid encoding the mutant von Willebrand Factor A1 protein of the invention. The invention provides for a vector containing such a nucleic acid. The invention provides for an animal expressing such a nucleic acid to express the mutant VWF protein.

The invention also provides a method for treating von Willebrand Disease (VWD) in a subject in need thereof, the method comprising administering to the subject an effective amount of a compound that promotes platelet adhesion in the subject, wherein the compound increases the dissociation rate between VWF-A1 protein and GPIb-alpha protein by at least two-fold, thereby administration of the compound increases blood coagulation in the subject. In one embodiment, coagulation is measured by a coagulation factor assay, an ex-vivo flow chamber assay, or a combination thereof.

The invention provides a method for rapidly detecting an internal vascular injury site in a subject. The method comprises: administering to a subject a targeted molecular imaging agent, wherein the molecule circulates for an effective period of time in order to bind to the injury site within the subject; tracking a deposition of the labeled targeted molecular imaging agent in the subject; and identifying the site of a thrombus formation in the subject by imaging the targeted molecular imaging agent, thereby the deposition of the targeted molecular imaging agent at the internal vascular injury site is indicative of internal bleeding within a subject. In one embodiment, the targeted molecular imaging agent is administered by subcutaneous, intra-muscular, intra-peritoneal, or intravenous injection; infusion; by oral, nasal, or topical delivery; or a combination of the routes listed. In another embodiment, the targeted molecular imaging agent comprises a nanoparticle, a fluorophore, a quantum dot, a microcrystal, a radiolabel, a dye, a gold biolabel, an antibody, a peptide, a small molecule ligand, or a combination of the agents listed. In a further embodiment, the nanoparticle comprises a perfluorocarbon, while in particular embodiments, the nanoparticle is coupled to an antibody, a small molecule, a peptide, or a receptor trap. In some embodiments, the targeted molecular imaging agent specifically binds to a platelet receptor, or a VWF protein, or a portion thereof. In other embodiments, the targeted molecular imaging agent has a $T_{1/2}$ of at least 30 minutes. In further embodiments, imaging comprises a PET scan, MRI, IR scan, ultrasound, nuclear imaging, or a combination of the methods listed. In a particular embodiment, the subject is further administered a prothrombotic compound. In a further embodiment, the compound increases the dissociation rate between VWF-A1 protein and GPIb-alpha protein by at least two-fold.

Considerable emphasis has been placed on elucidating the role of structural changes in the A1 domain of VWF in order to gain insight into mechanism(s) that may regulate its binding to platelet GPIb alpha. This invention concerns the contribution of the biophysical properties of this interaction in governing platelet adhesion under hydrodynamic conditions. It has been demonstrated that flow-dependent adhesion and rapid and force-driven kinetic properties define the GPIb alpha-VWF-A1 bond. The invention provides classification of subtypes of von Willebrand disease (vWD), such as platelet-type, type 2B or type 2M in terms of similarities in the alterations in the biophysical properties of bonds to better understand the clinical phenotypes associated with these bleeding disorders. The invention is directed to understanding the biomechanical and molecular mechanisms by which the VWF-A1 domain mediates adhesive interactions with GPIb alpha both in vitro and in vivo. This invention provides for mice with mutant A1 domains to demonstrate the importance of the intrinsic kinetic and mechanical properties of this receptor-ligand pair in preventing inappropriate platelet aggregation in circulating blood, to facilitate the study of human platelet biology, as well as to generate a humanized animal model of hemostasis and thrombosis. The animal model is also useful for the generation and testing of novel anti-thrombotic therapies designed to inhibit platelet-VWF interactions as well as those designed to correct the bleeding phenotype associated with a reduction in adhesion between this receptor-ligand pair.

The invention is directed to understanding the effect that alterations in platelet size and shape have on the force-driven kinetics of the GPIb alpha-VWF-A1 tether bond. Platelets can bind to and translocate on surface-immobilized VWF under shear forces that preclude selectin-dependent adhesion of leukocytes to the vessel wall, due to their small discoid shape and not as a consequence of the unique kinetic properties of the GPIb alpha-VWF-A1 tether bond. The contribution of particle geometry in supporting the interactions between this receptor-ligand pair, we is performed by evaluating the interaction between vWF-A1 coated microspheres, ranging from 4 to 12 μm in diameter (platelet to leukocyte size), with surface-immobilized platelets under physiologic flow conditions. The utility of using polystyrene microspheres with a uniform shape and size to permit determination of the relationship between wall shear stress and the force acting on the GPIb alpha-vWF-A1 tether bond has been demonstrated. Moreover, it has been shown that the "sidedness" of the receptor or ligand does not alter the kinetic properties of this bond. β1-tubulin deficient mice have a defect in the cytoskeleton of platelets that changes the shape of these cells from discoid to spherical. Preliminary data demonstrates that the "spherical" platelets have a >60% reduction in attachment at high shear rates as compare to wild-type (WT) platelets. No differences in the kinetics of the GPIb alpha-vWF-A1 tether bond for WT and mutant platelets have been found using our microsphere assay system. Thus, platelet shape and not alterations in the biophysical properties of the GPIb alpha-vWF-A1 tether bond are responsible for the defect in adhesion. Data generated from these experiments will be use to develop a computational algorithm designed to stimulate the adhesion of platelets to surface-immobilized vWF under various hydrodynamic conditions. Thus, the invention provides an in vivo method to test for defects in hemostasis and thrombus formation that result from abnormalities in platelet shape and size. It also provides for a method to test the ability of synthetic platelet substitutes, which may be of varying shapes and sizes, to support hemostasis.

The invention provides a method for determining whether platelet function or morphology in a subject is abnormal.

The method comprises: affixing a molecule comprising a murine VWF-A1 domain to a surface of a flow chamber, wherein the domain comprises at least one mutation at a position selected from the group consisting of 1263>S, 1269>D, 1274>R, 1287>R, 1302>D, 1308>R, 1313R>W, 1314>V, 1326>H, 1329>I, 1330>G, 1333>D, 1344>A, 1347>V, 1350>A, 1370>S, 1379>R, 1381>A, 1385>M 1391>Q, 1394>S, 1397>F, 1421>N, 1439>V, 1442>S, 1449>Q, 1466>P, 1469>L, 1472>H, 1473>M, 1475>Q, 1479>G, and any combination thereof, where the position corresponds to an amino acid position of human von Willebrand Factor A1 protein shown in SEQ ID NO: 6; perfusing through the flow chamber a volume of blood or plasma from a subject at a shear flow rate of at least about 100 s$^{-1}$; perfusing a targeted molecular imaging agent into the flow chamber; and comparing the flow rate of the blood or plasma from the subject as compared to a normal flow rate, so as to determine whether the subject's platelet function or morphology is abnormal.

In one embodiment, affixing comprises (i) affixing an antibody which specifically binds VWF-A1 domain, and (ii) perfusing murine mutant VWF-A1 protein in the flow chamber at a shear flow rate of at least 100 s$^{-1}$. In another embodiment, the targeted molecular imaging agent comprises a nanoparticle, a fluorophore, a quantum dot, a microcrystal, a radiolabel, a dye, a gold biolabel, an antibody, a peptide, a small molecule ligand, or a combination of the agents listed. In a further embodiment, the targeted molecular imaging agent binds to a platelet receptor, a platelet ligand, or any region of a VWF protein or a portion thereof. In a particular embodiment, the targeted molecular imaging agent comprises horseradish peroxidase (HRP) coupled to an antibody directed at VWF-A1. In other embodiments, the comparing comprises a platelet adhesion assay, fluorescence imaging, a chromogenic indicator assay, a microscopy morphology analysis, or any combination of the listed modes. In some embodiments, platelets bound to VWF-A1 are less than about 500 cells/mm$^2$. In particular embodiments, the platelets are substantially spherical. In further embodiments, the subject is a human, a canine, a feline, a murine, a porcine, an equine, or a bovine. In other embodiments, the VWF molecule is an antibody, a peptide, or a Fab fragment directed to a VWF polypeptide or a portion thereof.

The invention also provides for a method for producing von Willebrand Factor A1 protein that specifically binds human platelets, the method comprising: (a) providing an animal expressing a plasma VWF containing a mutant von Willebrand Factor A1 protein, wherein the mutation causes the animal's von Willebrand Factor A1 protein to bind preferentially to for human platelets; and (b) harvesting the mutant animal von Willebrand Factor A1 so as to produce von Willebrand Factor A1 protein that specifically binds human platelets. In one embodiment, the mutant animal von Willebrand Factor A1 protein comprises at least one mutation comprising 1263P>S, 1269N>D, 1274K>R, 1287M>R, 1302G>D, 1308H>R, 1313R>W, 1314I>V, 1326R>H, 1329L>I, 1330E>G, 1333A>D, 1344T>A, 1347I>V, 1350T>A, 1370G>S, 1379H>R, 1381T>A, 1385T>M 1391P>Q, 1394A>S, 1397L>F, 1421S>N, 1439L>V, 1442G>S, 1449R>Q, 1466A>P, 1469Q>L, 1472Q>H, 1473V>M, 1475H>Q, 1479S>G, or any combination thereof.

The invention provides a method for testing efficacy and toxicity of a gene therapy vector, wherein the method comprises: (a) introducing a gene therapy vector into the animal of claim 4, allowing sufficient time for expression of the vector; (b) perfusing platelets from a subject into the animal under a condition suitable for GPIb-alpha-VWF-A1 protein binding; and (c) determining whether or not a thrombotic event occurs in the animal. In one embodiment, the vector comprises a nucleic acid encoding a platelet receptor polypeptide, a platelet ligand polypeptide, or a VWF polypeptide, or a portion thereof. In another embodiment, the subject is a human, a dog, a cat, a horse, a pig, or a primate. In a particular embodiment, the platelets are not murine platelets. In a further embodiment, the thrombotic event comprises blood clotting, abnormal bleeding, abnormal clotting, death, or a combination thereof. In some embodiments, the determining comprises dynamic force microscopy, a coagulation factor assay, a platelet adhesion assay, thrombus imaging, a bleeding time assay, aggregometry, review of real-time video of blood flow, a Doppler ultrasound vessel occlusion assay, or a combination thereof. In other embodiments, perfusing platelets is followed by perfusion of a labeled agent. In further embodiments, the labeled agent comprises one or more of a nanoparticle, a fluorophore, a quantum dot, a microcrystal, a radiolabel, a dye, a gold biolabel, an antibody, or a small molecule ligand. In particular embodiments, the agent targets a platelet receptor, a VWF protein, or a portion thereof.

The invention also provides a method for calibrating an aggregometry device or a device for measuring clot formation or retraction, wherein the method comprises: (a) providing hematologic data obtained from a subject, wherein blood or platelets from the subject is assessed by the device; (b) determining whether or not a thrombotic event occurs in the animal described above, wherein the animal is perfused with a sample of blood or platelets from the subject; and (c) correlating data obtained from (b) with the data obtained in (a) so as to calibrate the device, wherein a certain data obtained from the device is indicative of the corresponding thrombotic outcome determined in the animal described above. In one embodiment, the thrombotic event comprises blood clotting, abnormal bleeding, abnormal clotting, death, or a combination thereof.

The invention provides for in vivo determination of intrinsic and mechanical properties of the GPIb alpha-vWF-A1 tether bond and to determine if they are indeed critical for regulating the adhesion between platelets and vWF and how they may be manipulated to impair or enhance hemostasis and/or thrombosis. The invention provides determination of whether animals that posses gain-of-function mutations in VWF-A1, for example, those associated with type 2B vWD, have a defect in platelet deposition at sites of vascular injury and/or a loss of high molecular weight multimers of vWF. The invention provides determination of whether animals that possess loss-of-function mutations in VWF-A1, for example, those associated type 2M vWD, have a defect in platelet deposition at sites of vascular injury. Based on the results obtained herein, mice are genetically engineered with 1) mutant A1 domains that increase or decrease the on- and/or off-rate of this receptor-ligand pair by varying degrees, 2) A1 domains containing both types of mutations to confirm whether specific regions within this domain are essential for the stabilization of GPIb alpha binding, and 3) mutations within the A1 domain that favor binding to human but not murine GPIb alpha to enable the study of human platelet behavior in an animal model of hemostasis or thrombosis.

The invention provides methods for determining the impact of altering the intrinsic bond kinetics and/or its mechanical properties of the GPIb alpha-VWF-A1 interaction on hemostasis and thrombosis, which comprises: measuring platelet counts, plasma levels of vWF, and bleeding times; performing multimer gel analysis of mutant vWF; measuring the affinity of mutant vWF for platelets using a fluid phase binding assay; evaluating in vitro platelet tethering, rolling, and thrombus formation on surface-immobilized murine plasma vWF containing mutant A1 domains under physiological flow conditions; determining the ability of thrombi to form at sites of vascular injury in vivo in mutant VWF mice using epifluorescent intravital microscopy in; measuring platelet tethering frequency and rolling velocities in vivo.

In certain embodiments, the subject is a human. In other embodiments, the subject is a non-human animal such as a canine, equine, feline, porcine, murine, bovine, foul, sheep, or any other animal in need of treatment. In certain embodiments, the pharmaceutical composition further comprises another active agent. The additional active agent can be, but is not limited to, an analgesic, an antioxidant, diuretic, or a combination thereof. In certain embodiments, the composition is in a capsule form, a granule form, a powder form, a solution form, a suspension form, a tablet form, or any other form suitable for use by the method of the present invention. In certain embodiments, the composition is administered via oral, sublingual, buccal, parenteral, intravenous, transdermal, inhalation, intranasal, vaginal, intramuscular, rectal administration or any other route of administration that is suitable for delivery of the compound.

DETAILED DESCRIPTION OF THE INVENTION

The invention provides methods for identifying and evaluating potential anti-thrombotic reagents and compounds. The invention provides methods for testing for undesirable thrombotic or bleeding side effects of reagents in the setting of preclinical testing. The invention provides an in vivo model to test the efficacy of potential anti-thrombotic drugs directed against receptors, ligands, and/or intracellular signaling pathways on or in human platelets prior to FDA approval. To date, in vitro models of thrombosis do not accurately recapitulate the hemodynamic conditions, cell-cell interactions, or cell-protein interactions that occur at sites of vascular injury in a living animal. Thus, the system provided by this invention provides a method to test drugs directed at inhibiting or altering human platelet function other than directly testing them in humans. The invention provides a great advantage of being able to test directly compounds that target human platelets in an in vivo system. The invention provides a method to test contrast agents for imaging of human platelets at sites of thrombosis. For instance, one could test the ability of nanoparticle contrast agents targeted to human platelets to identify areas of thrombosis or occult bleeding. The invention provides a method to test compounds that correct the bleeding phenotype associated with a reduction in interactions between GPIb alpha and VWF-A1. The invention provides a method to test gene therapies directed at correcting genetic mutations associated with von Willebrand disease. The invention provides a method to correlate results obtained with an in vitro assay designed to measure the effects of antithrombotics or markers of platelet activation in patients.

Terms

A "pharmaceutical composition" refers to a mixture of one or more of the compounds, or pharmaceutically acceptable salts, hydrates, polymorphs, or pro-drugs thereof, with other chemical components, such as physiologically acceptable carriers and excipients. The purpose of a pharmaceutical composition is to facilitate administration of a compound to an organism.

As used herein von Willdebrand factor is abbreviated "VWF" and, alternatively, "vWF".

A "pro-drug" refers to an agent which is converted into the parent drug in vivo. Pro-drugs are often useful because, in some situations, they are easier to administer than the parent drug. They are bioavailable, for instance, by oral administration whereas the parent drug is not. The pro-drug also has improved solubility in pharmaceutical compositions over the parent drug. For example, the compound carries protective groups which are split off by hydrolysis in body fluids, e.g., in the bloodstream, thus releasing active compound or is oxidized or reduced in body fluids to release the compound.

A compound of the present invention also can be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

The term "pharmaceutically acceptable salt" means a salt, which is suitable for or compatible with the treatment of a patient or a subject such as a human patient or an animal.

The term "pharmaceutically acceptable acid addition salt" as used herein means any non-toxic organic or inorganic salt of any base compounds of the invention or any of their intermediates. Illustrative inorganic acids which form suitable acid addition salts include hydrochloric, hydrobromic, sulfuric and phosphoric acids, as well as metal salts such as sodium monohydrogen orthophosphate and potassium hydrogen sulfate. Illustrative organic acids that form suitable acid addition salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed and such salts exist in either a hydrated, solvated or substantially anhydrous form. In general, the acid addition salts of compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, are used, for example, in the isolation of compounds of the invention for laboratory use or for subsequent conversion to a pharmaceutically acceptable acid addition salt.

As used herein and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

Arterial thrombosis is a pathological consequence of disease states such as atherosclerosis and remains a major cause of morbidity and mortality in the Western world with healthcare cost ranging in the billions of dollars in the USA alone (*Circulation* 2006; 113:e85). Central to this process is the inappropriate deposition and activation of platelets in diseased vessels that can ultimately occlude the lumen, thus impeding blood flow to vital organ such as the heart and brain. Another key player is VWF, a large plasma glycoprotein of complex multimeric structure, which under normal physiological conditions prevents excessive bleeding by promoting platelet deposition at sites of vascular injury, thus "sealing off" leaky blood vessels. In order for this event to occur, VWF must form a "bridge" between receptors expressed on circulating platelets and exposed components of the injured vessel wall. This is the function of the A1 and A3 domains of this plasma protein, respectively. Each is folded into a disulfide-bonded loop structure that is critical for optimal biological activity (FIG. 1A).

Figure 1B:
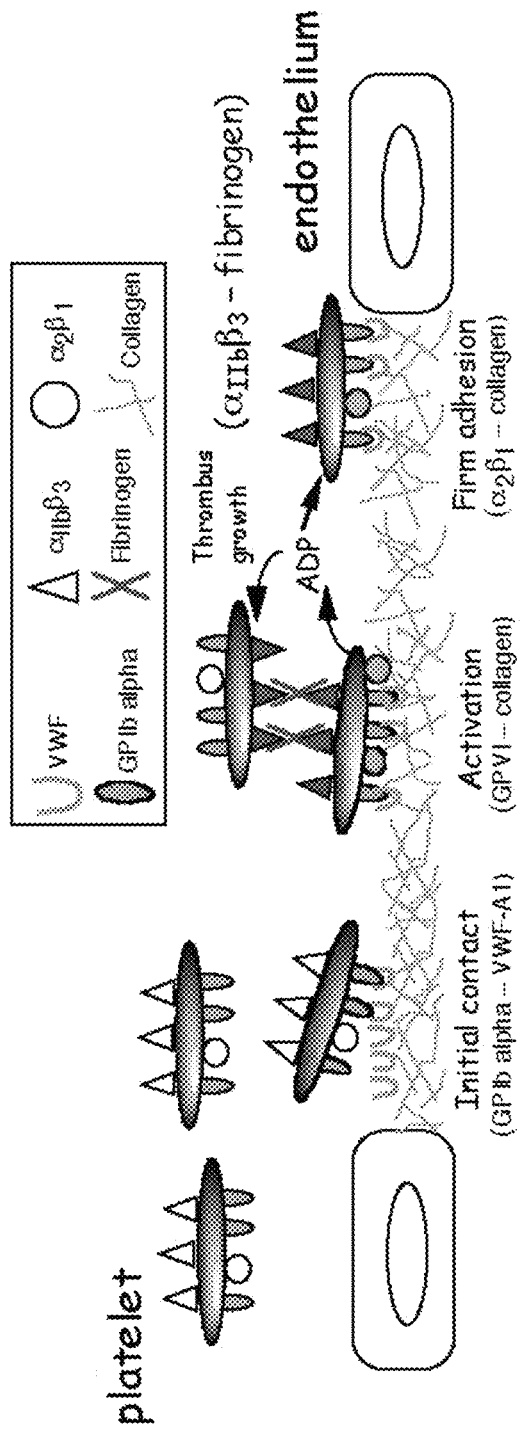
FIG. 1B is an illustration depicting the sequential adhesive and activation events that promote platelet deposition at sites of vascular injury.

It is the A1 domain that contains residues that compose the binding site for its receptor on platelets known as GPIb alpha, an adhesive event essential for the ability of these cells to rapidly attach to the injured vessel wall. The critical nature of this interaction is exemplified by the bleeding disorder, termed type 2M von Willebrand Disease (VWD), which results from the incorporation of loss-of-function point mutations within this domain that reduce the interaction between VWF-A1 and GPIb alpha (Sadler J E et al. (2006) *J. Thromb. Haemost.* 4: 2103-14). The A3 domain, on the other hand, is believed to be important in anchoring plasma VWF to sites where extracellular matrix components (i.e., collagen) are exposed as a result of disruption of the overlying vasculature endothelium (Wu D. et al. *Blood* 2002). Once in contact with exposed elements of the damaged vessel wall, platelets become "activated" through various signaling pathways (i.e. GPVI) enabling other adhesion molecules, such as α2β1 (collagen receptor) and αIIbβ3 (fibrinogen and VWF receptor) integrins, to firmly anchor these cells at the site of injury and to each other (FIG. 1B). In addition, ADP released from adherent platelets serves to amplify the activation of integrin receptors as well as other platelets leading to thrombus growth. Considerable emphasis has been placed on understanding the mechanism(s) that govern the interaction between GPIb alpha and the A1 domain of VWF and how it can be perturbed by point mutations associated with von Willebrand Disease, information relevant to the development of anti-thrombotic therapies.

von Willebrand Factor (VWF), the A1 Domain, and Related Diseases

During the past two decades, there has been considerable progress in understanding how VWF mediates platelet adhesion. Both the VWF cDNA and gene have been cloned and the primary structure of the VWF subunit (FIG. 1A) has been determined (13-16). It has been reported that ~59% of the mature VWF consists of repeated segments which are 29% to 43% homologous (17). These regions consist of domains that are triplicated (domains "A" and "B"), duplicated (domain "C") or quadruplicated (domain "D"). The triplicated A repeats encode for the central region of each VWF subunit. The A1 and A3 domains contain the sequences that mediate VWF's interaction with receptors on platelets or components of subendothelial extracellular matrix, respectively. Each is folded into a disulfide-bonded loop structure that is critical for optimal biological activity. The sequences of the amino terminal halves of each loop and the location of the cysteines forming the loop structure of each domain are highly conserved. It is the VWF-A1 domain (1260-1480) that contains sequences that provide binding sites for the platelet glycoprotein receptor Ib alpha, an interaction critical for the ability of these cells to rapidly attach and translocate at sites vascular injury (18,19). The role of the A3 domain, however, is believed to be in anchoring plasma VWF at sites where extracellular matrix components (i.e., collagen) are exposed as a result of disruption of the endothelium (20-25).

Figure 2:
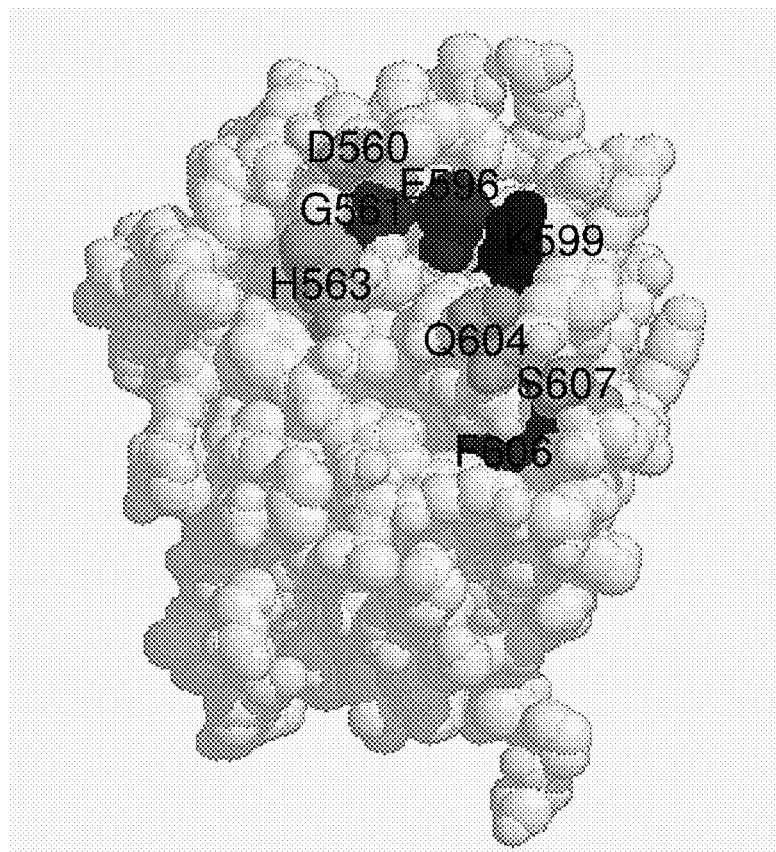
FIG. 2 is a model depicting the location of residues in the human VWF-A1 domain that if mutated, diminish GPIb alpha-mediated platelet binding in flow. Type 2M mutations are in red, residues identified by alanine scanning mutagenesis are in blue, and residues identified by crystal structure are in green.

With regard to mediating adhesive interactions with platelets, it has become increasingly evident that the VWF-A1 domain plays a crucial role in this process based on molecular genetic studies of individuals with type 2M or 2B VWD (26-31). In the majority of cases, patients with these designated genotypes have single point mutations contained within the disulfide loop (between Cys 1272 and Cys 1458) of this domain. With regard to type 2M VWD, afflicted individuals have significant impairments in hemostasis that appears to result from a lack of or reduced adhesive interactions between GPIb alpha and VWF at sites of vascular injury, and not from an alteration in VWF multimer structure. Structural and functional evidence has been provided in that type 2M mutations, such as 1324G>S, are localized within a region of the A1 domain (FIG. 5B), which is critical for supporting GPIb alpha-mediated platelet adhesion at physiological flow rates. Confirmation that this residue, as well as others predicted by our analysis of the crystal structure of the A1 domain, does contribute to GPIb alpha binding is suggested by studies evaluating the structure of the complex formed between this receptor-ligand pair (32, 33). Thus, it is possible to make accurate predictions about protein function from the three-dimensional protein structure and to confirm these postulates by site-specific mutagenesis and analysis under physiologically relevant flow conditions. The localization of some of the residues within the A1 domain that when mutated disrupt GPIb alpha binding is shown below (FIG. 2). The invention provides methods for evaluating the effect that loss-of-function mutations have on hemostasis and thrombus formation.

In contrast type 2M VWD, mutations associated with type 2B VWD are known to enhance the interaction between VWF-A1 and GPIb alpha, that is, they mitigate the requirement for exogenous modulators such as ristocetin or botrocetin to induce platelet agglutination (30). Moreover, these altered residues are localized in a region remote from the major GPIb alpha binding site that has been identified by mutagenesis (26; FIG. 3A-yellow). Clinically, this disease state is characterized by a loss of circulating high molecular weight VWF multimers (HMWM, FIG. 3B) together with a mild to moderate thrombocytopenia, which ultimately results in bleeding but not thrombosis (30, 31). It is the clearance of the HMWM of VWF from plasma that is believed to be responsible for the increased bleeding tendencies in patients with this disorder as they contribute to the majority of the hemostatic function associated with this plasma glycoprotein (34). The invention provides methods for evaluating the effect that gain-of-function mutations have on hemostasis, thrombus formation, and plasma levels of VWF.

Figures 4A, 4B, 4C:
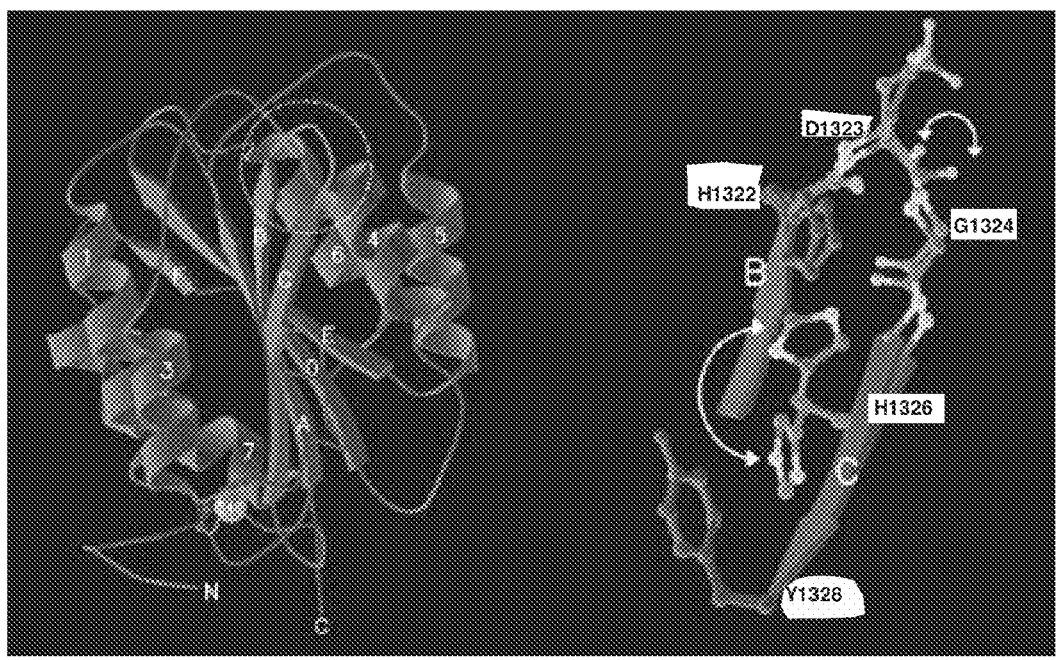
FIG. 4A shows structure models of the human VWF-A1 domain representing the location of the Ile1309 mutation and its proposed effects on residues critical for GPIb binding.
FIG. 4B shows the loss of the isoleucine methyl group allows a water molecule to enter, which ultimately results in changes in orientation of the G1324 peptide plane and the side chain of H1326 as depicted, residues critical for GPIb binding.
FIG. 4C shows a legend correlating standard nomenclature with nomenclature in the image of FIG. 4A.

Surface-immobilization of VWF and subsequent exposure to physiologically relevant shear forces appears to be a prerequisite for its ability to support interactions with platelets as this multimeric protein does not bind appreciably to these cells in the circulation. These hydrodynamic conditions are believed to promote structural changes within the A1 domain that in turn increases its affinity for GPIb alpha (35-37). Evidence suggested to support the existence of such an alteration in structure includes the ability of non-physiologic modulators such as the antibiotic ristocetin or the snake venom protein botrocetin to promote platelet agglutination in solution-based assays (38, 39). Moreover, this "on" and "off" conformation is exemplified by type 2B VWD. For instance, it was initially hypothesized that incorporation of type 2B mutations into the A1 domain shifted the equilibrium between two distinct tertiary conformations, analogous to those seen in crystal structures of the integrin I domain in ligand-free and collagen-bound states (40). The location of the type 2B mutants at sites distinct from the GPIb alpha binding site suggest that they disrupt a region responsible for regulation of binding affinity, thus affecting ligand binding allosterically. The crystal structure of a type 2B mutant A1 domain, 1309I>V, was determined and compared to its wild-type counterpart (41). A change was discovered in the structure of a loop, thought to be involved in GPIb alpha binding, lying on the surface distal to the mutation site. A similar finding has been observed for the VWF-A1 crystal structure containing the identical mutation (FIGS. 4A-4C).

This altered conformation represents a high affinity binding state of the A1 domain. However, the pathway of allosteric change proposed previously, involving the burial of a water molecule, cannot be a general feature of type 2B mutants, and the structural rearrangements appear too subtle to explain the altered kinetics. Interestingly, complex formation between botrocetin and VWF-A1 in which the type 2B mutation 1309I>V has been incorporated, and has demonstrated that most of these structural differences are reversed including: (1) loss of the buried water molecule at the mutation site; (2) the peptide plan between Asp 1323 and Gly 1324 flips back to a conformation similar to that in the WT structure; and (3) the side chain of His 1326 remains in the "mutant" position, although there is some evidence from electron density of an alternative conformation similar to WT. However, this reversion in structure does not correlate with a loss in the function-enhancing activity associated with the type 2B mutation. In fact, the addition of botrocetin further augments the interaction between the mutant A1 domain and platelets in flow (42). Thus, an alternative mechanism must account for function-enhancing nature of type 2B mutations. Moreover, these subtle alterations in structure did not compare to the large conformational changes in homologous integrin I-type domains that occur on ligand binding.

Figure 6:
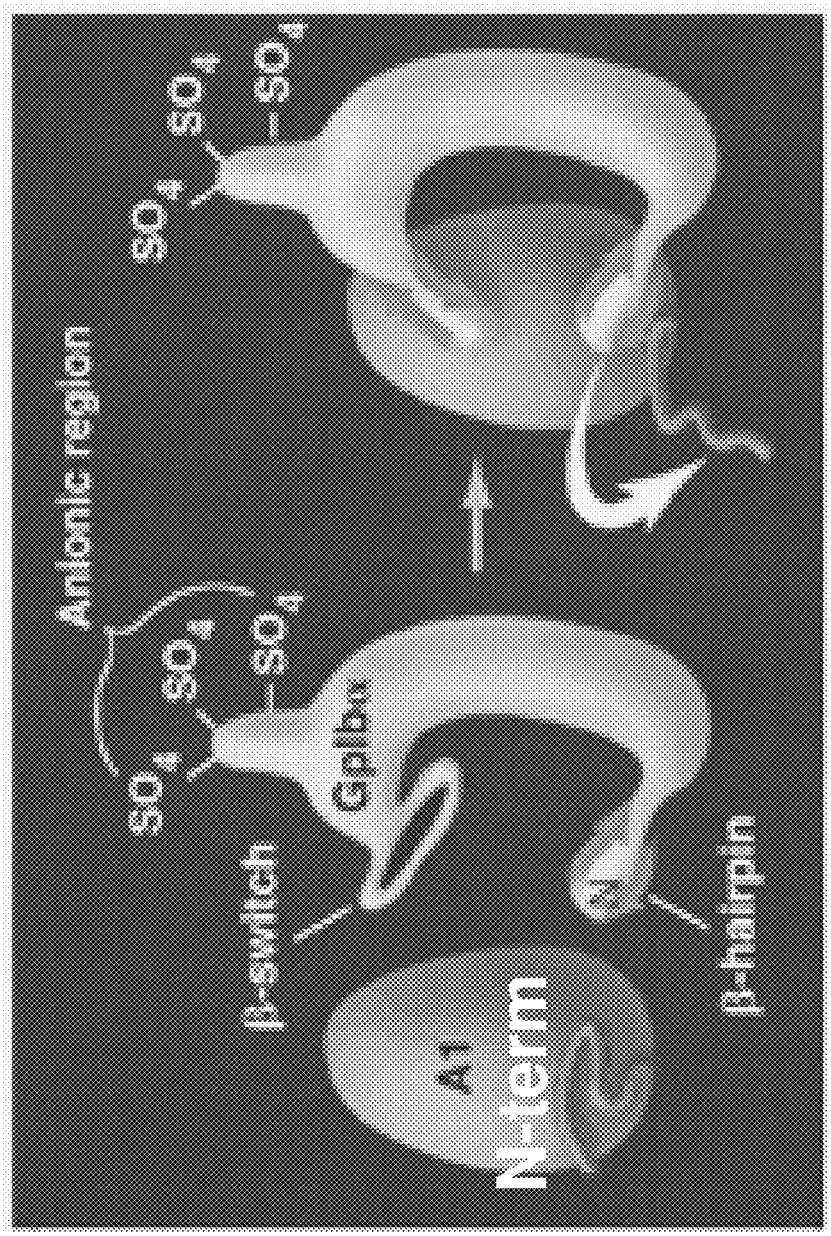
FIG. 6 is schematic wherein the uncomplexed A1 domain, an amino-terminal extension (pink) appears to block a binding site for the amino-terminal β-hairpin (orange arrows) of GPIb alpha. Binding requires the amino-terminal extension of A1 to move, and also induces the β-switch (yellow loop) of GPIb alpha to form a β-strand motif.

Recent findings provide support that type 2B mutations may stabilize the binding of a region of GPIb alpha known as the β-hairpin to an area near the location of these altered residues, distinct from that identified by site-directed mutagenesis. Type 2B mutations have been suggested to destabilize a network of interactions observed between the bottom face of the A1 domain and its terminal peptides in the wild type A1 structure, thereby making the binding site accessible (FIG. 6).

Progress has been made in understanding the structure of this receptor-ligand pair and potential alterations in conformation that may regulate this interaction. This model is non-limiting. However, the model permits determination of the kinetic and biomechanical basis for 1) the regulation of VWF-A1 domain activity in response to hydrodynamic forces, 2) the alterations in bond kinetics that result from incorporation of type 2B mutations into the VWF-A1 domain, and 3) the susceptibility of the kinetics of the GPIb alpha-VWF-A1 bond to an applied force.

Transgenic Animals

The invention provides for transgenic non-human animals that comprise a genome contains a nucleotide sequence (such as a gene) encoding a modified form of the A1 domain of VWF. The modification can be an amino acid residue substitution at a position involved with binding to GPIb alpha or in close proximity to this region such as, but not limited to, positions 1263, 1269, 1274, 1287, 1302, 1308, 1313, 1314, 1326, 1329, 1330, 1333, 1344, 1347, 1350, 1370, 1379, 1381, 1385 1391, 1394, 1397, 1421, 1439, 1442, 1449, 1466, 1469, 1472, 1473, 1475, 1479. It can also comprise a partial or full replacement of the animal A1 domain of VWF with the A1 domain of human VWF. It can also comprise a partial or full replacement of the entire VWF gene in an animal with the human VWF gene. Such non-human animals include vertebrates such as ovines, bovines, rodents, non-human primates, porcines, caprines, equines, ruminants, lagomorphs, canines, felines, aves, and the like. In one embodiment, non-human animals are selected from the order Rodentia that includes murines (such as rats and mice). In another embodiment, mice are particularly useful.

The transgenic non-human animals of the current invention are produced by experimental manipulation of the genome of the germline of the non-human animal (such as those animals described above). These genetically engineered non-human animals may be produced by several methods well known in the art which include the introduction of a "transgene" that comprises a nucleic acid (for example, DNA such as the A1 domain of VWF) integrated into a chromosome of the somatic and/or germ line cells of a non-human animal via methods known to one skilled in the art or into an embryonal target cell. A transgenic animal is an animal whose genome has been altered by the introduction of a transgene.

The term "transgene" as used herein refers to a foreign gene that is placed into an organism by introducing the foreign gene into newly fertilized eggs, embryonic stem (ES) cells, or early embryos. The term "foreign gene" refers to any nucleic acid (for example, a gene sequence) that is introduced into the genome of an animal by experimental manipulations. These nucleic acids may include gene sequences found in that animal so long as the introduced gene contains some modification (for example, the presence of a selectable marker gene, a point mutation—such as the base pair substitution mutant that contributes to the amino acid change at amino acid residue 1326 of the A1 domain of VWF—the presence of a loxP site, and the like) relative to the naturally-occurring gene.

The term "loxP site" refers to a short (34 bp) DNA sequence that is recognized by the Cre recombinase of the *E. coli* bacteriophage P1. In the presence of Cre recombinase, placement of two loxP sites in the same orientation on either side of a DNA segment can result in efficient excision of the intervening DNA segment, leaving behind only a single copy of the loxP site (Sauer and Henderson (1988) *Proc. Natl. Acad. Sci. USA* 85:5166).

In one embodiment, the invention provides for a targeting construct or vector that comprises a selectable marker gene flanked on either side by a modified A1 domain of VWF. The modification of the A1 domain can comprise an amino acid residue substitution at a position involved with binding to GPIb alpha (such as, but not limited to, positions 1263, 1269, 1274, 1287, 1302, 1308, 1313, 1314, 1326, 1329, 1330, 1333, 1344, 1347, 1350, 1370, 1379, 1381, 1385 1391, 1394, 1397, 1421, 1439, 1442, 1449, 1466, 1469, 1472, 1473, 1475, 1479) or can be a partial or full replacement of an animal (for example, a mouse) A1 domain of VWF with the A1 domain of human VWF. The targeting vector contains the modified A1 domain of VWF gene sequence sufficient to permit the homologous recombination of the targeting vector into at least one allele of the A1 domain of the VWF gene resident in the chromosomes of the target or recipient cell (for example, ES cells). The targeting vector will usually harbor 10 to 15 kb of DNA homologous to the A1 domain of the VWF gene, wherein this 10 to 15 kb of DNA will be divided more or less equally on each side of the selectable marker gene. The targeting vector can contain more than one selectable maker gene and when multiple selectable marker genes are utilized, the targeting vector usually contains a negative selectable marker (for example, the Herpes simplex virus tk (HSV-tk) gene) and a positive selectable marker (such as G418 or the neo gene). The positive selectable marker permits the selection of recipient cells containing an integrated copy of the targeting vector and but does not enable one skilled in the art to determine whether this integration occurred at the target site or at a random site. The presence of the negative selectable marker permits the identification of recipient cells containing the targeting vector at the targeted site (for example, which has integrated by virtue of homologous recombination into the target site). Cells growing in medium that selects against the expression of the negative selectable marker represents that the cells do not contain a copy of the negative selectable marker.

Targeting vectors can also be of the replacement-type wherein the integration of a replacement-type vector results in the insertion of a selectable marker into the target gene. Replacement-type targeting vectors may be employed to disrupt a gene (such as the VWF gene or the A1 domain of the VWF gene). This can result in the generation of a null allele; for example, an allele not capable of expressing a functional protein wherein the null alleles may be generated by deleting a portion of the coding region, deleting the entire gene, introducing an insertion and/or a frameshift mutation, and the like.

A selectable marker can include a gene which encodes an enzymatic activity that confers resistance to an antibiotic or drug upon the cell in which the selectable marker is expressed. Selectable markers may be positive. A positive selectable marker is usually a dominant selectable marker wherein the genes encode an enzymatic activity that can be detected in a mammalian cell or a cell line (including ES cells). Some non-limiting examples of dominant selectable markers include the bacterial xanthine-guanine phosphoribosyl transferase gene (also referred to as the gpt gene) which confers the ability to grow in the presence of mycophenolic acid, the bacterial hygromycin G phosphotransferase (hyg) gene which confers resistance to the antibiotic hygromycin, and the bacterial aminoglycoside 3' phosphotransferase gene (also referred to as the neo gene) which confers resistance to the drug G418 in mammalian cells. Selectable markers may also be negative. Negative selectable markers encode an enzymatic activity whose expression is toxic to the cell when grown in an appropriate selective medium. One non-limiting example of a negative selectable marker is the HSV-tk gene wherein HSV-tk expression in cells grown in the presence of gancyclovir or acyclovir is catatonic. Growth of cells in selective medium containing acyclovir or gancyclovir therefore selects against cells capable of expressing a functional HSV TK enzyme.

The ES cells suitable of the present invention utilized to generate transgenic animals can harbor introduced expression vectors (constructs), such as plasmids and the like. The expression vector constructs can be introduced via transfection, lipofection, transformation, injection, electroporation, or infection. The expression vectors can contain coding sequences, or portions thereof, encoding proteins for expression. Such expression vectors can include the required components for the transcription and translation of the inserted coding sequence. Expression vectors containing sequences encoding the produced proteins and polypeptides, as well as the appropriate transcriptional and translational control elements, can be generated using methods well known to and practiced by those skilled in the art. These methods include in vitro recombinant DNA techniques, synthetic techniques, and in vivo genetic recombination which are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y. In one embodiment, loxP expressing targeting vectors are used for transfection methods (such as pDNR-1r vector, pACD4K-C vector, and the like). In other embodiments, Cre-recombinase-expressing plasmids are also utilized (for example, crAVE cre recombinase vectors).

Introducing targeting vectors into embryonic stem (ES) cells can generate the mutant VWF-A1 transgenic animals of the present invention. ES cells are obtained by culturing pre-implantation embryos in vitro under appropriate conditions (Evans, et al. (1981) *Nature* 292:154-156; Bradley, et al. (1984) *Nature* 309:255-258; Gossler, et al. (1986) *Proc. Acad. Sci. USA* 83:9065-9069; and Robertson, et al. (1986) *Nature* 322:445-448). Using a variety of methods known to those skilled in the art, transgenes can be efficiently introduced into the ES cells via DNA transfection methods, which include (but are not limited to), protoplast or spheroplast fusion, electroporation, retrovirus-mediated transduction, calcium phosphate co-precipitation, lipofection, microinjection, and DEAE-dextran-mediated transfection. Following the introduction into the blastocoel of a blastocyst-stage embryo, transfected ES cells can thereafter colonize an embryo and contribute to the germ line of the resulting chimeric animal (see Jaenisch, (1988) *Science* 240:1468-1474). Assuming that the transgene provides a means for selection, the transfected ES cells may be subjected to various selection protocols to enrich for ES cells that have integrated the transgene prior to the introduction of transfected ES cells into the blastocoel. Alternatively, the polymerase chain reaction (PCR) may be used to screen for ES cells that have integrated the transgene and precludes the need for growth of the transfected ES cells under appropriate selective conditions prior to transfer into the blastocoel.

Alternative methods for the generation of transgenic animals (such as transgenic mice) containing an altered A1 domain of the VWF gene are established in the art. For example, embryonic cells at various stages of development can be used to introduce transgenes for the production of transgenic animals and different methods are used that depend on the stage of embryonic cell development. For microinjection methods, the zygote is best suited. In the mouse, the male pronucleus reaches the size of approximately 20 microns in diameter, which allows for reproducible injection of 1-2 picoliters (pl) of suspended DNA solution. A major advantage in using zygotes as a gene transfer target is that in most cases the injected DNA will be incorporated into the host genome before the first cleavage (Brinster, et al. (1985) *Proc. Natl. Acad. Sci. USA* 82:4438-4442). Thus, all cells of the transgenic non-human animal (such as a mouse) will carry the incorporated transgene (mutant A1 domain of the VWF gene), which can result in the efficient transmission of the transgene to the offspring of the founder since 50% of the germ cells will harbor the transgene (see U.S. Pat. No. 4,873,191).

Another method known in the art that can be used to introduce transgenes into a non-human animal is retroviral infection. The developing non-human embryo can be cultured in vitro to the blastocyst stage wherein during this time, the blastomeres can be targets for retroviral infection (Janenich (1976) *Proc. Natl. Acad. Sci. USA* 73:1260-1264). Enzymatic treatment to remove the zona pellucida can increase infection efficiency of the blastomeres (Hogan et al. (1986) in *Manipulating the Mouse Embryo*, Cold Spring Harbor Laboratory Press, Plainview, N.Y.). The viral vector system used by one skilled in the art in order to introduce the transgene is usually a replication-defective retrovirus that harbors the transgene (Jahner, D. et al. (1985) *Proc. Natl. Acad Sci. USA* 82:6927-6931; Van der Putten, et al. (1985) *Proc. Natl. Acad Sci. USA* 82:6148-6152). Transfection can be easily and efficiently obtained via culturing blastomeres on a monolayer of virus-producing cells (Van der Putten, supra; Stewart, et al. (1987) *EMBO J.* 6:383-388). Infection can also be performed at a later stage whereby virus or virus-producing cells are injected into the blastocoele (Jahner, D. et al. (1982) *Nature* 298:623-628). Most of the founder non-human animals will be mosaic for the transgene since incorporation occurs only in a subset of cells that form the transgenic animal and the founder may additionally contain various retroviral insertions of the transgene at different positions in the genome that generally will segregate in the offspring. Additional methods of using retroviruses or retroviral vectors to create transgenic animals known to those skilled in the art involves microinjecting mitomycin C-treated cells or retroviral particles producing retrovirus into the perivitelline space of fertilized eggs or early embryos (see Haskell and Bowen (1995) *Mol. Reprod. Dev.* 40:386).

In one embodiment of the invention, non-human transgenic animals can be generated that express a modified A1 domain of the VWF sequence. The modified A1 domain can contain an amino acid residue substitution at a position involved with binding of the VWF protein to GPIb alpha (such as, but not limited to, positions 1263, 1269, 1274, 1287, 1302, 1308, 1313, 1314, 1326, 1329, 1330, 1333, 1344, 1347, 1350, 1370, 1379, 1381, 1385 1391, 1394, 1397, 1421, 1439, 1442, 1449, 1466, 1469, 1472, 1473, 1475, 1479). In some embodiments, the VWF-A1 domain can comprise a single mutation, while in other embodiments, it can comprise 2 or more mutations.

In one embodiment of the invention, the modification of the A1 domain can be a partial or full replacement of an animal (for example, a mouse) A1 domain of VWF with the A1 domain of human VWF. In other words, the A1 domain in the animal VWF is removed and replaced with the human A1 sequence. In another embodiment, the animal VWF A1 domain may be partially replaced so that some portion of the human A1 domain replaces a portion of the animal A1 domain. For example, human A1 domain sequence could comprise at least 5%, 10%, 15%, 20%, 25%, 30%, 40%, 50%, 60%, 70%, 75%, 80%, 90%, 95%, 99%, or 100% of the animal A1 domain. The A1 domain of human VWF protein comprises SEQ ID NO: 1. In another embodiment, the animal can be a model for pre-clinical testing of compounds, wherein the animal expresses a mutant von Willebrand Factor (VWF) A1 protein containing one or more mutations, such that the binding specificity of the mutant VWF-A1 protein changes from being specific for the animal platelets to being specific for human platelets. In another embodiment, the mutation occurs in the VWF-A1 domain of a mouse. In particular embodiments, the murine mutant VWF-A1 protein comprises at least one mutation comprising 1263P>S, 1269N>D, 1274K>R, 1287M>R, 1302G>D, 1308H>R, 1313R>W, 1314I>V, 1326R>H, 1329L>I, 1330E>G, 1333A>D, 1344T>A, 1347I>V, 1350T>A, 1370G>S, 1379H>R, 1381T>A, 1385T>M 1391P>Q, 1394A>S, 1397L>F, 1421S>N, 1439L>V, 1442G>S, 1449R>Q, 1466A>P, 1469Q>L, 1472Q>H, 1473V>M, 1475H>Q, 1479S>G, or any combination thereof. In a particularly useful embodiment, the murine mutant VWF-A1 protein comprises a 1326R>H mutation, a 1314I>V mutation, or a combination thereof.

The modification of the A1 domain can be an amino acid substitution at residue 1326 (for example Arg for His in the mouse). In some embodiments, the non-human transgenic animal harbors a mutant construct wherein an amino acid residue substitution at a position involved affects binding to GPIb alpha (such as, but not limited to, positions 1263, 1269, 1274, 1287, 1302, 1308, 1313, 1314, 1326, 1329, 1330, 1333, 1344, 1347, 1350, 1370, 1379, 1381, 1385 1391, 1394, 1397, 1421, 1439, 1442, 1449, 1466, 1469, 1472, 1473, 1475, 1479). In yet other embodiments, non-human transgenic animals can successfully harbor a type 2B (Ile1309Val; 1309I>V) mutation and/or an Arg1326His (1326R>H) mutant construct. In another embodiment, the non-human transgenic animal expresses an Arg1326His (1326R>H) mutation wherein the mutant VWF-A1 domain comprises SEQ ID NO: 5, which corresponds to the His amino acid at the same position in humans, canines, chimpanzees, rat, porcine, felines, equines, bovine, and the like (Jenkins et al., (1998) *Blood* 91(6): 2032-44). In further embodiments of the invention, the non-human transgenic animal is a mouse. Example 3 below describes the transgenic animal of the current invention.

Molecular Manipulations of VWF-A1 and its Corresponding Mutants

The present invention utilizes conventional molecular biology, microbiology, and recombinant DNA techniques available to one of ordinary skill in the art. Such techniques are well known to the skilled worker and are explained fully in the literature. See, e.g., Maniatis, Fritsch & Sambrook, "*Molecular Cloning: A Laboratory Manual*" (1982): "*DNA Cloning: A Practical Approach*," Volumes I and II (D. N. Glover, ed., 1985); "Oligonucleotide Synthesis" (M. J. Gait, ed., 1984); "*Nucleic Acid Hybridization*" (B. D. Hames & S. J. Higgins, eds., 1985); "*Transcription and Translation*" (B. D. Hames & S. J. Higgins, eds., 1984); "*Animal Cell Culture*" (R. I. Freshney, ed., 1986); "*Immobilized Cells and Enzymes*" (IRL Press, 1986): B. Perbal, "*A Practical Guide to Molecular Cloning*" (1984), and Sambrook, et al., "*Molecular Cloning: a Laboratory Manual*" (1989).

The VWF sequences from mouse, human, have been aligned as shown in Jenkins et al. (1998) "Molecular Modeling of Ligand and Mutation Sites of the Type A Domains of Human von Willebrand Factor and Their Relevance to von Willebrand's Disease" Vol. 91, No. 6, *Blood*, pp. 2032-2044.

The DNA and polypeptide sequences of human VWF are readily available to those skilled in the art, under Genbank Accession No. X04385. The polypeptide sequence of the A1 domain of human VWF, which runs from amino acid residue number 1260 to amino acid residue number 1480 of the nucleotide sequence of SEQ ID NO:6, is shown in SEQ ID NO: 1. The polypeptide sequence of the A1 domain of mouse VWF, which runs from amino acid residue number 1260 to amino acid residue number 1480 of the of SEQ ID NO:8, is shown in SEQ ID NO: 2.

SEQ ID NO: 1 is the human wild type amino acid sequence corresponding to the A1 domain of VWF. The residues shown in SEQ ID NO: 1 are residues 1260-1480, the A1 domain, of SEQ ID NO: 6.

SEQ ID NO: 1:
EDISEPPLHDFYCSRLLDLVFLLDGSSRLSEAEFEVLKAFVVDMMERLRI
SQKWVRVAVVEYHDGSHAYIGLKDRKRPSELRRIASQVKYAGSQVASTSE
VLKYTLFQIFSKIDRPEASRIALLLMASQEPQRMSRNFVRYVQGLKKKKV
IVIPVGIGPHANLKQIRLIEKQAPENKAFVLSSVDELEQQRDEIVSYLCD
LAPEAPPPTLPPHMAQVTVGP

SEQ ID NO: 2 is the mouse wild type amino acid sequence corresponding to the A1 domain of VWF. The residues shown in SEQ ID NO:2 are residue numbers 1260-1480 from the full length mouse VWF shown in SEQ ID NO: 8.

SEQ ID NO: 2:
EDTPEPPLHNFYCSKLLDLVFLLDGSSMLSEAEFEVLKAFVVGMMERLH
ISQKRIRVAVVEYHDGSRAYLELKARKRPSELRRITSQIKYTGSQVAST
SEVLKYTLFQIFGKIDRPEASHITLLLTASQEPPRMARNLVRYVQGLKK
KKVIVIPVGIGPHASLKQIRLIEKQAPENKAFLLSGVDELEQRRDEIVS
YLCDLAPEAPAPTQPPQVAHVTVSP

The nucleotide sequence of the A1 domain of human VWF corresponding to amino acid residues 1260-1480 is shown in SEQ ID NO: 3 and of mouse VWF is shown in SEQ ID NO: 4 below.

SEQ ID NO: 3 is the human wild type nucleotide sequence corresponding to the A1 domain of VWF:
GAGGACATCTCGGAACCGCCGTTGCACGATTTCTACTGCAGCAGGCTAC
TGGACCTGGTCTTCCTGCTGGATGGCTCCTCCAGGCTGTCCGAGGCTGA
GTTTGAAGTGCTGAAGGCCTTTGTGGTGGACATGATGGAGCGGCTGCGC
ATCTCCCAGAAGTGGGTCCGCGTGGCCGTGGTGGAGTACCACGACGGCT
CCCACGCCTACATCGGGCTCAAGGACCGGAAGCGACCGTCAGAGCTGCG
GCGCATTGCCAGCCAGGTGAAGTATGCGGGCAGCCAGGTGGCCTCCACC
AGCGAGGTCTTGAAATACACACTGTTCCAAATCTTCAGCAAGATCGACC
GCCCTGAAGCCTCCCGCATCGCCCTGCTCCTGATGGCCAGCCAGGAGCC
CCAACGGATGTCCCGGAACTTTGTCCGCTACGTCCAGGGCCTGAAGAAG
AAGAAGGTCATTGTGATCCCGGTGGGCATTGGGCCCCATGCCAACCTCA
AGCAGATCCGCCTCATCGAGAAGCAGGCCCCTGAGAACAAGGCCTTCGT
GCTGAGCAGTGTGGATGAGCTGGAGCAGCAAAGGGACGAGATCGTTAGC
TACCTCTGTGACCTTGCCCCTGAAGCCCCTCCTCCTACTCTGCCCCCCC
ACATGGCACAAGTCACTGTGGGCCCG SEQ ID NO: 4 is the mouse wild type nucleotide sequence corresponding to the A1 domain of VWF:
GAGGATACCCCCGAGCCCCCCCTGCACAACTTCTACTGCAGCAAGCTGC
TGGATCTTGTCTTCCTGCTGGATGGCTCCTCTATGTTGTCCGAGGCTGA
GTTTGAAGTGCTCAAAGCTTTTGTGGTGGGCATGATGGAGAGGTTACAC
ATCTCTCAGAAGCGCATCCGCGTGGCAGTGGTAGAGTACCATGATGGCT
CCCGTGCCTACCTTGAGCTCAAGGCCCGGAAGCGACCCTCAGAGCTTCG
GCGCATCACCAGCCAGATTAAGTATACAGGCAGCCAGGTGGCCTCTACC
AGTGAGGTTTTGAAGTACACACTGTTCCAGATCTTTGGCAAAATTGACC
GCCCTGAAGCCTCCCATATCACTCTGCTCCTGACTGCTAGCCAGGAGCC
CCCACGGATGGCTAGGAATTTGGTCCGCTATGTCCAAGGTCTGAAGAAG
AAGAAGGTTATCGTGATCCCTGTGGGCATTGGGCCCCACGCCAGCCTCA
AACAGATCCGCCTCATCGAGAAGCAGGCCCCTGAAAACAAGGCTTTTCT
GCTCAGTGGGGTGGATGAGCTGGAGCAGAGAAGAGATGAGATAGTCAGC
TACCTCTGTGACCTTGCTCCCGAGGCCCCAGCCCCAACTCAGCCTCCAC
AGGTAGCCCACGTCACCGTGAGTCCA Human mRNA for pre-pro-von Willebrand factor:

SEQ ID NO: 6: Amino Acid Sequence Human VWF-(residue 1 to residue 2813)
```
  1 MIPARFAGVL LALALILPGT LCAEGTRGRS STARCSLFGS DFVNTFDGSM YSFAGYCSYL
 61 LAGGCQKRSF SIIGDFQNGK RVSLSVYLGE FFDIHLFVNG TVTQGDQRVS MPYASKGLYL
121 ETEAGYYKLS GEAYGFVARI DGSGNFQVLL SDRYFNKTCG LCGNFNIFAE DDFMTQEGTL
181 TSDPYDFANS WALSSGEQWC ERASPPSSSC NISSGEMQKG LWEQCQLLKS TSVFARCHPL
241 VDPEPFVALC EKTLCECAGG LECACPALLE YARTCAQEGM VLYGWTDHSA CSPVCPAGME
301 YRQCVSPCAR TCQSLHINEM CQERCVDGCS CPEGQLLDEG LCVESTECPC VHSGKRYPPG
361 TSLSRDCNTC ICRNSQWICS NEECPGECLV TGQSHFKSFD NRYFTFSGIC QYLLARDCQD
421 HSFSIVIETV QCADDRDAVC TRSVTVRLPG LHNSLVKLKH GAGVAMDGQD IQLPLLKGDL
481 RIQHTVTASV RLSYGEDLQM DWDGRGRLLV KLSPVYAGKT CGLCGNYNGN QGDDFLTPSG
541 LAEPRVEDFG NAWKLHGDCQ DLQKQHSDPC ALNPRMTRFS EEACAVLTSP TFEACHRAVS
601 PLPYLRNCRY DVCSCSDGRE CLCGALASYA AACAGRGVRV AWREPGRCEL NCPKGQVYLQ
661 CGTPCNLTCR SLSYPDEECN EACLEGCFCP PGLYMDERGD CVPKAQCPCY YDGEIFQPED
```

```
 721 IFSDHHTMCY CEDGFMHCTM SGVPGSLLPD AVLSSPLSHR SKRSLSCRPP MVKLVCPADN
 781 LRAEGLECTK TCQNYDLECM SMGCVSGCLC PPGMVRHENR CVALERCPCF HQGKEYAPGE
 841 TVKIGCNTCV CRDRKWNCTD HVCDATCSTI GMAHYLTFDG LKYLFPGECQ YVLVQDYCGS
 901 NPGTFRILVG NKGCSHPSVK CKKRVTILVE GGEIELFDGE VNVKRPMKDE THFEVVESGR
 961 YIILLLGKAL SVVWDRHLSI SVVLKQTYQE KVCGLCGNFD GIQNNDLTSS NLQVEEDPVD
1021 FGNSWKVSSQ CADTRKVPLD SSPATCHNNI MKQTMVDSSC RILTSDVFQD CNKLVDPEPY
1081 LDVCIYDTCS CESIGDCACF CDTIAAYAHV CAQHGKVVTW RTATLCPQSC EERNLRENGY
1141 ECEWRYNSCA PACQVTCQHP EPLACPVQCV EGCHAHCPPG KILDELLQTC VDPEDCPVCE
1201 VAGRRFASGK KVTLNPSDPE HCQICHCDVV NLTCEACQEP GGLVVPPTDA PVSPTTLYVE
1261 DISEPPLHDF YCSRLLDLVF LLDGSSRLSE AEFEVLKAFV VDMMERLRIS QKWVRVAVVE
1321 YHDGSHAYIG LKDRKRPSEL RRIASQVKYA GSQVASTSEV LKYTLFQIFS KIDRPEASRI
1381 ALLLMASQEP QRMSRNFVRY VQGLKKKKVI VIPVGIGPHA NLKQIRLIEK QAPENKAFVL
1441 SSVDELEQQR DEIVSYLCDL APEAPPPTLP PHMAQVTVGP GLLGVSTLGP KRNSMVLDVA
1501 FVLEGSDKIG EADFNRSKEF MEEVIQRMDV GQDSIHVTVL QYSYMVTVEY PFSEAQSKGD
1561 ILQRVREIRY QGGNRTNTGL ALRYLSDHSF LVSQGDREQA PNLVYMVTGN PASDEIKRLP
1621 GDIQVVPIGV GPNANVQELE RIGWPNAPIL IQDFETLPRE APDLVLQRCC SGEGLQIPTL
1681 SPAPDCSQPL DVILLLDGSS SFPASYFDEM KSFAKAFISK ANIGPRLTQV SVLQYGSITT
1741 IDVPWNVVPE KAHLLSLVDV MQREGGPSQI GDALGFAVRY LTSEMHGARP GASKAVVILV
1801 TDVSVDSVDA AADAARSNRV TVFPIGIGDR YDAAQLRILA GPAGDSNVVK LQRIEDLPTM
1861 VTLGNSFLHK LCSGFVRICM DEDGNEKRPG DVWTLPDQCH TVTCQPDGQT LLKSHRVNCD
1921 RGLRPSCPNS QSPVKVEETC GCRWTCPCVC TGSSTRHIVT FDGQNFKLTG SCSYVLFQNK
1981 EQDLEVILHN GACSPGARQG CMKSIEVKHS ALSVELHSDM EVTVNGRLVS VPYVGGNMEV
2041 NVYGAIMHEV RFNHLGHIFT FTPQNNEFQL QLSPKTFASK TYGLCGICDE NGANDFMLRD
2101 GTVTTDWKTL VQEWTVQRPG QTCQPILEEQ CLVPDSSHCQ VLLLPLFAEC HKVLAPATFY
2161 AICQQDSCHQ EQVCEVIASY AHLCRTNGVC VDWRTPDFCA MSCPPSLVYN HCEHGCPRHC
2221 DGNVSSCGDH PSEGCFCPPD KVMLEGSCVP EEACTQCIGE DGVQHQFLEA WVPDHQPCQI
2281 CTCLSGRKVN CTTQPCPTAK APTCGLCEVA RLRQNADQCC PEYECVCDPV SCDLPPVPHC
2341 ERGLQPTLTN PGECRPNFTC ACRKEECKRV SPPSCPPHRL PTLRKTQCCD EYECACNCVN
2401 STVSCPLGYL ASTATNDCGC TTTTCLPDKV CVHRSTIYPV GQFWEEGCDV CTCTDMEDAV
2461 MGLRVAQCSQ KPCEDSCRSG FTYVLHEGEC CGRCLPSACE VVTGSPRODS QSSWKSVGSQ
2521 WASPENPCLI NECVRVKEEV FIQQRNVSCP QLEVPVCPSG FQLSCKTSAC CPSCRCERME
2581 ACMLNGTVIG PGKTVMIDVC TTCRCMVQVG VISGFKLECR KTTCNPCPLG YKEENNTGEC
2641 CGRCLPTACT IQLRGGQIMT LKRDETLQDG CDTHFCKVNE RGEYFWEKRV TGCPPPFDEHK
2701 CLAEGGKIMK IPGTCCDTCE EPECNDITAR LQYVKVGSCK SEVEVDIHYC QGKCASKAMY
2761 SIDINDVQDQ CSCCSPTRTE PMQVALHCTN GSVVYHEVLN AMECKCSPRK CSK
VWF mature peptide (AA 763-2790)
VWF pro polypeptide (AA 1-2790)

SEQ ID NO: 7 Nucleic acid sequence-human VWF
    1 agctcacagc tattgtggtg ggaaagggag ggtggttggt ggatgtcaca gcttgggctt
   61 tatctccccc agcagtgggg actccacagc ccctgggcta cataacagca agacagtccg
  121 gagctgtagc agacctgatt gagcctttgc agcagctgag agcatggcct agggtgggcg
```

-continued

```
 181 gcaccattgt ccagcagctg agtttcccag ggaccttgga gatagccgca gccctcattt
 241 gcaggggaag gcaccattgt ccagcagctg agtttcccag ggaccttgga gatagccgca
 301 gccctcattt atgattcctg ccagatttgc cggggtgctg cttgctctgg ccctcatttt
 361 gccagggacc ctttgtgcag aaggaactcg cggcaggtca tccacggccc gatgcagcct
 421 tttcggaagt gacttcgtca cacctttga tgggagcatg tacagctttg cgggatactg
 481 cagttacctc ctggcagggg gctgccagaa acgctccttc tcgattattg gggacttcca
 541 gaatggcaag agagtgagcc tctccgtgta tcttgggaa tttttttgaca tccatttgtt
 601 tgtcaatggt accgtgacac aggggggacca aagagtctcc atgccctatg cctccaaagg
 661 gctgtatcta gaaactgagg ctgggtacta caagctgtcc ggtgaggcct atggctttgt
 721 ggccaggatc gatgcagcgc gcaactttca gtcctgctgt cagacagat acttcaacaa
 781 gacctgcggg ctgtgtggca actttaacat ctttgctgaa gatgacttta tgacccaaga
 841 agggaccttg acctcggacc cttatgactt tgccaactca tgggctctga gcagtggaga
 901 acagtggtgt gaacgggcat ctcctcccag cagctcatgc aacatctcct ctggggaaat
 961 gcagaagggc ctgtgggagc agtgccagct tctgaagagc acctcggtgt ttgcccgctg
1021 ccaccctctg gtgaccccg agccttttgt ggccctgtgt gagaagactt tgtgtgagtg
1081 tgctgggggg ctggagtgcg cctgccctgc cctcctggag tacgcccgga cctgtgccca
1141 ggagggaatg gtgctgtacg gctggaccga ccacagcgcg tgcagcccag tgtgccctgc
1201 tggtatggag tataggcagt gtgtgtcccc ttgcgccagg acctgccaga gcctgcacat
1261 caatgaaatg tgtcaggagc gatgcgtgga tggctgcagc tgccctgagg acagctcct
1321 ggatgaaggc ctctgcgtgg agagcaccga gtgtccctgc gtgcattccg gaaagcgcta
1381 ccctcccggc acctccctct ctcgagactg caacacctgc atttgccgaa acgccagtg
1441 gatctgcagc aatgaagaat gtccagggga gtgccttgtc actggtcaat cccacttcaa
1501 gagcttttgac aacagatact tcaccttcag tgggatctgc cagtacctgc tgcccggga
1561 ttgccaggac cactccttct ccattgtcat tgagactgtc cagtgtgctg atgaccgcga
1621 cgctgtgtgc acccgctccg tcaccgtccg gctgcctggc ctgcacaaca gccttgtgaa
1681 actgaagcat ggggcaggag ttgccatgga tggccaggac atccagctcc ccctcctgaa
1741 aggtgacctc cgcatccagc atacagtgac ggcctccgtg cgcctcagct acggggagga
1801 cctgcagatg gactgggatg ccgcgggag gctgctggtg aagctgtccc ccgtctacgc
1861 cgggaagacc tgcggcctgt gtgggaatta caatggcaac cagggcgacg acttccttac
1921 ccctctgggg ctggcagagc ccgggtgga ggacttcggg aacgcctgga gctgcacgg
1981 ggactgccag gacctgcaga agcagcacag cgatccctgc gccctcaacc cgcgcatgac
2041 caggttctcc gaggaggcgt gcgcggtcct gacgtccccc acattcgagg cctgccatcg
2101 tgccgtcagc ccgctgccct acctgcggaa ctgccgctac gacgtgtgct cctgctcgga
2161 cggccgcgag tgcctgtgcg gcgccctggc cagctatgcc gcggcctgcg cggggagagg
2221 cgtgcgcgtc gcgtggcgcg agccaggccg ctgtgagctg aactgcccga aaggccaggt
2281 gtacctgcag tgcgggaccc cctgcaacct gacctgccgc tctctctctt acccggatga
2341 ggaatgcaat gaggcctgcc tggagggctg cttctgcccc ccagggctct acatggatga
2401 gagggggggac tgcgtgccca aggcccagtg ccctgttac tatgacggtg agatcttcca
2461 gccagaagac atcttctcag accatcacac catgtgctac tgtgaggatg gcttcatgca
2521 ctgtaccatg agtggagtcc ccggaagctt gctgcctgac gctgtcctca gcagtcccct
2581 gtctcatcgc agcaaaagga gcctatcctg tcggcccccc atggtcaagc tggtgtgtcc
```

```
2641 cgctgacaac ctgcgggctg aagggctcga gtgtaccaaa acgtgccaga actatgacct
2701 ggagtgcatg agcatgggct gtgtctctgg ctgcctctgc ccccgggca tggtccggca
2761 tgagaacaga tgtgtggccc tggaaaggtg tccctgcttc catcagggca aggagtatgc
2821 ccctggagaa acagtgaaga ttggctgcaa cacttgtgtc tgtcgggacc ggaagtggaa
2881 ctgcacagac catgtgtgtg atgccacgtg ctccacgatc ggcatggccc actacctcac
2941 cttcgacggg ctcaaatacc tgttccccgg ggagtgccag tacgttctgg tgcaggatta
3001 ctgcggcagt aaccctggga cctttcggat cctagtgggg aataagggat gcagccaccc
3061 ctcagtgaaa tgcaagaaac gggtcaccat cctggtgag ggaggagaga ttgagctgtt
3121 tgacggggag gtgaatgtga agaggcccat gaaggatgag actcactttg aggtggtgga
3181 gtctggccgg tacatcattc tgctgctggg caaagccctc tccgtggtct gggaccgcca
3241 cctgagcatc tccgtggtcc tgaagcagac ataccaggag aaagtgtgtg gcctgtgtgg
3301 gaattttgat ggcatccaga acaatgacct caccagcagc aacctccaag tggaggaaga
3361 ccctgtggac tttgggaact cctggaaagt gagctcgcag tgtgctgaca ccagaaaagt
3421 gcctctggac tcatcccctg ccacctgcca taacaacatc atgaagcaga cgatggtgga
3481 ttcctcctgt agaatcctta ccagtgacgt cttccaggac tgcaacaagc tggtggaccc
3541 cgagccatat ctggatgtct gcatttacga cacctgctcc tgtgagtcca ttggggactg
3601 cgcctgcttc tgcgacacca ttgctgccta tgcccacgtg tgtgccagc atggcaaggt
3661 ggtgacctgg aggacggcca cattgtgccc ccagagctgc gaggagagga atctccggga
3721 gaacgggtat gagtgtgagt ggcgctataa cagctgtgca cctgcctgtc aagtcacgtg
3781 tcagcaccct gagccactgg cctgccctgt gcagtgtgtg gagggctgcc atgcccactg
3841 ccctccaggg aaaatcctgg atgagctttt gcagacctgc gttgaccctg aagactgtcc
3901 agtgtgtgag gtggctggcc ggcgttttgc ctcaggaaag aaagtcacct gaatcccag
3961 tgaccctgag cactgccaga tttgccactg tgatgttgtc aacctcacct gtgaagcctg
4021 ccaggagccg ggaggcctgg tggtgcctcc cacagatgcc ccggtgagcc ccaccactct
4081 gtatgtggag gacatctcgg aaccgccgtt gcacgatttc tactgcagca ggctactgga
4141 cctggtcttc ctgctggatg ctcctccag gctgtccgag gctgagtttg aagtgctgaa
4201 ggccttttgtg gtggacatga tggagcggct gcgcatctcc cagaagtggg tccgcgtggc
4261 cgtggtggag taccacgacg gctcccacgc ctacatcggg ctcaaggacc ggaagcgacc
4321 gtcagagctg cggcgcattg ccagccaggt gaagtatgcg ggcagccagg tggcctccac
4381 cagcgaggtc ttgaaataca cactgttcca aatcttcagc aagatcgacc gccctgaagc
4441 ctcccgcatc gccctgctcc tgatggccag ccaggagccc caacggatgt cccggaactt
4501 tgtccgctac gtccagggcc tgaagaagaa aaggtcatt gtgatcccgg tgggcattgg
4561 gccccatgcc aacctcaagc agatccgcct catcgagaag caggcccctg agaacaaggc
4621 cttcgtgctg agcagtgtgg atgagctgga gcagcaaagg gacgagatcg ttagctacct
4681 ctgtgacctt gcccctgaag cccctcctcc tactctgccc ccccacatgg cacaagtcac
4741 tgtgggcccg gggctcttgg gggtttcgac cctggggccc aagaggaact ccatggttct
4801 ggatgtggcg ttcgtcctgg aaggatcgga caaaattggt gaagccgact tcaacaggag
4861 caaggagttc atggaggagg tgattcagcg gatggatgtg gccaggaca gcatccacgt
4921 cacggtgctg cagtactcct acatggtgac cgtggagtac cccttcagcg aggcacagtc
4981 caaaggggac atcctgcagc gggtgcgaga gatccgctac cagggcggca acaggaccaa
```

-continued

```
5041 cactgggctg ccctgcggt acctctctga ccacagcttc ttggtcagcc agggtgaccg 5101 ggagcaggcg cccaacctgg tctacatggt caccggaaat cctgcctctg atgagatcaa 5161 gaggctgcct ggagacatcc aggtggtgcc cattggagtg ggccctaatg ccaacgtgca 5221 ggagctggag aggattggct ggcccaatgc ccctatcctc atccaggact ttgagacgct 5281 cccccgagag gctcctgacc tggtgctgca gaggtgctgc tccggagagg ggctgcagat 5341 ccccacccctc tccctgcac ctgactgcag ccagcccctg acgtgatcc ttctcctgga 5401 tggctcctcc agtttcccag cttcttattt tgatgaaatg aagagtttcg ccaaggcttt 5461 catttcaaaa gccaatatag ggcctcgtct cactcaggtg tcagtgctgc agtatggaag 5521 catcaccacc attgacgtgc catggaacgt ggtcccggag aaagcccatt tgctgagcct 5581 tgtggacgtc atgcagcggg agggaggccc cagccaaatc ggggatgcct gggctttgc 5641 tgtgcgatac ttgacttcag aaatgcatgg tgccaggccg ggagcctcaa aggcggtggt 5701 catcctggtc acggacgtct ctgtggattc agtggatgca gcagctgatg ccgccaggtc 5761 caacagagtg acagtgttcc ctattggaat tggagatcgc tacgatgcag cccagctacg 5821 gatcttggca ggcccagcag gcgactccaa cgtggtgaag ctccagcgaa tcgaagacct 5881 ccctaccatg gtcaccttgg gcaattcctt cctccacaaa ctgtgctctg gatttgttag 5941 gatttgcatg gatgaggatg ggaatgagaa gaggcccggg gacgtctgga ccttgccaga 6001 ccagtgccac accgtgactt gccagccaga tggccagacc ttgctgaaga gtcatcgggt 6061 caactgtgac cgggggctga ggccttcgtg ccctaacagc cagtcccctg ttaaagtgga 6121 agagacctgt ggctgccgct ggacctgccc ctgcgtgtgc acaggcagct ccactcggca 6181 catcgtgacc tttgatgggc agaatttcaa gctgactggc agctgttctt atgtcctatt 6241 tcaaaacaag gagcaggacc tggaggtgat tctccataat ggtgcctgca gccctggagc 6301 aaggcagggc tgcatgaaat ccatcgaggt gaagcacagt gccctctccg tcgagctgca 6361 cagtgacatg gaggtgacgg tgaatgggag actggtctct gttccttacg tgggtgggaa 6421 catggaagtc aacgtttatg gtgccatcat gcatgaggtc agattcaatc accttggtca 6481 catcttcaca ttcactccac aaaacaatga gttccaactg cagctcagcc caagacttt 6541 tgcttcaaag acgtatggtc tgtgtgggat ctgtgatgag aacggagcca atgacttcat 6601 gctgagggat ggcacagtca ccacagactg gaaaacactt gttcaggaat ggactgtgca 6661 gcggccaggg cagacgtgcc agcccatcct ggaggagcag tgtcttgtcc ccgacagctc 6721 ccactgccag gtcctcctct taccactgtt tgctgaatgc acaaggtcc tggctccagc 6781 cacattctat gccatctgcc agcaggacag ttgccaccag gagcaagtgt gtgaggtgat 6841 cgcctcttat gcccacctct gtcggaccaa cggggtctgc gttgactgga ggacacctga 6901 tttctgtgct atgtcatgcc caccatctct ggtctacaac cactgtgagc atggctgtcc 6961 ccggcactgt gatggcaacg tgagctcctg tggggaccat ccctccgaag gctgtttctg 7021 ccctccagat aaagtcatgt ggaaggcag ctgtgtccct gaagaggcct gcactcagtg 7081 cattggtgag gatggagtcc agcaccagtt cctggaagcc tgggtcccgg accaccagcc 7141 ctgtcagatc tgcacatgcc tcagcgggcg gaaggtcaac tgcacaacgc agccctgccc 7201 cacggccaaa gctcccacgt gtggcctgtg tgaagtagcc cgcctccgcc agaatgcaga 7261 ccagtgctgc cccgagtatg agtgtgtgtg tgacccagtg agctgtgacc tgcccccagt 7321 gcctcactgt gaacgtggcc tccagcccac actgaccaac cctggcgagt gcagacccaa 7381 cttcacctgc gcctgcagga aggaggagtg caaaagagtg tccccaccct cctgccccc 7441 gcaccgtttg cccaccttc ggaagaccca gtgctgtgat gagtatgagt gtgcctgcaa
```

-continued

```
7501 ctgtgtcaac tccacagtga gctgtcccct tgggtacttg gcctcaaccg ccaccaatga
7561 ctgtggctgt accacaacca cctgccttcc cgacaaggtg tgtgtccacc gaagcaccat
7621 ctaccctgtg ggccagttct gggaggaggg ctgcgatgtg tgcacctgca ccgacatgga
7681 ggatgccgtg atgggcctcc gcgtggccca gtgctcccag aagccctgtg aggacagctg
7741 tcggtcgggc ttcacttacg ttctgcatga aggcgagtgc tgtggaaggt gcctgccatc
7801 tgcctgtgag gtggtgactg gctcaccgcg gggggactcc cagtcttcct ggaagagtgt
7861 cggctcccag tgggcctccc cggagaaccc ctgcctcatc aatgagtgtg tccgagtgaa
7921 ggaggaggtc tttatacaac aaaggaacgt ctcctgcccc cagctggagg tccctgtctg
7981 ccccctcggg tttcagctga gctgtaagac ctcagcgtgc tgcccaagct gtcgctgtga
8041 gcgcatggag gcctgcatgc tcaatggcac tgtcattggg cccgggaaga ctgtgatgat
8101 cgatgtgtgc acgacctgcc gctgcatggt gcaggtgggg gtcatctctg gattcaagct
8161 ggagtgcagg aagaccacct gcaaccccctg cccccctgggt tacaaggaag aaaataacac
8221 aggtgaatgt tgtgggagat gtttgcctac ggcttgcacc attcagctaa gaggaggaca
8281 gatcatgaca ctgaagcgtg atgagacgct ccaggatggc tgtgatactc acttctgcaa
8341 ggtcaatgag agaggagagt acttctggga agagggtc acaggctgcc caccctttga
8401 tgaacacaag tgtctggctg agggaggtaa aattatgaaa attccaggca cctgctgtga
8461 cacatgtgag gagcctgagt gcaacgacat cactgccagg ctgcagtatg tcaaggtggg
8521 aagctgtaag tctgaagtag aggtggatat ccactactgc cagggcaaat gtgccagcaa
8581 agccatgtac tccattgaca tcaacgatgt gcaggaccag tgctcctgct gctctccgac
8641 acggacggag cccatgcagg tggccctgca ctgcaccaat ggctctgttg tgtaccatga
8701 ggttctcaat gccatggagt gcaaatgctc ccccaggaag tgcagcaagt gaggctgctg
8761 cagctgcatg ggtgcctgct gctgcctgcc ttggcctgat ggccaggcca gagtgctgcc
8821 agtcctctgc atgttctgct cttgtgccct tctgagccca caataaaggc tgagctctta
8881 tcttgctgca tgttctgctc ttgtgccctt ctgagcccac aat
```

Mus musculus strain CASA/RkJ VWF (Vwf) mRNA
SEQ ID NO: 8 Amino Acid Sequence of Mouse VWF (residue no. 1 to residue no. 2813)

```
  1 MNPFRYEICL LVLALTWPGT LCTEKPRDRP STARCSLFGD DFINTFDETM YSFAGGCSYL
 61 LAGDCQKRSF SILGNFQDGK RMSLSVYLGE FFDIHLFANG TVTQGDQSIS MPYASQGLYL
121 EREAGYYKLS SETFGFAARI DONGNFQVLM SDRHFNKTCG LCGDFNIFAE DDFRTQEGTL
181 TSDPYDFANS WALSSEEQRC KRASPPSRNC ESSSGDMHQA MWEQCQLLKT ASVFARCHPL
241 VDPESFVALC EKILCTCATG PECACPVLLE YARTCAQEGM VLYGWTDHSA CRPACPAGME
301 YKECVSPCPR TCQSLSINEV CQQQCVDGCS CPEGELLDED RCVQSSDCPC VHAGKRYPPG
361 TSLSQDCNTC ICRNSLWICS NEECPGECLV TGQSHEKSED NRYFTFSGIC QYLLARDCED
421 HTFSIVIETM QCADDPDAVC TRSVSVRLSA LHNSLVKLKH GGAVGIDGQD VQLPFLQGDL
481 RIQHTVMASV RLSYAEDLQM DWDGRGRLLV KLSPVYSGKT CGLCGNYNGN KGDDFLTPAG
541 LVEPLVVDFG NAWKLQGDCS DLRRQHSDPC SLNPRLTRFA EEACALLTSS KFEACHHAVS
601 PLPYLQNCRY DVCSCSDSRD CLCNAVANYA AECARKGVHI GWREPGFCAL GCPQGQVYLQ
661 CGNSCNLTCR SLSLPDEECS EVCLEGCYCP PGLYQDERGD CVPKAQCPCY YDGELFQPAD
721 IFSDHHTMCY CEDGFMHCTT SGTLGSLLPD TVLSSPLSHR SKRSLSCRPP MVKLVCPADN
781 PRAQGLECAK TCQNYDLECM SLGCVSGCLC PPGMVRHENK CVALERCPCF HQGAEYAPGD
841 TVKIGCNTCV CRERKWNCTN HVCDATCSAI GMAHYLTFDG LKYLFPGECQ YVLVQDYCGS
```

-continued

```
 901 NPGTFQILVG NEGCSYPSVK CRKRVTILVD GGELELFDGE VNVKRPLRDE SHFEVVESGR

961 YVILLLGQAL SVVWDHHLSI SVVLKHTYQE QVCGLCGNFD GIQNNDFTTS SLQVEEDPVN

1021 FGNSWKVSSQ CADTRKLSLD VSPATCHNNI MKQTMVDSAC RILTSDVFQG CNRLVDPEPY

1081 LDICIYDTCS CESIGDCACF CDTIAAYAHV CAQHGQVVAW RTPTLCPQSC EEKNVRENGY

1141 ECEWRYNSCA PACPVTCQHP EPLACPVQCV EGCHAHCPPG RILDELLQTC VDPQDCPVCE

1201 VAGRRLAPGK KITLSPDDPA HCQNCHCDGV NLTCEACQEP GGLVAPPTDA PVSSTTPYVE

1261 DTPEPPLHNF YCSKLLDLVF LLDGSSMLSE AEFEVLKAFV VGMMERLHIS QKRIRVAVVE

1321 YHDGSRAYLE LKARKRPSEL RRITSQIKYT GSQVASTSEV LKYTLFQIFG KIDRPEASHI

1381 TLLLTASQEP PRMARNLVRY VQGLKKKKVI VIPVGIGPHA SLKQIRLIEK QAPENKAFLL

1441 SGVDELEQRR DEIVSYLCDL APEAPAPTQP PQVAHVTVSP GIAGISSPGP KRKSMVLDVV

1501 FVLEGSDEVG EANFNKSKEF VEEVIQRMDV SPDATRISVL QYSYTVTMEY AFNGAQSKEE

1561 VLRHVREIRY QGGNRTNTGQ ALQYLSEHSF SPSQGDRVEA PNLVYMVTGN PASDEIKRLP

1621 GDIQVVPIGV GPHANMQELE RISRPIAPIF IRDFETLPRE APDLVLQTCC SKEGLQLPTL

1681 PPLPDCSQPL DVVLLLDGSS SLPESSFDKM KSFAKAFISK ANIGPHLTQV SVIQYGSINT

1741 IDVPWNVVQE KAHLQSLVDL MQQEGGPSQI GDALAFAVRY VTSQIHGARP GASKAVVIII

1801 MDTSLDPVDT AADAARSNRV AVFPVGVGDR YDEAQLRILA GPGASSNVVK LQQVEDLSTM

1861 ATLGNSFFHK LCSGFSGVCV DEDGNEKRPG DVWTLPDQCH TVTCLANGQT LLQSHRVNCD

1921 HGPRPSCANS QSPVRVEETC GCRWTCPCVC TGSSTRHIVT FDGQNFKLTG SCSYVIFQNK

1981 EQDLEVLLHN GACSPGAKQA CMKSIEIKHA GVSAELHSNM EMAVDGRLVL APYVGENMEV

2041 SIYGAIMYEV RFTHLGHILT YTPQNNEFQL QLSPKTFASK MHGLCGICDE NGANDFTLRD

2101 GTVTTDWKRL VQEWTVQQPG YTCQAVPEEQ CPVSDSSHCQ VLLSASFAEC HKVIAPATFH

2161 TICQQDSCHQ ERVCEVIASY AHLCRTSGVC VDWRTTDFCA MSCPPSLVYN HCERGCPRHC

2221 DGNTSFCGDH PSEGCFCPQH QVFLEGSCVP EEACTQCVGE DGVRHQFLET WVPDHQPCQI

2281 CMCLSGRKIN CTAQPCPTAR APTCGPCEVA RLKQSTNLCC PEYECVCDLF NCNLPPVPPC

2341 EGGLQPTLTN PGECRPTFTC ACRKEECKRV SPPSCPPHRT PTLRKTQCCD EYECACSCVN

2401 STLSCPLGYL ASATTNDCGC TTTTCLPDKV CVHRGTVYPV GQFWEEGCDT CTCTDMEDTV

2461 VGLRVVQCSQ RPCEDSCQPG FSYVLHEGEC CGRCLPSACK VVAGSLRGDS HSSWKSVGSR

2521 WAVPENPCLV NECVRVEDAV FVQQRNISCP QLAVPTCPTG FQLNCETSEC CPSCHCEPVE

2581 ACLLNGTIIG PGKSVMVDLC TTCRCIVQTD AISRFKLECR KTTCEACPMG YREEKSQGEC

2641 CGRCLPTACT IQLRGGRIMT LKQDETFQDG CDSHLCRVNE RGEYIWEKRV TGCPPFDEHK

2701 CLAEGGKIVK IPGTCCDTCE EPDCKDITAK VQYIKVGDCK SQEEVDIHYC QGKCASKAVY

2761 SIDIEDVQEQ CSCCLPSRTE PMRVPLHCTN GSVVYHEVIN AMQCRCSPRN CSK
SEQ ID NO: 9-Nucleic Acid Seguence of Mouse VWF
    1 agtagcggct gggtttcctc aagggacctt ggagatacag cccctgtttg tatgggcaag 61 atgaacccct tcaggtatga gatctgcctg cttgttctgg ccctcacctg gccagggacc 121 ctctgcacag aaaagcccccg tgacaggccg tcgacggccc gatgcagcct ctttggggac 181 gacttcatca acacgtttga tgagaccatg tacagctttg caggggctg cagttatctc 241 ctggctgggg actgccagaa acgttcctc tccattctcg gaacttcca agatggcaag 301 agaatgagcc tgtctgtgta tcttggggag ttttttgaca tccatttgtt tgccaatggc 361 accgtaacgc agggtgacca agcatctcc atgccctacg cctcccaagg actctaccta 421 gaacgcgagg ctgggtacta taagctctcc agtgagacct ttggctttgc ggccagaatc
```

-continued

```
 481 gatggcaatg gcaacttcca agtcctgatg tcagacagac acttcaacaa gacctgtggg
 541 ctgtgcggtg attttaacat cttcgcggaa gatgatttta ggacgcagga ggggaccttg
 601 acctcagacc cctatgattt tgccaactcc tgggccctga gcagtgagga acagcggtgt
 661 aaacgggcat ctcctcccag caggaactgc gagagctctt ctggggacat gcatcaggcc
 721 atgtgggagc aatgccagct actgaagacg gcatcggtgt tgcccgctg ccaccctctg
 781 gtggatcccg agtcctttgt ggctctgtgt gagaagattt tgtgtacgtg tgctacgggg
 841 ccagagtgcg catgtcctgt actccttgag tatgcccgaa cctgcgccca ggaagggatg
 901 gtgctgtacg gctggactga ccacagtgcc tgtcgtccag cttgcccagc tggcatggaa
 961 tataaggagt gtgtgtctcc ttgccccaga acctgccaga gcctgtctat caatgaagtg
1021 tgtcagcagc aatgtgtaga cggctgtagc tgccctgagg gagagctctt ggatgaagac
1081 cgatgtgtgc agagctccga ctgtccttgc gtgcacgctg ggaagcggta ccctcctggc
1141 acctccctct ctcaggactg caacacttgt atctgcagaa acagcctatg gatctgcagc
1201 aatgaggaat gcccagggga gtgtcttgtc acaggccaat cgcacttcaa gagcttcgac
1261 aacaggtact tcaccttcag tgggatctgc caatatctgc tggccccggga ctgcgaggat
1321 cacactttct ccattgtcat agagaccatg cagtgtgccg atgaccctga tgctgtctgc
1381 acccgctcgg tcagtgtgcg gctctctgcc ctgcacaaca gcctggtgaa actgaagcac
1441 gggggagcag tgggcatcga tggtcaggat gtccagctcc ccttcctgca aggtgacctc
1501 cgcatccagc acacagtgat ggcttctgta cgcctcagct atgcggagga cctgcagatg
1561 gactgggatg gccgtgggcg gctactggtt aagctgtccc cagtctattc tgggaagacc
1621 tgtggcttgt gtgggaatta caacggcaac aagggagacg acttcctcac gccggccggc
1681 ttggtggagc ccctggtggt agacttcgga aacgcctgga agcttcaagg ggactgttcg
1741 gacctgcgca ggcaacacag cgacccctgc agcctgaatc cacgcttgac caggtttgca
1801 gaggaggctt gtgcgctcct gacgtcctcc aagttcgagg cctgccacca cgcagtcagc
1861 cctctgccct atctgcagaa ctgccgttat gatgtttgct cctgctccga cagccgggat
1921 tgcctgtgta acgcagtagc taactatgct gccgagtgtg cccgaaaagg cgtgcacatc
1981 gggtggcggg agcctggctt ctgtgctctg ggctgtccac agggccaggt gtacctgcag
2041 tgtgggaatt cctgcaacct gacctgccgc tccctctccc tcccggatga agaatgcagt
2101 gaagtctgtc ttgaaggctg ctactgccca ccagggctct accaggatga agagggggac
2161 tgtgtgccca aggcccagtg cccctgctac tacgatggtg agctcttcca gcctgcggac
2221 attttctcag accaccatac catgtgttac tgtgaagatg gcttcatgca ctgtaccaca
2281 agtggcaccc tggggagcct gttgcctgac actgtcctca gcagtccccct gtctcaccgt
2341 agcaaaagga gcctttcctg ccggccaccc atggtcaagc tggtgtgtcc tgctgacaac
2401 ccacgggctc aagggctgga gtgtgctaag acgtgccaga actacgacct ggagtgtatg
2461 agcctgggct gtgtgtctgg ctgcctctgt ccccaggca tggtccggca cgaaaacaag
2521 tgtgtggcct tggagcggtg tccctgcttc catcagggtg cagagtacgc cccgggagac
2581 acagtgaaga ttggctgcaa cacctgtgtc tgccgggagc ggaagtggaa ctgcacgaac
2641 catgtgtgtg acgccacttg ctctgccatt ggtatggccc actacctcac cttcgatgga
2701 ctcaagtacc tgttcccggg ggagtgccag tatgttctgg tgcaggatta ctgtggcagt
2761 aaccctggga cctttcagat cctggtggga aatgagggtt gcagctatcc ctcggtgaag
2821 tgcaggaagc gggtgaccat cctggtggat ggagggggagc ttgaactgtt tgacggagag
```

-continued

```
2881 gtgaacgtta agaggcccct gagagatgaa tctcactttg aggtggtgga gtcgggccgg
2941 tacgtcatcc tgctgctggg tcaggccctt tctgtggtct gggaccacca cctcagcatc
3001 tctgtggtcc tgaagcacac ataccaggaa caggtgtgtg gcctctgcgg aactttgat
3061 ggcatccaga acaatgactt caccactagc agcctccagg tggaggaaga ccccgtcaac
3121 tttgggaact cctggaaagt gagctcacag tgtgctgaca cgagaaagct gtcactagat
3181 gtttcccctg ccacttgcca caacaacatc atgaaacaga cgatggtgga ctcagcctgc
3241 agaatcctta ccagtgacgt cttccagggc tgcaacaggc tggtggaccc tgagccatac
3301 ctggacatct gtatttatga cacttgctcc tgtgagtcca tcggggactg cgcctgtttc
3361 tgtgacacca ttgctgccta tgcccacgtg tgtgcccagc atggccaggt ggtagcctgg
3421 aggacaccca cactgtgccc ccagagctgt gaagaaaaga atgttcggga aatggctat
3481 gagtgtgagt ggcgttataa cagctgtgcg cctgcttgcc cagtcacgtg tcagcaccct
3541 gagcctctgg cttgccctgt gcagtgtgtg gagggttgtc atgcacattg ccctccaggg
3601 agaatcctgg atgaacttct gcagacctgc gtagacccc aagactgccc cgtgtgtgag
3661 gtggctggtc ggcgcttggc tcctggaaag aaaatcacct tgagtcctga tgaccctgca
3721 cactgtcaga attgtcactg tgatggtgtg aaccttacgt gtgaagcctg ccaagagccc
3781 ggaggcctgg tggcaccccc aactgatgcc ccagtcagct ctaccacccc atatgttgag
3841 gataccccg agccccccct gcacaacttc tactgcagca agctgctgga tcttgtcttc
3901 ctgctggatg ctcctctat gttgtccgag gctgagtttg aagtgctcaa agcttttgtg
3961 gtgggcatga tggagaggtt acacatctct cagaagcgca tccgcgtggc agtggtagag
4021 taccatgatg gctcccgtgc ctaccttgag ctcaaggccc ggaagcgacc ctcagagctt
4081 cggcgcatca ccagccagat taagtataca ggcagccagg tggcctctac cagtgaggtt
4141 ttgaagtaca cactgttcca gatctttggc aaaattgacc gccctgaagc ctcccatatc
4201 actctgctcc tgactgctag ccaggagccc ccacggatgg ctaggaattt ggtccgctat
4261 gtccaaggtc tgaagaagaa gaaggttatc gtgatccctg tgggcattgg gccccacgcc
4321 agcctcaaac agatccgcct catcgagaag caggcccctg aaaacaaggc ttttctgctc
4381 agtggggtgg atgagctgga gcagagaaga gatgagatag tcagctacct ctgtgacctt
4441 gctcccgagg ccccagcccc aactcagcct ccacaggtag cccacgtcac cgtgagtcca
4501 gggatcgctg gatctcgtc accgggacca aaacggaagt ccatggttct ggatgtggtg
4561 tttgtcctgg aggggtcaga cgaagttggt gaagccaact tcaataagag caaggagttc
4621 gtggaggagg taatccagcg catggacgtg agcccggatg caacgcgcat ctcagtactg
4681 cagtattcct acacggtaac catggagtat gccttcaatg ggcccagtc caaggaggag
4741 gtgctgcggc acgtgcgaga gatccgctac cagggcggca ataggacaaa cactgggcag
4801 gccctgcagt accttcctga gcacagcttc tctcccagcc aaggggaccg ggtagaggca
4861 cctaacctgg tctacatggt cacgggggaac cccgcctctg atgagatcaa gaggttgcct
4921 ggagacatcc aggtggtacc cattggggtg ggccccccatg ccaacatgca ggaactggag
4981 aggatcagca ggcccatcgc tcccatcttc atccgggact ttgagacact tccccgagag
5041 gctcctgacc tggtcctgca gacatgttgc tccaaggagg gtctgcaact gcccacccc
5101 cccctctcc ctgactgcag ccaaccctg gatgtggtcc tgctcctgga tggctcctct
5161 agcttgccag agtcttcctt tgataaaatg aagagttttg ccaaggcttt catttcaaag
5221 gccaacattg ggccccacct cacacaggtg tccgtgatac agtatggaag catcaatacc
5281 attgatgtac catggaatgt ggttcaggag aaagcccatc tacagagttt ggtggacctc
```

```
5341  atgcagcagg agggtggccc cagccagatt ggggatgctc tggcctttgc cgtgcgctat 5401  gtaacttcac aaatccacgg agccaggcct ggggcctcca aagcagtggt catcatcatc 5461  atggatacct ccttggatcc cgtggacaca gcagcagatg ctgccagatc caaccgagtg 5521  gcagtgtttc ccgttggggt tggggatcgg tatgatgaag cccagctgag gatcttggca 5581  ggccctgggg ccagctccaa tgtggtaaag ctccagcaag ttgaagacct ctccaccatg 5641  gccaccctgg gcaactcctt cttccacaaa ctgtgttctg ggttttctgg agtttgtgtg 5701  gatgaagatg ggaatgagaa gaggcctggg gatgtctgga ccttgccgga tcagtgccac 5761  acagtgactt gcttggcaaa tggccagacc ttgctgcaga gtcatcgtgt caattgtgac 5821  catggacccc ggccttcatg tgccaacagc cagtctcctg ttcgggtgga ggagacgtgt 5881  ggctgccgct ggacctgccc ttgtgtgtgc acgggcagtt ccactcggca catcgtcacc 5941  ttcgatgggc agaatttcaa gcttactggt agctgctcct atgtcatctt caaaacaag 6001  gagcaggacc tggaagtgct cctccacaat ggggcctgca gccccgggggc aaaacaagcc 6061  tgcatgaagt ccattgagat taagcatgct ggcgtctctg ctgagctgca cagtaacatg 6121  gagatggcag tggatgggag actggtcctt gccccgtacg ttggtgaaaa catggaagtc 6181  agcatctacg gcgctatcat gtatgaagtc aggtttaccc atcttggcca catcctcaca 6241  tacacgccac aaaacaacga gttccaactg cagcttagcc ccaagacctt tgcttcgaag 6301  atgcatggtc tttgcggaat ctgtgatgaa aacggggcca atgacttcac gttgcgagat 6361  ggcacggtca ccacagactg gaaaaggctt gtccaggaat ggacggtgca gcagccaggg 6421  tacacatgcc aggctgttcc cgaggagcag tgtcccgtct ctgacagctc ccactgccag 6481  gtcctcctct cagcgtcgtt tgctgaatgc cacaaggtca tcgctccagc cacattccat 6541  accatctgcc agcaagacag ttgccaccag gagcgagtgt gtgaggtgat tgcttcttac 6601  gcccatctct gtcggaccag tggggtctgt gttgattgga ggacaactga tttctgtgct 6661  atgtcatgcc caccgtccct ggtgtataac cactgtgagc gtggctgccc tcggcactgc 6721  gatgggaaca ctagcttctg tggggaccat ccctcagaag gctgcttctg tccccaacac 6781  caagttttc tggaaggcag ctgtgtcccc gaggaggcct gcactcagtg tgttggcgag 6841  gatggagttc gacatcagtt cctggagacc tgggtcccag accatcagcc ctgtcagatc 6901  tgtatgtgcc tcagtgggag aaagattaac tgcactgccc agccgtgtcc cacagcccga 6961  gctcccacgt gtggcccatg tgaagtggct cgcctcaagc agagcacaaa cctgtgctgc 7021  ccagagtatg agtgtgtgtg tgacctgttc aactgcaact tgcctccagt gcctccgtgt 7081  gaaggagggc tccagccaac cctgaccaac cctggagaat gcagacccac ctttacctgt 7141  gcctgcagga agaagagtg caaaagagtg tccccaccct cctgcccccc tcaccggaca 7201  cccactctcc ggaagaccca gtgctgtgat gaatacgagt gtgcttgcag ctgtgtcaac 7261  tccacgctga gctgcccact tggctacctg gcctcagcca ctaccaatga ctgtggctgc 7321  accacgacca cctgtctccc tgacaaggtt tgtgtccacc gaggcaccgt ctaccctgtg 7381  ggccagttct gggagaggg ctgtgacacg tgcacctgta cggacatgga ggatactgtc 7441  gtgggcctgc gtgtggtcca gtgctctcaa aggccctgtg aagacagctg tcagccaggt 7501  ttttcttatg ttctccacga aggcgagtgc tgtggaaggt gcctgccctc tgcttgcaag 7561  gtggtggctg gctcactgcg gggcgattcc cactcttcct ggaaaagtgt tggatctcgg 7621  tgggctgttc ctgagaaccc ctgcctcgtc aacgagtgtg tccgcgtgga ggatgcagtg 7681  tttgtgcagc agaggaacat ctcctgccca cagctggctg tccctacctg tcccacaggc
```

```
-continued
7741 ttccaactga actgtgagac ctcagagtgc tgtcctagct gccactgtga gcctgtggag 7801 gcctgcctgc tcaatggcac catcattggg cccgggaaga gtgtgatggt tgacctatgc 7861 acgacctgcc gctgcatcgt gcagacagag gccatctcca gattcaagct ggagtgcagg 7921 aagactacct gtgaggcctg ccccatgggc tatcgggaag agaagagcca gggtgaatgc 7981 tgtgggagat gcttgcctac agcttgcact attcagctaa gaggaggacg gatcatgacc 8041 ctgaagcaag atgagacatt ccaggatggc tgtgacagtc atttgtgcag ggtcaacgag 8101 agaggagagt acatctggga gaagagggtc acgggctgcc caccatttga tgaacacaag 8161 tgtctggctg aaggaggcaa aatcgtgaaa attccaggca cctgctgtga cacatgtgag 8221 gagcctgatt gcaaagacat cacagccaag gtgcagtaca tcaaagtggg agattgtaag 8281 tcccaagagg aagtggacat tcattactgc cagggaaagt gtgccagcaa agctgtgtac 8341 tccattgaca tcgaggatgt gcaggagcaa tgctcctgct gcctgccctc gaggacggag 8401 cccatgcgcg tgcccttgca ctgcaccaat ggctctgtcg tgtaccacga ggtcatcaac 8461 gccatgcagt gcaggtgttc tccccggaac tgcagcaagt gaggcctgtg cagctacagc 8521 ggattcctac tgatacc
```

DNA sequences or oligonucleotides having specific sequences can be synthesized chemically or isolated by one of several approaches established in art. The basic strategies for identifying, amplifying, and isolated desired DNA sequences as well as assembling them into larger DNA molecules containing the desired sequence domains in the desired order, are well known to those of ordinary skill in the art. See, e.g., Sambrook, et al., (1989) *Nature* November 16; 342(6247):224-5; Perbal, B. et al., (1983) *J Virol.* March; 45(3):925-40. DNA segments corresponding to all or a portion of the VWF sequence may be isolated individually using the polymerase chain reaction (M. A. Innis, et al., "PCR Protocols: A Guide To Methods and Applications," Academic Press, 1990). A complete sequence may be assembled from overlapping oligonucleotides prepared by standard methods and assembled into a complete coding sequence. See, e.g., Edge (1981), *Nature,* 292:756; Nambiar, et al. (1984), *Science,* 223:1299; Jay et al. (1984), *J. Biol. Chem.,* 259:6311.

The assembled nucleotide sequence can be cloned into a suitable vector or replicon and maintained in said carrier in a composition that is substantially free of vectors that do not contain the assembled sequence, thus providing a reservoir of the assembled sequence wherein the entire sequence can be extracted from the reservoir via excising it from DNA material with restriction enzymes or by PCR amplification. Those of ordinary skill in the art are familiar with numerous cloning vectors, and the selection of an appropriate cloning vector is a matter of choice. The construction of vectors containing desired nucleotide sequences linked by appropriate DNA sequences is accomplished by discussed above. These vectors may be constructed to contain additional DNA sequences, such as bacterial origins of replication to make shuttle vectors in order to shuttle between prokaryotic hosts and mammalian hosts.

Procedures for construction and expression of mutant proteins of defined sequence are well known in the art. A DNA sequence encoding a mutant form of VWF or a fragment thereof can be synthesized chemically or prepared from the wild-type sequence by one of several approaches, including primer extension, linker insertion and PCR (see, e.g., Sambrook, et al., (1989) *Nature* November 16; 342 (6247):224-5; Maniatis, Fritsch & Sambrook, "Molecular Cloning: A Laboratory Manual" (1982): "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986): B. Perbal, "A Practical Guide to Molecular Cloning" (1984), and Sambrook, et al., "Molecular Cloning: a Laboratory Manual" (1989)). Mutants can be prepared by these techniques having additions, deletions, and substitutions in the wild-type sequence (for example, the mouse VWF-A1 1326R>H mutant of SEQ ID NO: 5). To confirm that the mutant contains the desired changes, one skilled in the art can confirm the changes of interest via sequence-by-sequence analysis and/or by methods available to one skilled in the art.

In one embodiment, modification of the A1 domain can contain an amino acid residue substitution at a position involved with binding to GPIb alpha (such as, but not limited to, positions 1263, 1269, 1274, 1287, 1302, 1308, 1313, 1314, 1326, 1329, 1330, 1333, 1344, 1347, 1350, 1370, 1379, 1381, 1385 1391, 1394, 1397, 1421, 1439, 1442, 1449, 1466, 1469, 1472, 1473, 1475, 1479). In further embodiments, the modification of the A1 domain can be a partial or full replacement of an animal (such as a mouse) A1 domain of VWF with the A1 domain of human VWF. In other embodiments of the invention, the modification of the A1 domain can be an amino acid substitution at residue 1326 (for example HIS for ARG) such as depicted in SEQ ID NO: 5.

SEQ ID NO: 5 is the sequence for the mouse VWF-A1 1326 R>H mutant, wherein the modified amino acid sequence corresponds to the A1 domain of mouse VWF (residues 1260-1480) having an amino acid substitution at residue 1326 of HIS for ARG (in Bold):

EDTPEPPLHNFYCSKLLDLVFLLDGSSMLSEAEFEVLKAFVVGMMERLH

ISQKRIRVAVVEYHDGSHAYLELKARKRPSELRRITSQIKYTGSQVAST

-continued

SEVLKYTLFQIFGKIDRPEASHITLLLTASQEPPRMARNLVRYVQGLKK

KKVIVIPVGIGPHASLKQIRLIEKQAPENKAFLLSGVDELEQRRDEIVS

YLCDLAPEAPAPTQPPQVAHVTVSP

An expression vector containing a nucleotide sequence encoding a protein of interest, such as a mutant VWF-A1 molecule described above, is transfected into a host cell, either eukaryotic (for example, yeast, mammalian, or insect cells) or prokaryotic, by conventional techniques well established in the art. Transfection techniques carried out depend on the host cell used. For example, mammalian cell transfection can be accomplished using lipofection, protoplast fusion, DEAE-dextran mediated transfection, $CaPO_4$ co-precipitation, electroporation, direct microinjection, as well as other methods known in the art which can comprise: scraping, direct uptake, osmotic or sucrose shock, lysozyme fusion or erythrocyte fusion, indirect microinjection such as via erythrocyte-mediated techniques, and/or by subjecting host cells to electric currents. Some of the techniques mentioned above are also applicable to unicellular organisms, such as bacteria or yeast. As other techniques for introducing genetic information into host cells will be developed, the above-mentioned list of transfection methods is not considered to be exhaustive. The transfected cells are then cultured by conventional techniques to produce a mutant VWF-A1 molecule harboring at least one of the mutations previously described.

One skilled in the art understands that expression of desired protein products in prokaryotes is most often carried out in *E. coli* with vectors that contain constitutive or inducible promoters. Some non-limiting examples of bacterial cells for transformation include the bacterial cell line *E. coli* strains DH5a or MC1061/p3 (Invitrogen Corp., San Diego, Calif.), which can be transformed using standard procedures practiced in the art, and colonies can then be screened for the appropriate plasmid expression. Some *E. coli* expression vectors (also known in the art as fusion-vectors) are designed to add a number of amino acid residues, usually to the N-terminus of the expressed recombinant protein. Such fusion vectors can serve three functions: 1) to increase the solubility of the desired recombinant protein; 2) to increase expression of the recombinant protein of interest; and 3) to aid in recombinant protein purification by acting as a ligand in affinity purification. In some instances, vectors, which direct the expression of high levels of fusion protein products that are readily purified, may also be used. Some non-limiting examples of fusion expression vectors include pGEX, which fuse glutathione S-tranferase to desired protein; pcDNA 3.1/V5-His A B & C (Invitrogen Corp, Carlsbad, Calif.) which fuse 6×-His to the recombinant proteins of interest; pMAL (New England Biolabs, MA) which fuse maltose E binding protein to the target recombinant protein; the *E. coli* expression vector pUR278 (Ruther et al., (1983) *EMBO* 12:1791), wherein the coding sequence may be ligated individually into the vector in frame with the lac Z coding region in order to generate a fusion protein; and pIN vectors (Inouye et al., (1985) *Nucleic Acids Res.* 13:3101-3109; Van Heeke et al., (1989) *J. Biol. Chem.* 24:5503-5509. Fusion proteins generated by the likes of the above-mentioned vectors are generally soluble and can be purified easily from lysed cells via adsorption and binding to matrix glutathione agarose beads subsequently followed by elution in the presence of free glutathione. For example, the pGEX vectors are designed to include thrombin or factor Xa protease cleavage sites so that the cloned target can be released from the GST moiety.

Other suitable cell lines, in addition to microorganisms such as bacteria (e.g., *E. coli* and *B. subtilis*) transformed with recombinant bacteriophage DNA, plasmid DNA or cosmid DNA expression vectors containing coding sequences for a mutant VWF-A1 molecule described above, may alternatively be used to produce the molecule of interest. Non-limiting examples include plant cell systems infected with recombinant virus expression vectors (for example, tobacco mosaic virus, TMV; cauliflower mosaic virus, CaMV) or transformed with recombinant plasmid expression vectors (e.g., Ti plasmid) containing coding sequences for a mutant VWF-A1 molecule described above; insect cell systems infected with recombinant virus expression vectors (e.g., baculovirus) containing coding sequences for a mutant VWF-A1 molecule described above; yeast (for example, *Saccharomyces* sp., *Pichia* sp.) transformed with recombinant yeast expression vectors containing coding sequences for a mutant VWF-A1 molecule described above; or mammalian cell lines harboring a vector that contains coding sequences for a mutant VWF-A1 molecule described above.

Mammalian cells (such as BHK cells, VERO cells, CHO cells and the like) can also contain an expression vector (for example, one that harbors a nucleotide sequence encoding a mutant VWF-A1 molecule described above) for expression of a desired product. Expression vectors containing such a nucleic acid sequence linked to at least one regulatory sequence in a manner that allows expression of the nucleotide sequence in a host cell can be introduced via methods known in the art, as described above. To those skilled in the art, regulatory sequences are well known and can be selected to direct the expression of a protein of interest in an appropriate host cell as described in Goeddel, *Gene Expression Technology* (1990) *Methods in Enzymology* 185, Academic Press, San Diego, Calif.). Regulatory sequences can comprise the following: enhancers, promoters, polyadenylation signals, and other expression control elements. Practitioners in the art understand that designing an expression vector can depend on factors, such as the choice of host cell to be transfected and/or the type and/or amount of desired protein to be expressed.

Animal or mammalian host cells capable of harboring, expressing, and secreting large quantities of a mutant VWF-A1 molecule (described above) of interest into the culture medium for subsequent isolation and/or purification include, but are not limited to, Chinese hamster ovary cells (CHO), such as CHO-K1 (ATCC CCL-61), DG44 (Chasin et al., (1986) *Som. Cell Molec. Genet,* 12:555-556; Kolkekar et al., (1997) *Biochemistry,* 36:10901-10909; and WO 01/92337 A2), dihydrofolate reductase negative CHO cells (CHO/dhfr-, Urlaub et al., (1980) *Proc. Natl. Acad. Sci. U.S.A.,* 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293 cells subcloned for growth in suspension culture, Graham et al., (1977) *J. Gen. Virol.,* 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4; Mather (1980) *Biol. Reprod.,* 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather (1982) *Annals NY Acad. Sci.*, 383:44-68); MCR 5 cells; FS4 cells. A cell line transformed to produce a mutant VWF-A1 molecule described above can also be an immortalized mammalian cell line of lymphoid origin, which include but are not limited to, a myeloma, hybridoma, trioma or quadroma cell line. The cell line can also comprise a normal lymphoid cell, such as a B cell, which has been immortalized by transformation with a virus, such as the Epstein Barr virus (such as a myeloma cell line or a derivative thereof).

A host cell strain, which modulates the expression of the inserted sequences, or modifies and processes the nucleic acid in a specific fashion desired also may be chosen. Such modifications (for example, glycosylation and other post-translational modifications) and processing (for example, cleavage) of protein products may be important for the function of the protein. Different host cell strains have characteristic and specific mechanisms for the post-translational processing and modification of proteins and gene products. As such, appropriate host systems or cell lines can be chosen to ensure the correct modification and processing of the foreign protein expressed, such as a mutant VWF-A1 molecule described above. Thus, eukaryotic host cells possessing the cellular machinery for proper processing of the primary transcript, glycosylation, and phosphorylation of the gene product may be used. Non-limiting examples of mammalian host cells include 3T3, W138, BT483, Hs578T, CHO, VERY, BHK, Hela, COS, BT2O, T47D, NSO (a murine myeloma cell line that does not endogenously produce any immunoglobulin chains), CRL7O3O, MDCK, 293, HTB2, and HsS78Bst cells.

For protein recovery, isolation and/or purification, the cell culture medium or cell lysate is centrifuged to remove particulate cells and cell debris. The desired polypeptide molecule (for example, a mutant VWF-A1 protein) is isolated or purified away from contaminating soluble proteins and polypeptides by suitable purification techniques. Non-limiting purification methods for proteins include: separation or fractionation on immunoaffinity or ion-exchange columns; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anion-exchange resins, in which the more acidic fraction(s) is/are collected.

In one embodiment, the protein isolated is a mutant human von Willebrand Factor A1 protein comprising one or more of the following mutations: 1263S>P, 1269D>N, 1274R>K, 1287R>M, 1302D>G, 1308R>H, 1313W>R, 1314V>I, 1326H>R, 1329I>L, 1330G>E, 1333D>A, 1344A>T, 1347V>I, 1350A>T, 1370S>G, 1379R>H, 1381A>T, 1385M>T 1391Q>P, 1394S>A, 1397F>L, 1421N>S, 1439V>L, 1442S>G, 1449Q>R, 1466P>A, 1469L>Q, 1472H>Q, 1473M>V, 1475Q>H, or 1479G>S. In another embodiment, the protein isolated is a mutant human von Willebrand Factor A1 protein comprising a 1263S>P, 1269D>N, 1274R>K, 1287R>M, 1302D>G, 1308R>H, 1313W>R, 1314V>I, 1326H>R, 1329I>L, 1330G>E, 1333D>A, 1344A>T, 1347V>I, 1350A>T, 1370S>G, 1379R>H, 1381A>T, 1385M>T, 1391Q>P, 1394S>A, 1397F>L, 1421N>S, 1439V>L, 1442S>G, 1449Q>R, 1466P>A, 1469L>Q, 1472H>Q, 1473M>V, 1475Q>H, or a 1479G>S mutation. In a particular embodiment, the protein isolated is a mutant human von Willebrand Factor A1 protein comprising a 1326H>R mutation.

The invention also provides a method for producing mutant von Willebrand Factor A1 protein that specifically binds human platelets. For example, an animal expressing a mutant von Willebrand Factor A1 (VWF-A1) protein can be provided, wherein the mutation causes the platelet binding specificity of the animal VWF-A1 protein to change to be specific for human platelets. VWF plasma protein containing the mutant A1 domain from an animal (such as from a mouse) can then be subsequently harvested. In one embodiment, the animal von Willebrand Factor A1 protein contains at least one mutation at amino acid position 1263, 1269, 1274, 1287, 1302, 1308, 1313, 1314, 1326, 1329, 1330, 1333, 1344, 1347, 1350, 1370, 1379, 1381, 1385, 1391, 1394, 1397, 1421, 1439, 1442, 1449, 1466, 1469, 1472, 1473, 1475, or 1479. In another embodiment, the mutations occur in a murine VWF-A1 protein. In particular embodiments, the mutant murine von Willebrand Factor A1 protein comprises at least one mutation comprising 1263P>S, 1269N>D, 1274K>R, 1287M>R, 1302G>D, 1308H>R, 1313R>W, 1314I>V, 1326R>H, 1329L>I, 1330E>G, 1333A>D, 1344T>A, 1347I>V, 1350T>A, 1370G>S, 1379H>R, 1381T>A, 1385T>M 1391P>Q, 1394A>S, 1397L>F, 1421S>N, 1439L>V, 1442G>S, 1449R>Q, 1466A>P, 1469Q>L, 1472Q>H, 1473V>M, 1475H>Q, 1479S>G, or any combination thereof.

Pre-Screening Evaluation of Anti-Thrombotics and Associated Diseases

Diversity libraries, such as random or combinatorial peptide or non-peptide libraries can be screened for small molecules and compounds that specifically bind to a VWF-A1 protein. Many libraries are known in the art that can be used such as, e.g., chemically synthesized libraries, recombinant (e.g., phage display) libraries, and in vitro translation-based libraries.

Any screening technique known in the art can be used to screen for agonist (i.e., compounds that promote platelet adhesion) or antagonist molecules (such as anti-thrombotics) directed at a target of interest (e.g., VWF-A1). The present invention contemplates screens for small molecule ligands or ligand analogs and mimics, as well as screens for natural ligands that bind to and modulate VWF-A1 binding to GPIb-alpha, such as via examining the degree of thrombus formation, platelet adhesion, coagulation, blood flow, vessel occlusion, or bleeding times. For example, natural products libraries can be screened using assays of the invention for molecules that modulate the activity of a molecule of interest, such as a VWF-A1 binding to GPIb-alpha.

Knowledge of the primary sequence of a molecule of interest, such as a VWF-A1, can provide an initial clue as to proteins that can modulate VWF-A1 binding to GPIb-alpha. Identification and screening of modulators is further facilitated by determining structural features of the protein, e.g., using X-ray crystallography, neutron diffraction, nuclear magnetic resonance spectrometry, and other techniques for structure determination. These techniques provide for the rational design or identification of such modulators.

Test compounds, such as test modulators of VWF-A1 binding to GPIb-alpha, are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) *Tib Tech* 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups. Screening compound libraries listed above [also see EXAMPLE 6 and U.S. Patent Application Publication No. 2005/0009163, which is hereby incorporated by reference], in combination with dynamic force microscopy, a coagulation factor assay, a platelet adhesion assay, thrombus imaging, a bleeding time assay, aggregometry, review of real-time video of blood flow, a Doppler ultrasound vessel occlusion assay, or a combination of these assays (for example, those assays described in EXAMPLES 1-4) can be used to identify modulators of VWF-A1 binding to GPIb-alpha, wherein the compound abbreviates or increases off-rate ($k_{off}$) binding kinetics between VWF-A1 and GPIb-alpha by at least two-fold (Lew et al., (2000) *Curr. Med. Chem.* 7(6):663-72; Werner et al., (2006) *Brief Funct. Genomic Proteomic* 5(1):32-6).

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

Examples of chemically synthesized libraries are described in Fodor et al., (1991) *Science* 251:767-773; Houghten et al., (1991) *Nature* 354:84-86; Lam et al., (1991) *Nature* 354:82-84; Medynski, (1994) *BioTechnology* 12:709-710; Gallop et al., (1994) *J. Medicinal Chemistry* 37(9):1233-1251; Ohlmeyer et al., (1993) *Proc. Natl. Acad. Sci. USA* 90:10922-10926; Erb et al., (1994) *Proc. Natl. Acad. Sci. USA* 91:11422-11426; Houghten et al., (1992) *Biotechniques* 13:412; Jayawickreme et al., (1994) *Proc. Natl. Acad. Sci. USA* 91:1614-1618; Salmon et al., (1993) *Proc. Natl. Acad. Sci. USA* 90:11708-11712; PCT Publication No. WO 93/20242, dated Oct. 14, 1993; and Brenner et al., (1992) *Proc. Natl. Acad. Sci. USA* 89:5381-5383.

Screening methods of the invention allowed for the identification of potential compounds that modulate VWF-A1 binding to GPIb-alpha. In some embodiments of the invention, the compound comprises one or more compounds having a structure depicted in Table 8 below.

Examples of phage display libraries are described in Scott et al., (1990) *Science* 249:386-390; Devlin et al., (1990) *Science*, 249:404-406; Christian, et al., (1992) *J. Mol. Biol.* 227:711-718; Lenstra, (1992) *J. Immunol. Meth.* 152:149-157; Kay et al., (1993) *Gene* 128:59-65; and PCT Publication No. WO 94/18318.

In vitro translation-based libraries include but are not limited to those described in PCT Publication No. WO 91/05058; and Mattheakis et al., (1994) *Proc. Natl. Acad. Sci. USA* 91:9022-9026.

In one non-limiting example, non-peptide libraries, such as a benzodiazepine library (see e.g., Bunin et al., (1994) *Proc. Natl. Acad. Sci. USA* 91:4708-4712), can be screened. Peptoid libraries, such as that described by Simon et al., (1992) *Proc. Natl. Acad. Sci. USA* 89:9367-9371, can also be used. Another example of a library that can be used, in which the amide functionalities in peptides have been permethylated to generate a chemically transformed combinatorial library, is described by Ostresh et al. (1994), *Proc. Natl. Acad. Sci. USA* 91:11138-11142.

Screening the libraries can be accomplished by any variety of commonly known methods. See, for example, the following references, which disclose screening of peptide libraries: Parmley and Smith, (1989) *Adv. Exp. Med. Biol.* 251:215-218; Scott and Smith, (1990) *Science* 249:386-390; Fowlkes et al., (1992) *BioTechniques* 13:422-427; Oldenburg et al., (1992) *Proc. Natl. Acad. Sci. USA* 89:5393-5397; Yu et al., (1994) *Cell* 76:933-945; Staudt et al., (1988) *Science* 241:577-580; Bock et al., (1992) *Nature* 355:564-566; Tuerk et al., (1992) *Proc. Natl. Acad. Sci. USA* 89:6988-6992; Ellington et al., (1992) *Nature* 355:850-852; U.S. Pat. Nos. 5,096,815; 5,223,409; and 5,198,346, all to Ladner et al.; Rebar et al., (1993) *Science* 263:671-673; and PCT Pub. WO 94/18318.

The invention provides a method for identifying a compound that modulates VWF-A1 binding to GPIb-alpha. In one embodiment, the method can comprise providing an electronic library of test compounds stored on a computer (such as those libraries described above); providing atomic coordinates for at least 10 amino acid residues of the A1 domain of the VWF protein listed in Table 8, where the coordinates having a root mean square deviation therefrom, with respect to at least 50% of the Ca atoms, of not greater than about 2.5 Å, in a computer readable format; converting the atomic coordinates into electrical signals readable by a computer processor to generate a three dimensional model of the VWF-A1 domain; performing a data processing method, wherein electronic test compounds from the library are superimposed upon the three dimensional model of the A1 domain of VWF; and determining which test compound fits within the binding pocket of the three dimensional model of the VWF-A1 protein. Thus, compounds can be identified that would modulate the binding of VWF-A1 to GPIb-alpha.

In another embodiment, the method can comprise providing an electronic library of test compounds stored on a computer; and providing atomic coordinates listed in Table 8 in a computer readable format for at least 10, 15, 20, 25, 30, 35, or 40 amino acid residues of the A1 domain of the VWF protein, wherein the residues can comprise 2 or more of the following residues: Pro1391, Arg1392, Arg1395, Val1398, Arg1399, Gln1402, Lys1406, Lys1423, Gln1424, Leu1427, Lys1430, or Glu1431; converting the atomic coordinates into electrical signals readable by a computer processor to generate a three dimensional model of the A1 domain of the VWF protein; performing a data processing method, wherein electronic test compounds from the library are superimposed upon the three dimensional model of the A1 domain of the VWF protein; and determining which test compound fits within the binding pocket of the three dimensional model of the VWF-A1 protein. Thus, compounds can be identified that would modulate the binding of VWF-A1 to GPIb-alpha.

In a further embodiment, the method can comprise providing an electronic library of test compounds stored on a computer (such as those libraries described above); providing atomic coordinates for at least 10 amino acid residues of the Botrocetin-VWF-A1 complex listed in accession entry 1IJK (http://www.rcsb.org/pdb/explore.do?structureId=1IJK), where coordinates having a root mean square deviation therefrom, with respect to at least 50% of the Cα atoms, not more than about 3 Å, in a computer readable format; converting the atomic coordinates into electrical signals readable by a computer processor to generate a three dimensional model of the Botrocetin-VWF-A1 complex; performing a data processing method, wherein electronic test compounds from the library are superimposed upon Botrocetin within the three dimensional model of the Botrocetin-VWF-A1 complex; and determining which test compound fits within the binding pocket of the three dimensional model of the VWF-A1 protein and best overlays the three-dimensional model generated above. Thus, compounds can be identified that would modulate the binding of VWF-A1 to GPIb-alpha.

In other embodiments, the method can comprise providing an electronic library of test compounds stored on a computer; providing atomic coordinates listed in accession entry 1IJK (http://www.rcsb.org/pdb/explore.do?structureId=1IJK) in a computer readable format for at least 10, 15, 20, 25, 30, 35, or 40 amino acid residues of the Botrocetin-murine VWF-A1 complex, wherein the residues comprise 2 or more of the following residues: Pro1391, Arg1392, Arg1395, Val1398, Arg1399, Gln1402, Lys1406, Lys1423, Gln1424, Leu1427, Lys1430, or Glu1431; converting the atomic coordinates into electrical signals readable by a computer processor to generate a three dimensional model of the Botrocetin-VWF-A1 complex; performing a data processing method, wherein electronic test compounds from the library are superimposed upon Botrocetin within the three dimensional model of the Botrocetin-VWF-A1 complex; and determining which test compound fits within the binding pocket of the three dimensional model of the VWF-A1 protein and best overlays the three-dimensional model generated above. Thus, compounds can be identified that would modulate the binding of VWF-A1 to GPIb-alpha.

The invention also provides for a compound identified by the method described above. In one embodiment, the compound inhibits thrombosis formation or promotes platelet adhesion.

The present invention provides methods for evaluating potential anti-thrombotic reagents in pre-clinical testing using a non-human transgenic animal (for example, non-human animals include, but are not limited to, vertebrates such as ovines, bovines, rodents, non-human primates, porcines, caprines, equines, ruminants, lagomorphs, canines, felines, ayes, and the like). There are three main classes of antithrombotic drugs that can be screened using the transgenic mouse model of the invention: Anticoagulant drugs (such as Heparins; Vitamin K antagonists, which are currently the only anticoagulants that can be administered orally; and direct thrombin inhibitors), Antiplatelet drugs (such as cyclooxygenase inhibitors like aspirin; phosphodiesterase inhibitors like ticlopidine (Ticlid); adenosine diphosphate receptor inhibitors like clopidogrel (Plavix); tirofiban (Aggrastat); adenosine reuptake inhibitors, and inhibitors of integrins on platelets (for example, alpha IIb Beta3) like eptifibatide (Integrilin)), and Thrombolytic or fibrinolytic drugs (such as t-PA (alteplase Activase); reteplase (Retavase); urokinase (Abbokinase); streptokinase (Kabikinase, Streptase); tenectaplase; lanoteplase; and anistreplase (Eminase)).

The invention provides an in vivo model to test the efficacy of potential anti-thrombotic drugs against human platelets prior to FDA approval. To date, in vitro models of thrombosis do not accurately recapitulate the hemodynamic conditions, cell-cell interactions, or cell-protein interactions that occur at sites of vascular injury in a living animal. Thus, anti-thrombotics can be identified and their potential therapeutic effects can be assessed for treatment of abnormal thrombotic events associated with atherothrombotic arterial diseases and venous thrombotic diseases (such as abnormal bleeding and/or abnormal clotting).

Atherothrombotic arterial diseases can include, but is not limited to, coronary artery disease, (for example, acute myocardial infarction, acute coronary syndromes (such as unstable angina pectoris) and stable angina pectoris); mesenteric ischemia, "abdominal angina," and mesenteric infarction; cerebral vascular disease, including acute stroke and transient ischemic attack; mesenteric arterial disease; as well as peripheral arterial disease, including acute peripheral arterial occlusion and intermittent claudication. Anti-thrombotic compounds identified by the pre-clinical testing method of the present invention can also be useful for the treatment of coronary artery disease (which includes, but is not limited to anti-thrombotic therapy during coronary angioplasty, anti-thrombotic therapy during cardiopulmonary bypass, and limiting of platelet activation during ischemia reperfusion) as well as venous thrombotic diseases (which include, but are not limited to deep venous thrombosis and pulmonary thromboembolism). Anti-thrombotic compounds identified by the pre-clinical testing method of the present invention can also be useful in anti-thrombotic therapy for pulmonary hypertension.

The invention provides a method for testing a compound that modulates VWF-A1 binding to GPIb-alpha. The method can entail obtaining or synthesizing a compound identified in the screens previously described above; contacting VWF-A1 with the compound under a condition suitable for GPIb-alpha-VWF-A1 binding; and determining whether the compound can modulate GPIb-alpha-VWF-A1 binding using a diagnostic assay. In one embodiment, contacting can comprise perfusing platelets into a flow chamber at a shear flow rate of at least 100 s$^{-1}$, wherein mutant murine VWF-A1 protein is immobilized on a bottom surface of the chamber. In another embodiment, contacting can comprise perfusing platelets into a transgenic non-human, for example the transgenic mouse described in EXAMPLE 3. In some embodiments, of the invention, contacting first occurs in vitro by way of the flow chamber described above, subsequently followed by in vivo testing of the compound's efficiency to modulate GPIb-alpha binding to VWF-A1 after the compound was determined to have a purported effect in modulating such binding in vitro. Thus, the invention provides a great advantage of being able to test directly compounds that target human platelets in an in vivo system. The transgenic mouse (which, for example, can harbor the 1326R>H mutation in the A1 domain of VWF of SEQ ID NO: 5) displays a bleeding phenotype, thus serves as a model for screening potential anti-thrombotic compounds useful for humans when the mouse is perfused with human platelets. Since the 1326R>H mutation in VWF-A1 in the mouse model (SEQ ID NO: 5) has been shown to support human platelet binding and it corresponds to the His amino acid at the same position in human VWF-A1 (as well as in canines, chimpanzees, rat, porcine, felines, equines, bovine, and the like (Jenkins et al., (1998) *Blood* 91(6): 2032-44)), the test compounds screened using this mouse model (while subject to perfusion with platelets from human, dog, cat, or other relevant organism) will be applicable to multiple species.

After perfusion with human platelets, a test compound (such as a purported anti-thrombotic that would minimize blood clotting or a compound that could promote platelet adhesion) can be administered to the animal subsequent to vessel injury in order to determine whether blood clotting is minimized or if it is enhanced. In one embodiment, the platelets infused are human platelets while in other embodiments the platelets infused are not murine platelets. In some embodiments, the compound can slow the on-rate, and/or increase the off-rate ($k_{off}$) binding kinetics, and/or reduce bond strength of the interaction between VWF-A1 and GPIb-alpha by at least two-fold, thus resulting in a decreased lifetime of the bond(s). Such compounds could reduce thrombosis formation. In other embodiments, the compound can abbreviate off-rate ($k_{off}$) binding kinetics between VWF-A1 and GPIb-alpha by at least two-fold, thus resulting in a prolongation in the lifetime of the bond(s). Such compounds could promote platelet adhesion due to the compound stabilizing an interaction between VWF-A1 and GPIb-alpha. To assess binding efficiency between VWF-A1 and GPIb-alpha, binding kinetics can be determined by measuring translocation velocity, tethering frequency, and bond strength (Fukuda, K., et al., (2005) *Nat. Struct. Mol. Biol.* 12:152-159; Doggett, et al., (2003) *Blood* 102(10): 152-60; Doggett, T. A. et al. (2002) *Biophys. J.* 83, 194-205; Schmidtke and Diamond (2000) *J Cell Bio* 149(3): 719-29; Mody et al., (2005) *Biophys. J.* 88: 1432-43, all of which are incorporated by reference in their entirety).

The compound identified and tested using the methods described above can be an anti-platelet drug. In one embodiment, the anti-platelet drug can be a cyclooxygenase inhibitor, a phosphodiesterase inhibitor, an adenosine diphosphate receptor inhibitor, a PI3K inhibitor, an adenosine reuptake inhibitors, thrombin receptor inhibitor or inhibitor of any intracellular signaling pathway in platelets, an alphaIIb beta3 inhibitor, an alpha2 beta1 inhibitor, a glycoprotein V inhibitor, a glycoprotein VI inhibitor, a PECAM-1 inhibitor or any adhesion molecule and/or activation pathway critical for human platelet function The diagnostic assay used in this method for testing a compound that modulates VWF-A1 binding to GPIb-alpha can assess whether an abnormal thrombotic event occurred in the subject. An abnormal thrombotic event can comprise abnormal bleeding, abnormal clotting, death, or a combination thereof. The assay can comprise dynamic force microscopy, a coagulation factor assay, a platelet adhesion assay, thrombus imaging, a bleeding time assay, aggregometry, review of real-time video of blood flow, a Doppler ultrasound vessel occlusion assay, or a combination thereof.

After perfusion with a purported anti-thrombotic or a compound that could promote platelet adhesion, a labeled agent can subsequently be perfused either into the flow chamber or to the animal. Such an agent would enable the visualization of either the presence or absence of a thrombus. In one embodiment, the labeled agent can comprise one or more of a nanoparticle, a fluorophore, a quantum dot, a microcrystal, a radiolabel, a dye, a gold biolabel, an antibody, or a small molecule ligand. In some embodiments, the agent can target a platelet receptor, a VWF protein, or a portion thereof.

Methods for Assessing Thrombotic Events In Vivo

The invention provides methods for detecting an internal vascular injury site (occult bleeding) in a subject. This could be useful in ER settings or on the battlefield in order to quickly identify sites of internal bleeding. For instance, the method can entail: administering to a subject a targeted molecular imaging agent, wherein the molecule circulates for an effective period of time in order to bind to the injury site within the subject; tracking a deposition of the labeled thrombosis-indicating-molecule in the subject; and identifying the site of a thrombus formation in the subject by imaging the labeled targeted molecular imaging agent. Thus, the deposition of the targeted molecular imaging agent at the internal vascular injury site can be indicative of internal bleeding within a subject. For example, a targeted molecular imaging agent can recognize constituents of thrombi that comprise a lipid, a protein, a cellular molecule, or a combination thereof. In one embodiment, the targeted molecular imaging agent is administered by subcutaneous, intra-muscular, intra-peritoneal, or intravenous injection; infusion; by oral, nasal, or topical delivery; or a combination of the listed routes of administration. In other embodiments, the targeted molecular imaging agent has a $T_{1/2}$ of at least 30 min. In some embodiments, the targeted molecular imaging agent can comprise an antibody, peptide, or Fab fragment directed to a platelet receptor, a VWF protein, or a portion thereof. In particular embodiments, the targeted molecular imaging agent can comprise a VWF-A1 or GPIb-alpha receptor trap. For example, a receptor trap is a decoy receptor that can comprise fusions between two distinct receptor components and the Fc region of an antibody molecule, which can result in the generation of a molecule with an increased affinity over single component reagents. This technology is available from Regeneron (Tarrytown, N.Y.) and is described in Wachsberger et al., (2007) *Int J Radiat Oncol Biol Phys.* 67(5):1526-37; Holash et al., (2002) *Proc Natl Acad Sci USA.* 2002 99(17):11393-8; Davis et al., (1996) *Cell.* 87(7): 1161-9; U.S. Pat. No. 7,087,411; and in United States Publication Applications 2004/0014667, 2005/0175610, 2005/0260203, 2006/0030529, 2006/0058234, which are all hereby incorporated by reference in their entirety.

To aid in the visualization of a site of thrombus formation, the targeted molecular imaging agent can further comprise a label. In one embodiment, the labeled thrombosis-indicating-molecule comprises a nanoparticle, a fluorophore, a quantum dot, a microcrystal, a radiolabel, a dye, a gold biolabel, an antibody, a peptide, a small molecule ligand, or a combination thereof. A fluorophore, for example green fluorescent protein, (such as GFP, RFP, YFP and the like; see Johnson and Johnson, (2007) *ACS Chem Biol.* 2(1):31-8) can be used as a biomarker. A quantum dot is a semiconductor nanocrystal, that can be as small as 2 to 10 nm or can 15-20 nm (for example, Q-dot nanocrystals; also see Kaji et al., (2007) *Anal Sci.* 23(1):21-4). Quantum dot fluorescence can be induced by exposure to ultraviolet light. Both a fluorescent protein and a quantum dot can be obtained commercially (for example, Molecular Probes-Invitrogen, Carlsbad, Calif. or Evident Technologies, Troy N.Y.). A fluorophore can also be generated in the laboratory according to molecular biology methods practiced in the art. A radiolabel is a radioactive isotope that can be used as a tracer. Non-limiting examples of radiolabels include: Technetium-99m, Iodine-123 and 131, Thallium-201, Gallium-67, Fluorine-18, -19, Indium-111, Xenon-133, and Krypton-81m. Radiolabels can be obtained commercially, for example, from SRI International (Menlo Park, Calif.). In one embodiment, the nanoparticle can comprise a perfluorocarbon (PFC). Non-limiting examples of perfluorocarbons include perfluorobutane, perfluorohexane, perfluorooctane, perfluorodecalin, perfluoromethyldecalin, and perfluoroperhydrophenanthrene. These can be synthesized according to the method described in EXAMPLE 5 or according to Partlow et al. (*FASEB J* (2007) Feb. 6 on-line publication, fj.06-6505com). The perfluorocarbon molecules can also be obtained commercially (F2 Chemicals Ltd.; Lancashire, UK). In another embodiment, the PFC nanoparticle can be coupled to a platelet receptor antibody (such as platelet receptor alpha-IIb beta3). In some embodiments, imaging can comprise a PET scan, a CT scan, an MRI, an IR scan, an ultrasound, nuclear imaging, or a combination thereof.

Since the usefulness of the method pertains to the swiftness in identifying sites of internal bleeding (for example in an ER setting or on the battlefield), the subject can be further administered a compound aid in the cessation of such bleeding. In one embodiment, the subject is further administered a thrombotic compound (for example, a compound identified in the screens described above or a compound comprising a structure depicted in Table 8). In some embodiments, the compound can abbreviate off-rate ($k_{off}$) binding kinetics, and/or slow the on-rate, and/or reduce the bond strength between VWF-A1 and GPIb-alpha by at least two-fold.

The invention also provides a method to test contrast agents for imaging of human platelets at sites of thrombosis. For instance, one could test the ability of nanoparticle contrast agents targeted to human platelets to identify areas of thrombosis or occult bleeding. In some embodiments, the prevention or reduction of thrombus formation at site of injury upon administration of a compound can be visually examined via tracking the localization of labeled platelets (such as with high resolution in vivo microscopy or MRI). In further embodiments, the platelets can be labeled with a nanoparticle, fluorophore, quantum dot, microcrystal, radiolabel, dye, or gold biolabel. The prevention or reduction of thrombus formation also can be readily determined by methods known to one skilled in the art, which include but are not limited to aggregometry, review of real-time video of blood flow in the animal, and determination of vessel occlusion, as well as by the examples provided below.

Additionally, the transgenic mouse's bleeding phenotype can be exploited to screen potential prothrombotic compounds, in addition to anti-thrombotics discussed above. A test compound (such as an alleged thrombotic that would induce and/or stimulate blood clotting) can be administered to the animal perfused with human platelets subsequent to vessel injury in order to determine whether blood clotting occurs. In some embodiments, the induction or stimulation of thrombus formation at site of injury upon administration of a compound can be visually examined via tracking the localization of labeled platelets (such as with high resolution in vivo microscopy or MRI). In further embodiments, the platelets can be labeled with a nanoparticle, fluorophore, quantum dot, microcrystal, radiolabel, dye, or gold biolabel. The prevention or reduction of thrombus formation also can be readily determined by methods known to one skilled in the art, which include but are not limited to aggregometry, ex-vivo flow chamber studies, review of real-time video of blood flow in the animal, and determination of vessel occlusion.

One of ordinary skill in the art can assess that the VWF-A1 mutants of this invention have the required properties of competitive binding to the GPIb platelet receptor in a manner that competes with the native VWF. Suitable assays are set forth in detail in the examples below, including ristocetin-induced platelet aggregation, platelet aggregation induced by ADP, thrombin, collagen, and platelet adhesion in a flow model.

In one embodiment of the invention, the non-human transgenic animal that expresses a modified A1 domain of the VWF sequence (for example, an amino acid residue substitution at a position involved with binding to GPIb alpha, such as, but not limited to, positions 1263, 1269, 1274, 1287, 1302, 1308, 1313, 1314, 1326, 1329, 1330, 1333, 1344, 1347, 1350, 1370, 1379, 1381, 1385 1391, 1394, 1397, 1421, 1439, 1442, 1449, 1466, 1469, 1472, 1473, 1475, 1479) can be used to validate new devices aimed at determining the effectiveness of antithrombotics in humans.

The non-human transgenic animal may also be used for determining the effectiveness of gene therapy (for example, assessing whether VWF-A1 protein targeting and protein expression was successful). Gene therapy refers to the insertion of genes into an individual's cells and tissues to treat a disease. For example, in a hereditary disease, a defective mutant allele is replaced with a functional one. The efficiency of VWF-A1 gene transfer by nonviral methodologies (i.e. lipofection) or viral methodologies (such as adenovirus infection described in U.S. Pat. No. 6,927,278 or United States Application Publication No. 2005/0169899) can be assessed using the non-transgenic mouse model described above via examining whether replacement of a portion or the whole VWF gene in a subject (such as a mutant VWF mouse of the invention) affects clot formation in vivo. Results obtained from such a mouse model can then be correlated with the likely effect to be observed in human subjects. For gene therapy reviews, see Zuckerbraun et al., (2002) *Arch Surg.* 137(7):854-61; Melo et al., (2004) *Arterioscler Thromb Vasc Biol.* 24(10):1761-74; and Dulak et al., (2006) *Cell Biochem Biophys.* 44(1):31-42, which are incorporated by reference in their entirety.

The invention provides a method for testing the efficiency of gene therapy in regulating thrombus formation in a subject. It also provides a method to test gene therapies directed at correcting genetic mutations associated with von Willebrand disease. The method can comprise the following steps: introducing a vector into the non-human transgenic animal of the invention described above, wherein the vector comprises a nucleic acid encoding a platelet receptor polypeptide, a platelet ligand polypeptide, or a VWF polypeptide, or a portion thereof; allowing sufficient time for expression of the polypeptide; perfusing platelets into the non-human transgenic animal that has one or more mutations in the VWF-A1 domain as previously described under a condition suitable for GPIb-alpha-VWF-A1 protein binding; and identifying an occurrence of a thrombotic event in the animal. For example, the vector introduced into the subject can be an adenovirus or DNA vector described in earlier sections utilizing methods discussed previously (see also Zuckerbraun et al., (2002) *Arch Surg.* 137(7):854-61; Melo et al., (2004) *Arterioscler Thromb Vasc Biol.* 24(10):1761-74; and Dulak et al., (2006) *Cell Biochem Biophys.* 44(1): 31-42). For example, the non-human animal that has one or more mutations in the VWF-A1 domain can be the murine model homozygous for the VWF-A1$^{1326R>H}$ mutation.

In one embodiment of the invention, the platelets can be human platelets. In particular, the platelets are not murine platelets. In some embodiments, the thrombotic event comprises blood clotting, abnormal bleeding, abnormal clotting, death, or a combination thereof. Such an event can be identified using dynamic force microscopy, a coagulation factor assay, a platelet adhesion assay, thrombus imaging, a bleeding time assay, aggregometry, review of real-time video of blood flow, a Doppler ultrasound vessel occlusion assay, or a combination of the techniques previously described. In a further embodiment, perfusing platelets can be followed by a perfusion of a labeled agent. Non-limiting examples of a labeled agent comprises one or more of a nanoparticle, a fluorophore, a quantum dot, a microcrystal, a radiolabel, a dye, a gold biolabel, an antibody, or a small molecule ligand. In some embodiments, the agent targets a platelet receptor, a VWF protein, or a portion thereof.

The invention also provides a method to correlate results obtained with an in vitro assay designed to measure the effects of antithrombotics or biomarkers of platelet activation in patients. For example, a biomarker is an indicator of a particular disease state or a particular state of an organism, such as when the subject experiences vascular vessel wall injury. Upon injury to the vessel wall and subsequent damage to the endothelial lining, exposure of the subendothelial matrix to blood flow results in deposition of platelets at the site of injury via binding to the collagen with the surface collagen-specific glycoprotein Ia/IIa receptor. This adhesion is strengthened further by the large multimeric circulating protein VWF, which forms links between the platelet glycoprotein Ib/IX/V and collagen fibrils. The platelets are then activated and release the contents of their granules into the plasma, in turn activating other platelets. For example, Glycoprotein VI (GP6) is a 58-kD platelet membrane glycoprotein that plays a crucial role in the collagen-induced activation and aggregation of platelets. The shedding of GP6 can act as a marker representing that a person is at risk of myocardial infarction. In one embodiment, platelets obtained from a subject determined to have an elevated biomarker level (for example, GP6) can be infused into the non-human transgenic animal described above according to previously described methods, wherein the occurrence of a thrombotic event can be evaluated. In another embodiment, platelets obtained from a subject undergoing an anti-thrombotic treatment can be infused into the non-human transgenic animal described above according to previously described methods, wherein the occurrence of a thrombotic event can then be evaluated.

Method of Screening and Treating Subjects with Abnormalities of Platelet Function The invention provides methods for treating subject with platelet function abnormalities, such as Von Willebrand disease (VWD), Bernard-Soulier syndrome, May-Hegglin anomaly, Chediak Higashi syndrome, and the like. In addition, the invention also provides methods for detecting abnormal platelet function or morphology in a subject.

VWD is a common hereditary coagulation abnormality that arises from a quantitative or qualitative deficiency of VWF). VWD affects humans, in addition to dogs and cats. There are three types of VWD: type 1, type 2, and type 3. Type 1 VWD is a quantitative defect, wherein decreased levels of VWF are detected but subjects may not have clearly impaired clotting, Type 2 VWD is a qualitative defect, wherein subjects have normal VWF levels but VWF multimers are structurally abnormal, or subgroups of large or small multimers are absent. Four subtypes exist: Type 2A, Type 2B, Type 2M, and Type 2N. Type 3 is rare and the most severe form of VWD (homozygous for the defective gene). (Braunwald et al., *Harrison's Principle of Internal Medicine*, 15$^{th}$ ed., (Chapter 116) 2001, McGraw Hill, Columbus, Ohio).

Bernard-Soulier Syndrome is a rare disorder caused by a deficiency of the surface platelet receptor GPIb alpha. As a result, platelets fail to stick and clump together at the site of the injury. Functional abnormalities have also been observed in some hereditary platelet disorders wherein the platelets are of abnormal size or shape, such as in May-Hegglin Anomaly and Chediak Higashi syndrome. (Braunwald et al., *Harrison's Principle of Internal Medicine*, 15$^{th}$ ed., (Chapter 116) 2001, McGraw Hill, Columbus, Ohio).

According to the invention, abnormal platelet function or morphology can be screened in a subject. The method can comprise the following steps: affixing a VWF-A1 molecule to a bottom surface of a flow chamber, or chip (such as a BIAcore chip), wherein the VWF-A1 molecule comprises at least one mutation at a position selected from the group consisting of 1263>S, 1269>D, 1274>R, 1287>R, 1302>D, 1308>R, 1313R>W, 1314>V, 1326>H, 1329>1, 1330>G, 1333>D, 1344>A, 1347>V, 1350>A, 1370>S, 1379>R, 1381>A, 1385>M 1391>Q, 1394>S, 1397>F, 1421>N, 1439>V, 1442>S, 1449>Q, 1466>P, 1469>L, 1472>H, 1473>M, 1475>Q, 1479>G, and any combination thereof, where the position corresponds to an amino acid position of human von Willebrand Factor A1 protein shown in SEQ ID NO: 6; perfusing a volume of whole blood or plasma over the surface-immobilized VWF-A1 molecule complexed to the murine mutant VWF-A1 protein in the flow chamber at a shear flow rate of at least 100 s$^{-1}$; perfusing a targeted molecular imaging agent into the flow chamber at a shear flow rate of at least 100 s$^{-1}$; determining whether platelets bind to the surface-immobilized-mutant-murine-VWF-A1 using a diagnostic assay; and comparing diagnostic assay results to a standard control, wherein the standard control sample was subjected to the steps described above. For example, the VWF molecule can be an antibody, a peptide, or a Fab fragment directed to a VWF polypeptide or a portion thereof. In one embodiment, the molecule can comprise a native or mutant VWF-A1 molecule, a purified native VWF or a mutant plasma VWF.

In one embodiment, whole blood or plasma sample can be perfused into the chamber or onto the chip, wherein the sample is obtained from the subject. For example, approximately 50 µl of whole blood can be perfused according to the method, or about 100 µl to about 150 µl of plasma can be perfused. As a standard control, the steps of the method described above can be performed using lyophilized non-self platelets, and can be subsequently compared to results obtained using the subjects' platelets. Here, the subject can be a human, a canine, a feline, a murine, a porcine, an equine, or a bovine.

In one embodiment, the targeted molecular imaging agent can comprise a nanoparticle, a fluorophore, a quantum dot, a microcrystal, a radiolabel, a dye, a gold biolabel, an antibody, a peptide, a small molecule ligand, or a combination thereof. In another embodiment, the targeted molecular imaging agent can bind to a platelet receptor, a platelet ligand, or any region of a VWF protein or a portion thereof. In a further embodiment, the targeted molecular imaging agent can comprise horseradish peroxidase (HRP) coupled to an antibody directed at VWF-A1. Following binding to VWF-A1, a reaction with diaminobenzadine (DAB) can be performed where DAB is reduced by HRP to produce a brown precipitate at the site of binding. This technique allows for enzymatic, colorimetric detection of binding that can be visualized by transmitted light microscopy. For example, if the antibody is directed at a platelet receptor, and colorimetric detection represents whether the antibody bound to the platelet-VWF-A1 complex, the absence of color would denote the lack of a complex formation, thus suggesting that platelets were unable to bind to VWF-A1. The lack of platelet binding could suggest functional defects in the subject's platelets. In one embodiment, platelets bound to VWF-A1 are less than about 500 cells/mm$^2$.

The normal platelet morphology is discoid with some spherical shaping. In one embodiment of the invention, the platelets obtained from the subject and that are subsequently screened are substantially spherical in shape. To further analyze platelet morphology, gross platelet histology can be assessed via light microscopy or electron microscopy. In another embodiment, platelets having an abnormal morphology are greater than about 2 μm in diameter. (Ross M H, *Histology: A text and atlas*, 3$^{rd}$ edition, Williams and Wilkins, 1995: Chapter 9). Various assays can be used to assess whether platelet function is normal, such as a platelet adhesion assay, fluorescence imaging, a chromogenic indication, microscopy morphology analysis, or those listed in *Harrison's Principle of Internal Medicine*, 15$^{th}$ ed., ((Chapter 116) 2001, McGraw Hill, Columbus, Ohio), which are hereby incorporated by reference.

The invention also provides a method of treating abnormalities in clotting due to a defect in the interaction between GPIb alpha and the A1 domain of VWF as occurs in certain types of von Willebrand Disease (VWD), where the method entails administering to the subject an effective amount of a compound that promotes platelet adhesion in the subject, wherein the compound abbreviates off-rate ($k_{off}$) and/or enhances the on-rate binding kinetics, and or strengthens the bond between between VWF-A1 and GPIb-alpha by at least two-fold. Thus, administration of the compound increases blood coagulation in the subject, for example, subjects diagnosed with VWD. In one embodiment, VWD is Type 1 or Type 2. In another embodiment, the compound is one identified by the screening methods described above. Coagulation can be measured by a coagulation factor assay, an ex-vivo flow chamber assay, a platelet adhesion [see EXAMPLES section] or those assays listed in *Harrison's Principle of Internal Medicine*, 15$^{th}$ ed., ((Chapter 116) 2001, McGraw Hill, Columbus, Ohio).

Therapeutic Formulations

Therapeutic compounds according to this invention are formulated in pharmaceutical compositions containing the compound and a pharmaceutically acceptable carrier. The pharmaceutical composition may contain other components so long as the other components do not reduce the effectiveness of the compound according to this invention so much that the therapy is negated. Some other components may have independent therapeutic effects. Pharmaceutically acceptable carriers are well known, and one skilled in the pharmaceutical art can easily select carriers suitable for particular routes of administration (see, e.g., *Remington's Pharmaceutical Sciences*, Mack Publishing Co., Easton, Pa., 1985).

The pharmaceutical compositions containing any of the compounds of this invention may be administered by a topical, oral, rectal, parenteral (such as subcutaneously, intramuscularly, intravenously, intraperitoneally, intrapleurally, intravesicularly or intrathecally), or nasal route, as compelled by the choice of drug and disease. One skilled in the pharmaceutical art can discern the optimal route of administration.

These compounds may also be applied topically or locally, in liposomes, solutions, gels, ointments, biodegradable microcapsules, or impregnated bandages. Compositions or dosage forms for topical application may include suspensions, dusting powder, solutions, lotions, suppositories, sprays, aerosols, biodegradable polymers, ointments, creams, gels, impregnated bandages and dressings, liposomes, and artificial skin.

Pharmaceutical carriers utilized by one skilled in the art which make up the foregoing compositions include petrolatum, polyethylene glycol, alginates, carboxymethylcellulose, methylcellulose, agarose, pectins, gelatins, collagen, vegetable oils, phospholipids, stearic acid, stearyl alcohol, polysorbate, mineral oils, polylactate, polyglycolate, polyanhydrides, polyvinylpyrrolidone, and the like.

Therapy dose and duration will depend on a variety of factors, such as the disease type, patient age, therapeutic index of the drugs, patient weight, and tolerance of toxicity. Initial dose levels will be selected based on their ability to achieve ambient concentrations shown to be effective in in vitro models (for example, a dose level used to determine therapeutic index), in vivo models, and in clinical trials. The skilled clinician using standard pharmacological approaches can determine the dose of a particular drug and duration of therapy for a particular patient in view of the above stated factors. The response to treatment can be monitored by analysis of body fluid or blood levels of the compound and the skilled clinician will adjust the dose and duration of therapy based on the response to treatment revealed by these measurements.

EXAMPLES

A number of Examples are provided below to facilitate a more complete understanding of the present invention. However, the scope of the invention is not limited to specific embodiments disclosed in these Examples, which are for purposes of illustration only.

Biophysical and molecular approaches are essential for understanding the structure:function relationship between a receptor and its ligand. Thus, the ability to study such interactions in an appropriate physiological and/or pathological setting is desirable. To do so, one requires an animal model that is amenable to genetic manipulation and has receptor-ligand interactions that closely resemble those found in humans. Thrombosis models in hamsters and guinea pigs have proven useful in pharmacological studies, but a mouse model would prove to be more beneficial based on the ability to insert or delete genes of interest, accessibility of tissues for study, and cost and ease of handling (49, 50). Regarding GPIb alpha-VWF interactions, two groups have significantly advanced the understanding of the importance of these interactions in mediating thrombosis by generating mice deficient in these proteins (51, 52). Yet, no information regarding the role of the biophysical properties of the GPIb alpha-VWF-A1 in regulating the processes of thrombosis and hemostasis will be obtained. Thus, the next logical approach is to generate animals with mutations within the VWF-A1 domain that change its kinetic properties in a desired manner and to correlate these biophysical alterations with the ability of these mice to maintain adequate hemostasis and to develop thrombi in response to vascular injury. Such information will be useful in designing therapies that reduce or enhance these processes.

Example 1

VWF Characterization

VWF Microsphere Studies

The association and dissociation kinetics of the GPIb alpha-VWF-A1 bond and the impact of fluid shear and particle size on these parameters can be determined by measuring the frequency and duration of transient adhesive events, known as transient tethers, that represent the smallest unit of interaction observable in a parallel-platelet flow chamber.

Production of Recombinant VWF-A1 Protein and Coating of Microspheres.

The generation of recombinant VWF-A1 protein (residues 1238 to 1472 of the mature, recombinant VWF) and its subsequent coupling to microspheres is performed as previously described (Doggett, T. A. et al. (2002) *Biophys. J.* 83, 194-205). Proper size, purity, and disulfide bonding of all proteins is assessed by Coomasie-blue staining of SDS-PAGE gels run under reducing and non-reducing conditions. Mass spectrometry is also employed to evaluate size and disulfide bonding pattern.

The resulting recombinant proteins are bound to polystyrene microspheres (goat anti-mouse IgG (FC); Bangs Lab, Inc., Fishers, Ind.) that were initially coated with a saturating concentration of mouse anti-6-HIS antibody as previously described in our publications. We have found this coating method to be superior to direct covalent coupling of the VWF-A1 to the beads as it prevents significant loss in protein function. Estimation of the amount of VWF-A1 bound to the beads is determined using a monoclonal antibody generated in our lab against the human and murine A1 domains, mAb AMD-1 and mAb AMD-2, respectively, and a calibrated microbead system (Quantum Simply Cellular; Flow Cytometry Standards Corp., San Juan, P.R.) following the manufacturer's instructions.

Laminar Flow Assays.

Figure 7A:
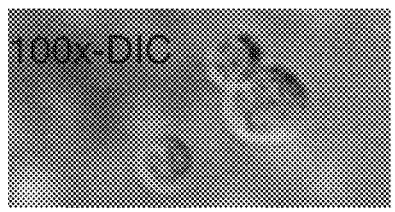
FIGS. 7A and 7B depict microscope images wherein the use of platelets in lieu of recombinant proteins or transfected cells as the immobilized substrate enables evaluation of GPIb alpha in its native form (i.e. correct orientation and proper post-translational modification). Platelet coverage of <10% can be bound in this manner and can remain relatively unactivated for up to 30 min as evident by morphology on light microscopic examination (FIG. 7A) and lack of expression of P-selectin by fluorescence microscopy (FIG. 7B).
Figure 7B:

In flow assays involving protein-coated microspheres, human or murine platelets purified by gel filtration are incubated with 10 mM sodium azide (NaN$_3$), 50 ng/ml prostaglandin E$_1$, and 10 µm indomethacin (Sigma Immunochemicals, St. Louis, Mo.) to reduce the possibility of activation and potential alterations in expression and/or distribution of GPIb alpha on their surface. Platelets are subsequently allowed to settle in stasis on Fab fragments of monoclonal antibodies that recognize either human (i.e., mAb 7E3) or murine (i.e., mAb NAD-1) alpha IIb/β$_3$ in order to form a reactive substrate. The use of platelets in lieu of recombinant proteins or transfected cells as the immobilized substrate enables evaluation of GPIb alpha in its native form (i.e. correct orientation and proper post-translational modification). Platelet coverage of <10% will be bound in this manner can remain relatively unactivated for up to 30 min as evident by morphology on light microscopic examination (FIG. 7A) and lack of expression of P-selectin by fluorescence microscopy (FIG. 7B).

Figure 8A:
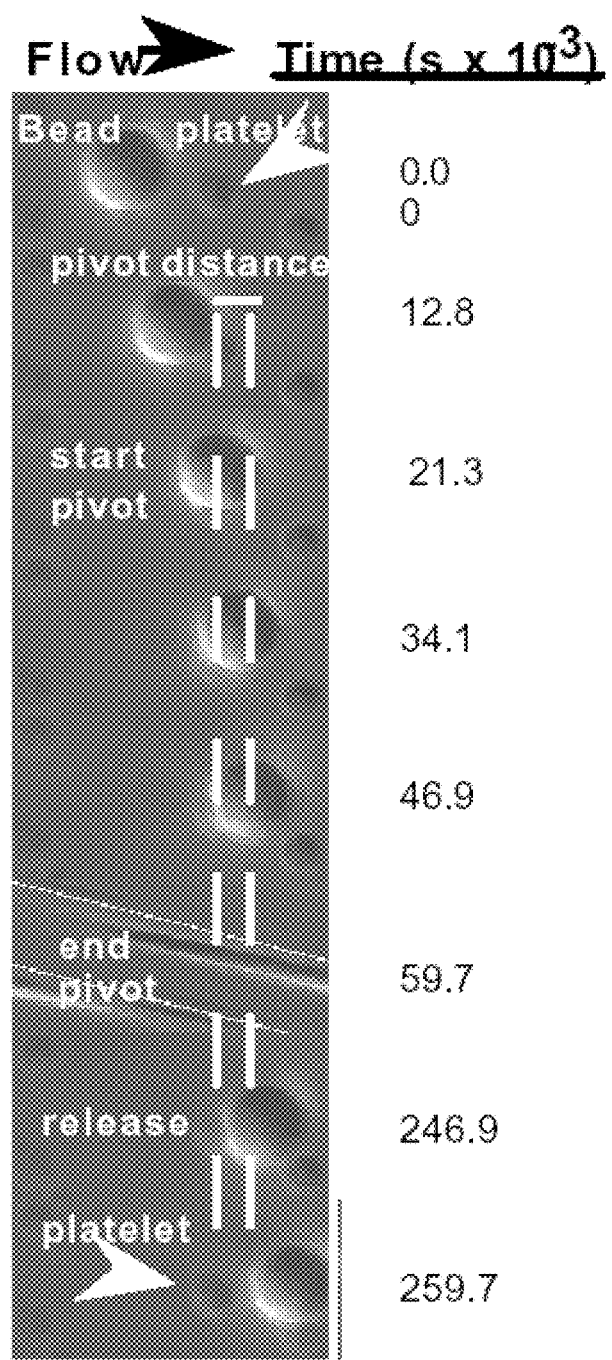
FIGS. 8A through 8D represent quantitations of bead-platelet interactions under flow.
Figure 8B:
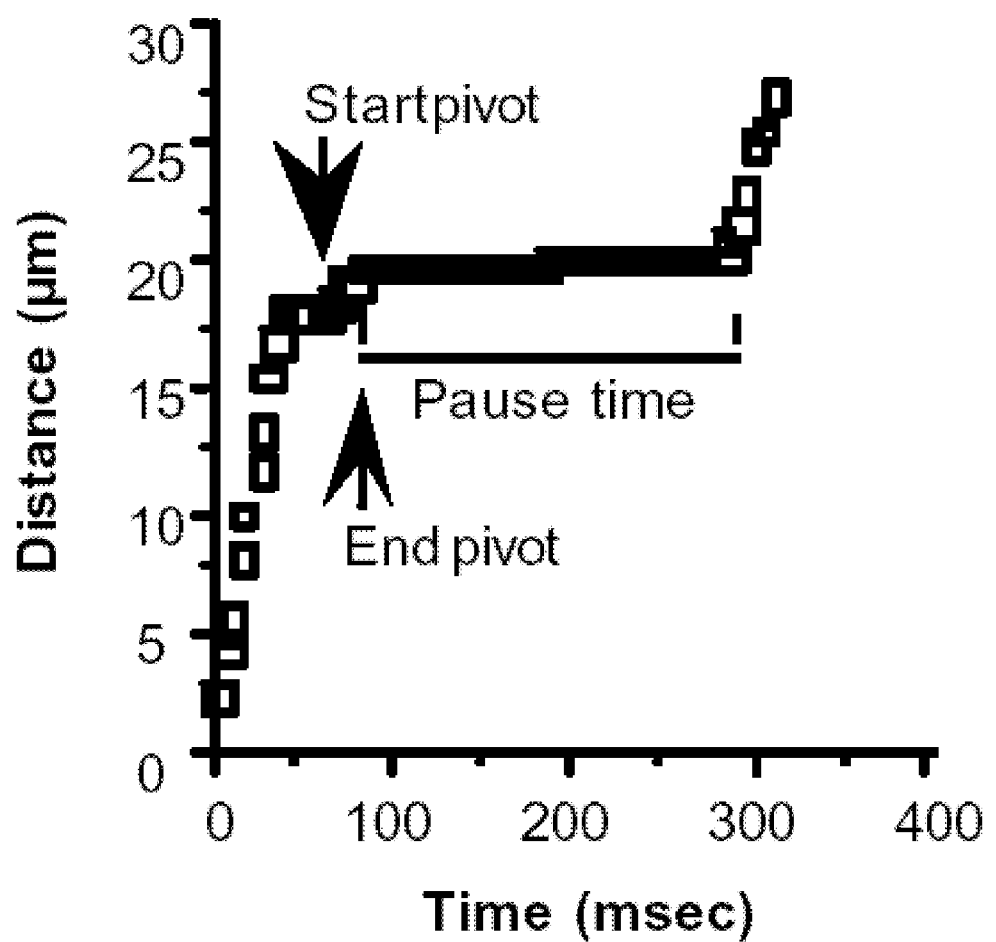
Figure 8D:
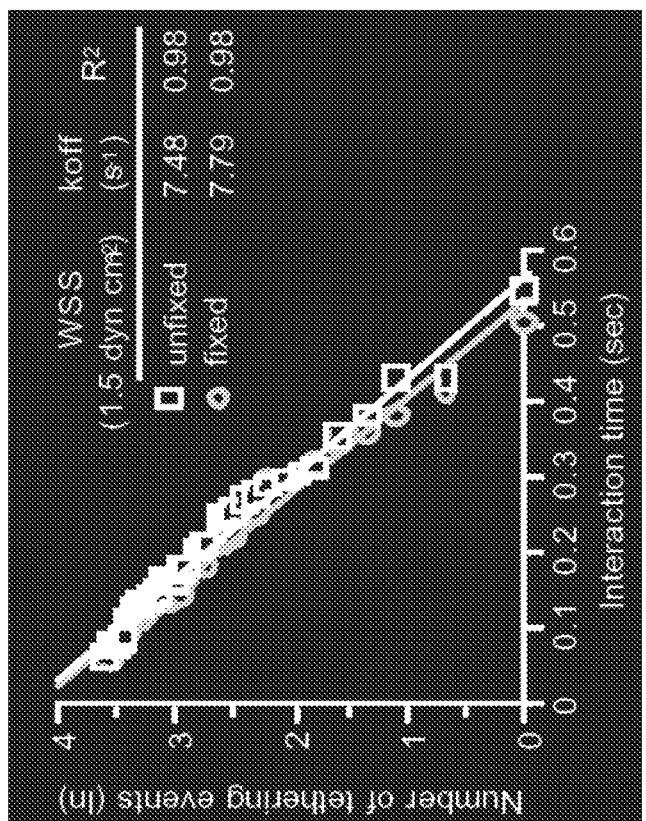
Figure 8C:
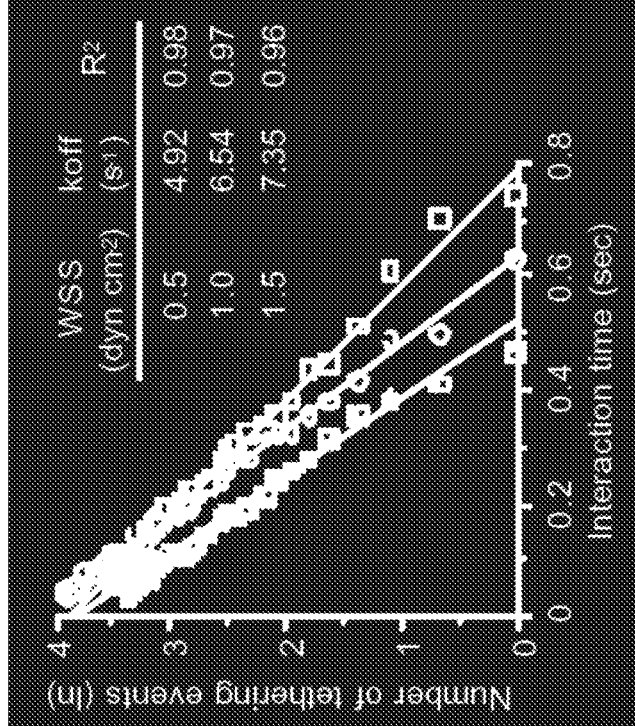

To reduce the possibility of multiple bond formation that would result in a prolongation in interaction times between the beads and immobilized platelets, the lowest site densities of VWF-A1 capable of supporting these brief interactions is used, a value we found to correspond to ~30 molecules µm$^2$. At this site density, we have shown that the formation of transient tethers between this receptor-ligand pair has distribution of bond lifetimes that obey first order dissociation kinetics. The duration of these interactions are measured by recording images from a Nikon X60 DIC objective (oil immersion) viewed at a frame rate of 235 fps (Speed Vision Technologies, San Diego, Calif.) and subjected to wall shear stresses (WSS) ranging from 0.5 to 3.0 dyn cm$^{-2}$. The cellular off-rates are determined by plotting the natural log of the number of VWF-A1 coated microspheres that interacted as a function of time after the initiation of tethering, the slope of the line=$-k_{off}$ (s$^{-1}$) which is the inverse of the bond lifetime. The force acting on the tether bond was calculated from force balance equations as stated above and $k_{off}$ plotted as a function of these forces. An example of the measurement of the duration of a transient tether and estimation of off-rates as a function of WSS is demonstrated below for WT human VWF-A1 (FIGS. 8A-8C). To demonstrate that our method for surface immobilization of platelets does not result in an alteration in the kinetics of the GPIb alpha-VWF-A1 tether bond, resting platelets were first fixed in paraformaldehyde prior to immobilization. As these platelets cannot activate, the kinetics should be reflective of GPIb alpha in the resting state. Indeed, analysis of the $k_{off}$ for this interaction using fixed platelets was identical to that observed for platelets treated with metabolic inhibitors (FIG. 8D).

The Structure-Function of Murine VWF-A1

To determine the structure and function of murine VWF-A1, its adhesive interactions with murine and human GPIb alpha, and whether the kinetics of this interaction mimic those reported in studies of its human counterpart, the domain was initially cloned by PCR from purified mouse genomic DNA. For the purpose of generating a mouse with a genetically modified VWF-A1 domain, a100-kb P1 clone was obtained from screening a 129/Svj DNA genomic library (Genomic Systems, St. Louis, Mo.) by polymerase chain reaction (PCR) using primers directed against a 200 bp region of exon 28. Sequence analysis of flanking regions (10 kb in size) as well as the A1 domain itself was performed and compared to those obtained from a BLAST search to confirm the fidelity of the clone. The deduced single-letter amino acid sequence of mouse VWF-A1 domain (M VWF) is shown compared to its human counterpart (H VWF) and encompasses amino acids 1260 to 1480 (FIG. 9). The locations of cysteines forming the loop structure are numbered (1272 and 1458) and differences in residues are highlighted in red. Conversion of the arginine (R) in the mouse A1 domain to histidine (H) as found in its human counterpart (blue χ) has been shown to enable mouse VWF to bind human platelets and simultaneously reduce the binding of mouse platelets. Locations of some, but not all, mutations known to affect human VWF-A1 function are also depicted.

Figures 10A, 10B:
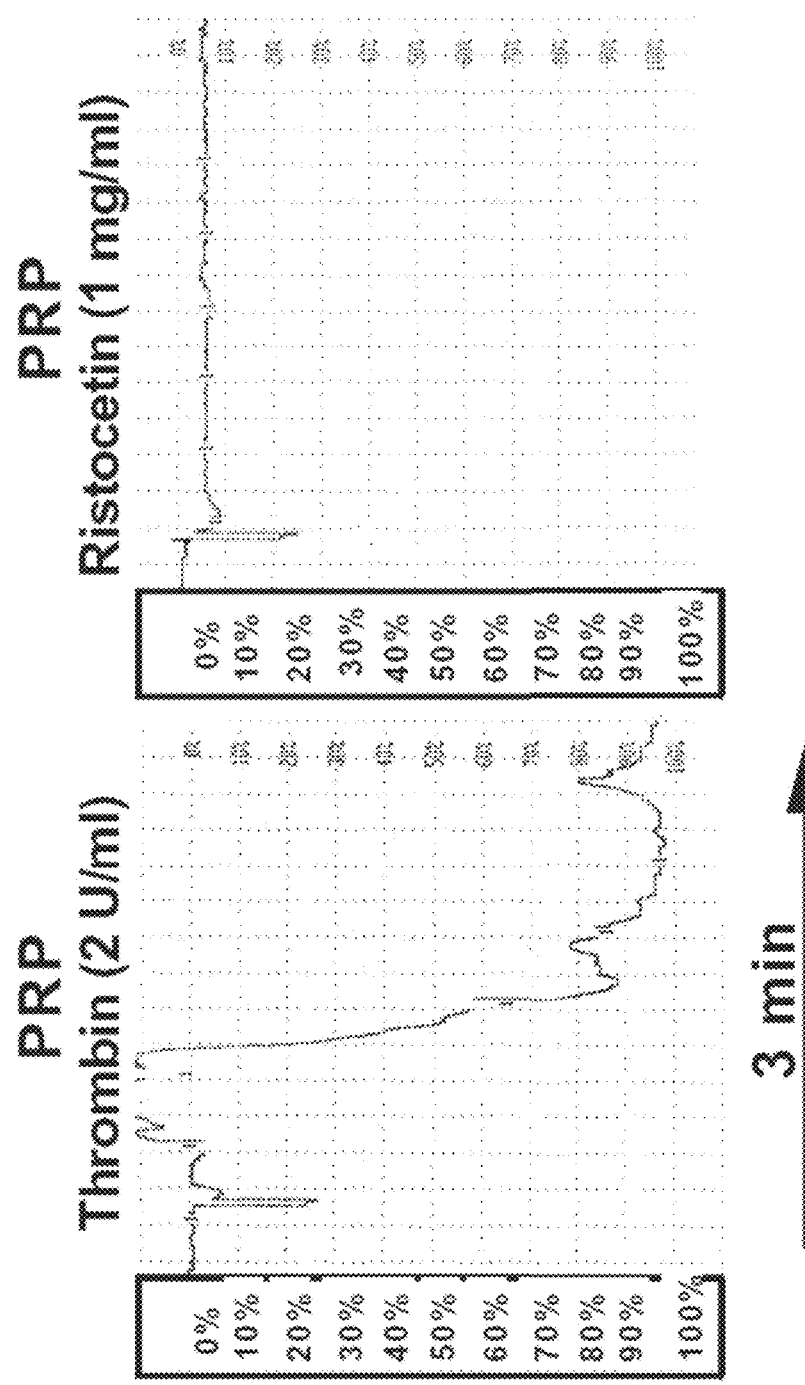

Although the amino acid sequence homology is ~85%, and preliminary studies suggest that functional differences do exist between human and murine VWF-A1 domains. In a Ristocetin-induced platelet aggregation assays, platelet GPIb alpha binding to wild type human VWF or mouse VWF was analyzed in the absence or presence of ristocetin as described by Inbal, et al. (1993, *Thromb. Haemost.*, 70:1058-1062). In this method, platelet rich plasma (PRP) is placed in a clear cuvette containing a stir bar and inserted into the aggregometer. Platelet aggregation is induced by the addition of ristocetin. In this ristocetin-induced platelet aggregation assay (RIPA), we observe that concentrations of this modulator that are known to cause agglutination of human platelets (~1.0 mg/ml) had no such effect using murine PRP (FIG. 10B). In fact, only at concentrations of ≥2.5 mg/ml was there any evidence of murine platelet aggregation observed (~30%, FIG. 10C). In comparison, incubation of murine PRP with thrombin resulted in >90% platelet aggregation (FIG. 10A).

Figure 11A:
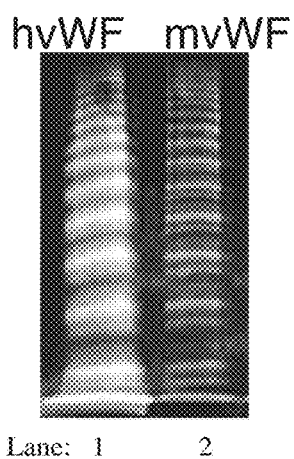
FIGS. 11A and 11B depict a multimer gel analysis of purified VWF from human (lane 1, FIG. 11A) and mouse (lane 2, FIG. 11A) plasma. The ability of human and mouse VWF to mediate platelet adhesion in flow was determined in order to evaluate platelet interactions between human and murine VWF with GPIb alpha, as depicted in the bar graph of FIG. 11B. Surface-immobilized murine VWF supports adhesion of syngeneic platelets (1×10$^8$/ml) at a shear rate encountered in the arterial circulation (1600 s$^{-1}$) as observed for the human plasma protein (FIG. 11B). In contrast, murine VWF did not support significant interactions with human platelets and vice versa.
Figure 11B:
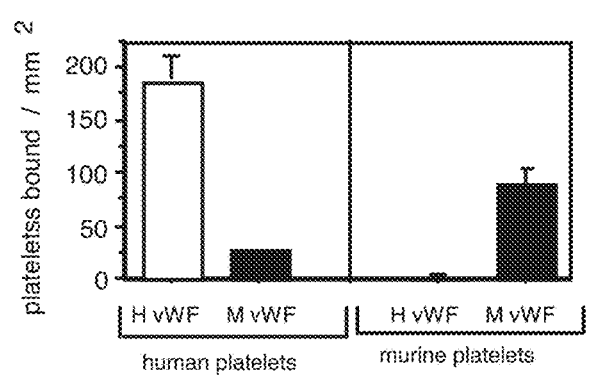

To better evaluate the above interactions and to compare functional relationships between human and murine VWF with GPIb alpha, VWF from human and mouse plasma was purified and its ability to mediate platelet adhesion in flow was determined. Multimer gel analysis did not reveal any differences between the two species, especially with regard to high molecular weight components (FIG. 11A). Moreover, surface-immobilized murine VWF could support adhesion of syngeneic platelets ($1 \times 10^8$/ml) at a shear rate encountered in the arterial circulation (1600 s$^{-1}$) as observed for the human plasma protein (FIG. 11B). In contrast, murine VWF did not support significant interactions with human platelets and vice versa. These results suggest that functional and possibly significant structural differences do exist between the A1 domains of murine and human VWF as primary attachment of platelets at this wall shear rate is dependent on its function. Thus, generation of a recombinant murine VWF-A1 domain is required to fully evaluate similarities and/or differences from its human counterpart.

Recombinant protein was expressed using a bacterial expression vector under the control of an inducible promoter (pQE9, Qiagen). Insertion of the murine fragment containing the majority of the VWF A1-domain (encoding for amino acids 1233 to 1471) into pQE9 produces an amino-terminal fusion protein containing 10 amino acids (including 6× histidine) contributed by the vector. After induction, inclusion bodies were harvested, washed, and solubilized according to previously published methods (32). The solubilized protein was diluted 40-fold in 50 mM Tris-HCl, 500 mM NaCl, 0.2% Tween 20, pH 7.8 and initially purified over a Ni$^{2+}$-chelated Sepharose (Pharmacia) column. To increase the yield of functional protein, the material purified from the Ni$^{2+}$ column was absorbed to and eluted from a Heparin-Sepharose column (Amersham Pharmacia Biotech).

Figure 12:
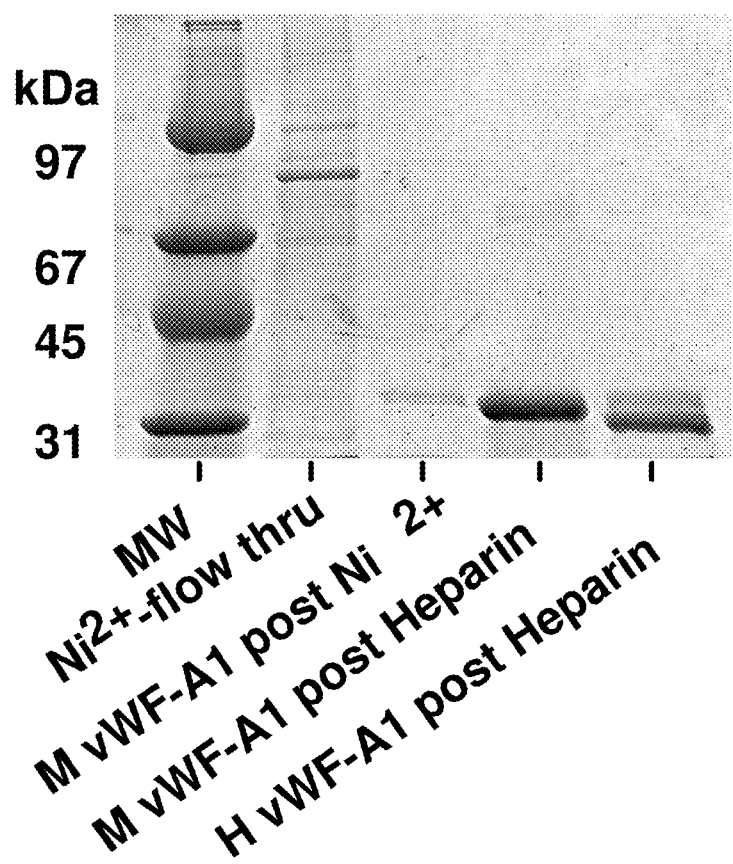
FIG. 12 is an image of a gel of mouse and human VWF-A1 highly purified protein, which was dialyzed against 25 mM Tris-HCl, 150 mM NaCl, 0.05% Tween 20, pH 7.8. SDS-PAGE analysis revealed a prominent protein band of ~34,000 Da for mouse VWF-A1 under non-reducing conditions.

The highly purified protein was dialyzed against 25 mM Tris-HCl, 150 mM NaCl, 0.05% Tween 20, pH 7.8. SDS-PAGE analysis revealed a prominent protein band of ~34,000 Da under non-reducing conditions (FIG. 12). The overall yield of protein obtained using the purification methods described above is ~2 mg/l of bacterial cells.

The protein was subsequently used in a series of in vitro flow chamber assays to assess function. Washed human or murine platelets ($5 \times 10^7$/ml) were infused through a parallel plate flow chamber containing glass cover slips coated with either human VWF-A1 or mouse VWF-A1 protein (100 µg/ml final concentration) at a shear rate of 800 s$^{-1}$. After 5 min of continuous flow, adherent platelets were quantified.

Figure 13B:
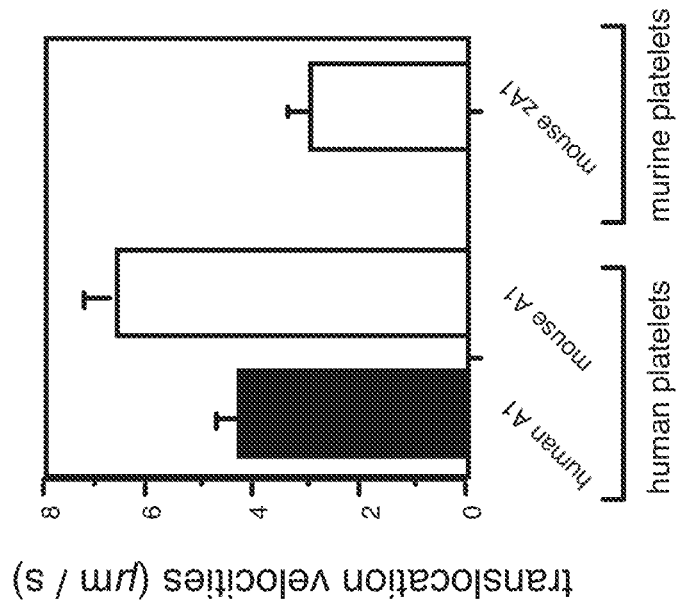
FIGS. 13A and 13B depict bar graphs of a series of in vitro flow chamber assays performed to assess platelet adhesion, wherein human or murine platelets (5×10$^7$/ml) were infused through a parallel plate flow chamber containing glass cover slips coated with either human (H) VWF-A1 or murine (M) VWF-A1 protein (100 μg/ml final concentration) at a shear rate of 800 s$^{-1}$. M VWF-A1 protein supported platelet adhesion as efficiently as its human counterpart under physiological flow conditions (FIG. 13A). The translocation of mouse platelets occurred to a similar degree as its human counterpart under physiological flow conditions (FIG. 13B). However, human platelets had a reduced capacity to interact with M VWF-A1 protein and mouse platelets had a reduced capacity to interact with H VWF-A1 protein in flow.
Figure 13A:
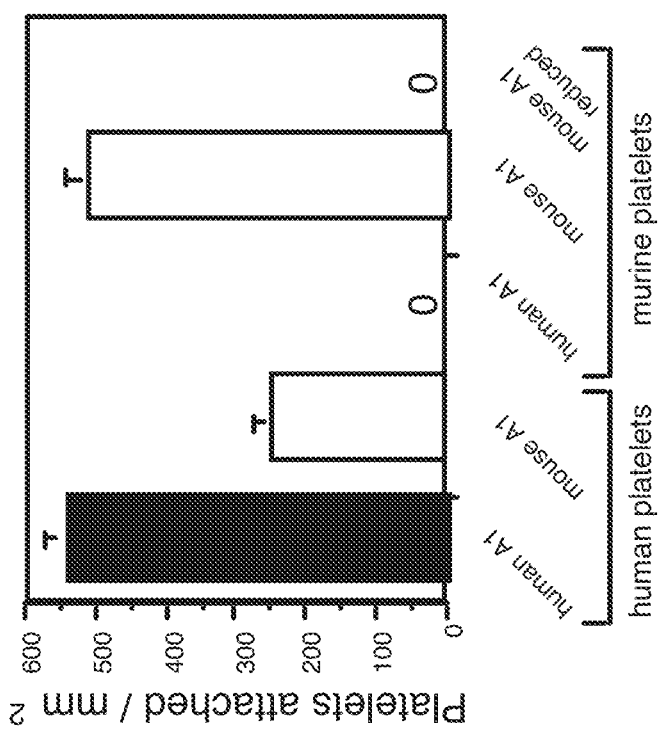

As shown in FIG. 13A, mouse VWF-A1 protein supported platelet adhesion as efficiently as its human counterpart under physiological flow conditions. To demonstrate the importance of the single disulfide bond formed by C1272 and C1458, reduced (DTT) and alkylated (iodoacetamide) mouse VWF-A1 was prepared and tested in flow. Reduction and alkylation of the protein abrogated attachment of murine platelets in flow. In addition, the limited ability of the native form of the protein to mediate adhesion of human platelets and lack of interaction between human VWF-A1 and mouse platelets suggests that structural/conformational differences exist between the species. However, this does not preclude the study of GPIb alpha-VWF-A1 interactions in mice as both proteins must share common kinetic attributes as they support rapid attachment and translocation of platelets to a similar degree under physiological flow conditions (FIG. 13B).

Figure 14B:
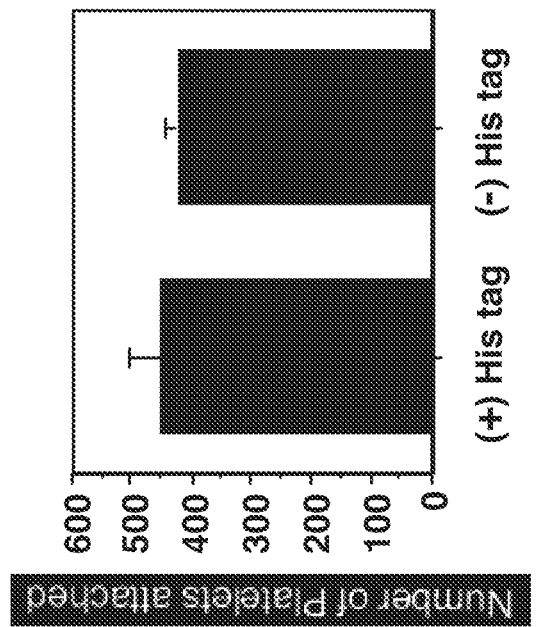
FIGS. 14A and 14B represent purified bacterial His-tagged VWF-A1 protein and non-His tagged VWF-A1 protein that was analyzed by SDS-PAGE (12.5%) under non-reducing and reducing conditions.
Figure 14A:
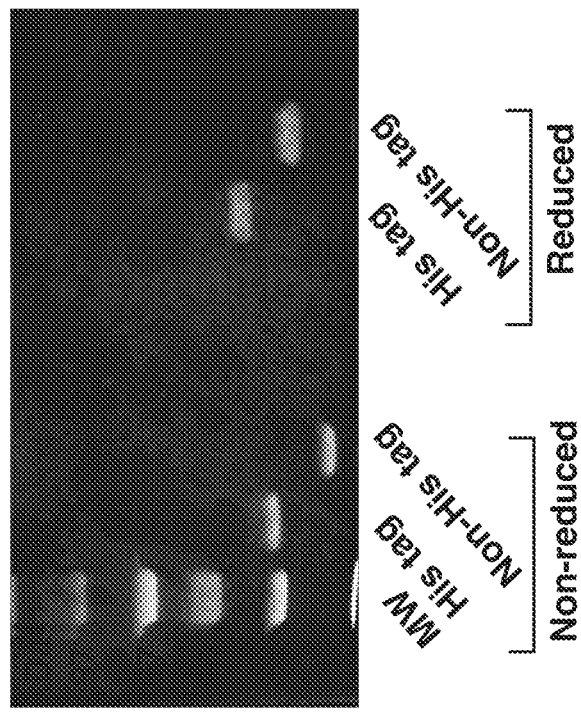

To demonstrate that the presence of the N-terminus His tag does not appear to affect the function of the recombinant protein, we compared the ability of a tagged vs. a non-tagged M VWF-A1 to support mouse platelet adhesion in flow. In the case of the latter, the murine A1 fragment was inserted into pET-11b (Stratagene) and purified as previously described (53). The purified bacterial non-His tag protein was analyzed by SDS-PAGE (12.5%) and found to migrate in an analogous manner to its tagged counterpart under non-reducing and reducing conditions (FIG. 14A). In addition, no differences were observed in the number of platelets that adhered to and translocated on either protein (449±53 platelets/mm$^2$ His-tag vs. 423±17 platelets/mm$^2$ non-His tag) at a shear rate of 800 s$^{-1}$ (FIG. 14B).

Characterization of the M VWF-A1 Domain.

Figure 15A:
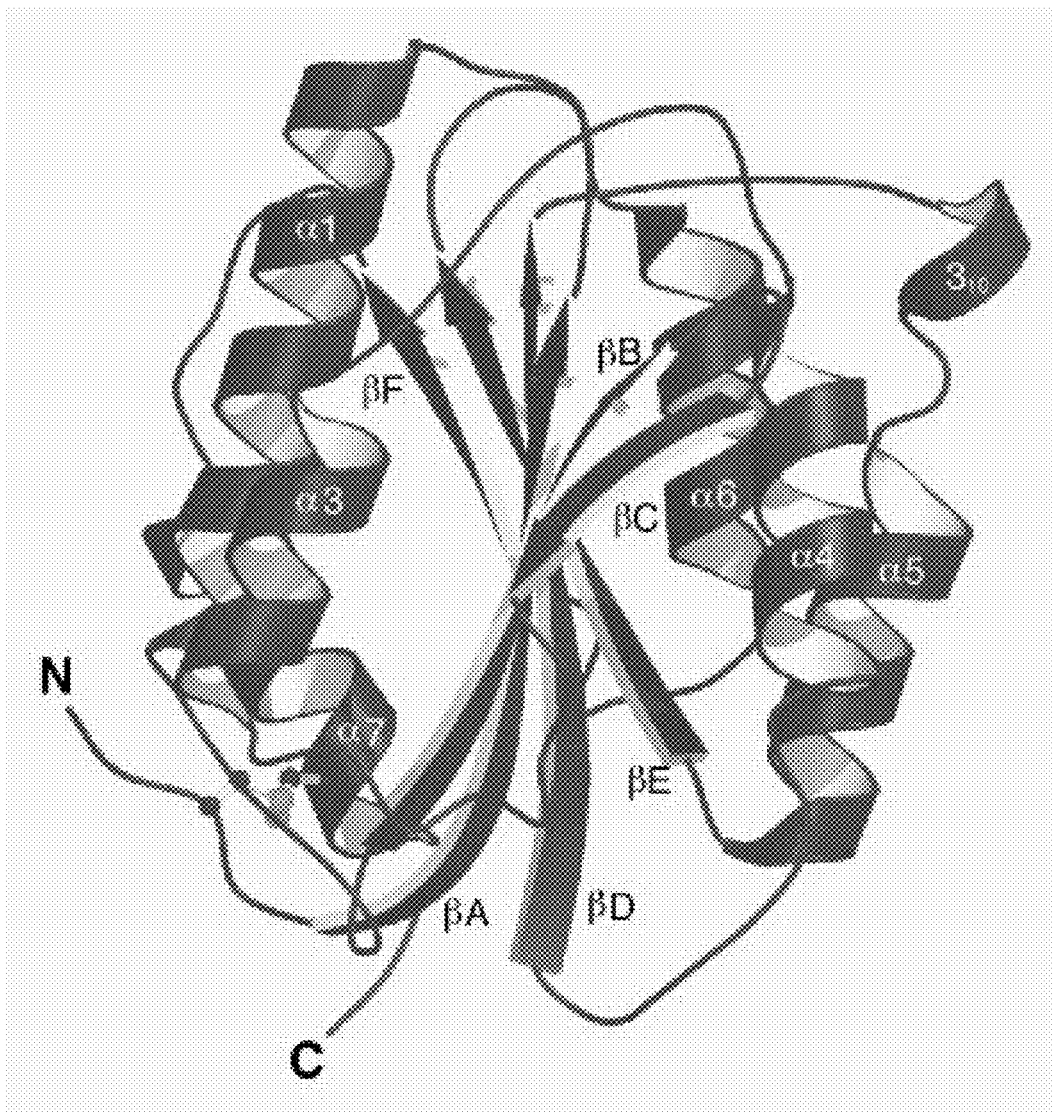
FIGS. 15A through 15C represents models of the crystal structure of VWF-A1 domains solved using a recombinant protein. The main chain schematic of the mouse VWF-A1 domain, with β-strands (arrows) and helices (coils), is shown in FIG. 15A. The two cysteines involved in the disulfide bridge are shown as yellow spheres.
Figure 15B:
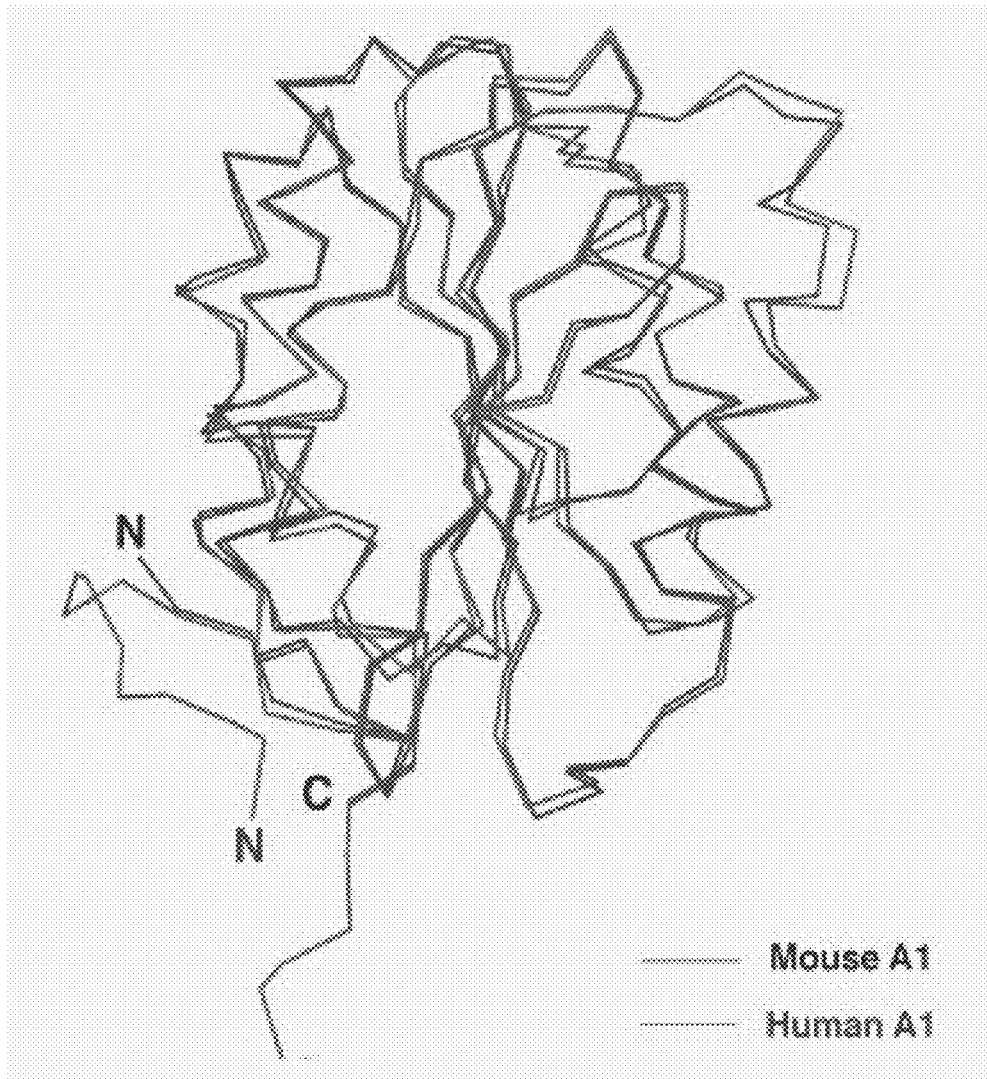

The A1 domains of human and mouse serve an identical purpose: to mediate primary attachment and translocation of platelets in flow. The crystal structure of the mouse A1 domain was solved using recombinant proteins (Fukuda, K., et al., (2005) *Nat. Struct. Mol. Biol.* 12:152-159). The main chain schematic of this domain, with β-strands (arrows) and helices (coils), is shown in FIG. 15A. The model was built from residues 1270 to 1463 of the murine VWF-A1 crystal. The two cysteines involved in the disulfide bridge are shown as yellow spheres (involving residues 1272 and 1458). The mouse and human A1 domains appear to overlap very closely, which suggests that only minor structural differences may account for the preferential binding of platelets from mice or man to their respective VWF-A1 proteins (FIG. 15B). In fact, the β-sheets of both species are identical within experimental error (a root mean square difference of 0.33 Å for Cα atoms). Thus, minor differences in residues, but not structure, most probably account for the inability of human platelets to interact with mouse VWF-A1 and vice versa.

Figure 15C:
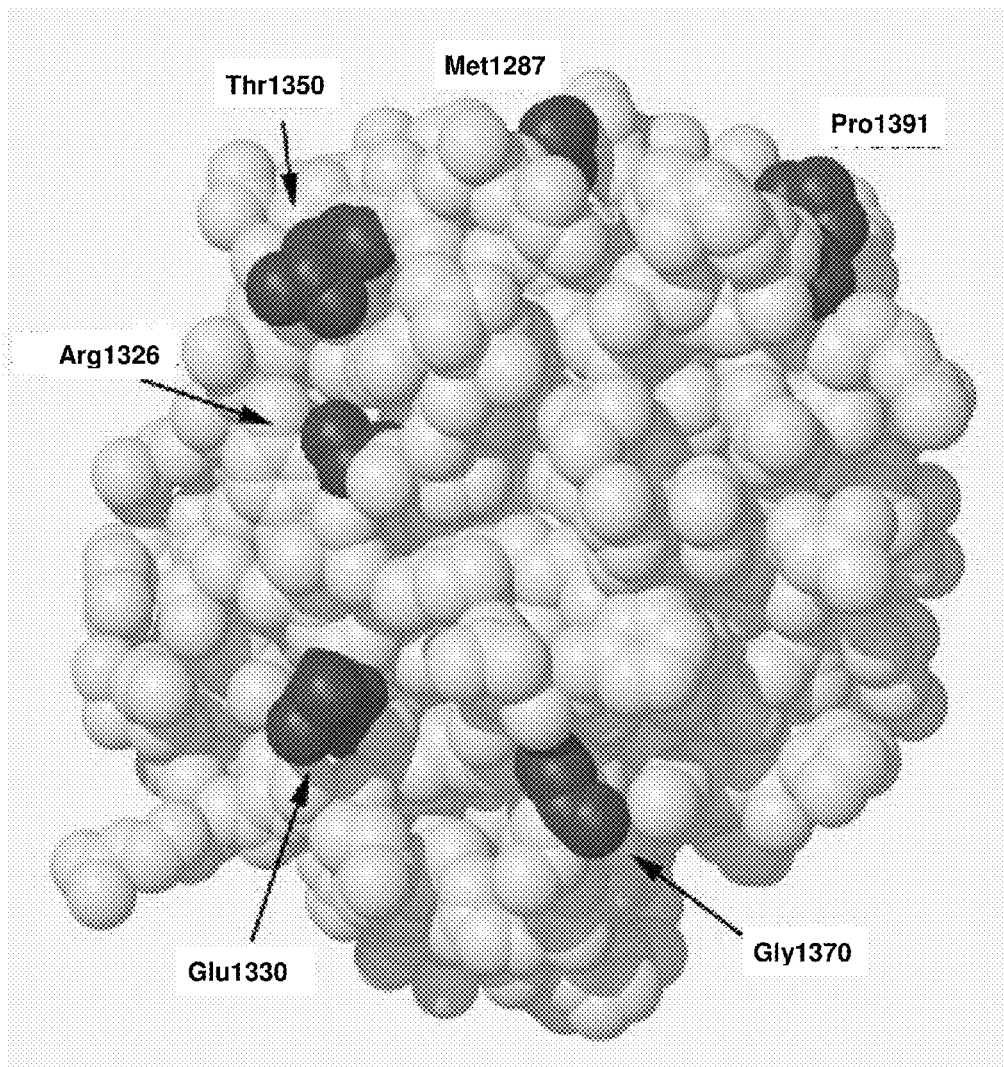

Support for this hypothesis is provided by mutagenesis studies. By analyzing the data obtained from the crystal structure of the murine VWF-A1 domain, we have identified several residues that may participate in interactions with GPIb alpha (FIG. 15C). Residue 1326 was initially chosen for study and was mutated to the corresponding amino acid at the identical location in its human counterpart (from Arg to His). Subsequently, the ability of murine and human platelets to interact with this mutant protein substrate was evaluated at a wall shear rate of 800 s$^{-1}$. Incorporation of a histidine for arginine at position 1326 in murine VWF-A1 reduced murine platelet adhesion by ~5-fold and increased translocation velocities of cells by ~7-fold as compared to the WT mouse protein (FIGS. 13A, 13B, 16A, and 16B). Interestingly, human platelet interactions with the mutated murine protein were comparable to that of WT human VWF-A1. Conversely, substitution of Arg for His in the human VWF-A1 protein resulted in an increased ability of murine platelets to attach and translocate in a manner similar to that observed for WT murine VWF-A1. These studies support the hypothesis that from a structural and functional standpoint, mouse and human VWF-A1 are very similar.

Thus, all that remains is to demonstrate that the kinetics of the interaction between the murine GPIb alpha and murine VWF-A1 are similar to its human counterpart and that mutations in man that cause functional alterations in platelet adhesion with VWF have the identical impact on the biophysical properties of the murine receptor-ligand pair.

The Kinetics of Murine VWF-A1

To determine whether the kinetics of the murine GPIb alpha interactions with the murine VWF-A1 domain is similar to that of the human receptor-ligand pair, we measured the dissociation of transient tethering events using VWF-A1 coated beads (7 μm diameter) interacting with surface-immobilized platelets. The use of beads with one uniform size and shape permits determination of the relationship between wall shear stress and the force directly acting on the GPIb alpha-VWF-A1 tether bond (Fb), a parameter difficult to estimate for discoid-shaped objects such as platelets. A coating concentration of VWF-A1 was chosen (5 μg/ml corresponding to 30 molecules/m$^2$) that supported tether bond formation at wall shear stresses ranging from 0.5 to 3 dyn cm$^{-2}$. Estimation of the site density of murine VWF-A1 on beads was performed using a monoclonal antibody generated in our laboratory designated as AMD-2. This antibody was made by immunizing Fischer 344 rats (3-4 months old) with recombinant WT protein. Following several injections of murine VWF-A1, serum was collected and screened by ELISA for anti-VWF-A1 antibodies. Spleens from animals with the highest antibody titers were harvested and splenocytes fused with Sp2/0 mouse myeloma cells (54).

Figure 17:
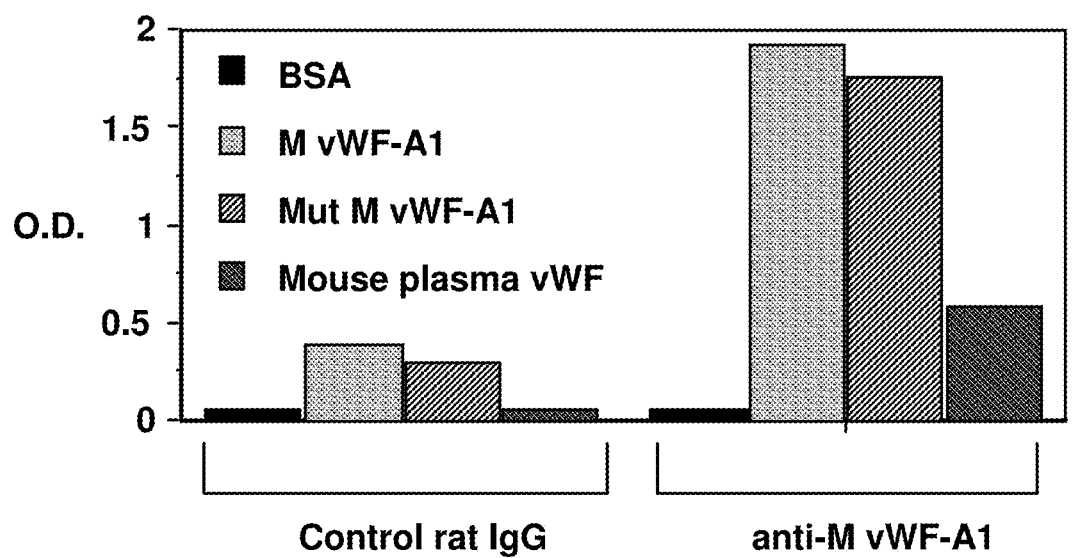
FIG. 17 represents data from an ELISA assay. Following several injections of mouse (M) VWF-A1, serum was collected from rats and screened by ELISA for anti-VWF-A1 antibodies. Spleens from animals with the highest antibody titers were harvested and splenocytes fused with Sp2/0 mouse myeloma cells (54). Supernatants of hybridomas were screened for reactivity to murine (M) VWF-A1 by ELISA. Pre-immune rat serum was used as control. Mabs to M VWF-A1 not only reacted with WT and mutant proteins (1324G>S) but also recognized native VWF purified from mouse plasma.

Supernatants of hybridomas were screened for reactivity to mouse VWF-A1 by ELISA (FIG. 17). Pre-immune rat serum was used as control. Monoclonal antibodies (Mabs) to murine VWF-A1 not only reacted with WT and mutant proteins (1324G>S) but also recognized native VWF purified from mouse plasma. Antibodies are currently being tested for function blocking capabilities to use in both in vitro and in vivo assays. Antibodies will also be used for epitope mapping.

Figures 18A, 18B:
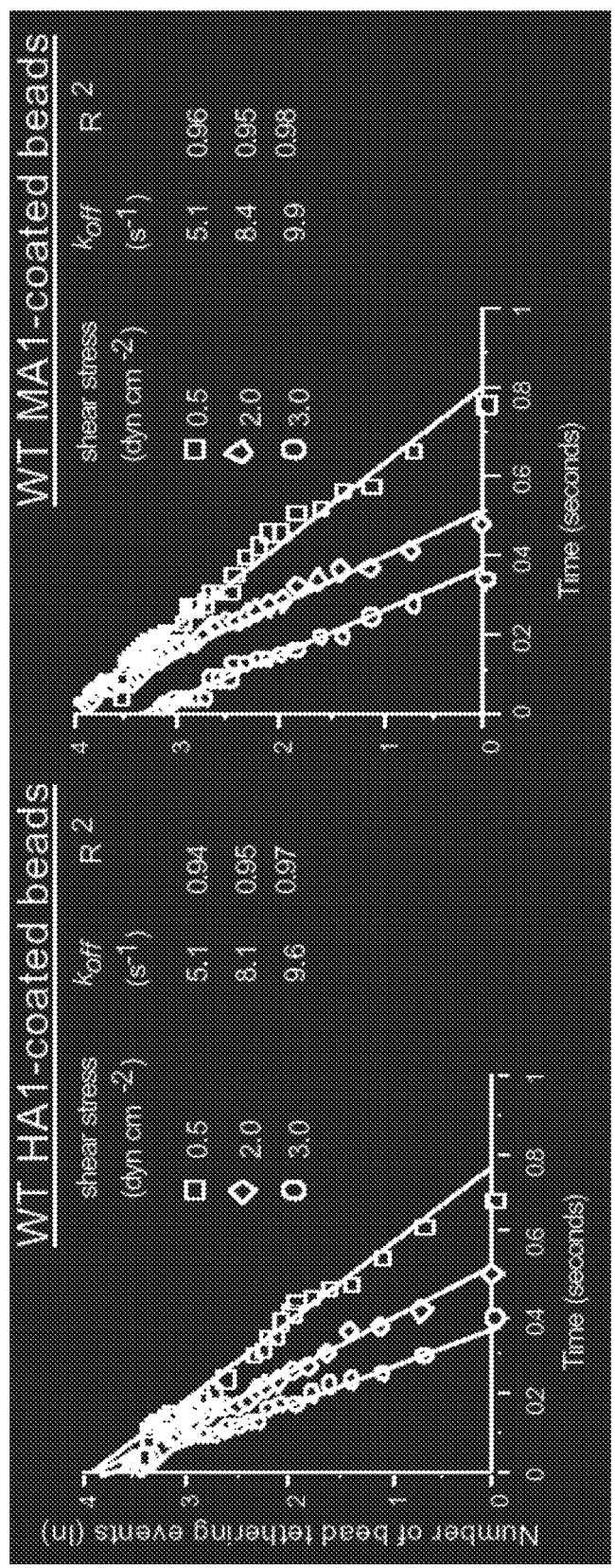
FIGS. 18A, 18B, and 18C show representative graphs depicting the distribution of interaction times for more than 35 individual transient attachment events at various times. Analysis of the distribution of interactions times between human or murine VWF-A1 coated beads and their respective platelet substrates, as measured by high temporal resolution video microscopy, indicate that >95% of all transient tether bonds events fit a straight line, the regressed slope of which corresponded to a single $k_{off}$, wherein the cellular off-rates of these quantal units of adhesion for the wild type human (H) and murine (M) proteins are found in FIGS. 18A, 18B, and 18C and M VWF-A1 protein containing the type 2B mutation I1309V (1309I>V) corresponds to FIG. 18C.
Figure 18C:
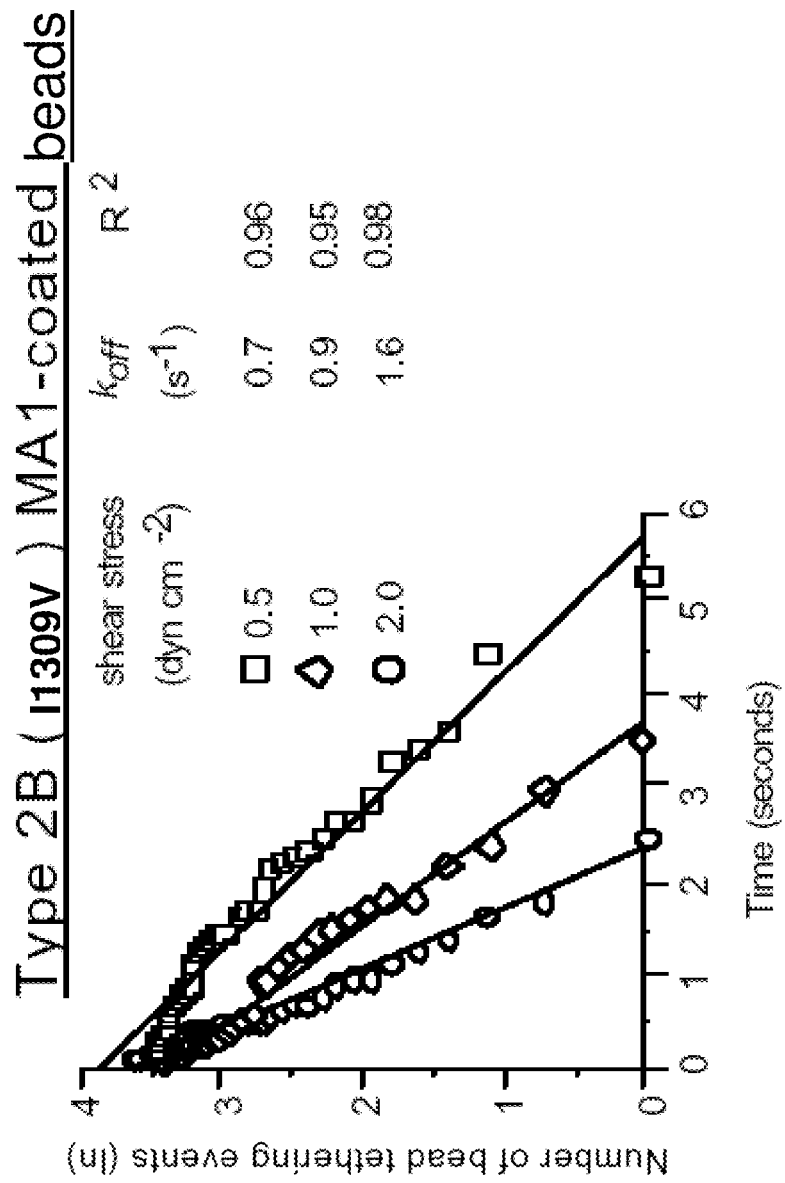

Analysis of the distribution of interactions times between human or murine VWF-A1 coated beads and their respective platelet substrates, as measured by high temporal resolution videomicroscopy, indicate that >95% of all transient tether bonds events fit a straight line, the regressed slope of which corresponded to a single $k_{off}$ (FIGS. 18A-C). Notably, the cellular off-rates of these quantal units of adhesion for the WT human and mouse proteins (FIGS. 18A and B) were quite similar, but were significantly higher than those observed for the murine VWF-A1 containing the type 2B mutation I1309V (1309I>V) (FIG. 18C). This is consistent with previous results obtained using the same mutation in the human protein (Table 1).

Based on these preliminary results, it appears that the dissociation kinetics of murine GPIb alpha interactions with murine VWF-A1 are nearly identical to its human counterpart and that type 2B mutations also prolongs the bond lifetime of this interaction as seen in man. A complete biophysical analysis is underway and in order to determine values for the intrinsic $k_{off}$ and susceptibility of the bond to force drive dissociation as performed previously for its human counterpart.

Example 2

VWF-A1 Mutagenesis

Preliminary results indicate that minor differences may exist between murine and human VWF that would preclude one from studying human platelet behavior in a mouse model of thrombosis. However, our findings that the estimated off-rate values and structure of these domains are similar suggest that one can investigate the role of the biophysical properties of the GPIb alpha-VWF-A1 bond in regulating platelet-VWF interactions in vivo using a mouse model. However, neither a delineation of the binding region for GPIb alpha within the murine VWF-A1 domain nor determination of the impact of mutations on the kinetics of this interaction has been performed to date. Thus, both murine and human A1 crystal structures can be exploited to 1) identify candidate residues involved in the binding site for murine GPIb alpha and to determine their impact on the kinetic properties of this receptor-ligand pair, 2) identify residues that confer species specificity, and 3) ascertain whether insertion of known point mutations that cause type 2M and 2B VWD in man alter the kinetic properties of the murine A1 domain in a similar manner. Critical residues can be classified in terms of their impact on the cellular association and dissociation rate constants. Information obtained from these studies can be used to generate mice with mutant A1 domains in order to establish the degree in alteration in the kinetics of the GPIb alpha-VWF-A1 bond that is necessary to perturb hemostasis.

Similar critical structural elements exist in murine A1 domain to those identified in its human counter-part that contribute to the biophysical properties of the bond formed with GPIb alpha. Thus, to identify structural elements within the murine VWF-A1 domain that impact on the kinetics of interaction with GPIb alpha, the hypothesis that only minor structural alterations in this domain are responsible for its reduced ability to support interactions with GPIb alpha receptor on human platelets will be tested.

Site-Specific Mutagenesis of Murine VWF-A1 Domain

Site-specific mutagenesis of murine VWF-A1 domain will be performed to define residues that contribute to GPIb alpha binding as well as those in that regulate this interaction. Studies will initially focus on amino acids that differ between human and mouse A1 that lie within the vicinity of the proposed GPIb alpha binding pocket.

To better define residues within murine VWF-A1 that are critical for binding of GPIb alpha on mouse platelets, mutations into VWF-A1 cDNA using a PCR-based strategy will be introduced and the resulting DNA will be sequenced to confirm the presence of the desired mutation(s). Muta-

TABLE 1

| SINGLE | H1326R* | G1330E* | R1287M* | Q1391P* | A1350T* | S1370G* | D1333A* | tions will be based on the murine A1 crystal structure and amino acid substitutions known to affect human VWF function such as those associated with Type 2M or 2B vWD (Tables 2-4). Several surface exposed residues have been identified within the murine A1 domain likely to participate in GPIb alpha binding. These are non-conserved residues in comparison to the human domain. Thus, we will convert these residues at first singly (then doubly and triply), into the murine VWF-A1 to those found in human VWF-A1*. Residues are chosen based on surface-exposure on the front and upper surfaces of the domain as understood by modeling and crystal structure analysis.

TABLE 2

| SINGLE | R1326 H* | E1350G* | M1287R* | P 1391 Q* | T1350A* | G1370S* | A1333D* |
|---|---|---|---|---|---|---|---|
| DOUBLE | | | R 1287 M* + Q 1391 P* | | | | |
| TRIPLE | | | H 1326 R* + G 1350 E* + A1333D* | | | | |

TABLE 3

| SINGLE | S1289R* | D1323R* | K1348E* | R1392E* |
|---|---|---|---|---|

Figures 5A, 5B:
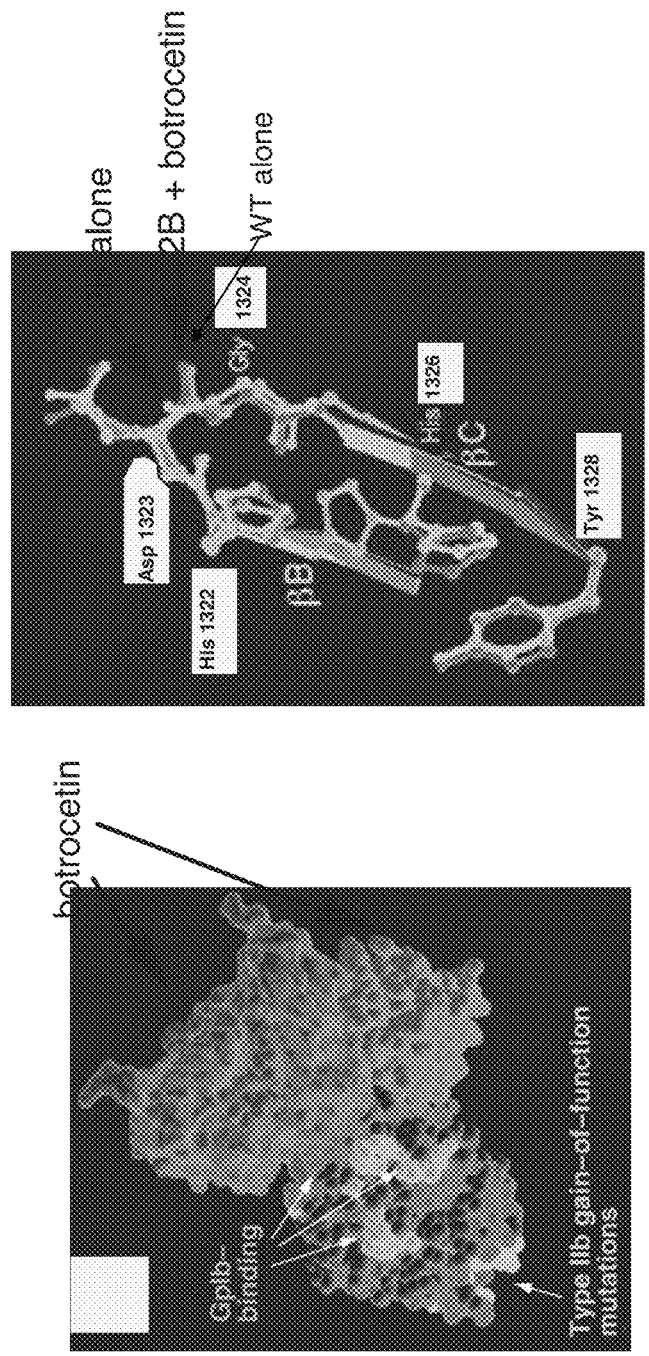
FIGS. 5A and 5B show a space-filling model of the botrocetin-A1 complex with sites involved in GPIb alpha binding and location of type 2B mutations indicated in FIG. 5A, wherein botrocetin does not alter the conformation of VWF-A1 and minor conformational changes in the A1 domain being represented by FIG. 5B with uncomplexed (blue) and complexed (green) mutant domains superimposed onto the WT structure (red).

Residues that perturb but do not abrogate platelet binding in the human VWF-A1 protein (Table 3, FIG. 5B).

TABLE 4

| TYPE 2M | G1324S* | Q1367R* | I1369F* | I1425F* |
|---|---|---|---|---|
| TYPE 2B | R1306L* | I1309V* | V1316M* | R1341L* |

Residues chosen based on their ability to abrogate or enhance interactions between human VWF and GPIb alpha (Table 4).

Type 2B mutations will also be combined with those that dramatically shorten the bond lifetime to determine (increase $k_{off}$) if these function-enhancing mutations can restore adhesion to that observed for WT VWF-A1.

Laminar flow assays will be performed to assess the impact of various mutations on platelet adhesion as well as the degree in alteration in the kinetic properties of the GPIb alpha-VWF-A1 bond.

Murine platelets will be purified as described above and stored in Tyrode's buffer containing 0.25% BSA, pH 7.4. For studies requiring human platelets, blood will be collected by venopuncture from healthy donors and cells obtained from centrifugation of PRP. All platelets will be used within 2 hours of purification.

To evaluate the impact of mutations on platelet adhesion, both human and murine platelets are perfused over high concentrations of murine VWF-A1 proteins (100 μg per ml) absorbed to glass cover slips in a parallel plate flow chamber at wall shear rates ranging from 20 to 1600 $s^{-1}$. An enzyme-linked immunosorbent assay is utilized to ensure that an equivalent amount of recombinant WT or mutant protein is immobilized. The number of platelets that attach per unit area per min and their velocity of forward motion (μm/s), termed translocation, is recorded on Hi-8 videotape using an inverted Nikon microscope with a plan 10× or 40× objective, respectively. In addition, whether the incorporated mutations alter the requirement for a critical level of hydrodynamic flow, termed the shear threshold phenomenon, to support interactions of platelets with the reactive substrate can be determined. It has been previously demonstrated that human attachment to immobilized VWF-A1 requires a minimum of >85 $s^{-1}$ of WSR to initiate and sustain this interaction. This phenomenon has also been well described for selectin-dependent adhesion and is believed to rely on a balance between the number of times a receptor encounters it ligand over a defined period of time and the rate at which a bond can form, parameters affected by shear rate, association rate constant, and receptor-ligand concentrations (59, 60). Once attached, however, the bond lifetime influences the velocity at which the cell will move on the reactive substrate in response to shear-induced force (61). Thus, it is likely that several mutations may perturb platelet accumulation on surface-bound VWF-A1 by altering the level of shear flow required to promote platelet attachment as well as the translocation velocities of these cells. For example, it has been shown that the type 2B mutation, Ile1309Val (1309I>V), promotes greater platelet attachment at low shear rates and reduces their translocation velocities as compared to the WT substrate. Similar results were observed upon incorporation of the identical mutation into murine VWF-A1. Demonstration that GPIb alpha on murine platelets is responsible for mediating interactions with recombinant A1 domains can be confirmed by antibody blocking experiments.

Determination of Tethering Frequencies, Translocation Velocities, Detachment Profiles, and Dissociation Rate Constants Using VWF-A1 Coated Microspheres.

To better ascertain the alteration in kinetics associated with the proposed mutations, the tethering frequency, translocation velocities, detachment profile, and off-rates of VWF-A1 coated beads (7 μm diameter) interacting with surface-immobilized platelets can be measured. As stated before, the use of beads with one uniform size and shape will permit determination of the relationship between wall shear stress and the force directly acting on the GPIb alpha-VWF-A1 tether bond (Fb), a parameter difficult to estimate for discoid shaped objects such as platelets. Platelet coverage >90% of the glass surface area is used in determining the tethering frequency (on rate driven phenomenon), translocation velocities (correlates with off-rate) and resistance to detachment forces (measure of bond strength) of VWF-A1 coated beads in flow. Recently, we have demonstrated that comparison of cellular on-rates and apparent bond strengths between WT and mutant forms of VWF-A1 can be achieved by limiting the concentration of these molecules as to prevent multiple bond formation, a process that can mimic an enhancement in either of these kinetic parameters. By using a similar strategy, we can determine whether the proposed mutations will alter the apparent on-rate of the GPIb alpha-VWF-A1 bond by evaluating the frequency of transient tethering events between microspheres coated with low site densities of VWF-A1 proteins and a platelet substrate. Results are expressed as the percentage of beads (per 10× field) that paused, but did not translocate, on over a range of wall shear rates that support such interactions (20 to 400 $s^{-1}$). Tethers per minute are divided by the flux of beads near the wall per minute to obtain the frequency of this adhesive interaction. Only one tethering event per bead is counted during the observation period.

For determining translocation velocities, beads (1×10⁶/ml), coated with a saturating concentration of VWF-A1 protein are infused into the parallel-plate flow chamber at 1.0 dyn $cm^{-2}$ and allowed to accumulate for 5 min. Subsequently, the wall shear stress is increased every 10 s to a maximum 36 dyn $cm^{-2}$ and the velocities of the beads determined.

For detachment assays, beads (1×10$^6$/ml), coated with the minimum but equal amounts of VWF-A1 required to support translocation, are infused into the parallel-plate flow chamber at 1.0 dyn cm$^{-2}$ and allowed to accumulate for 5 min. Subsequently, the wall shear stress is increased every 10 s to a maximum 36 dyn cm$^{-2}$. The number of beads remaining bound at the end of each incremental increase in wall shear stress is determined and expressed as the percentage of the total number of beads originally bound. Using this strategy, we were able to support our claim that type 2B mutations do not strengthen, and in fact may even weaken the interaction between GPIb alpha and VWF-A1 as suggested by the increase in reactive compliance as compared to the native complex (Table 1). In all studies, video images are recorded using a Hi8 VCR (Sony, Boston, Mass.) and analysis of performed using a PC-based image analysis system (Image Pro Plus).

For determining the kinetics of dissociation, we measure the duration of transient tethers between murine VWF-A1 coated microspheres and immobilized murine platelets as described herein. MC simulations are run and estimates of $k_{off}$ fit to the Bell model by standard linear regression to obtain the intrinsic off-rate ($k^0_{off}$) and the reactive compliance σ. Results are compared for all mutations to determine their impact on these kinetic parameters (i.e., increase or shorten the bond lifetime ($k^0_{off}$) and/or increase or decrease the susceptibility of the bond to hydrodynamic forces (σ).

These experiments complement recent work on identifying residues in human VWF-A1 domain critical for interacting with the GPIb alpha. Moreover, they allow for delineation of its binding site in murine VWF-A1. We believe this to be important, as this work will be essential for elucidating the role of the biophysical properties of this receptor-ligand pair in regulating platelet-VWF interactions in vivo. Furthermore, it will pave the way for the generation of mice with comparable types of human vWD (i.e., type 2B) and may even permit the study of human platelets in a mouse model of thrombosis.

Although our approach to mapping the GPIb alpha binding site is reasonable based on our previous studies, there is no guarantee that the introduction of mutations will not significantly perturb protein structure and thus function. The ability of murine VWF-A1 specific mAbs to recognize mutant proteins should clarify this matter. Similarly, our proposed gain/loss of function experiments involving swapping of residues between human and mouse VWF-A1 will also prove useful in avoiding this pitfall.

It is important to know whether the regions flanking the mouse A1 domain are important in mediating interactions with GPIb alpha. To this end, we plan to express full-length mouse VWF by inserting it into a mammalian expression vector and transfecting it into COS-7 cells (62). Mutations found to be critical for binding, will be inserted into the full-length construct. As we are in the process of generating the full-length cDNA, we will initially attempt to generate a recombinant protein containing the A1-A2-A3 domains to use in our studies. This will be accomplished using a baculovirus expression system as demonstrated for GPIb alpha.

The Relationship Between the Major and Minor Binding Sites for GPIb Alpha.

The recent results on the structure of GPIb alpha and its complex with VWF-A1 domain has not only confirmed our work as well as others with regard to the major binding site for this platelet receptor, but has shed new light into the mechanism by which type 2B mutations may enhance this critical interaction. As shown in FIG. 6, the concave face of GPIb alpha embraces the A1 domain in two distinct regions. The C-terminal loop of this receptor binds near the top of the domain (major binding site) and the N-terminal region known as the β-finger, at the bottom face (minor binding site) adjacent to the site where type 2B mutations are clustered. Based on these results that type 2B mutations appear to enhance the on-rate (reduced shear rate needed for formation of transient tethers in flow) and prolong the lifetime (5-6 fold) of the interaction between VWF-A1 and GPIb alpha, it is interesting to speculate whether similar alterations in bond kinetics would be observed with type 2B mutations if one interfered with the primary site. For instance, would inclusion of a type 2B with a type 2M mutation reconstitute adhesion, or is some finite interaction time required in the primary binding pocket for GPIb alpha before the effects of these mutations can be observed? These are important questions as they will guide the development of reagents that can either enhance or reduce the interaction between GPIb alpha and VWF-A1.

Figure 19A:
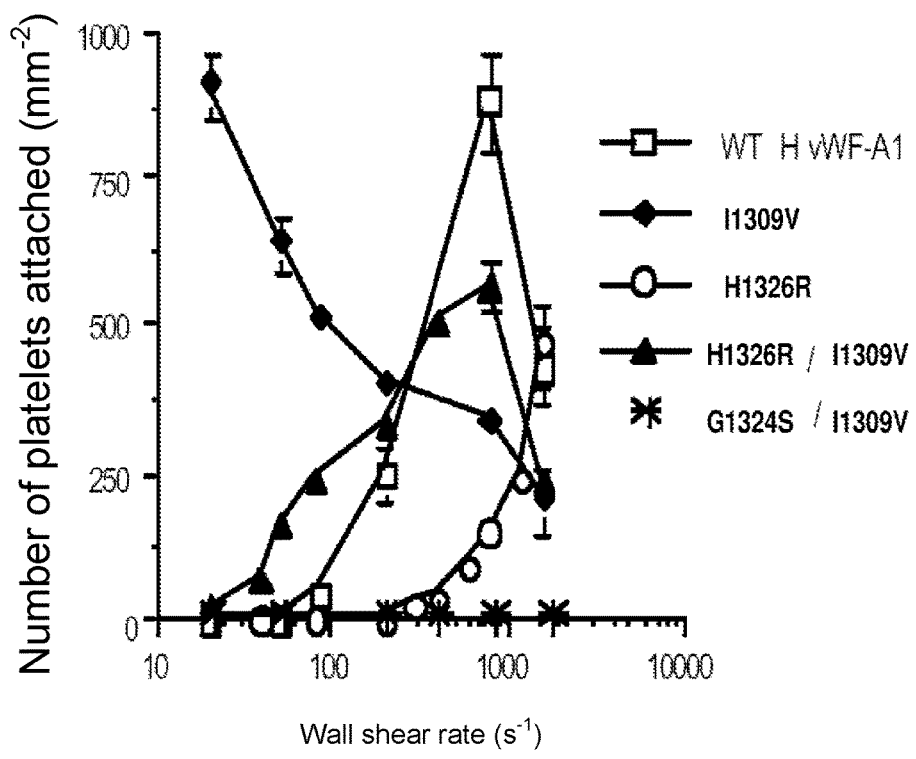
FIGS. 19A and 19B show graphs that represent an assessment of transient tether events (FIG. 19A) and analysis of the distribution of interactions times (FIG. 19B) between human VWF-A1 coated microspheres and human immobilized platelets. The type 2B mutation Ile1309Val (1309I>V) was incorporated into recombinant human (H) VWF-A1 containing either the type 2M mutation Gly1324Ser (1324G>S) or the function reducing mutation His1326Arg (1326H>R).

The type 2B mutation 1309I>V was incorporated into recombinant human VWF-A1 containing either the type 2M mutation Gly1324Ser (1324G>S) that completely abolishes adhesion or the function reducing mutation His1326Arg (1326H>R) and determined the ability of these doubly mutated proteins to support human platelet adhesion in flow. In comparison to WT, a ~3-fold increase in wall shear rate is required to promote platelet attachment to human VWF-A1 containing Arg at 1326 (FIG. 19A). Incorporation of the type 2B mutation, however, appeared to enhance the on-rate of this interaction as manifested by an increase in platelet binding at lower levels of shear flow, but not to levels observed for the type 2B mutation alone.

Figure 19B:
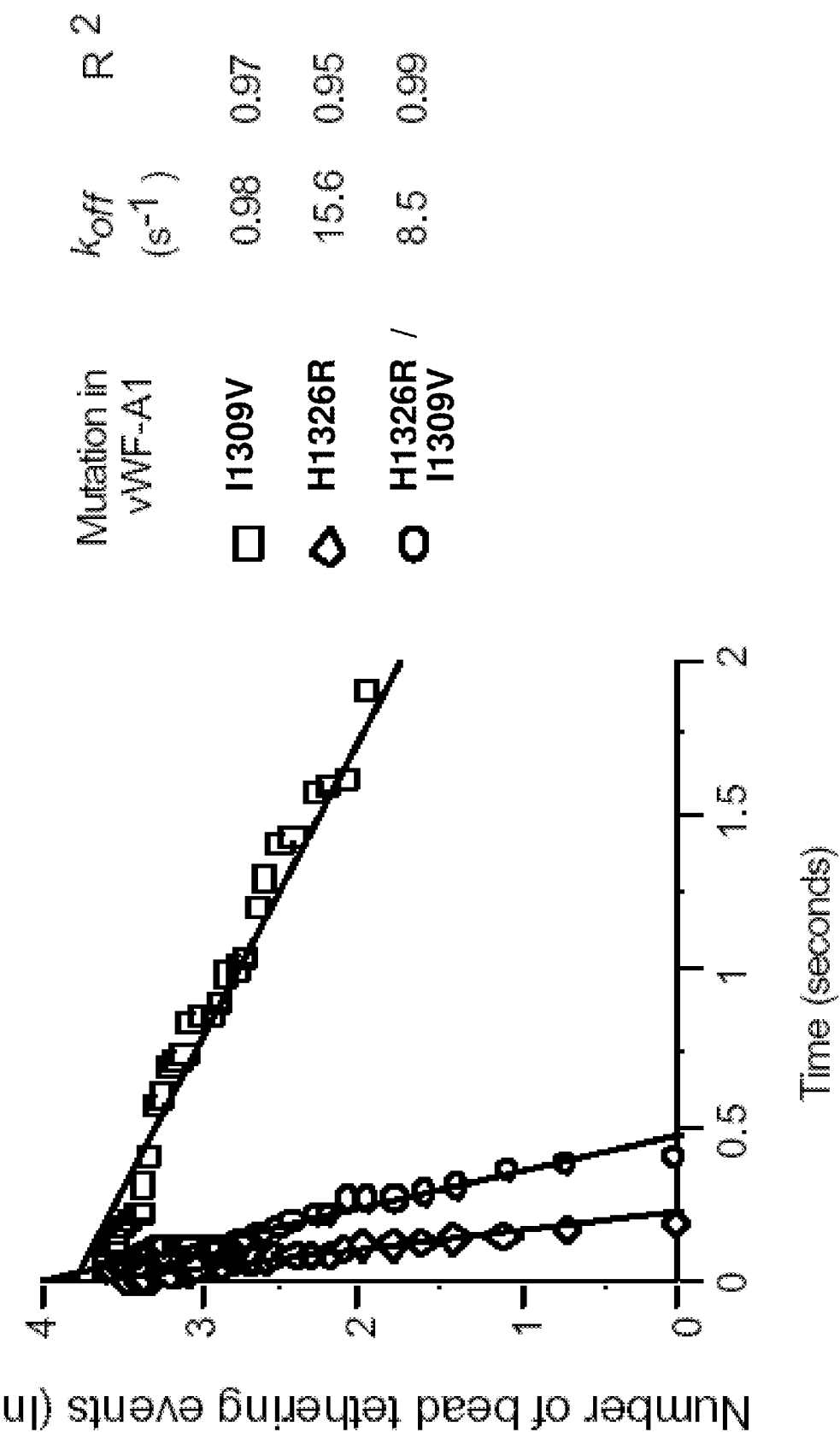

To determine whether the 1309 mutation would also prolong the lifetime of the interaction with GPIb alpha, the distribution of interactions times was analyzed between VWF-A1 coated beads and surface-immobilized platelets at a wall shear stress of 1 dyn cm$^{-2}$. Remarkably, a 2-fold reduction in $k_{off}$ was noted (from 15.6 to 8.5 s$^{-1}$) as compared to the single, function-diminishing mutation (FIG. 19B). This value is similar to that of the native receptor-ligand interaction with a $k_{off}$ of 6.5 s$^{-1}$ under identical flow conditions. By contrast, incorporation of Val for Be at residue 1309 in an A1 domain containing the type 2M mutation 1324G>S did not reconstitute platelet adhesion. Thus, these results suggest that it is essential for bond formation to occur in the primary GPIb alpha binding site (top face of the A1 domain). Moreover, the region of the A1 domain where type 2B mutations are clustered appears to be critical for stabilizing interactions with GPIb alpha. Similar findings were observed for murine VWF-A1 containing the identical type 2B mutation but with a change in Arg to His at residue 1326. A complete biophysical analysis is underway and in order to determine the full extent of the 1326 mutation on the intrinsic $k_{off}$, the susceptibility of the bond to force drive dissociation, and whether type 2B mutations can restore these parameters to levels obtained for the native receptor-ligand bond. In addition, it would be interesting to determine in vivo whether the enhancement in binding and increase in bond lifetime imparted by the type 2B mutation would correct any perturbation in hemostasis that may occur as a result of impacting on the function of the primary binding site for GPIb alpha.

Example 3

Genetically Modified VWF-A1 Mice

Recent kinetic evaluation of mutations associated with type 2B and platelet-type vWD suggests that the intrinsic properties of the GPIb alpha-VWF-A1 tether bond contribute to the regulation of platelet interactions with VWF. This is also supported by our preliminary studies investigating the impact of botrocetin on the biophysical properties of this receptor-ligand pair. Thus, by using the information obtained in Example 2, mutations can be incorporated into the murine A1 domain of the VWF gene that increase or decrease the intrinsic on- and off-rates by varying degrees in order to truly understand the importance of these kinetic parameters in controlling platelet adhesion. Moreover, the role of the minor binding site, where the majority of type 2B mutations have been identified, can be further delineated by combining such mutations with those that significantly shorten the lifetime of interaction between GPIb alpha and VWF-A1. Results indicate that substitution of the murine residue Arg at position 1326 for His at the same location in the human A1 domain results in a diminished on-rate as manifested by the increased requirement for shear flow to promote attachment and a significant increase in $k_{off}$ (shortening of bond lifetime). Subsequent incorporation of the type 2B mutation 1309I>V into this mutant domain significantly reverses the functional defect in adhesion and returns the off-rate closer to that observed for the WT domain. Similar results have been obtained with murine VWF-A1 in which Arg was replaced by His at residue 1326. Thus, introduction of these two mutations separately and then together into the mouse VWF gene will be the initial focus. This single amino acid substitution enables the mouse VWF-A1 domain to bind platelets at levels equivalent to its human counterpart. Thus, introduction of the two mutations separately (1326R>H or 1309I>V) and then together into the mouse VWF gene has been the target of recent studies. In addition, replacing >90% of the entire mouse A1 domain with its human counterpart is also central to current investigations. This model will enable one to test all potential therapies directed against this human domain in a mouse model of thrombosis.

Generation of mice that incorporate mutations into their A1 domain that significantly shorten the bond lifetime will be present with prolonged bleeding times and will be resistant to thrombus formation, while the additional incorporation of a type 2B mutation will correct these abnormalities by prolonging the tether bond lifetime to that observed for the WT domain. This should allow for sufficient time to form multiple bonds between platelets and VWF deposited at sites of vascular injury. Moreover, mice possessing the 1326R>H mutation should be able to support human platelet adhesion at sites of vascular injury. Thus, it will be demonstrated in vivo that the intrinsic properties of the GPIb alpha-VWF-A1 tether bond are indeed critical for regulating the interactions between platelets and VWF at sites of vascular injury.

By performing a detailed kinetic analysis of mutant VWF-A1 domains prior to the generation of animals with the identical substitutions in amino acids, we have greatly increased the likelihood of altering the interaction between platelets and VWF in a similar manner. We will be able to study the role of the intrinsic properties of the bonds formed between this receptor-ligand pair under complex hemodynamic conditions (i.e., in vivo). The initial choice of the 1326R>H mutation will be of benefit in two ways. First, it allows us to test our hypothesis that a critical interaction time between platelets and VWF is essential to maintaining adequate hemostasis. Secondly, the ability of this mutation to enhance human platelet adhesion will permit us to study their behavior in a mouse model of thrombosis. This is an intriguing concept as it may pave the way to test the impact of various pharmacological agents on human platelet adhesion at sites of vascular injury. For example, a substitution in which a single mutation in murine VWF-A1 (1260 to 1480) can be made in order to achieve human platelet bonding. In addition, a combination of two or more mutations that further perturb the kinetics of the interaction to achieve human platelet binding can also be made. In some instances, the entire mouse A1 domain in the mouse VWF gene with the human A1 domain found in the human VWF gene can be replaced.

Generation and Characterization of Mice Expressing a Mutant VWF-A1 Domain

Mutant Mouse.

Figure 20A:
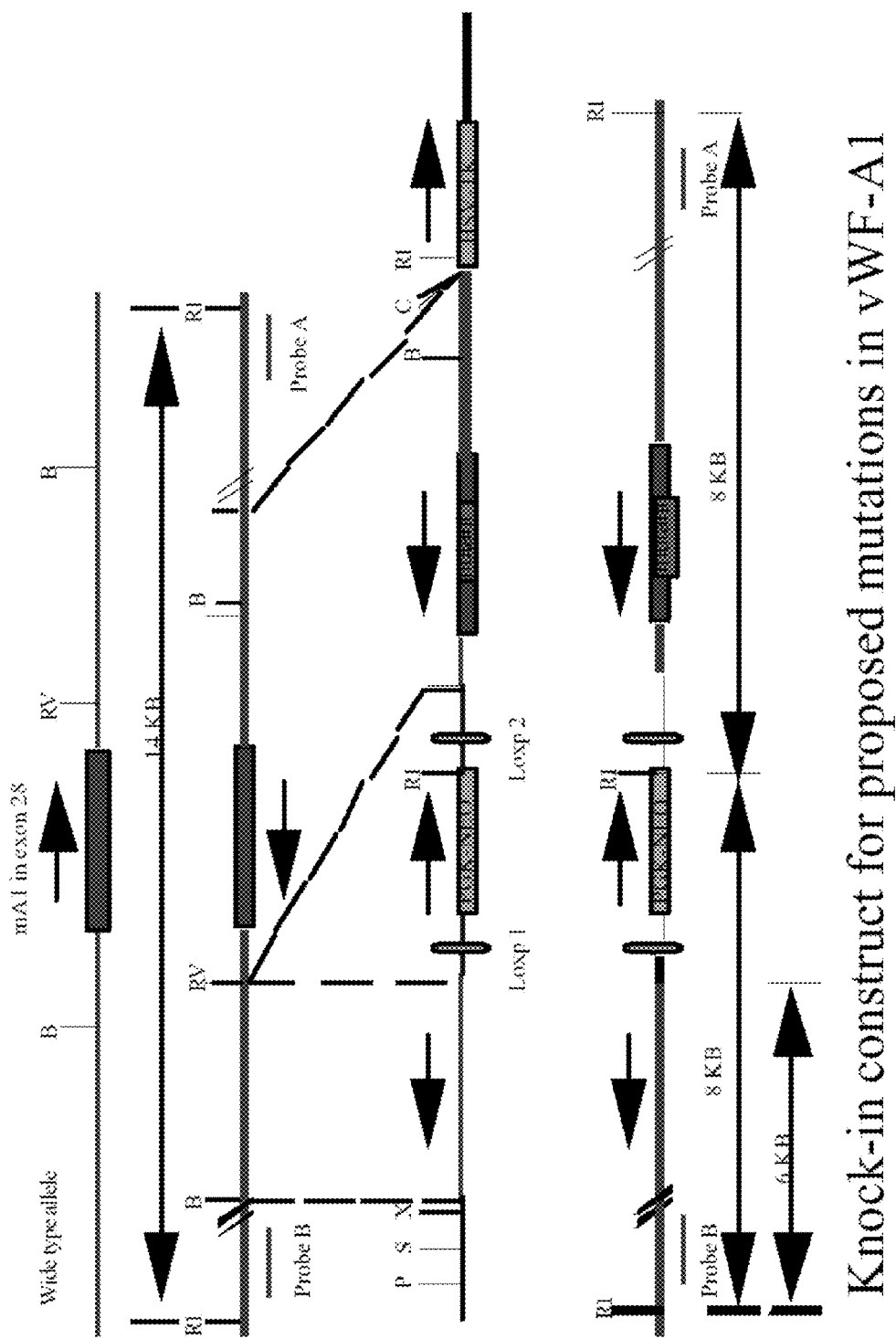
FIGS. 20A and 20B show a scheme for generating transgenic mice with mutant VWF-A1 domains.
Figure 20B:
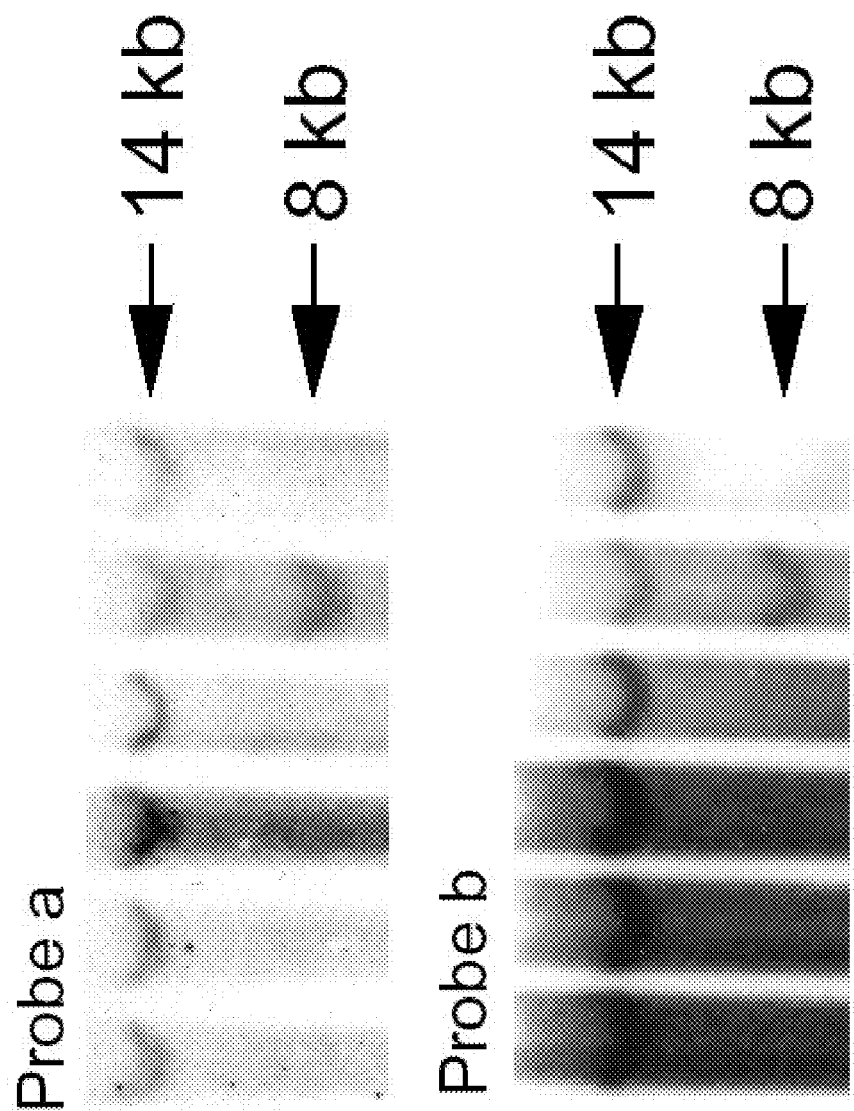

As mentioned previously, a 100-kb P1 clone containing the majority of the VWF gene (Genomic Systems, St. Louis, Mo.) was obtained. Digestion with Bam H1 resulted in a ~5.3 kb fragment containing part of intron 28 (including the splice sites), all of exon 28 and part of intron 29 which was the inserted into the pSP72 vector (Promega, Wis.). This was subsequently digested with Bam H1 and Eco R5 to yield a 2.9 kb (including exon 28) and a 2.4 kb fragment, designated Arm 1 and 2, respectively, both of which were subcloned back into pSP72 vector. This facilitated site-directed mutagenesis of the A1 domain contained within Arm 1. In addition, the 3' end of Arm 1 was extended 2 kb by PCR. Subsequently, Arms 1 and 2 were inserted into a lox P-targeting vector as shown below (FIGS. 20A and 20B). The fidelity of three constructs containing either the 1309I>V or 1326R>H substitutions or both mutations was confirmed by sequence analysis.

Figure 21:
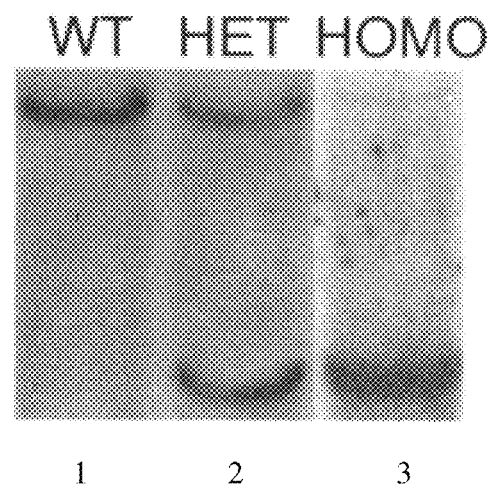
FIG. 21 represents Southern blot analysis wherein heterozygous and homozygous mice for the amino acid substitution at residue 1326 (R1326H; 1326R>H) display the Arg1326His mutation (lanes 2 and 3 respectively) while wild-type animals did not (lane 1).
Figure 22A:
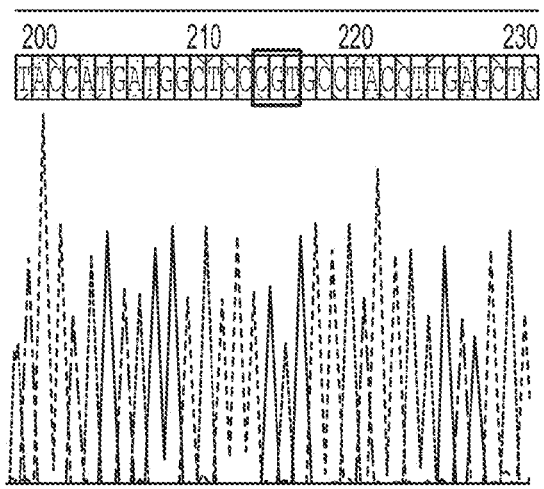
FIGS. 22A through 22C represent sequence analysis of purified PCR products of WT, heterozygous, or homozygous VWF-A1 domains wherein the red-boxed area denotes the conversion of Arg to His (CGT in FIG. 22A wherein the codon corresponds to Arg, CNT in FIG. 22B, and CAT in FIG. 22C wherein the codon corresponds to the amino acid His).
Figure 22B:
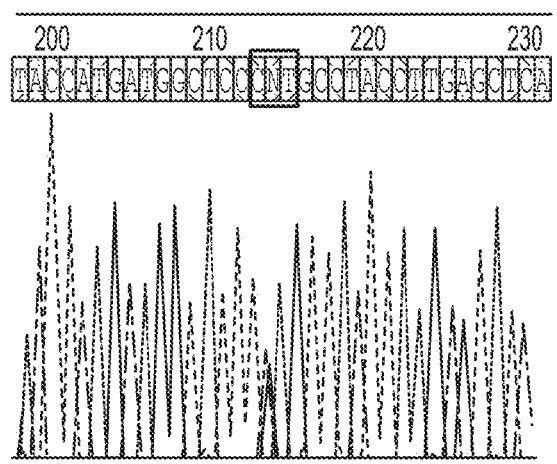
Figure 22C:
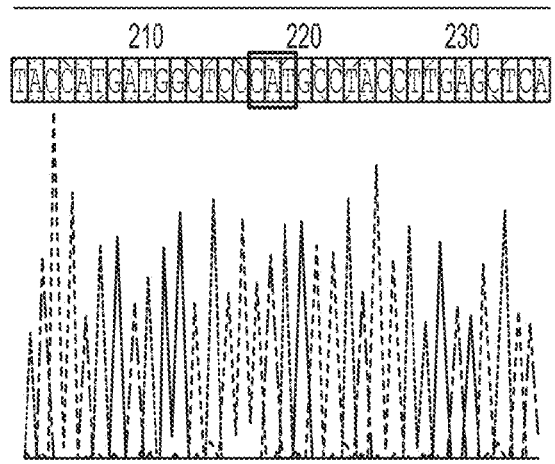

R1 embryonic stem cells derived from a 129/Sv×129/Sv-CP F1 3.5-day blastocysts were electroporated with 25 μg of linearized targeting construct and selected in both G418 (26 μmol/L) and gancyclovir (0.2 μmol/L). Genomic DNA from resistant clones were digested with EcoR1 or KpnI, and analyzed by Southern blot hybridization with probe "a" or "b", respectively, to determine if the construct was appropriately targeted (FIG. 20B). Targeting both the type 2B (Ile1309Val or 1309I>V) mutation and the Arg1326His (1326R>H) mutant constructs, have been successful. In a second step, embryonic stem cell clones that had undergone homologous recombination were transfected with 25 μg of Cre-recombinase-expressing plasmid and selected for G418. Clones in which the neo-cassette was deleted were identified by PCR and injected into C57BL/6 blastocysts (The Siteman Cancer Center Core Facility, Washington University). Male chimeric mice were bred to C57BL/6 Cre-recombinase (+) females to obtain heterozygous animals. Heterozygous mice lacking the neocassette, but containing the 1326R>H mutation, were interbred to obtain wild-type, heterozygous, and homozygous animals. Animals were identified by both Southern analysis (FIG. 21) and by PCR of the A1 domain (FIGS. 22A-22C; red boxed area denotes the conversion of Arg to His).

Determination of the Multimeric Composition of Murine VWF.

For platelet counts, whole blood will be collected into heparinized tubes and 100 μl volumes will be analyzed on a Hemavet (CBC Tech, Oxford, Conn., USA) Coulter Counter. The multimeric structure of murine VWF will be assayed by using the Pharmacia Phast Gel System (Pharmacia LKB Biotechnology). Briefly, samples diluted in 10 mmol/L Tris/HCl, 1 mmol/L EDTA, 2% SDS, 8 mol/L urea, and 0.05% bromophenol blue, pH 8.0, will be applied to a 1.7% agarose gel (LE, Seakem, FMC Bioproducts) in 0.5 mol/L Tris/HCl, pH 8.8, and 0.1% SDS with a stacking gel consisting of 0.8% agarose (HGT, Seakem) in 0.125 mol/L Tris/HCl, pH 6.8, and 0.1% SDS. After electrophoresis the protein will be transferred to a polyvinylidene fluoride membrane (Immobilon P, Millipore) by diffusion blotting for 1 hour at 60° C. The membrane will be blocked with 5% nonfat dry milk protein solution for 1 hour at room temperature. After washing with PBS/T, pH 7.4, the blot will be incubated with a polyclonal antibody raised in rabbits against murine VWF at a dilution of 1:500, washed, and incubated with a goat anti-rabbit horseradish peroxidase (Sigma) diluted 1:2000 in PBS/T. After three washes with PBS/T, the membrane will be incubated with the substrate solution (25 mg 3,3'-diaminobenzidine tetrahydrochloride (Sigma) in 50 mL PBS with 10 μL 30% $H_2O_2$). The enzyme reaction will be stopped by washing the membrane with distilled water.

Figure 23:
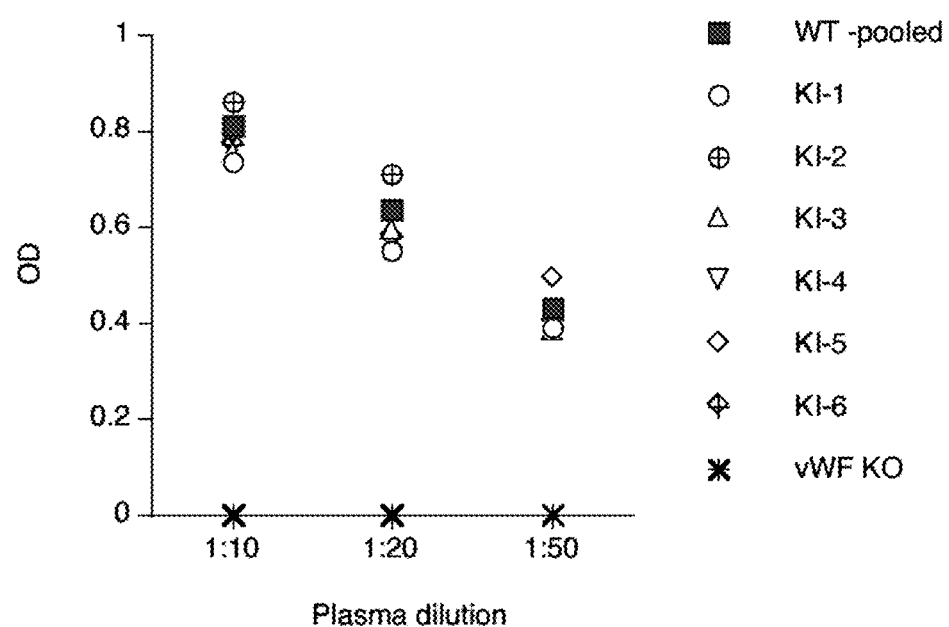
FIG. 23 is a graph of an ELISA assay which demonstrated that conversion of Arg to His in the mouse A1 domain did not alter plasma protein levels of VWF in mutant mice nor its ability to form multimers. The ELISA assay detected mouse VWF in plasma obtained from WT and homozygous (KI) animals, but not from plasma obtained from animals deficient in VWF (VWF KO).
Figure 24:
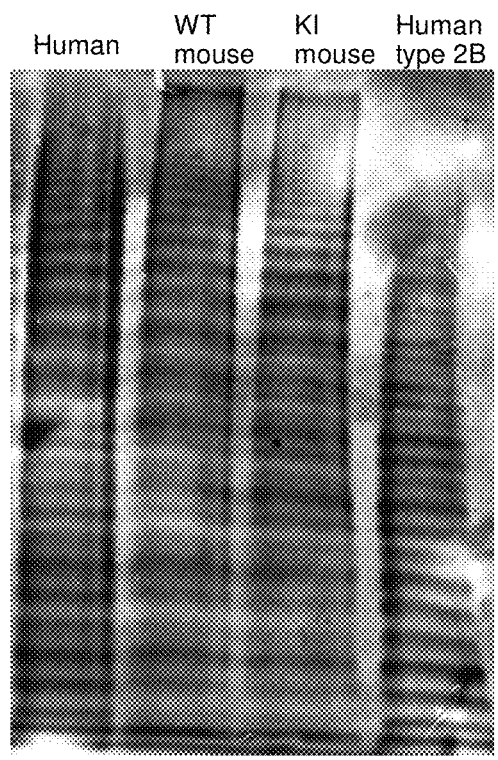
FIG. 24 is a gel image of multimer gel analysis of plasma VWF that revealed an identical banding pattern between mouse and human VWF. Incorporation of His at position 1326 in the mouse A1 domain had no effect on multimerization of VWF in mutant mice.

To demonstrate that conversion of Arg to His in the mouse A1 domain at position 1326 did not alter plasma protein levels of VWF nor its ability to form multimers, we performed an ELISA to detect mouse VWF in plasma obtained from WT and homozygous animals (FIG. 23). As shown in FIG. 23, plasma levels of VWF from homozygous mice (KI) were comparable to WT at all dilutions tested. Moreover, multimer gel analysis of plasma VWF revealed an identical banding pattern between mouse and human VWF. Incorporation of His at position 1326 in the mouse A1 domain had no effect on multimerization of VWF (FIG. 24). Thus, we are the first to successfully introduce a point mutation into mouse VWF A1 domain.

Bleeding Time for Human Platelet-Induced Hemostasis:

This assay provides an indirect measure of the ability of platelets and VWF to support hemostasis by interacting with the injured vessel wall. It also indirectly determines the function of multiple receptors and ligands on platelets that are required to form a hemostatic plug. That said, it provides direct evidence that the bleeding defect in our animals can be corrected by the administration of human platelets (FIG. 12). It is performed by immersing the severed tip (10 mm) of the animal's tail in isotonic saline at 37° C. and monitoring the length of time required for bleeding to cease. Homozygous mutant mice will be infused with an equal volume of either saline or purified human platelets. Platelet specific antibodies or drugs will be administered as described above and their ability to prolong bleeding time evaluated. All experiments will be stopped at 10 min by cauterizing the tail (51).

Figure 25:
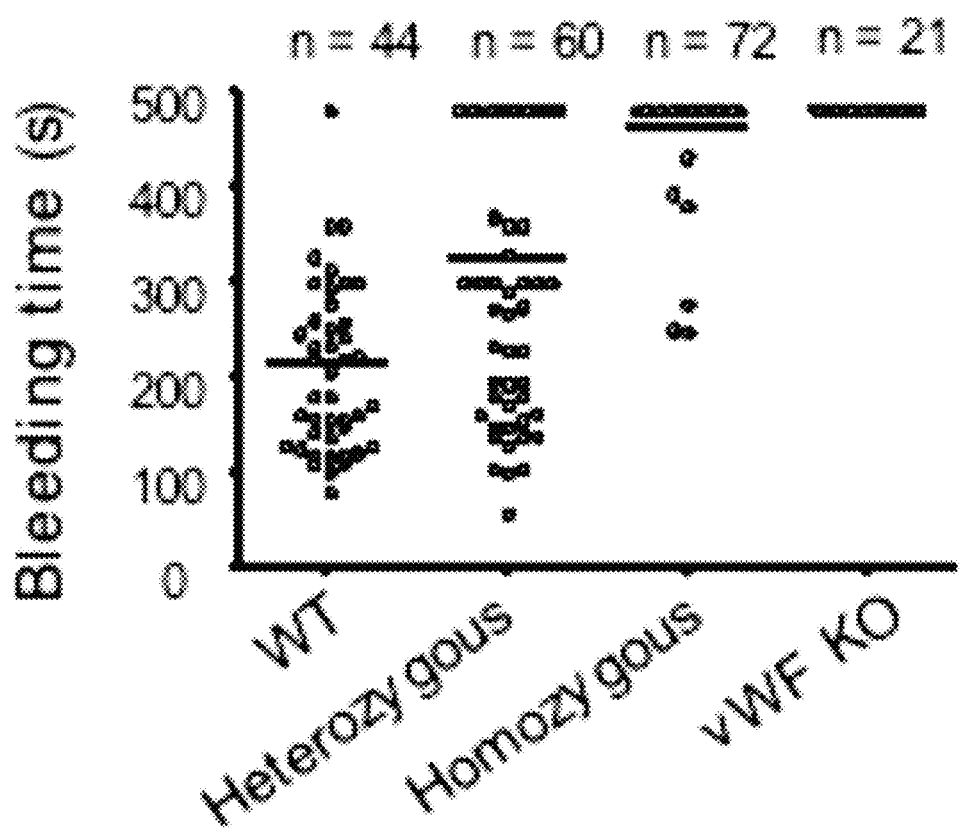
FIG. 25 is a graphical representation of the bleeding times (s) observed in the mutant VWF-A1 mice that are either heterozygous or homozygous for the 1326R>H mutation. Results are compared to normal counterparts and VWF-deficient mice. Tail cut=1 cm.
Figure 26:
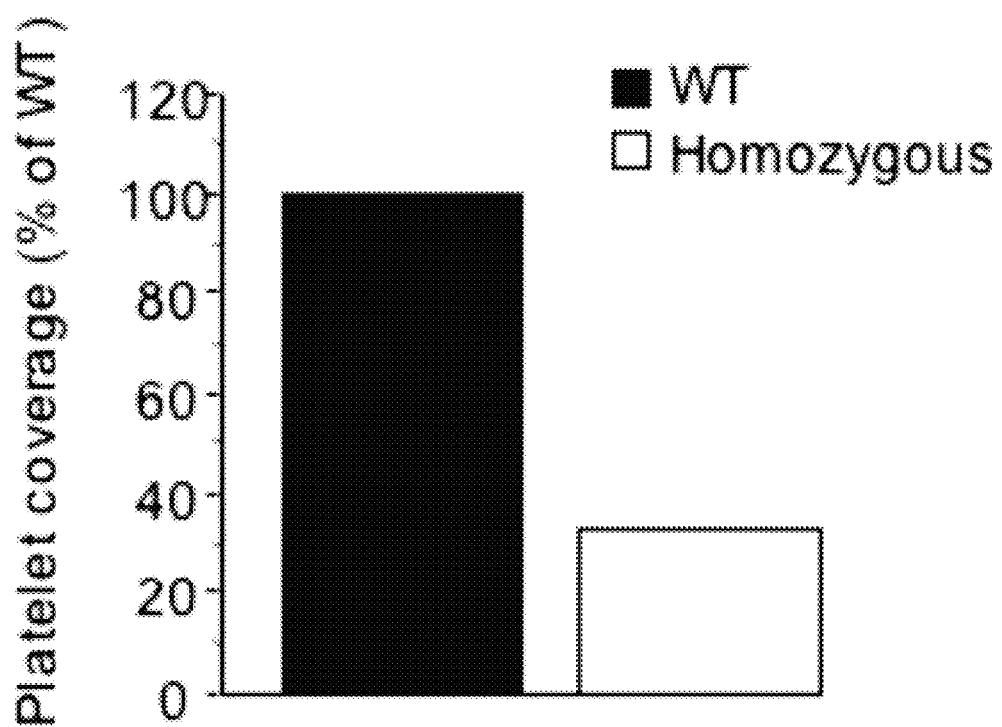
FIG. 26 is a bar graph depicting thrombus formation induced by perfusion of whole blood from either wild type (WT) or homozygous mutant mice over surface-immobilized collagen in vitro wherein an ~80% reduction in thrombus formation was observed compared to WT controls.

Although homozygous mice bearing the 1326R>H mutation are viable, they demonstrate a bleeding phenotype similar to that of animals deficient in VWF (KO) only when 10 mm of the tail is cut (FIG. 25 and FIG. 35B). Over 90% of these mice bled for a minimum of 8 minutes (end point) in contrast to 3.5 minutes for WT animals as measured by severing 1 cm of their tail. Moreover, thrombus formation induced by perfusion of whole blood from mutant mice over surface-immobilized collagen in vitro was reduced by ~80% as compared to WT controls (FIG. 26). To further characterize the bleeding phenotype depicted in FIG. 35B, standard techniques known in the art were employed, which involves removal of a minimal amount of the animal's tail (~5 mm). A slight, but statistically significant (P<0.01), increase in bleeding was observed in the homozygous 1326R>H mutant mice as compared to WT littermates, but not to the extent of the VWF knockout mouse (a mouse model that bleeds profusely due to complete lack of this plasma glycoprotein). In the homozygous 1326R>H mutant mouse, a larger cut (~10 mm) is needed in order to see a bleeding phenotype comparable to the VWF deficient mouse. Since these mice continue to bleed, the experiment is stopped at 8 min in order to prevent death. This phenotype observed in the 1326R>H mutant mouse is similar to the bleeding observed in human patients who have type 2M VWF disease. As not all type 2M mutations result in a complete loss of interaction between GPIb alpha and VWF-A1, but resemble the adhesion defects outlined for the 1326R>H mutant mouse, this genetically modified mouse model will be useful for directing therapies aimed at patients that have a partial but not complete defect in binding between GPIb alpha and VWF-A1.

Platelet Adhesion Studies in Mice Expressing a Mutant VWF-A1 Domain

Figure 27:
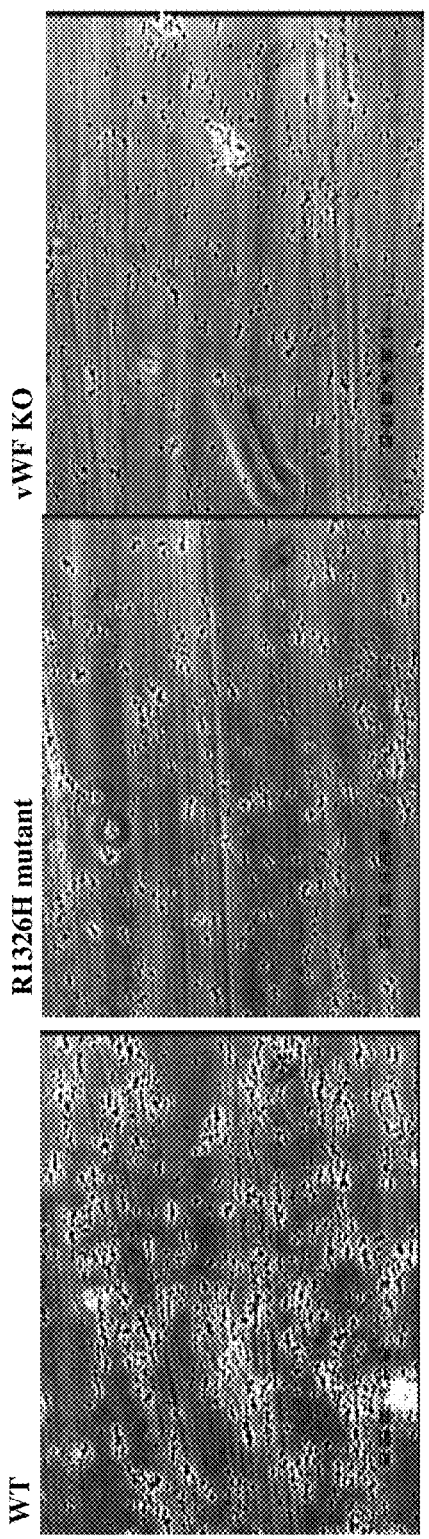
FIG. 27 are micrographs that demonstrate reduced thrombus formation occurring when whole blood from either the knock-in animals (homozygous for the R1326H mutation) or WT is perfused over collagen-coated cover slips at a shear rate of 1600 $s^{-1}$ indicating a 70% reduction in thrombi formed on collagen as compared to WT controls.

One goal of the work is to generate mice with mutant A1 domains that alter the kinetics of its interactions with GPIb alpha on mouse platelets. The first mutation we chose to introduce was the substitution of histidine for arginine at position 1326. This mutation was chosen based on our crystal structure analysis of the mouse and human A1 domains, which suggested that the location of this amino acid is central to GPIb alpha binding. Mice bearing this mutation are viable and demonstrate a bleeding phenotype, albeit not as severe as those lacking VWF (VWF KO) (FIGS. 35A and 35B). This was not unexpected as VWF is still present, but has a reduced ability to interact with platelets at high shear rates (>1600 $s^{-1}$). FIG. 27 demonstrates reduced thrombus formation that occurs when whole blood from these knock-in animals is perfused over collagen-coated cover slips at a shear rate of 1600 $s^{-1}$. Results thus far indicate a 70% reduction in thrombi formed on collagen as compared to WT controls.

Figures 28A, 28B:
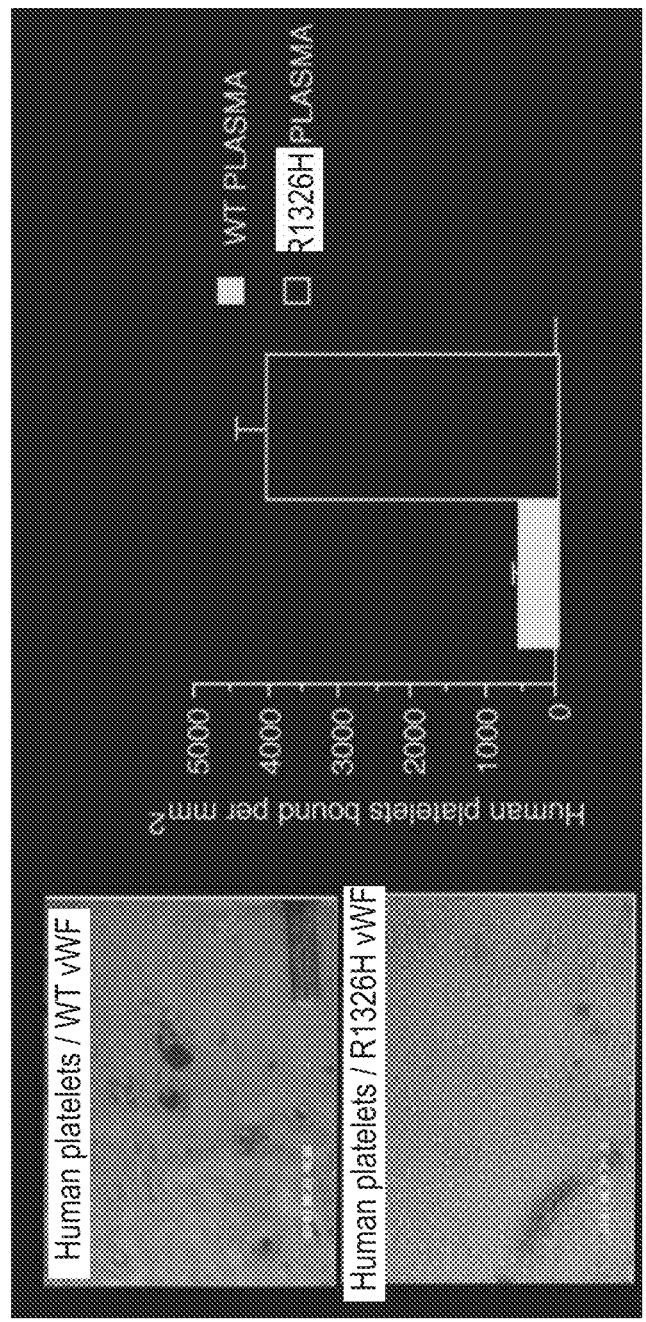
FIGS. 28A and 28B demonstrate a platelet adhesion assay in flow. R1326H mutant mouse VWF promotes interactions with human platelets under physiologic flow conditions, wherein anticoagulated human blood was infused over surface-immobilized WT or mutant mouse plasma VWF at 1600 $s^{-1}$ as shown in the micrographs of FIG. 28A.
Figures 29A, 29B:
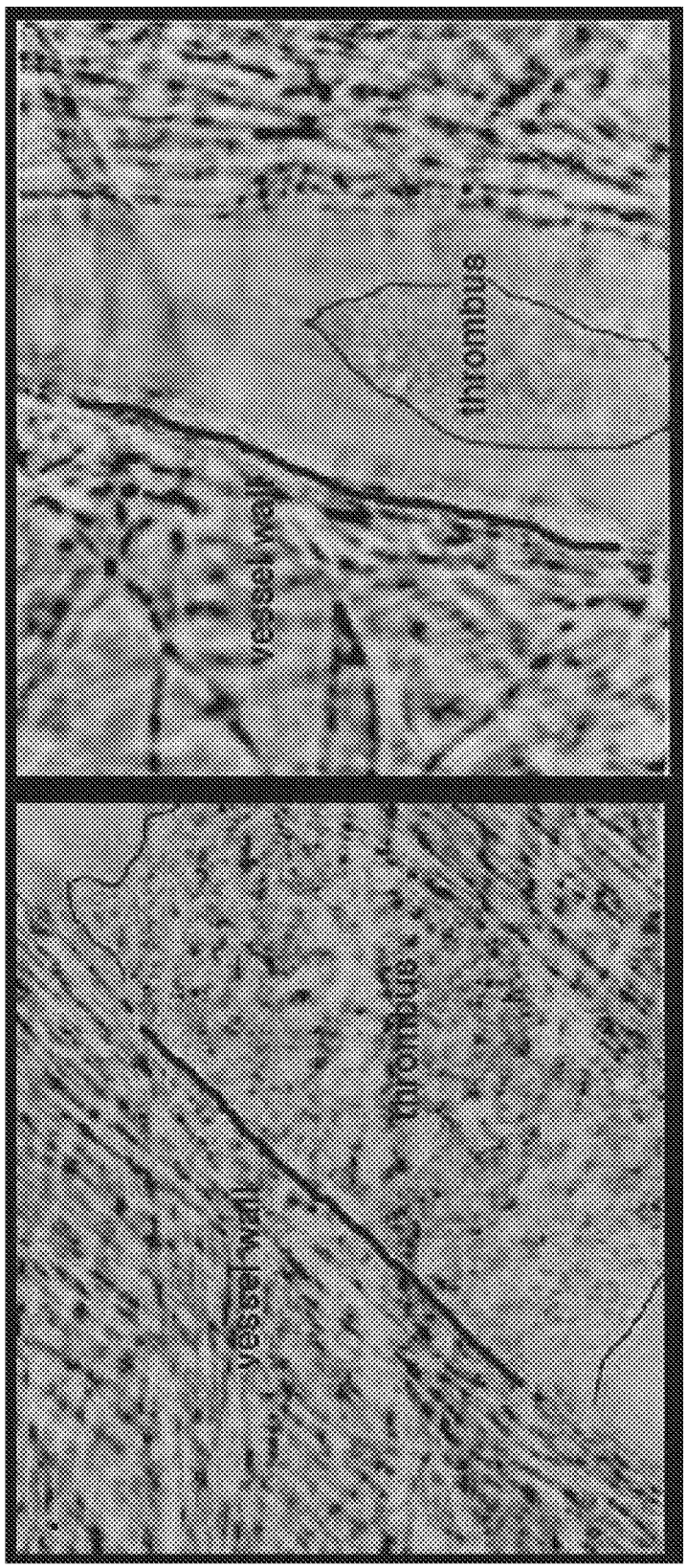
FIGS. 29A and 29B are transmitted light micrographs demonstrating that homozygous mutant mice infused with human (FIG. 29A) but not mouse platelets (FIG. 29B) were able to generate an arterial thrombus that occludes the vessel lumen in response to laser-induced vascular injury as depicted by intravital microscopy.

To demonstrate that the 1326R>H mutant in the A1 domain of mouse VWF (wherein the mutant VWF-A1 domain comprises SEQ ID NO: 5) is far superior to promoting interactions with human platelets under physiologic flow conditions, anticoagulated human blood was infused over surface-immobilized WT or mutant mouse plasma VWF at 1600 $s^{-1}$ (FIGS. 28A and 28B). Results indicate that the mutant form of mouse VWF can support human platelet attachment to levels observed for its human counterpart, thus making it an ideal system to evaluate human platelet behavior and the impact of novel anti-thrombotic drugs in an animal model. Moreover, this observation was not limited to ex vivo studies, as homozygous mutant mice infused with human (FIG. 29A) but not mouse platelets (FIG. 29B) were able to generate an arterial thrombus that occludes the vessel lumen in response to laser-induced vascular injury as depicted by intravital microscopy (transmitted light). Preliminary results indicate that mouse and human A1 domains are structurally similar and serve an identical functional role in the initiation of thrombus formation. Moreover, the ability of the "humanized" mouse A1 domain to support human platelet adhesion to the same degree as its human VWF-A1 counterpart ex-vivo, as well as its preferential binding of human platelets in vivo (FIG. 29A), suggests that our animal model will be an ideal system for preclinical screening of therapies directed at limiting the interactions between GPIb alpha and the VWF-A1 domain. Moreover, as both hemostasis and thrombosis also rely other key adhesion receptors on human platelets, such as those that interact with collagen OR fibrinogen FIG. 1B), this model can also be used for testing therapies directed against other human platelet receptors and ligands critical for these processes.

Figure 30:
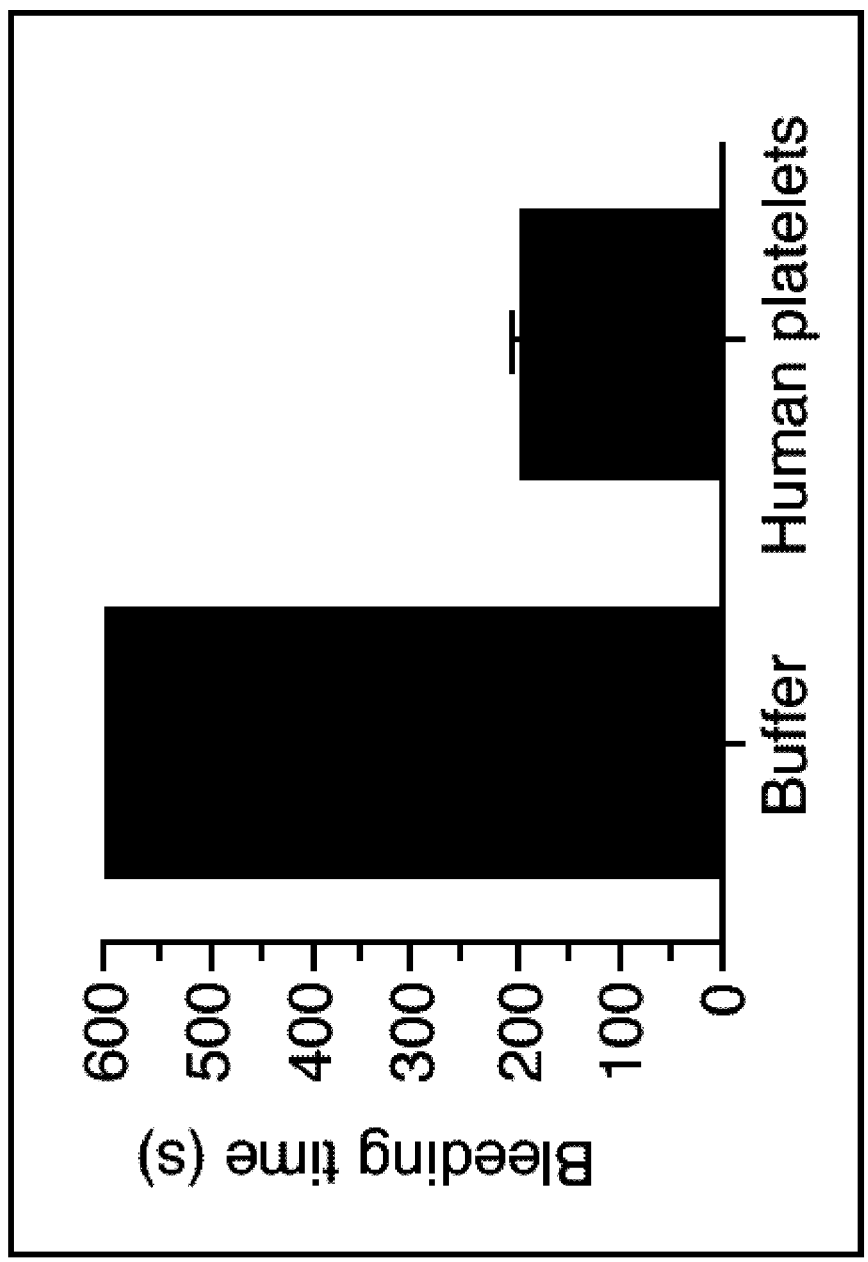
FIG. 30 is a bar graph that depicts the average bleeding time for mice receiving blood-banked human platelets (~3 minutes for a 1 cm tail cut) or given an intravenous infusion of a physiological buffered saline solution (10 minutes (end point)).

To assess the biological significance of this finding in terms of its effect on hemostasis, homozygous mutant animals received an infusion of blood-banked human platelets and bleeding time was subsequently measured by severing 1 cm of their tail. Average bleeding time for mice that received human platelets was ~3 minutes vs. 10 minutes (end point)

for animals given an intravenous infusion of a physiological buffered saline solution (FIG. 30). Results indicate that not only can the mutant form of mouse VWF support human platelet adhesion both ex-vivo and in vivo assays, but it can also perform its biological function; supporting hemostasis in the context of vascular injury.

Evaluation of Platelet-VWF Behavior in Flow.

Blood will be collected by cardiac puncture from anesthetized mice and thrombin-mediated activation prevented by the addition of hirudin (160 U/ml, Sigma) (68). Platelet adhesion to a glass cover slip coated with 100 μg/ml of equine tendon collagen (Helena Laboratories, Beaumont, Tex.) will be assessed in a parallel-plate flow chamber apparatus. Whole blood will be infused through the chamber at a wall shear rate of 1600 $s^{-1}$ for 3 minutes. As platelet adhesion under these homodynamic conditions requires VWF deposition and subsequent interactions between its A1 domain and GPIb alpha, the extent of platelet coverage should provide a gross estimate of the degree in impairment between this receptor-ligand pair. In addition, plasma VWF will be purified from these animals to evaluate platelet attachment to this immobilized substrate in flow. The surface area covered by adherent platelets at the end of each experiment will be determined (Image Pro Plus software) and expressed as a percentage of platelet coverage using blood from WT littermates. To better isolate GPIb alpha-VWF A1 interactions, identical experiments can be performed using platelets isolated from alphaIIb beta 3 deficient animals and reconstituting them in platelet poor plasma from our mutant A1 knock-in mice.

Evaluation of Platelet-VWF Behavior In Vivo.

In addition to the proposed in vitro work, platelet-VWF interactions in vivo will also be studied using intravital microscopy (Falati et al. (2002) *Nature Medicine* 8(10): 1175-80). This is accomplished by using a murine model of thrombosis that involves laser-induced injury to microvessels contained within the mouse cremaster muscle. The surgical preparation of animals, insertion of lines for administration of cells and anesthesia, will be performed as previously described (69). Human platelets will be collected and prepared, fluorescently labeled, perfused into a mouse model (such as the transgenic mouse of the current invention) via an intravenous injection (Pozgajova et al., (2006) *Blood* 108(2):510-4).

Surgical Preparation of Animals: Insertion of Lines for Administration of Cells and Anesthesia.

Figure 31:
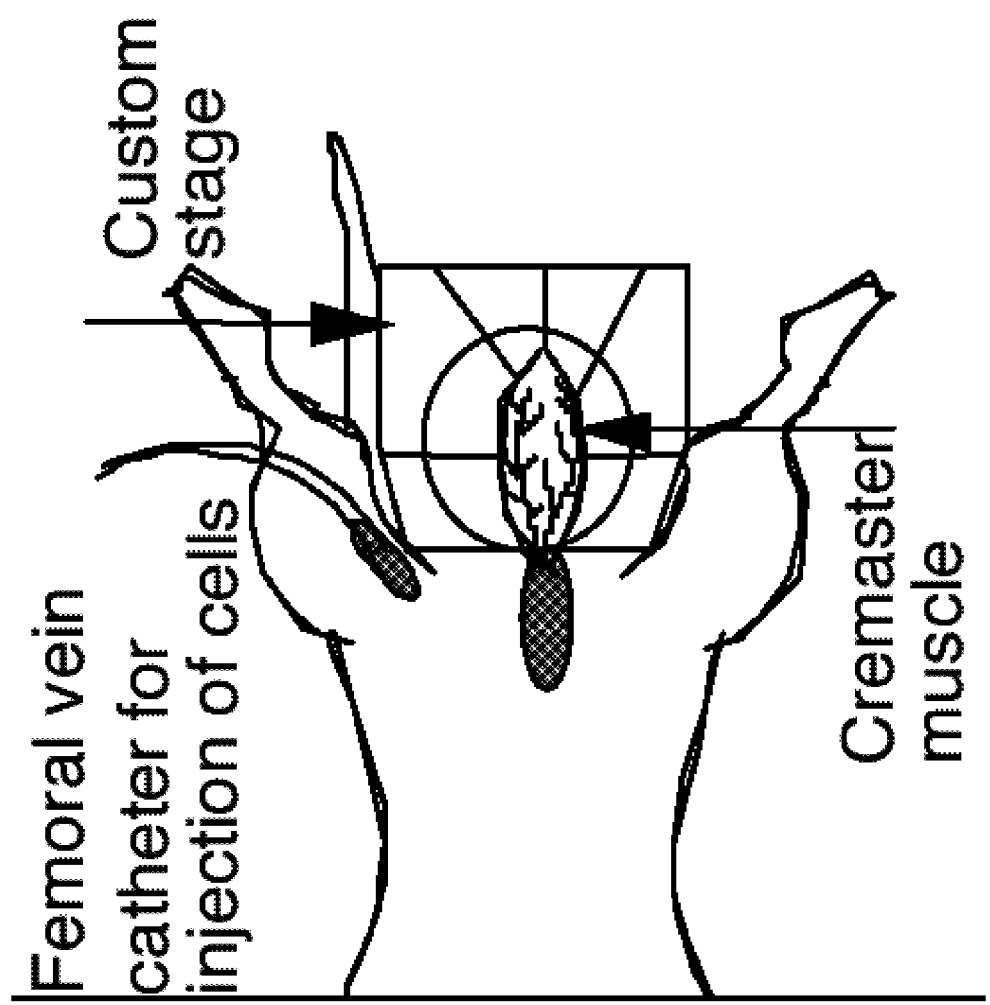
FIG. 31 is a schematic representing the isolation of the cremaster muscle and the catheter set-up used in intravital microscopy assays to assess thrombus formation.

Briefly, the skin covering the scrotum will be incised and the intact cremaster muscle dissected free from the connections to the subcutis. The mouse will be placed on a custom-built plexiglass board, and the exposed muscle positioned on a heated circular glass coverslip (25 mm) for viewing. The muscle will be slit along the ventral surface (using a thermal cautery), the testis excised, and the muscle spread across the coverslip with attached sutures (6/0 silk) (FIG. 31). The cremaster muscle will be kept continuously moistened by superfusion throughout the experiment with sterile, bicarbonate-buffered (pH 7.4), saline solution (37° C.) that is pregased with a 5% $CO_2$, 95% $N_2$ mixture for $O_2$ depletion. All parts of the setup in contact with the superfusion buffer will be presoaked with 1% Etoxaclean (Sigma Chemical Co., St. Louis, Mo.) overnight followed by extensive rinsing in 70% ethanol and endotoxin-free distilled water. The number of mice used for these experiments will be kept to the minimum necessary to establish statistically significant observations. Anesthetized animals will be euthanized after each experiment by $CO_2$ inhalation.

Vascular Trauma Will be Generated as Follows:

The segment of an arteriole will be visualized and recorded as "pre-injury". Subsequently, endothelial damage will be induced via a pulsed nitrogen dye laser at 440 nm applied through the microscope objective using the Micropoint laser system (Photonics Instruments, St. Charles, Ill.). The duration of exposure of the endothelium to the laser light will be varied to produce either a mild injury that supports the formation of a platelet monolayer or significant injury resulting in thrombus formation. The region of interest will then be videotaped and analyzed as described below.

Figure 32:
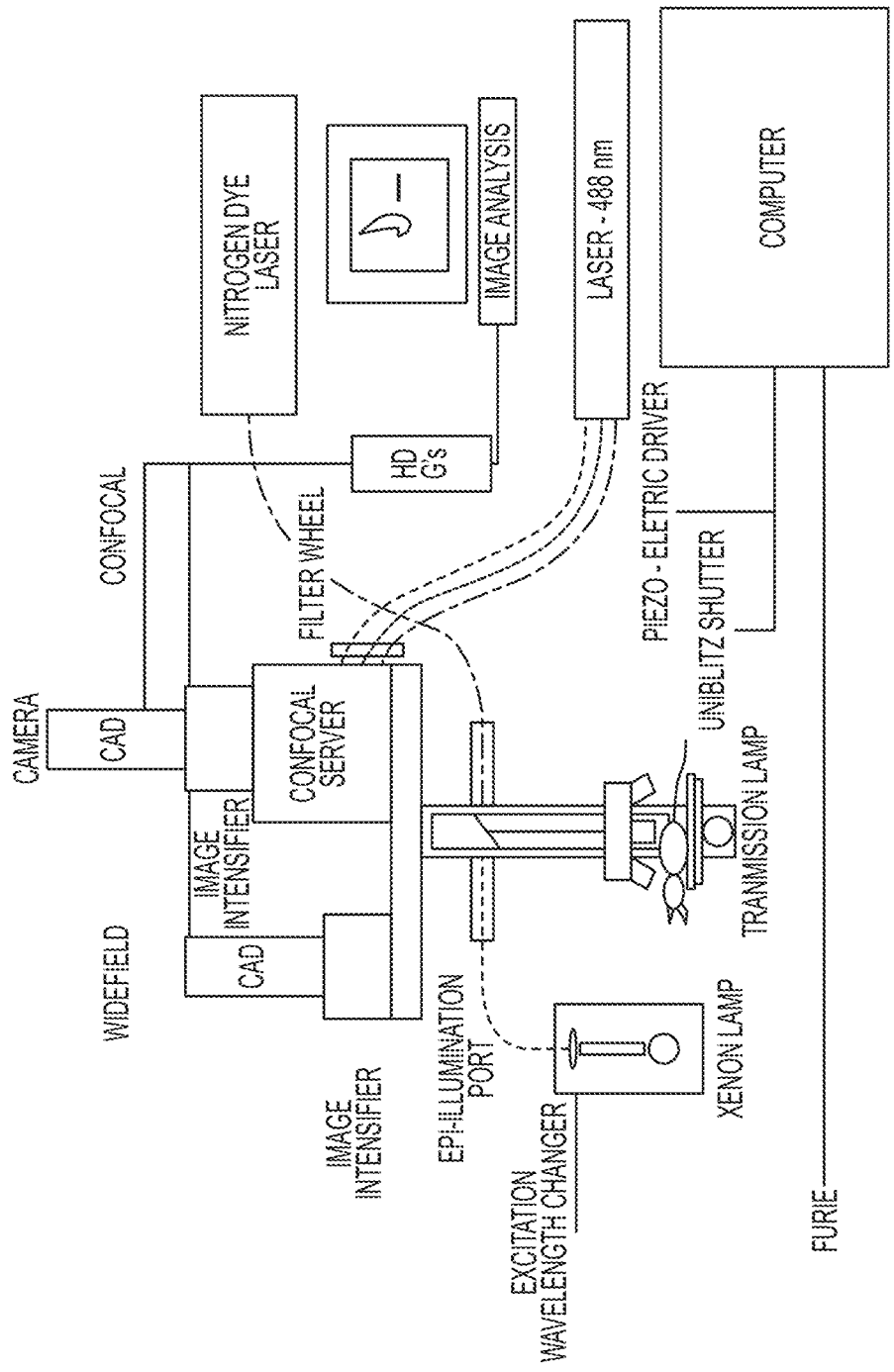
FIG. 32 is a schematic of an intravital microscopy method.

For example, vascular damage can subsequently be induced in arterioles contained within the cremaster muscle of mice by either 1) pulsed nitrogen dye laser applied through the objective of an intravital microscope (FIG. 32) or 2) standard application of a ferric chloride solution (Furie et al. *J. Clin. Invest.* 2005; 115:3355). The latter method has the advantage of exposing significant more subendothelial collagen, which will be beneficial for testing the role of the collagen receptors α2β1 in thrombus formation.

Figure 33A:
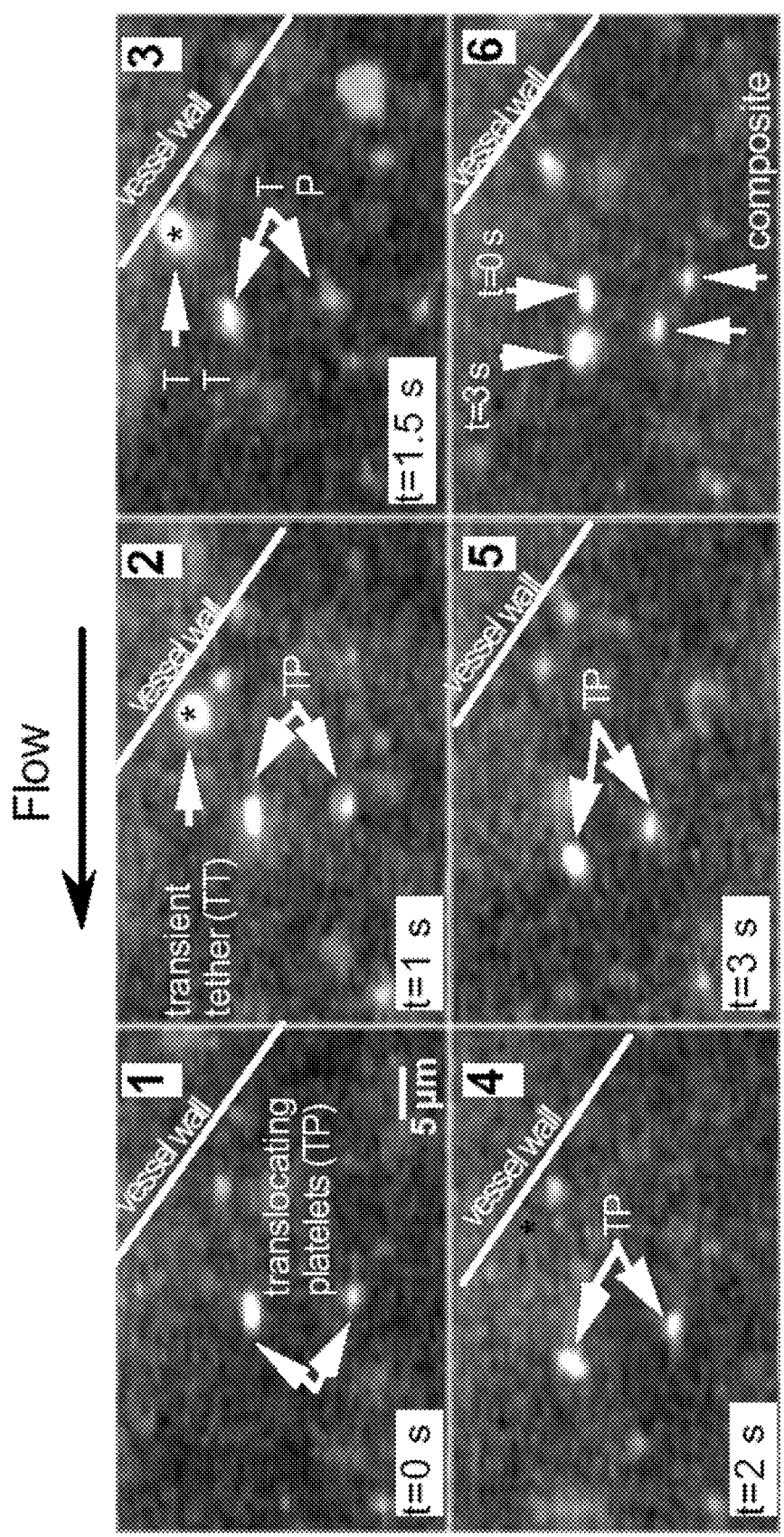
FIGS. 33A and 33B shows images of mouse platelet interactions and a bar graph of such interactions in a wild type animal.
Figure 33B:
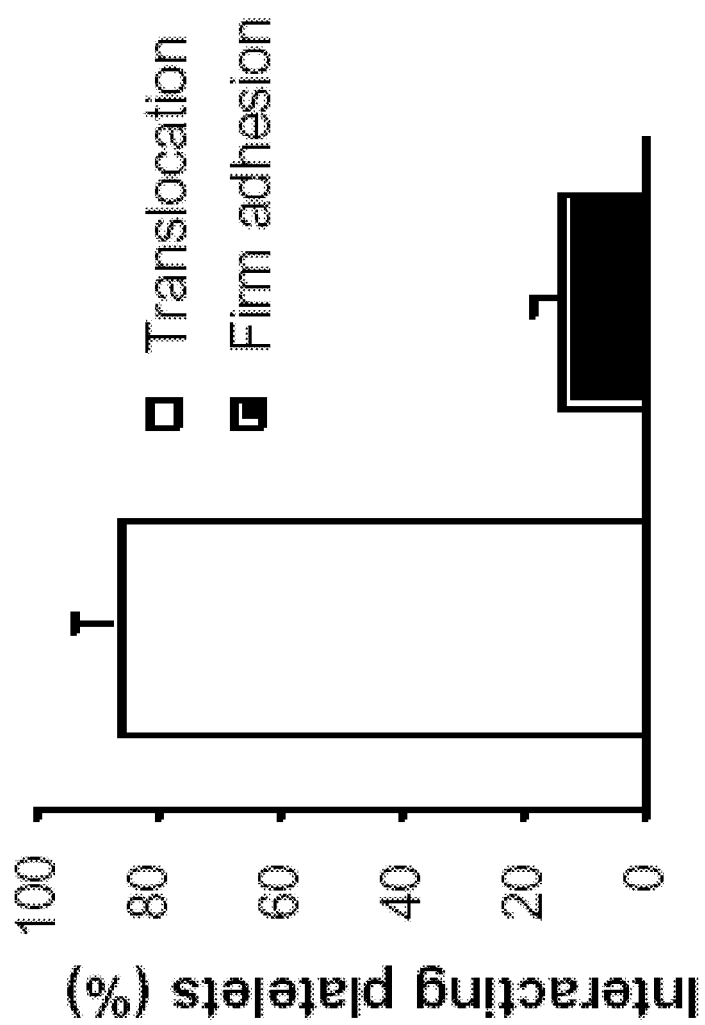
Figure 40:
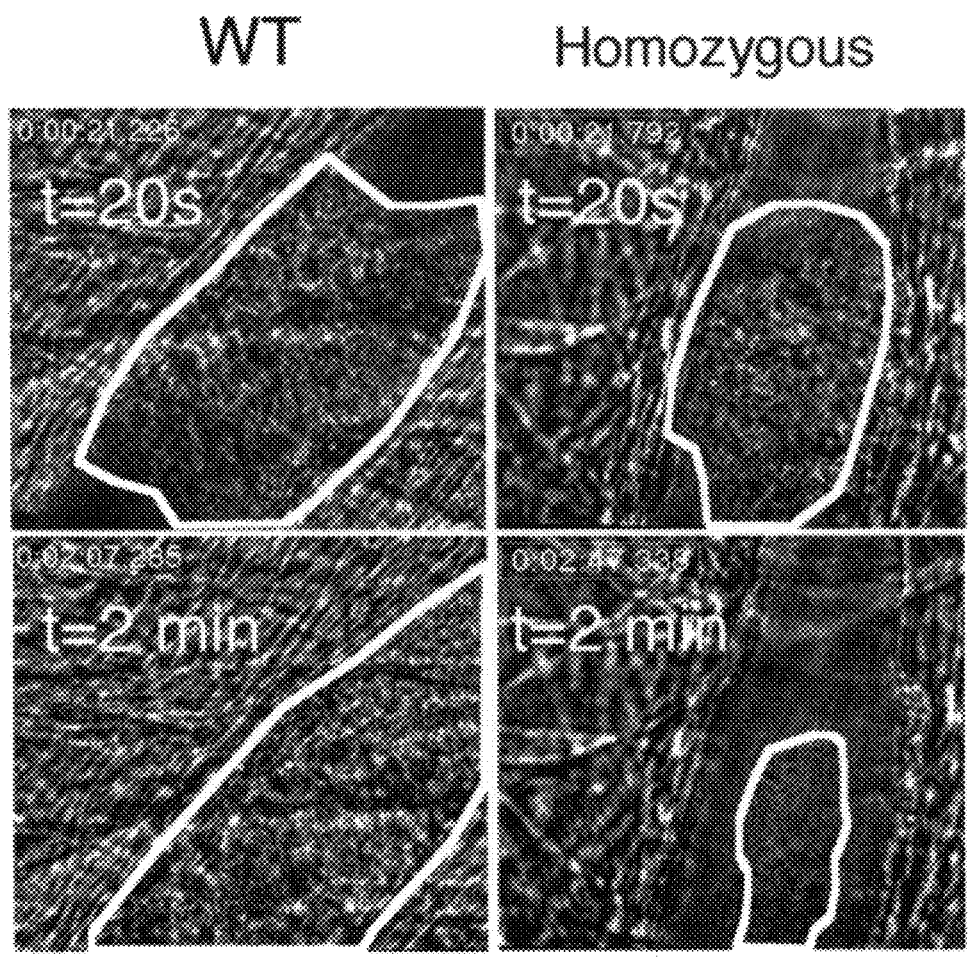
FIG. 40 depicts representative photomicrographs showing murine platelet accumulation at sites of laser-induced arteriolar injury in WT or homozygous mutant animals 20 s and 2 min post-injury. White lines demarcate the extent of the thrombus.

For studies analyzing the dynamic interactions between individual platelets and the injured vessel wall (attachment, translocation, and sticking), cells purified from genetically altered mice will be labeled ex-vivo with a derivative of carboxyfluorescein (BCECF, Molecular Probes) (Diacovo et al. *Science.* 1996). A human thrombus generated in the mutant mouse can also be visualized by this technique, thus allowing to distinguish human platelets from endogenous circulating mouse platelets upon illumination with an appropriate laser light source (see FIG. 40). Cells ($1\times10^7$/g of BWT) will be subsequently injected intravenously into mice bearing WT mouse (control) or the "humanized" A1 domains and their behavior visualized in the microcirculation using an intravital microscope (Zeiss, Axiotech Vario; IV500, Mikron Instruments, San Diego, Calif.; and the like) equipped with an iXON EM camera or a silicon-intensified camera (VE1000SIT; Dage mti, Michigan City, Ind.), a Yokogawa CSU22confocal head, and a 488 nm laser line (Andor Technology, Revolution series). A Xenon arc stroboscope (Chadwick Helmuth, El Monte, Calif.) will serve as the light source and fluorescent cells will be viewed through 60× or 100× water immersion objectives (Acroplan, Carl Zeiss Inc.). A tethered platelet will be defined as a cell establishing initial contact with the vessel wall (FIG. 33A, panel 2-3; FIG. 33B). The translocating fraction will be defined as number of tethered platelets that move at a velocity significantly lower than the centerline velocity for >1 s. The sticking fraction will be defined as the number of translocating cells that become stationary for >30 s post-tethering. Second order arterioles (up to 50 μm in diameter) will be evaluated for platelet interactions before and after the injury. Evaluation of platelet circulation in larger arterioles may be less accurate secondary to hemoglobin-mediated quenching of fluorescence emitted from platelets traveling in an area of the blood stream distal to the focal plane of the objective. Epi-illumination will only be used during video recordings to minimize possible phototoxic effects on tissue.

Figure 34B:
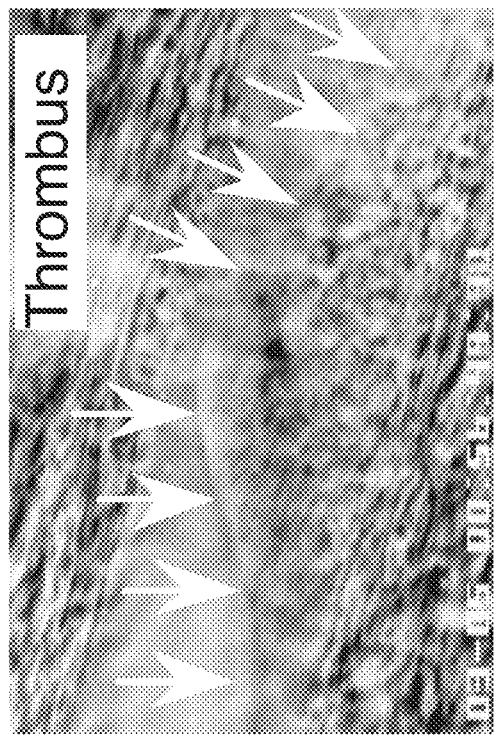
FIGS. 34A and 34B represents photomicrographs that depict the vessel wall in a wild type mouse in the (FIG. 34A) absence of injury or (FIG. 34B) post-laser-induced injury as visualized under transillumination (40× objective). Thrombus is indicated by the arrows.
Figure 34A:
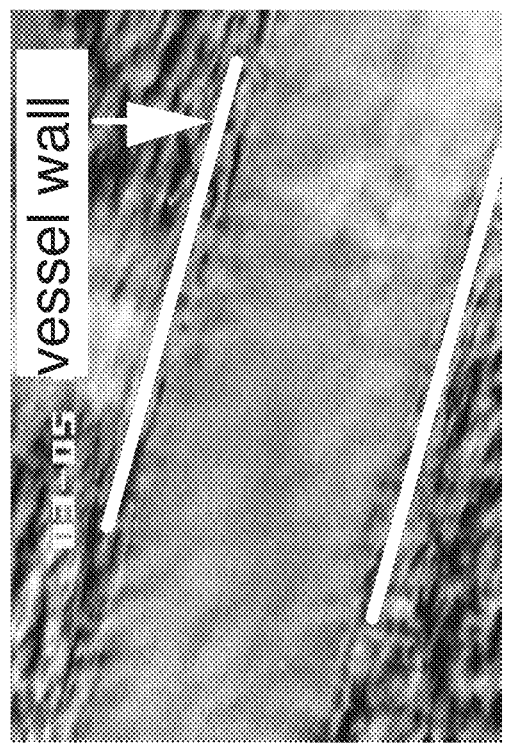

A role for GPIb alpha as well as the collagen (α2β1) and the fibrinogen (αIIb (33) receptors can be evaluated by using function-blocking antibodies to these proteins. Moreover, FDA approved anti-thrombotics (such as clopidogrel and tirofiban) can be examined as to whether the drugs inhibit human platelets from forming a thrombus in vivo, validating the mouse model for use in pre-clinical screening. The effect that antibodies and drugs have on altering the interaction between GPIb alpha-VWF-A1 interaction is determined by evaluating whether thrombus formation in the proposed mice is reduced or augmented upon arteriolar injury (FIGS. 34A and 34B).

For all experiments, the centerline erythrocyte velocity (Vrbc) is measured using an optical doppler velocimeter (Microcirculation Research Institute, Texas A&M College of Medicine, College Station, Tex.) prior to and after inducing the injury. Shear rate (SR) is then calculated based on Poiseulle's law for a Newtonian fluid: SR=8(Vmean/Dv), where Dv is the diameter of the vessel and Vmean is estimated from the measured Vrbc (Vmean=Vrbc/1.6).

Characterization of Thrombus Formation:

Thrombus formation can be characterized as follows: (1) Early individual platelet interactions with the damaged vessel wall (number of fluorescently labeled human platelets that attach during the first minute post-injury); (2) time required for thrombus generation of >20 μm diameter; (3) the ability of thrombi to remain at the initial site of vascular injury and not break free (measure of stability); (4) time until vessel occlusion; and (5) site of vessel occlusion, that is, at the site of injury or downstream from it. Platelet-vessel wall interactions can be viewed through 40× or 60× water immersion objectives. To standardize in vivo conditions, the velocity of flowing blood (shear rate) pre-injury is determined by measuring the centerline erythrocyte velocity (Vrbc) using an optical doppler velocimeter. Shear rate (SR) can then be calculated based on Poiseulle's law for a Newtonian fluid: SR=8×(Vmean/Dv), where Dv is the diameter of the vessel and Vmean is estimated from the measured Vrbc (Vmean=Vrbc/1.6). Vessel and thrombus diameters are measured using imaging software (ImagePro Plus).

Administration of Antibodies:

Function-blocking monoclonal antibodies 6D1 (anti-human GPIb alpha), 6F1 (anti-human α2β1) and 7E3 (anti-human αIIbβ3) have been generously provided by Dr. Barry Coller (Rockefeller University, NY). All antibodies are converted to F(ab')2 fragments to limit Fc receptor interactions in vivo. An intravenous dose of 10 μg/g body weight is given approximately 10 minutes after the injection of human platelets but 30 minutes prior to inducing vascular injury. Non-function blocking antibodies to these receptors is used as negative controls and administered under identical conditions. To ensure optimal ligand availability for the collagen and fibrinogen receptors on human platelet, mice possessing the A1 domain mutation have been bred with animals genetically deficient in α2β1 or αIIbβ3. Thus, endogenous platelets in these animals not only have a reduced ability to interact with the VWF-A1 domain, but also are incapable of binding to collagen or fibrinogen, respectively. Although human platelets have been shown to circulate in mice for a maximum of 24 hours, we can ensure that an equivalent percentage of human platelets are present at the time of vascular injury under each experimental condition (Xu et al. *J. Clin. Invest.* 2006; 116:769). Thus, 50 μl is obtained from an inserted venous catheter and flow cytometric analysis will be performed to determine the percentage of circulating fluorescently-labeled human platelets.

Administration of Drugs:

In comparison to aspirin, clopidogrel (Plavix) is the second most commonly used anti-thrombotic drug that targets one of the ADP receptors (P2Y12) on platelets, causing irreversible inhibition (Hankey et al. *Med. J. Aust.* 2003; 178:568). ADP is a potent mediator of platelet activation and aggregate formation, and thus considerable effort and funds have been devoted to inhibiting this activation pathway in platelets. Clopidogrel was approved by the FDA in 1997 for clinical use and was found to be of benefit in the secondary prevention of major vascular events in patients with a history of cerebrovascular and coronary artery diseases and major cardiac events post coronary artery stent placement (Gachet et al. *Semin. Thromb. Hemost.* 2005; 31:162). Disadvantages of this drug are: 1) It must be metabolized in the liver to generate an active metabolite, thus limiting its effectiveness in acute settings, and 2) irreversible inhibition that results in a marked prolongation of bleeding time.

Clopidogrel has been shown to reduce thrombus size and delay its formation in mice with a maximal effective dose of 50 mg/kg given the day before and 2 hours prior to experimentation (Lenain et al. *J. Throm. Haemost.* 2003; 1:1133). This drug will be obtained from the hospital pharmacy and tablets will be dissolved in sterile water for oral administration. Control animals will receive water in lieu of drug. The effectiveness of this treatment regime will be confirmed by first measuring the responsiveness of platelets isolated from drug-treated WT animals to ADP-induced aggregation using an optical aggregometer (Chrono-Log Corp.) as previously described (Leon et al. *J. Clin. Invest.* 1999; 104: 1731). As our mutant VWF-A1 domain mice also have a defect in platelet aggregation, these animals cannot be used for the purpose of testing to ADP-induced aggregation ex-vivo. However, this additional phenotype will be advantageous for us as it limits potential competition between human and mouse platelets for binding to ligands exposed at sites of vascular injury. Human platelets will be administered 30 minutes prior to vascular injury and 50 μl of blood drawn to determine the percentage of circulating cells as described above. Platelet rich plasma will also be purified from control and drug treated animals that receive human platelets to evaluate the effectiveness of clopidogrel on preventing ADP-induced aggregation of these cells ex-vivo.

Tirofiban (Aggrastat) is a non-peptide inhibitor of the fibrinogen receptor αIIbβ3 that limits the ability of platelets to form aggregates, an event required for thrombus progression. It has a plasma half-life of approximately 2 hours but only remains bound to platelets for seconds, thus necessitating continuous intravenous administration. It is currently approved for short-term treatment of patients with acute coronary syndrome that require interventional catheterization. Thus, the animals will be dosed based on that given for interventional procedures such as angioplasty, which consists of a 25 μg/kg bolus over 3 minutes followed by a continuous maintenance infusion of 0.15 μg/kg/min until the completion of the experiment (Valgimigli et al. *JAMA*. 2005; 293:2109). Human platelets will be administered 30 minutes prior to vascular injury and 50 μl of blood drawn to determine the percentage of circulating cells as described above.

Platelet Donors.

Mice are used as platelet donors. A means to evaluate murine platelet interactions with wild type and mutant VWF-A1 proteins is via in vitro flow chamber assays. Blood from ~10 mice are required to purify adequate numbers of platelets per assay. Blood from donor animals is obtained from the retro-orbital plexus using a heparinized glass pipette. Mice will be anesthetized with Ketamine and Xylazine prior to the procedure and are euthanized by $CO_2$ inhalation upon completion.

Bleeding Time for Human Platelet Induced Hemostasis.

This assay is carried out as described above.

Solution-Phase Binding Assay.

For type 2B mutant VWF, its capacity to bind to platelet GPIb alpha in solution can be determined. Plasma is harvested from these mice and VWF purified. Various concentrations of the plasma glycoprotein will be indirectly labeled using a non-function blocking, $^{125}$I-labeled mAb to its A1 domain as previously described (67). After a 30 min. incubation, a quantity of this mixture will be incubated with platelets purified from beta 3 deficient mice so to prevent integrin-mediated binding to VWF. After incubation period of 1 hour, an aliquot of this mixture will be added to a sucrose gradient and centrifuged to pellet the platelets. Radioactivity associated with the pellet vs. supernatant will be determined in a γ-scintillation counter, and the binding estimated as the percent of total radioactivity.

Example 4

Defining the In Vivo Role of the Von Willebrand Factor A1 Domain by Modifying a Species-Divergent Bond Proteins containing von Willebrand Factor (VWF) A domains contribute to human health and disease by promoting adhesive interactions between cells (Whittaker, C. A., & Hynes, R O. *Mol. Biol. Cell.* 13, 3369-3387 (2002)). The VWF-A1 domain is thought to play a critical role in hemostasis by initiating the rapid deposition of platelets at sites of vascular damage by binding to the platelet receptor glycoprotein Ib alpha (GPIbα) at high shear rates (Roth, G. J. *Blood* 77, 5-19 (1991); Cruz, M. A., et al., *J. Biol. Chem.* 268, 21238-21245 (1993); Sugimoto, M. et al., *Biochemistry* 30, 5202-5209 (1991); Pietu, G. et al., *Biochem. Biophys. Res. Commun.* 164, 1339-1347 (1989)). Although congenital absence of VWF in humans has established a role for this plasma glycoprotein in hemostasis (Sadler, J. E. et al. *J. Thromb. Haemost.* 4, 2103-2114 (2006)), the contribution of its A1 domain in clot formation has been questioned in a mouse model of vascular injury (Denis, C. et al. *Proc. Natl. Acad. Sci. USA* 95, 9524-9529 (1998)).

In this example, murine plasma VWF or its A1 domain fails to support significant interactions with human platelets (and likewise human VWF with murine platelets) under flow conditions. Atomic models of GPIbα-VWF-A1 complexes suggest that the structural basis for this behavior arises primarily from an electrostatic "hot-spot" at the binding interface. Introduction of a single point mutation within this region of murine VWF-A1 is sufficient to switch its binding specificity from murine to human platelets. In addition, introduction of a single point mutation within the electrostatic "hot-spot" region of human VWF-A1 is sufficient to switch its binding specificity from human to murine platelets. Moreover, mice possessing the 1326R>H mutation in their VWF have a bleeding phenotype distinct from VWF-deficient animals, and can be corrected by the administration of human platelets. Mechanistically, mutant animals can generate but not maintain thrombi at sites of vascular injury, whereas those infused with human platelets can form stable thrombi, a process that relies on GPIbα-VWF-A1 interaction. Thus, interspecies differences at protein interfaces can provide insight into the biological importance of a receptor-ligand bond, and aid in the development of an animal model to study human platelet behavior and drug therapies.

Methods

Generation of VWF$^{1326R>H}$ Mice.

Figure 38A:
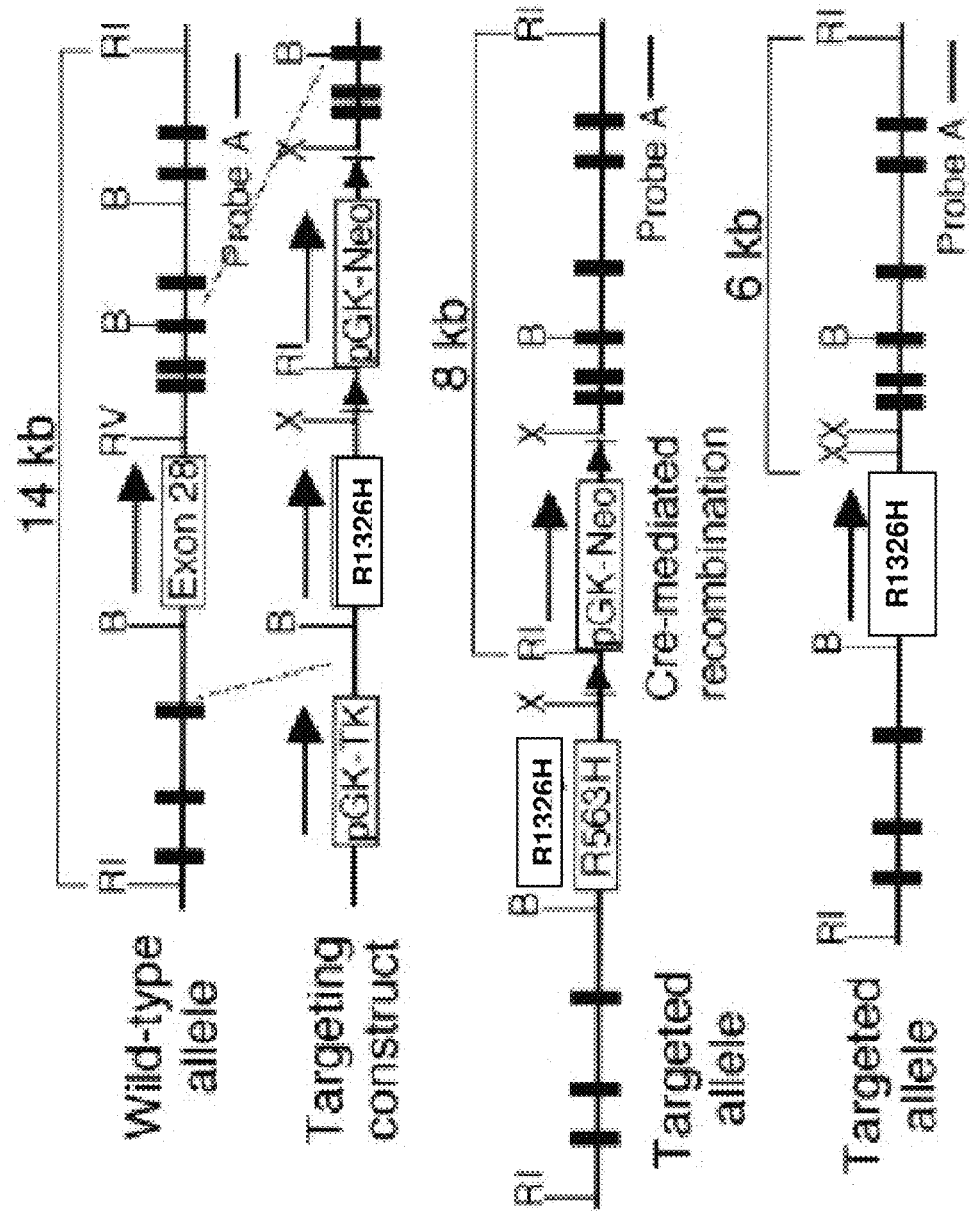
FIG. 38A is schematic for the generation of the $VWF^{1326R>H}$ mouse that represents the targeting strategy for insertion of exon 28 containing adenine in lieu of guanine at position 3977 of the cDNA for murine VWF. RI, EcoRI; RV; EcoRV; B, BamHI; X, XhoI; pGK-TK, pGK-Neo, thymidine kinase/neomycin resistance cassette; ◀, loxP sites.
Figure 38B:
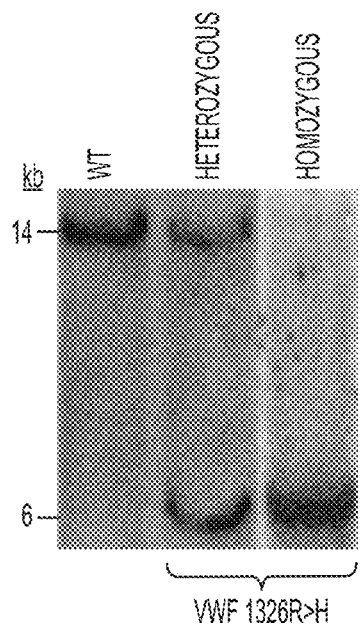
FIG. 38B is a blot of a Southern analysis of tailed DNA digested with EcoR1. Wild-type (WT) allele, 14 kb; mutant allele, 6 kb using Probe A.
Figure 38C:
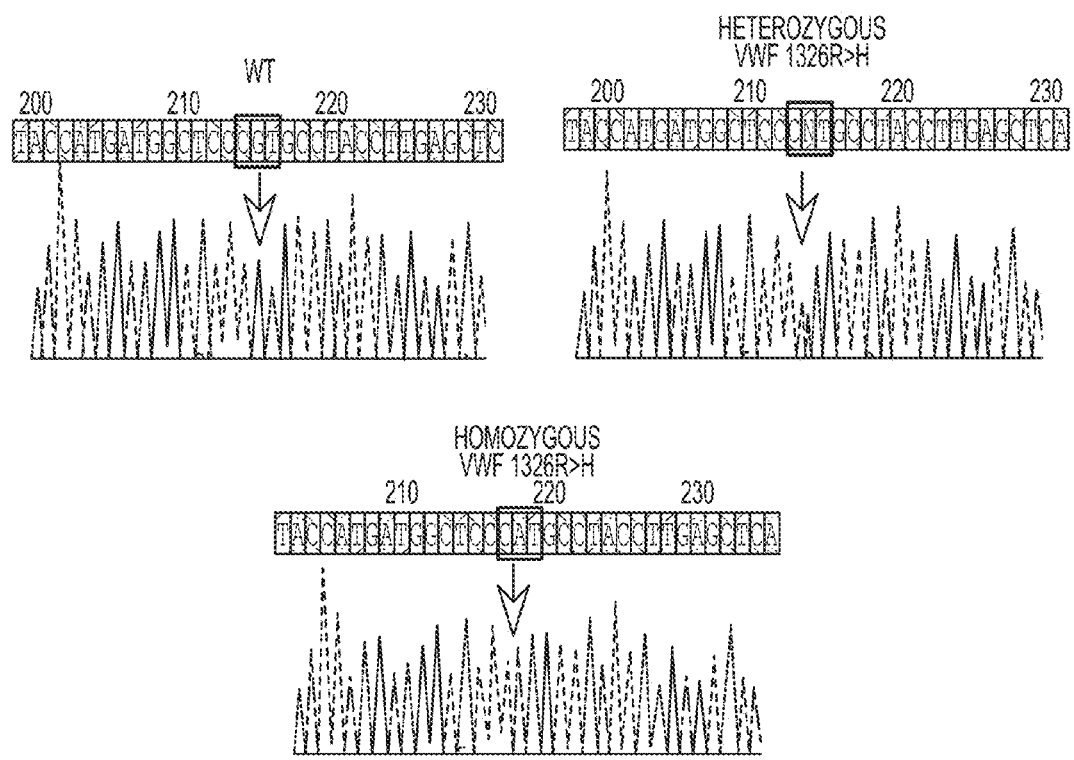
FIG. 38C represents the DNA sequencing of the tailed DNA demonstrating successful incorporation of adenine at position 3977 in heterozygous and homozygous animals (CGT>CAT). Sequence analysis of genomic DNA from these animals, 2 kb upstream and 6 kb downstream of exon 28, did not reveal any other alterations in nucleotide base pairs that would affect VWF production and/or function.
Figure 39A:
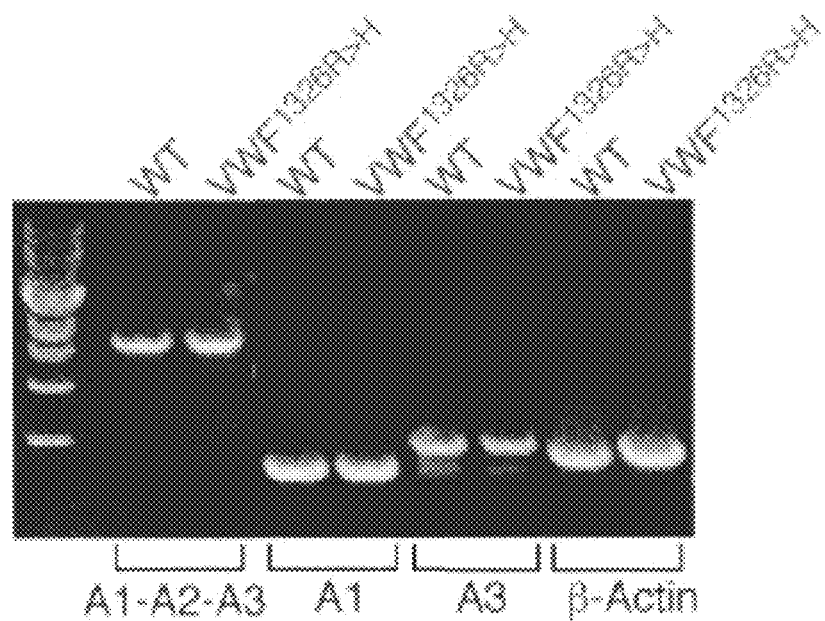
FIGS. 39A and 39B represent the analysis of VWF gene transcription and translation.
Figure 39B:
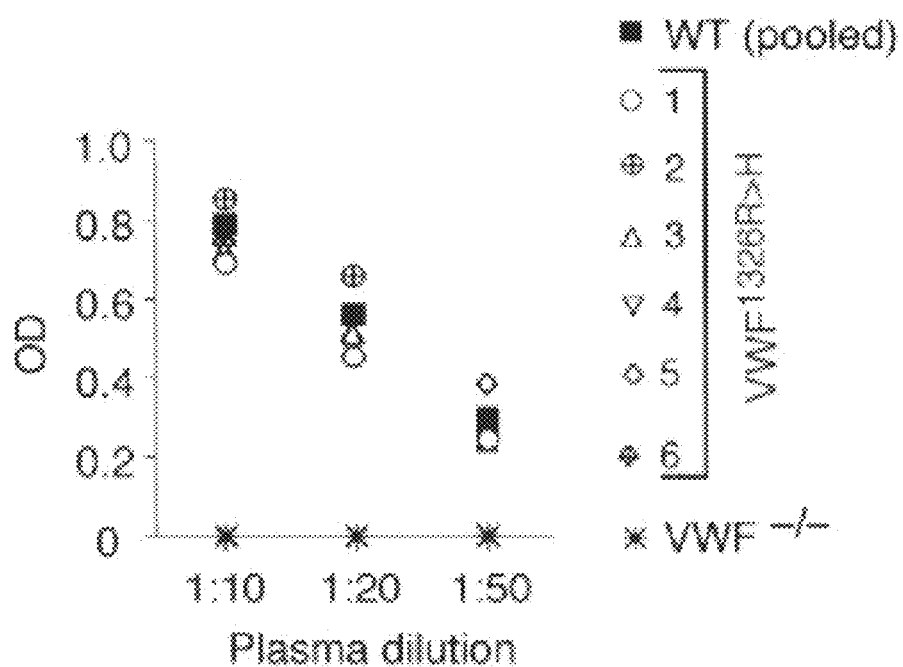
Figure 39C:
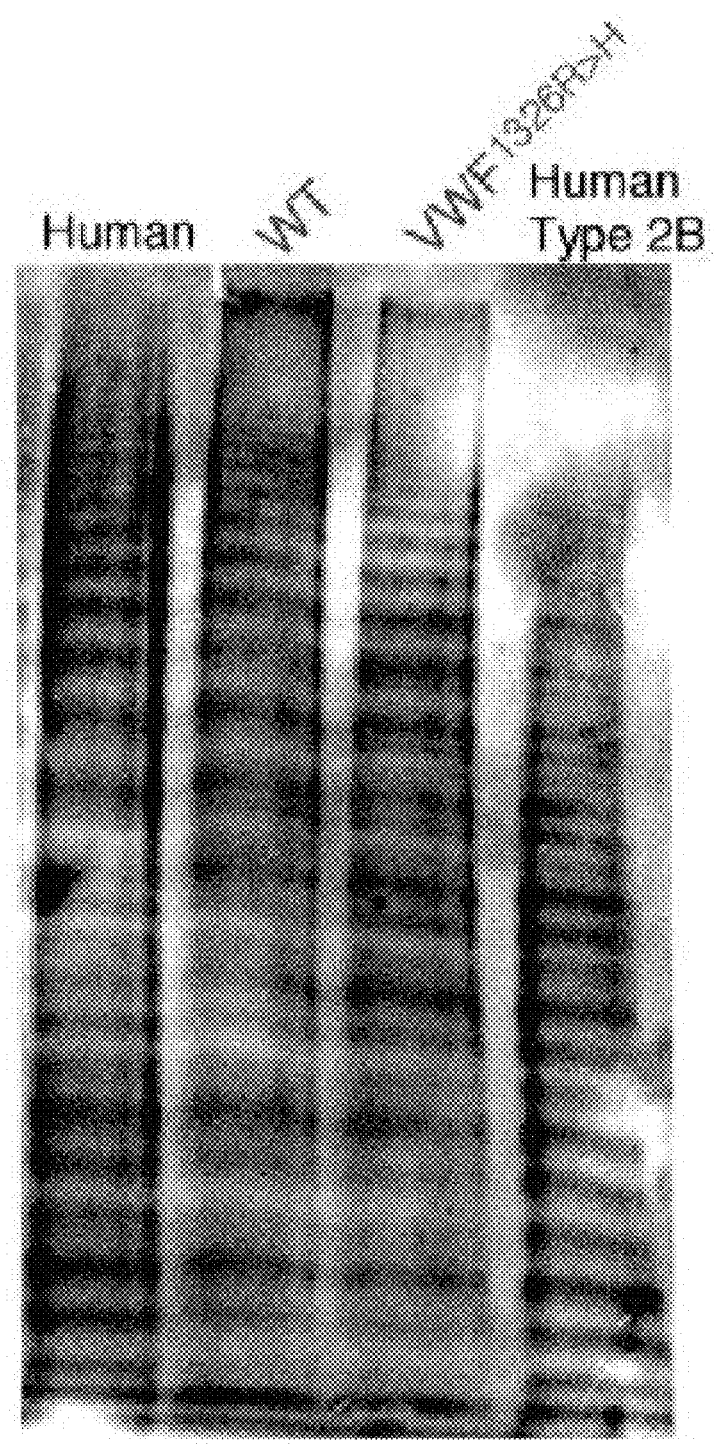
FIG. 39C is a gel showing the analysis of VWF multimers in plasma from WT or homozygous mutant animals. Normal human plasma as well as that obtained from a patient with type 2B VWD is shown for comparison.

The VWF$^{1326R>H}$ targeting vector (FIG. 38A) was prepared from a 129/SvJ mouse genomic library. The clone was identified by PCR using primers specific for exon 28 of the mouse VWF gene and sequence fidelity of the region to be targeted validated by comparison to published sequence for chromosome 6 (GenBank accession number NW_001030811). The targeting vector is identical to the corresponding region in the mouse genome, except the 1326R>H mutation was created in exon 28 and the Neo cassette flanked by loxP sites was inserted into intron 28. This resulted in the loss of an EcoRV site and the introduction of a new EcoR1 and two new XhoI sites. The construct was electroporated into an embryonic stem (ES) cell line, and potential clones identified by continued growth of cells in G418 and Gancyclovir supplemented media. DNA was isolated from surviving colonies, digested with EcoRI, and screened by Southern analysis using a 1.5 kb probe (A) corresponding to a DNA sequence downstream of the targeting construct. Chimeric mice generated from vwF$^{1326R>H}$ targeted ES cell lines were subsequently bred to a Cre transgenic mouse (C57BL/6 background) and animals containing the 1326R>H mutation, but without the Neo cassette, subsequently identified by both PCR and Southern analysis. WT and homozygous animals were the product of matings between heterozygous mice.

Analysis of VWF Transcripts, Antigen Levels, Multimers, and Collagen Binding.

Detection of transcripts from the A1-A2-A3 domains of murine VWF was performed by RT-PCR. Briefly, mRNA was isolated from lung tissue harvested from either homozygous VWF-A1$^{1326R>H}$ mice or aged-mated WT littermate controls (Oligotex®, Qiagen). Generation of cDNA and PCR-amplification of desired transcripts was performed using SuperScript™ One-Step RT-PCR (Invitrogen) and oligos specific for the A domains of VWF.

Functional factor VIII levels were determined by a mechanical clot detection method using the STA automated coagulation analyzer (Diagnostica Stago, Parsippany, N.J.). A log-log calibration curve was established by measuring the activated partial Thromboplastin time (aPTT) of varying dilutions of reference plasma. The aPTT of a 1:10 dilution of sample plasma mixed with factor VIII deficient plasma was determined, compared to the calibration curve, and the activity expressed as a percent of normal.

Evaluation of VWF antigen levels was performed as previously described (Denis, C. et al. *Proc. Natl. Acad. Sci. USA* 95, 9524-9529 (1998)). For multimer analysis, plasma from sodium citrate treated whole blood was diluted 1:5 in electrophoresis sample buffer (final concentration 10 mM Tris-HCl pH 8.0, 2% SDS, 1 mM EDTA) and heated at 56° C. for 30 minutes. Electrophoresis was carried out overnight (64 volts, 15° C.) through a horizontal SDS-agarose gel in 1.2% agarose (Ruggeri, Z. M. & Zimmerman, T. S. *Blood* 57, 1140-1143 (1981)). The gel was then electrophoretically transferred (150 mA, 90 minutes) to Immobilon (Millipore) followed by blocking (2 h) with 5% powdered milk in TBST (Tris HCl pH 8.0, 0.15M NaCl, 0.05% Tween-20). The membrane was incubated with a 1:500 dilution of rabbit anti-human VWF antiserum (DAKO) for 1 h, washed in TBST, and then incubated with a 1:10,000 dilution of HRP-conjugated mouse anti-rabbit IgG (Calbiochem). Bands were subsequently detected by chemiluminescence system (GE Healthcare). For comparison, a sample containing pooled human plasma from normals or patients with type 2B VWD was also loaded on the gel. Binding of VWF to surface-immobilized collagen was performed as previously described (Smith, C. et al. (2000) *J. Biol. Chem.* 275, 4205-4209). Briefly, 100 µg/ml of acid soluble type I collagen from human placenta (Sigma) was added to a 96 well microtiter plate and allowed to incubate overnight (4° C.). After washing and blocking with TBS containing 3% BSA and 0.05% Tween 20, varying concentration of platelet poor plasma harvested and pooled from WT, homozygous vWF$^{1326R>H}$, and VWF deficient mice was added to the wells and incubated for 1 h (37° C.). Wells were then washed and bound VWF detected by an ELISA as described above.

Ex Vivo Platelet Adhesion Studies.

Experiments were performed in a parallel-plate flow chamber as previously described (Offermanns, S. (2006) *Circ. Res.* 99, 1293-1304). For studies involving plasma VWF, a polyclonal anti-VWF antibody (Dako) was absorbed overnight (4° C.) to a six well tissue culture plate. Subsequently, the plate was washed and non-specific interactions blocked by the addition of TBS containing 3% BSA, pH 7.4 (1 h, 37° C.). Human or murine plasma obtained from heparinized whole blood was added and the plates placed at 37° C. for an additional 2 h. Generation, purification, and surface-immobilization of recombinant VWF-A1 proteins was performed as previously described (Doggett, T. A. et al. *Biophys. J.* 83, 194-205 (2002)). Both human and murine VWF-A1 constructs consist of amino acid residues 1238 to 1471, with a single intra-disulfide bond formed between residues 1272 and 1458 and were generated in bacteria. Citrated whole blood (150 µl) collected via cardiac puncture from anesthetized homozygous VWF$^{1326R>H}$ or WT mice or from venopuncture from human volunteers was perfused over the immobilized substrates at a wall shear rate of 1600 s$^{-1}$ for 4 min, followed by washing with Tyrode's buffer under the identical flow conditions. The number of platelets attached per unit area (0.07 mm$^2$) and translocation velocities were determined by off-line analysis (Image-Pro Plus, Media Cybernetics). For GPIbα inhibition studies, the function-blocking mAb 6D1 (20 µg/ml) or mAb SZ2 (20 µg/ml; Beckman Coulter) was added to anticoagulated human blood for 30 min prior to use. Experiments were performed in triplicate on two separate days. An ELISA was used to ensure equivalent coating concentration of plasma and recombinant proteins (Denis, C. et al. (1998) *Proc. Natl. Acad. Sci. USA* 95, 9524-9529).

In Vivo Thrombus Formation.

Administration of anesthesia, insertion of venous and arterial catheters, fluorescent labeling and administration of human platelets (5×10$^8$/ml), and surgical preparation of the cremaster muscle in mice have been previously described (Doggett, T. A. et al. *Biophys. J.* 83, 194-205 (2002); Diacovo, T. G., et al., *Science* 273, 252-255 (1996)). Injury to the vessel wall of arterioles (~40-65 µm diameter) was performed using a pulsed nitrogen dye laser (440 nm, Photonic Instruments) applied through a 20× water-immersion Olympus objective (LUMPlanFI, 0.5 NA) of a Zeiss Axiotech vario microscope. Mouse platelet- and human platelet-vessel wall interactions were visualized using either bright field or fluorescence microscopy. The latter utilized a fluorescent microscope system equipped with a Yokogawa CSU-22 spinning disk confocal scanner and 488 nm laser line (Revolution XD, Andor™ Technology). The extent of thrombus formation was assessed for 2 min post injury and the area (µm$^2$) of coverage determined (Image IQ, Andor™ Technology). For GPIbα or αIIbβ3 inhibition studies, the function-blocking mAb 6D1 or 7E3 (20 µg/ml), respectively (from B. Coller, Rockefeller University), was added to purified human platelets for 30 min prior to administration.

Tail Bleeding Assay.

Bleeding times were measured in 7-week old mice after amputating 1 cm of the tail tip as previously described (Denis, C. et al. (1998) *Proc. Natl. Acad. Sci. USA* 95, 9524-9529). In studies involving human platelets, platelet concentrates were obtained from Columbia Presbyterian Hospital Blood Bank, washed and resuspended in normal saline (1.5×10$^9$/300 µl) before administering through a catheter inserted into the right internal jugular vein. Tail cuts were performed 5 min after completion of the infusion of platelets. PLAVIX and ReoPro® were obtained from the research pharmacy at CUMC. For studies involving PLAVIX, animals received a 50 mg/kg oral dose of the drug the day before and 2 h prior to the administration of human platelets. ReoPro® was given initially as an intravenous bolus (0.25 mg/kg) 5 min after the administration of human platelets, followed by a continuous infusion (0.125 µg/kg/min) as per the manufacturer's recommendations.

Structural Modeling.

There are three crystal structures of the GPIbα-VWF-A1 complex: two are WT except for mutated N-glycosylation sites in GPIbα(Fukuda, K. et al., (2005) *Nat. Struct. Mol. Biol.* 12, 152-159; Dumas, J. J. et al. (2004) *J. Biol. Chem.* 279, 23327-23334), and one is a gain-of-function mutant (Huizinga, E. G. et al. (2002) *Science* 297, 1176-1179). The structures have only small differences that are not the result of the presence of mutations or botrocetin binding (Fukuda, K., et al., (2005) *Nat. Struct. Mol. Biol.* 12, 152-159). Both N-glycosylation sites in human GPIbα lie on the well-ordered upper ridge of the LRR, 18 Å and 27 Å (Cα-Cα) from the nearest VWF-A1 residue, so their absence is unlikely to affect the structure of the complex. Murine GPIbα has no predicted N-glycosylation sites.

Human GPIbα contains sulfated tyrosines implicated in binding VWF within an acidic loop just C-terminal to the sequence included in the crystal structures. Murine GPIbα has a predicted sulfation site in the same loop, so that the differential binding of human vs. murine GPIbα to VWF-A1 is also likely to be small. The interfacial regions are otherwise highly conserved between species, with the exception of three salt bridges (See FIGS. 37C-G). The conformation of the β-switch region is highly constrained, as noted in the main text. The only change to a buried interfacial residue is M239T (human to mouse), which lies in an invariant pocket. Notably, the crystal structure of the human "gain-of-function" mutant, M239V, shows no perturbations in this region, and given that valine is isosteric with threonine, this species difference is unlikely to affect either the complex structure or interspecies binding.

We used a consensus model of the human complex to build the murine model. We first overlaid murine A1 onto human A1 by fitting the central β-sheets (RMSD 0.3 Å; within experimental error); the only notable difference is the location of helix α4, which is shifted by 2-3 Å away from the GPIbα interface in the mouse owing to a larger residue on the buried face of this helix. For the GPIbα model, only the side-chains were altered, since the human and murine LRRs have identical lengths. Consensus rotamers with minimal steric clashes were chosen, followed by manual adjustment where necessary to create sensible van der waals interactions and H-bonding, using TURBOFRODO (Bio-Graphics, Marseille, France). Molecular overlays were optimized using LSQKAB (Collaborative Computational Project, No. 4. *Acta Crystallogr.* D50, 760-763 (1994)); molecular figures were created using MOLSCRIPT (Esnouf, R. M. *J. Mol. Graph. Model.* 15, 132-136 (1997)) and OPENGL (http://www.rush3d.com/reference/opengl-bluebook-1.0)

Statistics.

An unpaired, two-tailed Student t test was used for multiple comparisons.

Results and Discussion

As the interaction between GPIbα and VWF-A1 is a prerequisite for effective thrombus formation in the arterial circulation, we first tested the ex vivo ability of surface-bound murine plasma VWF or its recombinant A1 domain (rVWF-A1) to support human platelet adhesion under physiologically relevant flow conditions: that is at a shear rate exceeding 1000 s$^{-1}$ using a parallel-plate flow chamber (Ruggeri, Z. M. et al., (2006) *Blood.* 108, 1903-1910). The adhesive properties of VWF are tightly regulated such that it preferentially binds to platelets only when immobilized to sites of vascular injury and under hydrodynamic conditions encountered on the arterial side of the circulation (Sakariassen et al., (1979) *Nature* 279, 636-638; Ruggeri, Z. M. et al., (2006) *Blood.* 108, 1903-1910). Perfusion of human whole blood over murine plasma VWF or rVWF-A1 resulted in limited platelet deposition (10 to 25%, respectively) as compared with same-species controls (FIGS. 36A and 36B). Similarly, human VWF proteins had a diminished capacity to support murine platelet accumulation under identical conditions (FIG. FIG. 36C-D). This interspecies incompatibility would seem to preclude the study of human platelet behavior in a mouse model of arterial thrombosis.

In order to gain insight into the structural origins of this species incompatibility, we built models of murine-murine and human-murine GPIbα-VWF-A1 complexes based on the crystal structures of the human complex (Fukuda, K., et al., *Nat. Struct. Mol. Biol.* 12, 152-159 (2005); Dumas, J. J. et al., *J. Biol. Chem.* 279, 23327-23334 (2004); Huizinga, E. G. et al., *Science* 297, 1176-1179 (2002)) and human and murine VWF-A1 (Fukuda, K., et al., *Nat. Struct. Mol. Biol.* 12, 152-159 (2005)) (FIGS. 37A through 37E; see Methods).

Figure 37A:
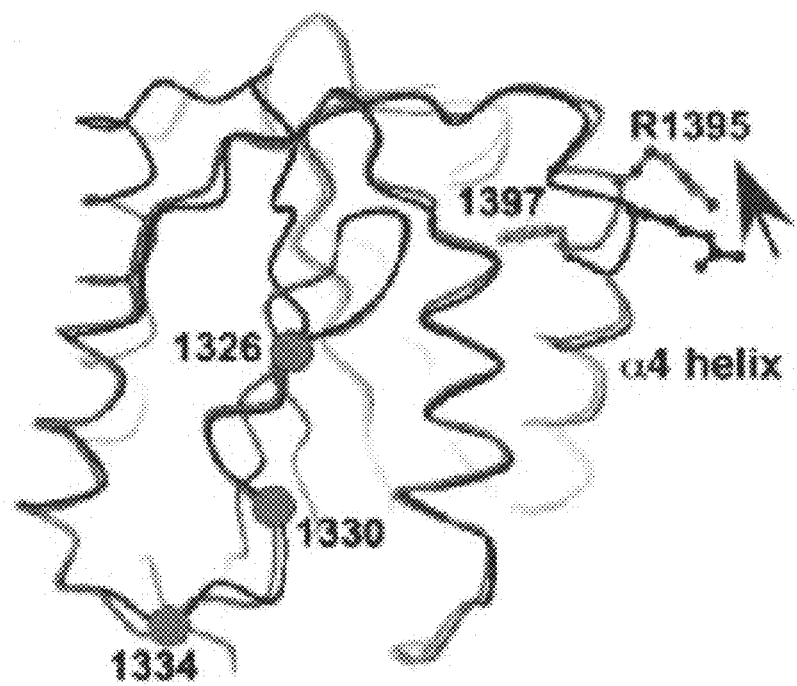
FIGS. 37A and 37B are structural representations of human and murine VWF-A1 domains.
Figure 37B:
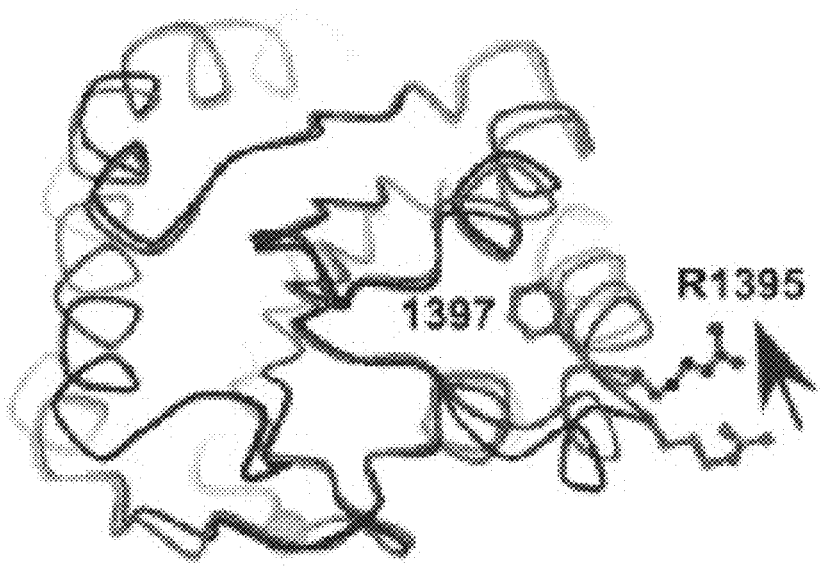

The A1 domain comprises a Rossmann-like fold with a central, mostly parallel β-sheet flanked on both sides by α-helices (Fukuda, K., et al., *Nat. Struct. Mol. Biol.* 12, 152-159 (2005)). Human and murine VWF-A1 share considerable sequence (86% identity) and structure homology; in fact, the β-sheets of both species are identical within experimental error (a root mean square difference of 0.33 Å for Cα-atoms). The only major difference is the location of helix α4 (nomenclature as previously described in Dumas, J. J. et al., *J. Biol. Chem.* 279, 23327-23334 (2004)), which is shifted 2-3 Å away from the GPIbα binding site in the mouse, owing to a difference in a buried hydrophobic residue (FIGS. 37A-37B). Although neither the structure of murine GPIbα nor its complex with the VWF-A1 domain are known, the high sequence similarity of the murine and human proteins (including the complex interface), as well as the rigid architecture of the leucine-rich repeats (LRR) of GPIbα, provide high confidence that their 3D structures will be highly homologous.

Figure 37C:
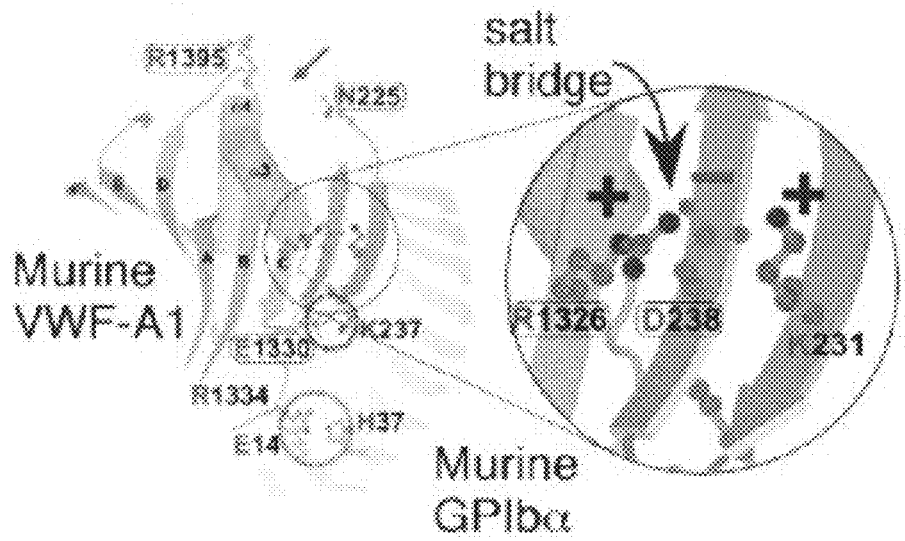
FIGS. 37C and 37D are structural representations of human and murine GPIbα-VWF-A1 complexes.
Figure 37D:
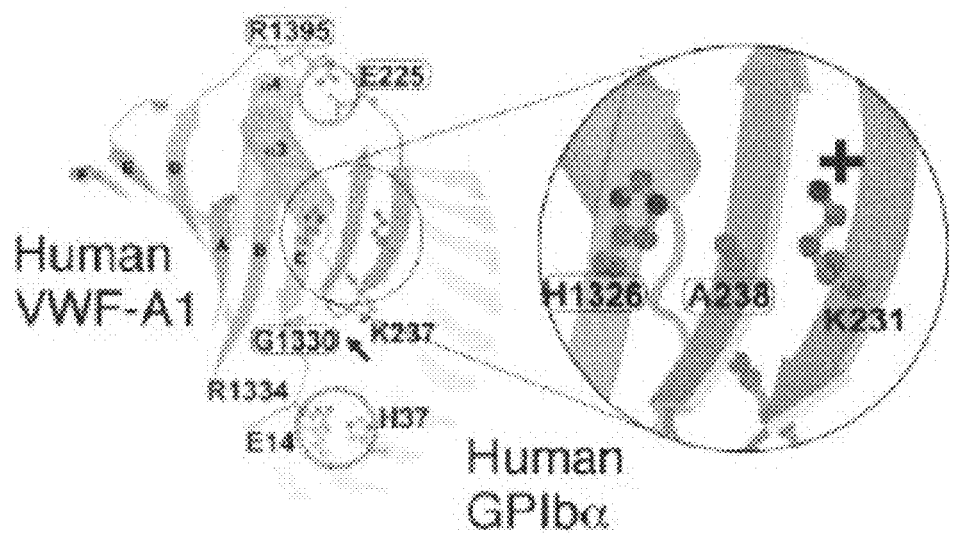

In the complexes, the major contact region involves the "β-switch" region (residues 227 to 241 in the C-terminal flank of GPIb alpha), which forms a β-hairpin that augments the β-sheet of the VWF-A1 domain. On its other side, this region of GPIbα packs tightly against the concave face of the LRR, which highly constrains it movement. Residues in mouse and human are mostly invariant on both sides of this interface. Notable exceptions are at position 1326 in VWF-A1, which is histidine (H) in humans versus an arginine (R) in mouse, and at position 238 in GPIb alpha, which is alanine (A) in humans versus an aspartic acid (D) in mouse (FIGS. 37C and 37D). A model of the murine complex suggests that these changes are complementary, since D238 can form an intermolecular salt-bridge with R1326; D238 in murine GPIb alpha also shields the positively charged flanking lysine (K) at position 231 (a conserved residue in both species) from unfavorable interactions with R1326 in murine VWF-A1. This salt-bridge cannot form in the human complex due to the presence of a histidine at 1326. However, an intermolecular salt-bridge can occur between R1395 and E225 located at the top of the human complex, which may compensate for this loss (FIG. 37D). No such interaction can occur in the murine complex (FIG. 37C).

Figure 37E:
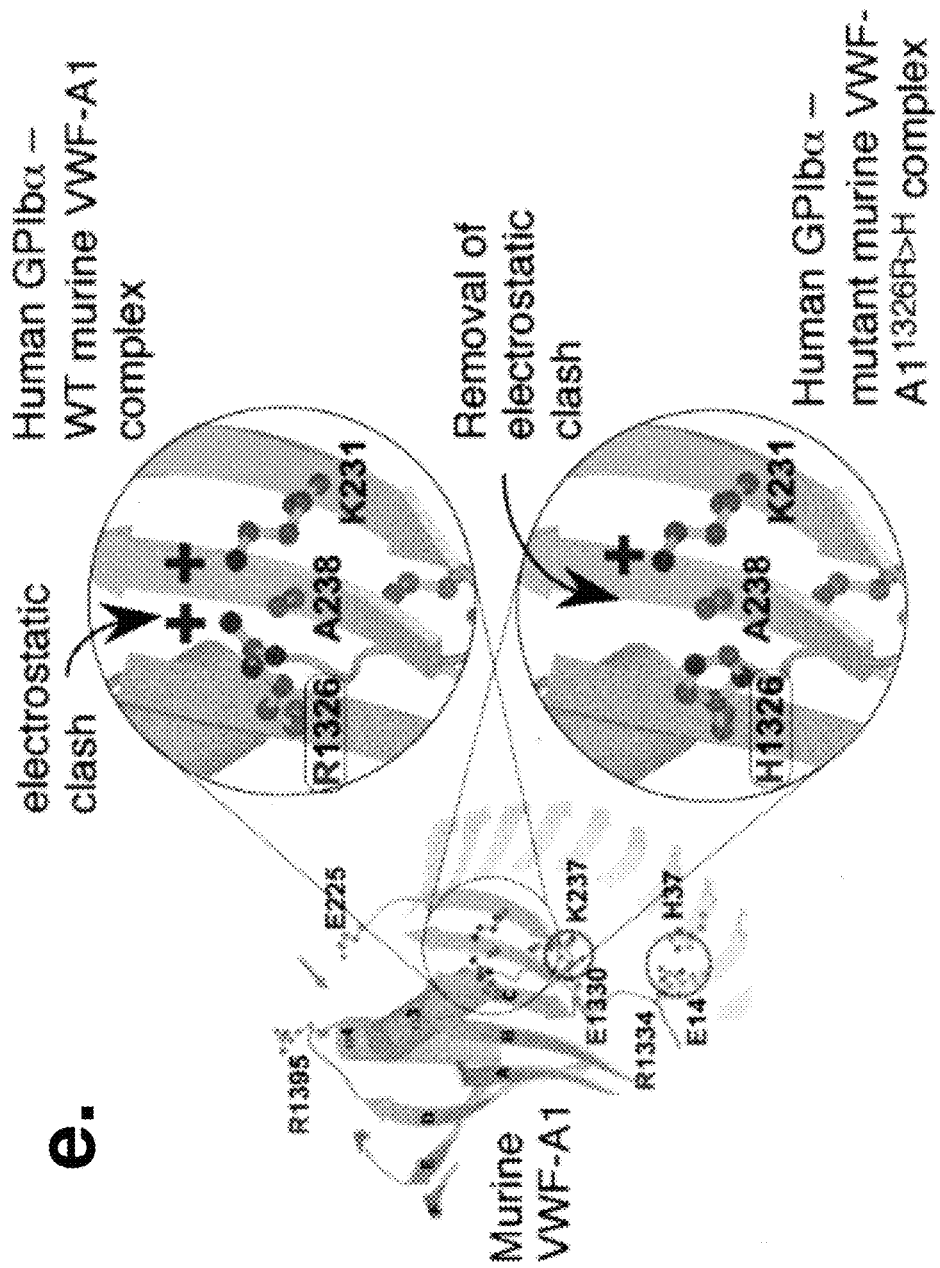
FIG. 37E is a model of the human GPIbα-murine A1 complex, showing the loss (green arrow) and gain (blue circle) of salt-bridges. The upper zoom shows the interspecies interface at the β-switch region, revealing the electrostatic clash. The lower zoom shows the murine VWF-A1 point mutant 1326R>H, which removes the electrostatic clash and now closely resembles the human-human complex.
Figure 37F:
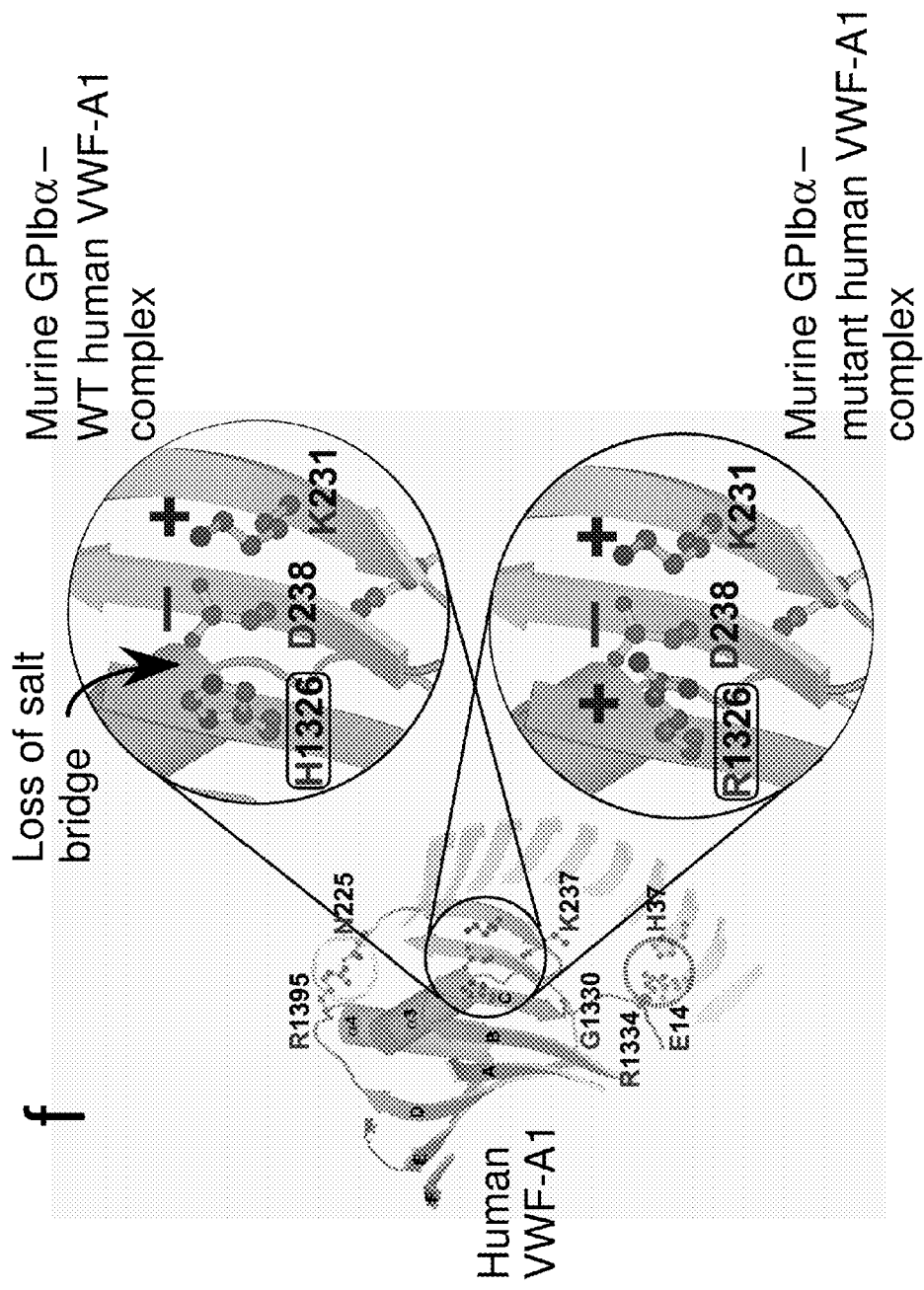
FIG. 37F is a model of the murine GPIbα-human VWF-A1 complex. Two salt-bridges are lost as compared to the murine complex; murine GPIbαD238 with residue 1326 due to the R>H change in human VWF-A1, and murine GPIbαK237 with residue 1330 owing to the E>G change in the human protein. Moreover, neither the chimeric nor murine complex forms a salt-bridge between residues 225 and 1395 on GPIbα and VWF-A1, respectively, as compared to its human counterpart (green circle). The upper zoom shows the interspecies interface at the β-switch region; there is no electrostatic clash but no salt-bridge can form with H1326. The lower zoom shows the human point mutant 1326H>R, which adds a salt-bridge and now closely resembles the murine-murine complex.

In the human GPIb alpha-murine VWF-A1 interspecies complex, we predict that the two positively charged residues (GPIb alpha K231 and VWF-A1 R1326) create an electrostatic clash that impedes binding, owing to the lack of a negatively charged group at position 238 (FIG. 37E). In the murine GPIb alpha-human VWF-A1 interspecies complex, however, no such electrostatic clash occurs despite the absence of the salt-bridge. There is, however, an overall change in net charge in the binding interface compared with the murine GPIb alpha-murine VWF-A1 complex (FIG. 37F). This, together with the loss of critical salt-bridges, most likely accounts for the reduced interaction between mouse platelets and human VWF (See Tables 5 and 6).

TABLE 5

Predicted effect of species differences in residues on the human GPIb alpha-murine VWF-A1 interspecies complex.

| mVWF-A1 | hGPIb-alpha partner | hGPIb alpha-mVWF-A1 | Reason |
|---|---|---|---|
| R1326 | A238 | (−) | Permits electrostatic clash of R1326 with K231 in GPIb alpha |
| E1330 | K237 | (+) | New salt-bridge E1330-K237 |
| G1370 | none | 0 | No interactions |
| R1395 (shifts position) | E225 | (−) | Loss of salt-bridge |

(+) = net positive,
(−) = net negative,
0 = minimal effect compared with syngeneic complexes.

TABLE 6

Predicted effect of species differences in residues on the murine GPIb alpha-human VWF-A1 interspecies complex.

| hVWF-A1 | mGPIb-alpha partner | hGPIb-alpha-mVWF-A1 | Reason |
|---|---|---|---|
| H1326 | D238 | (−) | Loss of R1326-D238 salt-bridge |
| G1330 | K237 | (−) | Loss of E1330-K237 salt-bridge |
| S1370 | none | 0 | No interactions |
| R1395 (shifts position) | N225 | (+) | New polar interactions with R1395 |

(+) = net positive,
(−) = net negative,
0 = minimal effect compared with syngeneic complexes.

Figure 37G:
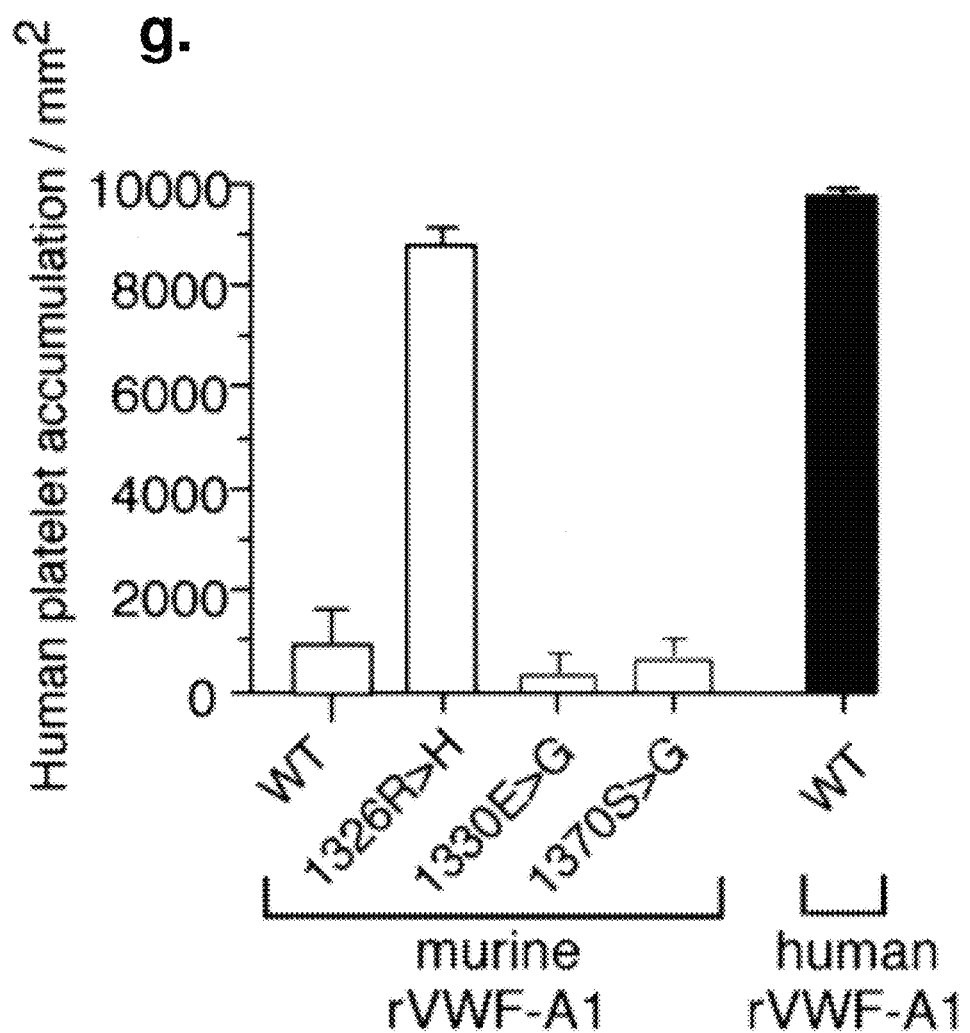
FIG. 37G is a graph that shows the accumulation of human platelets on surface-immobilized recombinant WT murine VWF-A1 domain proteins, those containing the selected mutations 1326R>H, 1330E>G and 1370S>G, or WT human VWF-A1 protein (shear rate of 1600 $s^{-1}$). Data are representative of three separate experiments performed in triplicate (mean±s.e.m.).
Figure 41A:
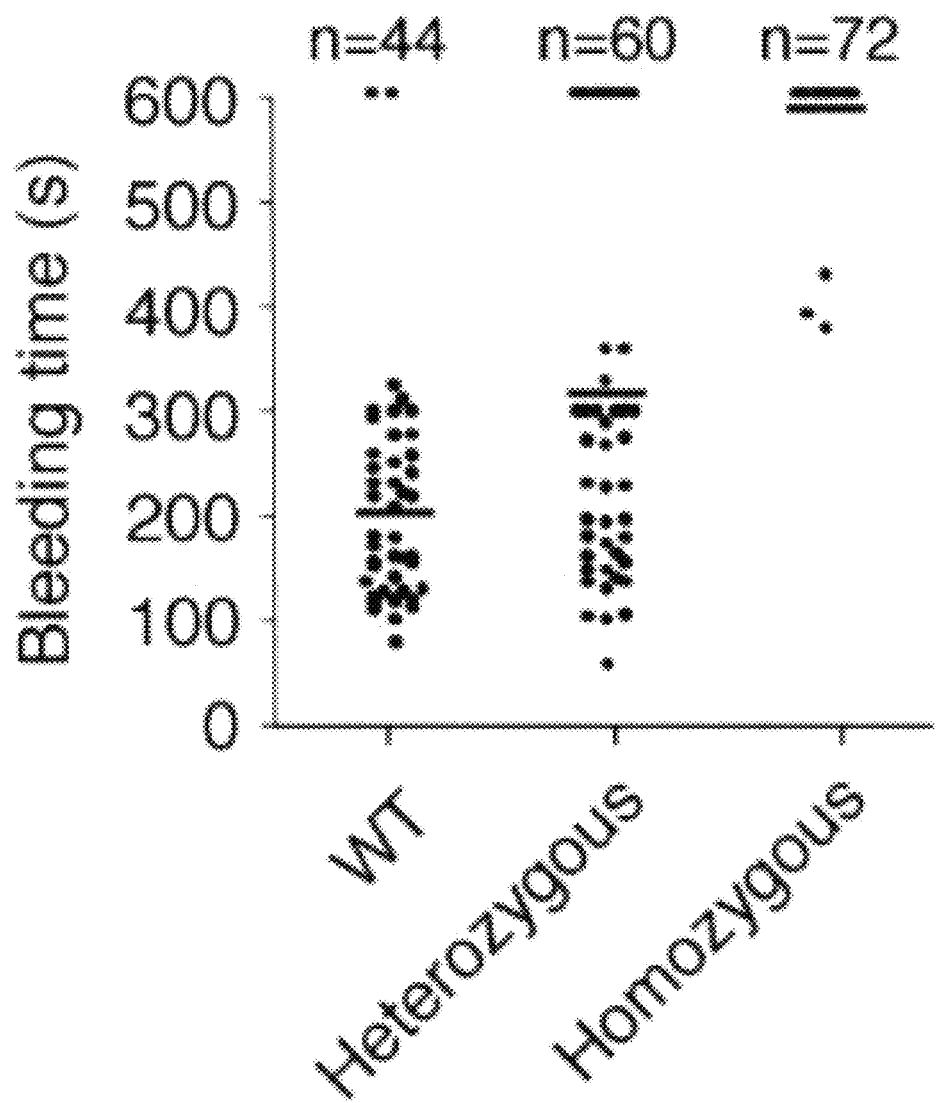
FIG. 41A is a graphical representation of the tail bleeding times (s) for heterozygous and homozygous VWF$^{1326R>H}$ and WT mice when tails were cut 1 cm from the tip of the tail. Each point represents one individual mouse and experiments were performed on five separate days.
Figure 41B:
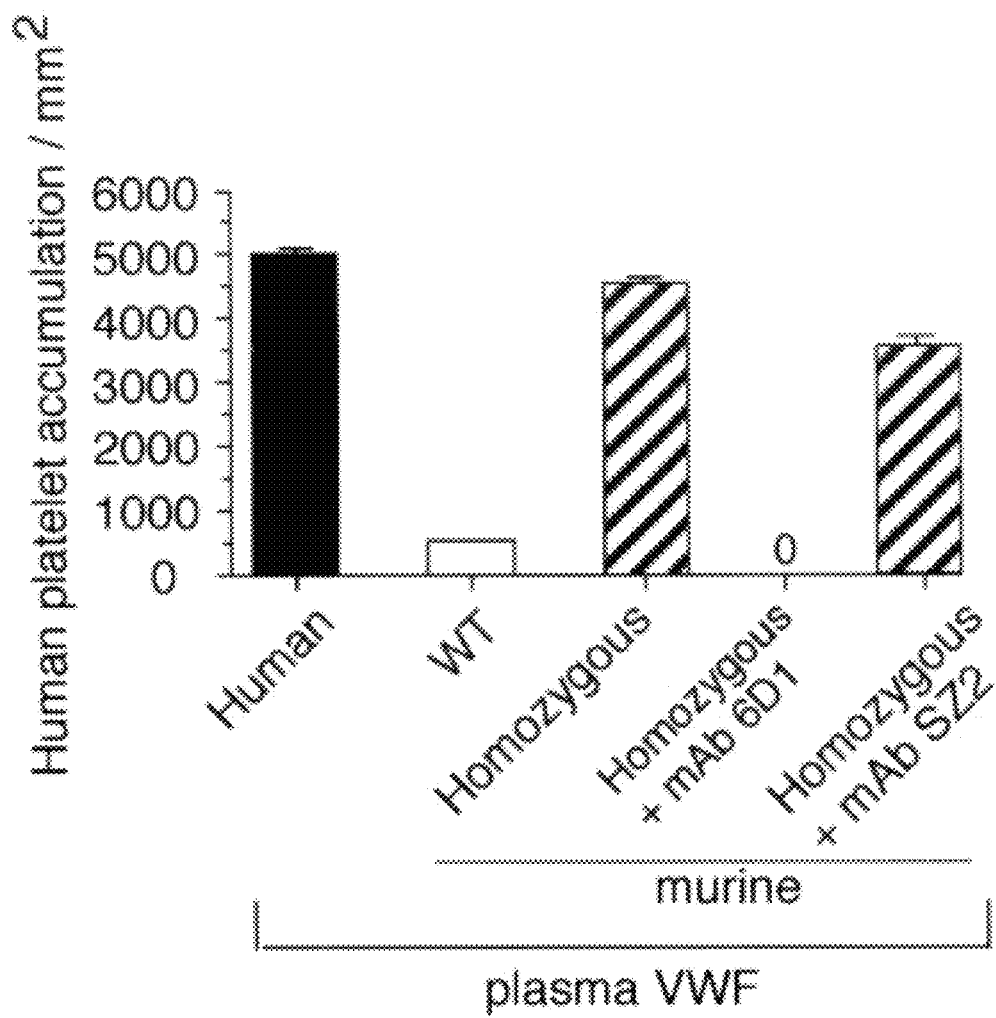
FIG. 41B is an ex vivo analysis of human platelet interactions with surface-immobilized plasma VWF$^{1326R>H}$ at a shear rate of 1,600 s$^{-1}$. A role for GPIb alpha on human platelets is demonstrated by the function-blocking antibody to this platelet receptor (mAb 6D1) to prevent adhesion in flow.
Figure 41C:
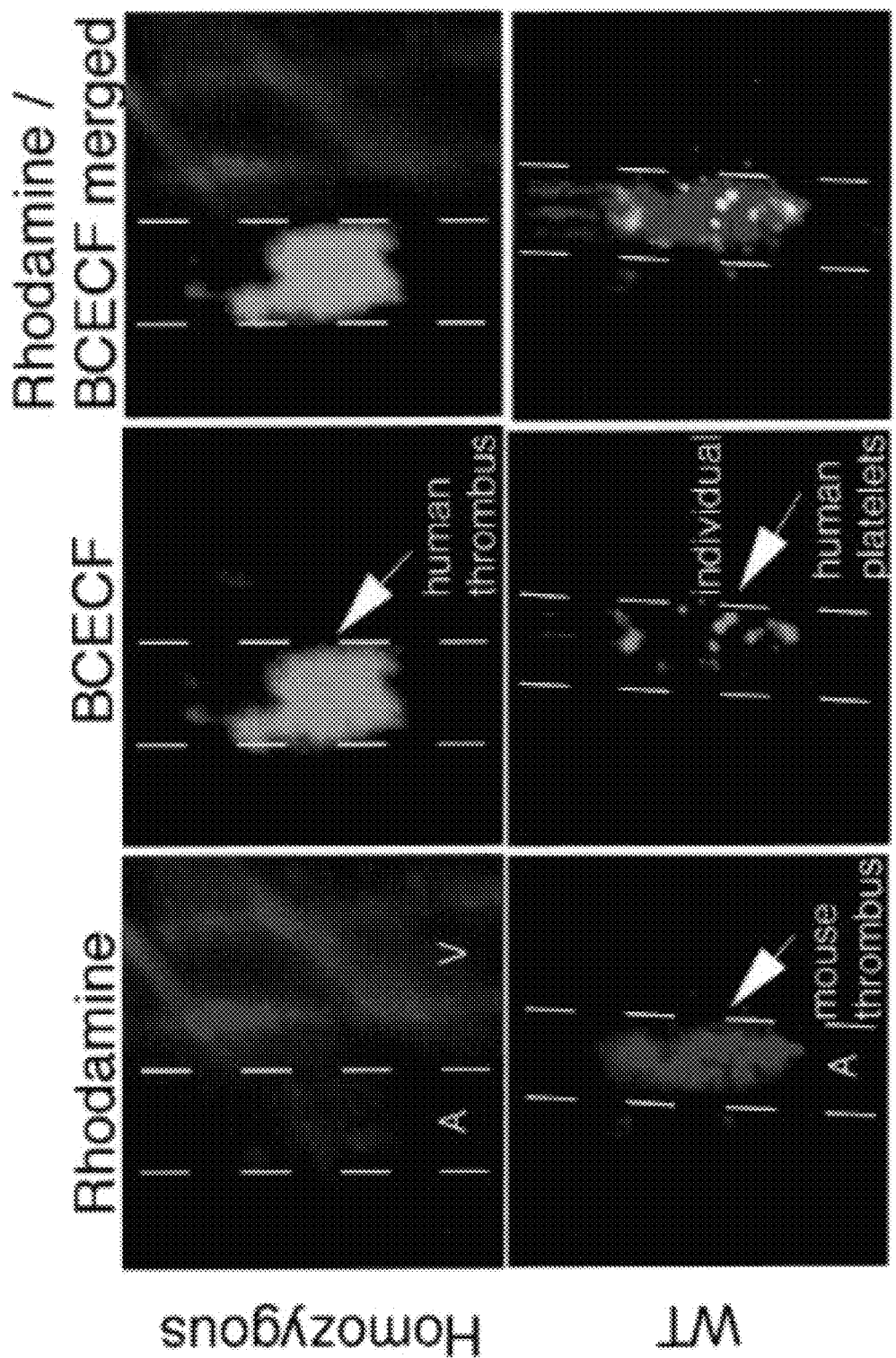
FIG. 41C are microscopy images of in vivo analysis of human platelet interactions with murine plasma VWF$^{1326R>H}$ using infused fluorescently labeled human platelets into the vasculature of the cremaster muscle of mice. Human platelet accumulation was examined at sites of laser-induced arteriolar injury in WT (n=10) or homozygous mutant animals (n=12) using 2 channel confocal microscopy with excitation wavelengths of 488 nm (BCECF) and 561 nm (rhodamine 6G). Representative composite images of fluorescent images depicting human thrombus formation in homozygous mutant (upper panels) or WT (lower panels) mice (V=venule; A=arteriole). Rhodamine and BCECF are depicted in red and green, respectively, and merged is presented in yellow.
Figure 41D:
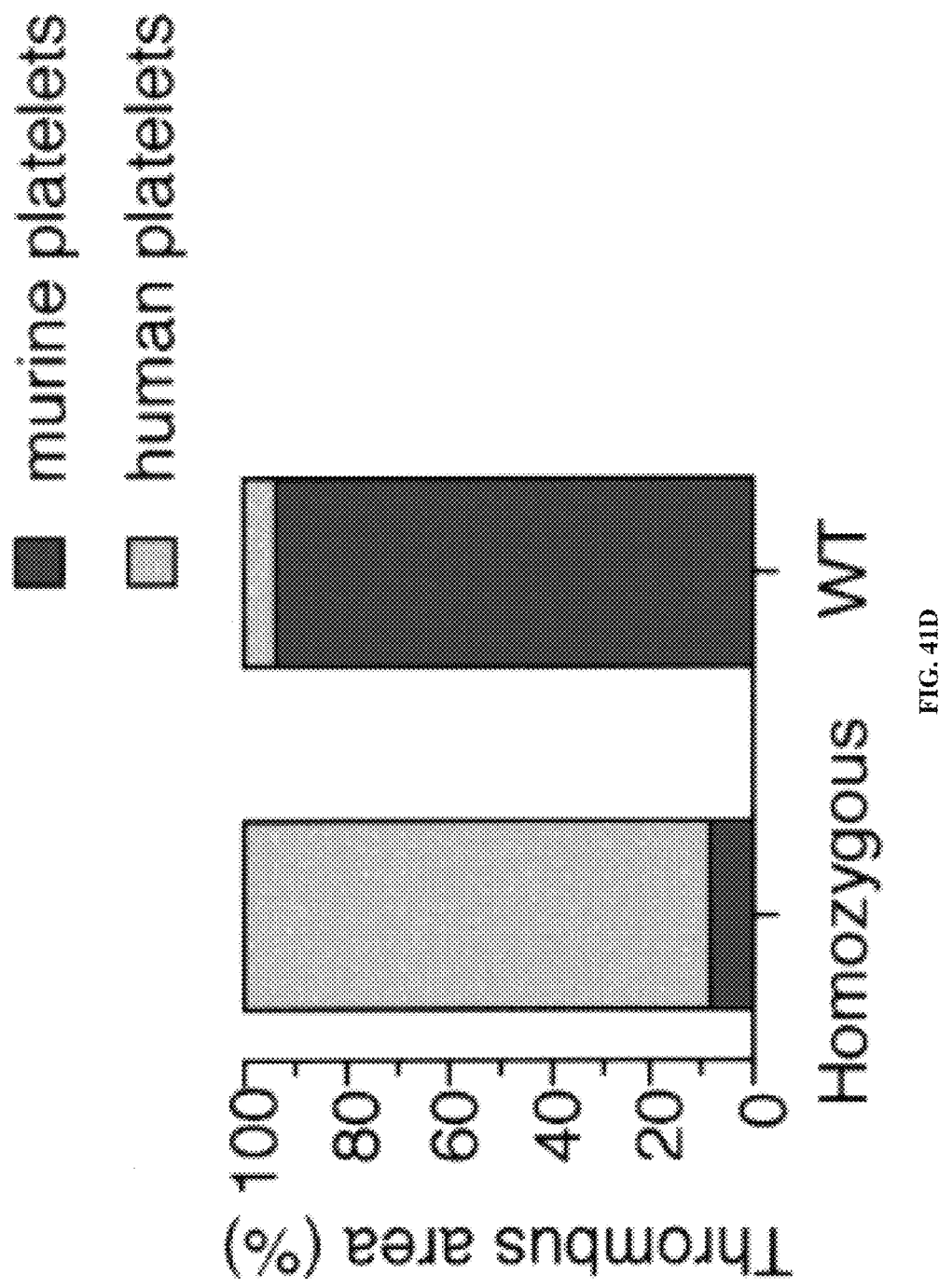
FIG. 41D is a bar graph depicting the composition of thrombi (% of total area) in WT or homozygous mutant animals.
Figure 41E:
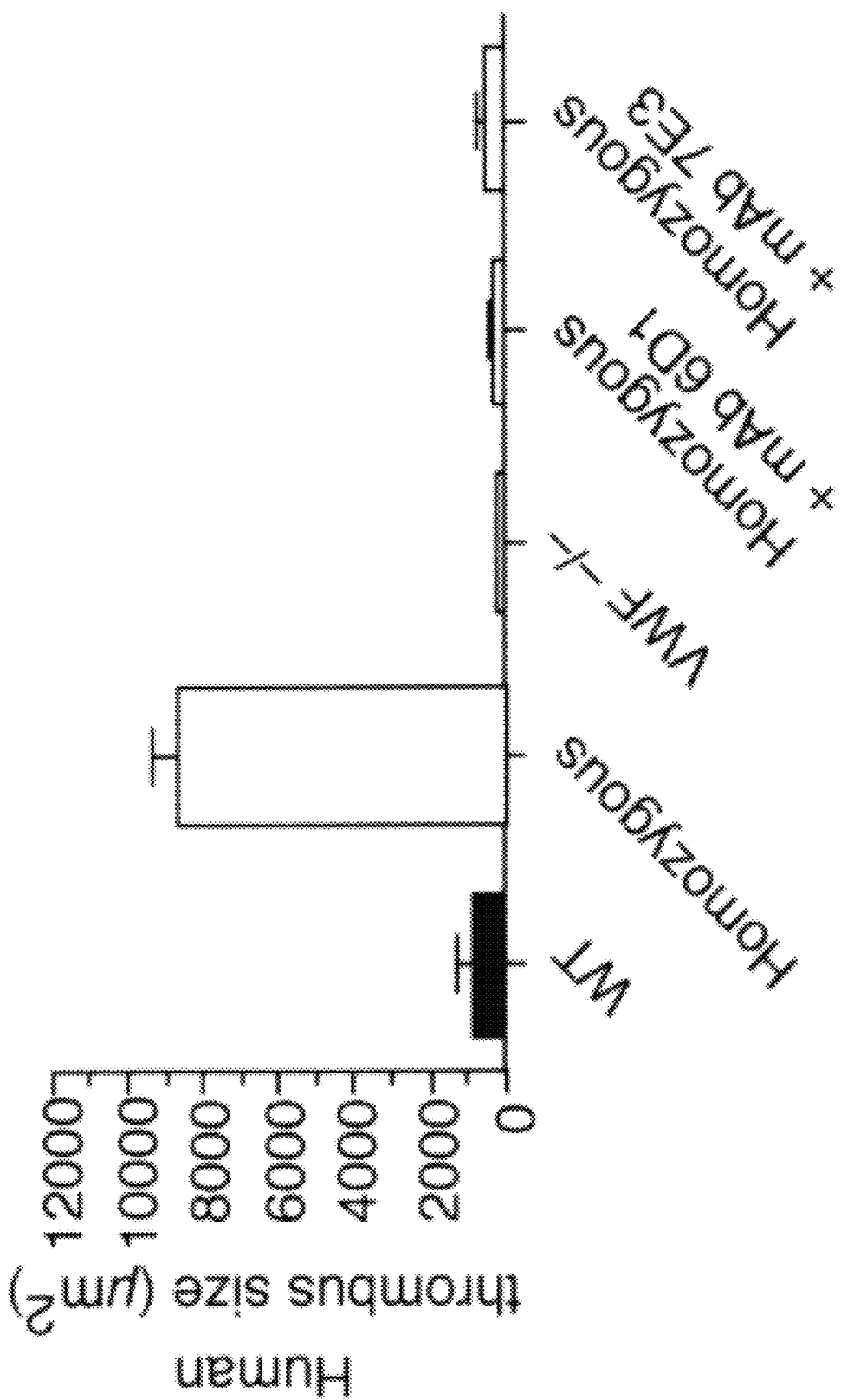
FIG. 41E is a bar graph measuring thrombus size during an in vivo study of human platelet interactions with plasma VWF$^{1326R>H}$ to determine the effect of GPIbα or αIIbβ3 blockade on human platelet adhesion in vivo. The requirement for GPIb alpha-mediated adhesion is shown by the ability of a function-blocking antibody (mAB 6D1 or mAb 7E3) to GPIb alpha to prevent human platelet thrombus formation in vivo. Fluorescently labeled human platelet accumulation was examined at sites of laser-induced arteriolar injury in WT (n=6) or homozygous mutant animals (n=8). Data represent the mean±s.e.m.
Figure 41F:
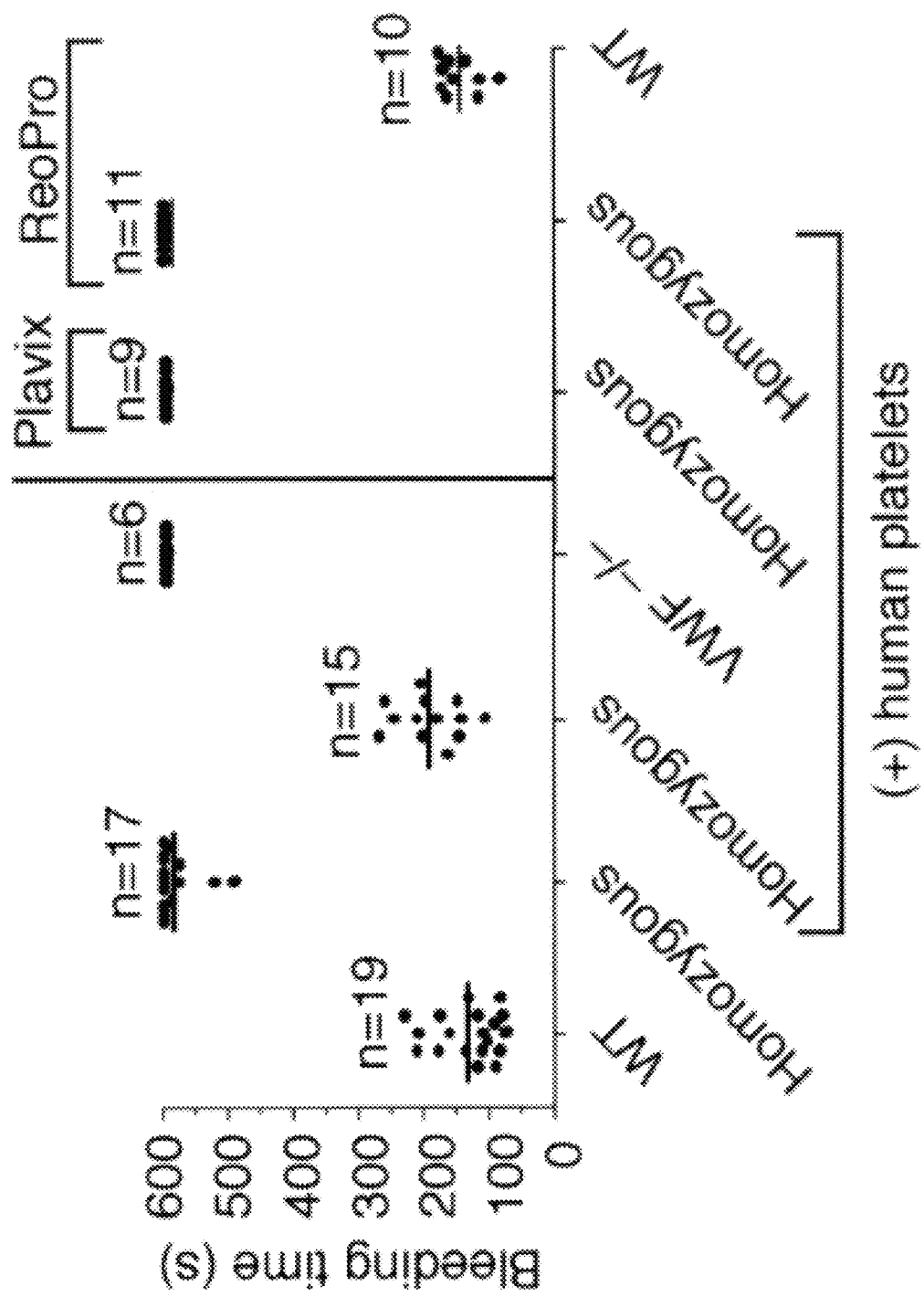
FIG. 41F is a graphical representation of tail bleeding times (s) for homozygous VWF$^{1326R>H}$ that received an infusion of either normal saline or human platelets prior to severing 10 mm of distal tail, wherein the ability of human platelets to restore hemostasis in homozygous VWF$^{1326R>H}$ and the effect of PLAVIX or ReoPro® on this process was examined. Each point represents one individual mouse and experiments were performed on 3 separate days.

To explore the importance of the electrostatic mismatches in destabilizing the interspecies complexes, we substituted human residues into murine rVWF-A1 at positions 1326 (R>H), 1330 (E>G), and 1370 (S>G), and analyzed the ability of the mutant proteins to support human platelet accumulation under flow. As expected, amino acid substitutions at positions 1330 (predicted to remove a salt-bridge) and 1370 (predicted to have no effect) failed to promote the interaction between murine rVWF-A1 and human GPIbα. However, the 1326R>H mutation, which eliminates the electrostatic clash with K231, rendered murine A1 capable of supporting interactions at a level comparable to its wild-type (WT) human counterpart (FIG. 37G). Similarly, conversion of 1326H>R in the human rVWF-A1 protein promoted the binding of mouse platelets, while the reverse substitution in its murine counterpart reduced adhesion by ~75%. That a single residue change is sufficient for shifting the binding preferences across species supports the notion that this contact region is a "hot-spot" in the protein interface (Bogan, A. A. & Thorn, K. S. *J. Mol. Biol.* 280, 1-9 (1998)).

In order to determine the ability of full-length murine VWF containing the 1326R>H mutation ($VWF^{1326R>H}$) to support human platelet interactions and ultimately thrombus formation in vivo, we genetically modified mice to express $VWF^{1326R>H}$ (FIGS. 38B-38C). Both homozygous and heterozygous animals were viable, fertile, born at the expected Mendelian ratio, and had platelet counts comparable to WT littermate controls. Moreover, reverse transcription-PCR (RT-PCR) of lung tissue from mutant mice with primers specific for the A1, A2, and/or A3 domains of VWF amplified cDNAs of the correct size and of similar intensity as compared to WT littermate controls (FIG. 39A). VWF antigen levels, Factor VIII function, as well as VWF multimer pattern in homozygous mutant plasma were found to be equivalent to WT controls (FIGS. 39B-39C). These results indicate that VWF gene translation, transcription, and posttranslational modifications were not perturbed by our targeting strategy. The ability of plasma VWF to bind to collagen was also not affected by the introduction of the point mutation.

Hemostasis relies on platelet adhesion and activation at sites of vascular injury, which ultimately results in the formation of a hemostatic plug. To demonstrate the importance of VWF-A1 in this process, we measured bleeding times for mice possessing the 1326R>H mutation by removing 1 cm of distal tail (FIG. 41A). In contrast to their WT counterparts, the vast majority of homozygous $VWF^{1326R>H}$ mice were incapable of forming an effective hemostatic plug, as they continued to bleed profusely throughout the duration of the experiment (10 min). Moreover, a smaller but statistically significant increase in bleeding time was noted for heterozygous animals (1.9-fold compared with WT; P=0.0055). Thus, disruption of a single salt bridge between murine VWF-A1 and GPIbα is sufficient to impair hemostasis.

To gain insight into how the 1326R>H mutation alterations hemostasis, we evaluated murine platelet adhesion at sites of vascular damage in vivo. A laser-induced vascular injury model was utilized to initiate platelet deposition in arterioles located in the microcirculation of the cremaster muscle of WT and homozygous mutant mice (Furie, B. & Furie., B. C. (2005) *J. Clin. Invest.* 115, 3355-3362). Although $VWF^{1326R>H}$ animals can initially form thrombi that fill the vessel lumen, they rapidly dissipated under the prevailing hydrodynamic conditions (FIG. 40). By contrast, thrombi in WT mice continue to enlarge and eventually occlude blood flow under identical conditions.

To demonstrate that the removal of the electrostatic clash between residues 1326 and 231 in murine VWF-A1 and human GPIb alpha, respectively, promotes substantial interactions between this chimeric receptor-ligand pair, we perfused human whole blood over surface-immobilized plasma VWF obtained from mice homozygous for $VWF^{1326R>H}$. Remarkably, mutant murine VWF bound human platelets at levels comparable with its human counterpart (FIG. 41B). Moreover, a function-blocking antibody 6D1, which binds exclusively to human GPIbα at the fourth LRR (Shen, Y. et al. (2000) *Blood.* 95, 903-910), inhibited platelet adhesion, demonstrating a key role for the platelet receptor in adhesion to $VWF^{1326R>H}$.

By contrast, the antibody SZ2 that recognizes the anionic-sulfated tyrosine sequence of GPIbα (residues 276 to 282) had a minimal affect on platelet accumulation, results consistent with a previous report (Fredrickson et al., (1998) *Blood.* 92, 3684-3693). The A1 domain also possesses the ability to support the movement of attached platelets in the direction of the prevailing hydrodynamic force owing to rapid and reversible interactions with GPIbα (Savage et al., (1996) *Cell* 84, 289-297; Doggett, T. A. et al. (2002) *Biophys. J.* 83, 194-205). We therefore compared translocation velocities of human platelets on either human or mutant murine VWF. Translocation velocities of human platelets on either homozygous mutant murine or native human plasma VWF were also similar (3.5±0.1 μm/sec vs. 3.2±0.1 μm/sec, respectively; mean±s.e.m, n=4), demonstrating that $VWF^{1326R->H}$ functions in a manner indistinguishable from its human counterpart.

We next tested the ability of murine $VWF^{1326R>H}$ to support human platelet adhesion in vivo. The ability of human platelets to preferentially support thrombus formation was monitored simultaneously by labeling purified human cells with BCECF ex-vivo, and mouse platelets with rhodamine 6G by intravenous administration. Fluorescently-labeled human platelets were infused continuously via a catheter inserted into the femoral artery, resulting in a high local concentration of these cells within the microcirculation of the cremaster muscle. Their behavior in response to laser-induced vascular injury was monitored in real-time using confocal intravital microscopy (Furie, B. & Furie., B. C. (2005) *J. Clin. Invest.* 115, 3355-3362). Upon induction of laser damage to the vessel wall of arterioles in mice homozygous for $VWF^{1326R>H}$, human platelets rapidly adhered to the site of injury, forming large thrombi composed mainly of human cells (91.7±1.2%; mean±s.e.m) (FIGS. 41C-41D); average thrombus size was 8,950±1,620 $\mu m^2$ (mean±s.e.m.). In WT mice, by contrast, human platelets had only a limited capacity to bind to the damaged vessel wall, accounting for only 5.7±0.4% of total thrombus area (mean±s.e.m.) (FIGS. 41C-41D).

Consistent with the critical role of platelet GPIb alpha in mediating interactions with VWF-A1, pre-treatment of human platelets with mAb 6D1 greatly reduced thrombus size in the vasculature of $VWF^{1326R>H}$ mice (265±125 $\mu m^2$; mean±s.e.m.) (FIG. 41E). This was also validated by our observations that human platelet deposition at sites of arterial injury is limited in VWF-deficient mice (185±35 $\mu m^2$; mean±s.e.m.), demonstrating that the A1 domain of this plasma protein serves as the major ligand for GPIbα in our humanized animal model of thrombosis.

Although GPIbα initiates platelet deposition at arterial shear rates, it is ultimately the platelet integrin αIIbβ3 that supports thrombus growth by promoting platelet-platelet interactions. The contribution of human αIIbβ3 in this process is demonstrated by the ability of the function blocking antibody 7E3 to also limit thrombus size (529±150 $\mu m^2$) (FIG. 41E). Confirmation that the interaction formed between human platelets and murine $VWF^{1326R>H}$ is sufficient to promote effective hemostasis is provided by the ability of infused human cells to restore bleeding times in mutant mice to a level observed for their WT counterparts (182±14.5 s vs. 131.5±11.2 s, respectively; mean±s.e.m.) (FIG. 41F). Importantly, human platelet-induced hemostatic clot formation can be completely disrupted in these animals by the preadministration of either clopidogrel (PLAVIX), an inhibitor of ADP-induced platelet activation, or abciximab (ReoPro®), a Fab fragment of the chimeric human-mouse monoclonal antibody 7E3, which blocks the function of αIIbβ3 on human but not murine platelets (Hankey, G. J. &

Eikelboom, J. W. Antiplatelet drugs. *Med. J. Aust.* 178, 568-574; Bennett, J. S. (2001) *Annu. Rev. Med.* 52, 161-184) (FIG. 41F).

In summary, these studies demonstrate how one can effectively utilize atomic models of interspecies complexes to identify a binding hot spot where a disproportionate amount of the binding free energy is localized, such that a single amino acid substitution significantly affects the interaction (Bogan, A. A. & Thorn, K. S. (1998) *J. Mol. Biol.* 280, 1-9), and in this case switches species specificity. Moreover, a subtle and localized change of this nature limits the possibility of inducing structural perturbations that impact on the function of other domains contained within VWF. These show that human platelet adhesion to VWF$^{1326R>H}$ is dependent on GPIbα binding to VWF-A1, with other potential ligands for this receptor playing a subservient role in this process (Bergmeier, W. et al. (2006) *Proc. Natl. Acad. Sci. USA.* 103, 16900-16905). The reliance of human thrombus formation on the integrin αIIbβ3, as well as the ability of the FDA approved drugs PLAVIX and ReoPro® to impair human platelet-mediated hemostasis indicate that downstream adhesive and activation events known to be critical for clot formation and stability are intact in the mutant VWF animals. Thus, we anticipate that the VWF$^{1326R>H}$ knock-in mice will prove useful in the preclinical evaluation of new antithrombotic therapeutics designed ultimately for human use. These results also have implications for advancing both knowledge of human platelet biology and in preclinical testing of antithrombotic therapies in vivo.

Example 5

Use of "Humanized" VWF-A1 Animal for Developing Technologies to Image Sites of Occult Bleeding or Thrombus Formation in Humans Perfluorocarbon Nanoparticle Based Imaging Platform.

Figure 42:
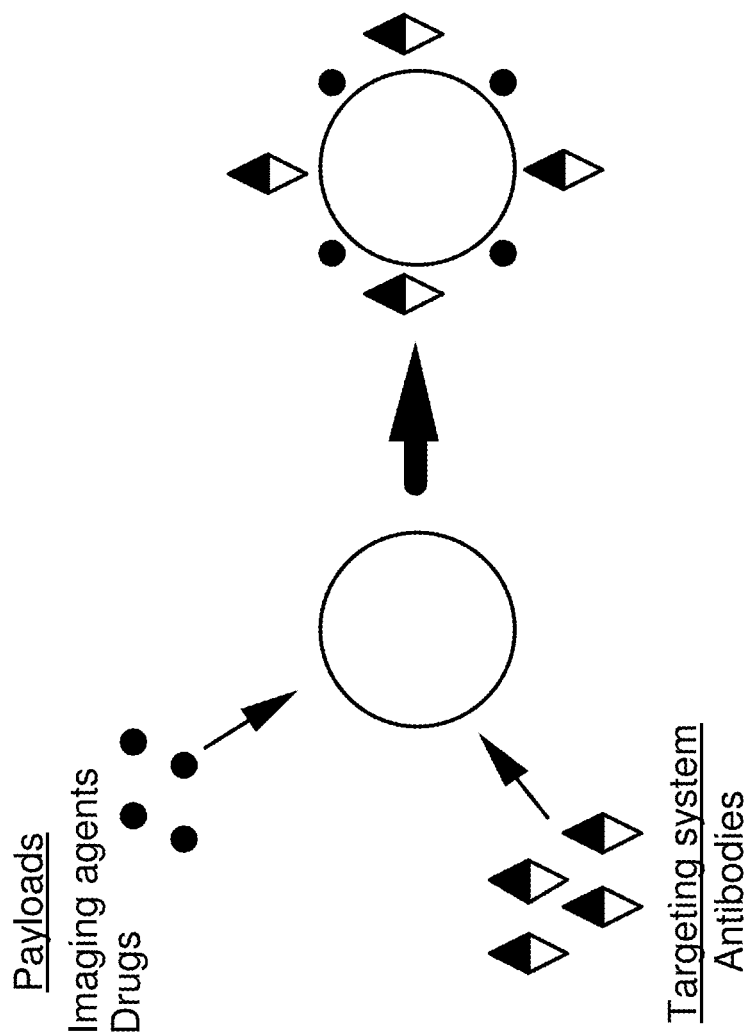
FIG. 42 is a schematic depicting a perfluorocarbon nanoparticle capable of incorporating imaging agents (Gd$^{+3}$, $^{99m}$Tc) and chemotherapeutics into the outer layers. Antibodies complexed to the surface of the particle can target the agent to specific sites within the body.

The ability of a VWF-A1 mutant animal, such as our 1326R>H mutant mouse, to generate thrombi composed of human platelets at sites of vascular injury in vivo, provides a means for developing imaging technologies designed to detect sites of occult bleeding or thrombus formation in humans. For example, such technologies may prove useful expediting the discovery of sites of internal bleeding in humans as a result of injuries obtained form a motor vehicle accident. Similarly, it may be useful in detecting injuries obtained in a military battle. Suitable probes include antibodies, small molecules, peptides that recognize molecules expressed on human platelets or the various domains of VWF. However, coupling contrast agents directly to antibodies is cumbersome and insufficient for detection of such complexes in the body by various imaging modalities (i.e. MRI) due to low signal to noise output. Thus, an ideal candidate for detection would not only preserve the specificity associated with monoclonal antibodies, small molecules, or peptides but also have the following properties: 1) high signal-to-noise ratio, 2) long circulating half-life, 3) acceptable toxicity profile, 4) ease of use and production, and 5) compatibility with standard commercially available imaging modalities. Perfluorocarbon Nanoparticle (PNP) may provide the answer. This proposal will take advantage of a novel nanoparticle contrast agent that can be imaged by ultrasound, magnetic resonance, and nuclear imaging (Lanza et al., (2000) *Invest Radiol*, 35: 227-234; Lanza et al., (1997) *Ultrasound Med Biol*, 23: 863-870; Yu et al., (2000) *Magn Reson Med.* 44(6):867-72). This agent is a small (~150-250 nanometer diameter), lipid encapsulated, perfluorocarbon emulsion that can be administered by vein. Importantly, monoclonal antibodies as well as small molecules and peptides that recognize platelets and/or VWF can be covalently coupled to PNPs. Moreover, PNPs can also be potentially used for targeted drug delivery (FIG. 42).

PNPs have been shown to remain stable in the circulation with a half-life of >1 hour, which permits rapid binding and local contrast enhancement sufficient for diagnostic imaging within 30-60 minutes. PNPs are cleared by the liver and spleen, and are similar to "artificial blood" formulations used to enhance oxygen, which have acceptable safety profiles for clinical use at 10 times greater dose than would be required for targeted contrast enhancement. In addition, perfluorocarbon to be used in this study (perfluorooctylbromide) has an extensive tract record for human safety in clinical trials (i.e., Oxygent, Alliance Pharmaceuticals). Thus, this nanoparticle platform provides an ideal opportunity to prove that contrast agents can be targeted specifically to sites of human thrombus formation.

Preparation of Fluorescently-Labeled Antibody Targeted Nanoparticles.

The basic method for formulating perfluorocarbon nanoparticles comprised of perfluorooctyl bromide (40% w/v), a surfactant co-mixture (2.0%, w/v) and glycerin 9(1.7%, w/v) has been well described (Lanza et al., (2000) *Invest Radiol*, 35: 227-234; Lanza et al., (1997) *Ultrasound Med Biol*, 23: 863-870).

Figure 43:
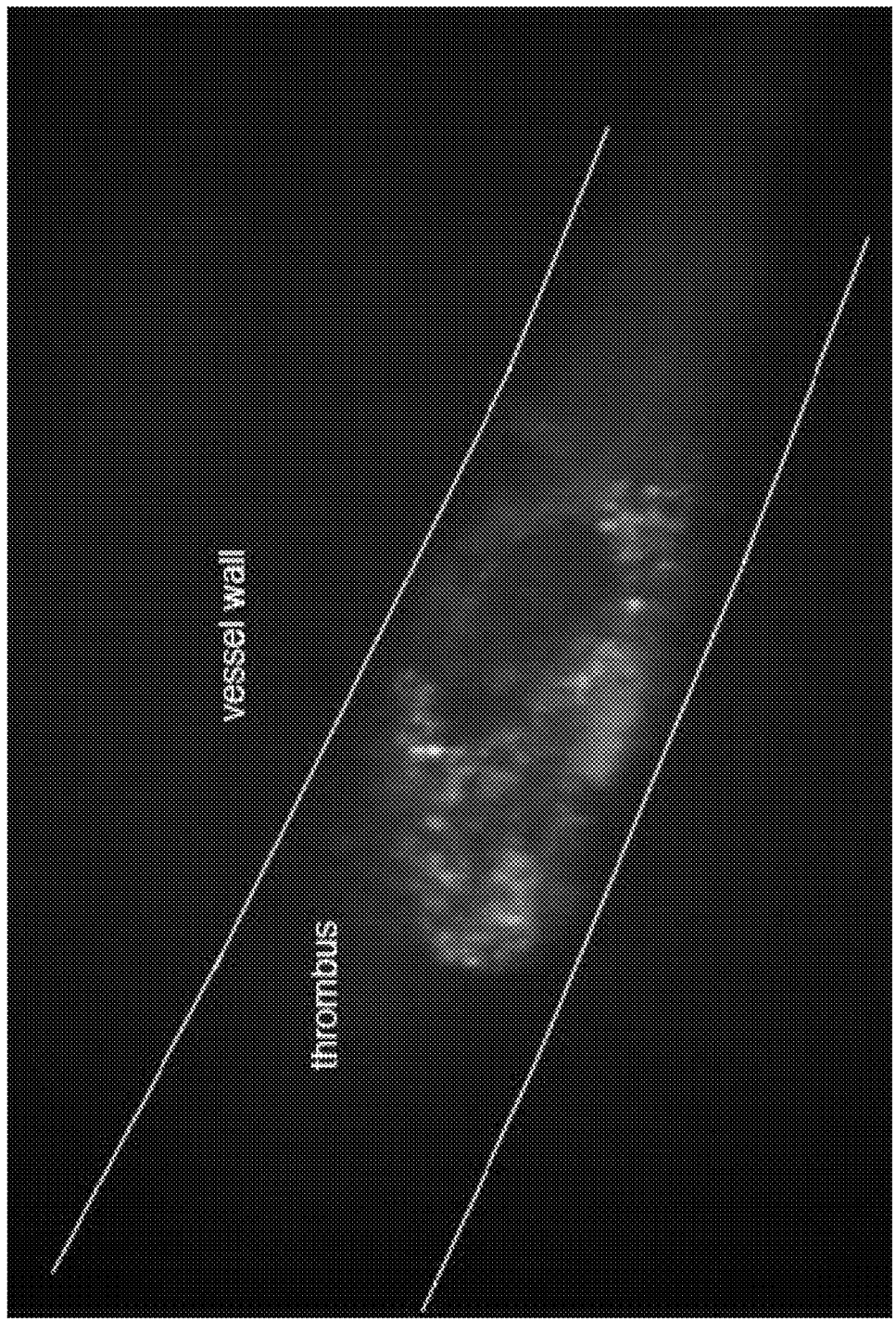
FIG. 43 is a photographic image depicting the accumulation of fluorescent PNP, coupled to an antibody that recognizes human alphaIIb beta 3 on the surface of human platelets, at a site of vascular injury in homozygous 1326R>H mutant mice infused with human platelets.

Briefly, the surfactant co-mixture is dissolved in chloroform/methanol, evaporated under reduced pressure, dried in a 50° C. vacuum oven, and finally dispersed into water by sonication. The suspension is combined with perfluorocarbon and then emulsified at 20,000 PSI. Fluorescent nanoparticles are manufactured by including in the lipid mixture 0.1 mole % Fluorescence-FITC or PE prior to the emulsification step. Coupling of monoclonal antibodies involves the introduction of a sulfhydrl group onto the protein by modification of amines with N-succinimidyl S-acetylthioacetate (SATA), which then is reacted with nanoparticles containing activated maleimide. We coupled an antibody that recognizes the human, but not mouse, platelet receptor alphaIIb beta$_3$ and determined the ability of FITC-labeled PNPs to detect a thrombus composed of human platelets at a site of laser-induced vascular injury in the cremaster muscle of a mouse homozygous for the 1326R>H mutation. These antibody-coupled PNPs rapidly and selectively accumulated at the site of the developing human thrombus (FIG. 43).

Example 6

Identification of Small Molecules that Mitigate Binding Between GPIb Alpha and the VWF-A1 Domain Small molecules, often with molecular weights of 500 or below, have proven to be extremely important to researchers to explore function at the molecular, cellular, and in vivo level. Such compounds have also been proven to be valuable as drugs to treat diseases, and most medicines marketed today are from this class (i.e., Aggrastat-see above). As the interaction between GPIb alpha and VWF-A1 is essential for the platelet deposition in damaged arterioles, it is a reasonable to assume that disruption of this adhesive event will inhibit or ameliorate thrombus formation. Moreover, we speculate that only partial inhibition is required to achieve this goal based on the phenotype of our mutant A1 domain mice, the inability to form stable thrombi in vivo.

Computational Design Based on the Structure of the Binary Complex.

Traditional approaches to small molecule discovery typically rely on a step-wise synthesis and screening program for large numbers of compounds to optimize activity profiles. Over the past decade, scientists have used computer models to aid in the development of new chemical agonists or antagonists as well as to better define activity profiles and binding affinities of such compounds. In particular, these tools are being successfully used, in conjunction with traditional research techniques, to examine the structural properties of existing compounds in order to predict their ability to alter the function of biologically relevant proteins. For this approach to be successful, one must have high quality crystal structures of the biological molecule(s) in order to generate an accurate 3-dimensional model so that it can then be used to identify binding regions for small molecules.

Figure 44B:
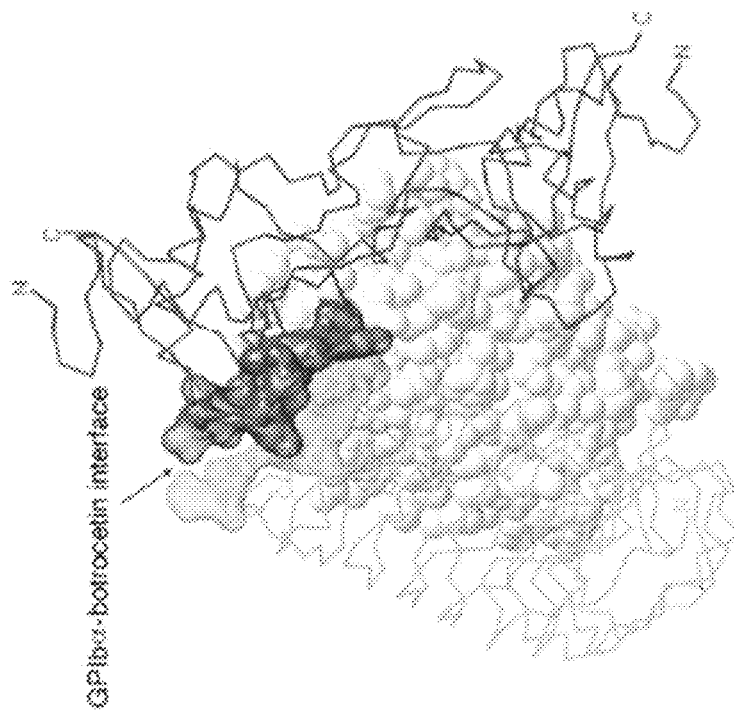
FIGS. 44A and 44B graphical representations of the structure of the VWF-A1-GPIb alpha-botrocetin ternary complex.
Figure 44A:
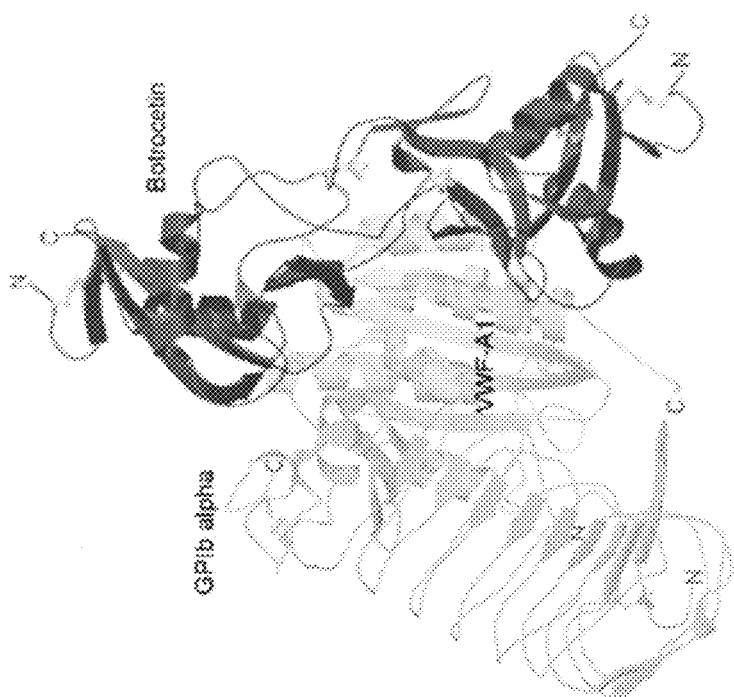

The structure of the binary complex formed when GPIb alpha binds to the A1 domain of VWF can be determined using such methods. For example, a mechanism by which the snake venom protein botrocetin enhances the interaction between GPIb alpha and the VWF-A1 in order to promote spontaneous platelet aggregation, resulting in death has been elucidated. Botrocetin was known to bind with high affinity to the A1 domain [see Table 7 for the crystallization data summary and Table 8 for atomic coordinate data], but was not thought to interact directly with GPIb alpha. This snake venom has the capacity to form a small, but distinct interface with this platelet receptor so to prevent its release from the A1 domain, thus facilitating platelet aggregation (FIGS. 44A and 44B). In a sense, nature has created a molecule that modifies the behavior of a known biological interaction, suggesting that one may be able to target man-made structures to this domain as well.

TABLE 7

Summary of Crystallization data (from PDB access no. 1AUQ and *J Biol Chem* (1998) 273(17):10396-10401)

| Structure | Free enzyme (see Table 8) |
| --- | --- |
| Space Group | $P6_1$ |
| Maximum resolution (Å) | 2.3 |
| Resolution range for refinement | 10-2.3 |
| Number of reflections | 11,849 |
| Completeness (%) | 85.4 |
| R factor$^2$ (%) | 18.6 |
| Free R factor$^2$ (%) | 23.8 |
| rms deviation in bond lengths (Å) | 0.011 |
| rms deviation in bond angles (°) | 1.43 |

TABLE 8

Atomic Coordinates for Residues of a Crystal of murine VWF-A1 (SEQ ID NO: 10).

| CRYST1 | 86.395 | | 86.395 | 68.125 | 90.00 | 90.00 | 120.00 | P 61 | 6 |
| --- | --- | --- | --- | --- | --- | --- | --- | --- | --- |
| ATOM | 1 | N | ASP 498 | 22.142 | 52.453 | -14.520 | 1.00 | 83.59 | N |
| ATOM | 2 | CA | ASP 498 | 20.770 | 52.768 | -14.026 | 1.00 | 83.86 | C |
| ATOM | 3 | C | ASP 498 | 20.803 | 53.068 | -12.522 | 1.00 | 81.16 | C |
| ATOM | 4 | O | ASP 498 | 20.978 | 52.165 | -11.696 | 1.00 | 81.93 | O |
| ATOM | 5 | CB | ASP 498 | 19.821 | 51.597 | -14.327 | 1.00 | 87.23 | C |
| ATOM | 6 | CG | ASP 498 | 18.352 | 51.961 | -14.133 | 1.00 | 88.94 | C |
| ATOM | 7 | OD1 | ASP 498 | 18.022 | 53.171 | -14.084 | 1.00 | 88.91 | O |
| ATOM | 8 | OD2 | ASP 498 | 17.521 | 51.027 | -14.033 | 1.00 | 90.11 | O |
| ATOM | 9 | N | ILE 499 | 20.620 | 54.343 | -12.190 | 1.00 | 76.43 | N |
| ATOM | 10 | CA | ILE 499 | 20.649 | 54.829 | -10.809 | 1.00 | 70.82 | C |
| ATOM | 11 | C | ILE 499 | 19.237 | 55.126 | -10.255 | 1.00 | 64.40 | C |
| ATOM | 12 | O | ILE 499 | 18.888 | 56.265 | -9.941 | 1.00 | 62.53 | O |
| ATOM | 13 | CB | ILE 499 | 21.596 | 56.076 | -10.724 | 1.00 | 75.17 | C |
| ATOM | 14 | CG1 | ILE 499 | 21.872 | 56.476 | -9.278 | 1.00 | 77.18 | C |
| ATOM | 15 | CG2 | ILE 499 | 21.030 | 57.256 | -11.527 | 1.00 | 77.54 | C |
| ATOM | 16 | CD1 | ILE 499 | 23.010 | 57.485 | -9.141 | 1.00 | 79.34 | C |
| ATOM | 17 | N | SER 500 | 18.445 | 54.071 | -10.111 | 1.00 | 58.81 | N |
| ATOM | 18 | CA | SER 500 | 17.073 | 54.170 | -9.616 | 1.00 | 52.67 | C |
| ATOM | 19 | C | SER 500 | 16.771 | 52.914 | -8.797 | 1.00 | 46.03 | C |
| ATOM | 20 | O | SER 500 | 17.477 | 51.915 | -8.928 | 1.00 | 46.10 | O |
| ATOM | 21 | CB | SER 500 | 16.085 | 54.306 | -10.779 | 1.00 | 55.03 | C |
| ATOM | 22 | OG | SER 500 | 14.814 | 54.747 | -10.320 | 1.00 | 55.43 | O |
| ATOM | 23 | N | GLU 501 | 15.690 | 52.946 | -8.017 | 1.00 | 39.21 | N |
| ATOM | 24 | CA | GLU 501 | 15.341 | 51.839 | -7.124 | 1.00 | 33.62 | C |
| ATOM | 25 | C | GLU 501 | 13.826 | 51.632 | -6.967 | 1.00 | 33.73 | C |
| ATOM | 26 | O | GLU 501 | 13.055 | 52.575 | -7.148 | 1.00 | 35.42 | O |
| ATOM | 27 | CB | GLU 501 | 16.025 | 52.088 | -5.772 | 1.00 | 27.09 | C |
| ATOM | 28 | CG | GLU 501 | 15.928 | 53.517 | -5.328 | 1.00 | 23.81 | C |
| ATOM | 29 | CD | GLU 501 | 17.036 | 53.971 | -4.394 | 1.00 | 22.26 | C |
| ATOM | 30 | OE1 | GLU 501 | 18.150 | 53.442 | -4.407 | 1.00 | 23.46 | O |
| ATOM | 31 | OE2 | GLU 501 | 16.790 | 54.912 | -3.645 | 1.00 | 19.78 | O |
| ATOM | 32 | N | PRO 502 | 13.390 | 50.408 | -6.585 | 1.00 | 32.77 | N |
| ATOM | 33 | CA | PRO 502 | 11.980 | 50.038 | -6.406 | 1.00 | 33.37 | C |
| ATOM | 34 | C | PRO 502 | 11.257 | 50.886 | -5.377 | 1.00 | 36.76 | C |
| ATOM | 35 | O | PRO 502 | 11.881 | 51.657 | -4.655 | 1.00 | 40.35 | O |
| ATOM | 36 | CB | PRO 502 | 12.056 | 48.588 | -5.911 | 1.00 | 32.84 | C |
| ATOM | 37 | CG | PRO 502 | 13.426 | 48.154 | -6.188 | 1.00 | 30.80 | C |
| ATOM | 38 | CD | PRO 502 | 14.248 | 49.372 | -5.994 | 1.00 | 33.53 | C |
| ATOM | 39 | N | PRO 503 | 9.921 | 50.743 | -5.283 | 1.00 | 38.50 | N |
| ATOM | 40 | CA | PRO 503 | 9.095 | 51.495 | -4.332 | 1.00 | 36.00 | C |
| ATOM | 41 | C | PRO 503 | 9.217 | 50.861 | -2.962 | 1.00 | 33.78 | C |
| ATOM | 42 | O | PRO 503 | 9.351 | 49.642 | -2.870 | 1.00 | 33.98 | O |
| ATOM | 43 | CB | PRO 503 | 7.670 | 51.270 | -4.844 | 1.00 | 35.94 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 44 | CG | PRO | 503 | 7.844 | 50.708 | −6.240 | 1.00 | 36.76 | C |
| ATOM | 45 | CD | PRO | 503 | 9.074 | 49.889 | −6.137 | 1.00 | 37.21 | C |
| ATOM | 46 | N | LEU | 504 | 9.225 | 51.670 | −1.910 | 1.00 | 32.48 | N |
| ATOM | 47 | CA | LEU | 504 | 9.284 | 51.120 | −0.562 | 1.00 | 31.29 | C |
| ATOM | 48 | C | LEU | 504 | 7.869 | 50.821 | −0.120 | 1.00 | 31.74 | C |
| ATOM | 49 | O | LEU | 504 | 7.663 | 50.104 | 0.847 | 1.00 | 34.42 | O |
| ATOM | 50 | CB | LEU | 504 | 9.857 | 52.133 | 0.427 | 1.00 | 27.31 | C |
| ATOM | 51 | CG | LEU | 504 | 11.346 | 52.216 | 0.633 | 1.00 | 20.47 | C |
| ATOM | 52 | CD1 | LEU | 504 | 11.608 | 53.354 | 1.577 | 1.00 | 16.31 | C |
| ATOM | 53 | CD2 | LEU | 504 | 11.865 | 50.886 | 1.213 | 1.00 | 22.70 | C |
| ATOM | 54 | N | HIS | 505 | 6.892 | 51.433 | −0.779 | 1.00 | 32.33 | N |
| ATOM | 55 | CA | HIS | 505 | 5.508 | 51.234 | −0.382 | 1.00 | 33.59 | C |
| ATOM | 56 | C | HIS | 505 | 4.574 | 50.872 | −1.506 | 1.00 | 37.41 | C |
| ATOM | 57 | O | HIS | 505 | 4.980 | 50.817 | −2.669 | 1.00 | 38.66 | O |
| ATOM | 58 | CB | HIS | 505 | 4.977 | 52.504 | 0.277 | 1.00 | 30.39 | C |
| ATOM | 59 | CG | HIS | 505 | 5.799 | 52.956 | 1.432 | 1.00 | 24.50 | C |
| ATOM | 60 | ND1 | HIS | 505 | 6.533 | 54.118 | 1.413 | 1.00 | 26.88 | N |
| ATOM | 61 | CD2 | HIS | 505 | 6.041 | 52.377 | 2.628 | 1.00 | 22.75 | C |
| ATOM | 62 | CE1 | HIS | 505 | 7.195 | 54.235 | 2.543 | 1.00 | 22.86 | C |
| ATOM | 63 | NE2 | HIS | 505 | 6.915 | 53.193 | 3.297 | 1.00 | 23.78 | N |
| ATOM | 64 | N | ASP | 506 | 3.323 | 50.612 | −1.125 | 1.00 | 39.57 | N |
| ATOM | 65 | CA | ASP | 506 | 2.254 | 50.291 | −2.072 | 1.00 | 41.22 | C |
| ATOM | 66 | C | ASP | 506 | 1.600 | 51.614 | −2.482 | 1.00 | 39.47 | C |
| ATOM | 67 | O | ASP | 506 | 1.306 | 51.826 | −3.651 | 1.00 | 42.48 | O |
| ATOM | 68 | CB | ASP | 506 | 1.231 | 49.325 | −1.443 | 1.00 | 44.20 | C |
| ATOM | 69 | CG | ASP | 506 | 1.831 | 47.941 | −1.106 | 1.00 | 47.68 | C |
| ATOM | 70 | OD1 | ASP | 506 | 2.837 | 47.508 | −1.730 | 1.00 | 48.34 | O |
| ATOM | 71 | OD2 | ASP | 506 | 1.276 | 47.272 | −0.209 | 1.00 | 49.92 | O |
| ATOM | 72 | N | PHE | 507 | 1.367 | 52.497 | −1.507 | 1.00 | 38.50 | N |
| ATOM | 73 | CA | PHE | 507 | 0.800 | 53.830 | −1.756 | 1.00 | 35.03 | C |
| ATOM | 74 | C | PHE | 507 | 2.016 | 54.527 | −2.406 | 1.00 | 36.00 | C |
| ATOM | 75 | O | PHE | 507 | 3.086 | 54.637 | −1.780 | 1.00 | 35.29 | O |
| ATOM | 76 | CB | PHE | 507 | 0.408 | 54.471 | −0.418 | 1.00 | 32.75 | C |
| ATOM | 77 | CG | PHE | 507 | −0.252 | 55.810 | −0.552 | 1.00 | 32.71 | C |
| ATOM | 78 | CD1 | PHE | 507 | −1.605 | 55.915 | −0.866 | 1.00 | 33.60 | C |
| ATOM | 79 | CD2 | PHE | 507 | 0.471 | 56.969 | −0.343 | 1.00 | 29.61 | C |
| ATOM | 80 | CE1 | PHE | 507 | −2.216 | 57.157 | −0.962 | 1.00 | 31.49 | C |
| ATOM | 81 | CE2 | PHE | 507 | −0.132 | 58.205 | −0.437 | 1.00 | 29.32 | C |
| ATOM | 82 | CZ | PHE | 507 | −1.477 | 58.298 | −0.750 | 1.00 | 33.05 | C |
| ATOM | 83 | N | TYR | 508 | 1.839 | 55.032 | −3.624 | 1.00 | 35.32 | N |
| ATOM | 84 | CA | TYR | 508 | 2.955 | 55.578 | −4.396 | 1.00 | 32.82 | C |
| ATOM | 85 | C | TYR | 508 | 2.445 | 56.499 | 5.515 | 1.00 | 33.01 | C |
| ATOM | 86 | O | TYR | 508 | 1.484 | 56.154 | −6.200 | 1.00 | 39.06 | O |
| ATOM | 87 | CB | TYR | 508 | 3.612 | 54.364 | −5.053 | 1.00 | 27.12 | C |
| ATOM | 88 | CG | TYR | 508 | 5.027 | 54.464 | −5.529 | 1.00 | 31.57 | C |
| ATOM | 89 | CD1 | TYR | 508 | 6.041 | 54.922 | −4.680 | 1.00 | 35.35 | C |
| ATOM | 90 | CD2 | TYR | 508 | 5.389 | 53.946 | −6.771 | 1.00 | 28.70 | C |
| ATOM | 91 | CE1 | TYR | 508 | 7.397 | 54.848 | −5.054 | 1.00 | 36.51 | C |
| ATOM | 92 | CE2 | TYR | 508 | 6.730 | 53.862 | −7.154 | 1.00 | 33.58 | C |
| ATOM | 93 | CZ | TYR | 508 | 7.735 | 54.309 | −6.294 | 1.00 | 36.83 | C |
| ATOM | 94 | OH | TYR | 508 | 9.075 | 54.176 | −6.649 | 1.00 | 40.00 | O |
| ATOM | 95 | N | CYS | 509 | 3.046 | 57.662 | −5.717 | 1.00 | 28.11 | N |
| ATOM | 96 | CA | CYS | 509 | 2.593 | 58.516 | −6.822 | 1.00 | 27.15 | C |
| ATOM | 97 | C | CYS | 509 | 3.509 | 58.310 | −8.009 | 1.00 | 25.32 | C |
| ATOM | 98 | O | CYS | 509 | 4.717 | 58.512 | −7.909 | 1.00 | 30.67 | O |
| ATOM | 99 | CB | CYS | 509 | 2.572 | 59.997 | −6.464 | 1.00 | 25.77 | C |
| ATOM | 100 | SG | CYS | 509 | 1.888 | 61.004 | −7.834 | 1.00 | 21.50 | S |
| ATOM | 101 | N | SER | 510 | 2.939 | 57.837 | −9.102 | 1.00 | 23.50 | N |
| ATOM | 102 | CA | SER | 510 | 3.686 | 57.590 | −10.321 | 1.00 | 25.91 | C |
| ATOM | 103 | C | SER | 510 | 3.052 | 58.414 | −11.475 | 1.00 | 25.38 | C |
| ATOM | 104 | O | SER | 510 | 2.384 | 57.882 | −12.364 | 1.00 | 32.01 | O |
| ATOM | 105 | CB | SER | 510 | 3.687 | 56.087 | −10.612 | 1.00 | 24.85 | C |
| ATOM | 106 | OG | SER | 510 | 4.275 | 55.783 | −11.867 | 1.00 | 29.60 | O |
| ATOM | 107 | N | ARG | 511 | 3.236 | 59.726 | −11.434 | 1.00 | 19.35 | N |
| ATOM | 108 | CA | ARG | 511 | 2.689 | 60.596 | −12.451 | 1.00 | 16.16 | C |
| ATOM | 109 | C | ARG | 511 | 3.757 | 61.589 | −12.810 | 1.00 | 20.03 | C |
| ATOM | 110 | O | ARG | 511 | 4.825 | 61.584 | −12.191 | 1.00 | 24.48 | O |
| ATOM | 111 | CB | ARG | 511 | 1.439 | 61.310 | −11.952 | 1.00 | 13.51 | C |
| ATOM | 112 | CG | ARG | 511 | 0.300 | 60.358 | −11.708 | 1.00 | 13.74 | C |
| ATOM | 113 | CD | ARG | 511 | −0.994 | 61.084 | −11.674 | 1.00 | 12.03 | C |
| ATOM | 114 | NE | ARG | 511 | −2.111 | 60.169 | −11.505 | 1.00 | 12.96 | N |
| ATOM | 115 | CZ | ARG | 511 | −3.388 | 60.547 | −11.582 | 1.00 | 16.84 | C |
| ATOM | 116 | NH1 | ARG | 511 | −3.700 | 61.814 | −11.841 | 1.00 | 18.71 | N |
| ATOM | 117 | NH2 | ARG | 511 | −4.361 | 59.680 | −11.342 | 1.00 | 18.41 | N |
| ATOM | 118 | N | LEU | 512 | 3.482 | 62.427 | −13.810 | 1.00 | 16.95 | N |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 119 | CA | LEU | 512 | 4.457 | 63.400 | −14.279 | 1.00 | 17.28 | C |
| ATOM | 120 | C | LEU | 512 | 4.337 | 64.645 | −13.434 | 1.00 | 16.82 | C |
| ATOM | 121 | O | LEU | 512 | 3.544 | 65.534 | −13.715 | 1.00 | 18.14 | O |
| ATOM | 122 | CB | LEU | 512 | 4.220 | 63.668 | −15.756 | 1.00 | 18.43 | C |
| ATOM | 123 | CG | LEU | 512 | 4.357 | 62.372 | −16.556 | 1.00 | 17.02 | C |
| ATOM | 124 | CD1 | LEU | 512 | 3.947 | 62.602 | −17.993 | 1.00 | 15.13 | C |
| ATOM | 125 | CD2 | LEU | 512 | 5.796 | 61.865 | −16.461 | 1.00 | 16.19 | C |
| ATOM | 126 | N | LEU | 513 | 5.226 | 64.748 | −12.458 | 1.00 | 19.32 | N |
| ATOM | 127 | CA | LEU | 513 | 5.162 | 65.827 | −11.501 | 1.00 | 18.08 | C |
| ATOM | 128 | C | LEU | 513 | 6.506 | 66.390 | −11.089 | 1.00 | 15.12 | C |
| ATOM | 129 | O | LEU | 513 | 7.477 | 65.655 | −10.948 | 1.00 | 14.11 | O |
| ATOM | 130 | CB | LEU | 513 | 4.454 | 65.273 | −10.257 | 1.00 | 19.36 | C |
| ATOM | 131 | CG | LEU | 513 | 4.260 | 66.123 | −9.012 | 1.00 | 20.52 | C |
| ATOM | 132 | CD1 | LEU | 513 | 3.338 | 67.259 | −9.353 | 1.00 | 18.37 | C |
| ATOM | 133 | CD2 | LEU | 513 | 3.698 | 65.270 | −7.902 | 1.00 | 12.16 | C |
| ATOM | 134 | N | ASP | 514 | 6.534 | 67.699 | −10.853 | 1.00 | 16.07 | N |
| ATOM | 135 | CA | ASP | 514 | 7.735 | 68.384 | −10.383 | 1.00 | 16.17 | C |
| ATOM | 136 | C | ASP | 514 | 7.257 | 68.946 | 9.041 | 1.00 | 15.61 | C |
| ATOM | 137 | O | ASP | 514 | 6.480 | 69.890 | 9.014 | 1.00 | 16.76 | O |
| ATOM | 138 | CB | ASP | 514 | 8.136 | 69.530 | −11.327 | 1.00 | 15.99 | C |
| ATOM | 139 | CG | ASP | 514 | 9.016 | 69.076 | −12.511 | 1.00 | 18.33 | C |
| ATOM | 140 | OD1 | ASP | 514 | 9.255 | 67.874 | −12.736 | 1.00 | 17.22 | O |
| ATOM | 141 | OD2 | ASP | 514 | 9.492 | 69.961 | −13.240 | 1.00 | 25.18 | O |
| ATOM | 142 | N | LEU | 515 | 7.660 | 68.338 | −7.929 | 1.00 | 15.44 | N |
| ATOM | 143 | CA | LEU | 515 | 7.205 | 68.808 | −6.623 | 1.00 | 14.64 | C |
| ATOM | 144 | C | LEU | 515 | 8.282 | 69.524 | −5.802 | 1.00 | 14.01 | C |
| ATOM | 145 | O | LEU | 515 | 9.382 | 68.995 | −5.603 | 1.00 | 8.40 | O |
| ATOM | 146 | CB | LEU | 515 | 6.613 | 67.625 | −5.853 | 1.00 | 14.99 | C |
| ATOM | 147 | CG | LEU | 515 | 6.168 | 67.788 | −4.396 | 1.00 | 9.59 | C |
| ATOM | 148 | CD1 | LEU | 515 | 5.054 | 68.775 | 4.249 | 1.00 | 5.58 | C |
| ATOM | 149 | CD2 | LEU | 515 | 5.714 | 66.455 | 3.924 | 1.00 | 8.85 | C |
| ATOM | 150 | N | VAL | 516 | 7.975 | 70.743 | −5.355 | 1.00 | 10.50 | N |
| ATOM | 151 | CA | VAL | 516 | 8.927 | 71.514 | −4.566 | 1.00 | 13.88 | C |
| ATOM | 152 | C | VAL | 516 | 8.504 | 71.601 | −3.100 | 1.00 | 14.19 | C |
| ATOM | 153 | O | VAL | 516 | 7.400 | 72.059 | −2.796 | 1.00 | 14.17 | O |
| ATOM | 154 | CB | VAL | 516 | 9.103 | 72.966 | −5.111 | 1.00 | 15.97 | C |
| ATOM | 155 | CG1 | VAL | 516 | 10.134 | 73.711 | −4.278 | 1.00 | 14.88 | C |
| ATOM | 156 | CG2 | VAL | 516 | 9.580 | 72.947 | −6.570 | 1.00 | 14.16 | C |
| ATOM | 157 | N | PHE | 517 | 9.359 | 71.127 | −2.191 | 1.00 | 17.00 | N |
| ATOM | 158 | CA | PHE | 517 | 9.072 | 71.205 | −0.747 | 1.00 | 13.51 | C |
| ATOM | 159 | C | PHE | 517 | 9.776 | 72.469 | −0.179 | 1.00 | 12.08 | C |
| ATOM | 160 | O | PHE | 517 | 11.009 | 72.587 | −0.233 | 1.00 | 10.17 | O |
| ATOM | 161 | CB | PHE | 517 | 9.602 | 69.968 | −0.024 | 1.00 | 15.54 | C |
| ATOM | 162 | CG | PHE | 517 | 8.940 | 68.662 | −0.426 | 1.00 | 11.63 | C |
| ATOM | 163 | CD1 | PHE | 517 | 7.805 | 68.200 | 0.230 | 1.00 | 13.47 | C |
| ATOM | 164 | CD2 | PHE | 517 | 9.517 | 67.852 | −1.400 | 1.00 | 9.53 | C |
| ATOM | 165 | CE1 | PHE | 517 | 7.256 | 66.952 | −0.075 | 1.00 | 10.36 | C |
| ATOM | 166 | CE2 | PHE | 517 | 8.989 | 66.625 | −1.703 | 1.00 | 8.49 | C |
| ATOM | 167 | CZ | PHE | 517 | 7.847 | 66.164 | −1.036 | 1.00 | 10.76 | C |
| ATOM | 168 | N | LEU | 518 | 9.005 | 73.405 | 0.378 | 1.00 | 12.33 | N |
| ATOM | 169 | CA | LEU | 518 | 9.574 | 74.643 | 0.926 | 1.00 | 12.65 | C |
| ATOM | 170 | C | LEU | 518 | 9.420 | 74.659 | 2.453 | 1.00 | 11.22 | C |
| ATOM | 171 | O | LEU | 518 | 8.333 | 74.940 | 2.959 | 1.00 | 15.25 | O |
| ATOM | 172 | CB | LEU | 518 | 8.884 | 75.865 | 0.287 | 1.00 | 9.93 | C |
| ATOM | 173 | CG | LEU | 518 | 8.791 | 75.956 | −1.244 | 1.00 | 8.05 | C |
| ATOM | 174 | CD1 | LEU | 518 | 7.840 | 77.076 | −1.640 | 1.00 | 3.79 | C |
| ATOM | 175 | CD2 | LEU | 518 | 10.166 | 76.182 | −1.857 | 1.00 | 10.27 | C |
| ATOM | 176 | N | LEU | 519 | 10.514 | 74.399 | 3.168 | 1.00 | 7.04 | N |
| ATOM | 177 | CA | LEU | 519 | 10.518 | 74.319 | 4.635 | 1.00 | 7.57 | C |
| ATOM | 178 | C | LEU | 519 | 10.795 | 75.567 | 5.440 | 1.00 | 4.28 | C |
| ATOM | 179 | O | LEU | 519 | 11.867 | 76.131 | 5.339 | 1.00 | 10.10 | O |
| ATOM | 180 | CB | LEU | 519 | 11.544 | 73.283 | 5.090 | 1.00 | 6.92 | C |
| ATOM | 181 | CG | LEU | 519 | 11.188 | 71.821 | 4.925 | 1.00 | 10.92 | C |
| ATOM | 182 | CD1 | LEU | 519 | 11.011 | 71.550 | 3.470 | 1.00 | 8.66 | C |
| ATOM | 183 | CD2 | LEU | 519 | 12.295 | 70.951 | 5.489 | 1.00 | 7.00 | C |
| ATOM | 184 | N | ASP | 520 | 9.891 | 75.908 | 6.352 | 1.00 | 11.69 | N |
| ATOM | 185 | CA | ASP | 520 | 10.051 | 77.081 | 7.217 | 1.00 | 13.58 | C |
| ATOM | 186 | C | ASP | 520 | 11.330 | 76.914 | 8.057 | 1.00 | 14.38 | C |
| ATOM | 187 | O | ASP | 520 | 11.469 | 75.933 | 8.775 | 1.00 | 18.86 | O |
| ATOM | 188 | CB | ASP | 520 | 8.813 | 77.201 | 8.116 | 1.00 | 15.76 | C |
| ATOM | 189 | CG | ASP | 520 | 8.737 | 78.528 | 8.839 | 1.00 | 14.91 | C |
| ATOM | 190 | OD1 | ASP | 520 | 9.744 | 78.970 | 9.394 | 1.00 | 15.53 | O |
| ATOM | 191 | OD2 | ASP | 520 | 7.671 | 79.143 | 8.870 | 1.00 | 15.00 | O |
| ATOM | 192 | N | GLY | 521 | 12.272 | 77.847 | 7.958 | 1.00 | 12.62 | N |
| ATOM | 193 | CA | GLY | 521 | 13.514 | 77.720 | 8.713 | 1.00 | 12.88 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 194 | C | GLY | 521 | 13.617 | 78.637 | 9.919 | 1.00 | 17.26 | C |
| ATOM | 195 | O | GLY | 521 | 14.690 | 78.785 | 10.508 | 1.00 | 16.89 | O |
| ATOM | 196 | N | SER | 522 | 12.500 | 79.256 | 10.291 | 1.00 | 16.08 | N |
| ATOM | 197 | CA | SER | 522 | 12.452 | 80.168 | 11.420 | 1.00 | 17.98 | C |
| ATOM | 198 | C | SER | 522 | 12.484 | 79.424 | 12.750 | 1.00 | 18.81 | C |
| ATOM | 199 | O | SER | 522 | 12.359 | 78.197 | 12.792 | 1.00 | 17.50 | O |
| ATOM | 200 | CB | ER | 522 | 11.158 | 80.967 | 11.371 | 1.00 | 12.88 | C |
| ATOM | 201 | OG | SER | 522 | 10.069 | 80.128 | 11.708 | 1.00 | 12.60 | O |
| ATOM | 202 | N | SER | 523 | 12.547 | 80.206 | 13.628 | 1.00 | 17.68 | N |
| ATOM | 203 | CA | SER | 523 | 12.558 | 79.701 | 15.187 | 1.00 | 20.71 | C |
| ATOM | 204 | C | SER | 523 | 11.141 | 79.389 | 15.694 | 1.00 | 20.97 | C |
| ATOM | 205 | O | SER | 523 | 10.971 | 78.999 | 16.833 | 1.00 | 27.46 | O |
| ATOM | 206 | CB | SER | 523 | 13.253 | 80.693 | 16.111 | 1.00 | 21.32 | C |
| ATOM | 207 | OG | SER | 523 | 12.701 | 81.986 | 15.933 | 1.00 | 26.32 | O |
| ATOM | 208 | N | ARG | 524 | 10.117 | 79.590 | 14.872 | 1.00 | 16.19 | N |
| ATOM | 209 | CA | ARG | 524 | 8.765 | 79.240 | 15.278 | 1.00 | 19.04 | C |
| ATOM | 210 | C | ARG | 524 | 8.655 | 77.734 | 15.460 | 1.00 | 20.87 | C |
| ATOM | 211 | O | ARG | 524 | 7.724 | 77.235 | 16.106 | 1.00 | 22.79 | O |
| ATOM | 212 | CB | ARG | 524 | 7.758 | 79.709 | 14.246 | 1.00 | 20.78 | C |
| ATOM | 213 | CC | ARG | 524 | 7.654 | 81.183 | 14.225 | 1.00 | 22.74 | C |
| ATOM | 214 | CD | ARG | 524 | 7.449 | 81.671 | 15.627 | 1.00 | 23.78 | C |
| ATOM | 215 | NE | ARG | 524 | 7.265 | 83.107 | 15.661 | 1.00 | 29.27 | N |
| ATOM | 216 | CZ | ARG | 524 | 7.116 | 83.815 | 16.774 | 1.00 | 29.96 | C |
| ATOM | 217 | NH1 | ARG | 524 | 7.140 | 83.218 | 17.959 | 1.00 | 25.48 | N |
| ATOM | 218 | NH2 | ARG | 524 | 6.899 | 85.118 | 16.686 | 1.00 | 26.64 | N |
| ATOM | 219 | N | LEU | 525 | 9.561 | 77.014 | 14.804 | 1.00 | 19.12 | N |
| ATOM | 220 | CA | LEU | 525 | 9.645 | 75.571 | 14.915 | 1.00 | 17.29 | C |
| ATOM | 221 | C | LEU | 525 | 10.942 | 75.381 | 15.674 | 1.00 | 22.24 | C |
| ATOM | 222 | O | LEU | 525 | 11.950 | 76.041 | 15.374 | 1.00 | 21.49 | O |
| ATOM | 223 | CB | LEU | 525 | 9.817 | 74.913 | 13.546 | 1.00 | 19.88 | C |
| ATOM | 224 | CG | LEU | 525 | 8.695 | 74.845 | 12.523 | 1.00 | 15.92 | C |
| ATOM | 225 | CD1 | LEU | 525 | 9.236 | 74.241 | 11.253 | 1.00 | 11.38 | C |
| ATOM | 226 | CD2 | LEU | 525 | 7.556 | 73.989 | 13.080 | 1.00 | 16.42 | C |
| ATOM | 227 | N | SER | 526 | 10.912 | 74.519 | 16.682 | 1.00 | 23.55 | N |
| ATOM | 228 | CA | SER | 526 | 12.113 | 74.240 | 17.460 | 1.00 | 24.19 | C |
| ATOM | 229 | C | SER | 526 | 12.873 | 73.147 | 16.725 | 1.00 | 25.31 | C |
| ATOM | 230 | O | SER | 526 | 12.342 | 72.534 | 15.797 | 1.00 | 26.87 | O |
| ATOM | 231 | CB | SER | 526 | 11.737 | 73.746 | 18.855 | 1.00 | 22.27 | C |
| ATOM | 232 | OG | SER | 526 | 10.926 | 72.579 | 18.785 | 1.00 | 18.28 | O |
| ATOM | 233 | N | GLU | 527 | 14.093 | 72.868 | 17.160 | 1.00 | 26.48 | N |
| ATOM | 234 | CA | GLU | 527 | 14.900 | 71.829 | 16.539 | 1.00 | 26.18 | C |
| ATOM | 235 | C | GLU | 527 | 14.144 | 70.514 | 16.449 | 1.00 | 25.55 | C |
| ATOM | 236 | O | GLU | 527 | 14.134 | 69.859 | 15.406 | 1.00 | 30.55 | O |
| ATOM | 237 | CB | GLU | 527 | 16.172 | 71.620 | 17.349 | 1.00 | 28.26 | C |
| ATOM | 238 | CG | GLU | 527 | 17.025 | 70.471 | 16.880 | 1.00 | 37.14 | C |
| ATOM | 239 | CD | GLU | 527 | 18.417 | 70.909 | 16.459 | 1.00 | 44.14 | C |
| ATOM | 240 | OE1 | GLU | 527 | 19.082 | 71.637 | 17.238 | 1.00 | 44.73 | O |
| ATOM | 241 | OE2 | GLU | 527 | 18.853 | 70.506 | 15.351 | 1.00 | 47.92 | O |
| ATOM | 242 | N | ALA | 528 | 13.458 | 70.159 | 17.526 | 1.00 | 23.12 | N |
| ATOM | 243 | CA | ALA | 528 | 12.733 | 68.901 | 17.580 | 1.00 | 19.11 | C |
| ATOM | 244 | C | ALA | 528 | 11.547 | 68.875 | 16.650 | 1.00 | 19.81 | C |
| ATOM | 245 | O | ALA | 528 | 11.237 | 67.834 | 16.078 | 1.00 | 24.34 | O |
| ATOM | 246 | CB | ALA | 528 | 12.301 | 68.609 | 18.992 | 1.00 | 11.67 | C |
| ATOM | 247 | N | GLU | 529 | 10.873 | 70.015 | 16.518 | 1.00 | 19.26 | N |
| ATOM | 248 | CA | GLU | 529 | 9.697 | 70.126 | 15.659 | 1.00 | 19.04 | C |
| ATOM | 249 | C | GLU | 529 | 10.146 | 70.132 | 14.212 | 1.00 | 21.14 | C |
| ATOM | 250 | O | GLU | 529 | 9.491 | 69.543 | 13.358 | 1.00 | 26.65 | O |
| ATOM | 251 | CB | GLU | 529 | 8.908 | 71.403 | 15.974 | 1.00 | 17.25 | C |
| ATOM | 252 | CG | GLU | 529 | 8.144 | 71.355 | 17.292 | 1.00 | 12.54 | C |
| ATOM | 253 | CD | GLU | 529 | 7.447 | 72.663 | 17.624 | 1.00 | 18.73 | C |
| ATOM | 254 | OE1 | GLU | 529 | 8.120 | 73.725 | 17.576 | 1.00 | 16.59 | O |
| ATOM | 255 | OE2 | GLU | 529 | 6.236 | 72.623 | 17.966 | 1.00 | 18.64 | O |
| ATOM | 256 | N | PHE | 530 | 11.292 | 70.750 | 13.945 | 1.00 | 17.88 | N |
| ATOM | 257 | CA | PHE | 530 | 11.828 | 70.807 | 12.600 | 1.00 | 18.23 | C |
| ATOM | 258 | C | PHE | 530 | 12.139 | 69.383 | 12.147 | 1.00 | 21.70 | C |
| ATOM | 259 | O | PHE | 530 | 11.848 | 69.007 | 11.003 | 1.00 | 28.22 | O |
| ATOM | 260 | CB | PHE | 530 | 13.083 | 71.658 | 12.571 | 1.00 | 17.84 | C |
| ATOM | 261 | CG | PHE | 530 | 13.534 | 72.028 | 11.196 | 1.00 | 19.34 | C |
| ATOM | 262 | CD1 | PHE | 530 | 12.696 | 72.758 | 10.342 | 1.00 | 17.07 | C |
| ATOM | 263 | CD2 | PHE | 530 | 14.806 | 71.685 | 10.759 | 1.00 | 16.08 | C |
| ATOM | 264 | CE1 | PHE | 530 | 13.127 | 73.139 | 9.089 | 1.00 | 12.46 | C |
| ATOM | 265 | CE2 | PHE | 530 | 15.248 | 72.066 | 9.492 | 1.00 | 13.83 | C |
| ATOM | 266 | CZ | PHE | 530 | 14.413 | 72.789 | 8.664 | 1.00 | 11.80 | C |
| ATOM | 267 | N | GLU | 531 | 12.650 | 68.563 | 13.052 | 1.00 | 18.89 | N |
| ATOM | 266 | CA | GLU | 531 | 12.932 | 67.182 | 12.695 | 1.00 | 21.46 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 269 | C | GLU | 531 | 11.660 | 66.478 | 12.263 | 1.00 | 17.63 | C |
| ATOM | 270 | O | GLU | 531 | 11.711 | 65.606 | 11.397 | 1.00 | 22.80 | O |
| ATOM | 271 | CB | GLU | 531 | 13.556 | 66.414 | 13.862 | 1.00 | 19.16 | C |
| ATOM | 272 | CG | GLU | 531 | 14.685 | 66.955 | 14.274 | 1.00 | 24.82 | C |
| ATOM | 273 | CD | GLU | 531 | 15.827 | 67.120 | 13.105 | 1.00 | 28.99 | C |
| ATOM | 274 | OE1 | GLU | 531 | 16.177 | 66.101 | 12.469 | 1.00 | 24.87 | O |
| ATOM | 275 | OE2 | GLU | 531 | 16.211 | 68.282 | 12.831 | 1.00 | 35.27 | O |
| ATOM | 276 | N | VAL | 532 | 10.529 | 66.840 | 12.864 | 1.00 | 15.71 | N |
| ATOM | 277 | CA | VAL | 532 | 9.257 | 66.211 | 12.509 | 1.00 | 15.96 | C |
| ATOM | 278 | C | VAL | 532 | 8.820 | 66.691 | 11.133 | 1.00 | 18.38 | C |
| ATOM | 279 | O | VAL | 532 | 8.234 | 65.921 | 10.357 | 1.00 | 22.15 | O |
| ATOM | 280 | CB | VAL | 532 | 8.149 | 66.493 | 13.551 | 1.00 | 15.96 | C |
| ATOM | 281 | CG1 | VAL | 532 | 6.825 | 65.847 | 13.117 | 1.00 | 6.01 | C |
| ATOM | 282 | CG2 | VAL | 532 | 8.575 | 65.950 | 14.908 | 1.00 | 13.74 | C |
| ATOM | 283 | N | LEU | 533 | 9.150 | 67.943 | 10.821 | 1.00 | 14.73 | N |
| ATOM | 284 | CA | LEU | 533 | 8.826 | 68.530 | 9.536 | 1.00 | 14.97 | C |
| ATOM | 285 | C | LEU | 533 | 9.602 | 67.771 | 8.476 | 1.00 | 16.19 | C |
| ATOM | 286 | O | LEU | 533 | 9.044 | 67.348 | 7.458 | 1.00 | 18.03 | O |
| ATOM | 287 | CB | LEU | 533 | 9.243 | 70.008 | 9.496 | 1.00 | 14.45 | C |
| ATOM | 288 | CG | LEU | 533 | 8.780 | 70.717 | 8.220 | 1.00 | 12.15 | C |
| ATOM | 289 | CD1 | LEU | 533 | 7.283 | 70.472 | 8.038 | 1.00 | 14.73 | C |
| ATOM | 290 | CD2 | LEU | 533 | 9.060 | 72.183 | 8.282 | 1.00 | 8.85 | C |
| ATOM | 291 | N | LYS | 534 | 10.899 | 67.640 | 8.704 | 1.00 | 12.22 | N |
| ATOM | 292 | CA | LYS | 534 | 11.766 | 66.936 | 7.785 | 1.00 | 13.88 | C |
| ATOM | 293 | C | LYS | 534 | 11.337 | 65.492 | 7.592 | 1.00 | 13.67 | C |
| ATOM | 294 | O | LYS | 534 | 11.356 | 64.974 | 6.478 | 1.00 | 19.68 | O |
| ATOM | 295 | CB | LYS | 534 | 13.210 | 67.016 | 8.282 | 1.00 | 17.43 | C |
| ATOM | 296 | CG | LYS | 534 | 13.819 | 68.393 | 8.100 | 1.00 | 13.24 | C |
| ATOM | 297 | CD | LYS | 534 | 15.OD2 | 68.635 | 9.036 | 1.00 | 18.41 | C |
| ATOM | 298 | CE | LYS | 534 | 15.936 | 67.455 | 9.114 | 1.00 | 20.81 | C |
| ATOM | 299 | NZ | LYS | 534 | 17.017 | 67.696 | 10.101 | 1.00 | 18.52 | N |
| ATOM | 300 | N | ALA | 535 | 10.871 | 64.858 | 8.656 | 1.00 | 13.06 | N |
| ATOM | 301 | CA | ALA | 535 | 10.442 | 63.472 | 8.563 | 1.00 | 9.85 | C |
| ATOM | 302 | C | ALA | 535 | 9.164 | 63.382 | 7.745 | 1.00 | 13.30 | C |
| ATOM | 303 | O | ALA | 535 | 8.911 | 62.361 | 7.082 | 1.00 | 15.28 | O |
| ATOM | 304 | CB | ALA | 535 | 10.254 | 62.901 | 9.923 | 1.00 | 8.53 | C |
| ATOM | 305 | N | PHE | 536 | 8.348 | 64.428 | 7.797 | 1.00 | 13.50 | N |
| ATOM | 306 | CA | PHE | 536 | 7.117 | 64.490 | 6.996 | 1.00 | 11.73 | C |
| ATOM | 307 | C | PHE | 536 | 7.537 | 64.558 | 5.521 | 1.00 | 14.75 | C |
| ATOM | 308 | O | PHE | 536 | 6.962 | 63.887 | 4.654 | 1.00 | 17.83 | O |
| ATOM | 309 | CB | PHE | 536 | 6.369 | 65.756 | 7.350 | 1.00 | 6.75 | C |
| ATOM | 310 | CG | PHE | 536 | 5.252 | 66.076 | 6.419 | 1.00 | 12.43 | C |
| ATOM | 311 | CD1 | PHE | 536 | 4.113 | 65.288 | 6.388 | 1.00 | 13.94 | C |
| ATOM | 312 | CD2 | PHE | 536 | 5.314 | 67.191 | 5.585 | 1.00 | 10.83 | C |
| ATOM | 313 | CE1 | PHE | 536 | 3.040 | 65.604 | 5.534 | 1.00 | 15.05 | C |
| ATOM | 314 | CE2 | PHE | 536 | 4.260 | 67.511 | 4.736 | 1.00 | 11.68 | C |
| ATOM | 315 | CZ | PHE | 536 | 3.114 | 66.720 | 4.711 | 1.00 | 9.74 | C |
| ATOM | 316 | N | VAL | 537 | 8.550 | 65.375 | 5.250 | 1.00 | 13.66 | N |
| ATOM | 317 | CA | VAL | 537 | 9.068 | 65.549 | 3.903 | 1.00 | 14.58 | C |
| ATOM | 318 | C | VAL | 537 | 9.593 | 64.209 | 3.418 | 1.00 | 16.40 | C |
| ATOM | 319 | O | VAL | 537 | 9.176 | 63.735 | 2.376 | 1.00 | 21.04 | O |
| ATOM | 320 | CB | VAL | 537 | 10.143 | 66.684 | 3.858 | 1.00 | 12.13 | C |
| ATOM | 321 | CG1 | VAL | 537 | 10.864 | 66.706 | 2.527 | 1.00 | 7.80 | C |
| ATOM | 322 | CG2 | VAL | 537 | 9.459 | 68.040 | 4.070 | 1.00 | 2.11 | C |
| ATOM | 323 | N | VAL | 538 | 10.397 | 63.541 | 4.231 | 1.00 | 17.90 | N |
| ATOM | 324 | CA | VAL | 538 | 10.929 | 62.228 | 3.867 | 1.00 | 15.91 | C |
| ATOM | 325 | C | VAL | 538 | 9.842 | 61.187 | 3.559 | 1.00 | 17.55 | C |
| ATOM | 326 | O | VAL | 538 | 9.946 | 60.4 91 | 2.538 | 1.00 | 15.35 | O |
| ATOM | 327 | CB | VAL | 538 | 11.893 | 61.693 | 4.948 | 1.00 | 17.65 | C |
| ATOM | 328 | CG1 | VAL | 538 | 12.129 | 60.169 | 4.791 | 1.00 | 9.43 | C |
| ATOM | 329 | CG2 | VAL | 538 | 13.200 | 62.447 | 4.849 | 1.00 | 9.34 | C |
| ATOM | 330 | N | ASP | 539 | 6.618 | 61.040 | 4.410 | 1.00 | 17.17 | N |
| ATOM | 331 | CA | ASP | 539 | 7.798 | 60.050 | 4.068 | 1.00 | 21.22 | C |
| ATOM | 332 | C | ASP | 539 | 6.892 | 60.418 | 2.919 | 1.00 | 17.63 | C |
| ATOM | 333 | O | ASP | 539 | 6.313 | 59.526 | 2.305 | 1.00 | 20.04 | O |
| ATOM | 334 | CB | ASP | 539 | 7.048 | 59.412 | 5.257 | 1.00 | 29.14 | C |
| ATOM | 335 | CG | ASP | 539 | 6.636 | 60.345 | 6.384 | 1.00 | 35.47 | C |
| ATOM | 336 | OD1 | ASP | 539 | 6.283 | 61.428 | 6.128 | 1.00 | 44.75 | O |
| ATOM | 337 | OD2 | ASP | 539 | 7.219 | 59.993 | 7.523 | 1.00 | 36.63 | O |
| ATCM | 338 | N | MET | 540 | 6.610 | 61.709 | 2.601 | 1.00 | 16.39 | N |
| ATOM | 339 | CA | MET | 540 | 6.063 | 62.172 | 1.423 | 1.00 | 13.96 | C |
| ATOM | 340 | C | MET | 540 | 6.857 | 61.593 | 0.269 | 1.00 | 10.86 | C |
| ATOM | 341 | O | MET | 540 | 6.333 | 60.862 | −0.539 | 1.00 | 14.71 | O |
| ATOM | 342 | CB | MET | 540 | 6.159 | 63.688 | 1.294 | 1.00 | 22.58 | C |
| ATOM | 343 | CG | MET | 540 | 5.149 | 64.497 | 2.065 | 1.00 | 31.44 | C |

TABLE 8-continued

Atomic Coordinates for Residues of a Crystal of murine VWF-A1 (SEQ ID NO: 10).

| CRYST1 | 86.395 | | 86.395 | 68.125 | 90.00 | 90.00 | 120.00 | P 61 | 6 |
|---|---|---|---|---|---|---|---|---|---|
| ATOM | 344 | SD | MET 540 | 3.503 | 64.541 | 1.326 | 1.00 | 45.37 | S |
| ATOM | 345 | CE | MET 540 | 3.679 | 65.729 | 0.060 | 1.00 | 31.22 | C |
| ATOM | 346 | N | MET 541 | 8.163 | 61.870 | 0.261 | 1.00 | 13.18 | N |
| ATOM | 347 | CA | MET 541 | 9.116 | 61.398 | −0.751 | 1.00 | 10.35 | C |
| ATOM | 348 | C | MET 541 | 9.107 | 59.895 | −0.969 | 1.00 | 16.49 | C |
| ATOM | 349 | O | MET 541 | 9.225 | 59.438 | −2.111 | 1.00 | 20.40 | O |
| ATOM | 350 | CB | MET 541 | 10.537 | 61.813 | −0.370 | 1.00 | 9.58 | C |
| ATOM | 351 | CG | MET 541 | 10.820 | 63.276 | −0.620 | 1.00 | 11.21 | C |
| ATOM | 352 | SD | MET 541 | 12.434 | 63.842 | −0.058 | 1.00 | 12.89 | S |
| ATOM | 353 | CE | MET 541 | 13.392 | 63.835 | −1.500 | 1.00 | 15.28 | C |
| ATOM | 354 | N | GLU 542 | 8.985 | 59.119 | 0.107 | 1.00 | 16.56 | N |
| ATOM | 355 | CA | GLU 542 | 8.971 | 57.657 | −0.008 | 1.00 | 13.92 | C |
| ATOM | 356 | C | GLU 542 | 7.759 | 57.174 | −0.818 | 1.00 | 14.26 | C |
| ATOM | 357 | O | GLU 542 | 7.789 | 56.104 | −1.430 | 1.00 | 15.31 | O |
| ATOM | 358 | CB | GLU 542 | 8.925 | 57.018 | 1.382 | 1.00 | 12.65 | C |
| ATOM | 359 | CG | GLU 542 | 10.175 | 57.228 | 2.230 | 1.00 | 15.01 | C |
| ATOM | 360 | CD | GLU 542 | 10.155 | 56.422 | 3.528 | 1.00 | 13.47 | C |
| ATOM | 361 | OE1 | GLU 542 | 9.181 | 55.694 | 3.785 | 1.00 | 18.27 | O |
| ATOM | 362 | OE2 | GLU 542 | 11.109 | 56.518 | 4.308 | 1.00 | 15.89 | O |
| ATOM | 363 | N | ARG 543 | 6.688 | 57.961 | −0.789 | 1.00 | 12.61 | N |
| ATOM | 364 | CA | ARG 543 | 5.451 | 57.633 | −1.473 | 1.00 | 10.82 | C |
| ATOM | 365 | C | ARG 543 | 5.388 | 58.327 | −2.827 | 1.00 | 11.37 | C |
| ATOM | 366 | O | ARG 543 | 4.310 | 58.574 | −3.373 | 1.00 | 13.23 | O |
| ATOM | 367 | CB | ARG 543 | 4.285 | 58.069 | −0.593 | 1.00 | 9.75 | C |
| ATOM | 368 | CG | ARG 543 | 4.168 | 57.203 | 0.632 | 1.00 | 8.93 | C |
| ATOM | 369 | CD | ARG 543 | 3.353 | 57.841 | 1.737 | 1.00 | 9.66 | C |
| ATOM | 370 | NE | ARG 543 | 3.241 | 56.878 | 2.835 | 1.00 | 17.05 | N |
| ATOM | 371 | CZ | ARG 543 | 4.196 | 56.652 | 3.737 | 1.00 | 12.00 | C |
| ATOM | 372 | NH1 | ARG 543 | 5.341 | 57.332 | 3.697 | 1.00 | 9.90 | N |
| ATOM | 373 | NH2 | ARG 543 | 4.044 | 55.681 | 4.634 | 1.00 | 15.47 | N |
| ATOM | 374 | N | LEU 544 | 6.554 | 58.559 | −3.401 | 1.00 | 13.34 | N |
| ATOM | 375 | CA | LEU 544 | 6.676 | 59.214 | −4.688 | 1.00 | 15.24 | C |
| ATOM | 376 | C | LEU 544 | 7.606 | 58.388 | −5.574 | 1.00 | 16.79 | C |
| ATOM | 377 | O | LEU 544 | 8.633 | 57.871 | −5.103 | 1.00 | 17.01 | O |
| ATOM | 378 | CB | LEU 544 | 7.318 | 60.578 | −4.465 | 1.00 | 12.06 | C |
| ATOM | 379 | CG | LEU 544 | 6.539 | 61.886 | −4.546 | 1.00 | 11.78 | C |
| ATOM | 380 | CD1 | LEU 544 | 5.138 | 61.769 | −4.046 | 1.00 | 11.41 | C |
| ATOM | 381 | CD2 | LEU 544 | 7.315 | 62.896 | −3.751 | 1.00 | 8.97 | C |
| ATOM | 382 | N | ARG 545 | 7.283 | 58.269 | −6.855 | 1.00 | 15.28 | N |
| ATOM | 383 | CA | ARG 545 | 8.187 | 57.551 | −7.740 | 1.00 | 15.08 | C |
| ATOM | 384 | C | ARG 545 | 9.110 | 58.627 | −8.278 | 1.00 | 17.33 | C |
| ATOM | 385 | O | ARG 545 | 8.794 | 59.266 | −9.283 | 1.00 | 19.41 | O |
| ATOM | 386 | CB | ARG 545 | 7.431 | 56.887 | −8.875 | 1.00 | 16.99 | C |
| ATOM | 387 | CG | ARG 545 | 8.327 | 56.142 | −9.837 | 1.00 | 20.50 | C |
| ATOM | 388 | CD | ARG 545 | 7.453 | 55.4 93 | 10.868 | 1.00 | 26.46 | C |
| ATOM | 389 | NE | ARG 545 | 8.195 | 54.796 | −11.903 | 1.00 | 28.51 | N |
| ATOM | 390 | CZ | ARG 545 | 7.644 | 53.877 | −12.690 | 1.00 | 33.26 | C |
| ATOM | 391 | NH1 | ARG 545 | 6.357 | 53.572 | −12.541 | 1.00 | 31.05 | N |
| ATOM | 392 | NH2 | ARG 545 | 8.368 | 53.259 | −13.617 | 1.00 | 30.37 | N |
| ATOM | 393 | N | ILE 546 | 10.205 | 58.879 | −7.556 | 1.00 | 16.27 | N |
| ATOM | 394 | CA | ILE 546 | 11.177 | 59.909 | −7.919 | 1.00 | 18.03 | C |
| ATOM | 395 | C | ILE 546 | 12.039 | 59.480 | −9.084 | 1.00 | 19.30 | C |
| ATOM | 396 | O | ILE 546 | 12.750 | 58.477 | −9.014 | 1.00 | 20.66 | O |
| ATOM | 397 | CB | ILE 546 | 12.065 | 60.290 | −6.714 | 1.00 | 13.91 | C |
| ATOM | 398 | CG1 | ILE 546 | 11.234 | 60.956 | −5.622 | 1.00 | 10.37 | C |
| ATOM | 399 | CG2 | ILE 546 | 13.134 | 61.243 | −7.134 | 1.00 | 10.93 | C |
| ATOM | 400 | CD1 | ILE 546 | 11.981 | 61.088 | 4.306 | 1.00 | 8.23 | C |
| ATOM | 401 | N | SER 547 | 11.986 | 60.270 | −10.152 | 1.00 | 20.13 | N |
| ATOM | 402 | CA | SER 547 | 12.725 | 59.968 | −11.360 | 1.00 | 16.38 | C |
| ATOM | 403 | C | SER 547 | 12.518 | 61.108 | −12.343 | 1.00 | 20.11 | C |
| ATOM | 404 | O | SER 547 | 11.443 | 61.710 | −12.407 | 1.00 | 19.86 | O |
| ATOM | 405 | CB | SER 547 | 12.191 | 58.664 | −11.956 | 1.00 | 19.67 | C |
| ATOM | 406 | OG | SER 547 | 12.939 | 58.238 | −13.078 | 1.00 | 24.56 | O |
| ATOM | 407 | N | GLN 548 | 13.542 | 61.364 | −13.156 | 1.00 | 21.04 | N |
| ATOM | 408 | CA | GLN 548 | 13.527 | 62.426 | −14.159 | 1.00 | 22.05 | C |
| ATOM | 409 | C | GLN 548 | 12.335 | 62.253 | −15.121 | 1.00 | 23.36 | C |
| ATOM | 410 | O | GLN 548 | 11.802 | 63.236 | −15.645 | 1.00 | 26.68 | O |
| ATOM | 411 | CB | GLN 548 | 14.869 | 62.399 | −14.905 | 1.00 | 23.09 | C |
| ATOM | 412 | CG | GLN 548 | 15.601 | 63.727 | −15.086 | 1.00 | 25.87 | C |
| ATOM | 413 | CD | GLN 548 | 15.738 | 64.560 | −13.825 | 1.00 | 27.98 | C |
| ATOM | 414 | OE1 | GLN 548 | 15.630 | 65.783 | −13.890 | 1.00 | 34.12 | O |
| ATOM | 415 | NE2 | GLN 548 | 15.977 | 63.925 | −12.684 | 1.00 | 25.55 | N |
| ATOM | 416 | N | LYS 549 | 11.894 | 61.009 | −15.304 | 1.00 | 21.82 | N |
| ATOM | 417 | CA | LYS 549 | 10.766 | 60.701 | −16.182 | 1.00 | 21.44 | C |
| ATOM | 418 | C | LYS 549 | 9.453 | 60.554 | −15.390 | 1.00 | 22.62 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 419 | O | LYS | 549 | 8.374 | 60.330 | −15.971 | 1.00 | 18.28 | O |
| ATOM | 420 | CB | LYS | 549 | 11.041 | 59.406 | −16.955 | 1.00 | 24.39 | C |
| ATOM | 421 | CG | LYS | 549 | 12.431 | 59.320 | −17.575 | 1.00 | 34.15 | C |
| ATOM | 422 | CD | LYS | 549 | 12.762 | 60.573 | −18.390 | 1.00 | 44.91 | C |
| ATOM | 423 | CE | LYS | 549 | 14.154 | 60.513 | −19.044 | 1.00 | 51.62 | C |
| ATOM | 424 | NZ | LYS | 549 | 15.302 | 60.529 | −18.076 | 1.00 | 53.07 | N |
| ATOM | 425 | N | TRP | 550 | 9.535 | 60.665 | −14.064 | 1.00 | 19.15 | N |
| ATOM | 426 | CA | TRP | 550 | 8.350 | 60.544 | −13.241 | 1.00 | 18.15 | C |
| ATOM | 427 | C | TRP | 550 | 8.178 | 61.740 | −12.313 | 1.00 | 17.14 | C |
| ATOM | 428 | O | TRP | 550 | 7.755 | 62.808 | −12.759 | 1.00 | 17.54 | O |
| ATOM | 429 | CB | TRP | 550 | 8.383 | 59.219 | −12.473 | 1.00 | 22.31 | C |
| ATOM | 430 | CG | TRP | 550 | 8.360 | 58.034 | −13.381 | 1.00 | 24.07 | C |
| ATOM | 431 | CD1 | TRP | 550 | 9.420 | 57.250 | −13.752 | 1.00 | 25.74 | C |
| ATOM | 432 | CD2 | TRP | 550 | 7.228 | 57.533 | −14.096 | 1.00 | 23.63 | C |
| ATOM | 433 | NE1 | TRP | 550 | 9.016 | 56.302 | −14.667 | 1.00 | 25.59 | N |
| ATOM | 434 | CE2 | TRP | 550 | 7.665 | 56.461 | −14.894 | 1.00 | 25.02 | C |
| ATOM | 435 | CE3 | TRP | 550 | 5.875 | 57.905 | −14.136 | 1.00 | 23.56 | C |
| ATOM | 436 | CZ2 | TRP | 550 | 6.807 | 55.743 | −15.734 | 1.00 | 25.72 | C |
| ATOM | 437 | CZ3 | TRP | 550 | 5.017 | 57.196 | −14.970 | 1.00 | 25.40 | C |
| ATOM | 438 | CH2 | TRP | 550 | 5.487 | 56.125 | −15.758 | 1.00 | 24.34 | C |
| ATOM | 439 | N | VAL | 551 | 8.465 | 61.572 | −11.022 | 1.00 | 18.80 | N |
| ATOM | 440 | CA | VAL | 551 | 8.321 | 62.674 | −10.069 | 1.00 | 16.63 | C |
| ATOM | 441 | C | VAL | 551 | 9.695 | 63.240 | −9.739 | 1.00 | 14.99 | C |
| ATOM | 442 | O | VAL | 551 | 10.599 | 62.501 | −9.362 | 1.00 | 15.74 | O |
| ATOM | 443 | CB | VAL | 551 | 7.614 | 62.214 | −8.731 | 1.00 | 16.18 | C |
| ATOM | 444 | CG1 | VAL | 551 | 7.477 | 63.406 | −7.761 | 1.00 | 10.00 | C |
| ATOM | 445 | CG2 | VAL | 551 | 6.231 | 61.611 | −9.016 | 1.00 | 12.35 | C |
| ATOM | 446 | N | ARG | 552 | 9.876 | 64.536 | −9.950 | 1.00 | 14.51 | N |
| ATOM | 447 | CA | ARG | 552 | 11.142 | 65.180 | −9.612 | 1.00 | 14.95 | C |
| ATOM | 448 | C | ARG | 552 | 10.860 | 66.010 | −8.358 | 1.00 | 14.50 | C |
| ATOM | 449 | O | ARG | 552 | 9.756 | 66.543 | −8.188 | 1.00 | 12.82 | O |
| ATOM | 450 | CB | ARG | 552 | 11.639 | 66.066 | −10.757 | 1.00 | 13.60 | C |
| ATOM | 451 | CG | ARG | 552 | 11.890 | 65.318 | −12.052 | 1.00 | 14.38 | C |
| ATOM | 452 | CD | ARG | 552 | 12.686 | 66.146 | −13.018 | 1.00 | 14.42 | C |
| ATOM | 453 | NE | ARG | 552 | 11.980 | 67.368 | −13.388 | 1.00 | 22.75 | N |
| ATOM | 454 | CZ | ARG | 552 | 12.544 | 68.383 | −14.035 | 1.00 | 19.53 | C |
| ATOM | 455 | NH1 | ARG | 552 | 13.824 | 68.318 | −14.381 | 1.00 | 24.67 | N |
| ATOM | 456 | NH2 | ARG | 552 | 11.823 | 69.436 | −14.383 | 1.00 | 12.20 | N |
| ATOM | 457 | N | VAL | 553 | 11.844 | 66.108 | −7.469 | 1.00 | 18.50 | N |
| ATOM | 458 | CA | VAL | 553 | 11.654 | 66.840 | −6.209 | 1.00 | 19.75 | C |
| ATOM | 459 | C | VAL | 553 | 12.740 | 67.861 | −5.972 | 1.00 | 19.66 | C |
| ATOM | 460 | O | VAL | 553 | 13.872 | 67.695 | −6.406 | 1.00 | 22.27 | O |
| ATOM | 461 | CB | VAL | 553 | 11.677 | 65.886 | −4.956 | 1.00 | 16.81 | C |
| ATOM | 462 | CG1 | VAL | 553 | 10.441 | 64.952 | −4.920 | 1.00 | 7.54 | C |
| ATOM | 463 | CG2 | VAL | 553 | 12.966 | 65.070 | 4.942 | 1.00 | 19.00 | C |
| ATOM | 464 | N | ALA | 554 | 12.385 | 68.930 | −5.279 | 1.00 | 17.64 | N |
| ATOM | 465 | CA | ALA | 554 | 13.356 | 69.958 | 4.924 | 1.00 | 16.45 | C |
| ATOM | 466 | C | ALA | 554 | 13.038 | 70.208 | −3.450 | 1.00 | 14.99 | C |
| ATOM | 467 | O | ALA | 554 | 11.882 | 70.006 | −3.030 | 1.00 | 12.08 | O |
| ATOM | 468 | CB | ALA | 554 | 13.153 | 71.224 | −5.764 | 1.00 | 6.96 | C |
| ATOM | 469 | N | VAL | 555 | 14.063 | 70.516 | −2.651 | 1.00 | 13.54 | N |
| ATOM | 470 | CA | VAL | 555 | 13.879 | 70.778 | −1.220 | 1.00 | 14.53 | C |
| ATOM | 471 | C | VAL | 555 | 14.590 | 72.068 | −0.892 | 1.00 | 11.41 | C |
| ATOM | 472 | O | VAL | 555 | 15.769 | 72.191 | −1.175 | 1.00 | 10.57 | O |
| ATOM | 473 | CB | VAL | 555 | 14.402 | 69.594 | −0.318 | 1.00 | 14.50 | C |
| ATOM | 474 | CG1 | VAL | 555 | 14.355 | 69.980 | 1.182 | 1.00 | 10.37 | C |
| ATOM | 475 | CG2 | VAL | 555 | 13.491 | 68.358 | −0.515 | 1.00 | 11.88 | C |
| ATOM | 476 | N | VAL | 556 | 13.857 | 73.044 | −0.359 | 1.00 | 11.91 | N |
| ATOM | 477 | CA | VAL | 556 | 14.424 | 74.337 | −0.026 | 1.00 | 14.48 | C |
| ATOM | 478 | C | VAL | 556 | 13.996 | 74.729 | 1.394 | 1.00 | 18.03 | C |
| ATOM | 479 | O | VAL | 556 | 12.807 | 74.771 | 1.717 | 1.00 | 18.24 | O |
| ATOM | 480 | CB | VAL | 556 | 13.929 | 75.435 | −0.999 | 1.00 | 16.63 | C |
| ATOM | 481 | CG1 | VAL | 556 | 14.721 | 76.700 | −0.812 | 1.00 | 12.12 | C |
| ATOM | 482 | CG2 | VAL | 556 | 14.022 | 74.948 | −2.450 | 1.00 | 17.97 | C |
| ATOM | 483 | N | GLU | 557 | 14.977 | 75.023 | 2.228 | 1.00 | 15.76 | N |
| ATOM | 484 | CA | GLU | 557 | 14.750 | 75.431 | 3.594 | 1.00 | 16.18 | C |
| ATOM | 485 | C | GLU | 557 | 14.810 | 76.937 | 3.456 | 1.00 | 19.44 | C |
| ATOM | 486 | O | GLU | 557 | 15.751 | 77.448 | 2.847 | 1.00 | 20.78 | O |
| ATOM | 487 | CB | GLU | 557 | 15.922 | 74.921 | 4.451 | 1.00 | 21.73 | C |
| ATOM | 488 | CG | GLU | 557 | 16.042 | 75.479 | 5.890 | 1.00 | 22.98 | C |
| ATOM | 489 | CD | GLU | 557 | 17.093 | 76.581 | 6.011 | 1.00 | 26.66 | C |
| ATOM | 490 | OE1 | GLU | 557 | 18.322 | 76.271 | 6.047 | 1.00 | 27.04 | O |
| ATOM | 491 | OE2 | GLU | 557 | 16.666 | 77.755 | 6.075 | 1.00 | 18.13 | O |
| ATOM | 492 | N | TYR | 558 | 13.823 | 77.668 | 3.964 | 1.00 | 16.82 | N |
| ATOM | 493 | CA | TYR | 558 | 13.878 | 79.117 | 3.826 | 1.00 | 19.30 | C |

TABLE 8-continued

Atomic Coordinates for Residues of a Crystal of murine VWF-A1 (SEQ ID NO: 10).

| CRYST1 | 86.395 | | 86.395 | 68.125 | 90.00 | 90.00 | 120.00 | P 61 | 6 |
|---|---|---|---|---|---|---|---|---|---|
| ATOM | 494 | C | TYR 558 | 13.894 | 79.898 | 5.123 | 1.00 | 21.56 | C |
| ATOM | 495 | O | TYR 558 | 13.367 | 79.450 | 6.146 | 1.00 | 18.80 | O |
| ATOM | 496 | CB | TYR 558 | 12.769 | 79.638 | 2.903 | 1.00 | 18.20 | C |
| ATOM | 497 | CG | TYR 558 | 11.350 | 79.457 | 3.414 | 1.00 | 21.51 | C |
| ATOM | 498 | CD1 | TYR 558 | 10.681 | 78.250 | 3.251 | 1.00 | 19.46 | C |
| ATOM | 499 | CD2 | TYR 558 | 10.662 | 80.511 | 4.037 | 1.00 | 17.80 | C |
| ATOM | 500 | CE1 | TYR 558 | 9.360 | 78.101 | 3.689 | 1.00 | 17.32 | C |
| ATOM | 501 | CE2 | TYR 558 | 9.361 | 80.361 | 4.462 | 1.00 | 11.71 | C |
| ATOM | 502 | CZ | TYR 558 | 8.727 | 79.158 | 4.289 | 1.00 | 14.15 | C |
| ATOM | 503 | OH | TYR 558 | 7.443 | 78.997 | 4.727 | 1.00 | 21.33 | O |
| ATOM | 504 | N | HIS 559 | 14.548 | 81.054 | 5.077 | 1.00 | 22.82 | N |
| ATOM | 505 | CA | HIS 559 | 14.659 | 81.942 | 6.228 | 1.00 | 22.57 | C |
| ATOM | 506 | C | HIS 559 | 14.761 | 83.343 | 5.632 | 1.00 | 24.28 | C |
| ATOM | 507 | O | HIS 559 | 13.803 | 83.820 | 5.035 | 1.00 | 24.51 | O |
| ATOM | 508 | CB | HIS 559 | 15.877 | 81.580 | 7.084 | 1.00 | 23.05 | C |
| ATOM | 509 | CG | HIS 559 | 17.138 | 81.409 | 6.295 | 1.00 | 31.12 | C |
| ATOM | 510 | ND1 | HIS 559 | 17.327 | 80.384 | 5.400 | 1.00 | 35.63 | N |
| ATOM | 511 | CD2 | HIS 559 | 18.274 | 82.154 | 6.254 | 1.00 | 35.29 | C |
| ATOM | 512 | CE1 | HIS 559 | 18.512 | 80.499 | 4.841 | 1.00 | 34.53 | C |
| ATOM | 513 | NE2 | HIS 559 | 19.109 | 81.564 | 5.342 | 1.00 | 33.84 | N |
| ATOM | 514 | N | ASP 560 | 15.895 | 84.013 | 5.788 | 1.00 | 29.85 | N |
| ATOM | 515 | CA | ASP 560 | 16.077 | 85.336 | 5.194 | 1.00 | 37.48 | C |
| ATOM | 516 | C | ASP 560 | 16.114 | 85.132 | 3.676 | 1.00 | 36.28 | C |
| ATOM | 517 | O | ASP 560 | 15.522 | 85.892 | 2.912 | 1.00 | 39.28 | O |
| ATOM | 518 | CB | ASP 560 | 17.391 | 85.957 | 5.686 | 1.00 | 46.15 | C |
| ATOM | 519 | CG | ASP 560 | 17.242 | 87.430 | 6.059 | 1.00 | 55.52 | C |
| ATOM | 520 | OD1 | ASP 560 | 16.086 | 87.905 | 6.195 | 1.00 | 60.53 | O |
| ATOM | 521 | OD2 | ASP 560 | 18.286 | 88.112 | 6.218 | 1.00 | 59.22 | O |
| ATOM | 522 | N | GLY 561 | 16.849 | 84.101 | 3.271 | 1.00 | 34.51 | N |
| ATOM | 523 | CA | GLY 561 | 16.973 | 83.729 | 1.879 | 1.00 | 29.45 | C |
| ATOM | 524 | C | GLY 561 | 16.599 | 82.261 | 1.769 | 1.00 | 28.57 | C |
| ATOM | 525 | O | GLY 561 | 15.991 | 81.698 | 2.689 | 1.00 | 25.19 | O |
| ATOM | 526 | N | SER 562 | 17.044 | 81.614 | 0.700 | 1.00 | 27.35 | N |
| ATOM | 527 | CA | SER 562 | 16.730 | 80.216 | 0.502 | 1.00 | 26.74 | C |
| ATOM | 528 | C | SER 562 | 17.984 | 79.376 | 0.408 | 1.00 | 28.35 | C |
| ATOM | 529 | O | SER 562 | 18.981 | 79.803 | −0.164 | 1.00 | 29.74 | O |
| ATOM | 530 | CB | SER 562 | 15.903 | 80.028 | −0.770 | 1.00 | 25.65 | C |
| ATOM | 531 | OG | SER 562 | 14.733 | 80.834 | −0.746 | 1.00 | 25.69 | O |
| ATOM | 532 | N | HIS 563 | 17.952 | 78.221 | 1.058 | 1.00 | 26.61 | N |
| ATOM | 533 | CA | HIS 563 | 19.052 | 77.273 | 1.016 | 1.00 | 28.05 | C |
| ATOM | 534 | C | HIS 563 | 18.452 | 76.026 | 0.354 | 1.00 | 25.45 | C |
| ATOM | 535 | O | HIS 563 | 17.662 | 75.317 | 0.977 | 1.00 | 26.54 | O |
| ATOM | 536 | CB | HIS 563 | 19.565 | 76.923 | 2.425 | 1.00 | 33.01 | C |
| ATOM | 537 | CG | HIS 563 | 20.592 | 77.879 | 2.971 | 1.00 | 42.56 | C |
| ATOM | 538 | ND1 | HIS 563 | 21.368 | 77.586 | 4.081 | 1.00 | 41.44 | N |
| ATOM | 539 | CD2 | HIS 563 | 20.950 | 79.129 | 2.588 | 1.00 | 41.45 | C |
| ATOM | 540 | CE1 | HIS 563 | 22.148 | 78.615 | 4.351 | 1.00 | 39.61 | C |
| ATOM | 541 | NE2 | HIS 563 | 21.919 | 79.566 | 3.466 | 1.00 | 38.40 | N |
| ATOM | 542 | N | ALA 564 | 18.736 | 75.824 | −0.929 | 1.00 | 22.09 | N |
| ATOM | 543 | CA | ALA 564 | 18.220 | 74.671 | −1.653 | 1.00 | 20.28 | C |
| ATOM | 544 | C | ALA 564 | 19.183 | 73.513 | −1.505 | 1.00 | 18.53 | C |
| ATOM | 545 | O | ALA 564 | 20.359 | 73.650 | −1.785 | 1.00 | 21.05 | O |
| ATOM | 546 | CB | ALA 564 | 18.040 | 75.005 | −3.108 | 1.00 | 16.92 | C |
| ATOM | 547 | N | TYR 565 | 18.675 | 72.384 | −1.028 | 1.00 | 18.56 | N |
| ATOM | 548 | CA | TYR 565 | 19.463 | 71.183 | −0.840 | 1.00 | 15.69 | C |
| ATOM | 549 | C | TYR 565 | 19.236 | 70.245 | −2.021 | 1.00 | 16.43 | C |
| ATOM | 550 | O | TYR 565 | 20.096 | 69.461 | −2.376 | 1.00 | 14.38 | O |
| ATOM | 551 | CB | TYR 565 | 19.035 | 70.473 | 0.434 | 1.00 | 18.28 | C |
| ATOM | 552 | CG | TYR 565 | 19.373 | 71.214 | 1.691 | 1.00 | 20.29 | C |
| ATOM | 553 | CD1 | TYR 565 | 18.609 | 72.296 | 2.105 | 1.00 | 19.07 | C |
| ATOM | 554 | CD2 | TYR 565 | 20.450 | 70.816 | 2.485 | 1.00 | 24.63 | C |
| ATOM | 555 | CE1 | TYR 565 | 18.899 | 72.966 | 3.277 | 1.00 | 23.97 | C |
| ATOM | 556 | CE2 | TYR 565 | 20.752 | 71.476 | 3.670 | 1.00 | 25.91 | C |
| ATOM | 557 | CZ | TYR 565 | 19.971 | 72.552 | 4.061 | 1.00 | 24.70 | C |
| ATOM | 558 | OH | TYR 565 | 20.247 | 73.212 | 5.240 | 1.00 | 28.07 | O |
| ATOM | 559 | N | ILE 566 | 18.050 | 70.302 | −2.599 | 1.00 | 16.43 | N |
| ATOM | 560 | CA | ILE 566 | 17.720 | 69.445 | −3.721 | 1.00 | 16.83 | C |
| ATOM | 561 | C | ILE 566 | 17.121 | 70.236 | −4.876 | 1.00 | 14.70 | C |
| ATOM | 562 | O | ILE 566 | 16.222 | 71.044 | −4.662 | 1.00 | 16.54 | O |
| ATOM | 563 | CB | ILE 566 | 16.690 | 68.368 | −3.301 | 1.00 | 15.97 | C |
| ATOM | 564 | CG1 | ILE 566 | 17.187 | 67.570 | −2.097 | 1.00 | 18.44 | C |
| ATOM | 565 | CG2 | ILE 566 | 16.392 | 67.432 | −4.446 | 1.00 | 16.90 | C |
| ATOM | 566 | CD1 | ILE 566 | 18.416 | 66.752 | −2.370 | 1.00 | 28.29 | C |
| ATOM | 567 | N | GLY 567 | 17.667 | 70.052 | −6.075 | 1.00 | 14.70 | N |
| ATOM | 568 | CA | GLY 567 | 17.123 | 70.694 | −7.261 | 1.00 | 14.69 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 569 | C | GLY | 567 | 16.372 | 69.660 | −8.106 | 1.00 | 15.85 | C |
| ATOM | 570 | O | GLY | 567 | 16.730 | 68.469 | −8.109 | 1.00 | 16.56 | O |
| ATOM | 571 | N | LEU | 568 | 15.392 | 70.097 | −8.892 | 1.00 | 17.74 | N |
| ATOM | 572 | CA | LEU | 568 | 14.622 | 69.174 | −9.722 | 1.00 | 16.77 | C |
| ATOM | 573 | C | LEU | 568 | 15.471 | 68.292 | −10.628 | 1.00 | 18.54 | C |
| ATOM | 574 | O | LEU | 568 | 15.177 | 67.117 | −10.807 | 1.00 | 24.33 | O |
| ATOM | 575 | CB | LEU | 568 | 13.591 | 69.935 | −10.559 | 1.00 | 11.30 | C |
| ATOM | 576 | CG | LEU | 568 | 12.456 | 70.603 | −9.767 | 1.00 | 11.42 | C |
| ATOM | 577 | CD1 | LEU | 568 | 11.744 | 71.638 | −10.640 | 1.00 | 6.22 | C |
| ATOM | 578 | CD2 | LEU | 568 | 11.508 | 69.583 | −9.227 | 1.00 | 3.91 | C |
| ATOM | 579 | N | LYS | 569 | 16.512 | 68.864 | −11.212 | 1.00 | 23.19 | N |
| ATOM | 580 | CA | LYS | 569 | 17.393 | 68.123 | −12.124 | 1.00 | 23.15 | C |
| ATOM | 581 | C | LYS | 569 | 18.459 | 67.248 | −11.458 | 1.00 | 23.97 | C |
| ATOM | 582 | O | LYS | 569 | 19.272 | 66.623 | −12.149 | 1.00 | 21.55 | O |
| ATOM | 583 | CB | LYS | 569 | 18.087 | 69.098 | −13.067 | 1.00 | 23.83 | C |
| ATOM | 584 | CG | LYS | 569 | 17.154 | 69.828 | −14.027 | 1.00 | 29.42 | C |
| ATOM | 585 | CD | LYS | 569 | 17.882 | 71.015 | −14.638 | 1.00 | 32.89 | C |
| ATOM | 586 | CE | LYS | 569 | 16.994 | 71.782 | −15.588 | 1.00 | 36.32 | C |
| ATOM | 587 | NZ | LYS | 569 | 17.497 | 71.604 | −16.981 | 1.00 | 42.82 | N |
| ATOM | 588 | N | ASP | 570 | 18.477 | 67.207 | −10.128 | 1.00 | 24.14 | N |
| ATOM | 589 | CA | ASP | 570 | 19.476 | 66.409 | −9.435 | 1.00 | 26.34 | C |
| ATOM | 590 | C | ASP | 570 | 19.300 | 64.950 | −9.749 | 1.00 | 31.25 | C |
| ATOM | 591 | O | ASP | 570 | 18.335 | 64.336 | −9.314 | 1.00 | 34.28 | O |
| ATOM | 592 | CB | ASP | 570 | 19.389 | 66.624 | −7.930 | 1.00 | 23.64 | C |
| ATOM | 593 | CG | ASP | 570 | 20.081 | 67.890 | −7.493 | 1.00 | 24.59 | C |
| ATOM | 594 | OD1 | ASP | 570 | 20.678 | 68.575 | −8.352 | 1.00 | 27.05 | O |
| ATOM | 595 | OD2 | ASP | 570 | 20.041 | 68.200 | −6.289 | 1.00 | 24.49 | O |
| ATOM | 596 | N | ARG | 571 | 20.223 | 64.390 | −10.523 | 1.00 | 34.80 | N |
| ATOM | 597 | CA | ARG | 571 | 20.126 | 62.983 | −10.869 | 1.00 | 35.48 | C |
| ATOM | 598 | C | ARG | 571 | 20.829 | 62.155 | −9.817 | 1.00 | 30.97 | C |
| ATOM | 599 | O | ARG | 571 | 22.025 | 61.861 | −9.922 | 1.00 | 29.82 | O |
| ATOM | 600 | CB | ARG | 571 | 20.710 | 62.721 | −12.246 | 1.00 | 46.16 | C |
| ATOM | 601 | CG | ARG | 571 | 20.453 | 61.315 | −12.743 | 1.00 | 60.41 | C |
| ATOM | 602 | CD | ARG | 571 | 21.501 | 60.929 | −13.762 | 1.00 | 70.06 | C |
| ATOM | 603 | NE | ARG | 571 | 21.379 | 59.540 | −14.198 | 1.00 | 76.92 | N |
| ATOM | 604 | CZ | ARG | 571 | 22.061 | 59.032 | −15.218 | 1.00 | 82.89 | C |
| ATOM | 605 | NH1 | ARG | 571 | 22.910 | 59.802 | −15.892 | 1.00 | 86.30 | N |
| ATOM | 606 | NH2 | ARG | 571 | 21.877 | 57.770 | −15.579 | 1.00 | 85.49 | N |
| ATOM | 607 | N | LYS | 572 | 20.093 | 61.876 | −8.750 | 1.00 | 23.93 | N |
| ATOM | 608 | CA | LYS | 572 | 20.588 | 61.086 | −7.634 | 1.00 | 20.81 | C |
| ATOM | 609 | C | LYS | 572 | 19.511 | 60.067 | −7.365 | 1.00 | 16.06 | C |
| ATOM | 610 | O | LYS | 572 | 18.381 | 60.237 | −7.789 | 1.00 | 17.31 | O |
| ATOM | 611 | CB | LYS | 572 | 20.843 | 61.966 | −6.393 | 1.00 | 18.06 | C |
| ATOM | 612 | CG | LYS | 572 | 22.004 | 62.929 | −6.578 | 1.00 | 20.31 | C |
| ATOM | 613 | CD | LYS | 572 | 22.138 | 63.949 | −5.468 | 1.00 | 23.14 | C |
| ATOM | 614 | CE | LYS | 572 | 23.202 | 64.988 | −5.836 | 1.00 | 24.18 | C |
| ATOM | 615 | NZ | LYS | 572 | 23.545 | 65.977 | −4.755 | 1.00 | 20.57 | N |
| ATOM | 616 | N | ARG | 573 | 19.857 | 58.956 | −6.750 | 1.00 | 20.74 | N |
| ATOM | 617 | CA | ARG | 573 | 18.834 | 57.949 | −6.475 | 1.00 | 22.56 | C |
| ATOM | 618 | C | ARG | 573 | 17.883 | 58.457 | −5.379 | 1.00 | 20.74 | C |
| ATOM | 619 | O | ARG | 573 | 18.280 | 59.311 | −4.565 | 1.00 | 23.29 | O |
| ATOM | 620 | CB | ARG | 573 | 19.498 | 56.617 | −6.138 | 1.00 | 27.37 | C |
| ATOM | 621 | CG | ARG | 573 | 20.682 | 56.741 | −5.228 | 1.00 | 35.56 | C |
| ATOM | 622 | CD | ARG | 573 | 21.369 | 55.399 | −5.040 | 1.00 | 44.36 | C |
| ATOM | 623 | NE | ARG | 573 | 22.340 | 55.095 | −6.087 | 1.00 | 49.02 | N |
| ATOM | 624 | CZ | ARG | 573 | 22.261 | 54.052 | −6.916 | 1.00 | 54.28 | C |
| ATOM | 625 | NH1 | ARG | 573 | 21.240 | 53.191 | −6.847 | 1.00 | 56.03 | N |
| ATOM | 626 | NH2 | ARG | 573 | 23.226 | 53.851 | −7.805 | 1.00 | 52.89 | N |
| ATOM | 627 | N | PRO | 574 | 16.610 | 57.997 | −5.375 | 1.00 | 17.46 | N |
| ATOM | 628 | CA | PRO | 574 | 15.610 | 58.412 | −4.392 | 1.00 | 12.01 | C |
| ATOM | 629 | C | PRO | 574 | 16.092 | 58.327 | −2.953 | 1.00 | 14.44 | C |
| ATOM | 630 | O | PRO | 574 | 15.816 | 59.220 | −2.163 | 1.00 | 17.36 | O |
| ATOM | 631 | CB | PRO | 574 | 14.472 | 57.442 | −4.650 | 1.00 | 16.28 | C |
| ATOM | 632 | CG | PRO | 574 | 14.547 | 57.219 | −6.088 | 1.00 | 11.38 | C |
| ATOM | 633 | CD | PRO | 574 | 16.024 | 57.OD2 | −6.291 | 1.00 | 18.26 | C |
| ATOM | 634 | N | SER | 575 | 16.880 | 57.305 | −2.639 | 1.00 | 13.89 | N |
| ATOM | 635 | CA | SER | 575 | 17.394 | 57.104 | −1.289 | 1.00 | 15.54 | C |
| ATOM | 636 | C | SER | 575 | 18.385 | 58.170 | −0.880 | 1.00 | 18.01 | C |
| ATOM | 637 | O | SER | 575 | 18.394 | 58.619 | 0.269 | 1.00 | 19.91 | O |
| ATOM | 638 | CB | SER | 575 | 18.052 | 55.742 | −1.163 | 1.00 | 11.08 | C |
| ATOM | 639 | OG | SER | 575 | 19.038 | 55.601 | −2.157 | 1.00 | 15.54 | O |
| ATOM | 640 | N | GLU | 576 | 19.221 | 58.599 | −1.810 | 1.00 | 19.82 | N |
| ATOM | 641 | CA | GLU | 576 | 20.180 | 59.616 | −1.445 | 1.00 | 19.22 | C |
| ATOM | 642 | C | GLU | 576 | 19.456 | 60.923 | −1.244 | 1.00 | 19.69 | C |
| ATOM | 643 | O | GLU | 576 | 19.754 | 61.678 | −0.322 | 1.00 | 21.30 | O |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 644 | CB | GLU | 576 | 21.287 | 59.774 | −2.483 | 1.00 | 24.50 | C |
| ATOM | 645 | CG | GLU | 576 | 22.414 | 60.647 | −1.930 | 1.00 | 34.07 | C |
| ATOM | 646 | CD | GLU | 576 | 23.375 | 61.108 | −2.979 | 1.00 | 44.16 | C |
| ATOM | 647 | OE1 | GLU | 576 | 23.681 | 60.305 | 3.893 | 1.00 | 48.95 | O |
| ATOM | 648 | OE2 | GLU | 576 | 23.816 | 62.283 | −2.891 | 1.00 | 50.40 | O |
| ATOM | 649 | N | LEU | 577 | 18.495 | 61.191 | −2.106 | 1.00 | 18.39 | N |
| ATOM | 650 | CA | LEU | 577 | 17.734 | 62.419 | −1.993 | 1.00 | 18.06 | C |
| ATOM | 651 | C | LEU | 577 | 17.042 | 62.469 | −0.640 | 1.00 | 15.66 | C |
| ATOM | 652 | O | LEU | 577 | 17.081 | 63.482 | 0.056 | 1.00 | 16.14 | O |
| ATOM | 653 | CB | LEU | 577 | 16.715 | 62.518 | −3.141 | 1.00 | 14.46 | C |
| ATOM | 654 | CG | LEU | 577 | 17.362 | 62.681 | −4.522 | 1.00 | 13.01 | C |
| ATOM | 655 | CD1 | LEU | 577 | 16.309 | 62.686 | −5.592 | 1.00 | 12.16 | C |
| ATOM | 656 | CD2 | LEU | 577 | 18.182 | 63.963 | −4.564 | 1.00 | 10.44 | C |
| ATOM | 657 | N | ARG | 578 | 16.431 | 61.356 | −0.258 | 1.00 | 18.03 | N |
| ATOM | 658 | CA | ARG | 578 | 15.721 | 61.282 | 1.013 | 1.00 | 16.42 | C |
| ATOM | 659 | C | ARG | 578 | 16.656 | 61.533 | 2.177 | 1.00 | 18.59 | C |
| ATOM | 660 | O | ARG | 578 | 16.276 | 62.207 | 3.136 | 1.00 | 23.30 | O |
| ATOM | 661 | CB | ARG | 578 | 15.005 | 59.939 | 1.169 | 1.00 | 14.49 | C |
| ATOM | 662 | CG | ARG | 578 | 13.822 | 59.783 | 0.220 | 1.00 | 9.10 | C |
| ATOM | 663 | CD | ARG | 578 | 12.924 | 58.631 | 0.583 | 1.00 | 7.18 | C |
| ATOM | 664 | NE | ARG | 578 | 13.668 | 57.391 | 0.758 | 1.00 | 13.10 | N |
| ATOM | 665 | CZ | ARG | 578 | 13.780 | 56.455 | −0.164 | 1.00 | 11.87 | C |
| ATOM | 666 | NH1 | ARG | 578 | 13.191 | 56.622 | −1.340 | 1.00 | 9.76 | N |
| ATOM | 667 | NH2 | ARG | 578 | 14.501 | 55.368 | 0.083 | 1.00 | 14.50 | N |
| ATOM | 668 | N | ARG | 579 | 17.889 | 61.046 | 2.070 | 1.00 | 17.36 | N |
| ATOM | 669 | CA | ARG | 579 | 18.879 | 61.248 | 3.119 | 1.00 | 17.76 | C |
| ATOM | 670 | C | ARG | 579 | 19.246 | 62.719 | 3.237 | 1.00 | 18.99 | C |
| ATOM | 671 | O | ARG | 579 | 19.372 | 63.252 | 4.341 | 1.00 | 21.54 | O |
| ATOM | 672 | CB | ARG | 579 | 20.132 | 60.414 | 2.833 | 1.00 | 18.77 | C |
| ATOM | 673 | CG | ARG | 579 | 21.347 | 60.787 | 3.684 | 1.00 | 24.17 | C |
| ATOM | 674 | CD | ARG | 579 | 22.532 | 59.857 | 3.461 | 1.00 | 26.24 | C |
| ATOM | 675 | NE | ARG | 579 | 22.856 | 59.678 | 2.045 | 1.00 | 36.84 | N |
| ATOM | 676 | CZ | ARG | 579 | 22.428 | 58.654 | 1.296 | 1.00 | 39.67 | C |
| ATOM | 677 | NH1 | ARG | 579 | 21.640 | 57.703 | 1.800 | 1.00 | 37.99 | N |
| ATOM | 678 | NH2 | ARG | 579 | 22.861 | 58.521 | 0.052 | 1.00 | 40.49 | N |
| ATOM | 679 | N | ILE | 580 | 19.433 | 63.377 | 2.101 | 1.00 | 18.54 | N |
| ATOM | 680 | CA | ILE | 580 | 19.784 | 64.790 | 2.098 | 1.00 | 14.36 | C |
| ATOM | 681 | C | ILE | 580 | 18.681 | 65.556 | 2.800 | 1.00 | 14.39 | C |
| ATOM | 682 | O | ILE | 580 | 18.956 | 66.396 | 3.643 | 1.00 | 15.74 | O |
| ATOM | 683 | CB | ILE | 580 | 19.969 | 65.315 | 0.673 | 1.00 | 10.89 | C |
| ATOM | 684 | CG1 | ILE | 580 | 21.209 | 64.682 | 0.067 | 1.00 | 16.10 | C |
| ATOM | 685 | CG2 | ILE | 580 | 20.087 | 66.835 | 0.663 | 1.00 | 13.34 | C |
| ATOM | 686 | CD1 | ILE | 580 | 21.457 | 65.030 | −1.408 | 1.00 | 15.50 | C |
| ATOM | 687 | N | ALA | 581 | 17.432 | 65.208 | 2.508 | 1.00 | 16.77 | N |
| ATOM | 688 | CA | ALA | 581 | 16.294 | 65.881 | 3.121 | 1.00 | 16.31 | C |
| ATOM | 689 | C | ALA | 581 | 16.252 | 65.723 | 4.646 | 1.00 | 17.47 | C |
| ATOM | 690 | O | ALA | 581 | 15.942 | 66.670 | 5.350 | 1.00 | 18.94 | O |
| ATOM | 691 | CB | ALA | 581 | 14.991 | 65.386 | 2.487 | 1.00 | 12.38 | C |
| ATOM | 692 | N | SER | 582 | 16.559 | 64.539 | 5.167 | 1.00 | 21.47 | N |
| ATOM | 693 | CA | SER | 582 | 16.516 | 64.344 | 6.617 | 1.00 | 22.46 | C |
| ATOM | 694 | C | SER | 582 | 17.700 | 64.984 | 7.295 | 1.00 | 23.44 | C |
| ATOM | 695 | O | SER | 582 | 17.673 | 65.229 | 8.497 | 1.00 | 29.23 | O |
| ATOM | 696 | CB | SER | 582 | 16.469 | 62.867 | 6.974 | 1.00 | 21.25 | C |
| ATOM | 697 | OG | SER | 582 | 17.659 | 62.228 | 6.577 | 1.00 | 25.04 | O |
| ATOM | 698 | N | GLN | 583 | 18.728 | 65.293 | 6.522 | 1.00 | 22.77 | N |
| ATOM | 699 | CA | GLN | 583 | 19.919 | 65.910 | 7.077 | 1.00 | 23.36 | C |
| ATOM | 700 | C | GLN | 583 | 19.874 | 67.425 | 6.981 | 1.00 | 21.29 | C |
| ATOM | 701 | O | GLN | 583 | 20.812 | 68.117 | 7.416 | 1.00 | 20.02 | O |
| ATOM | 702 | CB | GLN | 583 | 21.177 | 65.369 | 6.398 | 1.00 | 30.71 | C |
| ATOM | 703 | CG | GLN | 583 | 21.524 | 63.939 | 6.797 | 1.00 | 42.85 | C |
| ATOM | 704 | CD | GLN | 583 | 22.843 | 63.455 | 6.192 | 1.00 | 55.80 | C |
| ATOM | 705 | OE1 | GLN | 583 | 23.589 | 62.715 | 6.839 | 1.00 | 62.99 | O |
| ATOM | 706 | NE2 | GLN | 583 | 23.141 | 63.873 | 4.950 | 1.00 | 59.38 | N |
| ATOM | 707 | N | VAL | 584 | 18.804 | 67.940 | 6.389 | 1.00 | 15.51 | N |
| ATOM | 708 | CA | VAL | 584 | 18.622 | 69.371 | 6.255 | 1.00 | 21.88 | C |
| ATOM | 709 | C | VAL | 584 | 18.891 | 70.018 | 7.615 | 1.00 | 26.42 | C |
| ATOM | 710 | O | VAL | 584 | 18.367 | 69.585 | 8.643 | 1.00 | 26.77 | O |
| ATOM | 711 | CB | VAL | 584 | 17.194 | 69.706 | 5.768 | 1.00 | 25.45 | C |
| ATOM | 712 | CG1 | VAL | 584 | 16.944 | 71.199 | 5.861 | 1.00 | 30.17 | C |
| ATOM | 713 | CG2 | VAL | 584 | 17.013 | 69.269 | 4.333 | 1.00 | 27.33 | C |
| ATOM | 714 | N | LYS | 585 | 19.690 | 71.073 | 7.597 | 1.00 | 30.58 | N |
| ATOM | 715 | CA | LYS | 585 | 20.108 | 71.788 | 8.798 | 1.00 | 33.89 | C |
| ATOM | 716 | C | LYS | 585 | 19.091 | 72.734 | 9.417 | 1.00 | 32.68 | C |
| ATOM | 717 | O | LYS | 585 | 18.570 | 73.641 | 8.747 | 1.00 | 33.70 | O |
| ATOM | 718 | CB | LYS | 585 | 21.398 | 72.551 | 8.497 | 1.00 | 41.79 | C |

TABLE 8-continued

Atomic Coordinates for Residues of a Crystal of murine VWF-A1 (SEQ ID NO: 10).

| CRYST1 | 86.395 | | 86.395 | 68.125 | 90.00 | 90.00 | 120.00 | P 61 | 6 |
|---|---|---|---|---|---|---|---|---|---|
| ATOM | 719 | CG | LYS 585 | 22.643 | 71.977 | 9.165 | 1.00 | 52.09 | C |
| ATOM | 720 | CD | LYS 585 | 22.693 | 72.340 | 10.657 | 1.00 | 63.92 | C |
| ATOM | 721 | CE | LYS 585 | 22.857 | 73.859 | 10.873 | 1.00 | 70.35 | C |
| ATOM | 722 | NZ | LYS 585 | 22.735 | 74.271 | 12.316 | 1.00 | 74.91 | N |
| ATOM | 723 | N | TYR 586 | 18.859 | 72.557 | 10.718 | 1.00 | 30.31 | N |
| ATOM | 724 | CA | TYR 586 | 17.928 | 73.416 | 11.454 | 1.00 | 29.54 | C |
| ATOM | 725 | C | TYR 586 | 18.583 | 74.776 | 11.564 | 1.00 | 29.75 | C |
| ATOM | 726 | O | TYR 586 | 19.696 | 74.885 | 12.079 | 1.00 | 30.67 | O |
| ATOM | 727 | CB | TYR 586 | 17.619 | 72.856 | 12.861 | 1.00 | 27.95 | C |
| ATOM | 728 | CG | TYR 586 | 16.772 | 73.793 | 13.721 | 1.00 | 26.56 | C |
| ATOM | 729 | CD1 | TYR 586 | 15.389 | 73.906 | 13.522 | 1.00 | 24.59 | C |
| ATOM | 730 | CD2 | TYR 586 | 17.361 | 74.604 | 14.699 | 1.00 | 21.69 | C |
| ATOM | 731 | CE1 | TYR 586 | 14.616 | 74.806 | 14.265 | 1.00 | 20.84 | C |
| ATOM | 732 | CE2 | TYR 586 | 16.590 | 75.508 | 15.457 | 1.00 | 17.53 | C |
| ATOM | 733 | CZ | TYR 586 | 15.222 | 75.601 | 15.233 | 1.00 | 23.50 | C |
| ATOM | 734 | OH | TYR 586 | 14.461 | 76.482 | 15.978 | 1.00 | 21.84 | O |
| ATOM | 735 | N | ALA 587 | 17.932 | 75.788 | 10.994 | 1.00 | 28.03 | N |
| ATOM | 736 | CA | ALA 587 | 18.433 | 77.150 | 11.016 | 1.00 | 27.73 | C |
| ATOM | 737 | C | ALA 587 | 17.945 | 77.932 | 12.220 | 1.00 | 27.05 | C |
| ATOM | 738 | O | ALA 587 | 18.735 | 78.601 | 12.870 | 1.00 | 26.39 | O |
| ATOM | 739 | CB | ALA 587 | 18.056 | 77.882 | 9.719 | 1.00 | 29.03 | C |
| ATOM | 740 | N | GLY 588 | 16.643 | 77.880 | 12.490 | 1.00 | 25.16 | N |
| ATOM | 741 | CA | GLY 588 | 16.093 | 78.606 | 13.619 | 1.00 | 24.35 | C |
| ATOM | 742 | C | GLY 588 | 16.224 | 80.115 | 13.484 | 1.00 | 26.00 | C |
| ATOM | 743 | O | GLY 588 | 16.582 | 80.806 | 14.429 | 1.00 | 27.67 | O |
| ATOM | 744 | N | SER 589 | 15.891 | 80.626 | 12.309 | 1.00 | 25.60 | N |
| ATOM | 745 | CA | SER 589 | 15.985 | 82.044 | 12.009 | 1.00 | 25.91 | C |
| ATOM | 746 | C | SER 589 | 14.916 | 82.905 | 12.679 | 1.00 | 27.91 | C |
| ATOM | 747 | O | SER 589 | 13.849 | 82.426 | 13.050 | 1.00 | 23.56 | O |
| ATOM | 748 | CB | SER 589 | 15.879 | 82.228 | 10.495 | 1.00 | 26.02 | C |
| ATOM | 749 | OG | SER 589 | 16.935 | 83.028 | 9.992 | 1.00 | 41.28 | O |
| ATOM | 750 | N | GLN 590 | 15.212 | 84.193 | 12.811 | 1.00 | 32.43 | N |
| ATOM | 751 | CA | GLN 590 | 14.256 | 85.130 | 13.373 | 1.00 | 37.48 | C |
| ATOM | 752 | C | GLN 590 | 13.253 | 85.476 | 12.296 | 1.00 | 35.55 | C |
| ATOM | 753 | O | GLN 590 | 12.160 | 85.937 | 12.588 | 1.00 | 38.88 | O |
| ATOM | 754 | CB | GLN 590 | 14.955 | 86.415 | 13.821 | 1.00 | 39.80 | C |
| ATOM | 755 | CG | GLN 590 | 15.288 | 86.435 | 15.295 | 1.00 | 56.15 | C |
| ATOM | 756 | CD | GLN 590 | 16.155 | 87.622 | 15.686 | 1.00 | 65.66 | C |
| ATOM | 757 | OE1 | GLN 590 | 15.649 | 88.723 | 15.932 | 1.00 | 71.38 | O |
| ATOM | 758 | NE2 | GLN 590 | 17.473 | 87.403 | 15.742 | 1.00 | 67.58 | N |
| ATOM | 759 | N | VAL 591 | 13.647 | 85.246 | 11.047 | 1.00 | 34.29 | N |
| ATOM | 760 | CA | VAL 591 | 12.832 | 85.570 | 9.880 | 1.00 | 30.91 | C |
| ATOM | 761 | C | VAL 591 | 12.827 | 84.471 | 8.809 | 1.00 | 26.09 | C |
| ATOM | 762 | O | VAL 591 | 13.885 | 84.022 | 8.392 | 1.00 | 23.24 | O |
| ATOM | 763 | CB | VAL 591 | 13.359 | 86.907 | 9.243 | 1.00 | 30.16 | C |
| ATOM | 764 | CG1 | VAL 591 | 13.067 | 86.983 | 7.758 | 1.00 | 33.78 | C |
| ATOM | 765 | CG2 | VAL 591 | 12.750 | 88.102 | 9.949 | 1.00 | 29.76 | C |
| ATOM | 766 | N | ALA 592 | 11.636 | 84.000 | 8.437 | 1.00 | 24.70 | N |
| ATOM | 767 | CA | ALA 592 | 11.462 | 83.007 | 7.372 | 1.00 | 20.42 | C |
| ATOM | 758 | C | ALA 592 | 10.529 | 83.712 | 6.375 | 1.00 | 23.74 | C |
| ATOM | 769 | O | ALA 592 | 9.320 | 83.852 | 6.629 | 1.00 | 19.55 | O |
| ATOM | 770 | CB | ALA 592 | 10.829 | 81.750 | 7.893 | 1.00 | 14.37 | C |
| ATOM | 771 | N | SER 593 | 11.104 | 84.209 | 5.277 | 1.00 | 22.94 | N |
| ATOM | 772 | CA | SER 593 | 10.349 | 84.951 | 4.270 | 1.00 | 23.81 | C |
| ATOM | 773 | C | SER 593 | 9.677 | 84.093 | 3.224 | 1.00 | 22.86 | C |
| ATOM | 774 | O | SER 593 | 10.336 | 83.470 | 2.401 | 1.00 | 22.82 | O |
| ATOM | 775 | CB | SER 593 | 11.232 | 85.974 | 3.569 | 1.00 | 23.57 | C |
| ATOM | 776 | OG | SER 593 | 10.496 | 86.636 | 2.556 | 1.00 | 14.43 | O |
| ATOM | 777 | N | THR 594 | 8.354 | 84.150 | 3.212 | 1.00 | 22.76 | N |
| ATOM | 778 | CA | THR 594 | 7.568 | 83.380 | 2.263 | 1.00 | 22.25 | C |
| ATOM | 779 | C | THR 594 | 7.608 | 84.069 | 0.898 | 1.00 | 21.75 | C |
| ATOM | 780 | O | THR 594 | 7.593 | 83.411 | −0.143 | 1.00 | 21.45 | O |
| ATOM | 781 | CB | THR 594 | 6.122 | 83.217 | 2.768 | 1.00 | 19.99 | C |
| ATOM | 782 | OG1 | THR 594 | 5.593 | 84.505 | 3.106 | 1.00 | 18.50 | O |
| ATOM | 783 | CG2 | THR 594 | 6.110 | 82.375 | 4.021 | 1.00 | 15.10 | C |
| ATOM | 784 | N | SER 595 | 7.663 | 85.400 | 0.901 | 1.00 | 21.20 | N |
| ATOM | 785 | CA | SER 595 | 7.738 | 86.164 | −0.334 | 1.00 | 18.60 | C |
| ATOM | 786 | C | SER 595 | 9.032 | 85.850 | −1.040 | 1.00 | 19.69 | C |
| ATOM | 787 | O | SER 595 | 9.044 | 85.513 | −2.228 | 1.00 | 22.57 | O |
| ATOM | 788 | CB | SER 595 | 7.661 | 87.653 | −0.037 | 1.00 | 11.10 | C |
| ATOM | 789 | OG | SER 595 | 6.344 | 87.985 | 0.326 | 1.00 | 19.37 | O |
| ATOM | 790 | N | GLU 596 | 10.122 | 85.922 | −0.294 | 1.00 | 21.05 | N |
| ATOM | 791 | CA | GLU 596 | 11.418 | 85.638 | −0.863 | 1.00 | 23.66 | C |
| ATOM | 792 | C | GLU 596 | 11.591 | 84.184 | −1.299 | 1.00 | 22.27 | C |
| ATOM | 793 | O | GLU 596 | 12.302 | 83.905 | −2.260 | 1.00 | 24.61 | O |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 794 | CB | GLU | 596 | 12.543 | 86.151 | 0.043 | 1.00 | 30.29 | C |
| ATOM | 795 | CG | GLU | 596 | 13.058 | 87.575 | −0.366 | 1.00 | 39.81 | C |
| ATOM | 796 | CD | GLU | 596 | 11.948 | 88.663 | −0.449 | 1.00 | 45.46 | C |
| ATOM | 797 | OE1 | GLU | 596 | 11.391 | 89.067 | 0.602 | 1.00 | 52.14 | O |
| ATOM | 798 | OE2 | GLU | 596 | 11.648 | 89.142 | −1.565 | 1.00 | 47.05 | O |
| ATOM | 799 | N | VAL | 597 | 10.886 | 83.257 | −0.661 | 1.00 | 19.54 | N |
| ATOM | 800 | CA | VAL | 597 | 10.993 | 81.869 | −1.079 | 1.00 | 14.34 | C |
| ATOM | 801 | C | VAL | 597 | 10.056 | 81.566 | −2.257 | 1.00 | 14.34 | C |
| ATOM | 802 | O | VAL | 597 | 10.322 | 80.677 | −3.047 | 1.00 | 15.50 | O |
| ATOM | 803 | CB | VAL | 597 | 10.768 | 80.893 | 0.077 | 1.00 | 10.95 | C |
| ATOM | 804 | CG1 | VAL | 597 | 9.297 | 80.603 | 0.266 | 1.00 | 9.01 | C |
| ATOM | 805 | CG2 | VAL | 597 | 11.555 | 79.624 | −0.172 | 1.00 | 10.66 | C |
| ATOM | 806 | N | LEU | 598 | 8.951 | 82.287 | −2.372 | 1.00 | 12.70 | N |
| ATOM | 807 | CA | LEU | 598 | 8.067 | 82.083 | −3.502 | 1.00 | 12.15 | C |
| ATOM | 808 | C | LEU | 598 | 8.749 | 82.749 | −4.699 | 1.00 | 17.31 | C |
| ATOM | 809 | O | LEU | 598 | 8.579 | 82.324 | −5.840 | 1.00 | 18.32 | O |
| ATOM | 810 | CB | LEU | 598 | 6.700 | 82.699 | −3.240 | 1.00 | 8.81 | C |
| ATOM | 811 | CG | LEU | 598 | 5.728 | 81.891 | −2.363 | 1.00 | 9.60 | C |
| ATOM | 812 | CD1 | LEU | 598 | 4.467 | 82.716 | −2.154 | 1.00 | 9.06 | C |
| ATOM | 813 | CD2 | LEU | 598 | 5.370 | 80.522 | −2.975 | 1.00 | 7.06 | C |
| ATOM | 814 | N | LYS | 599 | 9.552 | 83.777 | −4.432 | 1.00 | 18.09 | N |
| ATOM | 815 | CA | LYS | 599 | 10.288 | 84.442 | −5.492 | 1.00 | 20.39 | C |
| ATOM | 816 | C | LYS | 599 | 11.328 | 83.475 | −6.055 | 1.00 | 20.58 | C |
| ATOM | 817 | O | LYS | 599 | 11.552 | 83.432 | −7.260 | 1.00 | 23.57 | O |
| ATOM | 818 | CB | LYS | 599 | 11.OD1 | 85.693 | −4.982 | 1.00 | 21.30 | C |
| ATOM | 819 | CG | LYS | 599 | 11.836 | 86.366 | −6.063 | 1.00 | 20.62 | C |
| ATOM | 820 | CD | LYS | 599 | 12.331 | 87.732 | −5.633 | 1.00 | 28.26 | C |
| ATOM | 821 | CE | LYS | 599 | 13.674 | 87.677 | −4.914 | 1.00 | 28.15 | C |
| ATOM | 822 | NZ | LYS | 599 | 14.463 | 88.927 | −5.268 | 1.00 | 36.90 | N |
| ATOM | 823 | N | TYR | 600 | 11.972 | 82.712 | −5.184 | 1.00 | 15.33 | N |
| ATOM | 824 | CA | TYR | 600 | 12.975 | 81.739 | −5.605 | 1.00 | 14.72 | C |
| ATOM | 825 | C | TYR | 600 | 12.380 | 80.614 | −6.470 | 1.00 | 15.26 | C |
| ATOM | 826 | O | TYR | 600 | 13.031 | 80.110 | −7.394 | 1.00 | 14.23 | O |
| ATOM | 827 | CB | TYR | 600 | 13.659 | 81.159 | −4.369 | 1.00 | 10.22 | C |
| ATOM | 828 | CG | TYR | 600 | 14.763 | 80.168 | −4.658 | 1.00 | 13.36 | C |
| ATOM | 829 | CD1 | TYR | 600 | 16.091 | 80.594 | −4.820 | 1.00 | 9.42 | C |
| ATOM | 830 | CD2 | TYR | 600 | 14.488 | 78.791 | −4.745 | 1.00 | 9.40 | C |
| ATOM | 831 | CE1 | TYR | 600 | 17.123 | 79.670 | −5.066 | 1.00 | 8.00 | C |
| ATOM | 832 | CE2 | TYR | 600 | 15.502 | 77.874 | −4.987 | 1.00 | 11.12 | C |
| ATOM | 833 | CZ | TYR | 600 | 16.812 | 78.320 | −5.154 | 1.00 | 13.46 | C |
| ATOM | 834 | OH | TYR | 600 | 17.796 | 77.412 | −5.477 | 1.00 | 18.52 | O |
| ATOM | 835 | N | THR | 601 | 11.144 | 80.228 | −6.167 | 1.00 | 15.74 | N |
| ATOM | 836 | CA | THR | 601 | 10.449 | 79.163 | −6.887 | 1.00 | 16.26 | C |
| ATOM | 837 | C | THR | 601 | 10.062 | 79.658 | −8.291 | 1.00 | 18.06 | C |
| ATOM | 838 | O | THR | 601 | 10.189 | 78.942 | −9.297 | 1.00 | 20.51 | O |
| ATOM | 839 | CB | THR | 601 | 9.184 | 78.724 | −6.074 | 1.00 | 13.62 | C |
| ATOM | 840 | OG1 | THR | 601 | 9.583 | 78.361 | −4.745 | 1.00 | 14.88 | O |
| ATOM | 841 | CG2 | THR | 601 | 8.493 | 77.517 | −6.690 | 1.00 | 8.81 | C |
| ATOM | 842 | N | LEU | 602 | 9.660 | 80.914 | −8.358 | 1.00 | 18.80 | N |
| ATOM | 843 | CA | LEU | 602 | 9.239 | 81.517 | −9.594 | 1.00 | 12.28 | C |
| ATOM | 844 | C | LEU | 602 | 10.394 | 81.808 | −10.528 | 1.00 | 12.80 | C |
| ATOM | 845 | O | LEU | 602 | 10.365 | 81.445 | −11.686 | 1.00 | 15.88 | O |
| ATOM | 846 | CB | LEU | 602 | 8.497 | 82.800 | −9.259 | 1.00 | 7.41 | C |
| ATOM | 847 | CG | LEU | 602 | 7.971 | 83.645 | −10.410 | 1.00 | 4.81 | C |
| ATOM | 848 | CD1 | LEU | 602 | 7.137 | 82.788 | −11.305 | 1.00 | 11.16 | C |
| ATOM | 849 | CD2 | LEU | 602 | 7.163 | 84.783 | −9.881 | 1.00 | 3.73 | C |
| ATOM | 850 | N | PHE | 603 | 11.409 | 82.496 | −10.031 | 1.00 | 17.52 | N |
| ATOM | 851 | CA | PHE | 603 | 12.537 | 82.883 | −10.862 | 1.00 | 18.59 | C |
| ATOM | 852 | C | PHE | 603 | 13.743 | 81.966 | −10.844 | 1.00 | 21.46 | C |
| ATOM | 853 | O | PHE | 603 | 14.577 | 82.022 | −11.746 | 1.00 | 21.41 | O |
| ATOM | 854 | CB | PHE | 603 | 12.954 | 84.322 | −10.533 | 1.00 | 13.06 | C |
| ATOM | 855 | CG | PHE | 603 | 11.860 | 85.333 | −10.758 | 1.00 | 13.57 | C |
| ATOM | 856 | CD1 | PHE | 603 | 11.257 | 85.469 | −12.006 | 1.00 | 13.30 | C |
| ATOM | 857 | CD2 | PHE | 603 | 11.422 | 86.138 | −9.722 | 1.00 | 11.61 | C |
| ATOM | 858 | CE1 | PHE | 603 | 10.232 | 86.385 | −12.212 | 1.00 | 8.39 | C |
| ATOM | 859 | CE2 | PHE | 603 | 10.403 | 87.054 | −9.916 | 1.00 | 14.44 | C |
| ATOM | 860 | CZ | PHE | 603 | 9.804 | 87.180 | −11.160 | 1.00 | 14.78 | C |
| ATOM | 861 | N | GLN | 604 | 13.828 | 81.087 | −9.856 | 1.00 | 24.28 | N |
| ATOM | 862 | CA | GLN | 604 | 14.983 | 80.205 | −9.787 | 1.00 | 27.12 | C |
| ATOM | 863 | C | GLN | 604 | 14.687 | 78.739 | −10.058 | 1.00 | 24.50 | C |
| ATOM | 864 | O | GLN | 604 | 15.512 | 78.040 | −10.605 | 1.00 | 24.04 | O |
| ATOM | 865 | CB | GLN | 604 | 15.689 | 80.368 | −8.440 | 1.00 | 31.32 | C |
| ATOM | 866 | CG | GLN | 604 | 16.522 | 81.621 | −8.287 | 1.00 | 35.80 | C |
| ATOM | 867 | CD | GLN | 604 | 17.861 | 81.469 | −8.960 | 1.00 | 45.50 | C |
| ATOM | 868 | OE1 | GLN | 604 | 18.784 | 80.859 | −8.418 | 1.00 | 49.26 | O |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 869 | NE2 | GLN | 604 | 17.973 | 81.999 | −10.166 | 1.00 | 54.22 | N |
| ATOM | 870 | N | ILE | 605 | 13.521 | 78.260 | −9.660 | 1.00 | 23.49 | N |
| ATOM | 871 | CA | ILE | 605 | 13.196 | 76.859 | −9.881 | 1.00 | 22.06 | C |
| ATOM | 872 | C | ILE | 605 | 12.418 | 76.627 | −11.163 | 1.00 | 25.79 | C |
| ATOM | 873 | O | ILE | 605 | 12.635 | 75.633 | −11.861 | 1.00 | 28.80 | O |
| ATOM | 874 | CB | ILE | 605 | 12.425 | 76.243 | −8.678 | 1.00 | 18.12 | C |
| ATOM | 875 | CG1 | ILE | 605 | 13.356 | 76.119 | −7.470 | 1.00 | 16.09 | C |
| ATOM | 876 | CG2 | ILE | 605 | 11.862 | 74.874 | −9.035 | 1.00 | 15.46 | C |
| ATOM | 877 | CD1 | ILE | 605 | 12.661 | 75.604 | −6.225 | 1.00 | 12.12 | C |
| ATOM | 878 | N | PHE | 606 | 11.444 | 77.484 | −11.431 | 1.00 | 21.94 | N |
| ATOM | 879 | CA | PHE | 606 | 10.670 | 77.333 | −12.645 | 1.00 | 22.03 | C |
| ATOM | 880 | C | PHE | 606 | 10.903 | 78.556 | −13.533 | 1.00 | 22.92 | C |
| ATOM | 881 | O | PHE | 606 | 9.965 | 79.130 | −14.083 | 1.00 | 19.90 | O |
| ATOM | 882 | CB | PHE | 606 | 9.188 | 77.149 | −12.310 | 1.00 | 19.38 | C |
| ATOM | 883 | CG | PHE | 606 | 8.899 | 75.943 | −11.442 | 1.00 | 24.03 | C |
| ATOM | 884 | CD1 | PHE | 606 | 8.941 | 74.656 | −11.969 | 1.00 | 21.11 | C |
| ATOM | 885 | CD2 | PHE | 606 | 8.498 | 76.107 | −10.108 | 1.00 | 23.28 | C |
| ATOM | 886 | CE1 | PHE | 606 | 8.582 | 73.560 | −11.178 | 1.00 | 22.09 | C |
| ATOM | 887 | CE2 | PHE | 606 | 8.141 | 75.025 | −9.319 | 1.00 | 19.77 | C |
| ATOM | 888 | CZ | PHE | 606 | 8.175 | 73.749 | −9.850 | 1.00 | 22.92 | C |
| ATOM | 889 | N | SER | 607 | 12.165 | 78.971 | −13.641 | 1.00 | 27.16 | N |
| ATOM | 890 | CA | SER | 607 | 12.505 | 80.127 | −14.456 | 1.00 | 34.01 | C |
| ATOM | 891 | C | SER | 607 | 11.927 | 79.863 | −15.832 | 1.00 | 41.74 | C |
| ATOM | 892 | O | SER | 607 | 11.276 | 80.737 | −16.421 | 1.00 | 49.40 | O |
| ATOM | 893 | CB | SER | 607 | 13.997 | 80.342 | −14.543 | 1.00 | 29.88 | C |
| ATOM | 894 | OG | SER | 607 | 14.209 | 81.653 | −15.023 | 1.00 | 31.36 | O |
| ATOM | 895 | N | LYS | 608 | 12.279 | 78.717 | −16.404 | 1.00 | 43.35 | N |
| ATOM | 896 | CA | LYS | 608 | 11.647 | 78.316 | −17.648 | 1.00 | 46.17 | C |
| ATOM | 897 | C | LYS | 608 | 11.480 | 76.817 | −17.716 | 1.00 | 42.64 | C |
| ATOM | 898 | O | LYS | 608 | 12.365 | 76.029 | −17.390 | 1.00 | 40.78 | O |
| ATOM | 899 | CB | LYS | 608 | 12.195 | 78.939 | −18.935 | 1.00 | 54.48 | C |
| ATOM | 900 | CG | LYS | 608 | 11.035 | 79.221 | −19.979 | 1.00 | 55.51 | C |
| ATOM | 901 | CD | LYS | 608 | 9.997 | 80.303 | −19.504 | 1.00 | 54.84 | C |
| ATOM | 902 | CE | LYS | 608 | 8.628 | 79.732 | −19.088 | 1.00 | 53.13 | C |
| ATOM | 903 | NZ | LYS | 608 | 7.777 | 79.171 | −20.196 | 1.00 | 50.29 | N |
| ATOM | 904 | N | ILE | 609 | 10.244 | 76.475 | −18.018 | 1.00 | 38.42 | N |
| ATOM | 905 | CA | ILE | 609 | 9.753 | 75.134 | −18.077 | 1.00 | 32.87 | C |
| ATOM | 906 | C | ILE | 609 | 10.437 | 74.185 | −19.038 | 1.00 | 30.65 | C |
| ATOM | 907 | O | ILE | 609 | 10.108 | 74.152 | −20.208 | 1.00 | 34.42 | O |
| ATOM | 908 | CB | ILE | 609 | 8.235 | 75.198 | −18.302 | 1.00 | 31.16 | C |
| ATOM | 909 | CG1 | ILE | 609 | 7.626 | 76.217 | −17.324 | 1.00 | 30.77 | C |
| ATOM | 910 | CG2 | ILE | 609 | 7.595 | 73.836 | −18.148 | 1.00 | 32.93 | C |
| ATOM | 911 | CD1 | ILE | 609 | 8.177 | 76.152 | −15.893 | 1.00 | 27.01 | C |
| ATOM | 912 | N | ASP | 610 | 11.382 | 73.407 | −18.512 | 1.00 | 29.30 | N |
| ATOM | 913 | CA | ASP | 610 | 12.115 | 72.397 | −19.278 | 1.00 | 26.65 | C |
| ATOM | 914 | C | ASP | 610 | 11.296 | 71.090 | −19.348 | 1.00 | 24.52 | C |
| ATOM | 915 | O | ASP | 610 | 11.667 | 70.160 | −20.061 | 1.00 | 22.38 | O |
| ATOM | 916 | CB | ASP | 610 | 13.472 | 72.100 | −18.610 | 1.00 | 31.38 | C |
| ATOM | 917 | CG | ASP | 610 | 13.326 | 71.445 | −17.208 | 1.00 | 40.16 | C |
| ATOM | 918 | OD1 | ASP | 610 | 12.777 | 72.111 | −16.296 | 1.00 | 44.05 | O |
| ATOM | 919 | OD2 | ASP | 610 | 13.781 | 70.280 | −17.006 | 1.00 | 37.91 | O |
| ATOM | 920 | N | ARG | 611 | 10.207 | 71.023 | −18.586 | 1.00 | 20.53 | N |
| ATOM | 921 | CA | ARG | 611 | 9.338 | 69.847 | −18.523 | 1.00 | 17.10 | C |
| ATOM | 922 | C | ARG | 611 | 7.882 | 70.318 | −18.565 | 1.00 | 18.14 | C |
| ATOM | 923 | O | ARG | 611 | 7.147 | 70.151 | −17.579 | 1.00 | 17.77 | O |
| ATOM | 924 | CB | ARG | 611 | 9.555 | 69.117 | −17.188 | 1.00 | 15.35 | C |
| ATOM | 925 | CG | ARG | 611 | 10.090 | 67.715 | −17.279 | 1.00 | 19.43 | C |
| ATOM | 926 | CD | ARG | 611 | 9.053 | 66.659 | −16.878 | 1.00 | 17.95 | C |
| ATOM | 927 | NE | ARG | 611 | 9.225 | 66.220 | −15.507 | 1.00 | 15.53 | N |
| ATOM | 928 | CZ | ARG | 611 | 8.787 | 65.070 | −15.009 | 1.00 | 15.73 | C |
| ATOM | 929 | NH1 | ARG | 611 | 8.143 | 64.187 | −15.746 | 1.00 | 14.15 | N |
| ATOM | 930 | NH2 | ARG | 611 | 8.950 | 64.830 | −13.726 | 1.00 | 20.70 | N |
| ATOM | 931 | N | PRO | 612 | 7.410 | 70.799 | −19.734 | 1.00 | 18.33 | N |
| ATOM | 932 | CA | PRO | 612 | 6.023 | 71.278 | −19.846 | 1.00 | 18.14 | C |
| ATOM | 933 | C | PRO | 612 | 4.985 | 70.176 | −19.746 | 1.00 | 16.54 | C |
| ATOM | 934 | O | PRO | 612 | 3.800 | 70.458 | −19.694 | 1.00 | 18.83 | O |
| ATOM | 935 | CB | PRO | 612 | 6.003 | 71.928 | −21.226 | 1.00 | 20.27 | C |
| ATOM | 936 | CG | PRO | 612 | 6.909 | 70.998 | −22.015 | 1.00 | 21.20 | C |
| ATOM | 937 | CD | PRO | 612 | 8.066 | 70.757 | −21.054 | 1.00 | 19.55 | C |
| ATOM | 938 | N | GLU | 613 | 5.439 | 68.926 | −19.694 | 1.00 | 17.56 | N |
| ATOM | 939 | CA | GLU | 613 | 4.539 | 67.780 | −19.590 | 1.00 | 18.04 | C |
| ATOM | 940 | C | GLU | 613 | 4.265 | 67.341 | −18.137 | 1.00 | 20.09 | C |
| ATOM | 941 | O | GLU | 613 | 3.525 | 66.376 | −17.895 | 1.00 | 19.26 | O |
| ATOM | 942 | CB | GLU | 613 | 5.088 | 66.593 | −20.380 | 1.00 | 17.32 | C |
| ATOM | 943 | CG | GLU | 613 | 6.320 | 65.939 | −19.764 | 1.00 | 16.50 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 944 | CD | GLU | 613 | 7.622 | 66.575 | −20.203 | 1.00 | 17.75 | C |
| ATOM | 945 | OE1 | GLU | 613 | 7.609 | 67.682 | −20.775 | 1.00 | 21.13 | O |
| ATOM | 946 | OE2 | GLU | 613 | 8.680 | 65.949 | −19.979 | 1.00 | 18.68 | O |
| ATOM | 947 | N | ALA | 614 | 4.896 | 67.997 | −17.172 | 1.00 | 17.80 | N |
| ATOM | 948 | CA | ALA | 614 | 4.645 | 67.643 | −15.782 | 1.00 | 17.35 | C |
| ATOM | 949 | C | ALA | 614 | 3.998 | 68.805 | −15.068 | 1.00 | 17.82 | C |
| ATOM | 950 | O | ALA | 614 | 4.245 | 69.962 | −15.422 | 1.00 | 18.03 | O |
| ATOM | 951 | CB | ALA | 614 | 5.929 | 67.302 | −15.103 | 1.00 | 14.29 | C |
| ATOM | 952 | N | SER | 615 | 3.143 | 68.502 | −14.088 | 1.00 | 14.90 | N |
| ATOM | 953 | CA | SER | 615 | 2.532 | 69.553 | −13.297 | 1.00 | 13.08 | C |
| ATOM | 954 | C | SER | 615 | 3.622 | 70.036 | −12.347 | 1.00 | 14.27 | C |
| ATOM | 955 | O | SER | 615 | 4.577 | 69.304 | −12.056 | 1.00 | 17.25 | O |
| ATOM | 956 | CB | SER | 615 | 1.362 | 69.029 | −12.491 | 1.00 | 10.01 | C |
| ATOM | 957 | OG | SER | 615 | 0.379 | 68.502 | −13.348 | 1.00 | 13.32 | O |
| ATOM | 958 | N | ARG | 616 | 3.505 | 71.290 | −11.929 | 1.00 | 13.79 | N |
| ATOM | 959 | CA | ARG | 616 | 4.441 | 71.923 | −11.021 | 1.00 | 10.29 | C |
| ATOM | 950 | C | ARG | 616 | 3.696 | 72.218 | −9.722 | 1.00 | 8.30 | C |
| ATOM | 961 | O | ARG | 616 | 2.638 | 72.841 | −9.721 | 1.00 | 8.31 | O |
| ATOM | 962 | CB | ARG | 616 | 4.966 | 73.188 | −11.671 | 1.00 | 10.60 | C |
| ATOM | 963 | CG | ARG | 616 | 5.580 | 72.883 | −13.020 | 1.00 | 11.29 | C |
| ATOM | 964 | CD | ARG | 616 | 5.648 | 74.101 | −13.902 | 1.00 | 18.79 | C |
| ATOM | 965 | NE | ARG | 616 | 5.380 | 73.740 | −15.286 | 1.00 | 25.65 | N |
| ATOM | 956 | CZ | ARG | 616 | 4.217 | 73.955 | −15.877 | 1.00 | 28.89 | C |
| ATOM | 967 | NH1 | ARG | 616 | 3.238 | 74.543 | −15.223 | 1.00 | 36.05 | N |
| ATOM | 968 | NH2 | ARG | 616 | 3.977 | 73.463 | −17.075 | 1.00 | 37.22 | N |
| ATOM | 959 | N | ILE | 617 | 4.187 | 71.673 | −8.616 | 1.00 | 10.46 | N |
| ATOM | 970 | CA | ILE | 617 | 3.532 | 71.893 | −7.341 | 1.00 | 8.09 | C |
| ATOM | 971 | C | ILE | 617 | 4.549 | 72.311 | −6.289 | 1.00 | 9.44 | C |
| ATOM | 972 | O | ILE | 617 | 5.625 | 71.717 | −6.176 | 1.00 | 13.23 | O |
| ATOM | 973 | CB | ILE | 617 | 2.790 | 70.616 | −6.898 | 1.00 | 13.19 | C |
| ATOM | 974 | CG1 | ILE | 617 | 1.747 | 70.212 | −7.951 | 1.00 | 12.54 | C |
| ATOM | 975 | CG2 | ILE | 617 | 2.102 | 70.832 | −5.549 | 1.00 | 17.10 | C |
| ATOM | 976 | CD1 | ILE | 617 | 0.818 | 69.049 | −7.489 | 1.00 | 9.40 | C |
| ATOM | 977 | N | ALA | 618 | 4.241 | 73.396 | −5.587 | 1.00 | 11.26 | N |
| ATOM | 978 | CA | ALA | 618 | 5.092 | 73.932 | −4.523 | 1.00 | 9.88 | C |
| ATOM | 979 | C | ALA | 618 | 4.319 | 73.708 | −3.221 | 1.00 | 13.13 | C |
| ATOM | 980 | O | ALA | 618 | 3.164 | 74.135 | −3.084 | 1.00 | 13.87 | O |
| ATOM | 981 | CB | ALA | 618 | 5.332 | 75.403 | −4.747 | 1.00 | 6.93 | C |
| ATOM | 982 | N | LEU | 619 | 4.920 | 72.964 | −2.304 | 1.00 | 11.48 | N |
| ATOM | 983 | CA | LEU | 619 | 4.286 | 72.655 | −1.029 | 1.00 | 14.03 | C |
| ATOM | 984 | C | LEU | 619 | 4.900 | 73.622 | −0.022 | 1.00 | 12.75 | C |
| ATOM | 985 | O | LEU | 619 | 6.035 | 73.447 | 0.395 | 1.00 | 9.90 | O |
| ATOM | 986 | CB | LEU | 619 | 4.604 | 71.206 | −0.675 | 1.00 | 14.36 | C |
| ATOM | 987 | CG | LEU | 619 | 3.800 | 70.416 | 0.353 | 1.00 | 19.68 | C |
| ATOM | 988 | CD1 | LEU | 619 | 2.311 | 70.465 | 0.078 | 1.00 | 19.00 | C |
| ATOM | 989 | CD2 | LEU | 619 | 4.319 | 68.989 | 0.289 | 1.00 | 14.02 | C |
| ATOM | 990 | N | LEU | 620 | 4.186 | 74.700 | 0.281 | 1.00 | 11.45 | N |
| ATOM | 991 | CA | LEU | 620 | 4.706 | 75.711 | 1.201 | 1.00 | 14.00 | C |
| ATOM | 992 | C | LEU | 620 | 4.397 | 75.384 | 2.663 | 1.00 | 13.84 | C |
| ATOM | 993 | O | LEU | 620 | 3.271 | 75.581 | 3.123 | 1.00 | 10.40 | O |
| ATOM | 994 | CB | LEU | 620 | 4.156 | 77.095 | 0.823 | 1.00 | 11.10 | C |
| ATOM | 995 | CG | LEU | 620 | 4.779 | 78.300 | 1.525 | 1.00 | 10.11 | C |
| ATOM | 996 | CD1 | LEU | 620 | 6.276 | 78.366 | 1.250 | 1.00 | 10.19 | C |
| ATOM | 997 | CD2 | LEU | 620 | 4.089 | 79.568 | 1.058 | 1.00 | 11.71 | C |
| ATOM | 998 | N | LEU | 621 | 5.397 | 74.880 | 3.380 | 1.00 | 12.67 | N |
| ATOM | 999 | CA | LEU | 621 | 5.226 | 74.528 | 4.785 | 1.00 | 15.42 | C |
| ATOM | 1000 | C | LEU | 621 | 5.536 | 75.770 | 5.639 | 1.00 | 15.14 | C |
| ATOM | 1OD1 | O | LEU | 621 | 6.697 | 76.117 | 5.882 | 1.00 | 17.05 | O |
| ATOM | 1OD2 | CB | LEU | 621 | 6.117 | 73.327 | 5.100 | 1.00 | 11.95 | C |
| ATOM | 1003 | CG | LEU | 621 | 5.761 | 72.185 | 4.115 | 1.00 | 11.75 | C |
| ATOM | 1004 | CD1 | LEU | 621 | 6.957 | 71.338 | 3.727 | 1.00 | 7.16 | C |
| ATOM | 1005 | CD2 | LEU | 621 | 4.678 | 71.351 | 4.702 | 1.00 | 7.13 | C |
| ATOM | 1006 | N | MET | 622 | 4.467 | 76.390 | 6.131 | 1.00 | 13.49 | N |
| ATOM | 1007 | CA | MET | 622 | 4.538 | 77.624 | 6.899 | 1.00 | 17.11 | C |
| ATOM | 1008 | C | MET | 622 | 4.273 | 77.505 | 8.396 | 1.00 | 17.35 | C |
| ATOM | 1009 | O | MET | 622 | 3.211 | 77.062 | 8.803 | 1.00 | 18.55 | O |
| ATOM | 1010 | CB | MET | 622 | 3.499 | 78.593 | 6.341 | 1.00 | 19.32 | C |
| ATOM | 1011 | CG | MET | 622 | 3.634 | 78.898 | 4.878 | 1.00 | 19.64 | C |
| ATOM | 1012 | SD | MET | 622 | 2.174 | 79.715 | 4.255 | 1.00 | 22.75 | S |
| ATOM | 1013 | CE | MET | 622 | 2.302 | 81.305 | 4.988 | 1.00 | 20.32 | C |
| ATOM | 1014 | N | ALA | 623 | 5.199 | 78.003 | 9.204 | 1.00 | 16.59 | N |
| ATOM | 1015 | CA | ALA | 623 | 5.057 | 78.000 | 10.654 | 1.00 | 14.97 | C |
| ATOM | 1016 | C | ALA | 623 | 5.115 | 79.425 | 11.201 | 1.00 | 18.32 | C |
| ATOM | 1017 | O | ALA | 623 | 4.952 | 79.648 | 12.405 | 1.00 | 21.62 | O |
| ATOM | 1018 | CB | ALA | 623 | 6.167 | 77.173 | 11.279 | 1.00 | 15.96 | C |

TABLE 8-continued

Atomic Coordinates for Residues of a Crystal of murine VWF-A1 (SEQ ID NO: 10).

| CRYST1 | 86.395 | | 86.395 | 68.125 | 90.00 | 90.00 | 120.00 | P 61 | 6 |
|---|---|---|---|---|---|---|---|---|---|
| ATOM | 1019 | N | SER 624 | 5.300 | 80.397 | 10.323 | 1.00 | 19.46 | N |
| ATOM | 1020 | CA | SER 624 | 5.433 | 81.772 | 10.771 | 1.00 | 21.55 | C |
| ATOM | 1021 | C | SER 624 | 4.869 | 82.812 | 9.799 | 1.00 | 22.83 | C |
| ATOM | 1022 | O | SER 624 | 4.108 | 82.483 | 8.855 | 1.00 | 18.76 | O |
| ATOM | 1023 | CB | SER 624 | 6.921 | 82.065 | 11.026 | 1.00 | 18.76 | C |
| ATOM | 1024 | OG | SER 624 | 7.721 | 81.753 | 9.896 | 1.00 | 22.42 | O |
| ATOM | 1025 | N | GLN 625 | 5.152 | 84.075 | 10.122 | 1.00 | 22.23 | N |
| ATOM | 1026 | CA | GLN 625 | 4.776 | 85.204 | 9.282 | 1.00 | 27.39 | C |
| ATOM | 1027 | C | GLN 625 | 5.948 | 86.161 | 9.222 | 1.00 | 27.09 | C |
| ATOM | 1028 | O | GLN 625 | 6.583 | 86.445 | 10.227 | 1.00 | 27.21 | O |
| ATOM | 1029 | CB | GLN 625 | 3.498 | 85.908 | 9.742 | 1.00 | 27.20 | C |
| ATOM | 1030 | CG | GLN 625 | 3.294 | 86.097 | 11.206 | 1.00 | 33.26 | C |
| ATOM | 1031 | CD | GLN 625 | 1.881 | 86.577 | 11.507 | 1.00 | 32.60 | C |
| ATOM | 1032 | OE1 | GLN 625 | 1.168 | 85.979 | 12.305 | 1.00 | 41.09 | O |
| ATOM | 1033 | NE2 | GLN 625 | 1.471 | 87.647 | 10.854 | 1.00 | 32.88 | N |
| ATOM | 1034 | N | GLU 626 | 6.326 | 86.519 | 8.004 | 1.00 | 28.00 | N |
| ATOM | 1035 | CA | GLU 626 | 7.434 | 87.437 | 7.771 | 1.00 | 28.38 | C |
| ATOM | 1036 | C | GLU 626 | 7.013 | 88.885 | 8.071 | 1.00 | 29.02 | C |
| ATOM | 1037 | O | GLU 626 | 5.813 | 89.221 | 8.041 | 1.00 | 25.62 | O |
| ATOM | 1038 | CB | GLU 626 | 7.852 | 87.355 | 6.304 | 1.00 | 25.11 | C |
| ATOM | 1039 | CG | GLU 626 | 6.807 | 87.963 | 5.378 | 1.00 | 23.18 | C |
| ATOM | 1040 | CD | GLU 626 | 7.062 | 87.693 | 3.915 | 1.00 | 24.81 | C |
| ATOM | 1041 | OE1 | GLU 626 | 8.171 | 87.208 | 3.580 | 1.00 | 20.13 | O |
| ATOM | 1042 | OE2 | GLU 626 | 6.129 | 87.946 | 3.116 | 1.00 | 17.26 | O |
| ATOM | 1043 | N | PRO 627 | 7.995 | 89.762 | 8.367 | 1.00 | 29.70 | N |
| ATOM | 1044 | CA | PRO 627 | 7.708 | 91.173 | 8.653 | 1.00 | 31.82 | C |
| ATOM | 1045 | C | PRO 627 | 7.050 | 91.835 | 7.441 | 1.00 | 33.52 | C |
| ATOM | 1046 | O | PRO 627 | 7.505 | 91.662 | 6.310 | 1.00 | 33.48 | O |
| ATOM | 1047 | CB | PRO 627 | 9.096 | 91.759 | 8.947 | 1.00 | 28.98 | C |
| ATOM | 1048 | CG | PRO 627 | 10.037 | 90.803 | 8.297 | 1.00 | 31.86 | C |
| ATOM | 1049 | CD | PRO 627 | 9.420 | 89.477 | 8.587 | 1.00 | 29.78 | C |
| ATOM | 1050 | N | GLN 628 | 6.000 | 92.609 | 7.702 | 1.00 | 36.73 | N |
| ATOM | 1051 | CA | GLN 628 | 5.208 | 93.302 | 6.679 | 1.00 | 38.04 | C |
| ATOM | 1052 | C | GLN 628 | 6.026 | 93.896 | 5.542 | 1.00 | 35.21 | C |
| ATOM | 1053 | O | GLN 628 | 5.629 | 93.832 | 4.375 | 1.00 | 34.60 | O |
| ATOM | 1054 | CB | GLN 628 | 4.353 | 94.406 | 7.332 | 1.00 | 44.33 | C |
| ATOM | 1055 | CG | GLN 628 | 2.922 | 94.535 | 6.808 | 1.00 | 52.77 | C |
| ATOM | 1056 | CD | GLN 628 | 1.885 | 94.095 | 7.834 | 1.00 | 60.03 | C |
| ATOM | 1057 | OE1 | GLN 628 | 1.070 | 94.899 | 8.302 | 1.00 | 61.34 | O |
| ATOM | 1058 | NE2 | GLN 628 | 1.923 | 92.814 | 8.206 | 1.00 | 63.65 | N |
| ATOM | 1059 | N | ARG 629 | 7.180 | 94.448 | 5.884 | 1.00 | 32.79 | N |
| ATOM | 1060 | CA | ARG 629 | 8.051 | 95.067 | 4.898 | 1.00 | 34.31 | C |
| ATOM | 1061 | C | ARG 629 | 8.588 | 94.118 | 3.822 | 1.00 | 30.81 | C |
| ATOM | 1062 | O | ARG 629 | 8.919 | 94.556 | 2.723 | 1.00 | 36.74 | O |
| ATOM | 1063 | CB | ARG 629 | 9.209 | 95.784 | 5.592 | 1.00 | 38.79 | C |
| ATOM | 1064 | CG | ARG 629 | 10.042 | 94.861 | 6.431 | 1.00 | 47.03 | C |
| ATOM | 1065 | CD | ARG 629 | 11.399 | 95.422 | 6.687 | 1.00 | 49.94 | C |
| ATOM | 1066 | NE | ARG 629 | 12.324 | 94.336 | 6.978 | 1.00 | 58.97 | N |
| ATOM | 1067 | CZ | ARG 629 | 13.603 | 94.339 | 6.633 | 1.00 | 65.16 | C |
| ATOM | 1068 | NH1 | ARG 629 | 14.109 | 95.379 | 5.985 | 1.00 | 70.46 | N |
| ATOM | 1069 | NH2 | ARG 629 | 14.378 | 93.314 | 6.952 | 1.00 | 68.49 | N |
| ATOM | 1070 | N | MET 630 | 8.655 | 92.828 | 4.110 | 1.00 | 25.21 | N |
| ATOM | 1071 | CA | MET 630 | 9.171 | 91.879 | 3.134 | 1.00 | 23.72 | C |
| ATOM | 1072 | C | MET 630 | 8.061 | 91.297 | 2.268 | 1.00 | 24.23 | C |
| ATOM | 1073 | O | MET 630 | 8.346 | 90.631 | 1.270 | 1.00 | 25.88 | O |
| ATOM | 1074 | CB | MET 630 | 9.905 | 90.735 | 3.828 | 1.00 | 25.55 | C |
| ATOM | 1075 | CG | MET 630 | 11.078 | 91.153 | 4.687 | 1.00 | 28.67 | C |
| ATOM | 1076 | SD | MET 630 | 11.844 | 89.733 | 5.470 | 1.00 | 30.08 | S |
| ATOM | 1077 | CE | MET 630 | 13.015 | 89.228 | 4.233 | 1.00 | 33.64 | C |
| ATOM | 1078 | N | SER 631 | 6.811 | 91.617 | 2.606 | 1.00 | 23.98 | N |
| ATOM | 1079 | CA | SER 631 | 5.634 | 91.098 | 1.906 | 1.00 | 24.27 | C |
| ATOM | 1080 | C | SER 631 | 5.076 | 91.919 | 0.751 | 1.00 | 26.26 | C |
| ATOM | 1081 | O | SER 631 | 4.010 | 91.584 | 0.210 | 1.00 | 21.34 | O |
| ATOM | 1082 | CB | SER 631 | 4.504 | 90.879 | 2.911 | 1.00 | 22.54 | C |
| ATOM | 1083 | OG | SER 631 | 4.923 | 90.050 | 3.983 | 1.00 | 24.17 | O |
| ATOM | 1084 | N | ARG 632 | 5.797 | 92.967 | 0.357 | 1.00 | 29.47 | N |
| ATOM | 1085 | CA | ARG 632 | 5.348 | 93.865 | −0.711 | 1.00 | 27.92 | C |
| ATOM | 1086 | C | ARG 632 | 4.990 | 93.255 | −2.075 | 1.00 | 24.00 | C |
| ATOM | 1087 | O | ARG 632 | 4.013 | 93.653 | −2.698 | 1.00 | 19.20 | O |
| ATOM | 1088 | CB | ARG 632 | 6.350 | 95.003 | −0.869 | 1.00 | 32.62 | C |
| ATOM | 1089 | CG | ARG 632 | 6.093 | 96.167 | 0.064 | 1.00 | 38.66 | C |
| ATOM | 1090 | CD | ARG 632 | 7.198 | 97.197 | −0.041 | 1.00 | 48.62 | C |
| ATOM | 1091 | NE | ARG 632 | 8.267 | 96.958 | 0.932 | 1.00 | 58.66 | N |
| ATOM | 1092 | CZ | ARG 632 | 9.535 | 97.343 | 0.786 | 1.00 | 61.73 | C |
| ATOM | 1093 | NH1 | ARG 632 | 9.927 | 97.984 | −0.317 | 1.00 | 62.36 | N |

TABLE 8-continued

Atomic Coordinates for Residues of a Crystal of murine VWF-A1 (SEQ ID NO: 10).

| CRYST1 | 86.395 | | 86.395 | 68.125 | 90.00 | 90.00 | 120.00 | P 61 | 6 |
|---|---|---|---|---|---|---|---|---|---|
| ATOM | 1094 | NH2 | ARG 632 | 10.396 | 97.139 | 1.779 | 1.00 | 60.51 | N |
| ATOM | 1095 | N | ASN 633 | 5.754 | 92.267 | −2.520 | 1.00 | 22.34 | N |
| ATOM | 1096 | CA | ASN 633 | 5.501 | 91.630 | −3.812 | 1.00 | 23.39 | C |
| ATOM | 1097 | C | ASN 633 | 4.823 | 90.274 | −3.673 | 1.00 | 22.81 | C |
| ATOM | 1098 | O | ASN 633 | 4.613 | 89.592 | −4.665 | 1.00 | 20.30 | O |
| ATOM | 1099 | CB | ASN 633 | 6.815 | 91.430 | −4.583 | 1.00 | 19.08 | C |
| ATOM | 1100 | CG | ASN 633 | 7.352 | 92.708 | −5.169 | 1.00 | 17.97 | C |
| ATOM | 1101 | OD1 | ASN 633 | 6.663 | 93.724 | −5.197 | 1.00 | 12.49 | O |
| ATOM | 1102 | NO2 | ASN 633 | 8.602 | 92.667 | −5.644 | 1.00 | 17.03 | N |
| ATOM | 1103 | N | PHE 634 | 4.494 | 89.889 | −2.445 | 1.00 | 22.28 | N |
| ATOM | 1104 | CA | PHE 634 | 3.878 | 88.603 | −2.182 | 1.00 | 19.74 | C |
| ATOM | 1105 | C | PHE 634 | 2.821 | 88.172 | −3.190 | 1.00 | 18.80 | C |
| ATOM | 1106 | O | PHE 634 | 2.994 | 87.142 | −3.849 | 1.00 | 19.49 | O |
| ATOM | 1107 | CB | PHE 634 | 3.303 | 88.536 | −0.756 | 1.00 | 14.84 | C |
| ATOM | 1108 | CG | PHE 634 | 2.736 | 87.184 | −0.414 | 1.00 | 11.94 | C |
| ATOM | 1109 | CD1 | PHE 634 | 3.583 | 86.149 | −0.048 | 1.00 | 4.10 | C |
| ATOM | 1110 | CD2 | PHE 634 | 1.373 | 86.920 | −0.576 | 1.00 | 11.23 | C |
| ATOM | 1111 | CE1 | PHE 634 | 3.095 | 84.880 | 0.136 | 1.00 | 5.83 | C |
| ATOM | 1112 | CE2 | PHE 634 | 0.858 | 85.645 | −0.393 | 1.00 | 10.88 | C |
| ATOM | 1113 | CZ | PHE 634 | 1.719 | 84.617 | −0.040 | 1.00 | 9.89 | C |
| ATOM | 1114 | N | VAL 635 | 1.751 | 88.942 | −3.365 | 1.00 | 18.69 | N |
| ATOM | 1115 | CA | VAL 635 | 0.707 | 88.514 | −4.314 | 1.00 | 21.28 | C |
| ATOM | 1116 | C | VAL 635 | 1.214 | 88.374 | −5.751 | 1.00 | 21.28 | C |
| ATOM | 1117 | O | VAL 635 | 0.803 | 87.478 | −6.480 | 1.00 | 22.82 | O |
| ATOM | 1118 | CB | VAL 635 | −0.500 | 89.440 | −4.280 | 1.00 | 20.51 | C |
| ATOM | 1119 | CG1 | VAL 635 | −1.510 | 89.022 | −5.316 | 1.00 | 25.23 | C |
| ATOM | 1120 | CG2 | VAL 635 | −1.129 | 89.383 | −2.922 | 1.00 | 23.14 | C |
| ATOM | 1121 | N | ARG 636 | 2.160 | 89.227 | −6.111 | 1.00 | 18.25 | N |
| ATOM | 1122 | CA | ARG 636 | 2.778 | 89.239 | −7.420 | 1.00 | 13.92 | C |
| ATOM | 1123 | C | ARG 636 | 3.522 | 87.936 | −7.677 | 1.00 | 15.53 | C |
| ATOM | 1124 | O | ARG 636 | 3.419 | 87.366 | −8.760 | 1.00 | 19.16 | O |
| ATOM | 1125 | CB | ARG 636 | 3.719 | 90.446 | −7.480 | 1.00 | 13.52 | C |
| ATOM | 1126 | CG | ARG 636 | 2.923 | 91.760 | −7.492 | 1.00 | 21.06 | C |
| ATOM | 1127 | CD | ARG 636 | 3.742 | 92.986 | −7.115 | 1.00 | 31.89 | C |
| ATOM | 1128 | NE | ARG 636 | 3.059 | 94.231 | −7.497 | 1.00 | 34.04 | N |
| ATOM | 1129 | CZ | ARG 636 | 2.973 | 95.330 | −6.747 | 1.00 | 33.28 | C |
| ATOM | 1130 | NH1 | ARG 636 | 3.523 | 95.373 | −5.545 | 1.00 | 32.30 | N |
| ATOM | 1131 | NH2 | ARG 636 | 2.396 | 96.421 | −7.233 | 1.00 | 35.94 | N |
| ATOM | 1132 | N | TYR 637 | 4.249 | 87.439 | −6.683 | 1.00 | 12.24 | N |
| ATOM | 1133 | CA | TYR 637 | 4.969 | 86.187 | −6.837 | 1.00 | 13.29 | C |
| ATOM | 1134 | C | TYR 637 | 3.984 | 85.046 | −6.970 | 1.00 | 15.41 | C |
| ATOM | 1135 | O | TYR 637 | 4.176 | 84.141 | −7.789 | 1.00 | 17.67 | O |
| ATOM | 1136 | CB | TYR 637 | 5.912 | 85.942 | −5.654 | 1.00 | 16.02 | C |
| ATOM | 1137 | CG | TYR 637 | 7.003 | 86.987 | −5.572 | 1.00 | 17.66 | C |
| ATOM | 1138 | CD1 | TYR 637 | 7.556 | 87.512 | −6.726 | 1.00 | 23.47 | C |
| ATOM | 1139 | CD2 | TYR 637 | 7.438 | 87.486 | −4.356 | 1.00 | 23.35 | C |
| ATOM | 1140 | CE1 | TYR 637 | 8.507 | 88.512 | −6.684 | 1.00 | 24.21 | C |
| ATOM | 1141 | CE2 | TYR 637 | 8.398 | 88.493 | −4.296 | 1.00 | 25.27 | C |
| ATOM | 1142 | CZ | TYR 637 | 8.929 | 89.000 | −5.471 | 1.00 | 27.11 | C |
| ATOM | 1143 | OH | TYR 637 | 9.897 | 89.989 | −5.446 | 1.00 | 27.67 | O |
| ATOM | 1144 | N | VAL 638 | 2.892 | 85.114 | −6.212 | 1.00 | 17.90 | N |
| ATOM | 1145 | CA | VAL 638 | 1.866 | 84.073 | −6.264 | 1.00 | 15.71 | C |
| ATOM | 1146 | C | VAL 638 | 1.110 | 84.107 | −7.591 | 1.00 | 16.42 | C |
| ATOM | 1147 | O | VAL 638 | 0.730 | 83.057 | −8.121 | 1.00 | 13.74 | O |
| ATOM | 1148 | CB | VAL 638 | 0.879 | 84.189 | −5.070 | 1.00 | 14.51 | C |
| ATOM | 1149 | CG1 | VAL 638 | −0.224 | 83.196 | −5.201 | 1.00 | 10.64 | C |
| ATOM | 1150 | CG2 | VAL 638 | 1.623 | 83.907 | −3.762 | 1.00 | 15.68 | C |
| ATOM | 1151 | N | GLN 639 | 0.858 | 85.306 | −8.122 | 1.00 | 17.70 | N |
| ATOM | 1152 | CA | GLN 639 | 0.173 | 85.418 | −9.401 | 1.00 | 19.16 | C |
| ATOM | 1153 | C | GLN 639 | 1.132 | 84.973 | −10.494 | 1.00 | 20.06 | C |
| ATOM | 1154 | O | GLN 639 | 0.705 | 84.381 | −11.500 | 1.00 | 21.31 | O |
| ATOM | 1155 | CB | GLN 639 | −0.280 | 86.842 | −9.661 | 1.00 | 24.29 | C |
| ATOM | 1156 | CG | GLN 639 | −1.377 | 87.339 | −8.758 | 1.00 | 33.20 | C |
| ATOM | 1157 | CD | GLN 639 | −1.509 | 88.855 | −8.824 | 1.00 | 42.75 | C |
| ATOM | 1158 | OE1 | GLN 639 | −0.534 | 89.573 | −9.095 | 1.00 | 47.34 | O |
| ATOM | 1159 | NE2 | GLN 639 | −2.709 | 89.353 | −8.572 | 1.00 | 47.82 | N |
| ATOM | 1160 | N | GLY 640 | 2.428 | 85.212 | −10.272 | 1.00 | 19.08 | N |
| ATOM | 1161 | CA | GLY 640 | 3.465 | 84.789 | −11.212 | 1.00 | 16.51 | C |
| ATOM | 1162 | C | GLY 640 | 3.515 | 83.268 | −11.342 | 1.00 | 16.94 | C |
| ATOM | 1163 | O | GLY 640 | 3.492 | 82.740 | −12.454 | 1.00 | 19.48 | O |
| ATOM | 1164 | N | LEU 641 | 3.553 | 82.551 | −10.221 | 1.00 | 16.74 | N |
| ATOM | 1165 | CA | LEU 641 | 3.579 | 81.088 | −10.252 | 1.00 | 13.10 | C |
| ATOM | 1166 | C | LEU 641 | 2.269 | 80.555 | −10.792 | 1.00 | 13.33 | C |
| ATOM | 1167 | O | LEU 641 | 2.206 | 79.465 | −11.355 | 1.00 | 18.15 | O |
| ATOM | 1168 | CB | LEU 641 | 3.802 | 80.530 | −8.852 | 1.00 | 14.38 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 1169 | CG | LEU | 641 | 5.198 | 80.681 | −8.238 | 1.00 | 16.65 | C |
| ATOM | 1170 | CD1 | LEU | 641 | 5.139 | 80.462 | −6.733 | 1.00 | 18.86 | C |
| ATOM | 1171 | CD2 | LEU | 641 | 6.206 | 79.737 | −8.886 | 1.00 | 6.08 | C |
| ATOM | 1172 | N | LYS | 642 | 1.205 | 81.311 | −10.605 | 1.00 | 14.11 | N |
| ATOM | 1173 | CA | LYS | 642 | −0.101 | 80.898 | −11.096 | 1.00 | 16.06 | C |
| ATOM | 1174 | C | LYS | 642 | −0.150 | 80.870 | −12.623 | 1.00 | 16.97 | C |
| ATOM | 1175 | O | LYS | 642 | −0.809 | 80.019 | −13.210 | 1.00 | 19.62 | O |
| ATOM | 1176 | CB | LYS | 642 | −1.169 | 81.847 | −10.555 | 1.00 | 16.72 | C |
| ATOM | 1177 | CG | LYS | 642 | −2.558 | 81.585 | −11.078 | 1.00 | 18.86 | C |
| ATOM | 1178 | CD | LYS | 642 | −3.085 | 82.761 | −11.881 | 1.00 | 14.53 | C |
| ATOM | 1179 | CE | LYS | 642 | −4.522 | 82.498 | −12.267 | 1.00 | 25.13 | C |
| ATOM | 1180 | NZ | LYS | 642 | −5.053 | 83.581 | −13.128 | 1.00 | 33.85 | N |
| ATOM | 1181 | N | LYS | 643 | 0.517 | 81.829 | −13.256 | 1.00 | 17.23 | N |
| ATOM | 1182 | CA | LYS | 643 | 0.554 | 81.933 | −14.714 | 1.00 | 15.33 | C |
| ATOM | 1183 | C | LYS | 643 | 1.409 | 80.845 | −15.322 | 1.00 | 14.03 | C |
| ATOM | 1184 | O | LYS | 643 | 1.183 | 80.439 | −16.464 | 1.00 | 13.60 | O |
| ATOM | 1185 | CB | LYS | 643 | 1.127 | 83.281 | −15.127 | 1.00 | 16.90 | C |
| ATOM | 1186 | CG | LYS | 643 | 0.301 | 84.453 | −14.692 | 1.00 | 23.60 | C |
| ATOM | 1187 | CD | LYS | 643 | 0.990 | 85.751 | −15.080 | 1.00 | 29.59 | C |
| ATOM | 1188 | CE | LYS | 643 | 0.321 | 86.922 | −14.390 | 1.00 | 34.30 | C |
| ATOM | 1189 | NZ | LYS | 643 | 1.216 | 88.106 | −14.326 | 1.00 | 35.59 | N |
| ATOM | 1190 | N | LYS | 644 | 2.442 | 80.431 | −14.598 | 1.00 | 15.71 | N |
| ATOM | 1191 | CA | LYS | 644 | 3.321 | 79.373 | −15.059 | 1.00 | 15.56 | C |
| ATOM | 1192 | C | LYS | 644 | 2.720 | 78.041 | −14.644 | 1.00 | 13.62 | C |
| ATOM | 1193 | O | LYS | 644 | 3.351 | 77.009 | −14.825 | 1.00 | 16.26 | O |
| ATOM | 1194 | CB | LYS | 644 | 4.737 | 79.517 | −14.466 | 1.00 | 19.22 | C |
| ATOM | 1195 | CG | LYS | 644 | 5.710 | 80.398 | −15.264 | 1.00 | 22.27 | C |
| ATOM | 1196 | CD | LYS | 644 | 7.123 | 80.272 | −14.690 | 1.00 | 24.71 | C |
| ATOM | 1197 | CE | LYS | 644 | 8.123 | 81.299 | −15.260 | 1.00 | 31.85 | C |
| ATOM | 1198 | NZ | LYS | 644 | 9.118 | 81.871 | −14.243 | 1.00 | 23.70 | N |
| ATOM | 1199 | N | LYS | 645 | 1.502 | 78.076 | −14.098 | 1.00 | 10.95 | N |
| ATOM | 1200 | CA | LYS | 645 | 0.761 | 76.876 | −13.644 | 1.00 | 14.53 | C |
| ATOM | 1201 | C | LYS | 645 | 1.425 | 76.068 | −12.527 | 1.00 | 15.63 | C |
| ATOM | 1202 | O | LYS | 645 | 1.324 | 74.833 | −12.481 | 1.00 | 10.70 | O |
| ATOM | 1203 | CB | LYS | 645 | 0.397 | 75.957 | −14.803 | 1.00 | 14.90 | C |
| ATOM | 1204 | CG | LYS | 645 | −1.087 | 75.949 | −15.174 | 1.00 | 16.56 | C |
| ATOM | 1205 | CD | LYS | 645 | −1.866 | 75.078 | −14.228 | 1.00 | 19.52 | C |
| ATOM | 1206 | CE | LYS | 645 | −3.242 | 75.666 | −13.949 | 1.00 | 28.98 | C |
| ATOM | 1207 | NZ | LYS | 645 | −4.386 | 74.911 | −14.522 | 1.00 | 29.12 | N |
| ATOM | 1208 | N | VAL | 646 | 2.095 | 76.784 | −11.630 | 1.00 | 13.98 | N |
| ATOM | 1209 | CA | VAL | 646 | 2.745 | 76.182 | −10.481 | 1.00 | 17.17 | C |
| ATOM | 1210 | C | VAL | 646 | 1.723 | 76.303 | −9.379 | 1.00 | 17.08 | C |
| ATOM | 1211 | O | VAL | 646 | 1.333 | 77.413 | −9.028 | 1.00 | 15.83 | O |
| ATOM | 1212 | CB | VAL | 646 | 4.004 | 76.952 | −10.065 | 1.00 | 15.22 | C |
| ATOM | 1213 | CG1 | VAL | 646 | 4.628 | 76.308 | −8.805 | 1.00 | 14.08 | C |
| ATOM | 1214 | CG2 | VAL | 646 | 4.980 | 76.955 | −11.204 | 1.00 | 10.59 | C |
| ATOM | 1215 | N | ILE | 647 | 1.247 | 75.160 | −8.895 | 1.00 | 17.86 | N |
| ATOM | 1216 | CA | ILE | 647 | 0.235 | 75.107 | −7.852 | 1.00 | 15.74 | C |
| ATOM | 1217 | C | ILE | 647 | 0.858 | 75.303 | −6.464 | 1.00 | 15.68 | C |
| ATOM | 1218 | O | ILE | 647 | 1.785 | 74.592 | −6.086 | 1.00 | 17.61 | O |
| ATOM | 1219 | CB | ILE | 647 | −0.514 | 73.765 | −7.947 | 1.00 | 14.07 | C |
| ATOM | 1220 | CG1 | ILE | 647 | −1.094 | 73.600 | −9.364 | 1.00 | 17.76 | C |
| ATOM | 1221 | CG2 | ILE | 647 | −1.620 | 73.665 | −6.896 | 1.00 | 12.37 | C |
| ATOM | 1222 | CD1 | ILE | 647 | −1.913 | 74.795 | −9.865 | 1.00 | 11.46 | C |
| ATOM | 1223 | N | VAL | 648 | 0.400 | 76.298 | −5.722 | 1.00 | 16.62 | N |
| ATOM | 1224 | CA | VAL | 648 | 0.969 | 76.519 | −4.387 | 1.00 | 16.18 | C |
| ATOM | 1225 | C | VAL | 648 | 0.004 | 75.932 | −3.365 | 1.00 | 15.96 | C |
| ATOM | 1226 | O | VAL | 648 | −1.158 | 76.338 | −3.284 | 1.00 | 14.76 | O |
| ATOM | 1227 | CB | VAL | 648 | 1.258 | 78.035 | −4.079 | 1.00 | 12.13 | C |
| ATOM | 1228 | CG1 | VAL | 648 | 2.023 | 78.179 | −2.775 | 1.00 | 9.31 | C |
| ATOM | 1229 | CG2 | VAL | 648 | 2.078 | 78.678 | −5.223 | 1.00 | 11.58 | C |
| ATOM | 1230 | N | ILE | 649 | 0.456 | 74.906 | −2.659 | 1.00 | 15.66 | N |
| ATOM | 1231 | CA | ILE | 649 | −0.369 | 74.276 | −1.644 | 1.00 | 16.78 | C |
| ATOM | 1232 | C | ILE | 649 | 0.222 | 74.671 | −0.306 | 1.00 | 17.79 | C |
| ATOM | 1233 | O | ILE | 649 | 1.223 | 74.095 | 0.124 | 1.00 | 18.08 | O |
| ATOM | 1234 | CB | ILE | 649 | −0.376 | 72.747 | −1.769 | 1.00 | 14.88 | C |
| ATOM | 1235 | CG1 | ILE | 649 | −0.873 | 72.352 | −3.159 | 1.00 | 16.15 | C |
| ATOM | 1236 | CG2 | ILE | 649 | −1.297 | 72.142 | −0.708 | 1.00 | 16.62 | C |
| ATOM | 1237 | CD1 | ILE | 649 | −0.925 | 70.873 | −3.418 | 1.00 | 17.42 | C |
| ATOM | 1238 | N | PRO | 650 | −0.351 | 75.709 | 0.334 | 1.00 | 16.08 | N |
| ATOM | 1239 | CA | PRO | 650 | 0.076 | 76.238 | 1.627 | 1.00 | 12.67 | C |
| ATOM | 1240 | C | PRO | 650 | −0.300 | 75.297 | 2.775 | 1.00 | 15.98 | C |
| ATOM | 1241 | O | PRO | 650 | −1.478 | 74.921 | 2.940 | 1.00 | 13.96 | O |
| ATOM | 1242 | CB | PRO | 650 | −0.737 | 77.512 | 1.764 | 1.00 | 9.54 | C |
| ATOM | 1243 | CG | PRO | 650 | −1.475 | 77.687 | 0.465 | 1.00 | 13.54 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 1244 | CD | PRO | 650 | −1.626 | 76.326 | −0.068 | 1.00 | 16.46 | C |
| ATOM | 1245 | N | VAL | 651 | 0.693 | 74.893 | 3.553 | 1.00 | 14.32 | N |
| ATOM | 1246 | CA | VAL | 651 | 0.422 | 74.040 | 4.697 | 1.00 | 14.36 | C |
| ATOM | 1247 | C | VAL | 651 | 0.728 | 74.922 | 5.911 | 1.00 | 12.69 | C |
| ATOM | 1248 | O | VAL | 651 | 1.871 | 75.307 | 6.129 | 1.00 | 15.37 | O |
| ATOM | 1249 | CB | VAL | 651 | 1.293 | 72.782 | 4.691 | 1.00 | 14.81 | C |
| ATOM | 1250 | CG1 | VAL | 651 | 0.942 | 71.918 | 5.884 | 1.00 | 15.50 | C |
| ATOM | 1251 | CG2 | VAL | 651 | 1.075 | 72.004 | 3.392 | 1.00 | 10.07 | C |
| ATOM | 1252 | N | GLY | 652 | −0.307 | 75.355 | 6.617 | 1.00 | 9.84 | N |
| ATOM | 1253 | CA | GLY | 652 | −0.102 | 76.201 | 7.776 | 1.00 | 12.11 | C |
| ATOM | 1254 | C | GLY | 652 | 0.074 | 75.324 | 8.991 | 1.00 | 11.33 | C |
| ATOM | 1255 | O | GLY | 652 | −0.778 | 74.503 | 9.244 | 1.00 | 17.62 | O |
| ATOM | 1256 | N | ILE | 653 | 1.150 | 75.492 | 9.742 | 1.00 | 13.97 | N |
| ATOM | 1257 | CA | ILE | 653 | 1.397 | 74.679 | 10.931 | 1.00 | 18.24 | C |
| ATOM | 1258 | C | ILE | 653 | 1.481 | 75.547 | 12.197 | 1.00 | 21.88 | C |
| ATOM | 1259 | O | ILE | 653 | 2.468 | 76.273 | 12.417 | 1.00 | 19.90 | O |
| ATOM | 1260 | CB | ILE | 653 | 2.728 | 73.937 | 10.804 | 1.00 | 22.12 | C |
| ATOM | 1261 | CG1 | ILE | 653 | 2.805 | 73.167 | 9.478 | 1.00 | 18.02 | C |
| ATOM | 1262 | CG2 | ILE | 653 | 2.957 | 73.057 | 12.034 | 1.00 | 18.87 | C |
| ATOM | 1263 | CD1 | ILE | 653 | 4.217 | 72.868 | 9.064 | 1.00 | 14.43 | C |
| ATOM | 1264 | N | GLY | 654 | 0.445 | 75.491 | 13.023 | 1.00 | 17.34 | N |
| ATOM | 1265 | CA | GLY | 654 | 0.480 | 76.279 | 14.245 | 1.00 | 18.39 | C |
| ATOM | 1266 | C | GLY | 654 | −0.111 | 77.682 | 14.187 | 1.00 | 20.92 | C |
| ATOM | 1267 | O | GLY | 654 | −0.373 | 78.214 | 13.102 | 1.00 | 24.39 | O |
| ATOM | 1268 | N | PRO | 655 | −0.264 | 78.337 | 15.363 | 1.00 | 20.00 | N |
| ATOM | 1269 | CA | PRO | 655 | −0.806 | 79.684 | 15.601 | 1.00 | 15.28 | C |
| ATOM | 1270 | C | PRO | 655 | −0.034 | 80.794 | 14.911 | 1.00 | 16.41 | C |
| ATOM | 1271 | O | PRO | 655 | −0.588 | 81.825 | 14.552 | 1.00 | 18.28 | O |
| ATOM | 1272 | CB | PRO | 655 | −0.642 | 79.852 | 17.116 | 1.00 | 12.24 | C |
| ATOM | 1273 | CG | PRO | 655 | −0.672 | 78.460 | 17.630 | 1.00 | 13.05 | C |
| ATOM | 1274 | CD | PRO | 655 | 0.153 | 77.719 | 16.635 | 1.00 | 14.07 | C |
| ATOM | 1275 | N | HIS | 656 | 1.272 | 80.622 | 14.794 | 1.00 | 16.41 | N |
| ATOM | 1276 | CA | HIS | 656 | 2.082 | 81.667 | 14.194 | 1.00 | 18.52 | C |
| ATOM | 1277 | C | HIS | 656 | 2.109 | 81.703 | 12.664 | 1.00 | 17.35 | C |
| ATOM | 1278 | O | HIS | 656 | 2.603 | 82.672 | 12.084 | 1.00 | 17.65 | O |
| ATOM | 1279 | CB | HIS | 656 | 3.492 | 81.676 | 14.815 | 1.00 | 16.60 | C |
| ATOM | 1280 | CG | HIS | 656 | 3.498 | 82.026 | 16.283 | 1.00 | 18.39 | C |
| ATOM | 1281 | ND1 | HIS | 656 | 3.392 | 81.077 | 17.277 | 1.00 | 18.56 | N |
| ATOM | 1282 | CD2 | HIS | 656 | 3.554 | 83.224 | 16.915 | 1.00 | 16.46 | C |
| ATOM | 1283 | CE1 | HIS | 656 | 3.376 | 81.672 | 18.451 | 1.00 | 13.19 | C |
| ATOM | 1284 | NE2 | HIS | 656 | 3.474 | 82.972 | 18.258 | 1.00 | 16.12 | N |
| ATOM | 1285 | N | ALA | 657 | 1.504 | 80.703 | 12.027 | 1.00 | 17.30 | N |
| ATOM | 1286 | CA | ALA | 657 | 1.459 | 80.616 | 10.564 | 1.00 | 18.06 | C |
| ATOM | 1287 | C | ALA | 657 | 0.729 | 81.810 | 9.961 | 1.00 | 16.82 | C |
| ATOM | 1288 | O | ALA | 657 | −0.300 | 82.248 | 10.464 | 1.00 | 19.76 | O |
| ATOM | 1289 | CB | ALA | 657 | 0.808 | 79.297 | 10.121 | 1.00 | 13.90 | C |
| ATOM | 1290 | N | ASN | 658 | 1.277 | 82.340 | 8.877 | 1.00 | 19.53 | N |
| ATOM | 1291 | CA | ASN | 658 | 0.699 | 83.502 | 8.226 | 1.00 | 16.37 | C |
| ATOM | 1292 | C | ASN | 658 | −0.569 | 83.144 | 7.494 | 1.00 | 18.85 | C |
| ATOM | 1293 | O | ASN | 658 | −0.575 | 82.964 | 6.284 | 1.00 | 20.50 | O |
| ATOM | 1294 | CB | ASN | 658 | 1.704 | 84.142 | 7.276 | 1.00 | 11.24 | C |
| ATOM | 1295 | CG | ASN | 658 | 1.282 | 85.534 | 6.844 | 1.00 | 11.66 | C |
| ATOM | 1296 | OD1 | ASN | 658 | 0.098 | 85.829 | 6.766 | 1.00 | 14.75 | O |
| ATOM | 1297 | NO2 | ASN | 658 | 2.251 | 86.396 | 6.563 | 1.00 | 16.32 | N |
| ATOM | 1298 | N | LEU | 659 | −1.648 | 83.035 | 8.251 | 1.00 | 20.82 | N |
| ATOM | 1299 | CA | LEU | 659 | −2.943 | 82.704 | 7.700 | 1.00 | 19.30 | C |
| ATOM | 1300 | C | LEU | 659 | −3.460 | 83.699 | 6.664 | 1.00 | 20.85 | C |
| ATOM | 1301 | O | LEU | 659 | −4.230 | 83.317 | 5.782 | 1.00 | 22.69 | O |
| ATOM | 1302 | CB | LEU | 659 | −3.950 | 82.569 | 8.824 | 1.00 | 17.74 | C |
| ATOM | 1303 | CG | LEU | 659 | −4.579 | 81.198 | 8.897 | 1.00 | 21.02 | C |
| ATOM | 1304 | CD1 | LEU | 659 | −3.505 | 80.188 | 9.248 | 1.00 | 24.59 | C |
| ATOM | 1305 | CD2 | LEU | 659 | −5.665 | 81.212 | 9.935 | 1.00 | 27.06 | C |
| ATOM | 1306 | N | LYS | 660 | −3.078 | 84.968 | 6.782 | 1.00 | 22.50 | N |
| ATOM | 1307 | CA | LYS | 660 | −3.520 | 85.982 | 5.822 | 1.00 | 23.11 | C |
| ATOM | 1308 | C | LYS | 660 | −2.945 | 85.639 | 4.452 | 1.00 | 24.26 | C |
| ATOM | 1309 | O | LYS | 660 | −3.663 | 85.697 | 3.448 | 1.00 | 27.91 | O |
| ATOM | 1310 | CB | LYS | 660 | −3.068 | 87.361 | 6.251 | 1.00 | 21.43 | C |
| ATOM | 1311 | N | GLN | 661 | −1.667 | 85.240 | 4.420 | 1.00 | 21.76 | N |
| ATOM | 1312 | CA | GLN | 661 | −0.991 | 84.844 | 3.183 | 1.00 | 17.85 | C |
| ATOM | 1313 | C | GLN | 661 | −1.570 | 83.531 | 2.688 | 1.00 | 18.55 | C |
| ATOM | 1314 | O | GLN | 661 | −1.828 | 83.372 | 1.499 | 1.00 | 23.06 | O |
| ATOM | 1315 | CB | GLN | 661 | 0.525 | 84.730 | 3.377 | 1.00 | 12.86 | C |
| ATOM | 1316 | CG | GLN | 661 | 1.237 | 86.102 | 3.366 | 1.00 | 10.63 | C |
| ATOM | 1317 | CD | GLN | 661 | 2.755 | 86.013 | 3.544 | 1.00 | 14.73 | C |
| ATOM | 1318 | OE1 | GLN | 661 | 3.287 | 84.965 | 3.905 | 1.00 | 17.21 | O |

TABLE 8-continued

Atomic Coordinates for Residues of a Crystal of murine VWF-A1 (SEQ ID NO: 10).

| CRYST1 | | 86.395 | | 86.395 | | 68.125 | 90.00 | 90.00 | 120.00 | P 61 | 6 |
|---|---|---|---|---|---|---|---|---|---|---|---|
| ATOM | 1319 | NE2 | GLN | 661 | 3.451 | 87.118 | 3.305 | 1.00 | 15.89 | N | |
| ATOM | 1320 | N | ILE | 662 | −1.850 | 82.613 | 3.607 | 1.00 | 17.78 | N | |
| ATOM | 1321 | CA | ILE | 662 | −2.438 | 81.336 | 3.237 | 1.00 | 15.00 | C | |
| ATOM | 1322 | C | ILE | 662 | −3.775 | 81.610 | 2.537 | 1.00 | 19.04 | C | |
| ATOM | 1323 | O | ILE | 662 | −4.050 | 81.031 | 1.487 | 1.00 | 21.90 | O | |
| ATOM | 1324 | CB | ILE | 662 | −2.580 | 80.411 | 4.489 | 1.00 | 11.85 | C | |
| ATOM | 1325 | CG1 | ILE | 662 | −1.196 | 80.040 | 4.995 | 1.00 | 11.79 | C | |
| ATOM | 1326 | CG2 | ILE | 662 | −3.337 | 79.126 | 4.196 | 1.00 | 7.88 | C | |
| ATOM | 1327 | CD1 | ILE | 662 | −1.191 | 79.084 | 6.171 | 1.00 | 13.32 | C | |
| ATOM | 1328 | N | ARG | 663 | −4.558 | 82.560 | 3.047 | 1.00 | 20.47 | N | |
| ATOM | 1329 | CA | ARG | 663 | −5.850 | 82.874 | 2.436 | 1.00 | 20.44 | C | |
| ATOM | 1330 | C | ARG | 663 | −5.704 | 83.569 | 1.078 | 1.00 | 19.11 | C | |
| ATOM | 1331 | O | ARG | 663 | −6.548 | 83.416 | 0.195 | 1.00 | 19.37 | O | |
| ATOM | 1332 | CB | ARG | 663 | −6.733 | 83.701 | 3.390 | 1.00 | 23.96 | C | |
| ATOM | 1333 | CG | ARG | 663 | −7.123 | 82.987 | 4.686 | 1.00 | 32.86 | C | |
| ATOM | 1334 | CD | ARG | 663 | −7.800 | 81.612 | 4.456 | 1.00 | 41.17 | C | |
| ATOM | 1335 | NE | ARG | 663 | −7.818 | 80.785 | 5.672 | 1.00 | 43.59 | N | |
| ATOM | 1336 | CZ | ARG | 663 | −8.042 | 79.471 | 5.708 | 1.00 | 44.43 | C | |
| ATOM | 1337 | NH1 | ARG | 663 | −8.287 | 78.791 | 4.604 | 1.00 | 40.35 | N | |
| ATOM | 1338 | NH2 | ARG | 663 | −7.942 | 78.818 | 6.853 | 1.00 | 47.33 | N | |
| ATOM | 1339 | N | LEU | 664 | −4.641 | 84.338 | 0.911 | 1.00 | 20.67 | N | |
| ATOM | 1340 | CA | LEU | 664 | 4.400 | 85.016 | −0.351 | 1.00 | 23.77 | C | |
| ATOM | 1341 | C | LEU | 664 | −4.006 | 83.990 | −1.425 | 1.00 | 24.53 | C | |
| ATOM | 1342 | O | LEU | 664 | −4.470 | 84.066 | −2.570 | 1.00 | 25.26 | O | |
| ATOM | 1343 | CB | LEU | 664 | −3.287 | 86.048 | −0.200 | 1.00 | 22.42 | C | |
| ATOM | 1344 | CG | LEU | 664 | −3.695 | 87.458 | 0.188 | 1.00 | 23.55 | C | |
| ATOM | 1345 | CD1 | LEU | 664 | −2.434 | 88.240 | 0.463 | 1.00 | 22.20 | C | |
| ATOM | 1346 | CD2 | LEU | 664 | −4.517 | 88.113 | −0.910 | 1.00 | 21.42 | C | |
| ATOM | 1347 | N | ILE | 665 | −3.147 | 83.040 | −1.053 | 1.00 | 23.53 | N | |
| ATOM | 1348 | CA | ILE | 665 | −2.697 | 82.009 | −1.970 | 1.00 | 21.00 | C | |
| ATOM | 1349 | C | ILE | 665 | −3.895 | 81.209 | −2.462 | 1.00 | 22.09 | C | |
| ATOM | 1350 | O | ILE | 665 | −4.064 | 81.029 | −3.659 | 1.00 | 24.56 | O | |
| ATOM | 1351 | CB | ILE | 665 | −1.680 | 81.078 | −1.316 | 1.00 | 17.66 | C | |
| ATOM | 1352 | CG1 | ILE | 665 | −0.391 | 81.841 | −1.015 | 1.00 | 15.92 | C | |
| ATOM | 1353 | CG2 | ILE | 665 | −1.375 | 79.913 | −2.234 | 1.00 | 18.28 | C | |
| ATOM | 1354 | CD1 | ILE | 665 | 0.629 | 81.031 | −0.194 | 1.00 | 6.96 | C | |
| ATOM | 1355 | N | GLU | 666 | −4.732 | 80.747 | −1.549 | 1.00 | 23.35 | N | |
| ATOM | 1356 | CA | GLU | 666 | −5.917 | 79.983 | −1.918 | 1.00 | 19.08 | C | |
| ATOM | 1357 | C | GLU | 666 | −6.813 | 80.616 | −2.967 | 1.00 | 19.61 | C | |
| ATOM | 1358 | O | GLU | 666 | −7.341 | 79.920 | −3.827 | 1.00 | 18.02 | O | |
| ATOM | 1359 | CB | GLU | 666 | −6.784 | 79.754 | −0.704 | 1.00 | 17.71 | C | |
| ATOM | 1360 | CG | GLU | 666 | −6.367 | 78.618 | 0.172 | 1.00 | 26.16 | C | |
| ATOM | 1361 | CD | GLU | 666 | −7.515 | 78.164 | 1.049 | 1.00 | 28.97 | C | |
| ATOM | 1362 | OE1 | GLU | 666 | −7.910 | 78.950 | 1.944 | 1.00 | 22.27 | O | |
| ATOM | 1363 | OE2 | GLU | 666 | −8.030 | 77.036 | 0.815 | 1.00 | 30.15 | O | |
| ATOM | 1364 | N | LYS | 667 | −7.009 | 81.928 | −2.878 | 1.00 | 21.77 | N | |
| ATOM | 1365 | CA | LYS | 667 | −7.908 | 82.604 | −3.800 | 1.00 | 27.64 | C | |
| ATOM | 1366 | C | LYS | 667 | −7.336 | 83.042 | −5.140 | 1.00 | 28.79 | C | |
| ATOM | 1367 | O | LYS | 667 | −8.067 | 83.548 | −5.999 | 1.00 | 33.07 | O | |
| ATOM | 1368 | CB | LYS | 667 | −8.613 | 83.773 | −3.108 | 1.00 | 29.02 | C | |
| ATOM | 1369 | CG | LYS | 667 | −7.764 | 84.976 | −2.848 | 1.00 | 34.25 | C | |
| ATOM | 1370 | CD | LYS | 667 | −8.600 | 86.097 | −2.236 | 1.00 | 45.36 | C | |
| ATOM | 1371 | CE | LYS | 667 | −7.746 | 87.344 | −1.955 | 1.00 | 55.46 | C | |
| ATOM | 1372 | NZ | LYS | 667 | −8.130 | 88.070 | −0.688 | 1.00 | 58.49 | N | |
| ATOM | 1373 | N | GLN | 668 | −6.042 | 82.833 | −5.329 | 1.00 | 29.18 | N | |
| ATOM | 1374 | CA | GLN | 668 | −5.370 | 83.189 | −6.570 | 1.00 | 27.43 | C | |
| ATOM | 1375 | C | GLN | 668 | −5.720 | 82.143 | −7.648 | 1.00 | 27.44 | C | |
| ATOM | 1376 | O | GLN | 668 | −5.795 | 82.459 | −8.834 | 1.00 | 29.48 | O | |
| ATOM | 1377 | CB | GLN | 668 | −3.856 | 83.236 | −6.324 | 1.00 | 24.44 | C | |
| ATOM | 1378 | CG | GLN | 668 | −3.199 | 84.560 | −6.643 | 1.00 | 31.15 | C | |
| ATOM | 1379 | CD | GLN | 668 | −3.934 | 85.764 | −6.071 | 1.00 | 33.50 | C | |
| ATOM | 1380 | OE1 | GLN | 668 | −4.353 | 86.659 | −6.818 | 1.00 | 32.99 | O | |
| ATOM | 1381 | NE2 | GLN | 668 | −4.054 | 85.819 | −4.747 | 1.00 | 30.05 | N | |
| ATOM | 1382 | N | ALA | 669 | −5.930 | 80.895 | −7.231 | 1.00 | 23.35 | N | |
| ATOM | 1383 | CA | ALA | 669 | −6.275 | 79.816 | −8.153 | 1.00 | 21.93 | C | |
| ATOM | 1384 | C | ALA | 669 | −6.968 | 78.683 | −7.379 | 1.00 | 20.53 | C | |
| ATOM | 1385 | O | ALA | 669 | −6.590 | 78.375 | −6.267 | 1.00 | 22.44 | O | |
| ATOM | 1386 | CB | ALA | 669 | −5.010 | 79.303 | −8.854 | 1.00 | 21.51 | C | |
| ATOM | 1387 | N | PRO | 670 | −7.983 | 78.041 | −7.977 | 1.00 | 22.07 | N | |
| ATOM | 1388 | CA | PRO | 670 | −8.697 | 76.959 | −7.300 | 1.00 | 19.32 | C | |
| ATOM | 1389 | C | PRO | 670 | −7.916 | 75.769 | −6.744 | 1.00 | 24.31 | C | |
| ATOM | 1390 | O | PRO | 670 | −8.338 | 75.182 | −5.735 | 1.00 | 22.85 | O | |
| ATOM | 1391 | CB | PRO | 670 | −9.740 | 76.517 | −8.344 | 1.00 | 19.25 | C | |
| ATOM | 1392 | CG | PRO | 670 | −9.251 | 77.058 | −9.633 | 1.00 | 18.97 | C | |
| ATOM | 1393 | CD | PRO | 670 | −8.649 | 78.372 | −9.251 | 1.00 | 22.64 | C | |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 1394 | N | GLU | 671 | −6.765 | 75.444 | −7.332 | 1.00 | 21.90 | N |
| ATOM | 1395 | CA | GLU | 671 | −6.037 | 74.282 | −6.872 | 1.00 | 21.53 | C |
| ATOM | 1396 | C | GLU | 671 | −5.121 | 74.573 | −5.724 | 1.00 | 18.85 | C |
| ATOM | 1397 | O | GLU | 671 | −4.526 | 73.648 | −5.152 | 1.00 | 17.02 | O |
| ATOM | 1398 | CB | GLU | 671 | −5.237 | 73.622 | −7.996 | 1.00 | 28.16 | C |
| ATOM | 1399 | CG | GLU | 671 | −6.053 | 73.156 | −9.167 | 1.00 | 30.85 | C |
| ATOM | 1400 | CD | GLU | 671 | −6.052 | 74.163 | −10.295 | 1.00 | 40.33 | C |
| ATOM | 1401 | OE1 | GLU | 671 | −5.922 | 75.389 | −10.033 | 1.00 | 37.89 | O |
| ATOM | 1402 | OE2 | GLU | 671 | −6.181 | 73.718 | −11.456 | 1.00 | 49.39 | O |
| ATOM | 1403 | N | ASN | 672 | 4.915 | 75.849 | −5.440 | 1.00 | 16.70 | N |
| ATOM | 1404 | CA | ASN | 672 | −4.035 | 76.229 | −4.324 | 1.00 | 20.34 | C |
| ATOM | 1405 | C | ASN | 672 | −4.755 | 75.885 | −3.007 | 1.00 | 18.55 | C |
| ATOM | 1406 | O | ASN | 672 | −5.136 | 76.780 | −2.248 | 1.00 | 18.65 | O |
| ATOM | 1407 | CB | ASN | 672 | −3.751 | 77.739 | −4.359 | 1.00 | 19.53 | C |
| ATOM | 1408 | CG | ASN | 672 | −2.994 | 78.186 | −5.601 | 1.00 | 15.33 | C |
| ATOM | 1409 | OD1 | ASN | 672 | −2.466 | 77.384 | −6.369 | 1.00 | 12.87 | O |
| ATOM | 1410 | ND2 | ASN | 672 | −2.914 | 79.494 | −5.778 | 1.00 | 17.27 | N |
| ATOM | 1411 | N | LYS | 673 | −4.986 | 74.601 | −2.761 | 1.00 | 17.76 | N |
| ATOM | 1412 | CA | LYS | 673 | −5.708 | 74.178 | −1.568 | 1.00 | 21.07 | C |
| ATOM | 1413 | C | LYS | 673 | −4.820 | 74.299 | −0.335 | 1.00 | 20.99 | C |
| ATOM | 1414 | O | LYS | 673 | −3.655 | 73.896 | −0.360 | 1.00 | 26.08 | O |
| ATOM | 1415 | CB | LYS | 673 | −6.222 | 72.732 | −1.710 | 1.00 | 19.00 | C |
| ATOM | 1416 | CG | LYS | 673 | −7.480 | 72.469 | −0.858 | 1.00 | 30.07 | C |
| ATOM | 1417 | CD | LYS | 673 | −7.457 | 71.176 | −0.047 | 1.00 | 30.38 | C |
| ATOM | 1418 | CE | LYS | 673 | −7.751 | 69.983 | −0.913 | 1.00 | 36.80 | C |
| ATOM | 1419 | NZ | LYS | 673 | −7.645 | 68.682 | −0.181 | 1.00 | 45.16 | N |
| ATOM | 1420 | N | ALA | 674 | −5.357 | 74.891 | 0.727 | 1.00 | 18.75 | N |
| ATOM | 1421 | CA | ALA | 674 | −4.613 | 75.043 | 1.959 | 1.00 | 15.72 | C |
| ATOM | 1422 | C | ALA | 674 | −4.928 | 73.914 | 2.916 | 1.00 | 18.41 | C |
| ATOM | 1423 | O | ALA | 674 | −6.047 | 73.370 | 2.935 | 1.00 | 12.37 | O |
| ATOM | 1424 | CB | ALA | 674 | −4.938 | 76.362 | 2.607 | 1.00 | 14.82 | C |
| ATOM | 1425 | N | PHE | 675 | −3.916 | 73.577 | 3.716 | 1.00 | 20.72 | N |
| ATOM | 1426 | CA | PHE | 675 | −4.021 | 72.560 | 4.751 | 1.00 | 17.35 | C |
| ATOM | 1427 | C | PHE | 675 | −3.565 | 73.235 | 6.032 | 1.00 | 13.94 | C |
| ATOM | 1428 | O | PHE | 675 | −2.414 | 73.594 | 6.162 | 1.00 | 16.79 | O |
| ATOM | 1429 | CB | PHE | 675 | −3.148 | 71.357 | 4.421 | 1.00 | 17.30 | C |
| ATOM | 1430 | CG | PHE | 675 | −3.667 | 70.547 | 3.276 | 1.00 | 16.73 | C |
| ATOM | 1431 | CD1 | PHE | 675 | −3.357 | 70.890 | 1.961 | 1.00 | 18.39 | C |
| ATOM | 1432 | CD2 | PHE | 675 | −4.502 | 69.469 | 3.501 | 1.00 | 11.98 | C |
| ATOM | 1433 | CE1 | PHE | 675 | −3.880 | 70.177 | 0.880 | 1.00 | 11.40 | C |
| ATOM | 1434 | CE2 | PHE | 675 | −5.031 | 68.746 | 2.416 | 1.00 | 15.53 | C |
| ATOM | 1435 | CZ | PHE | 675 | −4.717 | 69.111 | 1.108 | 1.00 | 13.44 | C |
| ATOM | 1436 | N | VAL | 676 | −4.509 | 73.561 | 6.899 | 1.00 | 17.73 | N |
| ATOM | 1437 | CA | VAL | 676 | −4.176 | 74.211 | 8.163 | 1.00 | 19.36 | C |
| ATOM | 1438 | C | VAL | 676 | −4.128 | 73.145 | 9.260 | 1.00 | 20.91 | C |
| ATOM | 1439 | O | VAL | 676 | −5.035 | 72.324 | 9.395 | 1.00 | 19.66 | O |
| ATOM | 1440 | CB | VAL | 676 | −5.175 | 75.326 | 8.489 | 1.00 | 17.55 | C |
| ATOM | 1441 | CG1 | VAL | 676 | −4.779 | 76.031 | 9.769 | 1.00 | 18.65 | C |
| ATOM | 1442 | CG2 | VAL | 676 | −5.219 | 76.328 | 7.325 | 1.00 | 19.14 | C |
| ATOM | 1443 | N | LEU | 677 | −2.994 | 73.100 | 9.952 | 1.00 | 23.37 | N |
| ATOM | 1444 | CA | LEU | 677 | −2.740 | 72.122 | 11.003 | 1.00 | 21.69 | C |
| ATOM | 1445 | C | LEU | 677 | −2.362 | 72.830 | 12.284 | 1.00 | 17.44 | C |
| ATOM | 1446 | O | LEU | 677 | −1.870 | 73.965 | 12.263 | 1.00 | 11.94 | O |
| ATOM | 1447 | CB | LEU | 677 | −1.597 | 71.184 | 10.603 | 1.00 | 25.46 | C |
| ATOM | 1448 | CG | LEU | 677 | −1.766 | 70.099 | 9.540 | 1.00 | 25.42 | C |
| ATOM | 1449 | CD1 | LEU | 677 | −2.269 | 70.624 | 8.236 | 1.00 | 23.58 | C |
| ATOM | 1450 | CD2 | LEU | 677 | −0.422 | 69.495 | 9.346 | 1.00 | 30.67 | C |
| ATOM | 1451 | N | SER | 678 | −2.591 | 72.153 | 13.403 | 1.00 | 15.75 | N |
| ATOM | 1452 | CA | SER | 678 | −2.279 | 72.728 | 14.704 | 1.00 | 18.74 | C |
| ATOM | 1453 | C | SER | 678 | −0.805 | 72.690 | 15.096 | 1.00 | 15.98 | C |
| ATOM | 1454 | O | SER | 678 | −0.305 | 73.594 | 15.775 | 1.00 | 16.52 | O |
| ATOM | 1455 | CB | SER | 678 | −3.143 | 72.085 | 15.783 | 1.00 | 17.24 | C |
| ATOM | 1456 | OG | SER | 678 | −4.495 | 72.476 | 15.621 | 1.00 | 23.02 | O |
| ATOM | 1457 | N | SER | 679 | −0.095 | 71.679 | 14.621 | 1.00 | 15.13 | N |
| ATOM | 1458 | CA | SER | 679 | 1.305 | 71.550 | 14.954 | 1.00 | 16.64 | C |
| ATOM | 1459 | C | SER | 679 | 1.891 | 7C.526 | 13.993 | 1.00 | 16.28 | C |
| ATOM | 1460 | O | SER | 679 | 1.152 | 69.830 | 13.284 | 1.00 | 16.75 | O |
| ATOM | 1461 | CB | SER | 679 | 1.424 | 71.025 | 16.389 | 1.00 | 20.41 | C |
| ATOM | 1462 | OG | SER | 679 | C.924 | 69.683 | 16.472 | 1.00 | 15.18 | O |
| ATOM | 1463 | N | VAL | 680 | 3.212 | 70.389 | 14.023 | 1.00 | 14.70 | N |
| ATOM | 1464 | CA | VAL | 680 | 3.881 | 69.426 | 13.165 | 1.00 | 18.08 | C |
| ATOM | 1465 | C | VAL | 680 | 3.441 | 67.999 | 13.506 | 1.00 | 21.23 | C |
| ATOM | 1466 | O | VAL | 680 | 3.598 | 67.092 | 12.692 | 1.00 | 22.59 | O |
| ATOM | 1467 | CB | VAL | 680 | 5.421 | 69.505 | 13.291 | 1.00 | 15.16 | C |
| ATOM | 1468 | CG1 | VAL | 680 | 5.953 | 70.852 | 12.792 | 1.00 | 14.14 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 1469 | CG2 | VAL | 680 | 5.844 | 69.260 | 14.728 | 1.00 | 15.78 | C |
| ATOM | 1470 | N | ASP | 681 | 2.845 | 67.803 | 14.680 | 1.00 | 23.61 | N |
| ATOM | 1471 | CA | ASP | 681 | 2.431 | 66.465 | 15.090 | 1.00 | 20.29 | C |
| ATOM | 1472 | C | ASP | 681 | 1.267 | 65.967 | 14.292 | 1.00 | 17.46 | C |
| ATOM | 1473 | O | ASP | 681 | 1.021 | 64.758 | 14.254 | 1.00 | 19.43 | O |
| ATOM | 1474 | CB | ASP | 681 | 2.118 | 66.404 | 16.586 | 1.00 | 22.71 | C |
| ATOM | 1475 | CG | ASP | 681 | 3.360 | 66.605 | 17.455 | 1.00 | 27.60 | C |
| ATOM | 1476 | OD1 | ASP | 681 | 4.485 | 66.251 | 17.021 | 1.00 | 31.79 | O |
| ATOM | 1477 | OD2 | ASP | 681 | 3.205 | 67.117 | 18.585 | 1.00 | 30.83 | O |
| ATOM | 1478 | N | GLU | 682 | 0.559 | 66.891 | 13.648 | 1.00 | 19.92 | N |
| ATOM | 1479 | CA | GLU | 682 | −0.593 | 66.532 | 12.823 | 1.00 | 19.43 | C |
| ATOM | 1480 | C | GLU | 682 | −0.246 | 66.200 | 11.373 | 1.00 | 16.94 | C |
| ATOM | 1481 | O | GLU | 682 | −1.031 | 65.593 | 10.678 | 1.00 | 20.34 | O |
| ATOM | 1482 | CB | GLU | 682 | −1.664 | 67.616 | 12.904 | 1.00 | 19.71 | C |
| ATOM | 1483 | CG | GLU | 682 | −2.031 | 67.903 | 14.337 | 1.00 | 27.72 | C |
| ATOM | 1484 | CD | GLU | 682 | −3.385 | 68.541 | 14.516 | 1.00 | 32.65 | C |
| ATOM | 1485 | OE1 | GLU | 682 | −3.806 | 69.338 | 13.643 | 1.00 | 32.50 | O |
| ATOM | 1486 | OE2 | GLU | 682 | −4.013 | 68.250 | 15.567 | 1.00 | 36.39 | O |
| ATOM | 1487 | N | LEU | 683 | 0.968 | 66.533 | 10.953 | 1.00 | 19.46 | N |
| ATOM | 1488 | CA | LEU | 683 | 1.430 | 66.270 | 9.591 | 1.00 | 18.53 | C |
| ATOM | 1489 | C | LEU | 683 | 1.230 | 64.820 | 9.159 | 1.00 | 19.54 | C |
| ATOM | 1490 | O | LEU | 683 | 0.759 | 64.567 | 8.050 | 1.00 | 21.33 | O |
| ATOM | 1491 | CB | LEU | 683 | 2.913 | 66.629 | 9.458 | 1.00 | 9.01 | C |
| ATOM | 1492 | CG | LEU | 683 | 3.212 | 68.119 | 9.485 | 1.00 | 11.07 | C |
| ATOM | 1493 | CD1 | LEU | 683 | 4.725 | 68.380 | 9.521 | 1.00 | 6.20 | C |
| ATOM | 1494 | CD2 | LEU | 683 | 2.581 | 68.729 | 8.268 | 1.00 | 9.94 | C |
| ATOM | 1495 | N | GLU | 684 | 1.577 | 63.879 | 10.027 | 1.00 | 17.82 | N |
| ATOM | 1496 | CA | GLU | 684 | 1.449 | 62.470 | 9.701 | 1.00 | 21.58 | C |
| ATOM | 1497 | C | GLU | 684 | 0.026 | 62.043 | 9.404 | 1.00 | 20.80 | C |
| ATOM | 1498 | O | GLU | 684 | −0.204 | 61.216 | 8.521 | 1.00 | 21.28 | O |
| ATOM | 1499 | CB | GLU | 684 | 2.022 | 61.614 | 10.826 | 1.00 | 27.44 | C |
| ATOM | 1500 | CG | GLU | 684 | 1.799 | 60.112 | 10.601 | 1.00 | 42.61 | C |
| ATOM | 1501 | CD | GLU | 684 | 2.605 | 59.219 | 11.539 | 1.00 | 48.25 | C |
| ATOM | 1502 | OE1 | GLU | 684 | 2.910 | 59.655 | 12.683 | 1.00 | 46.17 | O |
| ATOM | 1503 | OE2 | GLU | 684 | 2.915 | 58.071 | 11.116 | 1.00 | 50.28 | O |
| ATOM | 1504 | N | GLN | 685 | −0.914 | 62.632 | 10.133 | 1.00 | 22.35 | N |
| ATOM | 1505 | CA | GLN | 685 | −2.349 | 62.353 | 10.005 | 1.00 | 25.85 | C |
| ATOM | 1506 | C | GLN | 685 | −2.958 | 62.892 | 8.709 | 1.00 | 22.14 | C |
| ATOM | 1507 | O | GLN | 685 | −4.089 | 62.579 | 8.381 | 1.00 | 25.03 | O |
| ATOM | 1508 | CB | GLN | 685 | −3.117 | 63.008 | 11.162 | 1.00 | 25.71 | C |
| ATOM | 1509 | CG | GLN | 685 | −2.414 | 62.982 | 12.509 | 1.00 | 34.50 | C |
| ATOM | 1510 | CD | GLN | 685 | −3.192 | 63.753 | 13.571 | 1.00 | 41.31 | C |
| ATOM | 1511 | OE1 | GLN | 685 | −4.338 | 64.167 | 13.356 | 1.00 | 40.86 | O |
| ATOM | 1512 | NE2 | GLN | 685 | −2.565 | 63.957 | 14.726 | 1.00 | 45.33 | N |
| ATOM | 1513 | N | GLN | 686 | −2.245 | 63.789 | 8.044 | 1.00 | 20.96 | N |
| ATOM | 1514 | CA | GLN | 686 | −2.715 | 64.404 | 6.813 | 1.00 | 23.16 | C |
| ATOM | 1515 | C | GLN | 686 | −1.882 | 64.075 | 5.583 | 1.00 | 19.32 | C |
| ATOM | 1516 | O | GLN | 686 | −2.328 | 64.299 | 4.456 | 1.00 | 22.21 | O |
| ATOM | 1517 | CB | GLN | 686 | −2.709 | 65.912 | 6.982 | 1.00 | 26.35 | C |
| ATOM | 1518 | CG | GLN | 686 | −3.709 | 66.416 | 7.948 | 1.00 | 35.22 | C |
| ATOM | 1519 | CD | GLN | 686 | −4.816 | 67.142 | 7.241 | 1.00 | 42.30 | C |
| ATOM | 1520 | OE1 | GLN | 686 | −4.941 | 68.365 | 7.350 | 1.00 | 45.54 | O |
| ATOM | 1521 | NE2 | GLN | 686 | −5.616 | 66.400 | 6.478 | 1.00 | 44.88 | N |
| ATOM | 1522 | N | ARG | 687 | −0.683 | 63.557 | 5.803 | 1.00 | 14.84 | N |
| ATOM | 1523 | CA | ARG | 687 | 0.238 | 63.225 | 4.731 | 1.00 | 17.34 | C |
| ATOM | 1524 | C | ARG | 687 | −0.364 | 62.511 | 3.524 | 1.00 | 17.95 | C |
| ATOM | 1525 | O | ARG | 687 | −0.248 | 62.982 | 2.402 | 1.00 | 18.16 | O |
| ATOM | 1526 | CB | ARG | 687 | 1.405 | 62.429 | 5.303 | 1.00 | 12.76 | C |
| ATOM | 1527 | CG | ARG | 687 | 2.512 | 62.076 | 4.320 | 1.00 | 12.31 | C |
| ATOM | 1528 | CD | ARG | 687 | 2.612 | 60.589 | 4.398 | 1.00 | 15.47 | C |
| ATOM | 1529 | NE | ARG | 687 | 2.836 | 60.134 | 5.786 | 1.00 | 27.33 | N |
| ATOM | 1530 | CZ | ARG | 687 | 2.343 | 58.985 | 6.234 | 1.00 | 25.36 | C |
| ATOM | 1531 | NH1 | ARG | 687 | 1.783 | 58.118 | 5.416 | 1.00 | 25.62 | N |
| ATOM | 1532 | NH2 | ARG | 687 | 2.342 | 58.744 | 7.535 | 1.00 | 34.14 | N |
| ATOM | 1533 | N | ASP | 688 | −1.044 | 61.397 | 3.749 | 1.00 | 22.35 | N |
| ATOM | 1534 | CA | ASP | 688 | −1.603 | 60.649 | 2.632 | 1.00 | 20.59 | C |
| ATOM | 1535 | C | ASP | 688 | −2.651 | 61.418 | 1.872 | 1.00 | 23.19 | C |
| ATOM | 1536 | O | ASP | 688 | −2.732 | 61.326 | 0.653 | 1.00 | 23.82 | O |
| ATOM | 1537 | CB | ASP | 688 | −2.128 | 59.301 | 3.096 | 1.00 | 21.54 | C |
| ATOM | 1538 | CG | ASP | 688 | −1.008 | 58.365 | 3.518 | 1.00 | 24.25 | C |
| ATOM | 1539 | OD1 | ASP | 688 | 0.172 | 58.697 | 3.266 | 1.00 | 31.52 | O |
| ATOM | 1540 | OD2 | ASP | 688 | −1.287 | 57.289 | 4.083 | 1.00 | 26.17 | O |
| ATOM | 1541 | N | GLU | 689 | −3.395 | 62.253 | 2.575 | 1.00 | 23.99 | N |
| ATOM | 1542 | CA | GLU | 689 | −4.419 | 63.045 | 1.927 | 1.00 | 26.49 | C |
| ATOM | 1543 | C | GLU | 689 | −3.796 | 64.142 | 1.054 | 1.00 | 25.62 | C |

TABLE 8-continued

Atomic Coordinates for Residues of a Crystal of murine VWF-A1 (SEQ ID NO: 10).

| CRYST1 | 86.395 | | 86.395 | | 68.125 | 90.00 | 90.00 | 120.00 | P 61 | 6 |
|---|---|---|---|---|---|---|---|---|---|---|
| ATOM | 1544 | O | GLU | 689 | −4.376 | 64.536 | 0.034 | 1.00 | 26.10 | O |
| ATOM | 1545 | CB | GLU | 689 | −5.334 | 63.663 | 2.981 | 1.00 | 34.19 | C |
| ATOM | 1546 | CG | GLU | 689 | −6.456 | 64.543 | 2.429 | 1.00 | 36.12 | C |
| ATOM | 1547 | CD | GLU | 689 | −7.358 | 65.061 | 3.527 | 1.00 | 42.19 | C |
| ATOM | 1548 | OE1 | GLU | 689 | −7.532 | 64.327 | 4.532 | 1.00 | 50.63 | O |
| ATOM | 1549 | OE2 | GLU | 689 | −7.895 | 66.189 | 3.385 | 1.00 | 42.61 | O |
| ATOM | 1550 | N | ILE | 690 | −2.645 | 64.665 | 1.478 | 1.00 | 21.08 | N |
| ATOM | 1551 | CA | ILE | 690 | −1.951 | 65.705 | 0.726 | 1.00 | 19.71 | C |
| ATOM | 1552 | C | ILE | 690 | −1.312 | 65.124 | −0.514 | 1.00 | 20.60 | C |
| ATOM | 1553 | O | ILE | 690 | −1.368 | 65.722 | −1.567 | 1.00 | 23.29 | O |
| ATOM | 1554 | CB | ILE | 690 | −0.881 | 66.388 | 1.572 | 1.00 | 20.01 | C |
| ATOM | 1555 | CG1 | ILE | 690 | −1.550 | 67.130 | 2.737 | 1.00 | 18.80 | C |
| ATOM | 1556 | CG2 | ILE | 690 | −0.054 | 67.322 | 0.713 | 1.00 | 19.33 | C |
| ATOM | 1557 | CD1 | ILE | 690 | −0.610 | 67.889 | 3.623 | 1.00 | 13.89 | C |
| ATOM | 1558 | N | VAL | 691 | −0.694 | 63.958 | −0.394 | 1.00 | 22.47 | N |
| ATOM | 1559 | CA | VAL | 691 | −0.083 | 63.301 | −1.543 | 1.00 | 21.73 | C |
| ATOM | 1560 | C | VAL | 691 | −1.144 | 62.902 | −2.579 | 1.00 | 20.40 | C |
| ATOM | 1561 | O | VAL | 691 | −0.923 | 63.076 | −3.767 | 1.00 | 22.98 | O |
| ATOM | 1562 | CB | VAL | 691 | 0.750 | 62.083 | −1.110 | 1.00 | 22.75 | C |
| ATOM | 1563 | CG1 | VAL | 691 | 1.147 | 61.263 | −2.296 | 1.00 | 29.43 | C |
| ATOM | 1564 | CG2 | VAL | 691 | 1.988 | 62.555 | −0.431 | 1.00 | 23.51 | C |
| ATOM | 1565 | N | SER | 692 | −2.296 | 62.407 | −2.139 | 1.00 | 17.46 | N |
| ATOM | 1566 | CA | SER | 692 | −3.371 | 62.031 | −3.054 | 1.00 | 15.69 | C |
| ATOM | 1567 | C | SER | 692 | −3.894 | 63.216 | −3.856 | 1.00 | 16.29 | C |
| ATOM | 1568 | O | SER | 692 | −4.106 | 63.117 | −5.060 | 1.00 | 19.86 | O |
| ATOM | 1569 | CB | SER | 692 | −4.532 | 61.435 | −2.283 | 1.00 | 15.65 | C |
| ATOM | 1570 | OG | SER | 692 | −4.134 | 60.230 | −1.674 | 1.00 | 28.15 | O |
| ATOM | 1571 | N | TYR | 693 | −4.129 | 64.319 | −3.168 | 1.00 | 16.74 | N |
| ATOM | 1572 | CA | TYR | 693 | −4.632 | 65.536 | −3.768 | 1.00 | 15.99 | C |
| ATOM | 1573 | C | TYR | 693 | −3.654 | 65.960 | −4.833 | 1.00 | 18.79 | C |
| ATOM | 1574 | O | TYR | 693 | −3.983 | 66.084 | −6.006 | 1.00 | 21.36 | O |
| ATOM | 1575 | CB | TYR | 693 | −4.725 | 66.619 | −2.702 | 1.00 | 11.55 | C |
| ATOM | 1576 | CG | TYR | 693 | −5.078 | 67.969 | −3.259 | 1.00 | 19.55 | C |
| ATOM | 1577 | CD1 | TYR | 693 | −6.374 | 68.238 | −3.748 | 1.00 | 20.06 | C |
| ATOM | 1578 | CD2 | TYR | 693 | −4.102 | 68.960 | −3.394 | 1.00 | 13.67 | C |
| ATOM | 1579 | CE1 | TYR | 693 | −6.665 | 69.458 | −4.365 | 1.00 | 14.61 | C |
| ATOM | 1580 | CE2 | TYR | 693 | −4.394 | 70.165 | −4.002 | 1.00 | 14.06 | C |
| ATOM | 1581 | CZ | TYR | 693 | −5.664 | 70.402 | −4.489 | 1.00 | 14.63 | C |
| ATOM | 1582 | OH | TYR | 693 | −5.911 | 71.592 | −5.123 | 1.00 | 17.27 | O |
| ATOM | 1583 | N | LEU | 694 | −2.416 | 66.070 | −4.401 | 1.00 | 21.64 | N |
| ATOM | 1584 | CA | LEU | 694 | −1.287 | 66.480 | −5.216 | 1.00 | 22.01 | C |
| ATOM | 1585 | C | LEU | 694 | −1.001 | 65.549 | −6.414 | 1.00 | 24.72 | C |
| ATOM | 1586 | O | LEU | 694 | −0.819 | 66.007 | −7.560 | 1.00 | 21.88 | O |
| ATOM | 1587 | CB | LEU | 694 | −0.131 | 66.631 | −4.229 | 1.00 | 19.20 | C |
| ATOM | 1588 | CG | LEU | 694 | 1.365 | 66.561 | −4.388 | 1.00 | 23.50 | C |
| ATOM | 1589 | CD1 | LEU | 694 | 1.939 | 67.326 | −3.227 | 1.00 | 20.23 | C |
| ATOM | 1590 | CD2 | LEU | 694 | 1.840 | 65.126 | −4.387 | 1.00 | 21.48 | C |
| ATOM | 1591 | N | CYS | 695 | −1.033 | 64.243 | −6.178 | 1.00 | 24.01 | N |
| ATOM | 1592 | CA | CYS | 695 | −0.805 | 63.264 | −7.230 | 1.00 | 23.59 | C |
| ATOM | 1593 | C | CYS | 695 | −1.913 | 63.363 | −8.266 | 1.00 | 23.92 | C |
| ATOM | 1594 | O | CYS | 695 | −1.662 | 63.443 | −9.476 | 1.00 | 20.77 | O |
| ATOM | 1595 | CB | CYS | 695 | −0.785 | 61.851 | −6.639 | 1.00 | 21.84 | C |
| ATOM | 1596 | SG | CYS | 695 | −0.122 | 60.600 | −7.770 | 1.00 | 25.31 | S |
| ATOM | 1597 | N | ASP | 696 | −3.141 | 63.401 | −7.775 | 1.00 | 25.04 | N |
| ATOM | 1598 | CA | ASP | 696 | −4.312 | 63.463 | −8.634 | 1.00 | 30.16 | C |
| ATOM | 1599 | C | ASP | 696 | −4.295 | 64.617 | −9.630 | 1.00 | 29.12 | C |
| ATOM | 1600 | O | ASP | 696 | −4.933 | 64.557 | −10.678 | 1.00 | 33.49 | O |
| ATOM | 1601 | CB | ASP | 696 | −5.569 | 63.536 | −7.775 | 1.00 | 33.29 | C |
| ATOM | 1602 | CG | ASP | 696 | −6.827 | 63.645 | −8.598 | 1.00 | 40.85 | C |
| ATOM | 1603 | OD1 | ASP | 696 | −7.215 | 62.641 | −9.244 | 1.00 | 44.44 | O |
| ATOM | 1604 | OD2 | ASP | 696 | −7.416 | 64.749 | −8.613 | 1.00 | 45.63 | O |
| ATOM | 1605 | N | LEU | 697 | −3.544 | 65.655 | −9.296 | 1.00 | 27.97 | N |
| ATOM | 1606 | CA | LEU | 697 | −3.421 | 66.863 | −10.108 | 1.00 | 23.65 | C |
| ATOM | 1607 | C | LEU | 697 | −2.498 | 66.673 | −11.297 | 1.00 | 21.19 | C |
| ATOM | 1608 | O | LEU | 697 | −2.676 | 67.307 | −12.337 | 1.00 | 23.84 | O |
| ATOM | 1609 | CB | LEU | 697 | −2.863 | 67.990 | −9.227 | 1.00 | 19.78 | C |
| ATOM | 1610 | CG | LEU | 697 | −3.679 | 69.216 | −8.812 | 1.00 | 18.30 | C |
| ATOM | 1611 | CD1 | LEU | 697 | −5.186 | 68.949 | −8.767 | 1.00 | 12.42 | C |
| ATOM | 1612 | CD2 | LEU | 697 | −3.128 | 69.715 | −7.478 | 1.00 | 11.15 | C |
| ATOM | 1613 | N | ALA | 698 | −1.467 | 65.864 | −11.106 | 1.00 | 20.21 | N |
| ATOM | 1614 | CA | ALA | 698 | −0.472 | 65.597 | −12.128 | 1.00 | 18.13 | C |
| ATOM | 1615 | C | ALA | 698 | −0.972 | 64.732 | −13.286 | 1.00 | 18.60 | C |
| ATOM | 1616 | O | ALA | 698 | −1.904 | 63.935 | −13.128 | 1.00 | 20.41 | O |
| ATOM | 1617 | CB | ALA | 698 | 0.746 | 64.965 | −11.481 | 1.00 | 16.85 | C |
| ATOM | 1618 | N | PRO | 699 | −0.362 | 64.887 | −14.479 | 1.00 | 15.84 | N |

TABLE 8-continued

Atomic Coordinates for Residues of a Crystal of murine VWF-A1 (SEQ ID NO: 10).

| CRYST1 | 86.395 | | 86.395 | 68.125 | 90.00 | 90.00 | 120.00 | P 61 | 6 |
|---|---|---|---|---|---|---|---|---|---|
| ATOM | 1619 | CA | PRO 699 | −0.802 | 64.081 | −15.622 | 1.00 | 14.86 | C |
| ATOM | 1620 | C | PRO 699 | −0.313 | 62.649 | −15.472 | 1.00 | 17.66 | C |
| ATOM | 1621 | O | PRO 699 | 0.687 | 62.397 | −14.808 | 1.00 | 18.33 | O |
| ATOM | 1622 | CB | PRO 699 | −0.131 | 64.763 | −16.817 | 1.00 | 10.16 | C |
| ATOM | 1623 | CG | PRO 699 | 0.224 | 66.151 | −16.293 | 1.00 | 11.52 | C |
| ATOM | 1624 | CD | PRO 699 | 0.636 | 65.888 | −14.889 | 1.00 | 12.64 | C |
| ATOM | 1625 | N | GLU 700 | −1.029 | 61.702 | −16.058 | 1.00 | 18.23 | N |
| ATOM | 1626 | CA | GLU 700 | −0.585 | 60.329 | −15.996 | 1.00 | 21.35 | C |
| ATOM | 1627 | C | GLU 700 | 0.318 | 60.141 | −17.171 | 1.00 | 24.65 | C |
| ATOM | 1628 | O | GLU 700 | 0.213 | 60.873 | −18.137 | 1.00 | 29.66 | O |
| ATOM | 1629 | CB | GLU 700 | −1.730 | 59.377 | −16.176 | 1.00 | 19.18 | C |
| ATOM | 1630 | CG | GLU 700 | −2.640 | 59.327 | −15.036 | 1.00 | 27.76 | C |
| ATOM | 1631 | CD | GLU 700 | −3.623 | 58.221 | −15.210 | 1.00 | 30.98 | C |
| ATOM | 1632 | OE1 | GLU 700 | −3.184 | 57.061 | −15.339 | 1.00 | 35.58 | O |
| ATOM | 1633 | OE2 | GLU 700 | −4.833 | 58.511 | −15.269 | 1.00 | 39.02 | O |
| ATOM | 1634 | N | ALA 701 | 1.223 | 59.173 | −17.083 | 1.00 | 33.25 | N |
| ATOM | 1635 | CA | ALA 701 | 2.109 | 58.864 | −18.203 | 1.00 | 34.46 | C |
| ATOM | 1636 | C | ALA 701 | 1.251 | 58.146 | −19.254 | 1.00 | 36.32 | C |
| ATOM | 1637 | O | ALA 701 | 0.277 | 57.456 | −18.916 | 1.00 | 30.64 | O |
| ATOM | 1638 | CB | ALA 701 | 3.251 | 57.962 | −17.739 | 1.00 | 32.72 | C |
| ATOM | 1639 | N | PRO 702 | 1.537 | 58.370 | −20.545 | 1.00 | 42.71 | N |
| ATOM | 1640 | CA | PRO 702 | 0.790 | 57.732 | −21.634 | 1.00 | 47.12 | C |
| ATOM | 1641 | C | PRO 702 | 1.089 | 56.237 | −21.591 | 1.00 | 49.56 | C |
| ATOM | 1642 | O | PRO 702 | 2.244 | 55.851 | −21.342 | 1.00 | 48.33 | O |
| ATOM | 1643 | CB | PRO 702 | 1.402 | 58.353 | −22.886 | 1.00 | 45.52 | C |
| ATOM | 1644 | CG | PRO 702 | 1.918 | 59.687 | −22.387 | 1.00 | 48.78 | C |
| ATOM | 1645 | CD | PRO 702 | 2.530 | 59.322 | −21.073 | 1.00 | 44.35 | C |
| ATOM | 1646 | N | PRO 703 | 0.080 | 55.383 | −21.849 | 1.00 | 51.95 | N |
| ATOM | 1647 | CA | PRO 703 | 0.189 | 53.922 | −21.841 | 1.00 | 54.88 | C |
| ATOM | 1648 | C | PRO 703 | 1.480 | 53.458 | −22.521 | 1.00 | 59.06 | C |
| ATOM | 1649 | O | PRO 703 | 1.819 | 53.929 | −23.616 | 1.00 | 56.81 | O |
| ATOM | 1650 | CB | PRO 703 | −1.057 | 53.477 | −22.606 | 1.00 | 53.66 | C |
| ATOM | 1651 | CG | PRO 703 | −2.041 | 54.516 | −22.235 | 1.00 | 53.29 | C |
| ATOM | 1652 | CD | PRO 703 | −1.240 | 55.790 | −22.379 | 1.00 | 53.11 | C |
| ATOM | 1653 | N | PRO 704 | 2.271 | 52.622 | −21.816 | 1.00 | 64.17 | N |
| ATOM | 1654 | CA | PRO 704 | 3.533 | 52.117 | −22.370 | 1.00 | 66.20 | C |
| ATOM | 1655 | C | PRO 704 | 3.250 | 51.526 | −23.741 | 1.00 | 67.33 | C |
| ATOM | 1656 | O | PRO 704 | 2.480 | 50.565 | −23.877 | 1.00 | 66.63 | O |
| ATOM | 1657 | CB | PRO 704 | 3.946 | 51.050 | −21.356 | 1.00 | 66.86 | C |
| ATOM | 1658 | CG | PRO 704 | 3.457 | 51.639 | −20.067 | 1.00 | 65.74 | C |
| ATOM | 1659 | CD | PRO 704 | 2.065 | 52.108 | −20.449 | 1.00 | 64.51 | C |
| ATOM | 1660 | N | THR 705 | 3.885 | 52.116 | −24.741 | 1.00 | 67.88 | N |
| ATOM | 1661 | CA | THR 705 | 3.712 | 51.735 | −26.130 | 1.00 | 68.43 | C |
| ATOM | 1662 | C | THR 705 | 5.009 | 51.114 | −26.688 | 1.00 | 68.19 | C |
| ATOM | 1663 | O | THR 705 | 4.932 | 50.046 | −27.340 | 1.00 | 66.67 | O |
| ATOM | 1664 | CB | THR 705 | 3.231 | 52.998 | −26.933 | 1.00 | 69.60 | C |
| ATOM | 1665 | OG1 | THR 705 | 2.672 | 52.619 | −28.198 | 1.00 | 70.05 | O |
| ATOM | 1666 | CG2 | THR 705 | 4.357 | 54.013 | −27.124 | 1.00 | 68.20 | C |
| ATOM | 1667 | OXT | THR 705 | 6.102 | 51.650 | −26.404 | 1.00 | 67.96 | O |

To demonstrate the feasibility of identifying potential small molecule inhibitors in silico, computational modeling software was utilized in conjunction with high-resolution crystal structure results to screen databases for existing compounds that would bind to the A1 domain where it interfaces with botrocetin (exogenous ligand binding site). Several small molecules predicted to bind with sub-micromolar $IC_{50}$s (concentration of drug required to inhibit the activity by 50%) and that could also severely disrupt binding of this snake venom protein were identified. Thus, potential candidate small molecules can be identified that may interfere with the interaction between GPIb alpha and the A1 domain of VWF.

Screening Small Molecule Library for Inhibitors.

Although the use of computational modeling is a state-of-the-art method for identifying lead compounds, it is not without its limitations. Thus, we will also screen an actual library of 20,000 small molecules manufactured by the Chembridge Corporation (San Diego, Calif.). The library consists of handcrafted drug-like organic molecules with molecular weights in a range of 25-550, which are soluble in DMSO at concentrations ranging from 10-20 mM. The structure and purity (>95%) of these compounds have been validated by NMR. The library is formatted in a 96 well plate for high throughput screening using instrumentation made available through the OCCC (under supervision of the Landry laboratory) and includes a robot plate reader (FLexStation II 384, Molecular Devices, Sunnyvale, Calif.), an 8-tip robotic pipettor (Multiprobe II Plus, Perkin Elmer, Shelton, Conn.), a 96-tip robotic pipettor (Mintrak, Perkin Elmer), and an automated 96 well plate washer (Perkin Elmer).

Figure 45A:
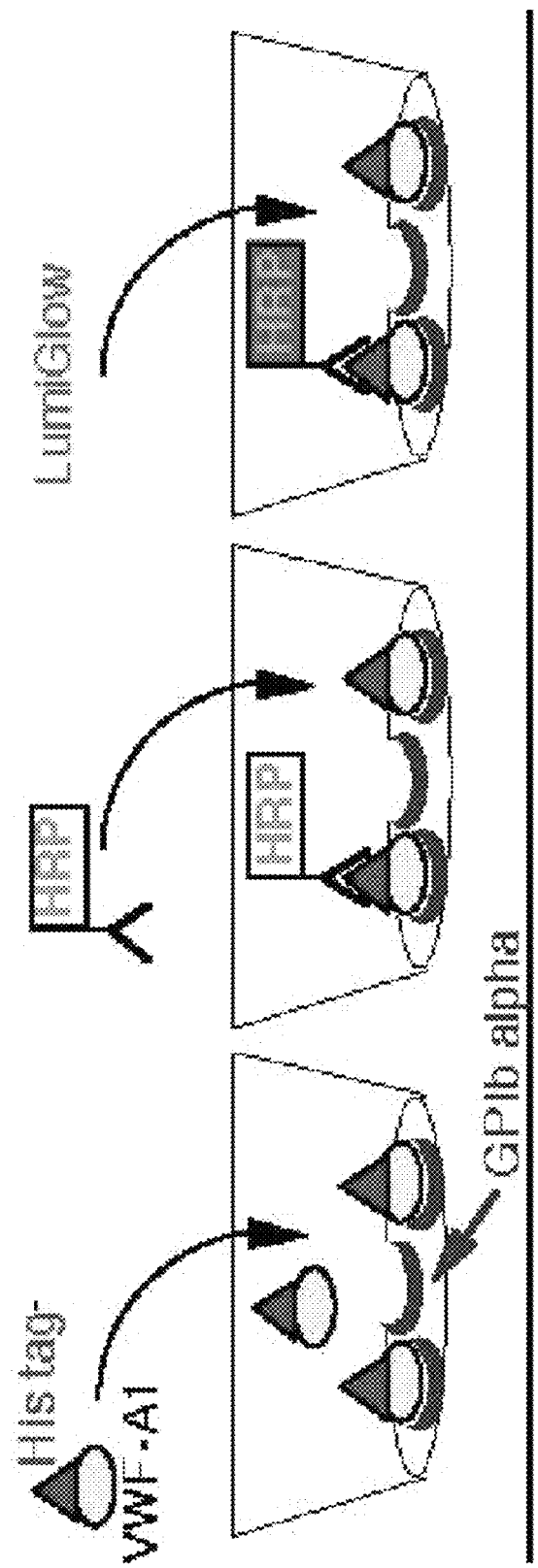
FIG. 45A is a schematic representation showing that Recombinant GPIb alpha is surface-immobilized in a 96 well format. After blocking potential non-specific binding sites, recombinant VWF-A1 containing a His tag is added to the wells and allowed to interact with GPIb alpha for a specified period of time. The unbound material is removed by washing the wells and the complex formed between the 2 proteins detected by the addition of a HRP-conjugated antibody that binds to the His tag on A1. The amount of bound A1 can then be quantified by either fluorescence (addition of LumiGlow) or by color change.

An ELISA based system will be used to screen for compounds that may inhibit the interaction between GPIb alpha and the VWF-A1 domain. Enzyme-Linked Immunosorbent Assay (ELISA) methods are immunoassay techniques used for detection or quantification of a substance. An example of this assay is demonstrated in FIG. 45A, where an antibody conjugated with horseradish peroxidase (HRP) was used to identify the presence of VWF. Depending on the substrate added, HRP enzyme activity can be detected by either a change in color (chromogenic product) or fluorescence (most sensitive indicator). Schematic representation of the proposed assay system to be used for screening is shown in FIG. 45A.

Assay System:

Recombinant GPIb alpha and VWF-A1 proteins will be generated and purified as described in the attached articles, with the latter containing a 6×His tag. Purified GPIb alpha will be absorbed overnight (4° C.) to PRO-BIND polystyrene 96-well assay plates (Falcon) at 10 µg/ml per well. Plates will be washed and non-specific binding sites blocked by the addition of TENTC buffer (50 mM Tris, 1 mM EDTA, 0.15M NaCl, 0.2% casein, 0.05% Tween 20, pH 8.0) for 1 hour at room temperature. Subsequently, plates will be washed with and resuspended in TBS buffer (50 mM Tris, 150 mM NaCl, pH 8.0) and 1 test compound per well added at a final concentration of 10 µM (final DMSO concentration 0.5%). After 30 min, recombinant His tagged VWF-A1 protein will be added at a 1:1 Molar ratio to that of GPIb alpha and left to incubate for 1 hour before washing with TBS buffer. VWF-A1 bound to surface-immobilized GPIb alpha will be determined by the addition of HRP-conjugated anti-His tag antibody and the A1-antibody conjugate detected by the addition of LumiGlow reagent (KPL, Gaithersburg, Md.). The resulting fluorescence will be quantified by of the number of luminescence emissions per second using a FLexStation II 384 plate reader. A sample will be considered positive when the luminescence (in counts per second) is more than 2 standard deviations above the mean value for negative-controls.

Figure 45B:
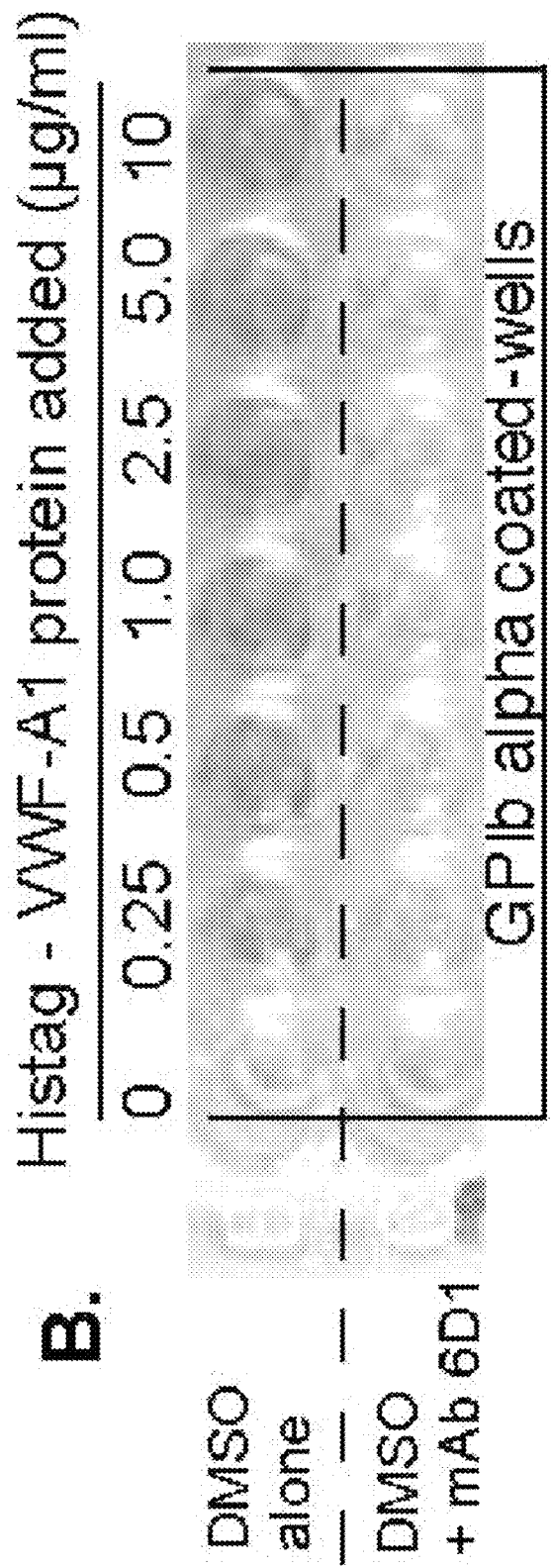
FIG. 45B is an image representing that the specificity of the interaction can be determined by the addition of the GPIb function blocking antibody 6D1 prior to the addition of recombinant VWF-A1. DMSO (0.5%) was added to illustrate that this reagent does not interfere with the assay.

Negative Controls:

Addition of mAb 6D1 to certain wells to prevent VWF-A1 binding to GPIb alpha or no addition of VWF-A1 protein (FIG. 45B). In either case, no significant fluorescence should be detected. Once compounds of interest have been identified, solubility of these molecules will be confirmed to rule out precipitation as the etiology for blocking interactions between GPIb alpha and VWF-A1. In addition, a dose effect curve will also be generated (1 nM to 100 µM) to obtain preliminary information regarding the IC50 of the inhibitor. Lead molecules will then be tested for their ability to limit human platelet interactions with plasma VWF in aggregometry and flow chamber assays as described in preliminary results. Ultimately, the most promising compound will be tested in our humanized mouse model of thrombosis.

Example 7

Effect of Plavix or ReoPro on Human Platelet-Induced Hemostasis in Homozygous $VWF^{1326R>H}$ Mice To demonstrate the feasibility of our $VWF^{1326R>H}$ mice to identify anti-thrombotic drugs capable of perturbing human platelet function in vivo, we tested the ability of 2 FDA approved drugs, Plavix and ReoPro, to prevent human platelet-induced hemostasis. Plavix is the second most commonly used anti-thrombotic drug that targets one of the ADP receptors (P2Y12) on platelets, causing irreversible inhibition (Hankey et al. Med. J. Aust. 2003; 178:568). ADP is a potent mediator of platelet activation and aggregate formation, and thus considerable effort and funds have been devoted to inhibiting this activation pathway in platelets. Clopidogrel was approved by the FDA in 1997 for clinical use and was found to be of benefit in the secondary prevention of major vascular events in patients with a history of cerebrovascular and coronary artery diseases and major cardiac events post coronary artery stent placement (Gachet et al. Semin. Thromb. Hemost. 2005; 31:162). Disadvantages of this drug are: 1) It must be metabolized in the liver to generate an active metabolite, thus limiting its effectiveness in acute settings, and 2) irreversible inhibition that results in a marked prolongation of bleeding time. Clopidogrel has been shown to reduce thrombus size and delay its formation in mice with a maximal effective dose of 50 mg/kg given the day before and 2 hours prior to experimentation. Homozygous $VWF^{1326R>H}$ mice that received this dosing schema, were unable to produce a hemostatic clot when administered human platelets in contrast to homozygous $VWF^{1326R>H}$ mice that received saline in lieu of drug.

Figures 46A, 46B:
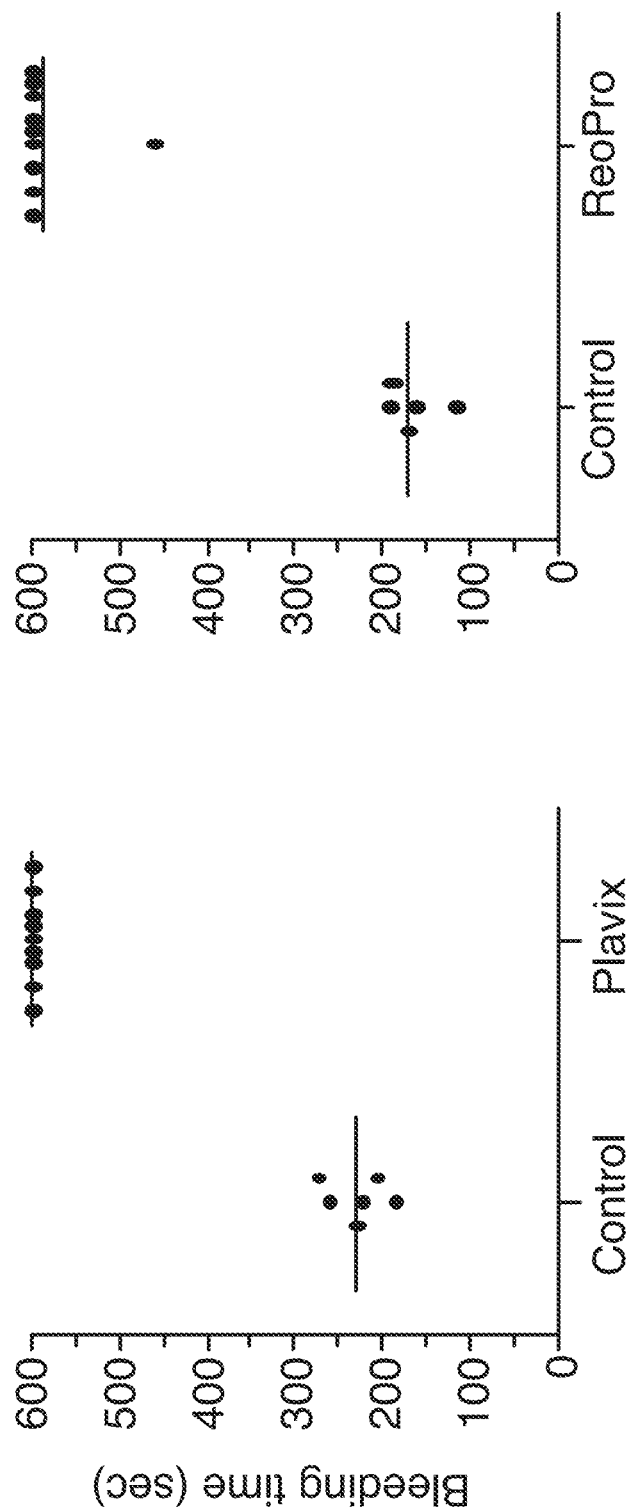
FIGS. 46A and 46B are graphs depicting the effect of Plavix (FIG. 46A) or ReoPro (FIG. 46B) on human platelet-induced hemostasis in homozygous VWF$^{1326R>H}$ mice.

As Plavix can also block the function of the ADP receptor on murine platelets (see FIG. 46A), we also tested the ability of ReoPro to prevent the formation of a hemostatic plug in homozygous $VWF^{1326R>H}$ mice. ReoPro is a Fab fragment of a human-murine chimeric monoclonal antibody that blocks fibrinogen binding to the platelet integrin receptor αIIbβ3, thus limiting thrombus growth (Bennett, J. S. Novel platelet inhibitors. Annu. Rev. Med. 52, 161-184 (2001)). It is currently approved for short-term treatment of patients with acute coronary syndrome that require interventional catheterization. It is administered by intravenously bolus (0.25 mg/kg), followed by an infusion of 0.125 µg/kg/min. This results in >80% αIIbβ3 occupancy, and disrupts platelet function for 24-36 h. It does not bind or disrupt the function of murine αIIbβ3. Administration of ReoPro to homozygous $VWF^{1326R>H}$ mice 5 minutes after the infusion of human platelets, prevented the formation of a hemostatic plug (mean bleeding time 579 sec) (FIG. 46B). By contrast, animals that received a non-function blocking antibody to human αIIbβ3 were able to form a hemostatic plug (mean bleeding 175 sec).

REFERENCES

1) Jaffe E A, Hoyer L W and Nachman R L Synthesis of antihemophilic factor antigen by cultured human endothelial cells. 1973. J Clin Invest. 52, 2757-2764.
2) Nachman R L., Levine R, Jaffe E A. Synthesis of factor VIII antigen by cultured guinea-pig megakaryocytes 1977. J Clin Invest. 60, 914-921.
3) Sporn L A, Chavin S I, Marder V J and Wagner, D D. Biosynthesis of von Willebrand protein by human megakaryocytes. 1985. J Clin Invest. 76, 1102-1106.
4) Sakariassen K S, Bolhuis P A and Sixma J J. human platelet adhesion to artery subendothelium is mediated by Factor VIII-von Willebrand factor bound to the subendothelium. 1979. Nature 279:636-638.
5) Meyer D, Baumgartner H R. Role of von Willebrand factor in platelet adhesion to subendothelium. 1983. Br J Haematol. 54:1-9.
6) Cruz M A, Yuan H, Lee J R, et al. Interaction of von Willebrand factor (vWF) with collagen. 1995. J Biol Chem. 270, 10822-10827.
7) Handa M, Titani K, Holland L Z, et al. The von Willebrand factor-binding domain of platelet membrane glycoprotein Ib. Characterization by monoclonal antibodies and partial amino acid sequence analysis of proteolytic fragments. 1986. J Biol Chem. 26, 12579-12585.
8) Murata M, Ware J, and Ruggeri Z M. Site-directed mutagenesis of a soluble recombinant fragment of platelet glycoprotein Ib alpha demonstrating negatively charged residues involved in von Willebrand factor binding. 1991. J Biol Chem. 266, 8149-8155.

9) Fressinaud E, Baruch, D, Girma J P, et al.: von Willebrand factor-mediate platelet adhesion to collagen involves platelet glycoprotein IIb/IIIa as well as glycoprotein Ib. 1988. J Lab Clin Med 112, 58-67.

10) Weiss H J, Sussman I I, Hoyer L W. Stabilization of factor VIII in plasma by the von Willebrand factor. 1977. J Clin Invest. 60, 390-404.

11) Ewenstein B M. von Willebrand's disease. 1997. Ann Rev Med 48, 525-542.

12) Sadler J E, Matsushita T, Dong Z, Tuley E A, Westfield L A. Molecular mechanism and classification of von Willebrand disease. 1995. Thromb and Haemost 74, 161-166.

13. Bonthron D T, Handin R I, Kaufman Rj et al. Structure of pre-pro-von Willebrand factor and its expression in heterologous cells. Nature 1986; 324:270-273.

14. Shelton-Inloes B B, Titani K, Sadler E. cDNA sequences for human von Willebrand factor reveal five types of repeated domains and five possible protein sequence polymorphisms. Biochemistry 1986; 25:3164-3171.

15. Verweij, C L, Diergaarde P J, Hart, M, et al. Full length von Willebrand factor (vWF) cDNA encodes a highly repetitive protein considerably larger than the mature vWF subunit. EMBO J. 1986; 5:1839-1863.

16. Mancuso D J, Tuley E A, Westfield L A et al. Structure of the gene for human von Willebrand factor. J Biol Chem. 1989; 264:19514-19527.

17. Sadler J E, Shelton-Inloes B B, Sorace J M, Harlan J et al. Cloning and characterization of two cDNAs coding for human von Willebrand factor. Proc Natl Acad Sci USA 1985; 82:6394-6398.

18) CRUZ M A, DIACOVO T G, EMSLEY J, LIDDINGTON R, HANDIN R I. 2000. MAPPING THE GPIB BINDING SITE IN THE VON WILLEBRAND FACTOR A1 DOMAIN. J BIOL CHEM. 275, 19098-19105.

19) Savage B, Saldivar E, Ruggeri Z M. 1996. Initiation of platelet adhesion by arrest onto fibrinogen or translocation on von Willebrand factor. Cell. 84, 289-297.

20) Kalafatis M, Takahashi Y, Girma J P, et al. Localization of the collagen-interactive domain of human von Willebrand factor between amino acid residues Gly 911 and Glu 1365. Blood 1987; 70:1577-1583.

21) Pareti F I, Niiya K, McPherson J M, et al. Isolation and characterization of two domains of human von Willebrand factor that interact with fibillar collagen types I and III. J Biol Chem. 1987; 262:13835-13841.

22) Roth G J, Titani K, Hoyer L W, et al. Localization of binding sites within human von Willebrand factor for monomeric type III collagen. Biochemistry 1986; 25:8357-8361.

23) Lankhof H, van Hoeij M, Schiphorst M E, Bracke M et al. A3 domain is essential for interaction of von Willebrand factor with collagen type III. Thromb Haemost. 1996; 75:950-958.

24) Pareti F I, Fujimura Y, Dent J A, et al. Isolation and characterization of a collagen binding domain in human von Willebrand factor. J Biol Chem. 1986; 261:15310-15315.

25) Pietu G, Meulien P, Cherel G, et al. Production in *Escherichia coli* of a biologically active subfragment of von Willebrand factor corresponding to the platelet glycoprotein Ib, collagen, and heparin binding domains. Biochem. Biophys. Res. Comm. 1989; 164:1339-1347.

26) Meyer D, Fressinaud E, Gaucher C, Lavergne J-M, Hilbert L, Ribba A S et al. Gene defects in 150 unrelated French cases with type 2 von Willebrand disease: from patient to gene. Thromb and Haemost. 1997; 78:451-456.

27) Ginsburg, D., and J. E. Sadler. 1993. von Willebrand disease: a database of point mutations, insertions, and deletions. For the Consortium on von Willebrand Factor Mutations and Polymorphisms, and the Subcommittee on von Willebrand Factor of the Scientific and Standardization Committee of the International Society on Thrombosis and Haemostasis. *Thromb. Haemost.* 69:177-184.

28) Hillery C A, Mancuso D J, Sadler J E, Ponder J W et al. Type 2M von Willebrand disease: F6061 and 1662F mutations in the glycoprotein Ib binding domain selectively impair ristocetin- but not botrocetin-mediated binding of von Willebrand factor to platelets. Blood 1998; 91:1572-15781.

29) Mancuso D J, Kroner P A, Christopherson P A et al. Type 2M:Milwaukee-1 von Willebrand disease: an in-frame deletion in the Cys509-Cys695 loop of von Willebrand factor A1 domain causes deficient binding of von Willebrand factor to platelets. Blood 1996; 88: 2559-2568.

30) Ruggeri, Z. M., F. I. Pareti, P. M. Mannucci, N., Ciavarella, and T. S. Zimmerman. 1980.
Heightened interaction between platelets and factor VIII/von Willebrand factor in a new subtype of von Willebrand's disease. *N. Engl. J. Med.* 302:1047-1051.

31) Cooney, K. A., and D. Ginsburg. 1996. Comparative analysis of type 2B von Willebrand disease mutations: implications for the mechanism of von Willebrand factor binding to platelets. *Blood* 87:2322-2328.

32) Cruz, M. A., T. G. Diacovo, J. Emsley, R. Liddington, and R. I. Handin. 2000. Mapping the glycoprotein Ib-binding site in the von willebrand factor A1 domain. *J Biol Chem.* 275:19098-19105.

33) Huizinga E G, Tsuji S, Romijn R A P, et al. Structures of Glycoprotein Ibα and its complex with von Willebrand Factor A1 domain. Science. 2002; 297:1176-1179.

34) Federici A B, Bader R, Pagani S, Colibretti M L, De Marco L, and Mannucci P M. Binding of von Willebrand factor to glycoproteins Ib and IIb/IIIa complex: affinity is related to multimeric size. Br J Haematol. 1989; 73:93-99.

35) Roth G J. Developing relationships: arterial platelet adhesion, glycoprotein Ib, and leucine-rich glycoproteins. Blood. 1991; 77:5-19.

36) Siedlecki C A, Lestini B J, Kottke-Marchant K K, Eppell S J, Wilson D L, and Marchant R E. Shear-dependent changes in the three-dimensional structure of human von Willebrand factor. Blood 1996; 88:2939-2950.

37) Ruggeri Z M, and Ware J. The structure and function of von Willebrand factor. Thromb Haemost. 1992; 67:594-599.

38) Howard M A, and Firkin B G. Ristocetin—a new tool in the investigation of platelet aggregation. Thromb Diath Haemorrh. 1971; 26:362-369.

39) Read M S, Smith S V, Lamb, M A, and Brinkhous K M. Role of botrocetin in platelet agglutination: formation of an activated complex of botrocetin and von Willebrand factor. Blood 1989; 74:1031-1035

40) Emsley J, Knight C G, Farndale R W, Barnes M J, and Liddington R C. Structural basis of collagen recognition by integrin alpha2 beta1. Cell 2000; 101:47-56.

41) CELIKEL R, RUGGERI Z M, AND VARUGHESE K I. VON WILLEBRAND FACTOR CONFORMATION AND ADHESIVE FUNCTION IS MODULATED BY AN INTERNALIZED WATER MOLECULE. NAT STRUCT BIOL. 2000; 7:881-884.

42) Fukuda K, Doggett T A, Bankston L A, Cruz M A, Diacovo T G, Liddington R C. Structural basis of von Willebrand factor activation by the snake toxin botrocetin. Structure. 2002; 10:943-950.
43) Sen U, Vasudevan S, Subbarao G, McClintock R A, Celikel R, Ruggeri Z M, Varughese K I. Crystal structure of the von Willebrand factor modulator botrocetin. Biochemistry. 2001; 40:345-352.
44) Andrews R K, Booth W J, Gorman J J, Castaldi P A, Berndt M C. Purification of botrocetin from Bothrops jararaca venom. Analysis of the botrocetin-mediated interaction between von Willebrand factor and the human platelet membrane glycoprotein Ib-IX complex. Biochemistry. 1989; 28:8317-8326.
45) Yoshida E, Fujimura Y, Miura S, Sugimoto M, Fukui H, Narita N, Usami Y, Suzuki M, Titani K. Alboaggregin-B and botrocetin, two snake venom proteins with highly homologous amino acid sequences but totally distinct functions on von Willebrand factor binding to platelets. Biochem Biophys Res Commun. 1993; 19:1386-1392.
46) Italiano J E Jr, Bergmeier W, Tiwari S, Falet H, Hartwig J H, Hoffmeister K M, Andre P, Wagner D D, Shivdasani R A. Mechanisms and implications of platelet discoid shape. Blood. 2003 Jun. 15; 101(12):4789-96. Epub 2003 Feb. 13.
47) Yoon, B. J., and S. Kim. 1990. A boundary collocation method for the motion of two spheroids in Stokes flow: Hydrodynamic and colloidal interactions. Int. J. Multiphase Flow. 16:639-649.
48) Chesla S E, Selvaraj P, Zhu C. Measuring two-dimensional receptor-ligand binding kinetics by micropipette. Biophys J. 1998; 75:1553-1572.
49) Yamamoto H, Vreys I, Stassen J M et al. Antagonism of vWF inhibits both injury induced arterial and venous thrombosis in the hamster. Thromb Haemost 1998: 79:202-210.
50) Azzam K, Garfinkel L I, Bal dit Sollier C et al. Antithrombotic effect of a recombinant von Willebrand factor, VCL, on nitrogen laser-induced thrombus formation in guinea pig mesenteric arteries. Thromb Haemost 1995: 73:318-323.
51) Denis C, Methia N, Frenette P S, et al. A mouse model of severe von Willebrand disease:defects in hemostasis and thrombosis. Proc Natl Acad Sci, USA. 1998; 95:9524-9529.
52) Ware J, Russell S, Ruggeri Z M. Generation and rescue of a murine model of platelet dysfunction: the Bernard-Soulier syndrome. Proc Natl Acad Sci USA. 2000 Mar. 14; 97(6):2803-8.
53) Miura, S., C. Q. Li, Z. Cao, H. Wang, M. R. Wardell, and J. E. Sadler. 2000. Interaction of von Willebrand factor domain A1 with platelet glycoprotein Ib alpha-(1-289). Slow intrinsic binding kinetics mediate rapid platelet adhesion. *J. Biol. Chem.* 275:7539-7546.
54) KOHLER G, MILSTEIN C: CONTINUOUS CULTURES OF FUSED CELLS SECRETING ANTIBODY OF PREDEFINED SPECIFICITY. NATURE 1975; 256: 495-497.
55) Alon R, Chen S, Fuhlbrigge R, Puri K D, Springer T A. The kinetics and shear threshold of transient and rolling interactions of L-selectin with its ligand on leukocytes. Proc Natl Acad Sci USA. 1998; 95:11631-1166.
56) Gillespie, D. T. 1976. A general method for numerically simulating the stochastic time evolution of coupled chemical reactions. *J. Comput. Phys.* 22:403-434.
57) Tees, D. F. J., and H. L. Goldsmith. 1996. Kinetics and locus of failure of receptor-ligand-mediated adhesion between latex spheres. I. Protein-carbohydrate bond. *Biophys. J.* 71:1102-1114.
58) Marshall B T, Long M, Piper J W, Yago T, McEver R P, Zhu C. Direct observation of catch bonds involving cell-adhesion molecules. Nature. 2003; 423:190-193.
59) CHEN S, SPRINGER T A. SELECTIN RECEPTOR-LIGAND BONDS: FORMATION LIMITED BY SHEAR RATE AND DISSOCIATION GOVERNED BY THE BELL MODEL. PROC NATL ACAD SCI USA. 2001; 98:950-955.
60) Greenberg A W, Brunk D K, Hammer D A. Cell-free rolling mediated by L-selectin and sialyl Lewis (x) reveals the shear threshold effect. Biophys J. 2002; 79:2391-2402.
61) Chen S and Springer T A. An automatic braking system that stabilizes leukocyte rolling by an increase in selectin bond number with shear. 1999. J Cell Biol. 144:185-200.
62) Cooney K A, Ginsburg D. Comparative analysis of type 2b von Willebrand disease mutations: implications for the mechanism of von Willebrand factor binding to platelets. Blood. 1996; 87:2322-2328.
63) Merkel R, Nassoy P, Leung A, Ritchie K, Evans E. Energy landscapes of receptor-ligand bonds explored with dynamic force spectroscopy. Nature. 1999 Jan. 7; 397 (6714):50-3.
64) Evans E, Leung A, Hammer D, Simon S. Chemically distinct transition states govern rapid dissociation of single L-selectin bonds under force. Proc Natl Acad Sci USA. 2001 Mar. 27; 98(7):3784-9. Epub 2001 Mar. 13.
65) Simson D A, Ziemann F, Strigl M, Merkel R. Micropipet-based pico force transducer: in depth analysis and experimental verification. Biophys J. 1998 April; 74(4): 2080-8.
66) Evans E, Berk D, Leung A. Detachment of agglutinin-bonded red blood cells. I. Forces to rupture molecular-point attachments, Biophys J. 1991 April; 59(4):838-48.
67) Ribba A S, Voorberg J, Meyer D, Pannekoek H, Pietu G. Related Articles, Links Free Full Text Characterization of recombinant von Willebrand factor corresponding to mutations in type IIA and type IIB von Willebrand disease. J Biol Chem. 1992; 267:23209-23215.
68) Andre P, Prasad K S, Denis C V, He M, Papalia J M, Hynes R O, Phillips D R, Wagner D D. CD40L stabilizes arterial thrombi by a beta3 integrin-dependent mechanism. Nat Med. 2002 March; 8(3):247-52.
69) Coxon, A., P. Rieu, F. J. Barkalow, S. Askari, A. H. Sharpe, U. H. von Andrian, M. A. Arnaout, and T. N. Mayadas. 1996. A novel role for the beta 2 integrin CD11b/CD18 in neutrophil apoptosis: a homeostatic mechanism in inflammation. *Immunity.* 5:653-666.
70) Ni H, Ramakrishnan V, Ruggeri Z M, Papalia J M, Phillips D R, Wagner D D. Increased thrombogenesis and embolus formation in mice lacking glycoprotein V Blood. 2001 Jul. 15; 98(2):368-73
71) King M R, Hammer D A. Multiparticle adhesive dynamics: hydrodynamic recruitment of rolling leukocytes. Proc Natl Acad Sci USA. 2001 Dec. 18; 98(26):14919-24.

Example 8

Figure 47:
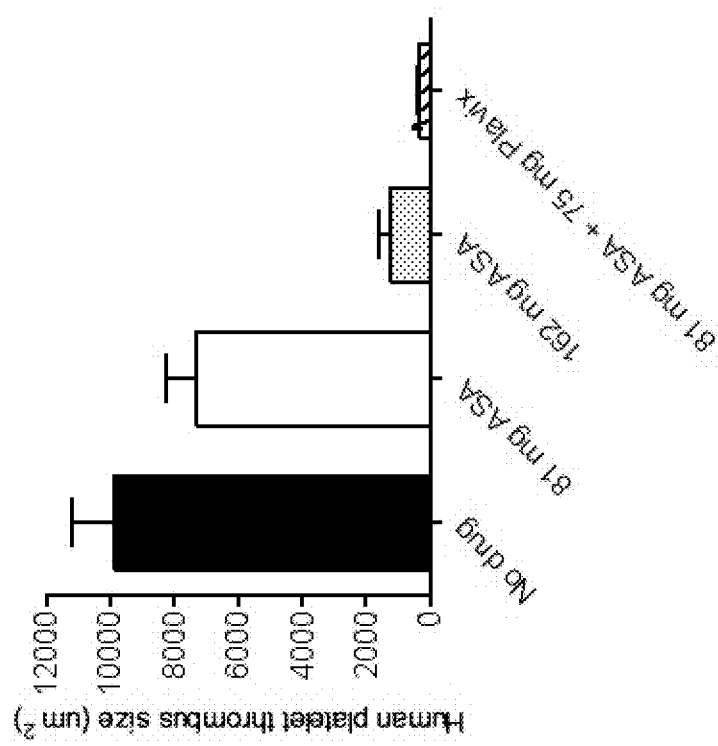
FIG. 47 is a graph showing the efficacy of anti-platelet drugs administered to patients by studying the ability of platelets harvested from patients on therapies in the VWF$^{1326R>H}$ mouse.

Determining the Efficacy of Anti-Platelet Drugs Administered to Patients by Studying the Ability of Platelets Harvested from Patients on Therapies in the $VWF^{1326R>H}$ Mouse Intravital microscopic study was carried out to evaluate the ability of the $VWF^{1326R>H}$ mouse to determine the efficacy of anti-platelet therapies given to patients at risk or with active cardiovascular disease. The typical prophylactic dose of aspirin (ASA) of 81 mg did not prevent laser-injury induced human platelet thrombus formation in the genetically modified animal while increasing the daily dose to 162 mg was preventative (FIG. 47). Similarly, platelets administered from a patient on 81 mg of ASA and 75 mg Plavix also prevented thrombus formation.

What is claimed is:

1. A transgenic mouse expressing a von Willebrand Factor A1 protein comprising an amino acid sequence at least 85% identical to SEQ ID NO: 2, wherein said von Willebrand Factor A1 protein comprises an arginine to histidine substitution at amino acid position 67.

2. The transgenic mouse of claim 1, wherein said von Willebrand Factor A1 protein is at least 90% identical to SEQ ID NO: 2 and wherein said von Willebrand Factor A1 protein comprises an arginine to histidine substitution at amino acid position 67.

3. The transgenic mouse of claim 1, wherein said von Willebrand Factor A1 protein is at least 95% identical to SEQ ID NO: 2, and wherein said von Willebrand Factor A1 protein comprises an arginine to histidine substitution at amino acid position 67.

4. The transgenic mouse of claim 1, wherein said von Willebrand Factor A1 protein is at least 99% identical to SEQ ID NO: 2 and wherein said von Willebrand Factor A1 protein comprises an arginine to histidine substitution at amino acid position 67.

* * * * *

```
                          SEQUENCE LISTING

<160> NUMBER OF SEQ ID NOS: 11

<210> SEQ ID NO 1
<211> LENGTH: 221
<212> TYPE: PRT
<213> ORGANISM: Homo sapiens

<400> SEQUENCE: 1

Glu Asp Ile Ser Glu Pro Pro Leu His Asp Phe Tyr Cys Ser Arg Leu
1               5                   10                  15

Leu Asp Leu Val Phe Leu Leu Asp Gly Ser Ser Arg Leu Ser Glu Ala
            20                  25                  30

Glu Phe Glu Val Leu Lys Ala Phe Val Val Asp Met Met Glu Arg Leu
        35                  40                  45

Arg Ile Ser Gln Lys Trp Val Arg Val Ala Val Val Glu Tyr His Asp
    50                  55                  60

Gly Ser His Ala Tyr Ile Gly Leu Lys Asp Arg Lys Arg Pro Ser Glu
65                  70                  75                  80

Leu Arg Arg Ile Ala Ser Gln Val Lys Tyr Ala Gly Ser Gln Val Ala
                85                  90                  95

Ser Thr Ser Glu Val Leu Lys Tyr Thr Leu Phe Gln Ile Phe Ser Lys
            100                 105                 110

Ile Asp Arg Pro Glu Ala Ser Arg Ile Ala Leu Leu Leu Met Ala Ser
        115                 120                 125

Gln Glu Pro Gln Arg Met Ser Arg Asn Phe Val Arg Tyr Val Gln Gly
    130                 135                 140

Leu Lys Lys Lys Lys Val Ile Val Ile Pro Val Gly Ile Gly Pro His
145                 150                 155                 160

Ala Asn Leu Lys Gln Ile Arg Leu Ile Glu Lys Gln Ala Pro Glu Asn
                165                 170                 175

Lys Ala Phe Val Leu Ser Ser Val Asp Glu Leu Glu Gln Gln Arg Asp
            180                 185                 190

Glu Ile Val Ser Tyr Leu Cys Asp Leu Ala Pro Glu Ala Pro Pro Pro
        195                 200                 205

Thr Leu Pro Pro His Met Ala Gln Val Thr Val Gly Pro
    210                 215                 220

<210> SEQ ID NO 2
<211> LENGTH: 221
<212> TYPE: PRT
<213> ORGANISM: Mus musculus

<400> SEQUENCE: 2

Glu Asp Thr Pro Glu Pro Pro Leu His Asn Phe Tyr Cys Ser Lys Leu
1               5                   10                  15

Leu Asp Leu Val Phe Leu Leu Asp Gly Ser Ser Met Leu Ser Glu Ala
            20                  25                  30

Glu Phe Glu Val Leu Lys Ala Phe Val Val Gly Met Met Glu Arg Leu
        35                  40                  45

His Ile Ser Gln Lys Arg Ile Arg Val Ala Val Val Glu Tyr His Asp
    50                  55                  60

Gly Ser Arg Ala Tyr Leu Glu Leu Lys Ala Arg Lys Arg Pro Ser Glu
65                  70                  75                  80
```

```
Leu Arg Arg Ile Thr Ser Gln Ile Lys Tyr Thr Gly Ser Gln Val Ala
                85                  90                  95

Ser Thr Ser Glu Val Leu Lys Tyr Thr Leu Phe Gln Ile Phe Gly Lys
            100                 105                 110

Ile Asp Arg Pro Glu Ala Ser His Ile Thr Leu Leu Thr Ala Ser
        115                 120                 125

Gln Glu Pro Pro Arg Met Ala Arg Asn Leu Val Arg Tyr Val Gln Gly
    130                 135                 140

Leu Lys Lys Lys Val Ile Val Ile Pro Val Gly Ile Gly Pro His
145                 150                 155                 160

Ala Ser Leu Lys Gln Ile Arg Leu Ile Glu Lys Gln Ala Pro Glu Asn
                165                 170                 175

Lys Ala Phe Leu Leu Ser Gly Val Asp Glu Leu Glu Gln Arg Arg Asp
            180                 185                 190

Glu Ile Val Ser Tyr Leu Cys Asp Leu Ala Pro Glu Ala Pro Ala Pro
        195                 200                 205

Thr Gln Pro Pro Gln Val Ala His Val Thr Val Ser Pro
    210                 215                 220

<210> SEQ ID NO 3
<211> LENGTH: 663
<212> TYPE: DNA
<213> ORGANISM: Homo sapiens

<400> SEQUENCE: 3
gaggacatct cggaaccgcc gttgcacgat ttctactgca gcaggctact ggacctggtc      60
ttcctgctgg atggctcctc caggctgtcc gaggctgagt ttgaagtgct gaaggccttt    120
gtggtggaca tgatggagcg gctgcgcatc tcccagaagt gggtccgcgt ggccgtggtg    180
gagtaccacg acggctccca cgcctacatc gggctcaagg accggaagcg accgtcagag    240
ctgcggcgca ttgccagcca ggtgaagtat gcgggcagcc aggtggcctc caccagcgag    300
gtcttgaaat acacactgtt ccaaatcttc agcaagatcg accgccctga agcctcccgc    360
atcgccctgc tcctgatggc cagccaggag ccccaacgga tgtcccggaa ctttgtccgc    420
tacgtccagg gcctgaagaa aagaaggtc attgtgatcc cggtgggcat gggccccat    480 gccaacctca gcagatccg cctcatcgag aagcaggccc ctgagaacaa ggccttcgtg    540
ctgagcagtg tggatgagct ggagcagcaa agggacgaga tcgttagcta cctctgtgac    600 cttgccctg aagcccctcc tcctactctg ccccccaca tggcacaagt cactgtgggc    660
ccg                                                                  663

<210> SEQ ID NO 4
<211> LENGTH: 663
<212> TYPE: DNA
<213> ORGANISM: Mus musculus

<400> SEQUENCE: 4 gaggatacccc ccgagccccc cctgcacaac ttctactgca gcaagctgct ggatcttgtc     60
ttcctgctgg atggctcctc tatgttgtcc gaggctgagt ttgaagtgct caaagctttt    120
gtggtgggca tgatggagag gttacacatc tctcagaagc gcatccgcgt ggcagtggta    180
gagtaccatg atggctcccg tgcctacctt gagctcaagg cccggaagcg accctcagag    240
cttcggcgca tcaccagcca gattaagtat acaggcagcc aggtggcctc taccagtgag    300
gttttgaagt acacactgtt ccagatcttt ggcaaaattg accgccctga agcctcccat    360
```

```
atcactctgc tcctgactgc tagccaggag cccccacgga tggctaggaa tttggtccgc    420
tatgtccaag gtctgaagaa gaagaaggtt atcgtgatcc ctgtgggcat tgggccccac    480
gccagcctca aacagatccg cctcatcgag aagcaggccc ctgaaaacaa ggctttctg     540 ctcagtgggg tggatgagct ggagcagaga agagatgaga tagtcagcta cctctgtgac    600
cttgctcccg aggccccagc cccaactcag cctccacagg tagcccacgt caccgtgagt    660
cca                                                                  663
```

```
<210> SEQ ID NO 5
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

Glu Asp Thr Pro Glu Pro Leu His Asn Phe Tyr Cys Ser Lys Leu
1               5                   10                  15

Leu Asp Leu Val Phe Leu Leu Asp Gly Ser Ser Met Leu Ser Glu Ala
                20                  25                  30

Glu Phe Glu Val Leu Lys Ala Phe Val Val Gly Met Met Glu Arg Leu
            35                  40                  45

His Ile Ser Gln Lys Arg Ile Arg Val Ala Val Val Glu Tyr His Asp
        50                  55                  60

Gly Ser His Ala Tyr Leu Glu Leu Lys Ala Arg Lys Arg Pro Ser Glu
65                  70                  75                  80

Leu Arg Arg Ile Thr Ser Gln Ile Lys Tyr Thr Gly Ser Gln Val Ala
                85                  90                  95

Ser Thr Ser Glu Val Leu Lys Tyr Thr Leu Phe Gln Ile Phe Gly Lys
                100                 105                 110

Ile Asp Arg Pro Glu Ala Ser His Ile Thr Leu Leu Leu Thr Ala Ser
            115                 120                 125

Gln Glu Pro Pro Arg Met Ala Arg Asn Leu Val Arg Tyr Val Gln Gly
        130                 135                 140

Leu Lys Lys Lys Lys Val Ile Val Ile Pro Val Gly Ile Gly Pro His
145                 150                 155                 160

Ala Ser Leu Lys Gln Ile Arg Leu Ile Glu Lys Gln Ala Pro Glu Asn
                165                 170                 175

Lys Ala Phe Leu Leu Ser Gly Val Asp Glu Leu Glu Gln Arg Arg Asp
            180                 185                 190

Glu Ile Val Ser Tyr Leu Cys Asp Leu Ala Pro Glu Ala Pro Ala Pro
        195                 200                 205

Thr Gln Pro Pro Gln Val Ala His Val Thr Val Ser Pro
        210                 215                 220

```
<210> SEQ ID NO 6
<211> LENGTH: 2813
<212> TYPE: PRT
<213> ORGANISM: Homo sapiens

<400> SEQUENCE: 6
```

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

-continued

```
Ala Arg Cys Ser Leu Phe Gly Ser Asp Phe Val Asn Thr Phe Asp Gly
         35                  40                  45

Ser Met Tyr Ser Phe Ala Gly Tyr Cys Ser Tyr Leu Leu Ala Gly Gly
 50                  55                  60

Cys Gln Lys Arg Ser Phe Ser Ile Ile Gly Asp Phe Gln Asn Gly Lys
 65                  70                  75                  80

Arg Val Ser Leu Ser Val Tyr Leu Gly Glu Phe Phe Asp Ile His Leu
                 85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
            195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445
```

```
Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
```

-continued

```
                865                 870                 875                 880
Leu Lys Tyr Leu Phe Pro Gly Glu Cys Gln Tyr Val Leu Val Gln Asp
                    885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Arg Val Thr Ile Leu
                915                 920                 925

Val Glu Gly Gly Glu Ile Glu Leu Phe Asp Gly Glu Val Asn Val Lys
            930                 935                 940

Arg Pro Met Lys Asp Glu Thr His Phe Glu Val Val Glu Ser Gly Arg
945                 950                 955                 960

Tyr Ile Ile Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                    980                 985                 990

Cys Gly Leu Cys Gly Asn Phe Asp  Gly Ile Gln Asn Asn  Asp Leu Thr
                    995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185

Thr Cys  Val Asp Pro Glu Asp  Cys Pro Val Cys Glu  Val Ala Gly
    1190                1195                1200

Arg Arg  Phe Ala Ser Gly Lys  Lys Val Thr Leu Asn  Pro Ser Asp
    1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro Thr
    1235                1240                1245

Asp Ala  Pro Val Ser Pro Thr  Thr Leu Tyr Val Glu  Asp Ile Ser
    1250                1255                1260

Glu Pro  Pro Leu His Asp Phe  Tyr Cys Ser Arg Leu  Leu Asp Leu
    1265                1270                1275
```

-continued

```
Val Phe Leu Leu Asp Gly Ser Ser Arg Leu Ser Glu Ala Glu Phe
            1280            1285            1290

Glu Val Leu Lys Ala Phe Val Asp Met Met Glu Arg Leu Arg
            1295            1300            1305

Ile Ser Gln Lys Trp Val Arg Val Ala Val Val Glu Tyr His Asp
            1310            1315            1320

Gly Ser His Ala Tyr Ile Gly Leu Lys Asp Arg Lys Arg Pro Ser
            1325            1330            1335

Glu Leu Arg Arg Ile Ala Ser Gln Val Lys Tyr Ala Gly Ser Gln
            1340            1345            1350

Val Ala Ser Thr Ser Glu Val Leu Lys Tyr Thr Leu Phe Gln Ile
            1355            1360            1365

Phe Ser Lys Ile Asp Arg Pro Glu Ala Ser Arg Ile Ala Leu Leu
            1370            1375            1380

Leu Met Ala Ser Gln Glu Pro Gln Arg Met Ser Arg Asn Phe Val
            1385            1390            1395

Arg Tyr Val Gln Gly Leu Lys Lys Lys Lys Val Ile Val Ile Pro
            1400            1405            1410

Val Gly Ile Gly Pro His Ala Asn Leu Lys Gln Ile Arg Leu Ile
            1415            1420            1425

Glu Lys Gln Ala Pro Glu Asn Lys Ala Phe Val Leu Ser Ser Val
            1430            1435            1440

Asp Glu Leu Glu Gln Gln Arg Asp Glu Ile Val Ser Tyr Leu Cys
            1445            1450            1455

Asp Leu Ala Pro Glu Ala Pro Pro Pro Thr Leu Pro Pro His Met
            1460            1465            1470

Ala Gln Val Thr Val Gly Pro Gly Leu Leu Gly Val Ser Thr Leu
            1475            1480            1485

Gly Pro Lys Arg Asn Ser Met Val Leu Asp Val Ala Phe Val Leu
            1490            1495            1500

Glu Gly Ser Asp Lys Ile Gly Glu Ala Asp Phe Asn Arg Ser Lys
            1505            1510            1515

Glu Phe Met Glu Glu Val Ile Gln Arg Met Asp Val Gly Gln Asp
            1520            1525            1530

Ser Ile His Val Thr Val Leu Gln Tyr Ser Tyr Met Val Thr Val
            1535            1540            1545

Glu Tyr Pro Phe Ser Glu Ala Gln Ser Lys Gly Asp Ile Leu Gln
            1550            1555            1560

Arg Val Arg Glu Ile Arg Tyr Gln Gly Gly Asn Arg Thr Asn Thr
            1565            1570            1575

Gly Leu Ala Leu Arg Tyr Leu Ser Asp His Ser Phe Leu Val Ser
            1580            1585            1590

Gln Gly Asp Arg Glu Gln Ala Pro Asn Leu Val Tyr Met Val Thr
            1595            1600            1605

Gly Asn Pro Ala Ser Asp Glu Ile Lys Arg Leu Pro Gly Asp Ile
            1610            1615            1620

Gln Val Val Pro Ile Gly Val Gly Pro Asn Ala Asn Val Gln Glu
            1625            1630            1635

Leu Glu Arg Ile Gly Trp Pro Asn Ala Pro Ile Leu Ile Gln Asp
            1640            1645            1650

Phe Glu Thr Leu Pro Arg Glu Ala Pro Asp Leu Val Leu Gln Arg
            1655            1660            1665
```

```
Cys Cys Ser Gly Glu Gly Leu Gln Ile Pro Thr Leu Ser Pro Ala
    1670                1675                1680

Pro Asp Cys Ser Gln Pro Leu Asp Val Ile Leu Leu Leu Asp Gly
    1685                1690                1695

Ser Ser Ser Phe Pro Ala Ser Tyr Phe Asp Glu Met Lys Ser Phe
    1700                1705                1710

Ala Lys Ala Phe Ile Ser Lys Ala Asn Ile Gly Pro Arg Leu Thr
    1715                1720                1725

Gln Val Ser Val Leu Gln Tyr Gly Ser Ile Thr Thr Ile Asp Val
    1730                1735                1740

Pro Trp Asn Val Val Pro Glu Lys Ala His Leu Leu Ser Leu Val
    1745                1750                1755

Asp Val Met Gln Arg Glu Gly Gly Pro Ser Gln Ile Gly Asp Ala
    1760                1765                1770

Leu Gly Phe Ala Val Arg Tyr Leu Thr Ser Glu Met His Gly Ala
    1775                1780                1785

Arg Pro Gly Ala Ser Lys Ala Val Val Ile Leu Val Thr Asp Val
    1790                1795                1800

Ser Val Asp Ser Val Asp Ala Ala Asp Ala Ala Arg Ser Asn
    1805                1810                1815

Arg Val Thr Val Phe Pro Ile Gly Ile Gly Asp Arg Tyr Asp Ala
    1820                1825                1830

Ala Gln Leu Arg Ile Leu Ala Gly Pro Ala Gly Asp Ser Asn Val
    1835                1840                1845

Val Lys Leu Gln Arg Ile Glu Asp Leu Pro Thr Met Val Thr Leu
    1850                1855                1860

Gly Asn Ser Phe Leu His Lys Leu Cys Ser Gly Phe Val Arg Ile
    1865                1870                1875

Cys Met Asp Glu Asp Gly Asn Glu Lys Arg Pro Gly Asp Val Trp
    1880                1885                1890

Thr Leu Pro Asp Gln Cys His Thr Val Thr Cys Gln Pro Asp Gly
    1895                1900                1905

Gln Thr Leu Leu Lys Ser His Arg Val Asn Cys Asp Arg Gly Leu
    1910                1915                1920

Arg Pro Ser Cys Pro Asn Ser Gln Ser Pro Val Lys Val Glu Glu
    1925                1930                1935

Thr Cys Gly Cys Arg Trp Thr Cys Pro Cys Val Cys Thr Gly Ser
    1940                1945                1950

Ser Thr Arg His Ile Val Thr Phe Asp Gly Gln Asn Phe Lys Leu
    1955                1960                1965

Thr Gly Ser Cys Ser Tyr Val Leu Phe Gln Asn Lys Glu Gln Asp
    1970                1975                1980

Leu Glu Val Ile Leu His Asn Gly Ala Cys Ser Pro Gly Ala Arg
    1985                1990                1995

Gln Gly Cys Met Lys Ser Ile Glu Val Lys His Ser Ala Leu Ser
    2000                2005                2010

Val Glu Leu His Ser Asp Met Glu Val Thr Val Asn Gly Arg Leu
    2015                2020                2025

Val Ser Val Pro Tyr Val Gly Gly Asn Met Glu Val Asn Val Tyr
    2030                2035                2040

Gly Ala Ile Met His Glu Val Arg Phe Asn His Leu Gly His Ile
    2045                2050                2055

Phe Thr Phe Thr Pro Gln Asn Asn Glu Phe Gln Leu Gln Leu Ser
```

-continued

```
            2060                2065                2070
Pro Lys Thr Phe Ala Ser Lys Thr Tyr Gly Leu Cys Gly Ile Cys
            2075                2080                2085
Asp Glu Asn Gly Ala Asn Asp Phe Met Leu Arg Asp Gly Thr Val
            2090                2095                2100
Thr Thr Asp Trp Lys Thr Leu Val Gln Glu Trp Thr Val Gln Arg
            2105                2110                2115
Pro Gly Gln Thr Cys Gln Pro Ile Leu Glu Glu Gln Cys Leu Val
            2120                2125                2130
Pro Asp Ser Ser His Cys Gln Val Leu Leu Pro Leu Phe Ala
            2135                2140                2145
Glu Cys His Lys Val Leu Ala Pro Ala Thr Phe Tyr Ala Ile Cys
            2150                2155                2160
Gln Gln Asp Ser Cys His Gln Glu Gln Val Cys Glu Val Ile Ala
            2165                2170                2175
Ser Tyr Ala His Leu Cys Arg Thr Asn Gly Val Cys Val Asp Trp
            2180                2185                2190
Arg Thr Pro Asp Phe Cys Ala Met Ser Cys Pro Pro Ser Leu Val
            2195                2200                2205
Tyr Asn His Cys Glu His Gly Cys Pro Arg His Cys Asp Gly Asn
            2210                2215                2220
Val Ser Ser Cys Gly Asp His Pro Ser Glu Gly Cys Phe Cys Pro
            2225                2230                2235
Pro Asp Lys Val Met Leu Glu Gly Ser Cys Val Pro Glu Glu Ala
            2240                2245                2250
Cys Thr Gln Cys Ile Gly Glu Asp Gly Val Gln His Gln Phe Leu
            2255                2260                2265
Glu Ala Trp Val Pro Asp His Gln Pro Cys Gln Ile Cys Thr Cys
            2270                2275                2280
Leu Ser Gly Arg Lys Val Asn Cys Thr Thr Gln Pro Cys Pro Thr
            2285                2290                2295
Ala Lys Ala Pro Thr Cys Gly Leu Cys Glu Val Ala Arg Leu Arg
            2300                2305                2310
Gln Asn Ala Asp Gln Cys Cys Pro Glu Tyr Glu Cys Val Cys Asp
            2315                2320                2325
Pro Val Ser Cys Asp Leu Pro Pro Val Pro His Cys Glu Arg Gly
            2330                2335                2340
Leu Gln Pro Thr Leu Thr Asn Pro Gly Glu Cys Arg Pro Asn Phe
            2345                2350                2355
Thr Cys Ala Cys Arg Lys Glu Glu Cys Lys Arg Val Ser Pro Pro
            2360                2365                2370
Ser Cys Pro Pro His Arg Leu Pro Thr Leu Arg Lys Thr Gln Cys
            2375                2380                2385
Cys Asp Glu Tyr Glu Cys Ala Cys Asn Cys Val Asn Ser Thr Val
            2390                2395                2400
Ser Cys Pro Leu Gly Tyr Leu Ala Ser Thr Ala Thr Asn Asp Cys
            2405                2410                2415
Gly Cys Thr Thr Thr Thr Cys Leu Pro Asp Lys Val Cys Val His
            2420                2425                2430
Arg Ser Thr Ile Tyr Pro Val Gly Gln Phe Trp Glu Glu Gly Cys
            2435                2440                2445
Asp Val Cys Thr Cys Thr Asp Met Glu Asp Ala Val Met Gly Leu
            2450                2455                2460
```

Arg Val Ala Gln Cys Ser Gln Lys Pro Cys Glu Asp Ser Cys Arg
2465                2470                2475

Ser Gly Phe Thr Tyr Val Leu His Glu Gly Glu Cys Cys Gly Arg
2480                2485                2490

Cys Leu Pro Ser Ala Cys Glu Val Val Thr Gly Ser Pro Arg Gly
2495                2500                2505

Asp Ser Gln Ser Ser Trp Lys Ser Val Gly Ser Gln Trp Ala Ser
2510                2515                2520

Pro Glu Asn Pro Cys Leu Ile Asn Glu Cys Val Arg Val Lys Glu
2525                2530                2535

Glu Val Phe Ile Gln Gln Arg Asn Val Ser Cys Pro Gln Leu Glu
2540                2545                2550

Val Pro Val Cys Pro Ser Gly Phe Gln Leu Ser Cys Lys Thr Ser
2555                2560                2565

Ala Cys Cys Pro Ser Cys Arg Cys Glu Arg Met Glu Ala Cys Met
2570                2575                2580

Leu Asn Gly Thr Val Ile Gly Pro Gly Lys Thr Val Met Ile Asp
2585                2590                2595

Val Cys Thr Thr Cys Arg Cys Met Val Gln Val Gly Val Ile Ser
2600                2605                2610

Gly Phe Lys Leu Glu Cys Arg Lys Thr Thr Cys Asn Pro Cys Pro
2615                2620                2625

Leu Gly Tyr Lys Glu Glu Asn Asn Thr Gly Glu Cys Cys Gly Arg
2630                2635                2640

Cys Leu Pro Thr Ala Cys Thr Ile Gln Leu Arg Gly Gly Gln Ile
2645                2650                2655

Met Thr Leu Lys Arg Asp Glu Thr Leu Gln Asp Gly Cys Asp Thr
2660                2665                2670

His Phe Cys Lys Val Asn Glu Arg Gly Glu Tyr Phe Trp Glu Lys
2675                2680                2685

Arg Val Thr Gly Cys Pro Pro Phe Asp Glu His Lys Cys Leu Ala
2690                2695                2700

Glu Gly Gly Lys Ile Met Lys Ile Pro Gly Thr Cys Cys Asp Thr
2705                2710                2715

Cys Glu Glu Pro Glu Cys Asn Asp Ile Thr Ala Arg Leu Gln Tyr
2720                2725                2730

Val Lys Val Gly Ser Cys Lys Ser Glu Val Glu Val Asp Ile His
2735                2740                2745

Tyr Cys Gln Gly Lys Cys Ala Ser Lys Ala Met Tyr Ser Ile Asp
2750                2755                2760

Ile Asn Asp Val Gln Asp Gln Cys Ser Cys Cys Ser Pro Thr Arg
2765                2770                2775

Thr Glu Pro Met Gln Val Ala Leu His Cys Thr Asn Gly Ser Val
2780                2785                2790

Val Tyr His Glu Val Leu Asn Ala Met Glu Cys Lys Cys Ser Pro
2795                2800                2805

Arg Lys Cys Ser Lys
    2810

<210> SEQ ID NO 7
<211> LENGTH: 8923
<212> TYPE: DNA
<213> ORGANISM: Homo sapiens

<400> SEQUENCE: 7

```
agctcacagc tattgtggtg ggaaagggag ggtggttggt ggatgtcaca gcttgggctt      60
tatctccccc agcagtgggg actccacagc ccctgggcta cataacagca agacagtccg     120
gagctgtagc agacctgatt gagcctttgc agcagctgag agcatggcct agggtgggcg     180
gcaccattgt ccagcagctg agtttcccag ggaccttgga gatagccgca gccctcattt     240
gcaggggaag gcaccattgt ccagcagctg agtttcccag ggaccttgga gatagccgca     300
gccctcattt atgattcctg ccagatttgc cggggtgctg cttgctctgg ccctcatttt     360
gccagggacc ctttgtgcag aaggaactcg cggcaggtca tccacggccc gatgcagcct     420
tttcggaagt gacttcgtca acacctttga tgggagcatg tacagctttg cgggatactg     480
cagttacctc ctggcagggg gctgccagaa acgctccttc tcgattattg gggacttcca     540
gaatggcaag agagtgagcc tctccgtgta tcttggggaa ttttttgaca tccatttgtt     600
tgtcaatggt accgtgacac aggggaccaa aagagtctcc atgccctatg cctccaaagg     660
gctgtatcta gaaactgagg ctgggtacta caagctgtcc ggtgaggcct atggctttgt     720
ggccaggatc gatggcagcg gcaactttca agtcctgctg tcagacagat acttcaacaa     780
gacctgcggg ctgtgtggca actttaacat ctttgctgaa gatgacttta tgacccaaga     840
agggaccttg acctcggacc cttatgactt tgccaactca tgggctctga gcagtggaga     900
acagtggtgt gaacgggcat ctcctcccag cagctcatgc aacatctcct ctggggaaat     960
gcagaagggc ctgtgggagc agtgccagct tctgaagagc acctcggtgt tgcccgctg    1020
ccaccctctg gtggacccg agccttttgt ggccctgtgt gagaagactt tgtgtgagtg    1080
tgctgggggg ctggagtgcg cctgccctgc cctcctggag tacgcccgga cctgtgccca    1140
ggagggaatg tgtgctatacg gctggaccga ccacagcgcg tgcagcccag tgtgccctgc    1200
tggtatggag tataggcagt gtgtgtcccc ttgcgccagg acctgccaga gcctgcacat    1260
caatgaaatg tgtcaggagc gatgcgtgga tgctgcagc tgccctgagg acagctcct    1320
ggatgaaggc ctctgcgtgg agagcaccga gtgtccctgc gtgcattccg gaaagcgcta    1380
ccctcccgga acctcctct ctcgagactg caacacctgc atttgccgaa acagccagtg    1440
gatctgcagc aatgaagaat gtccagggga gtgccttgtc actggtcaat cccacttcaa    1500
gagctttgac aacagatact tcaccttcag tgggatctgc cagtacctgc tggcccggga    1560
ttgccaggac cactccttct ccattgtcat tgagactgtc cagtgtgctg atgaccgcga    1620
cgctgtgtgc acccgctccg tcaccgtccg gctgcctggc ctgcacaaca gccttgtgaa    1680
actgaagcat ggggcaggag ttgccatgga tggccaggac atccagctcc ccctcctgaa    1740
aggtgacctc cgcatccagc atacagtgac ggcctccgtg cgcctcagct acggggagga    1800
cctgcagatg gactgggatg ccgcgggag gctgctggtg aagctgtccc ccgtctacgc    1860
cgggaagacc tgcggcctgt gtgggaatta caatggcaac cagggcgacg acttccttac    1920
ccctctgggg ctggcagagc ccgggtgga ggacttcggg aacgcctgga agctgcacgg    1980
ggactgccag gacctgcaga agcagcacag cgatccctgc gccctcaacc gcgcatgac    2040
caggttctcc gaggaggcgt gcgcggtcct gacgtccccc acattcgagg cctgccatcg    2100
tgccgtcagc ccgctgccct acctgcggaa ctgccgctac gacgtgtgct cctgctcgga    2160
cggccgcgag tgcctgtgcg gcgccctggc cagctatgcc gcggcctgcg cggggagagg    2220
cgtgcgcgtc gcgtggcgcg agccaggccg ctgtgagctg aactgcccga aaggccaggt    2280
gtacctgcag tgcgggaccc cctgcaacct gacctgccgc tctctctctt acccggatga    2340
```

```
ggaatgcaat gaggcctgcc tggagggctg cttctgcccc ccagggctct acatggatga    2400
gagggggggac tgcgtgccca aggcccagtg cccctgttac tatgacggtg agatcttcca   2460
gccagaagac atcttctcag accatcacac catgtgctac tgtgaggatg gcttcatgca    2520
ctgtaccatg agtggagtcc ccggaagctt gctgcctgac gctgtcctca gcagtcccct    2580
gtctcatcgc agcaaaagga gcctatcctg tcggccccc atggtcaagc tggtgtgtcc     2640
cgctgacaac ctgcgggctg aagggctcga gtgtaccaaa acgtgccaga actatgacct    2700
ggagtgcatg agcatgggct gtgtctctgg ctgcctctgc ccccgggca tggtccggca     2760
tgagaacaga tgtgtggccc tggaaaggtg tccctgcttc catcagggca aggagtatgc    2820
ccctggagaa acagtgaaga ttggctgcaa cacttgtgtc tgtcgggacc ggaagtggaa    2880
ctgcacagac catgtgtgtg atgccacgtg ctccacgatc ggcatggccc actacctcac    2940
cttcgacggg ctcaaatacc tgttccccgg ggagtgccag tacgttctgg tgcaggatta    3000
ctgcggcagt aaccctggga ccttcggat cctagtgggg aataagggat gcagccaccc     3060
ctcagtgaaa tgcaagaaac gggtcaccat cctggtggag ggaggagaga ttgagctgtt    3120
tgacggggag gtgaatgtga agaggcccat gaaggatgag actcactttg aggtggtgga    3180
gtctggccgg tacatcattc tgctgctggg caaagccctc tccgtggtct gggaccgcca    3240
cctgagcatc tccgtggtcc tgaagcagac ataccaggag aaagtgtgtg gcctgtgtgg   3300
gaattttgat ggcatccaga acaatgacct caccagcagc aacctccaag tggaggaaga   3360
ccctgtggac tttgggaact cctggaaagt gagctcgcag tgtgctgaca ccagaaaagt    3420
gcctctggac tcatcccctg ccacctgcca taacaacatc atgaagcaga cgatggtgga    3480
ttcctcctgt agaatcctta ccagtgacgt cttccaggac tgcaacaagc tggtggaccc   3540
cgagccatat ctggatgtct gcatttacga cacctgctcc tgtgagtcca ttggggactg   3600
cgcctgcttc tgcgacacca ttgctgccta tgcccacgtg tgtgcccagc atggcaaggt   3660
ggtgacctgg aggacggcca cattgtgccc ccagagctgc gaggagagga atctccggga   3720
gaacgggtat gagtgtgagt ggcgctataa cagctgtgca cctgcctgtc aagtcacgtg   3780
tcagcaccct gagccactgg cctgccctgt gcagtgtgtg gagggctgcc atgcccactg   3840
ccctccaggg aaaatcctgg atgagctttt gcagacctgc gttgaccctg aagactgtcc   3900
agtgtgtgag gtggctggcc ggcgttttgc ctcaggaaag aaagtcacct tgaatcccag   3960
tgaccctgag cactgccaga tttgccactg tgatgttgtc aacctcacct gtgaagcctg   4020
ccaggagccg ggaggcctgg tggtgcctcc cacagatgcc ccggtgagcc caccactct    4080
gtatgtggag gacatctcgg aaccgccgtt gcacgatttc tactgcagca ggctactgga   4140
cctggtcttc ctgctggatg gctcctccag gctgtccgag gctgagtttg aagtgctgaa   4200
ggcctttgtg gtggacatga tggagcggct gcgcatctcc cagaagtggg tccgcgtggc   4260
cgtggtggag taccacgacg gctcccacgc ctacatcggg ctcaaggacc ggaagcgacc   4320
gtcagagctg cggcgcattg ccagccaggt gaagtatgcg ggcagccagg tggcctccac   4380
cagcgaggtc ttgaaataca cactgttcca aatcttcagc aagatcgacc gcctgaagc    4440
ctcccgcatc gccctgctcc tgatggcag ccaggagccc caacggatgt cccggaactt    4500
tgtccgctac gtccagggcc tgaagaagaa gaaggtcatt gtgatcccgg tgggcattgg   4560
gccccatgcc aacctcaagc agatccgcct catcgagaag caggccctg agaacaaggc    4620
cttcgtgctg agcagtgtgg atgagctgga gcagcaaagg gacgagatcg ttagctacct   4680
```

```
ctgtgacctt gcccctgaag cccctcctcc tactctgccc cccacatgg cacaagtcac    4740 tgtgggcccg gggctcttgg gggtttcgac cctggggccc aagaggaact ccatggttct    4800
ggatgtggcg ttcgtcctgg aaggatcgga caaaattggt gaagccgact tcaacaggag    4860
caaggagttc atggaggagg tgattcagcg gatggatgtg ggccaggaca gcatccacgt    4920
cacggtgctg cagtactcct acatggtgac cgtggagtac cccttcagcg aggcacagtc    4980
caaaggggac atcctgcagc gggtgcgaga gatccgctac cagggcggca acaggaccaa    5040
cactgggctg gccctgcggt acctctctga ccacagcttc ttggtcagcc agggtgaccg    5100
ggagcaggcg cccaacctgg tctacatggt caccggaaat cctgcctctg atgagatcaa    5160
gaggctgcct ggagacatcc aggtggtgcc cattggagtg ggccctaatg ccaacgtgca    5220
ggagctggag aggattggct ggcccaatgc ccctatcctc atccaggact ttgagacgct    5280
cccccgagag gctcctgacc tggtgctgca gaggtgctgc tccggagagg ggctgcagat    5340
ccccaccctc tcccctgcac ctgactgcag ccagccctg gacgtgatcc ttctcctgga    5400
tggctcctcc agtttcccag cttcttattt tgatgaaatg aagagtttcg ccaaggcttt    5460
catttcaaaa gccaatatag ggcctcgtct cactcaggtg tcagtgctgc agtatggaag    5520
catcaccacc attgacgtgc catggaacgt ggtcccggag aaagcccatt tgctgagcct    5580
tgtggacgtc atgcagcggg agggaggccc cagccaaatc ggggatgcct gggctttgc    5640 tgtgcgatac ttgacttcag aaatgcatgg tgccaggccg ggagcctcaa aggcggtggt    5700
catcctggtc acggacgtct ctgtggattc agtggatgca gcagctgatg ccgccaggtc    5760
caacagagtg acagtgttcc ctattggaat tggagatcgc tacgatgcag cccagctacg    5820
gatcttggca ggcccagcag gcgactccaa cgtggtgaag ctccagcgaa tcgaagacct    5880
ccctaccatg gtcaccttgg gcaattcctt cctccacaaa ctgtgctctg gatttgttag    5940
gatttgcatg gatgaggatg ggaatgagaa gaggcccggg gacgtctgga ccttgccaga    6000
ccagtgccac accgtgactt gccagccaga tggccagacc ttgctgaaga gtcatcgggt    6060
caactgtgac cgggggctga ggccttcgtg ccctaacagc cagtcccctg ttaaagtgga    6120
agagacctgt ggctgccgct ggacctgccc ctgcgtgtgc acaggcagct ccactcggca    6180
catcgtgacc tttgatgggc agaatttcaa gctgactggc agctgttctt atgtcctatt    6240
tcaaaacaag gagcaggacc tggaggtgat tctccataat ggtgcctgca gccctggagc    6300
aaggcagggc tgcatgaaat ccatcgaggt gaagcacagt gccctctccg tcgagctgca    6360
cagtgacatg gaggtgacgg tgaatgggag actggtctct gttccttacg tgggtgggaa    6420
catggaagtc aacgtttatg gtgccatcat gcatgaggtc agattcaatc accttggtca    6480
catcttcaca ttcactccac aaaacaatga gttccaactg cagctcagcc ccaagacttt    6540
tgcttcaaag acgtatggtc tgtgtgggat ctgtgatgag aacggagcca atgacttcat    6600
gctgagggat ggcacagtca ccacagactg gaaaacactt gttcaggaat ggactgtgca    6660
gcggccaggg cagacgtgcc agcccatcct ggaggagcag tgtcttgtcc ccgacagctc    6720
ccactgccag gtcctcctct taccactgtt tgctgaatgc cacaaggtcc tggctccagc    6780
cacattctat gccatctgcc agcaggacag ttgccaccag gagcaagtgt gtgaggtgat    6840
cgcctcttat gcccacctct gtcggaccaa cggggtctgc gttgactgga ggacacctga    6900
tttctgtgct atgtcatgcc caccatctct ggtctacaac cactgtgagc atggctgtcc    6960
ccggcactgt gatggcaacg tgagctcctg tggggaccat ccctccgaag ctgtttctg    7020 ccctccagat aaagtcatgt tggaaggcag ctgtgtccct gaagaggcct gcactcagtg    7080
```

-continued

```
cattggtgag gatggagtcc agcaccagtt cctggaagcc tgggtcccgg accaccagcc      7140
ctgtcagatc tgcacatgcc tcagcgggcg aaggtcaac tgcacaacgc agccctgccc      7200
cacggccaaa gctcccacgt gtggcctgtg tgaagtagcc cgcctccgcc agaatgcaga      7260
ccagtgctgc cccgagtatg agtgtgtgtg tgacccagtg agctgtgacc tgccccccagt    7320
gcctcactgt gaacgtggcc tccagcccac actgaccaac cctggcgagt gcagacccaa     7380
cttcacctgc gcctgcagga aggaggagtg caaaagagtg tccccaccct cctgcccccc     7440
gcaccgtttg cccacccttc ggaagaccca gtgctgtgat gagtatgagt gtgcctgcaa     7500
ctgtgtcaac tccacagtga gctgtcccct tgggtacttg gcctcaaccg ccaccaatga    7560
ctgtggctgt accacaacca cctgccttcc cgacaaggtg tgtgtccacc gaagcaccat    7620
ctaccctgtg ggccagttct gggaggaggg ctgcgatgtg tgcacctgca ccgacatgga    7680
ggatgccgtg atgggcctcc gcgtggccca gtgctcccag aagccctgtg aggacagctg    7740
tcggtcgggc ttcacttacg ttctgcatga aggcgagtgc tgtggaaggt gcctgccatc    7800
tgcctgtgag gtggtgactg gctcaccgcg ggggactcc cagtcttcct ggaagagtgt    7860
cggctcccag tgggcctccc cggagaaccc ctgcctcatc aatgagtgtg tccgagtgaa    7920
ggaggaggtc tttatacaac aaaggaacgt ctcctgcccc cagctggagg tccctgtctg    7980
cccctcgggc tttcagctga gctgtaagac ctcagcgtgc tgcccaagct gtcgctgtga    8040
gcgcatggag gcctgcatgc tcaatggcac tgtcattggg cccgggaaga ctgtgatgat    8100
cgatgtgtgc acgacctgcc gctgcatggt gcaggtgggg gtcatctctg gattcaagct    8160
ggagtgcagg aagaccacct gcaacccctg cccctgggt tacaaggaag aaaataacac     8220
aggtgaatgt tgtgggagat gtttgcctac ggcttgcacc attcagctaa gaggaggaca   8280
gatcatgaca ctgaagcgtg atgagacgct ccaggatggc tgtgatactc acttctgcaa   8340
ggtcaatgag agaggagagt acttctggga agagggtc acaggctgcc caccctttga     8400
tgaacacaag tgtctggctg agggaggtaa aattatgaaa attccaggca cctgctgtga   8460
cacatgtgag gagcctgagt gcaacgacat cactgccagg ctgcagtatg tcaaggtggg   8520
aagctgtaag tctgaagtag aggtggatat ccactactgc cagggcaaat gtgccagcaa   8580
agccatgtac tccattgaca tcaacgatgt gcaggaccag tgctcctgct gctctccgac   8640
acggacggga cccatgcagg tggccctgca ctgcaccaat ggctctgttg tgtaccatga   8700
ggttctcaat gccatggagt gcaaatgctc ccccaggaag tgcagcaagt gaggctgctg   8760
cagctgcatg ggtgcctgct gctgcctgcc ttggcctgat ggccaggcca gagtgctgcc   8820
agtcctctgc atgttctgct cttgtgccct tctgagccca caataaaggc tgagctctta   8880
tcttgctgca tgttctgctc ttgtgccctt ctgagcccac aat                      8923
```

<210> SEQ ID NO 8
<211> LENGTH: 2813
<212> TYPE: PRT
<213> ORGANISM: Mus musculus

<400> SEQUENCE: 8

```
Met Asn Pro Phe Arg Tyr Glu Ile Cys Leu Leu Val Leu Ala Leu Thr
 1               5                  10                  15

Trp Pro Gly Thr Leu Cys Thr Glu Lys Pro Arg Asp Arg Pro Ser Thr
                20                  25                  30

Ala Arg Cys Ser Leu Phe Gly Asp Asp Phe Ile Asn Thr Phe Asp Glu
            35                  40                  45
```

```
Thr Met Tyr Ser Phe Ala Gly Gly Cys Ser Tyr Leu Leu Ala Gly Asp
    50                  55                  60
Cys Gln Lys Arg Ser Phe Ser Ile Leu Gly Asn Phe Gln Asp Gly Lys
 65                  70                  75                  80
Arg Met Ser Leu Ser Val Tyr Leu Gly Glu Phe Phe Asp Ile His Leu
                    85                  90                  95
Phe Ala Asn Gly Thr Val Thr Gln Gly Asp Gln Ser Ile Ser Met Pro
                100                 105                 110
Tyr Ala Ser Gln Gly Leu Tyr Leu Glu Arg Glu Ala Gly Tyr Tyr Lys
                115                 120                 125
Leu Ser Ser Glu Thr Phe Gly Phe Ala Ala Arg Ile Asp Gly Asn Gly
    130                 135                 140
Asn Phe Gln Val Leu Met Ser Asp Arg His Phe Asn Lys Thr Cys Gly
145                 150                 155                 160
Leu Cys Gly Asp Phe Asn Ile Phe Ala Glu Asp Asp Phe Arg Thr Gln
                165                 170                 175
Glu Gly Thr Leu Thr Ser Asp Pro Tyr Asp Phe Ala Asn Ser Trp Ala
                180                 185                 190
Leu Ser Ser Glu Glu Gln Arg Cys Lys Arg Ala Ser Pro Pro Ser Arg
    195                 200                 205
Asn Cys Glu Ser Ser Gly Asp Met His Gln Ala Met Trp Glu Gln
210                 215                 220
Cys Gln Leu Leu Lys Thr Ala Ser Val Phe Ala Arg Cys His Pro Leu
225                 230                 235                 240
Val Asp Pro Glu Ser Phe Val Ala Leu Cys Glu Lys Ile Leu Cys Thr
                245                 250                 255
Cys Ala Thr Gly Pro Glu Cys Ala Cys Pro Val Leu Leu Glu Tyr Ala
                260                 265                 270
Arg Thr Cys Ala Gln Glu Gly Met Val Leu Tyr Gly Trp Thr Asp His
            275                 280                 285
Ser Ala Cys Arg Pro Ala Cys Pro Ala Gly Met Glu Tyr Lys Glu Cys
    290                 295                 300
Val Ser Pro Cys Pro Arg Thr Cys Gln Ser Leu Ser Ile Asn Glu Val
305                 310                 315                 320
Cys Gln Gln Gln Cys Val Asp Gly Cys Ser Cys Pro Glu Gly Glu Leu
                325                 330                 335
Leu Asp Glu Asp Arg Cys Val Gln Ser Ser Asp Cys Pro Cys Val His
                340                 345                 350
Ala Gly Lys Arg Tyr Pro Pro Gly Thr Ser Leu Ser Gln Asp Cys Asn
    355                 360                 365
Thr Cys Ile Cys Arg Asn Ser Leu Trp Ile Cys Ser Asn Glu Glu Cys
    370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Glu Asp His Thr Phe Ser Ile Val Ile Glu Thr Met Gln Cys
                420                 425                 430
Ala Asp Asp Pro Asp Ala Val Cys Thr Arg Ser Val Ser Val Arg Leu
    435                 440                 445
Ser Ala Leu His Asn Ser Leu Val Lys Leu Lys His Gly Gly Ala Val
    450                 455                 460
```

-continued

```
Gly Ile Asp Gly Gln Asp Val Gln Leu Pro Phe Leu Gln Gly Asp Leu
465                 470                 475                 480

Arg Ile Gln His Thr Val Met Ala Ser Val Arg Leu Ser Tyr Ala Glu
            485                 490                 495

Asp Leu Gln Met Asp Trp Asp Gly Arg Gly Arg Leu Leu Val Lys Leu
        500                 505                 510

Ser Pro Val Tyr Ser Gly Lys Thr Cys Gly Leu Cys Gly Asn Tyr Asn
    515                 520                 525

Gly Asn Lys Gly Asp Asp Phe Leu Thr Pro Ala Gly Leu Val Glu Pro
530                 535                 540

Leu Val Val Asp Phe Gly Asn Ala Trp Lys Leu Gln Gly Asp Cys Ser
545                 550                 555                 560

Asp Leu Arg Arg Gln His Ser Asp Pro Cys Ser Leu Asn Pro Arg Leu
            565                 570                 575

Thr Arg Phe Ala Glu Glu Ala Cys Ala Leu Leu Thr Ser Ser Lys Phe
        580                 585                 590

Glu Ala Cys His His Ala Val Ser Pro Leu Pro Tyr Leu Gln Asn Cys
    595                 600                 605

Arg Tyr Asp Val Cys Ser Cys Ser Asp Ser Arg Asp Cys Leu Cys Asn
610                 615                 620

Ala Val Ala Asn Tyr Ala Ala Glu Cys Ala Arg Lys Gly Val His Ile
625                 630                 635                 640

Gly Trp Arg Glu Pro Gly Phe Cys Ala Leu Gly Cys Pro Gln Gly Gln
            645                 650                 655

Val Tyr Leu Gln Cys Gly Asn Ser Cys Asn Leu Thr Cys Arg Ser Leu
        660                 665                 670

Ser Leu Pro Asp Glu Glu Cys Ser Glu Val Cys Leu Glu Gly Cys Tyr
    675                 680                 685

Cys Pro Pro Gly Leu Tyr Gln Asp Glu Arg Gly Asp Cys Val Pro Lys
690                 695                 700

Ala Gln Cys Pro Cys Tyr Tyr Asp Gly Glu Leu Phe Gln Pro Ala Asp
705                 710                 715                 720

Ile Phe Ser Asp His His Thr Met Cys Tyr Cys Glu Asp Gly Phe Met
            725                 730                 735

His Cys Thr Thr Ser Gly Thr Leu Gly Ser Leu Leu Pro Asp Thr Val
        740                 745                 750

Leu Ser Ser Pro Leu Ser His Arg Ser Lys Arg Ser Leu Ser Cys Arg
    755                 760                 765

Pro Pro Met Val Lys Leu Val Cys Pro Ala Asp Asn Pro Arg Ala Gln
770                 775                 780

Gly Leu Glu Cys Ala Lys Thr Cys Gln Asn Tyr Asp Leu Glu Cys Met
785                 790                 795                 800

Ser Leu Gly Cys Val Ser Gly Cys Leu Cys Pro Pro Gly Met Val Arg
            805                 810                 815

His Glu Asn Lys Cys Val Ala Leu Glu Arg Cys Pro Cys Phe His Gln
        820                 825                 830

Gly Ala Glu Tyr Ala Pro Gly Asp Thr Val Lys Ile Gly Cys Asn Thr
    835                 840                 845

Cys Val Cys Arg Glu Arg Lys Trp Asn Cys Thr Asn His Val Cys Asp
850                 855                 860

Ala Thr Cys Ser Ala Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
```

-continued

```
                885                 890                 895
Tyr Cys Gly Ser Asn Pro Gly Thr Phe Gln Ile Leu Val Gly Asn Glu
                    900                 905                 910
Gly Cys Ser Tyr Pro Ser Val Lys Cys Arg Lys Arg Val Thr Ile Leu
                    915                 920                 925
Val Asp Gly Gly Glu Leu Glu Leu Phe Asp Gly Glu Val Asn Val Lys
    930                 935                 940
Arg Pro Leu Arg Asp Glu Ser His Phe Glu Val Val Glu Ser Gly Arg
945                 950                 955                 960
Tyr Val Ile Leu Leu Gly Gln Ala Leu Ser Val Val Trp Asp His
                    965                 970                 975
His Leu Ser Ile Ser Val Val Leu Lys His Thr Tyr Gln Glu Gln Val
                    980                 985                 990
Cys Gly Leu Cys Gly Asn Phe Asp  Gly Ile Gln Asn Asn  Asp Phe Thr
                    995                 1000                1005
Thr Ser  Ser Leu Gln Val Glu  Glu Asp Pro Val Asn  Phe Gly Asn
         1010                 1015                1020
Ser Trp  Lys Val Ser Ser Gln  Cys Ala Asp Thr Arg  Lys Leu Ser
         1025                 1030                1035
Leu Asp  Val Ser Pro Ala Thr  Cys His Asn Asn Ile  Met Lys Gln
         1040                 1045                1050
Thr Met  Val Asp Ser Ala Cys  Arg Ile Leu Thr Ser  Asp Val Phe
         1055                 1060                1065
Gln Gly  Cys Asn Arg Leu Val  Asp Pro Glu Pro Tyr  Leu Asp Ile
         1070                 1075                1080
Cys Ile  Tyr Asp Thr Cys Ser  Cys Glu Ser Ile Gly  Asp Cys Ala
         1085                 1090                1095
Cys Phe  Cys Asp Thr Ile Ala  Ala Tyr Ala His Val  Cys Ala Gln
         1100                 1105                1110
His Gly  Gln Val Val Ala Trp  Arg Thr Pro Thr Leu  Cys Pro Gln
         1115                 1120                1125
Ser Cys  Glu Glu Lys Asn Val  Arg Glu Asn Gly Tyr  Glu Cys Glu
         1130                 1135                1140
Trp Arg  Tyr Asn Ser Cys Ala  Pro Ala Cys Pro Val  Thr Cys Gln
         1145                 1150                1155
His Pro  Glu Pro Leu Ala Cys  Pro Val Gln Cys Val  Glu Gly Cys
         1160                 1165                1170
His Ala  His Cys Pro Pro Gly  Arg Ile Leu Asp Glu  Leu Leu Gln
         1175                 1180                1185
Thr Cys  Val Asp Pro Gln Asp  Cys Pro Val Cys Glu  Val Ala Gly
         1190                 1195                1200
Arg Arg  Leu Ala Pro Gly Lys  Lys Ile Thr Leu Ser  Pro Asp Asp
         1205                 1210                1215
Pro Ala  His Cys Gln Asn Cys  His Cys Asp Gly Val  Asn Leu Thr
         1220                 1225                1230
Cys Glu  Ala Cys Gln Glu Pro  Gly Gly Leu Val Ala  Pro Pro Thr
         1235                 1240                1245
Asp Ala  Pro Val Ser Ser Thr  Thr Pro Tyr Val Glu  Asp Thr Pro
         1250                 1255                1260
Glu Pro  Pro Leu His Asn Phe  Tyr Cys Ser Lys Leu  Leu Asp Leu
         1265                 1270                1275
Val Phe  Leu Leu Asp Gly Ser  Ser Met Leu Ser Glu  Ala Glu Phe
         1280                 1285                1290
```

```
Glu Val Leu Lys Ala Phe Val Val Gly Met Met Glu Arg Leu His
    1295                1300                1305

Ile Ser Gln Lys Arg Ile Arg Val Ala Val Val Glu Tyr His Asp
    1310                1315                1320

Gly Ser Arg Ala Tyr Leu Glu Leu Lys Ala Arg Lys Arg Pro Ser
    1325                1330                1335

Glu Leu Arg Arg Ile Thr Ser Gln Ile Lys Tyr Thr Gly Ser Gln
    1340                1345                1350

Val Ala Ser Thr Ser Glu Val Leu Lys Tyr Thr Leu Phe Gln Ile
    1355                1360                1365

Phe Gly Lys Ile Asp Arg Pro Glu Ala Ser His Ile Thr Leu Leu
    1370                1375                1380

Leu Thr Ala Ser Gln Glu Pro Pro Arg Met Ala Arg Asn Leu Val
    1385                1390                1395

Arg Tyr Val Gln Gly Leu Lys Lys Lys Val Ile Val Ile Pro
    1400                1405                1410

Val Gly Ile Gly Pro His Ala Ser Leu Lys Gln Ile Arg Leu Ile
    1415                1420                1425

Glu Lys Gln Ala Pro Glu Asn Lys Ala Phe Leu Leu Ser Gly Val
    1430                1435                1440

Asp Glu Leu Glu Gln Arg Arg Asp Glu Ile Val Ser Tyr Leu Cys
    1445                1450                1455

Asp Leu Ala Pro Glu Ala Pro Ala Pro Thr Gln Pro Pro Gln Val
    1460                1465                1470

Ala His Val Thr Val Ser Pro Gly Ile Ala Gly Ile Ser Ser Pro
    1475                1480                1485

Gly Pro Lys Arg Lys Ser Met Val Leu Asp Val Val Phe Val Leu
    1490                1495                1500

Glu Gly Ser Asp Glu Val Gly Glu Ala Asn Phe Asn Lys Ser Lys
    1505                1510                1515

Glu Phe Val Glu Glu Val Ile Gln Arg Met Asp Val Ser Pro Asp
    1520                1525                1530

Ala Thr Arg Ile Ser Val Leu Gln Tyr Ser Tyr Thr Val Thr Met
    1535                1540                1545

Glu Tyr Ala Phe Asn Gly Ala Gln Ser Lys Glu Glu Val Leu Arg
    1550                1555                1560

His Val Arg Glu Ile Arg Tyr Gln Gly Gly Asn Arg Thr Asn Thr
    1565                1570                1575

Gly Gln Ala Leu Gln Tyr Leu Ser Glu His Ser Phe Ser Pro Ser
    1580                1585                1590

Gln Gly Asp Arg Val Glu Ala Pro Asn Leu Val Tyr Met Val Thr
    1595                1600                1605

Gly Asn Pro Ala Ser Asp Glu Ile Lys Arg Leu Pro Gly Asp Ile
    1610                1615                1620

Gln Val Val Pro Ile Gly Val Gly Pro His Ala Asn Met Gln Glu
    1625                1630                1635

Leu Glu Arg Ile Ser Arg Pro Ile Ala Pro Ile Phe Ile Arg Asp
    1640                1645                1650

Phe Glu Thr Leu Pro Arg Glu Ala Pro Asp Leu Val Leu Gln Thr
    1655                1660                1665

Cys Cys Ser Lys Glu Gly Leu Gln Leu Pro Thr Leu Pro Pro Leu
    1670                1675                1680
```

```
Pro Asp Cys Ser Gln Pro Leu Asp Val Val Leu Leu Leu Asp Gly
    1685                1690                1695

Ser Ser Ser Leu Pro Glu Ser Ser Phe Asp Lys Met Lys Ser Phe
    1700                1705                1710

Ala Lys Ala Phe Ile Ser Lys Ala Asn Ile Gly Pro His Leu Thr
    1715                1720                1725

Gln Val Ser Val Ile Gln Tyr Gly Ser Ile Asn Thr Ile Asp Val
    1730                1735                1740

Pro Trp Asn Val Val Gln Glu Lys Ala His Leu Gln Ser Leu Val
    1745                1750                1755

Asp Leu Met Gln Gln Glu Gly Gly Pro Ser Gln Ile Gly Asp Ala
    1760                1765                1770

Leu Ala Phe Ala Val Arg Tyr Val Thr Ser Gln Ile His Gly Ala
    1775                1780                1785

Arg Pro Gly Ala Ser Lys Ala Val Val Ile Ile Ile Met Asp Thr
    1790                1795                1800

Ser Leu Asp Pro Val Asp Thr Ala Ala Asp Ala Ala Arg Ser Asn
    1805                1810                1815

Arg Val Ala Val Phe Pro Val Gly Val Gly Asp Arg Tyr Asp Glu
    1820                1825                1830

Ala Gln Leu Arg Ile Leu Ala Gly Pro Gly Ala Ser Ser Asn Val
    1835                1840                1845

Val Lys Leu Gln Gln Val Glu Asp Leu Ser Thr Met Ala Thr Leu
    1850                1855                1860

Gly Asn Ser Phe Phe His Lys Leu Cys Ser Gly Phe Ser Gly Val
    1865                1870                1875

Cys Val Asp Glu Asp Gly Asn Glu Lys Arg Pro Gly Asp Val Trp
    1880                1885                1890

Thr Leu Pro Asp Gln Cys His Thr Val Thr Cys Leu Ala Asn Gly
    1895                1900                1905

Gln Thr Leu Leu Gln Ser His Arg Val Asn Cys Asp His Gly Pro
    1910                1915                1920

Arg Pro Ser Cys Ala Asn Ser Gln Ser Pro Val Arg Val Glu Glu
    1925                1930                1935

Thr Cys Gly Cys Arg Trp Thr Cys Pro Cys Val Cys Thr Gly Ser
    1940                1945                1950

Ser Thr Arg His Ile Val Thr Phe Asp Gly Gln Asn Phe Lys Leu
    1955                1960                1965

Thr Gly Ser Cys Ser Tyr Val Ile Phe Gln Asn Lys Glu Gln Asp
    1970                1975                1980

Leu Glu Val Leu Leu His Asn Gly Ala Cys Ser Pro Gly Ala Lys
    1985                1990                1995

Gln Ala Cys Met Lys Ser Ile Glu Ile Lys His Ala Gly Val Ser
    2000                2005                2010

Ala Glu Leu His Ser Asn Met Glu Met Ala Val Asp Gly Arg Leu
    2015                2020                2025

Val Leu Ala Pro Tyr Val Gly Glu Asn Met Glu Val Ser Ile Tyr
    2030                2035                2040

Gly Ala Ile Met Tyr Glu Val Arg Phe Thr His Leu Gly His Ile
    2045                2050                2055

Leu Thr Tyr Thr Pro Gln Asn Asn Glu Phe Gln Leu Gln Leu Ser
    2060                2065                2070

Pro Lys Thr Phe Ala Ser Lys Met His Gly Leu Cys Gly Ile Cys
```

-continued

|  | 2075 |  |  |  | 2080 |  |  |  | 2085 |  |
|---|---|---|---|---|---|---|---|---|---|---|

Asp Glu Asn Gly Ala Asn Asp Phe Thr Leu Arg Asp Gly Thr Val
2090           2095                 2100

Thr Thr Asp Trp Lys Arg Leu Val Gln Glu Trp Thr Val Gln Gln
2105           2110                 2115

Pro Gly Tyr Thr Cys Gln Ala Val Pro Glu Glu Gln Cys Pro Val
2120           2125                 2130

Ser Asp Ser Ser His Cys Gln Val Leu Leu Ser Ala Ser Phe Ala
2135           2140                 2145

Glu Cys His Lys Val Ile Ala Pro Ala Thr Phe His Thr Ile Cys
2150           2155                 2160

Gln Gln Asp Ser Cys His Gln Glu Arg Val Cys Glu Val Ile Ala
2165           2170                 2175

Ser Tyr Ala His Leu Cys Arg Thr Ser Gly Val Cys Val Asp Trp
2180           2185                 2190

Arg Thr Thr Asp Phe Cys Ala Met Ser Cys Pro Pro Ser Leu Val
2195           2200                 2205

Tyr Asn His Cys Glu Arg Gly Cys Pro Arg His Cys Asp Gly Asn
2210           2215                 2220

Thr Ser Phe Cys Gly Asp His Pro Ser Glu Gly Cys Phe Cys Pro
2225           2230                 2235

Gln His Gln Val Phe Leu Glu Gly Ser Cys Val Pro Glu Glu Ala
2240           2245                 2250

Cys Thr Gln Cys Val Gly Glu Asp Gly Val Arg His Gln Phe Leu
2255           2260                 2265

Glu Thr Trp Val Pro Asp His Gln Pro Cys Gln Ile Cys Met Cys
2270           2275                 2280

Leu Ser Gly Arg Lys Ile Asn Cys Thr Ala Gln Pro Cys Pro Thr
2285           2290                 2295

Ala Arg Ala Pro Thr Cys Gly Pro Cys Glu Val Ala Arg Leu Lys
2300           2305                 2310

Gln Ser Thr Asn Leu Cys Cys Pro Glu Tyr Glu Cys Val Cys Asp
2315           2320                 2325

Leu Phe Asn Cys Asn Leu Pro Pro Val Pro Pro Cys Glu Gly Gly
2330           2335                 2340

Leu Gln Pro Thr Leu Thr Asn Pro Gly Glu Cys Arg Pro Thr Phe
2345           2350                 2355

Thr Cys Ala Cys Arg Lys Glu Glu Cys Lys Arg Val Ser Pro Pro
2360           2365                 2370

Ser Cys Pro Pro His Arg Thr Pro Thr Leu Arg Lys Thr Gln Cys
2375           2380                 2385

Cys Asp Glu Tyr Glu Cys Ala Cys Ser Cys Val Asn Ser Thr Leu
2390           2395                 2400

Ser Cys Pro Leu Gly Tyr Leu Ala Ser Ala Thr Thr Asn Asp Cys
2405           2410                 2415

Gly Cys Thr Thr Thr Thr Cys Leu Pro Asp Lys Val Cys Val His
2420           2425                 2430

Arg Gly Thr Val Tyr Pro Val Gly Gln Phe Trp Glu Glu Gly Cys
2435           2440                 2445

Asp Thr Cys Thr Cys Thr Asp Met Glu Asp Thr Val Val Gly Leu
2450           2455                 2460

Arg Val Val Gln Cys Ser Gln Arg Pro Cys Glu Asp Ser Cys Gln
2465           2470                 2475

```
Pro Gly Phe Ser Tyr Val Leu His Glu Gly Glu Cys Cys Gly Arg
    2480            2485                2490

Cys Leu Pro Ser Ala Cys Lys Val Val Ala Gly Ser Leu Arg Gly
    2495            2500                2505

Asp Ser His Ser Ser Trp Lys Ser Val Gly Ser Arg Trp Ala Val
    2510            2515                2520

Pro Glu Asn Pro Cys Leu Val Asn Glu Cys Val Arg Val Glu Asp
    2525            2530                2535

Ala Val Phe Val Gln Gln Arg Asn Ile Ser Cys Pro Gln Leu Ala
    2540            2545                2550

Val Pro Thr Cys Pro Thr Gly Phe Gln Leu Asn Cys Glu Thr Ser
    2555            2560                2565

Glu Cys Cys Pro Ser Cys His Cys Glu Pro Val Glu Ala Cys Leu
    2570            2575                2580

Leu Asn Gly Thr Ile Ile Gly Pro Gly Lys Ser Val Met Val Asp
    2585            2590                2595

Leu Cys Thr Thr Cys Arg Cys Ile Val Gln Thr Asp Ala Ile Ser
    2600            2605                2610

Arg Phe Lys Leu Glu Cys Arg Lys Thr Thr Cys Glu Ala Cys Pro
    2615            2620                2625

Met Gly Tyr Arg Glu Glu Lys Ser Gln Gly Glu Cys Cys Gly Arg
    2630            2635                2640

Cys Leu Pro Thr Ala Cys Thr Ile Gln Leu Arg Gly Gly Arg Ile
    2645            2650                2655

Met Thr Leu Lys Gln Asp Glu Thr Phe Gln Asp Gly Cys Asp Ser
    2660            2665                2670

His Leu Cys Arg Val Asn Glu Arg Gly Glu Tyr Ile Trp Glu Lys
    2675            2680                2685

Arg Val Thr Gly Cys Pro Pro Phe Asp Glu His Lys Cys Leu Ala
    2690            2695                2700

Glu Gly Gly Lys Ile Val Lys Ile Pro Gly Thr Cys Cys Asp Thr
    2705            2710                2715

Cys Glu Glu Pro Asp Cys Lys Asp Ile Thr Ala Lys Val Gln Tyr
    2720            2725                2730

Ile Lys Val Gly Asp Cys Lys Ser Gln Glu Glu Val Asp Ile His
    2735            2740                2745

Tyr Cys Gln Gly Lys Cys Ala Ser Lys Ala Val Tyr Ser Ile Asp
    2750            2755                2760

Ile Glu Asp Val Gln Glu Gln Cys Ser Cys Cys Leu Pro Ser Arg
    2765            2770                2775

Thr Glu Pro Met Arg Val Pro Leu His Cys Thr Asn Gly Ser Val
    2780            2785                2790

Val Tyr His Glu Val Ile Asn Ala Met Gln Cys Arg Cys Ser Pro
    2795            2800                2805

Arg Asn Cys Ser Lys
    2810

<210> SEQ ID NO 9
<211> LENGTH: 8537
<212> TYPE: DNA
<213> ORGANISM: Mus musculus

<400> SEQUENCE: 9
agtagcggct gggtttcctc aagggacctt ggagatacag cccctgtttg tatgggcaag     60
```

-continued

| | |
|---|---|
| atgaaccctt tcaggtatga gatctgcctg cttgttctgg ccctcacctg gccagggacc | 120 |
| ctctgcacag aaaagccccg tgacaggccg tcgacggccc gatgcagcct ctttggggac | 180 |
| gacttcatca acacgtttga tgagaccatg tacagctttg caggggctg cagttatctc | 240 |
| ctggctgggg actgccagaa acgttccttc tccattctcg gaacttcca agatggcaag | 300 |
| agaatgagcc tgtctgtgta tcttgggag tttttgaca tccatttgtt tgccaatggc | 360 |
| accgtaacgc agggtgacca aagcatctcc atgccctacg cctcccaagg actctaccta | 420 |
| gaacgcgagg ctgggtacta taagctctcc agtgagacct ttggctttgc ggccagaatc | 480 |
| gatggcaatg caacttcca gtcctgatg tcagacagac acttcaacaa gacctgtggg | 540 |
| ctgtgcggtg atttaacat cttcgcggaa gatgatttta ggacgcagga ggggaccttg | 600 |
| acctcagacc cctatgattt tgccaactcc tgggccctga gcagtgagga acagcggtgt | 660 |
| aaacgggcat ctcctcccag caggaactgc gagagctctt ctggggacat gcatcaggcc | 720 |
| atgtgggagc aatgccagct actgaagacg gcatcggtgt ttgcccgctg ccaccctctg | 780 |
| gtggatcccg agtcctttgt ggctctgtgt gagaagattt tgtgtacgtg tgctacgggg | 840 |
| ccagagtgcg catgtcctgt actccttgag tatgccgaa cctgcgccca ggaagggatg | 900 |
| gtgctgtacg gctggactga ccacagtgcc tgtcgtccag cttgcccagc tggcatggaa | 960 |
| tataaggagt gtgtgtctcc ttgccccaga acctgccaga gcctgtctat caatgaagtg | 1020 |
| tgtcagcagc aatgtgtaga cggctgtagc tgccctgagg gagagctctt ggatgaagac | 1080 |
| cgatgtgtgc agagctccga ctgtccttgc gtgcacgctg ggaagcggta ccctcctggc | 1140 |
| acctccctct ctcaggactg caacacttgt atctgcagaa acagcctatg gatctgcagc | 1200 |
| aatgaggaat gcccagggga gtgtcttgtc acaggccaat cgcacttcaa gagcttcgac | 1260 |
| aacaggtact tcaccttcag tgggatctgc caatatctgc tggcccggga ctgcgaggat | 1320 |
| cacactttct ccattgtcat agagaccatg cagtgtgccg atgaccctga tgctgtctgc | 1380 |
| acccgctcgg tcagtgtgcg gctctctgcc ctgcacaaca gcctggtgaa actgaagcac | 1440 |
| gggggagcag tgggcatcga tggtcaggat gtccagctcc ccttcctgca aggtgacctc | 1500 |
| cgcatccagc acacagtgat ggcttctgta cgcctcagct atgcggagga cctgcagatg | 1560 |
| gactgggatg gcgtggggcg gctactggtt aagctgtccc cagtctattc tgggaagacc | 1620 |
| tgtggcttgt gtgggaatta caacggcaac aagggagacg acttcctcac gccggccggc | 1680 |
| ttggtggagc ccctggtggt agacttcgga aacgcctgga agcttcaagg ggactgttcg | 1740 |
| gacctgcgca gcaacacag cgaccctgc agcctgaatc cacgcttgac caggtttgca | 1800 |
| gaggaggctt gtgcgctcct gacgtcctcc aagttcgagg cctgccacca cgcagtcagc | 1860 |
| cctctgccct atctgcagaa ctgccgttat gatgtttgct cctgctccga cagccgggat | 1920 |
| tgcctgtgta cgcagtagc taactatgct gccgagtgtg cccgaaaagg cgtgcacatc | 1980 |
| gggtggcggg agcctggctt ctgtgctctg ggctgtccac agggccaggt gtacctgcag | 2040 |
| tgtgggaatt cctgcaacct gacctgccgc tccctctccc tcccggatga agaatgcagt | 2100 |
| gaagtctgtc ttgaaggctg ctactgccca ccagggctct accaggatga aagaggggac | 2160 |
| tgtgtgccca aggccagtg cccctgctac acgatggta agctcttcca gcctgcggac | 2220 |
| atttctcag accaccatac catgtgttac tgtgaagatg gcttcatgca ctgtaccaca | 2280 |
| agtggcaccc tggggagcct gttgcctgac actgtcctca gcagtcccct gtctcaccgt | 2340 |
| agcaaaagga gcctttcctg ccggccaccc atggtcaagc tggtgtgtcc tgctgacaac | 2400 |

-continued

```
ccacgggctc aagggctgga gtgtgctaag acgtgccaga actacgacct ggagtgtatg    2460
agcctgggct gtgtgtctgg ctgcctctgt cccccaggca tggtccggca cgaaaacaag    2520
tgtgtggcct tggagcggtg tccctgcttc catcagggtg cagagtacgc cccgggagac    2580
acagtgaaga ttggctgcaa cacctgtgtc tgccgggagc ggaagtggaa ctgcacgaac    2640
catgtgtgtg acgccacttg ctctgccatt ggtatggccc actacctcac cttcgatgga    2700
ctcaagtacc tgttcccggg ggagtgccag tatgttctgg tgcaggatta ctgtggcagt    2760
aaccctggga cctttcagat cctggtggga aatgagggtt gcagctatcc ctcggtgaag    2820
tgcaggaagc gggtgaccat cctggtggat ggagggagc ttgaactgtt tgacggagag    2880
gtgaacgtta agaggcccct gagagatgaa tctcactttg aggtggtgga gtcgggccgg    2940
tacgtcatcc tgctgctggg tcaggccctt tctgtggtct ggaccacca cctcagcatc    3000
tctgtggtcc tgaagcacac ataccaggaa caggtgtgtg gcctctgcgg gaactttgat    3060
ggcatccaga caatgactt caccactagc agcctccagg tggaggaaga ccccgtcaac    3120
tttgggaact cctggaaagt gagctcacag tgtgctgaca cgagaaagct gtcactagat    3180
gtttccctg ccacttgcca caacaacatc atgaaacaga cgatggtgga ctcagcctgc    3240
agaatcctta ccagtgacgt cttccaggc tgcaacaggc tggtggaccc tgagcctac    3300
ctggacatct gtatttatga cacttgctcc tgtgagtcca tcggggactg cgcctgtttc    3360
tgtgacacca ttgctgccta tgcccacgtg tgtgcccagc atggccaggt ggtagcctgg    3420
aggacaccca cactgtgccc ccagagctgt gaagaaaaga atgttcggga aaatggctat    3480
gagtgtgagt ggcgttataa cagctgtgcg cctgcttgcc cagtcacgtg tcagcaccct    3540
gagcctctgg cttgccctgt gcagtgtgtg gagggttgtc atgcacattg ccctccaggg    3600
agaatcctgg atgaacttct gcagacctgc gtagaccccc aagactgccc cgtgtgtgag    3660
gtggctggtc ggcgcttggc tcctggaaag aaaatcacct tgagtcctga tgaccctgca    3720
cactgtcaga attgtcactg tgatggtgtg aaccttacgt gtgaagcctg ccaagagccc    3780
ggaggcctgg tggcaccccc aactgatgcc ccagtcagct ctaccacccc atatgttgag    3840
gataccccg agccccccct gcacaacttc tactgcagca agctgctgga tcttgtcttc    3900
ctgctggatg gctcctctat gttgtccgag gctgagtttg aagtgctcaa gcttttgtg    3960
gtgggcatga tggagaggtt acacatctct cagaagcgca tccgcgtggc agtggtagag    4020
taccatgatg gctcccgtgc ctaccttgag ctcaaggccc ggaagcgacc ctcagagctt    4080
cggcgcatca ccagccagat taagtataca ggcagccagg tggcctctac cagtgaggtt    4140
ttgaagtaca cactgttcca gatctttggc aaaattgacc gccctgaagc ctcccatatc    4200
actctgctcc tgactgctag ccaggagccc ccacggatgg ctaggaattt ggtccgctat    4260
gtccaaggtc tgaagaagaa gaaggttatc gtgatccctg tgggcattgg gccccacgcc    4320
agcctcaaac agatccgcct catcgagaag caggcccctg aaaacaaggc ttttctgctc    4380
agtggggtgg atgagctgga gcagagaaga gatgagatag tcagctacct ctgtgacctt    4440
gctcccgagg ccccagcccc aactcagcct ccacaggtag cccacgtcac cgtgagtcca    4500
gggatcgctg gatctcgtc accgggacca aaacggaagt ccatggttct ggatgtggtg    4560
tttgtcctgg aggggtcaga cgaagttggt gaagccaact tcaataagag caaggagttc    4620
gtggaggagg taatccagcg catggacgtg agcccggatg caacgcgcat ctcagtactg    4680
cagtattcct acacggtaac catggagtat gccttcaatg gggcccagtc caaggaggag    4740
gtgctgcggc acgtgcgaga gatccgctac cagggcggca ataggacaaa cactgggcag    4800
```

```
gccctgcagt acctttctga gcacagcttc tctcccagcc aaggggaccg ggtagaggca    4860
cctaacctgg tctacatggt cacggggaac cccgcctctg atgagatcaa gaggttgcct    4920
ggagacatcc aggtggtacc cattggggtg ggccccatg ccaacatgca ggaactggag     4980
aggatcagca ggcccatcgc tcccatcttc atccgggact tgagacact tccccgagag     5040
gctcctgacc tggtcctgca gacatgttgc tccaaggagg gtctgcaact gcccaccctc    5100
ccccctctcc ctgactgcag ccaacccctg gatgtggtcc tgctcctgga tggctcctct    5160
agcttgccag agtcttcctt tgataaaatg aagagttttg ccaaggcttt catttcaaag    5220
gccaacattg gccccacct cacacaggtg tccgtgatac agtatggaag catcaatacc     5280
attgatgtac catggaatgt ggttcaggag aaagcccatc tacagagttt ggtggacctc    5340
atgcagcagg agggtggccc cagccagatt ggggatgctc tggcctttgc cgtgcgctat    5400
gtaacttcac aaatccacgg agccaggcct ggggcctcca aagcagtggt catcatcatc    5460
atggatacct ccttggatcc cgtggacaca gcagcagatg ctgccagatc caaccgagtg    5520
gcagtgtttc ccgttggggt tggggatcgg tatgatgaag cccagctgag gatcttggca    5580
ggccctgggg ccagctccaa tgtggtaaag ctccagcaag ttgaagacct ctccaccatg    5640
gccaccctgg gcaactcctt cttccacaaa ctgtgttctg ggttttctgg agtttgtgtg    5700
gatgaagatg ggaatgagaa gaggcctggg gatgtctgga ccttgccgga tcagtgccac    5760
acagtgactt gcttggcaaa tggccagacc ttgctgcaga gtcatcgtgt caattgtgac    5820
catgaccccc ggccttcatg tgccaacagc cagtctcctg ttcgggtgga ggagacgtgt    5880
ggctgccgct ggacctgccc ttgtgtgtgc acgggcagtt ccactcggca catcgtcacc    5940
ttcgatgggc agaatttcaa gcttactggt agctgctcct atgtcatctt tcaaaacaag    6000
gagcaggacc tggaagtgct cctccacaat ggggcctgca gccccggggc aaaacaagcc    6060
tgcatgaagt ccattgagat taagcatgct ggcgtctctg ctgagctgca cagtaacatg    6120
gagatggcag tggatgggag actggtcctt gccccgtacg ttggtgaaaa catggaagtc    6180
agcatctacg gcgctatcat gtatgaagtc aggtttaccc atcttggcca catcctcaca    6240
tacacgccac aaaacaacga gttccaactg cagcttagcc ccaagacctt tgcttcgaag    6300
atgcatggtc tttgcggaat ctgtgatgaa acggggcca atgacttcac gttgcgagat    6360
ggcacggtca ccacagactg gaaaaggctt gtccaggaat ggacggtgca gcagccaggg    6420
tacacatgcc aggctgttcc cgaggagcag tgtcccgtct ctgacagctc ccactgccag    6480
gtcctcctct cagcgtcgtt tgctgaatgc acaaggtca tcgctccagc cacattccat     6540
accatctgcc agcaagacag ttgccaccag gagcgagtgt gtgaggtgat tgcttcttac    6600
gcccatctct gtcggaccag tggggtctgt gttgattgga ggacaactga tttctgtgct    6660
atgtcatgcc caccgtccct ggtgtataac cactgtgagc gtggctgccc tcggcactgc    6720
gatgggaaca ctagcttctg tgggggaccat ccctcagaag ctgcttctg tccccaacac    6780
caagtttttc tggaaggcag ctgtgtcccc gaggaggcct gcactcagtg tgttggcgag    6840
gatggagttc gacatcagtt cctggagacc tgggtcccag accatcagcc ctgtcagatc    6900
tgtatgtgcc tcagtgggag aaagattaac tgcactgccc agccgtgtcc cacagcccga    6960
gctcccacgt gtggcccatg tgaagtggct cgcctcaagc agagcacaaa cctgtgctgc    7020
ccagagtatg agtgtgtgtg tgacctgttc aactgcaact tgcctccagt gcctccgtgt    7080
gaaggagggc tccagccaac cctgaccaac cctggagaat gcagacccac ctttacctgt    7140
```

```
gcctgcagga aagaagagtg caaaagagtg tcccccaccct cctgcccccc tcaccggaca    7200
cccactctcc ggaagaccca gtgctgtgat gaatacgagt gtgcttgcag ctgtgtcaac    7260
tccacgctga gctgcccact tggctacctg gcctcagcca ctaccaatga ctgtggctgc    7320
accacgacca cctgtctccc tgacaaggtt tgtgtccacc gaggcaccgt ctaccctgtg    7380
ggccagttct gggaggaggg ctgtgacacg tgcacctgta cggacatgga ggatactgtc    7440
gtgggcctgc gtgtggtcca gtgctctcaa aggccctgtg aagacagctg tcagccaggt    7500
ttttcttatg ttctccacga aggcgagtgc tgtggaaggt gcctgccctc tgcttgcaag    7560
gtggtggctg gctcactgcg gggcgattcc cactcttcct ggaaaagtgt tggatctcgg    7620
tgggctgttc ctgagaaccc ctgcctcgtc aacgagtgtg tccgcgtgga ggatgcagtg    7680
tttgtgcagc agaggaacat ctcctgccca cagctggctg tccctacctg tcccacaggc    7740
ttccaactga actgtgagac ctcagagtgc tgtcctagct gccactgtga gcctgtggag    7800
gcctgcctgc tcaatggcac catcattggg cccgggaaga gtgtgatggt tgacctatgc    7860
acgacctgcc gctgcatcgt gcagacagac gccatctcca gattcaagct ggagtgcagg    7920
aagactacct gtgaggcctg ccccatgggc tatcgggaag agaagagcca gggtgaatgc    7980
tgtgggagat gcttgcctac agcttgcact attcagctaa gaggaggacg gatcatgacc    8040
ctgaagcaag atgagacatt ccaggatggc tgtgacagtc atttgtgcag ggtcaacgag    8100
agaggagagt acatctggga gaagagggtc acgggctgcc caccatttga tgaacacaag    8160
tgtctggctg aaggaggcaa aatcgtgaaa attccaggca cctgctgtga cacatgtgag    8220
gagcctgatt gcaaagacat cacagccaag gtgcagtaca tcaaagtggg agattgtaag    8280
tcccaagagg aagtggacat tcattactgc cagggaaagt gtgccagcaa agctgtgtac    8340
tccattgaca tcgaggatgt gcaggagcaa tgctcctgct gcctgccctc gaggacggaa    8400
cccatgcgcg tgcccttgca ctgcaccaat ggctctgtcg tgtaccacga ggtcatcaac    8460
gccatgcagt gcaggtgttc tccccggaac tgcagcaagt gaggcctgtg cagctacagc    8520
ggattcctac tgatacc                                                  8537
```

<210> SEQ ID NO 10
<211> LENGTH: 208
<212> TYPE: PRT
<213> ORGANISM: Mus musculus

<400> SEQUENCE: 10

```
Asp Ile Ser Glu Pro Pro Leu His Asp Phe Tyr Cys Ser Arg Leu Leu
1               5                   10                  15
Asp Leu Val Phe Leu Leu Asp Gly Ser Ser Arg Leu Ser Glu Ala Glu
            20                  25                  30
Phe Glu Val Leu Lys Ala Phe Val Val Asp Met Met Glu Arg Leu Arg
        35                  40                  45
Ile Ser Gln Lys Trp Val Arg Val Ala Val Val Glu Tyr His Asp Gly
    50                  55                  60
Ser His Ala Tyr Ile Gly Leu Lys Asp Arg Lys Arg Pro Ser Glu Leu
65                  70                  75                  80
Arg Arg Ile Ala Ser Gln Val Lys Tyr Ala Gly Ser Gln Val Ala Ser
                85                  90                  95
Thr Ser Glu Val Leu Lys Tyr Thr Leu Phe Gln Ile Phe Ser Lys Ile
            100                 105                 110
Asp Arg Pro Glu Ala Ser Arg Ile Ala Leu Leu Leu Met Ala Ser Gln
        115                 120                 125
```

```
Glu Pro Gln Arg Met Ser Arg Asn Phe Val Arg Tyr Val Gln Gly Leu
    130                 135                 140
Lys Lys Lys Val Ile Val Ile Pro Val Gly Ile Gly Pro His Ala
145                 150                 155                 160
Asn Leu Lys Gln Ile Arg Leu Ile Glu Lys Gln Ala Pro Glu Asn Lys
                165                 170                 175
Ala Phe Val Leu Ser Ser Val Asp Glu Leu Glu Gln Gln Arg Asp Glu
                180                 185                 190
Ile Val Ser Tyr Leu Cys Asp Leu Ala Pro Glu Ala Pro Pro Pro Thr
                195                 200                 205
```

```
<210> SEQ ID NO 11
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (10)..(10)
<223> OTHER INFORMATION: Asn or Asp
<220> FEATURE:
<221> NAME/KEY: MOD_RES
<222> LOCATION: (15)..(15)
<223> OTHER INFORMATION: Lys or Arg
<220> FEATURE:
<221> NAME/KEY: MOD_RES
<222> LOCATION: (28)..(28)
<223> OTHER INFORMATION: Met or Arg
<220> FEATURE:
<221> NAME/KEY: MOD_RES
<222> LOCATION: (43)..(43)
<223> OTHER INFORMATION: Gly or Asp
<220> FEATURE:
<221> NAME/KEY: MOD_RES
<222> LOCATION: (49)..(49)
<223> OTHER INFORMATION: His or Arg
<220> FEATURE:
<221> NAME/KEY: MOD_RES
<222> LOCATION: (54)..(54)
<223> OTHER INFORMATION: Arg or Trp
<220> FEATURE:
<221> NAME/KEY: MOD_RES
<222> LOCATION: (55)..(55)
<223> OTHER INFORMATION: Ile or Val
<220> FEATURE:
<221> NAME/KEY: MOD_RES
<222> LOCATION: (67)..(67)
<223> OTHER INFORMATION: Arg or His
<220> FEATURE:
<221> NAME/KEY: MOD_RES
<222> LOCATION: (70)..(70)
<223> OTHER INFORMATION: Leu or Ile
<220> FEATURE:
<221> NAME/KEY: MOD_RES
<222> LOCATION: (71)..(71)
<223> OTHER INFORMATION: Glu or Gly
<220> FEATURE:
<221> NAME/KEY: MOD_RES
<222> LOCATION: (74)..(74)
<223> OTHER INFORMATION: Ala or Asp
<220> FEATURE:
<221> NAME/KEY: MOD_RES
<222> LOCATION: (85)..(85)
<223> OTHER INFORMATION: Thr or Ala
<220> FEATURE:
<221> NAME/KEY: MOD_RES
<222> LOCATION: (88)..(88)
```

<223> OTHER INFORMATION: Ile or Val
<220> FEATURE:
<221> NAME/KEY: MOD_RES
<222> LOCATION: (91)..(91)
<223> OTHER INFORMATION: Thr or Ala
<220> FEATURE:
<221> NAME/KEY: MOD_RES
<222> LOCATION: (111)..(111)
<223> OTHER INFORMATION: Gly or Ser
<220> FEATURE:
<221> NAME/KEY: MOD_RES
<222> LOCATION: (120)..(120)
<223> OTHER INFORMATION: His or Arg
<220> FEATURE:
<221> NAME/KEY: MOD_RES
<222> LOCATION: (122)..(122)
<223> OTHER INFORMATION: Thr or Ala
<220> FEATURE:
<221> NAME/KEY: MOD_RES
<222> LOCATION: (126)..(126)
<223> OTHER INFORMATION: Thr or Met
<220> FEATURE:
<221> NAME/KEY: MOD_RES
<222> LOCATION: (132)..(132)
<223> OTHER INFORMATION: Pro or Gln
<220> FEATURE:
<221> NAME/KEY: MOD_RES
<222> LOCATION: (135)..(135)
<223> OTHER INFORMATION: Ala or Ser
<220> FEATURE:
<221> NAME/KEY: MOD_RES
<222> LOCATION: (138)..(138)
<223> OTHER INFORMATION: Leu or Phe
<220> FEATURE:
<221> NAME/KEY: MOD_RES
<222> LOCATION: (162)..(162)
<223> OTHER INFORMATION: Ser or Asn
<220> FEATURE:
<221> NAME/KEY: MOD_RES
<222> LOCATION: (180)..(180)
<223> OTHER INFORMATION: Leu or Val
<220> FEATURE:
<221> NAME/KEY: MOD_RES
<222> LOCATION: (183)..(183)
<223> OTHER INFORMATION: Gly or Ser
<220> FEATURE:
<221> NAME/KEY: MOD_RES
<222> LOCATION: (190)..(190)
<223> OTHER INFORMATION: Arg or Gln
<220> FEATURE:
<221> NAME/KEY: MOD_RES
<222> LOCATION: (207)..(207)
<223> OTHER INFORMATION: Ala or Pro
<220> FEATURE:
<221> NAME/KEY: MOD_RES
<222> LOCATION: (210)..(210)
<223> OTHER INFORMATION: Gln or Leu
<220> FEATURE:
<221> NAME/KEY: MOD_RES
<222> LOCATION: (213)..(213)
<223> OTHER INFORMATION: Gln or His
<220> FEATURE:
<221> NAME/KEY: MOD_RES
<222> LOCATION: (214)..(214)
<223> OTHER INFORMATION: Val or Met
<220> FEATURE:
<221> NAME/KEY: MOD_RES
<222> LOCATION: (216)..(216)
<223> OTHER INFORMATION: His or Gln
<220> FEATURE:
<221> NAME/KEY: MOD_RES
<222> LOCATION: (220)..(220)
<223> OTHER INFORMATION: Ser or Gly

<400> SEQUENCE: 11

Glu Asp Thr Xaa Glu Pro Pro Leu His Xaa Phe Tyr Cys Ser Xaa Leu
 1               5                  10                  15

-continued

```
Leu Asp Leu Val Phe Leu Leu Asp Gly Ser Ser Xaa Leu Ser Glu Ala
            20                  25                  30

Glu Phe Glu Val Leu Lys Ala Phe Val Val Xaa Met Met Glu Arg Leu
        35                  40              45

Xaa Ile Ser Gln Lys Xaa Xaa Arg Val Ala Val Val Glu Tyr His Asp
    50                  55                  60

Gly Ser Xaa Ala Tyr Xaa Xaa Leu Lys Xaa Arg Lys Arg Pro Ser Glu
65              70                  75                      80

Leu Arg Arg Ile Xaa Ser Gln Xaa Lys Tyr Xaa Gly Ser Gln Val Ala
                85                  90                  95

Ser Thr Ser Glu Val Leu Lys Tyr Thr Leu Phe Gln Ile Phe Xaa Lys
            100                 105                 110

Ile Asp Arg Pro Glu Ala Ser Xaa Ile Xaa Leu Leu Leu Xaa Ala Ser
            115                 120                 125

Gln Glu Pro Xaa Arg Met Xaa Arg Asn Xaa Val Arg Tyr Val Gln Gly
            130                 135                 140

Leu Lys Lys Lys Lys Val Ile Val Ile Pro Val Gly Ile Gly Pro His
145                 150                 155                 160

Ala Xaa Leu Lys Gln Ile Arg Leu Ile Glu Lys Gln Ala Pro Glu Asn
                165                 170                 175

Lys Ala Phe Xaa Leu Ser Xaa Val Asp Glu Leu Glu Gln Xaa Arg Asp
                180                 185                 190

Glu Ile Val Ser Tyr Leu Cys Asp Leu Ala Pro Glu Ala Pro Xaa Pro
            195                 200                 205

Thr Xaa Pro Pro Xaa Xaa Ala Xaa Val Thr Val Xaa Pro
    210                 215                 220
```

UNITED STATES PATENT AND TRADEMARK OFFICE
CERTIFICATE OF CORRECTION

| | | |
|---|---|---|
| PATENT NO. | : 9,686,971 B2 | Page 1 of 1 |
| APPLICATION NO. | : 15/047978 | |
| DATED | : June 27, 2017 | |
| INVENTOR(S) | : Thomas Diacovo and Jianchun Chen | |

It is certified that error appears in the above-identified patent and that said Letters Patent is hereby corrected as shown below:

In the Specification

Column 1, Line 26 paragraph should read --This invention was made with government support under Grant No. HL063244 awarded by the National Institutes of Health. The Government has certain rights in this invention.--

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*